(12) United States Patent
Xu et al.

(10) Patent No.: US 12,150,379 B2
(45) Date of Patent: Nov. 19, 2024

(54) ARYLAMINE COMPOUND, ORGANIC ELECTROLUMINESCENT DEVICE, AND ELECTRONIC APPARATUS

(71) Applicant: SHAANXI LIGHTE OPTOELECTRONICS MATERIAL CO., LTD., Xi'an (CN)

(72) Inventors: Xianbin Xu, Xi'an (CN); Lei Yang, Xi'an (CN)

(73) Assignee: Shaanxi Lighte Optoelectronics Material Co., Ltd., Xi'an (CN)

( * ) Notice: Subject to any disclaimer, the term of this patent is extended or adjusted under 35 U.S.C. 154(b) by 0 days.

(21) Appl. No.: 18/552,891

(22) PCT Filed: Nov. 28, 2022

(86) PCT No.: PCT/CN2022/134759
§ 371 (c)(1),
(2) Date: Sep. 27, 2023

(87) PCT Pub. No.: WO2024/007511
PCT Pub. Date: Jan. 11, 2024

(65) Prior Publication Data
US 2024/0298529 A1    Sep. 5, 2024

(30) Foreign Application Priority Data

Jul. 7, 2022  (CN) .......................... 202210794941.1

(51) Int. Cl.
*H10K 85/60*    (2023.01)
*C07D 413/12*   (2006.01)
*C07D 413/14*   (2006.01)
*C07D 417/12*   (2006.01)
*C09K 11/02*    (2006.01)
*H10K 50/11*    (2023.01)

(52) U.S. Cl.
CPC ......... H10K 85/636 (2023.02); C07D 413/12 (2013.01); C07D 413/14 (2013.01); C07D 417/12 (2013.01); C09K 11/02 (2013.01); H10K 85/633 (2023.02); H10K 85/615 (2023.02); H10K 85/622 (2023.02); H10K 85/626 (2023.02); H10K 85/6572 (2023.02); H10K 85/6574 (2023.02); H10K 85/6576 (2023.02)

(58) Field of Classification Search
CPC ................ C07D 413/12; C07D 413/14; C07D 417/12; C07D 417/14; H10K 85/636
See application file for complete search history.

(56) References Cited

FOREIGN PATENT DOCUMENTS

| CN | 113105420 A | | 7/2021 |
|---|---|---|---|
| CN | 113773314 A | * | 12/2021 |
| CN | 115109051 A | | 9/2022 |
| KR | 20210050474 A | * | 5/2021 |
| WO | WO-2021230714 A1 | * | 11/2021 |

* cited by examiner

*Primary Examiner* — Vu A Nguyen
(74) *Attorney, Agent, or Firm* — Rodney J. Fuller; BOOTH UDALL FULLER, PLC

(57) ABSTRACT

The present application provides an arylamine compound, an organic electroluminescent device containing the arylamine compound, and an electronic apparatus. The arylamine compound contains both a benzocarbazolyl group and a benzoxazolyl or benzothiazolyl group. The compound, when used in a mixed-type host material of an organic electroluminescent device, can significantly improve the efficiency and prolong service life of the device.

8 Claims, 1 Drawing Sheet

ARYLAMINE COMPOUND, ORGANIC ELECTROLUMINESCENT DEVICE, AND ELECTRONIC APPARATUS

CROSS-REFERENCE TO RELATED APPLICATIONS

This application is the U.S. National Stage of International Application No. PCT/CN2022/134759, filed on Nov. 28, 2022, which claims the benefit of Chinese patent application No. 202210794941.1 filed on Jul. 7, 2022, the contents of each of which are incorporated herein by reference in their entirety as a part of this application.

FIELD OF THE INVENTION

The present disclosure relates to the technical field of organic electroluminescent materials, and in particular to an arylamine compound, an organic electroluminescent device comprising the arylamine compound, and an electronic apparatus.

BACKGROUND OF THE INVENTION

With the development of electronic technology and the advancement of material science, electronic devices for achieving electroluminescence or photoelectric conversion have found an increasingly wide range of applications. An organic electroluminescent device typically includes a cathode and an anode that are disposed opposite to each other, and a functional layer disposed between the cathode and the anode. The functional layer consists of a plurality of organic or inorganic film layers, and generally comprises an organic light-emitting layer, a hole transport layer, an electron transport layer, etc. When a voltage is applied to the cathode and the anode, an electric field is formed between the two electrodes. Under the influence of the electric field, electrons on the cathode side migrate to the electroluminescent light-emitting layer, and holes on the anode side also migrate to the electroluminescent light-emitting layer. The electrons and the holes recombine in the electroluminescent light-emitting layer, forming excitons. The excitons in excited states release energy, causing the electroluminescent light-emitting layer to emit light to the outside.

Main problems with existing organic electroluminescent devices lie in their service life and efficiency. As display screens become larger and larger, driving voltages are increased accordingly, which necessitates improvement in luminous efficiency and current efficiency. It is therefore necessary to continue to develop new materials to further improve the performance of organic electroluminescent devices.

SUMMARY OF THE INVENTION

Directed against the above problems with the existing technology, the present disclosure aims at providing an arylamine compound, an organic electroluminescent device comprising the arylamine compound, and an electronic apparatus. The arylamine compound, when used in an organic electroluminescent device, can improve the performance of the device.

According to a first aspect of the present disclosure, there is provided an arylamine compound. The arylamine compound has a structure shown in Formula 1:

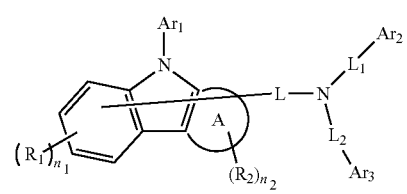

Formula 1 wherein:
ring A is a naphthalene ring;
L, $L_1$, and $L_2$ are identical or different, and are each independently selected from the group consisting of single bond, substituted or unsubstituted arylene having 6 to 30 carbon atoms, and substituted or unsubstituted heteroarylene having 3 to 30 carbon atoms;
$Ar_2$ is a group shown in Formula 2;

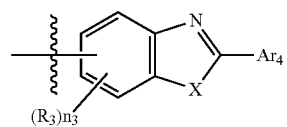

Formula 2

X is selected from O or S;
$Ar_1$, $Ar_3$, and $Ar_4$ are identical or different, and are each independently selected from the group consisting of substituted or unsubstituted aryl having 6 to 30 carbon atoms, and substituted or unsubstituted heteroaryl having 5 to 30 carbon atoms;
substituents in L, $L_1$, $L_2$, $Ar_1$, $Ar_3$, and $Ar_4$ are identical or different, and are each independently selected from the group consisting of deuterium, cyano, halogen, alkyl having 1 to 10 carbon atoms, haloalkyl having 1 to 10 carbon atoms, deuterated alkyl having 1 to 10 carbon atoms, alkoxy having 1 to 10 carbon atoms, alkylthio having 1 to 10 carbon atoms, trialkylsiyl having 3 to 12 carbon atoms, triphenylsilyl, aryl having 6 to 20 carbon atoms, heteroaryl having 3 to 20 carbon atoms, or cycloalkyl having 3 to 10 carbon atoms: optionally, any two adjacent substituents form a saturated or unsaturated 3 to 15-membered ring;
each $R_1$, each $R_2$, each $R_3$ is independently selected from the group consisting of deuterium, cyano, halogen, alkyl having 1 to 10 carbon atoms, haloalkyl having 1 to 10 carbon atoms, trialkylsiyl having 3 to 12 carbon atoms, triphenylsilyl, aryl having 6 to 20 carbon atoms, heteroaryl having 3 to 20 carbon atoms, or cycloalkyl having 3 to 10 carbon atoms; $n_1$ is selected from 0, 1, 2, 3, or 4: $n_2$ is selected from 0, 1, 2, 3, 4, 5, or 6; $n_3$ is selected from 0, 1, 2, or 3;
optionally, any two adjacent $R_3$ form a benzene ring.

According to a second aspect of the present disclosure, there is provided an organic electroluminescent device comprising an anode and a cathode that are disposed opposite to each other, and a functional layer disposed between the anode and the cathode. The functional layer comprises the arylamine compound described above.

According to a third aspect of the present disclosure, there is provided an electronic apparatus comprising the organic electroluminescent device described in the second aspect.

The structure of the arylamine compound of the present disclosure includes benzocarbazolyl and benzoxazolyl or benzothiazolyl groups. The benzocarbazolyl group has an excellent hole transport property, and the benzoxazolyl or benzothiazolylgroup has a relatively large conjugation plane, which is conducive to intermolecular accumulation and can further improve hole mobility in the compound of the present disclosure. A triarylamine compound, when used as a hole transport-type host material, can be oxidized to form free radical cations. The benzoxazolyl or benzothiazolyl group linked, directly or indirectly via a benzene ring, to the nitrogen atoms of the arylamine can stabilize theses free radical cations and improve the electrochemical stability of the compound. Therefore, the compound of the present disclosure, when used as a hole transport-type host material in a mixed-type host material of an organic electroluminescent device, can significantly improve the efficiency of the device and significantly prolong service life thereof.

BRIEF DESCRIPTION OF THE DRAWINGS

The accompanying drawings are intended to provide a further understanding of the present disclosure and form a part of the specification. The accompanying drawings, together with the following specific embodiments, are used to illustrate the present disclosure, but do not constitute any limitation on the present disclosure.

LIST OF REFERENCE SIGNS

Figure 1:
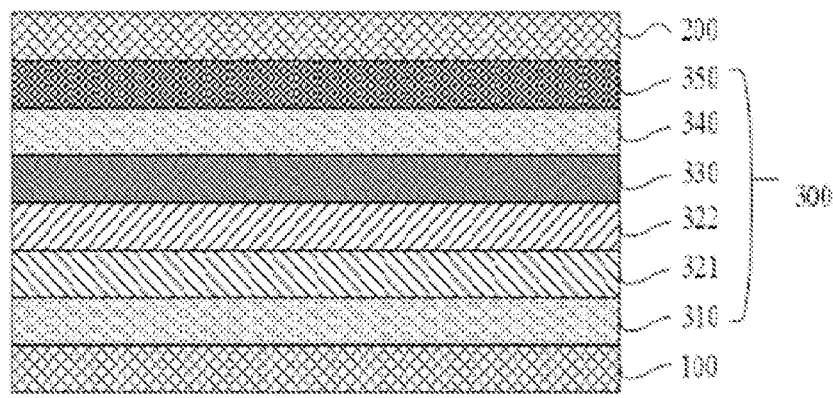
FIG. 1 is a schematic structural diagram of an organic electroluminescent device according to an embodiment of the present disclosure.

100; anode 200: cathode 300: functional layer 310: hole injection layer

321: hole transport layer 322: hole adjustment layer

330: organic light-emitting layer 340: electron transport layer

350: electron injection layer 400: electronic apparatus

DETAILED DESCRIPTION OF THE EMBODIMENTS

Exemplary embodiments will now be described more comprehensively with reference to the accompanying drawings. The exemplary embodiments, however, can be implemented in a variety of forms and should not be interpreted as being limited to the examples set forth herein. On the contrary, these embodiments are provided to make the present disclosure more comprehensive and complete, and to communicate the concepts of these exemplary embodiments fully to those skilled in the art. Features, structures, or characteristics described can be combined in one or more embodiments in any suitable manner. In the following description, many specific details are provided to give a full understanding of the embodiments of the present disclosure.

The present disclosure, in a first aspect, provides an arylamine compound. The arylamine compound has a structure shown in Formula 1;

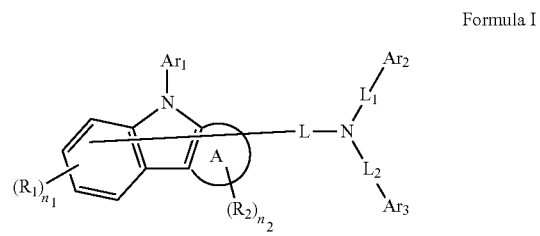

Formula I wherein:
ring A is a naphthalene ring;
L, $L_1$, and $L_2$ are identical or different, and are each independently selected from the group consisting of single bond, substituted or unsubstituted arylene having 6 to 30 carbon atoms, and substituted or unsubstituted heteroarylene having 3 to 30 carbon atoms;
$Ar_2$ is a group shown in Formula 2;

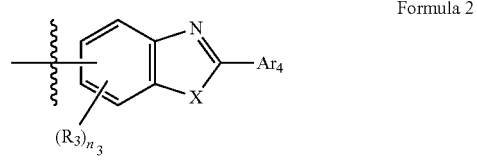

Formula 2

X is selected from O or S;
$Ar_1$, $Ar_3$, and $Ar_4$ are identical or different, and are each independently selected from the group consisting of substituted or unsubstituted aryl having 6 to 30 carbon atoms, and substituted or unsubstituted heteroaryl having 5 to 30 carbon atoms;
substituents in L, $L_1$, $L_2$, $Ar_1$, $Ar_3$, and $Ar_4$ are identical or different, and are each independently selected from the group consisting of deuterium, cyano, halogen, alkyl having 1 to 10 carbon atoms, haloalkyl having 1 to 10 carbon atoms, deuterated alkyl having 1 to 10 carbon atoms, alkoxy having 1 to 10 carbon atoms, alkylthio having 1 to 10 carbon atoms, trialkylsiyl having 3 to 12 carbon atoms, triphenylsilyl, aryl having 6 to 20 carbon atoms, heteroaryl having 3 to 20 carbon atoms, or cycloalkyl having 3 to 10 carbon atoms; optionally, any two adjacent substituents form a saturated or unsaturated 3 to 15-membered ring;
each $R_1$, each $R_2$, each $R_3$ is independently selected from the group consisting of deuterium, cyano, halogen, alkyl having 1 to 10 carbon atoms, haloalkyl having 1 to 10 carbon atoms, trialkylsiyl having 3 to 12 carbon atoms, triphenylsilyl, aryl having 6 to 20 carbon atoms, heteroaryl having 3 to 20 carbon atoms, or cycloalkyl having 3 to 10 carbon atoms; $n_1$ is selected from 0, 1, 2, 3, or 4; $n_2$ is selected from 0, 1, 2, 3, 4, 5, or 6; $n_3$ is selected from 0, 1, 2, or 3;
optionally, any two adjacent $R_3$ form a benzene ring.

In the present disclosure, the term "optional" or "optionally" means that the subsequently described event or circumstance may or may not occur. As an example, the expression "optionally, any two adjacent substituents form a saturated or unsaturated 3 to 15-membered ring" involve instances where any two adjacent substituents form a ring, and instances where any two adjacent substituents exist independently and do not form a ring. The expression "any two adjacent" may involve instances where there are two substituents on a same atom and also involve instances where there is one substituent on each of two adjacent atoms. When there are two substituents on a same atom, the two substituents, together with the atom to which they are attached, may form a saturated or unsaturated spiro ring; and when there is one substituent on each of two adjacent atoms, the two substituents may be fused into a ring.

In the present disclosure, the expression "each . . . independently" may be used interchangeably with the expressions " . . . independently", and " . . . each independently", and all these expressions should be interpreted in a broad sense. They can not only mean that, for same symbols in a same group, the selection of a specific option for one of the symbols and the selection of a specific option for another one of the symbols do not affect each other, but also mean that for same symbols in different groups, the selection of a specific option for one of the symbols and the selection of a specific option for another one of the symbols do not affect each other. Taking

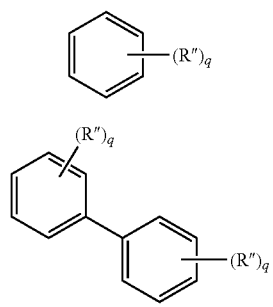

Q-1

Q-2 as an example, each q is independently selected from 0, 1, 2, or 3, and each R" is independently selected from hydrogen, deuterium, fluorine, and chlorine, which means: in Formula Q-1, there are q substituents R" on the benzene ring, wherein each of the substituent R" may be identical or different, with the selection of an option for one of the substituents R" and the selection of an option for another one of the substituents R" not affecting each other; and in Formula Q-2, there are q substituents R" on each of the two benzene rings of biphenyl, wherein the number q of the substituent R" on one benzene ring and the number q of the substituent R" on the other benzene ring may be identical or different, and each substituent R" may be identical or different, with the selection of an option for one of the substituents R" and the selection of an option for another one of the substituents R" not affecting each other.

In the present disclosure, the term "substituted or unsubstituted" means that the functional group defined by the term may or may not have a substituent (hereinafter referred to as Rc for ease of description). For example, "substituted or unsubstituted aryl" refers to aryl having a substituent Rc or aryl having no substituent. The foregoing substituent, namely Rc, may be, for example, deuterium, halogen, cyano, heteroaryl, aryl, trialkylsilyl, alkyl, haloalkyl, cycloalkyl, etc. The number of the substitutes may be one or more.

In the present disclosure, "more" means more than 2, such as 2, 3, 4, 5, 6, etc.

In the present disclosure, the number of carbon atoms of a substituted or unsubstituted functional group is the number of all carbon atoms.

Hydrogen atoms in the structure of the compound of the present disclosure include various isotopic atoms of hydrogen element, such as hydrogen (H), deuterium (D), or tritium (T).

"D" in a structural formula of a compound of the present disclosure represents "deuterated".

In the present disclosure, "aryl" refers to any functional group or substituent group derived from an aromatic carbon ring. An aryl group may be a monocyclic aryl group (e.g., phenyl) or a polycyclic aryl group. In other words, an aryl group may be a monocyclic aryl group, a fused aryl group, two or more monocyclic aryl groups linked by carbon-carbon bond conjugation, a monocyclic aryl group and a fused aryl group linked by carbon-carbon bond conjugation, or two or more fused aryl groups linked by carbon-carbon bond conjugation. That is, unless otherwise specified, two or more aromatic groups linked by carbon-carbon bond conjugation may also be regarded as an aryl group in the present disclosure. Among them, fused aryl groups may include, for example, bicyclic fused aryl groups (e.g., naphthyl), tricyclic fused aryl groups (e.g., phenanthryl, fluorenyl, anthryl) and the like. An aryl group does not contain heteroatoms such as B, N, O, S, P, Se, Si, etc. Examples of aryl may include, but are not limited to, phenyl, naphthyl, fluorenyl, spirodifluorenyl, anthryl, phenanthryl, biphenyl, terphenyl, triphenylene

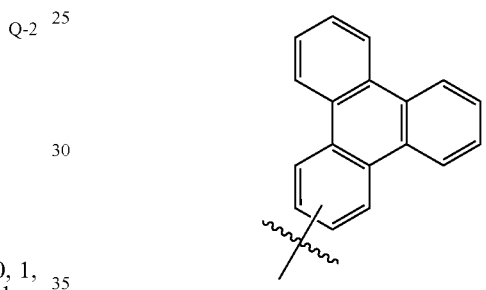

perylenyl, benzo[9,10]phenanthryl, pyrenyl, benzofluoranthenyl, chrysenyl, etc.

In the present disclosure, "arylene" refers to a divalent group formed by further removing one or more hydrogen atoms from an aryl group.

In the present disclosure, "terphenyl" includes

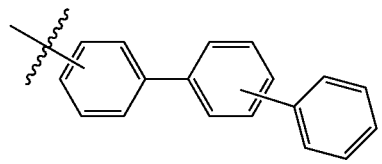

and

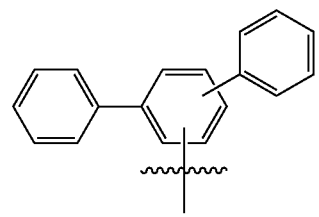

In the present disclosure, the number of carbon atoms of substituted or unsubstituted aryl (arylene) may be 6, 8, 10, 12, 13, 14, 15, 16, 17, 18, 19, 20, 21, 22, 23, 24, 25, or 30.

In some embodiments, substituted or unsubstituted aryl is substituted or unsubstituted aryl having 6 to 30 carbon atoms. In other embodiments, substituted or unsubstituted aryl is substituted or unsubstituted aryl having 6 to 25 carbon atoms. In other embodiments, substituted or unsubstituted aryl is substituted or unsubstituted aryl having 6 to 18 carbon atoms. In other embodiments, substituted or unsubstituted aryl is substituted or unsubstituted aryl having 6 to 15 carbon atoms.

In the present disclosure, fluorenyl may be substituted by one or more substituents. In the case where the above fluorenyl is substituted, the substituted fluorenyl may be, but is not limited to,

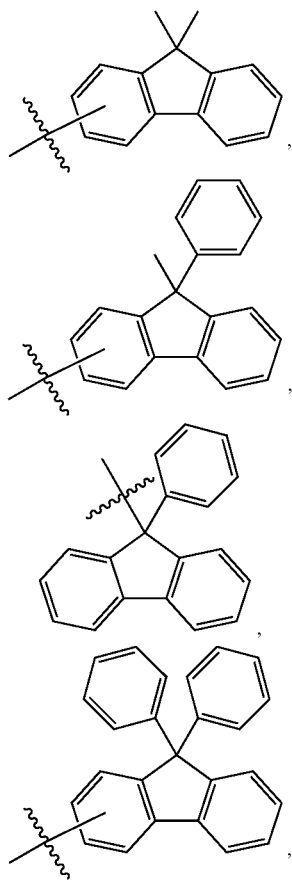

etc.

In the present disclosure, aryl, as a substituent of L, $L_1$, $L_2$, $Ar_1$, $Ar_3$, and $Ar_4$, may be, but is not limited to, phenyl, naphthyl, phenanthryl, biphenyl, fluorenyl, dimethylfluorenyl, etc.

In the present disclosure, "heteroaryl" refers to a monovalent aromatic ring containing 1, 2, 3, 4, 5, or 6 heteroatoms or a derivative thereof. The heteroatoms may be one or more selected from B, O, N, P, Si, Se, and S. A heteroaryl group may be a monocyclic heteroaryl group or polycyclic heteroaryl group. In other words, a heteroaryl group may be a single aromatic ring system, or a plurality of aromatic ring systems linked by carbon-carbon bond conjugation, with any of the aromatic ring systems being an aromatic monocyclic ring or a fused aromatic ring. For example, heteroaryl groups may include, but are not limited to, thienyl, furyl, pyrrolyl, imidazolyl, thiazolyl, oxazolyl, oxadiazolyl, triazolyl, pyridinyl, bipyridinyl, pyrimidyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silylfluorenyl, dibenzofuranyl, N-phenylcarbazolyl, N-pyridylcarbazolyl, N-methylcarbazolyl, etc.

In the present disclosure, "heteroarylene" is a divalent or polyvalent group formed by further removing one or more hydrogen atoms from a heteroaryl group.

In the present disclosure, the number of carbon atoms of substituted or unsubstituted heteroaryl (heteroarylene) may be 3, 4, 5, 6, 7, 8, 9, 10, 11, 12, 13, 14, 15, 16, 17, 18, 20, 21, 22, 23, 24, 25, 26, 27, 28, 29, or 30. In some embodiments, substituted or unsubstituted heteroaryl is substituted or unsubstituted heteroaryl having 12 to 18 carbon atoms. In other embodiments, substituted or unsubstituted heteroaryl is substituted or unsubstituted heteroaryl having 5 to 12 carbon atoms.

In the present disclosure, heteroaryl, as a substituent of L, $L_1$, $L_2$, $Ar_1$, $Ar_3$, and $Ar_4$, may be, but is not limited to, for example, pyridyl, carbazolyl, dibenzothienyl, dibenzofuranyl, benzoxazolyl, benzothiazolyl, and benzimidazolyl.

In the present disclosure, substituted heteroaryl may mean that one or more than two hydrogen atoms in the heteroaryl group are substituted by a group such as a deuterium atom, halogen, cyano, aryl, heteroaryl, trialkylsilyl, alkyl, cycloalkyl, haloalkyl, etc.

In the present disclosure, alkyl having 1 to 10 carbon atoms may include linear alkyl having 1 to 10 carbon atoms and branched alkyl having 3 to 10 carbon atoms. For example, the number of carbon atoms of alkyl may be, for example, 1, 2, 3, 4, 5, 6, 7, 8, 9, or 10. Specific examples of alkyl include, but are not limited to, methyl, ethyl, n-propyl, isopropyl, n-butyl, isobutyl, tert-butyl, n-pentyl, isopentyl, neopentyl, n-hexyl, etc.

In the present disclosure, halogen may be, for example, fluorine, chlorine, bromine, or iodine.

In the present disclosure, specific examples of trialkylsilyl include, but are not limited to, trimethylsilyl, triethylsilyl, etc.

In the present disclosure, specific examples of haloalkyl include, but are not limited to, trifluoromethyl.

In the present disclosure, the number of cycloalkyl having 3 to 10 carbon atoms may be, for example, 3, 4, 5, 6, 7, 8, or 10. Specific examples of cycloalkyl include, but are not limited to, cyclopentyl, cyclohexyl, adamantyl, etc.

In the present disclosure, the number of carbon atoms of deuterated alkyl having carbon atoms 1 to 10 is, for example, 1, 2, 3, 4, 5, 6, 7, 8 or 10. Specific examples of deuterated alkyl include, but are not limited to, trideuteromethyl.

In the present disclosure, the number of carbon atoms of haloalkyl having 1 to 10 carbon atoms is, for example, 1, 2, 3, 4, 5, 6, 7, 8 or 10. Specific examples of haloalkyl include, but are not limited to, trifluoromethyl.

In the present disclosure, a ring system formed by n atoms is an n-membered ring. For example, phenyl is a 6-membered ring. A 3 to 15-membered ring refers to a cyclic group having 3 to 15 ring atoms. A 3 to 15-membered ring may be, for example, cyclopentane, cyclohexane, a fluorene ring, a benzene ring, etc.

In the present disclosure,

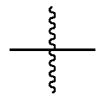

refers to a chemical bond linked with other groups.

In the present disclosure, a non-positional bond is single bond

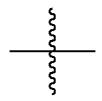

extending from a ring system, and it indicates that the linkage bond can be linked at one end thereof to any position in the ring system through which the bond passes, and linked at the other end thereof to the rest of the compound molecule. For example, as shown in Formula (f) below, the naphthalyl group represented by Formula (f) is linked to other positions of the molecule via two non-positional bonds passing through the two rings, which indicates any of possible linkages shown in Formulae (f-1) to (f-10):

(f)

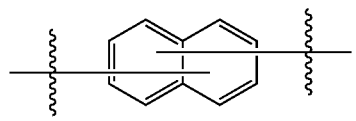

(f-1)

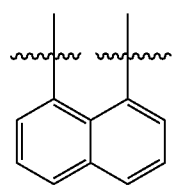

(f-2)

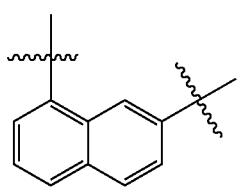

(f-3)

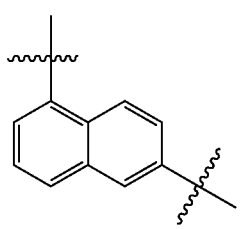

(f-4)

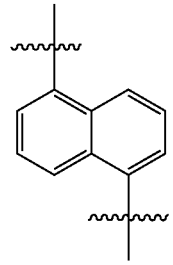

(f-5)

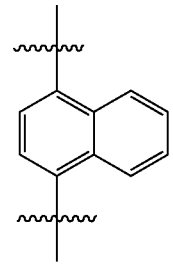

(f-6)

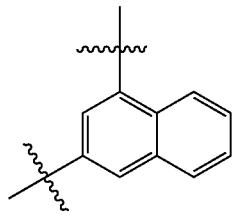

(f-7)

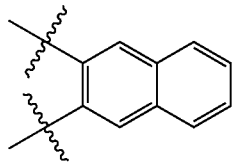

(f-8)

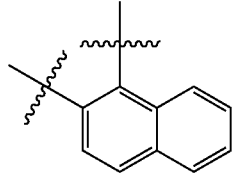

(f-9)

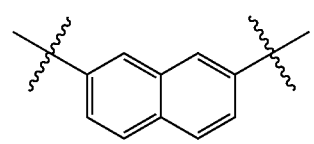

(f-10)

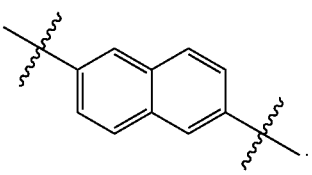

As another example, as shown in Formula (X') below, the dibenzofuranyl group represented by Formula (X') is linked to other positions of the molecule via a non-positional bond extending from the center of a side benzene ring, which indicates any of possible linkages shown in Formulae (X'-1) to (X'-4):

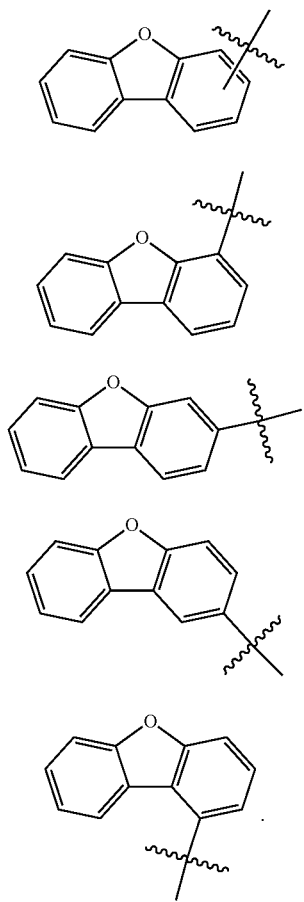

(X')

(X'-1)

(X'-2)

(X'-3)

(X'-4)

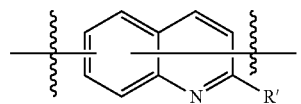

(Y-3)

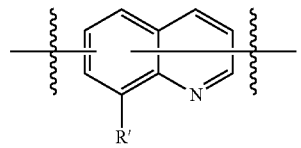

(Y-4)

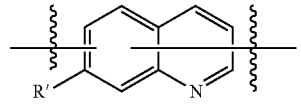

(Y-5)

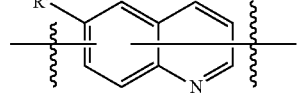

(Y-6)

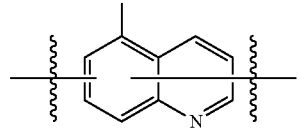

(Y-7)

In some embodiments, Formula 1 is specifically selected from structures shown in Formulae 1-1 to 1-3;

A non-positional substituent in the present disclosure refers to a substituent linked via single bond extending from the center of a ring system, and it means that the substituent may be linked to any possible position in the ring system. For example, as shown in Formula (Y) below, the substituent R' represented by Formula (Y) is linked to a quinoline ring via a non-positional bond, which indicates any of possible linkages shown in Formulae (Y-1) to (Y-7):

(Y)

(Y-1)

(Y-2)

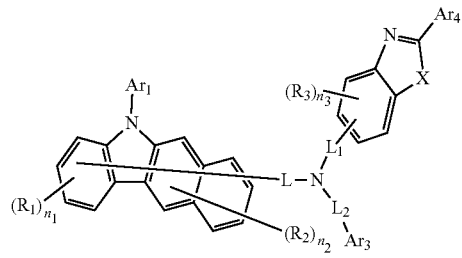

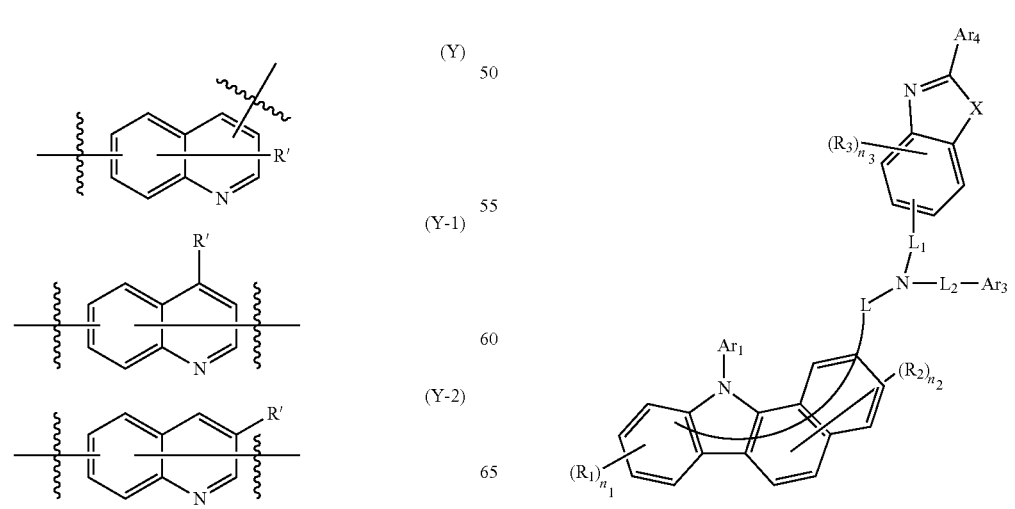

1-1

1-2

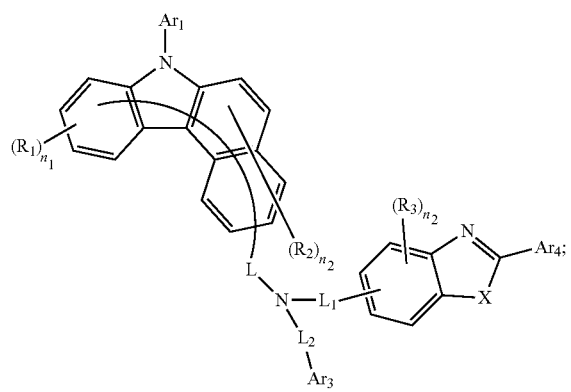
1-3
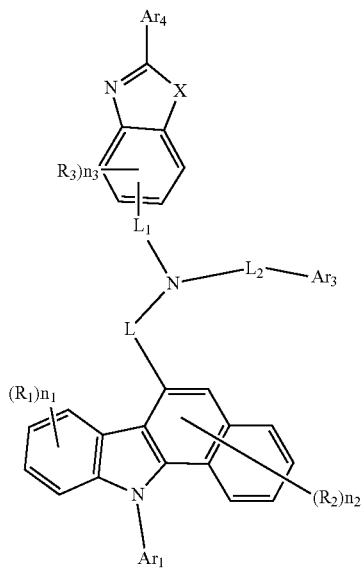
1-5
In the above Formulae 1-1 to 1-3, each symbol has a definition as it has in Formula 1.
A compound having the structure shown in Formula 1-2 or 1-3 requires a lower operating voltage.
In some embodiments, the compound shown in Formula 1 has a structure shown in the following Formulae 1-4 to 1-31;
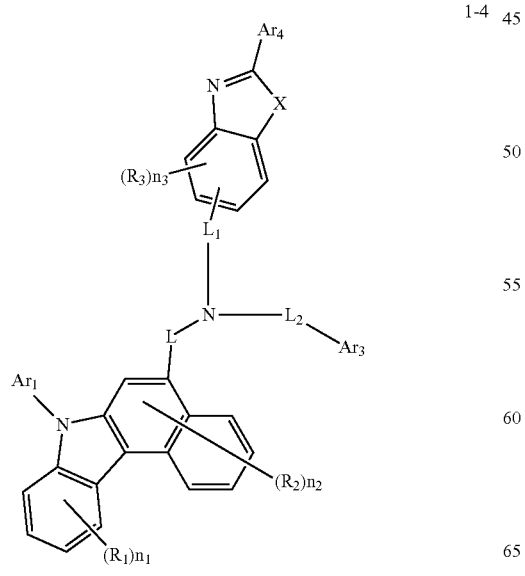
1-4
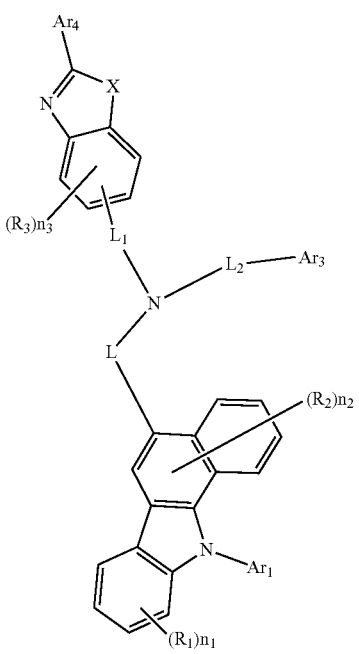
1-6

1-7
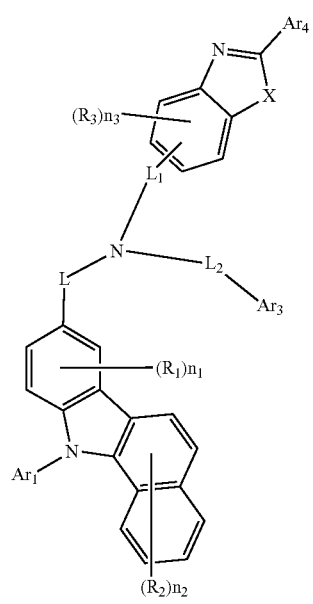
1-8
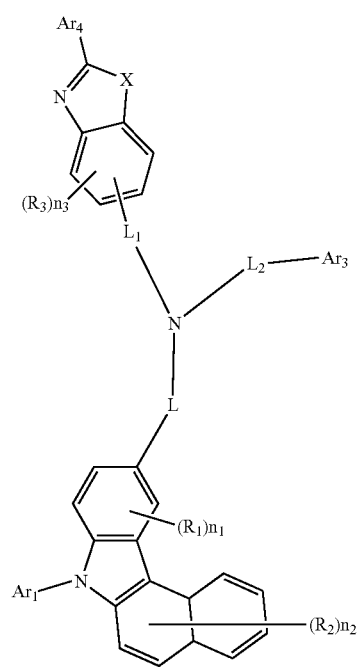
1-9
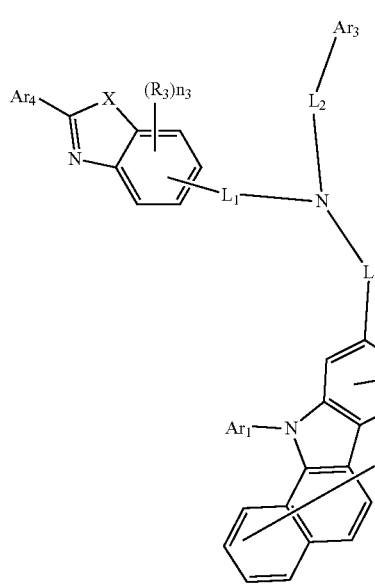
1-10
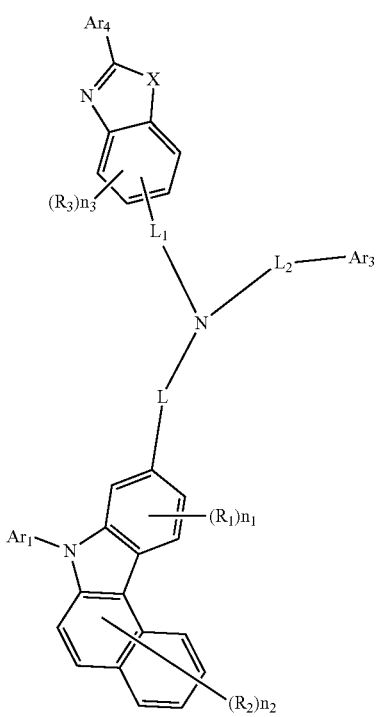

1-11
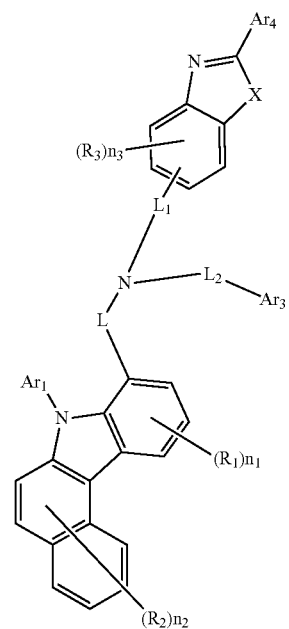
1-13
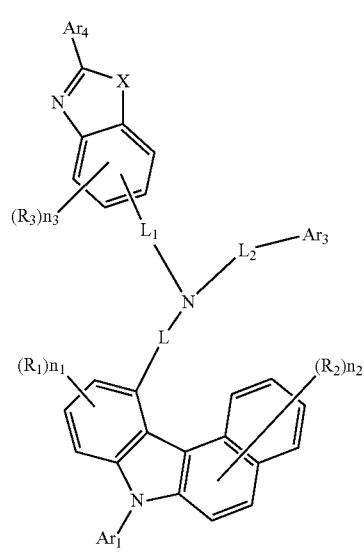
1-12
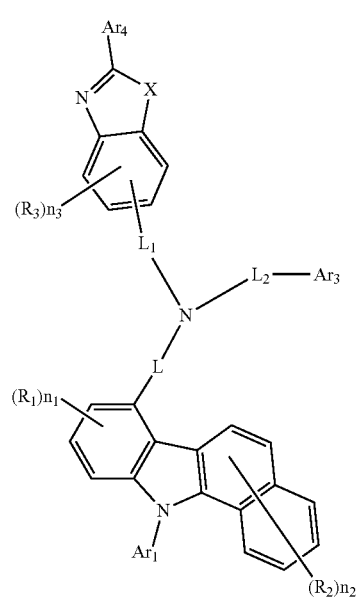
1-14
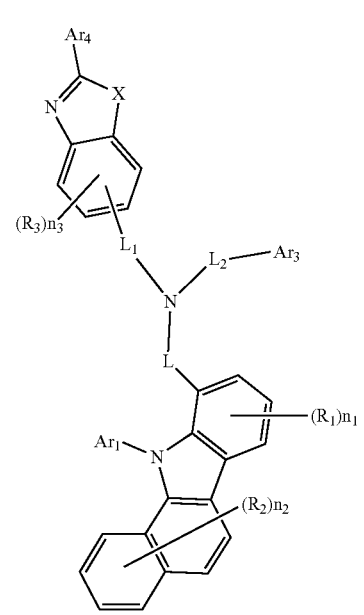

1-15
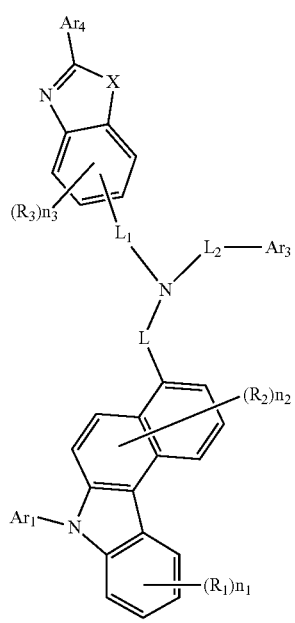
1-16
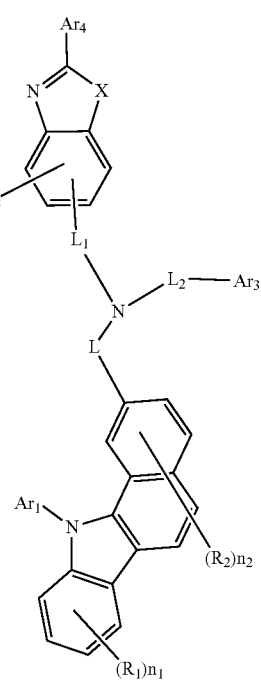
1-17
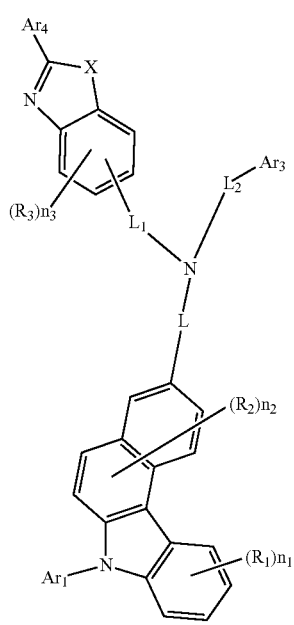
1-18
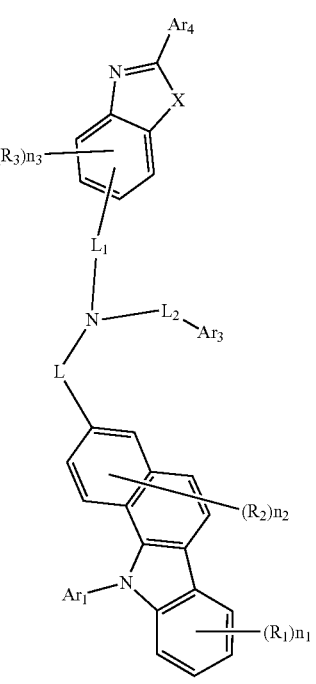

1-19
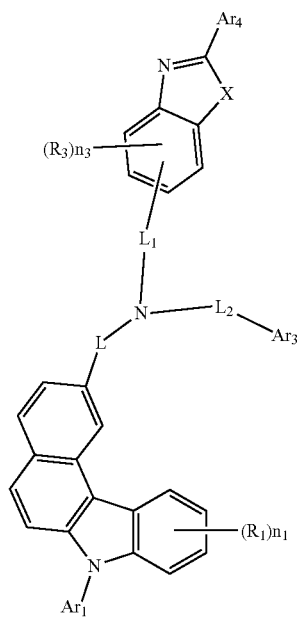
1-20
1-21
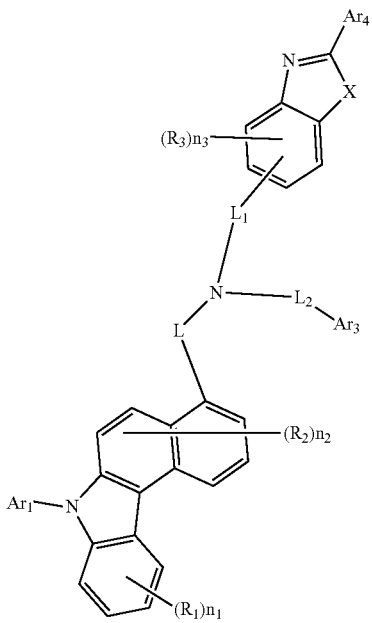
1-22
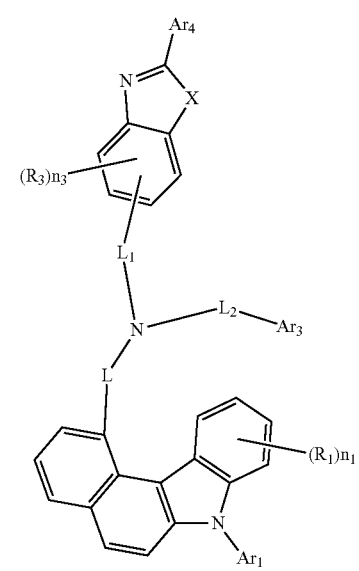

1-23
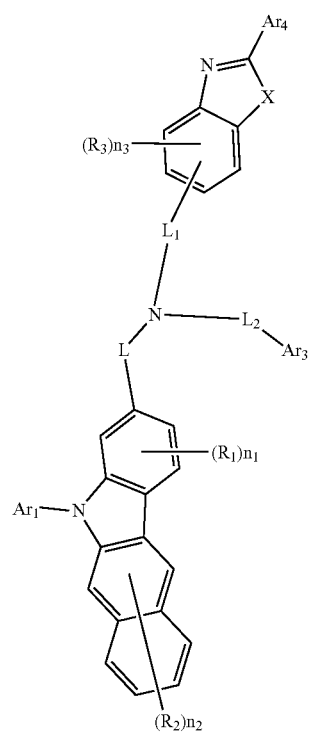
1-24
1-25
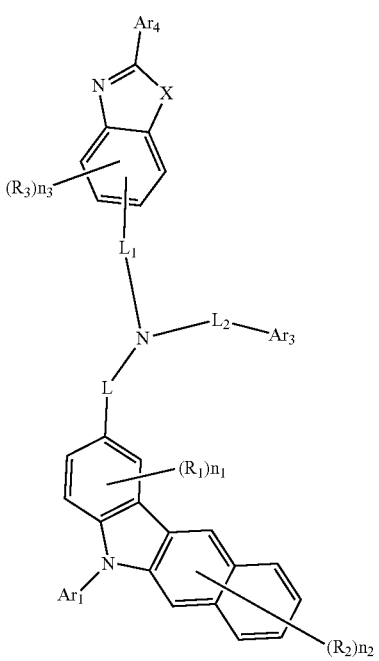
1-26
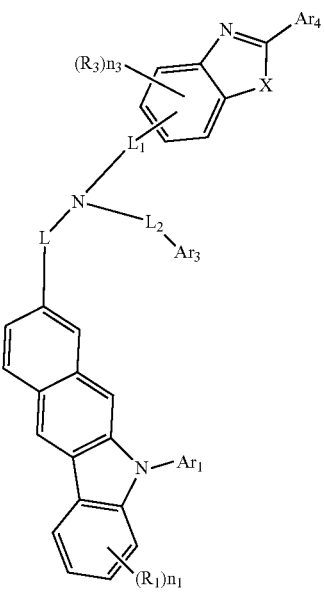

1-27
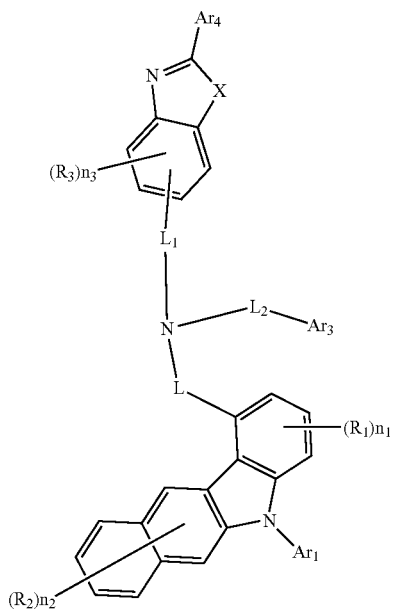
1-28
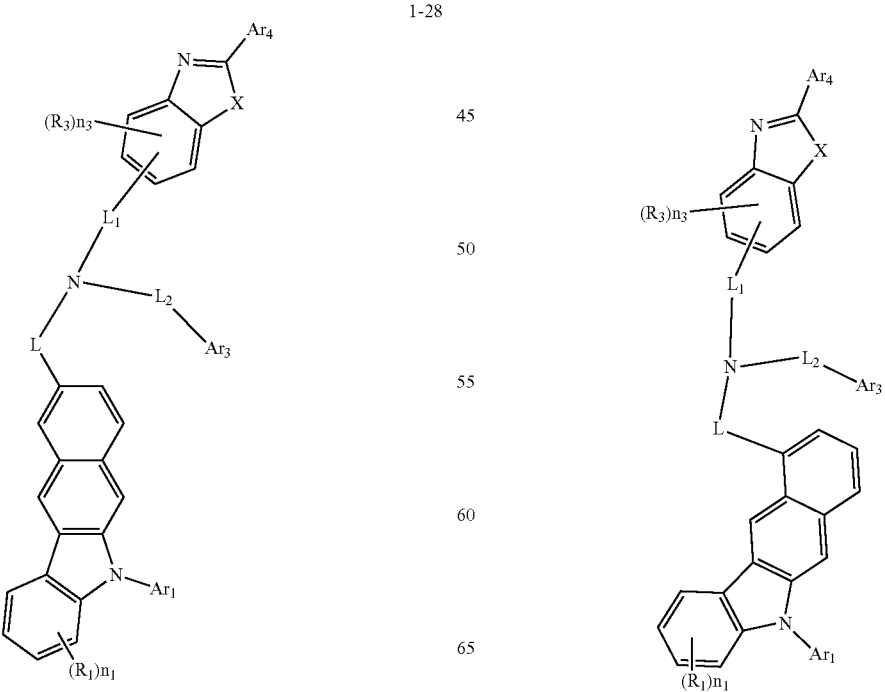
1-29
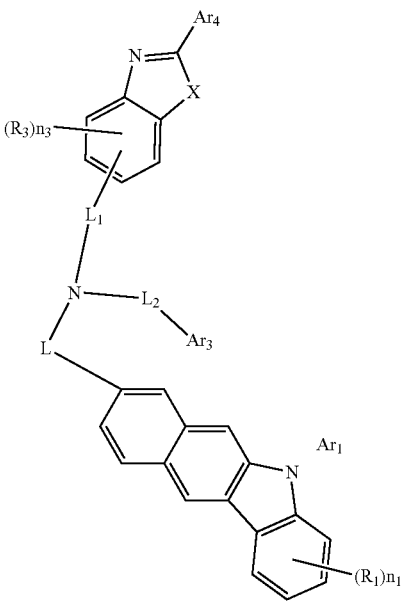
1-30

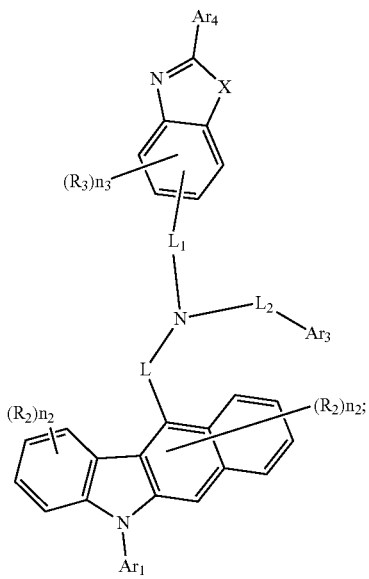

1-31

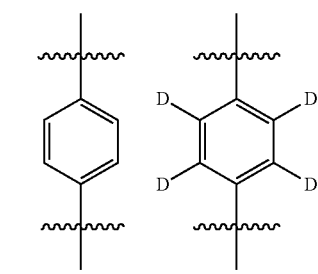
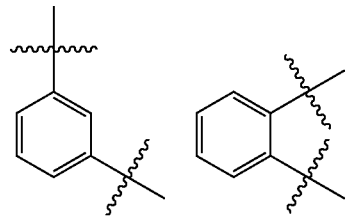
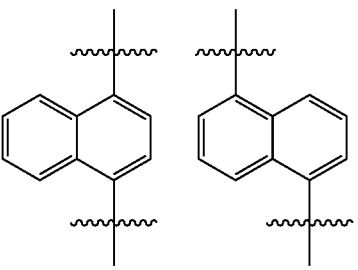
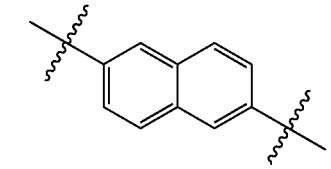
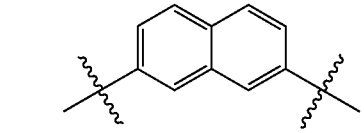
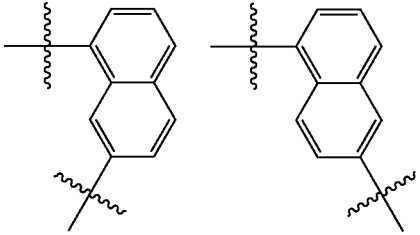

In the above Formulae 1-4 to 1-31, each symbol has a definition as it has in Formula 1.

In some embodiments, L, $L_1$, and $L_2$ are each independently selected from the group consisting of single bond, substituted or unsubstituted arylene having 6 to 15 carbon atoms, and substituted or unsubstituted heteroarylene having 12 to 18 carbon atoms.

In some embodiments, L, $L_1$, and $L_2$ are each independently selected from the group consisting of single bond, substituted or unsubstituted arylene having 6, 7, 8, 9, 10, 11, 12, 13, 14, or 15 carbon atoms, and substituted or unsubstituted heteroarylene having 12, 13, 14, 15, 16, 17, or 18 carbon atoms.

Optionally, the substituents in L, $L_1$, and $L_2$ are identical or different, and are each independently selected from the group consisting of deuterium, halogen, cyano, alkyl having 1 to 5 carbon atoms, haloalkyl having 1 to 5 carbon atoms, deuterated alkyl having 1 to 5 carbon atoms, trialkylsilyl having 3 to 8 carbon atoms, aryl having 6 to 10 carbon atoms, or heteroaryl having 5 to 12 carbon atoms.

In some embodiments, L, $L_1$, and $L_2$ are each independently selected from the group consisting of single bond, substituted or unsubstituted phenylene, substituted or unsubstituted naphthylene, substituted or unsubstituted biphenylene, substituted or unsubstituted fluorenylidene, substituted or unsubstituted phenanthrylene, substituted or unsubstituted anthrylene, substituted or unsubstituted carbazolylene, substituted or unsubstituted dibenzothienylene, and substituted or unsubstituted dibenzofuranylene.

Optionally, the substituents in L, $L_1$, and $L_2$ are each independently selected from the group consisting of deuterium, fluorine, cyano, trimethylsilyl, trideuteromethyl, trifluoromethyl, methyl, ethyl, isopropyl, tert-butyl, phenyl, or naphthyl.

In some embodiments, L and $L_1$ are each independently selected from the group consisting of single bond, phenylene, deuterated phenylene, or naphthylene.

In some embodiments, L and $L_1$ are each independently selected from the group consisting of single bond and the following groups:

In some embodiments, $L_2$ is selected from the group consisting of single bond, substituted or unsubstituted phenylene, substituted or unsubstituted naphthylene, substituted or unsubstituted biphenylene, substituted or unsubstituted carbazolylene, substituted or unsubstituted dibenzothienylene, substituted or unsubstituted dibenzofuranylene.

Optionally, the substituents in $L_2$ are each independently selected from the group consisting of deuterium, fluorine, cyano, trimethylsilyl, trideuteromethyl, trifluoromethyl, methyl, ethyl, isopropyl, tert-butyl, or phenyl.

In some embodiments, L$_2$ is selected from the group consisting of single bond and the following groups:
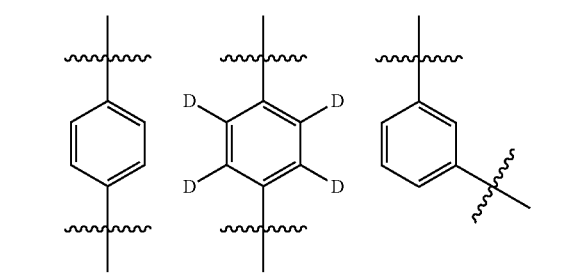
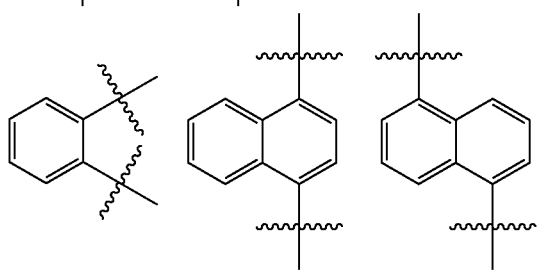
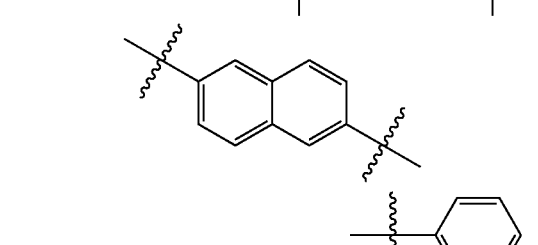
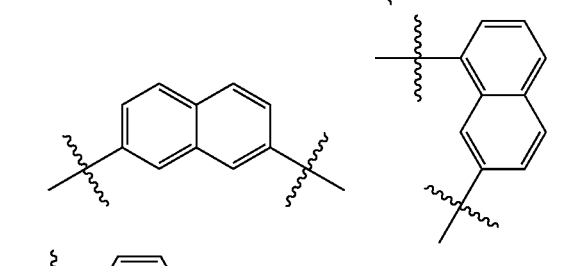
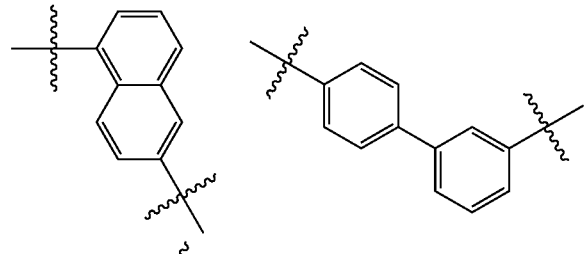
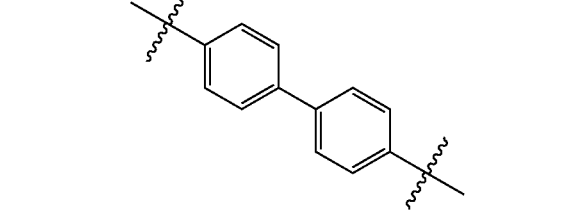
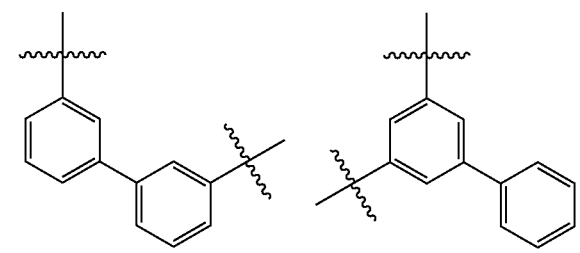
-continued
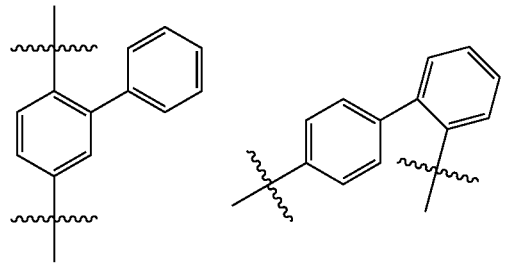
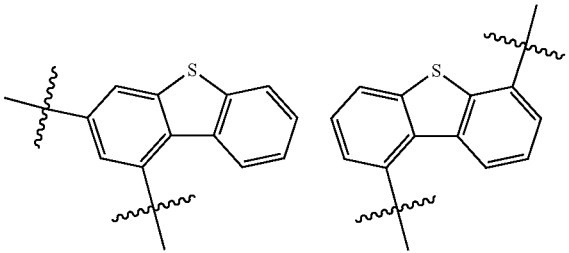
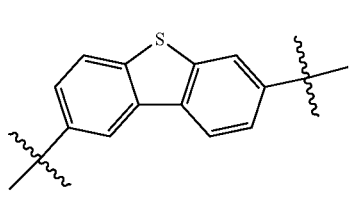
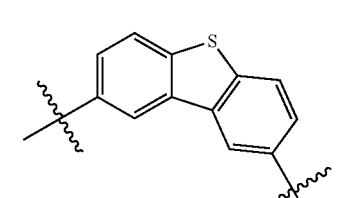
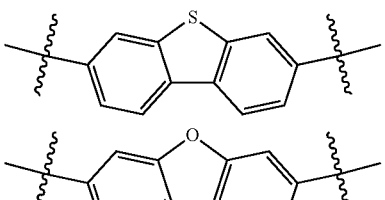
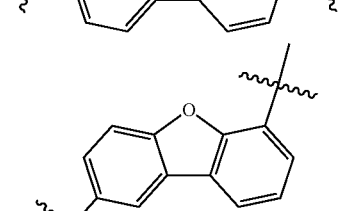
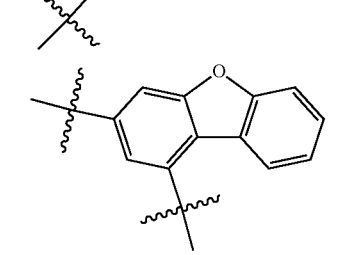

-continued

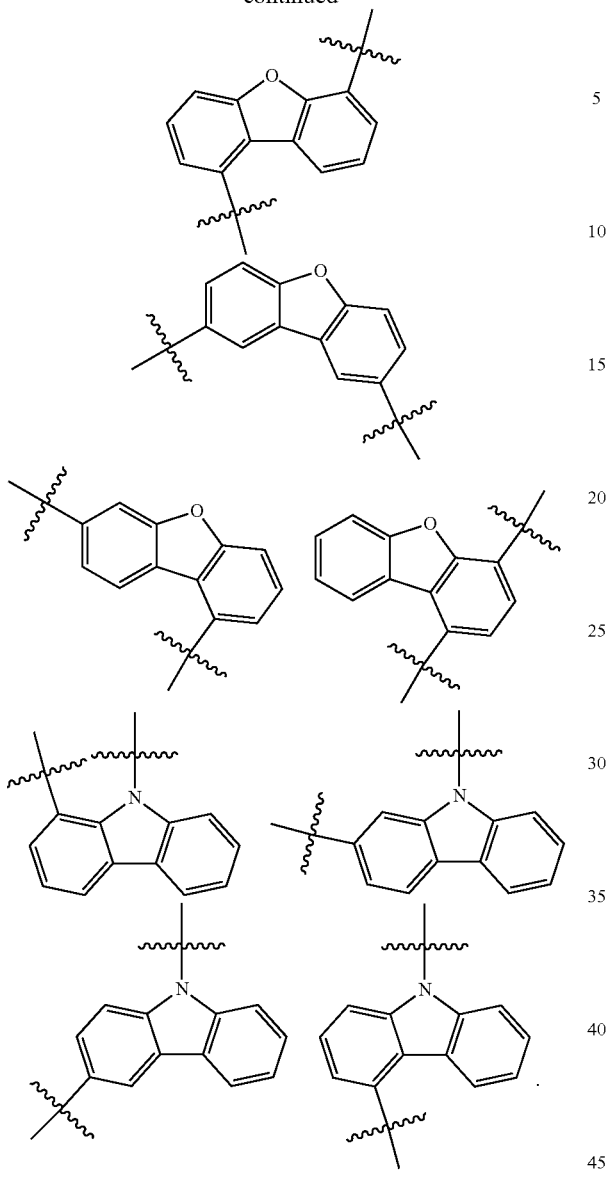

In some embodiments, $Ar_1$, $Ar_3$, and $Ar_4$ are each independently selected from the group consisting of substituted or unsubstituted aryl having 6 to 25 carbon atoms, and substituted or unsubstituted heteroaryl having 7 to 20 carbon atoms.

In some embodiments, $Ar_1$, $Ar_3$, and $Ar_4$ are each independently selected from the group consisting of substituted or unsubstituted aryl having 6, 7, 8, 9, 10, 11, 12, 13, 14, 15, 16, 17, 18, 19, 20, 21, 22, 23, 24, or 25 carbon atoms, and substituted or unsubstituted heteroaryl having 7, 8, 9, 10, 12, 13, 14, 15, 16, 17, 18, 19, or 20 carbon atoms.

In some embodiments, the substituents in $Ar_1$, $Ar_3$, and $Ar_4$ are each independently selected from the group consisting of deuterium, halogen, cyano, haloalkyl having 1 to 4 carbon atoms, deuterated alkyl having 1 to 4 carbon atoms, alkyl having 1 to 4 carbon atoms, cycloalkyl having 5 to 10 carbon atoms, aryl having 6 to 12 carbon atoms, heteroaryl having 5 to 12 carbon atoms, and trialkylsilyl having 3 to 8 carbon atoms; optionally, any two adjacent substituents form a benzene ring or a fluorene ring.

In some embodiments, $Ar_1$ and $Ar_3$ are each independently selected from substituted or unsubstituted group W, the unsubstituted group W is selected from the group consisting of the following groups:

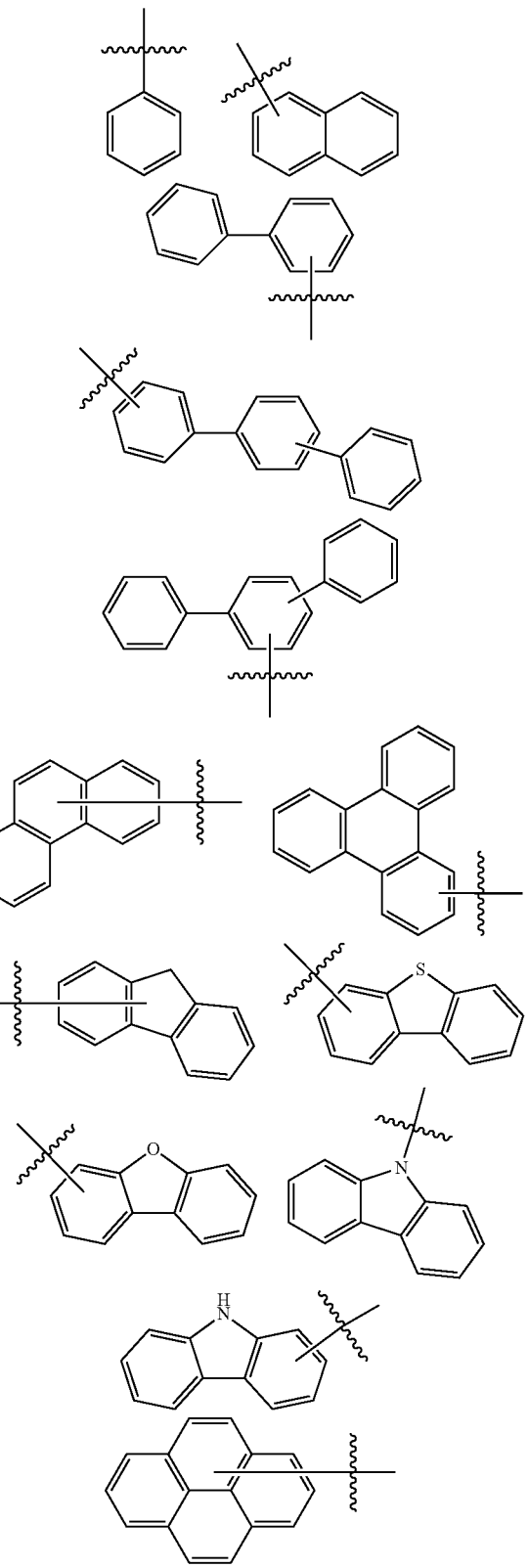

33
-continued

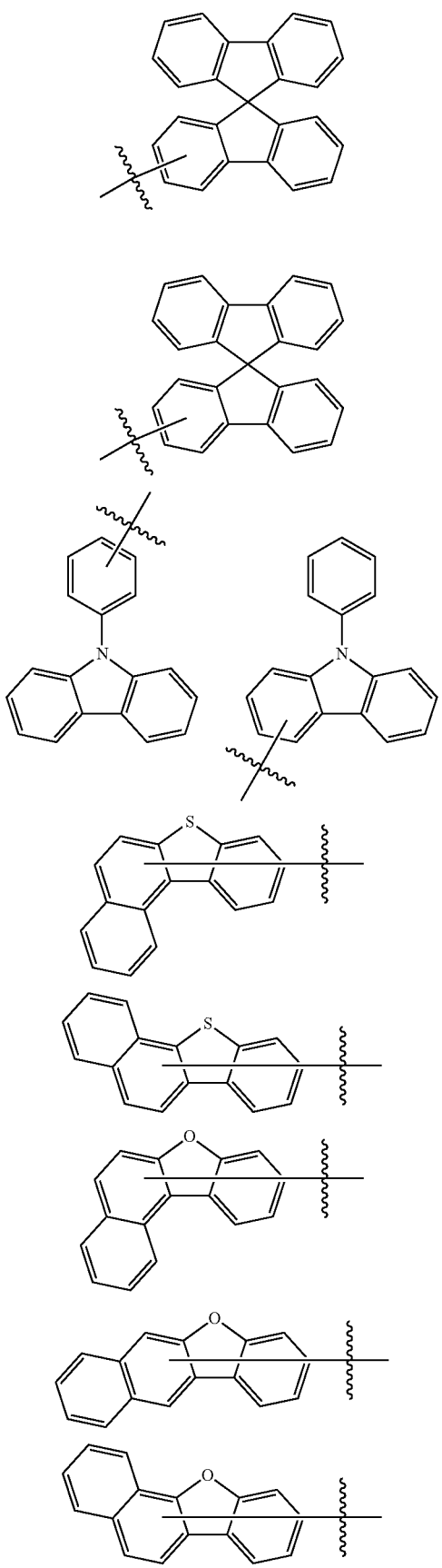

34
-continued

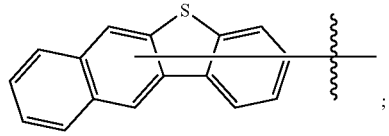

the substituted group W each has one or more substituents, the substituents being each independently selected from the group consisting of deuterium, fluorine, cyano, trimethylsilyl, triphenylsilyl, trifluoromethyl, cyclopentyl, cyclohexyl, methyl, ethyl, isopropyl, tert-butyl, adamantly, phenyl, naphthyl, pyridyl, dibenzofuranyl, dibenzothienyl, and carbazolyl; when the number of the substituents in group W is greater than 1, the substituents are identical or different.

In some embodiments, $Ar_1$ is selected from the group consisting of substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted dibenzofuranyl, substituted or unsubstituted dibenzothienyl, and substituted or unsubstituted carbazolyl.

Optionally, the substituents in $Ar_1$ are each independently selected from the group consisting of deuterium, fluorine, cyano, trimethylsilyl, triphenylsilyl, trideuteromethyl, trifluoromethyl, methyl, ethyl, isopropyl, tert-butyl, phenyl, naphthyl, dibenzofuranyl, dibenzothienyl, or carbazolyl.

In some embodiments, $Ar_1$ is selected from the following groups:

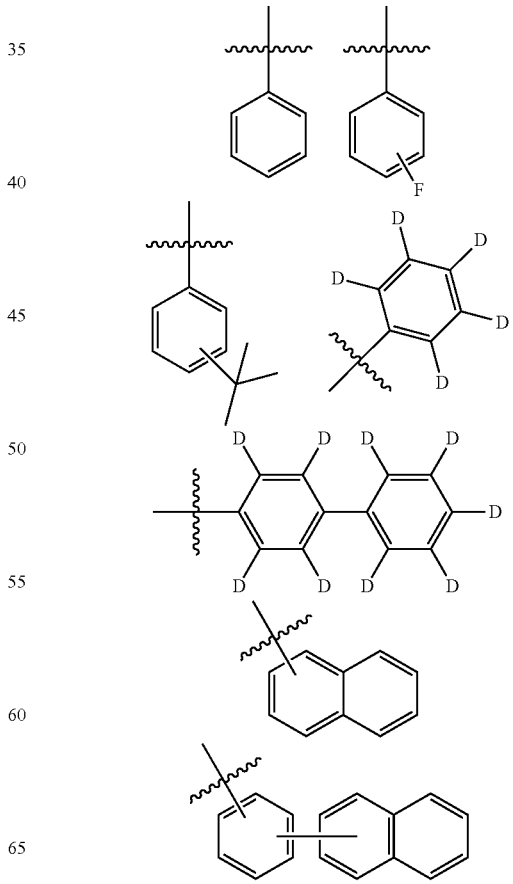

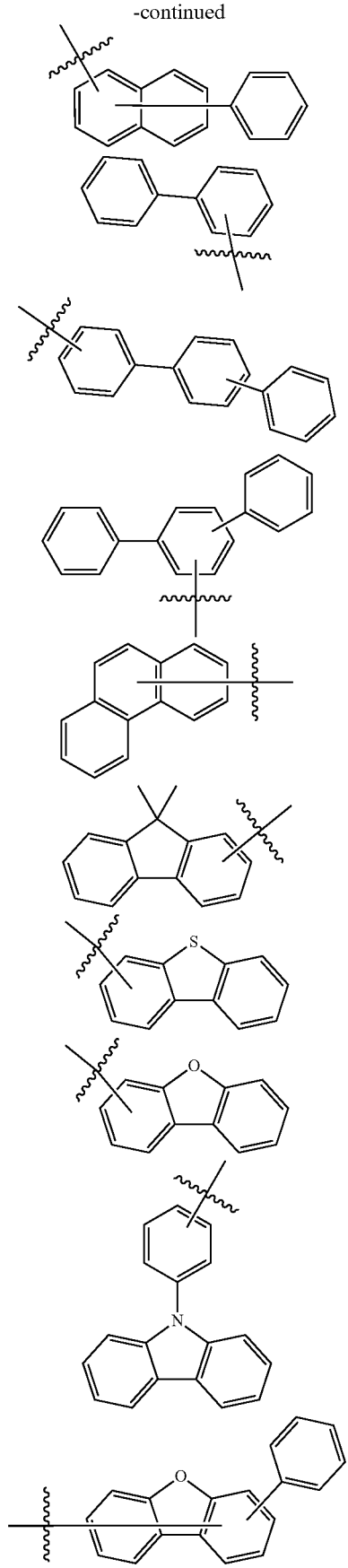
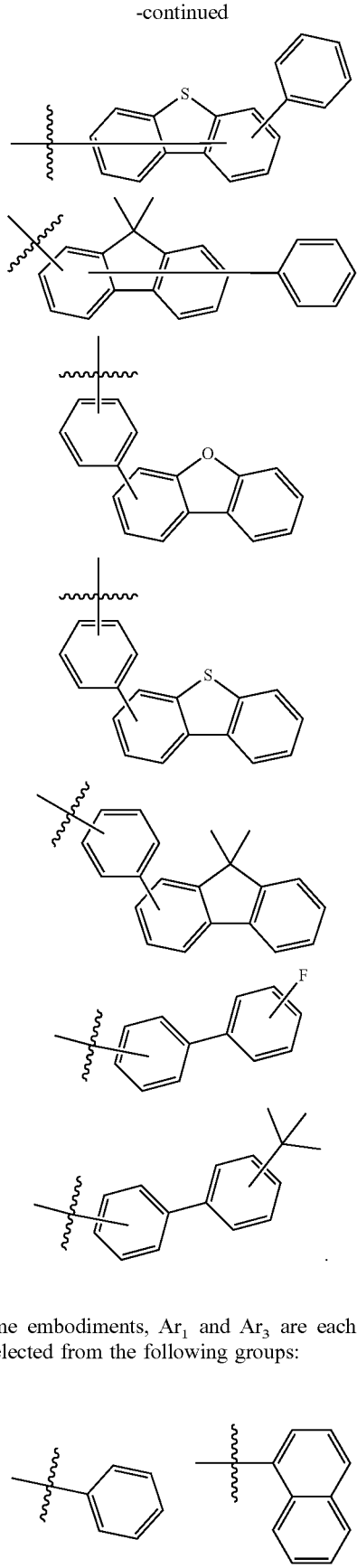
In some embodiments, Ar₁ and Ar₃ are each independently selected from the following groups:
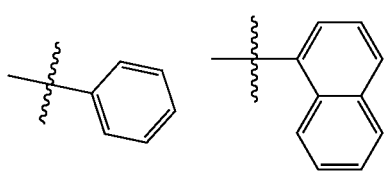

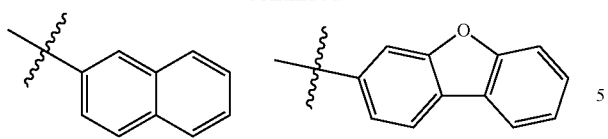
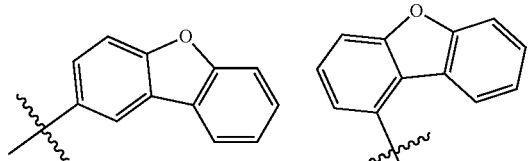
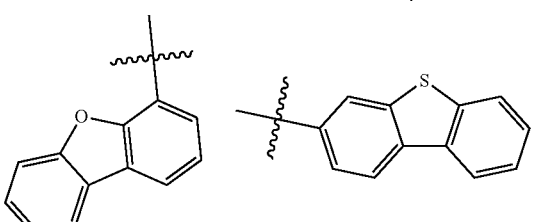
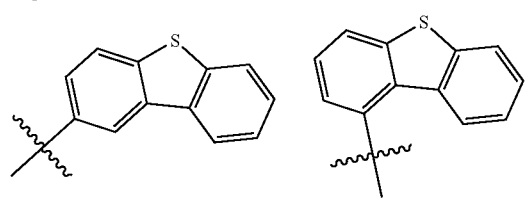
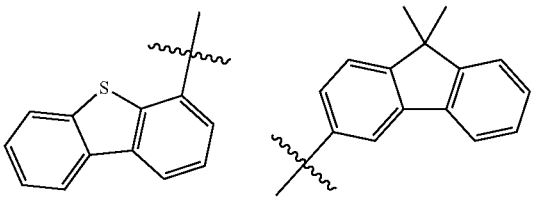
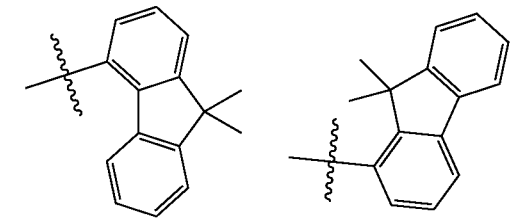
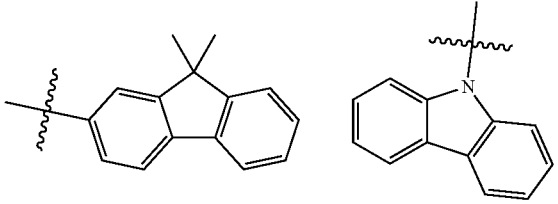
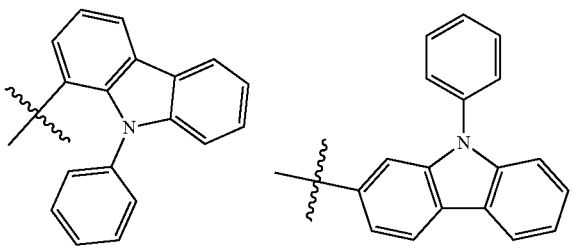
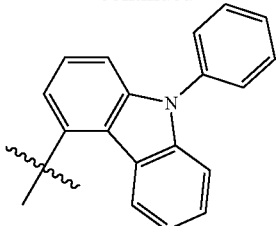
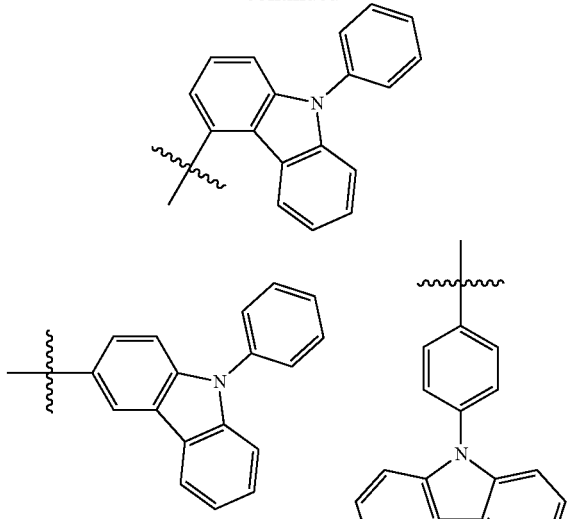
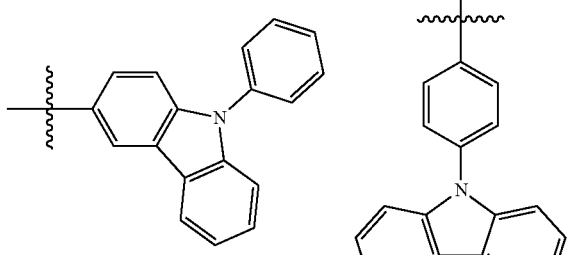
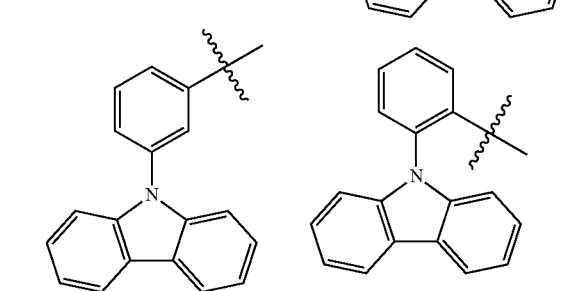
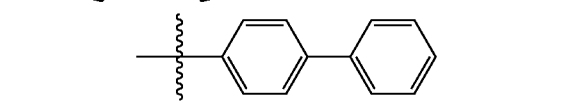
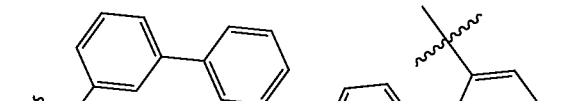
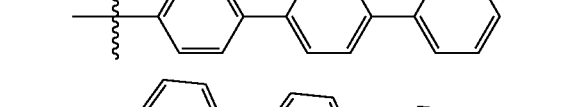
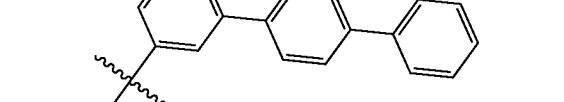
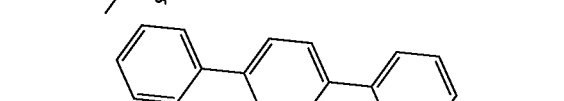
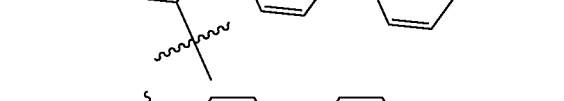

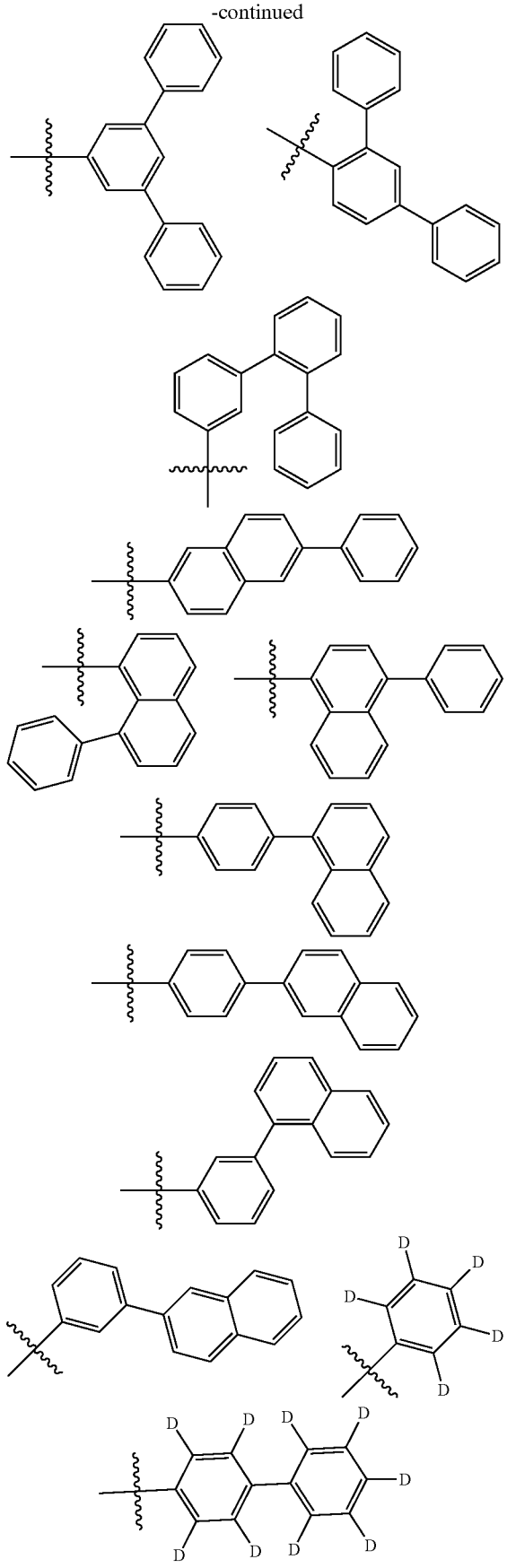
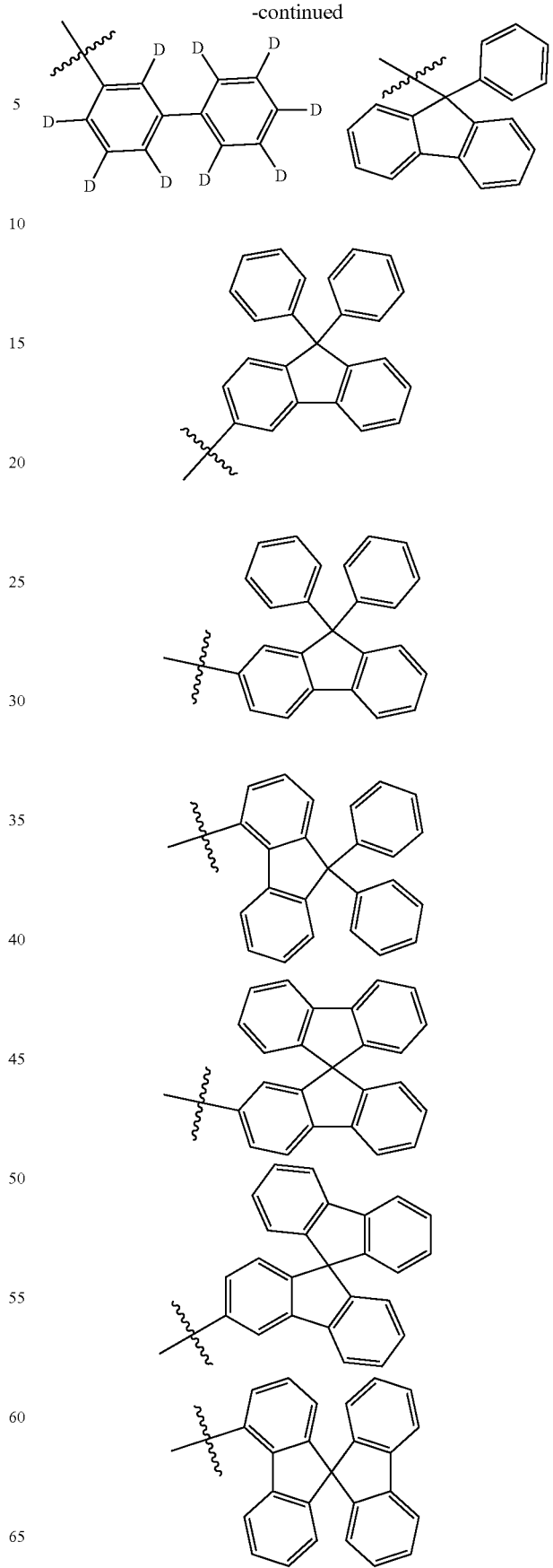

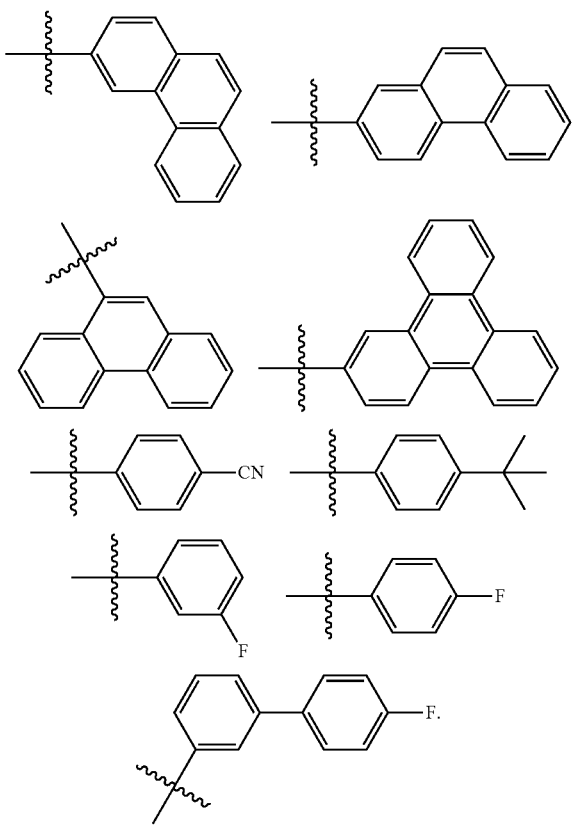

In some embodiments, Ar₄ is selected from the group consisting of substituted or unsubstituted phenyl, substituted or unsubstituted naphthyl, substituted or unsubstituted biphenyl, substituted or unsubstituted terphenyl, substituted or unsubstituted fluorenyl, substituted or unsubstituted phenanthryl, substituted or unsubstituted pyrenyl, substituted or unsubstituted triphenylene, substituted or unsubstituted dibenzofuranyl, substituted or unsubstituted dibenzothienyl, and substituted or unsubstituted carbazolyl.

Optionally, the substituents in Ar₄ are each independently selected from the group consisting of deuterium, fluorine, cyano, trimethylsilyl, triphenylsilyl, trideuteromethyl, trifluoromethyl, methyl, ethyl, isopropyl, tert-butyl, phenyl, naphthyl, biphenyl, dibenzofuranyl, dibenzothienyl, or carbazolyl.

In some embodiments, Ar₄ is selected from the following groups:

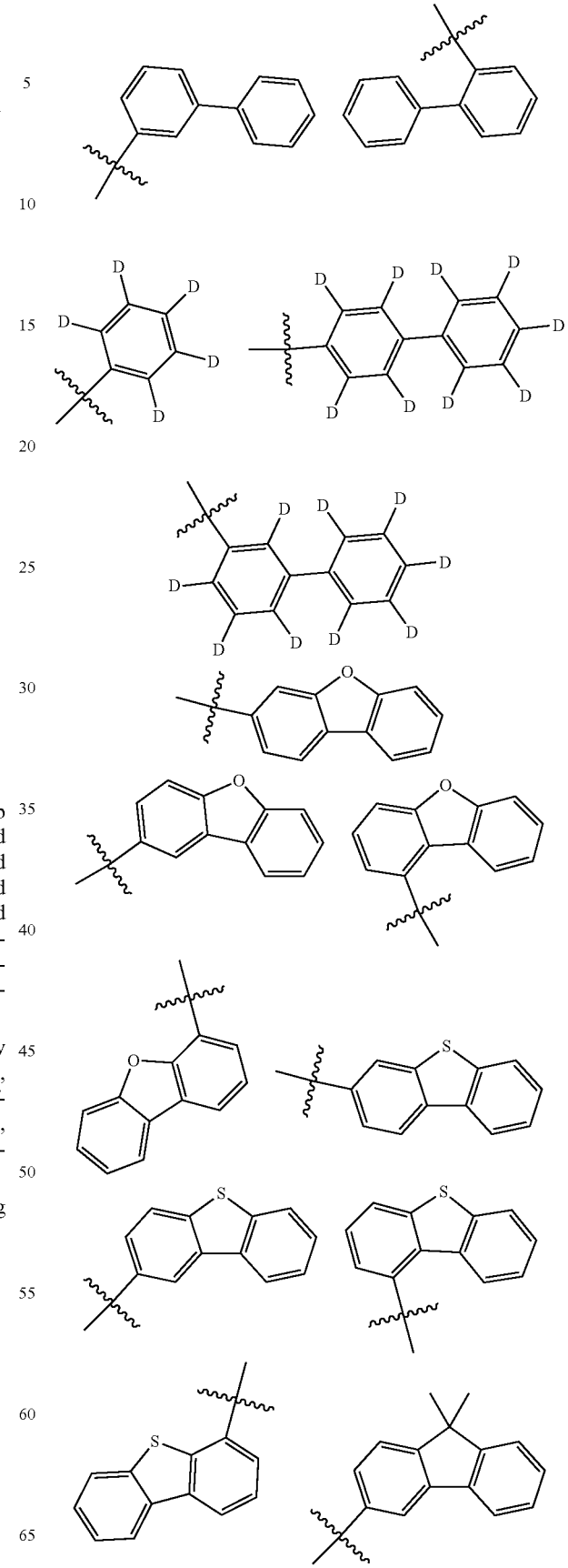

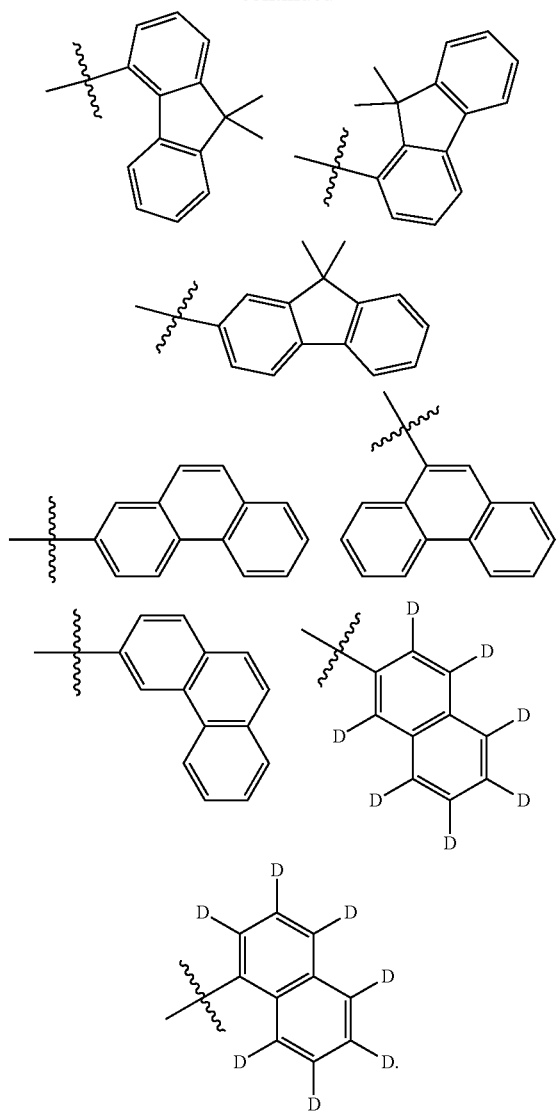
In some embodiments, Ar₂ is selected from the following groups:
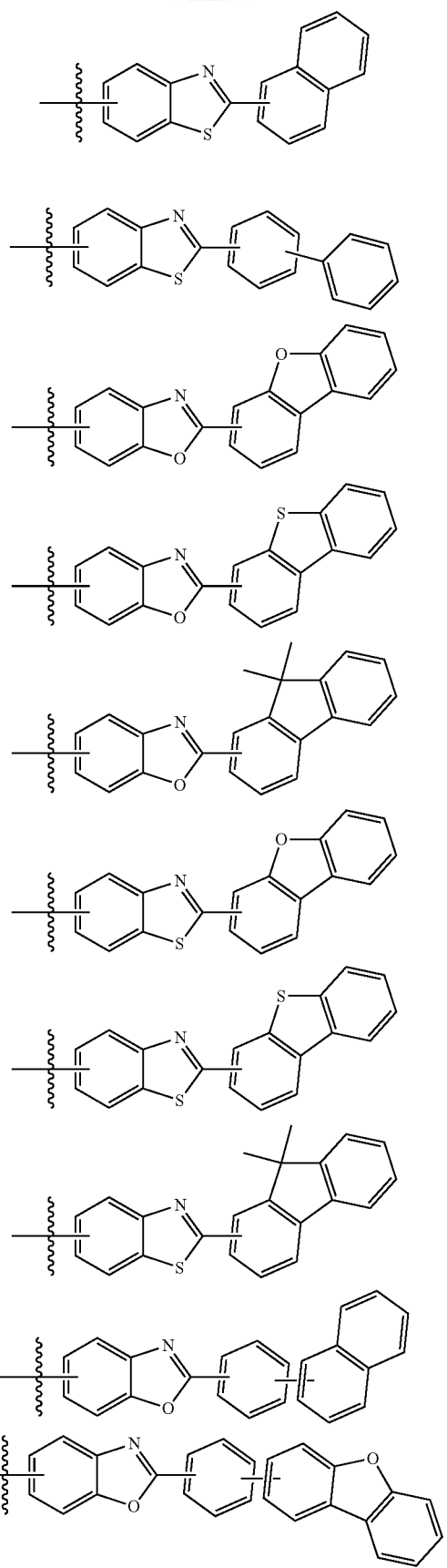

-continued
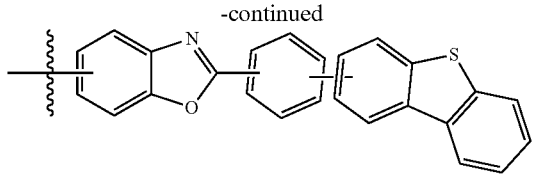
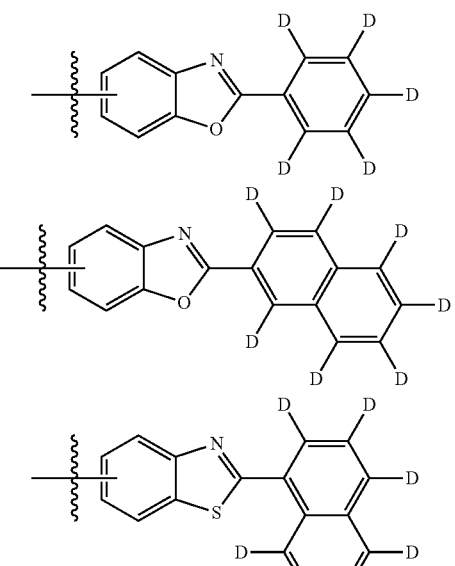
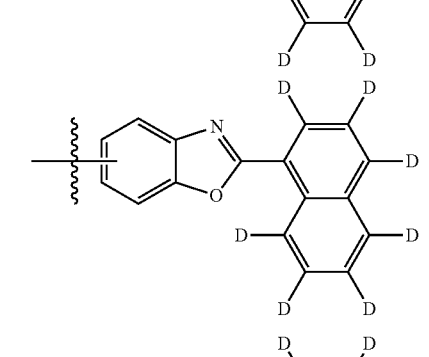
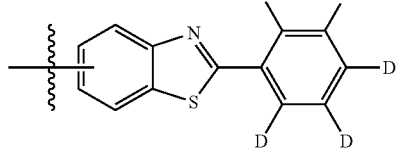
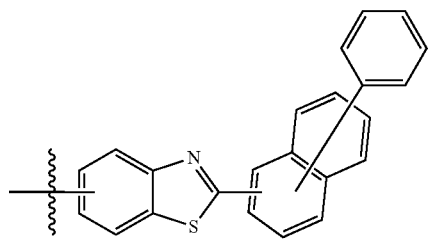
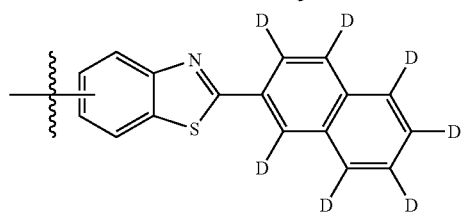
-continued
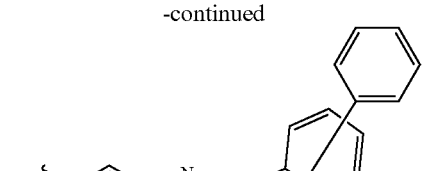
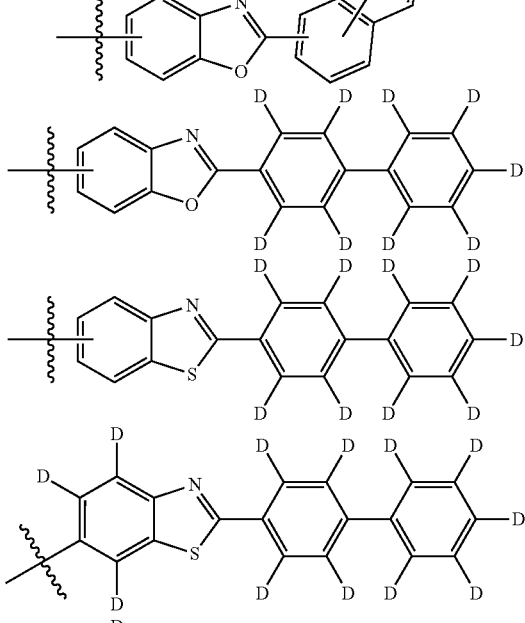
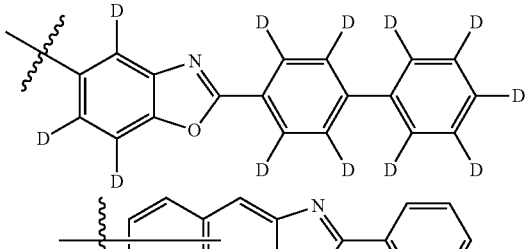
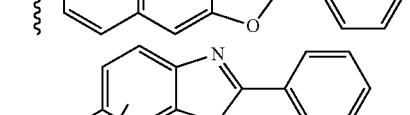
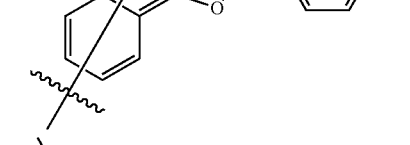
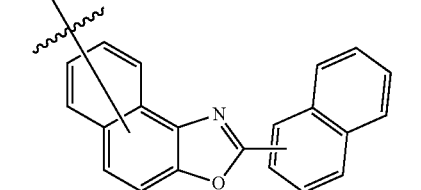
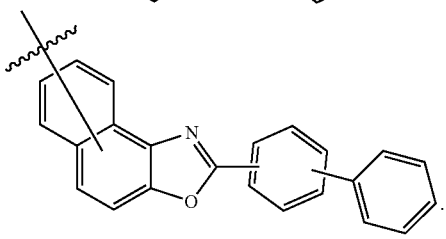

In some embodiments. Ar₂ is selected from the following groups:
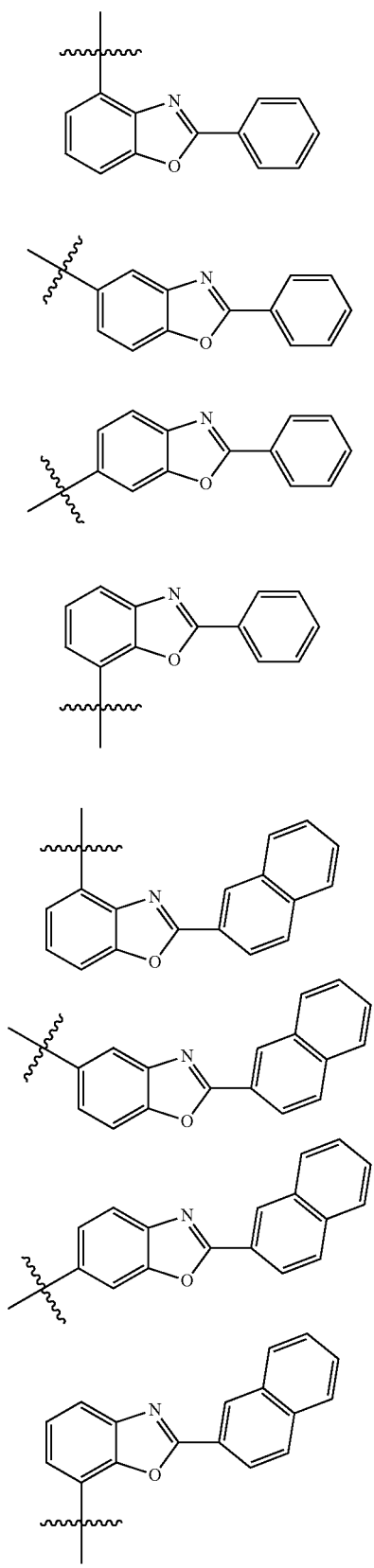
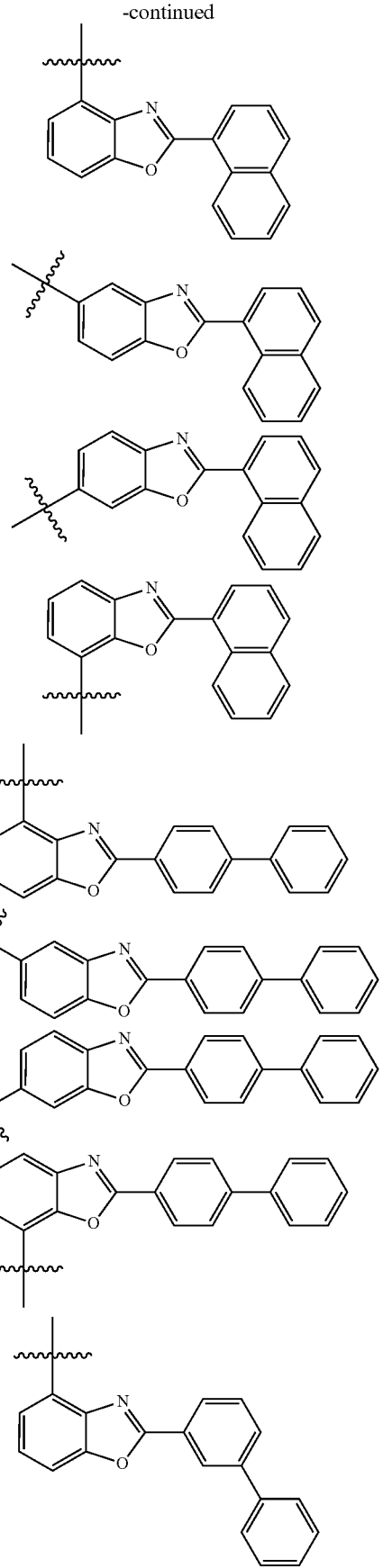

-continued
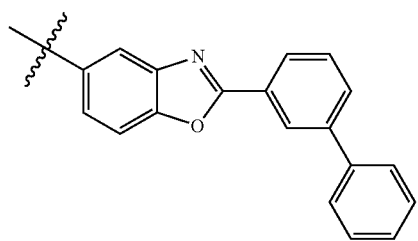
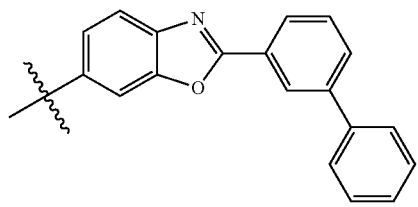
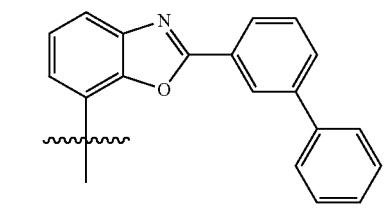
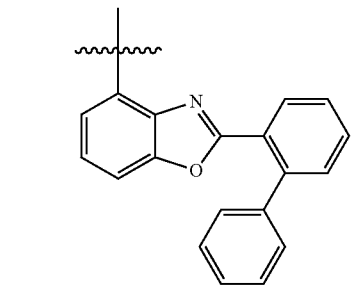
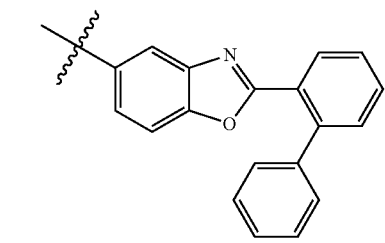
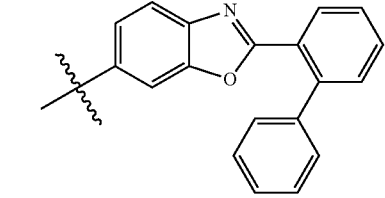
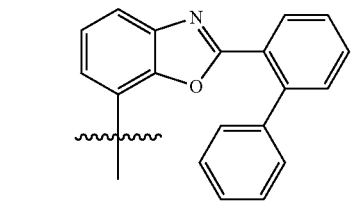
-continued
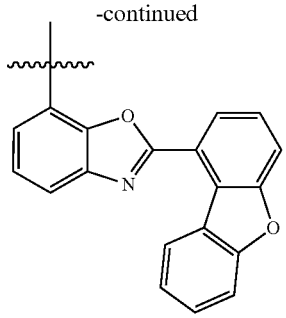
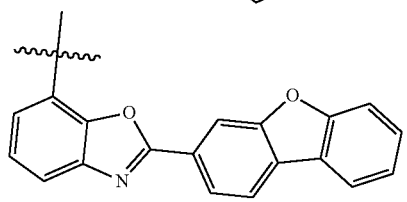
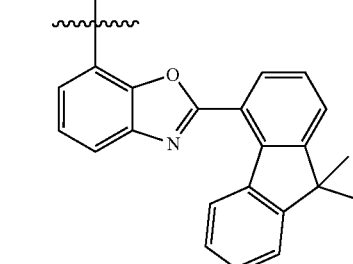
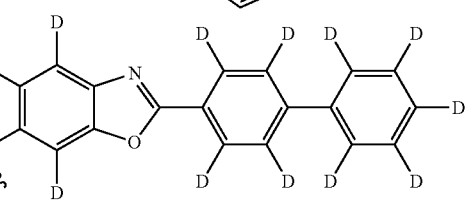
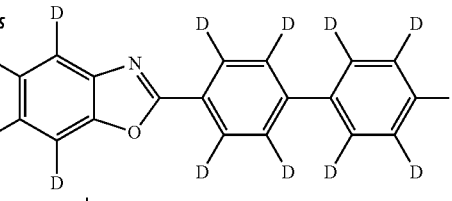
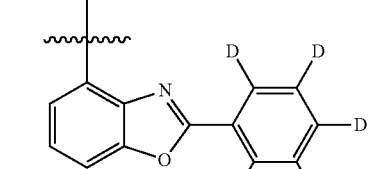
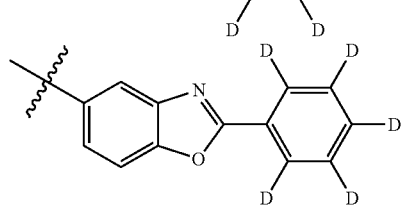
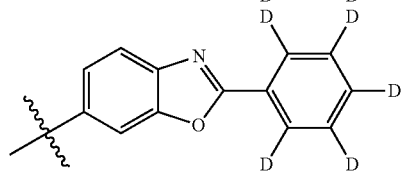

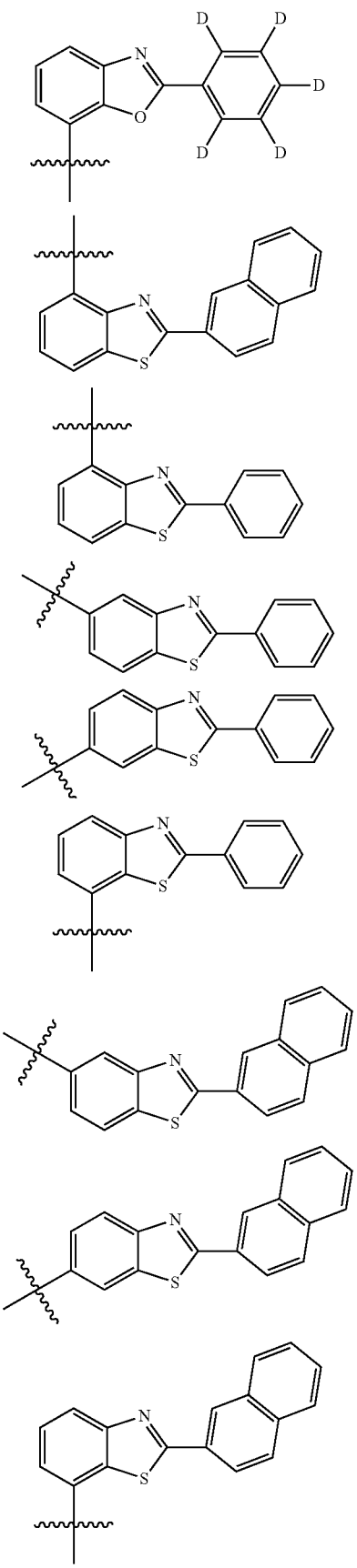
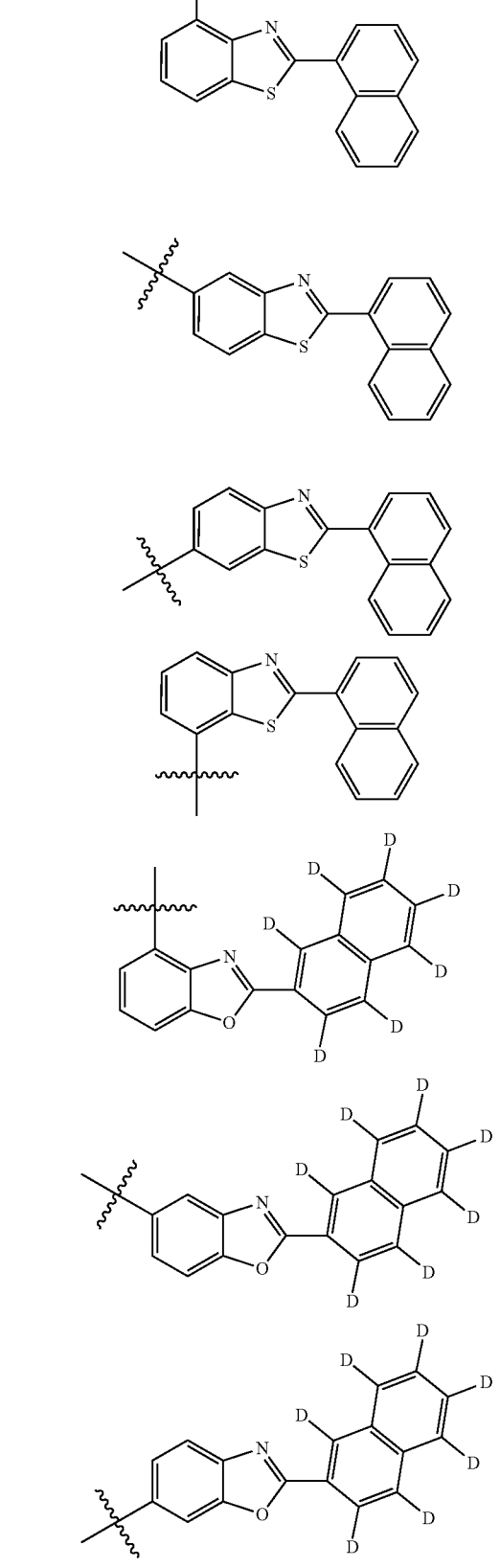

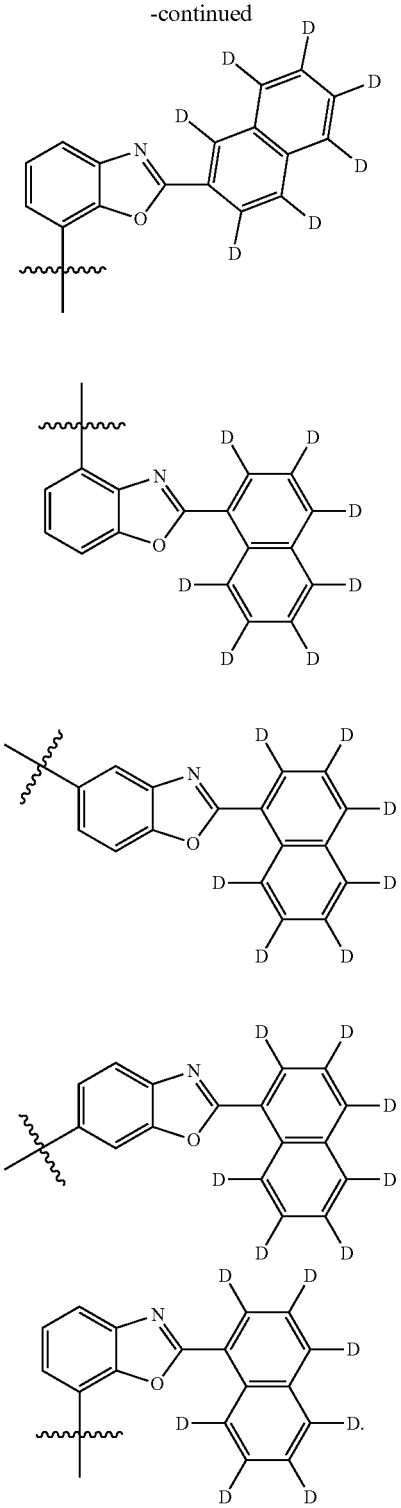
is selected from the following groups:
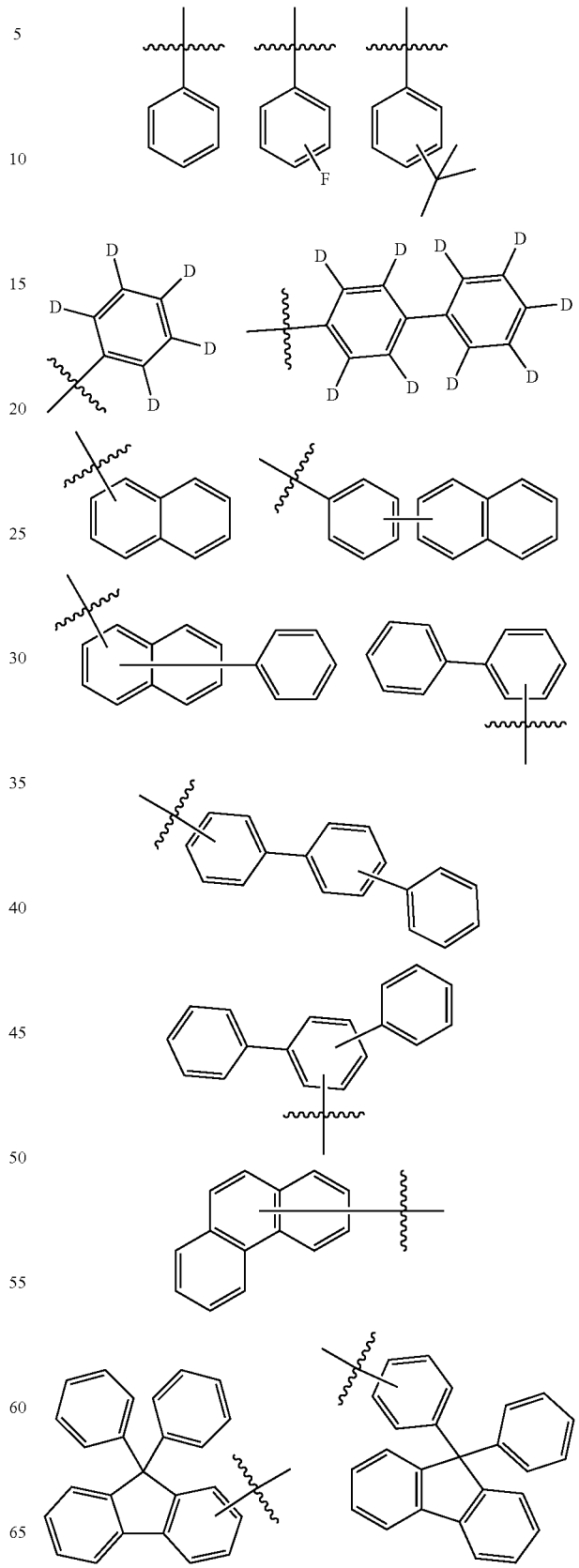
In some embodiments,
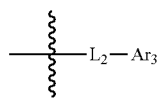

-continued
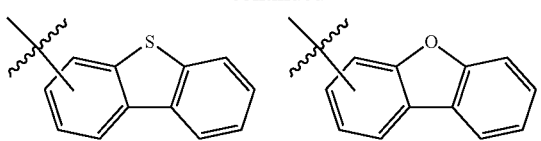
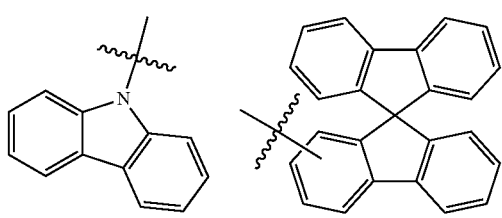
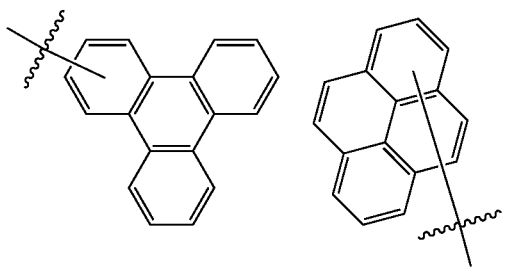
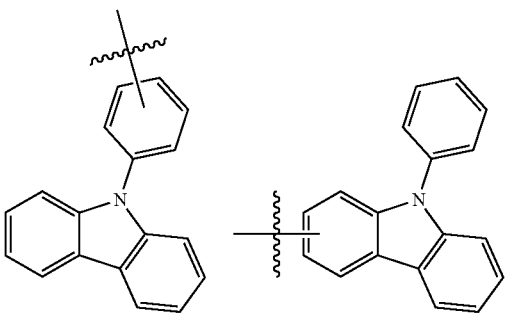
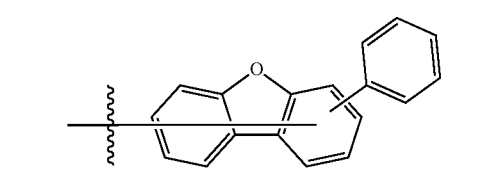
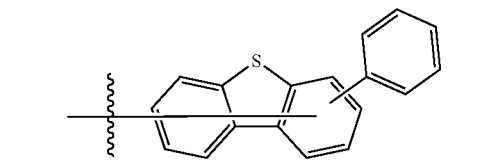
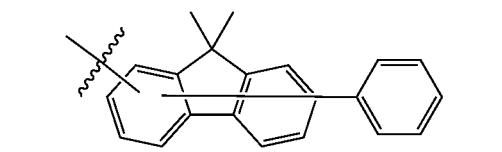
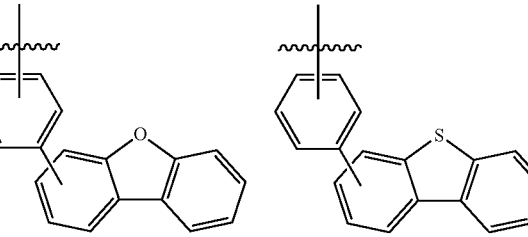
-continued
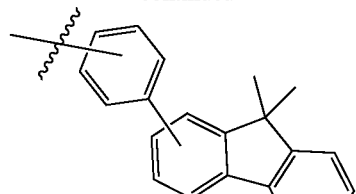
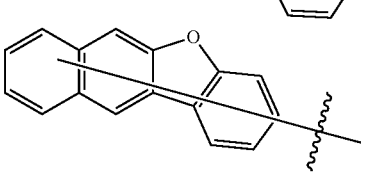
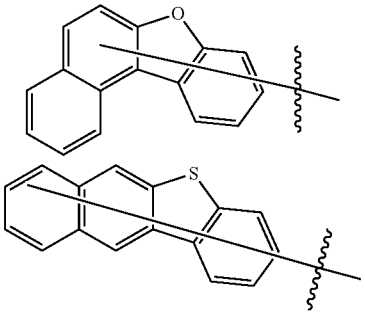
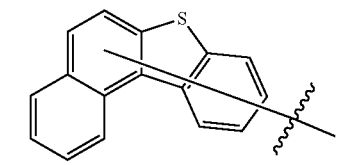
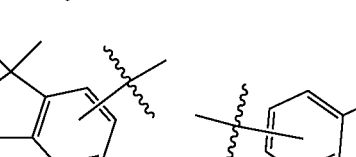
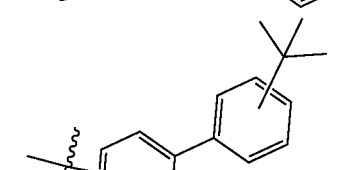
In some embodiments, each $R_1$, each $R_2$, each $R_3$ is identical or different, and is independently selected from the group consisting of deuterium, cyano, fluorine, trideuteromethyl, trimethylsilyl, methyl, ethyl, isopropyl, tert-butyl, phenyl, or naphthyl; optionally, any two adjacent $R_3$ form a benzene ring.
In some embodiments,
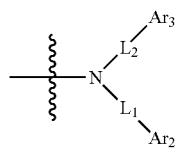

is selected from the following groups:
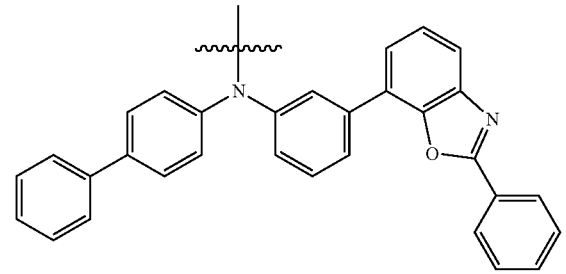
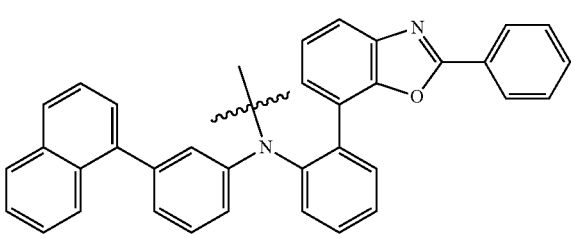
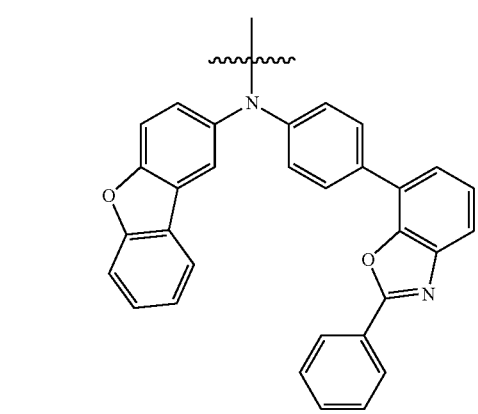
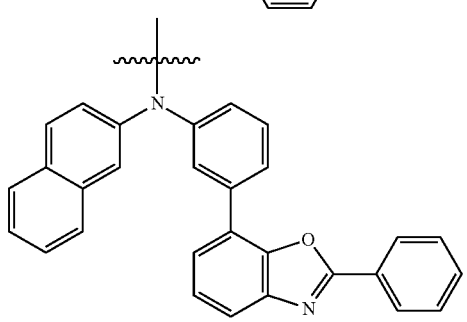
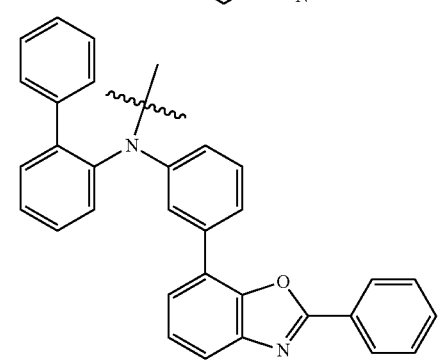
-continued
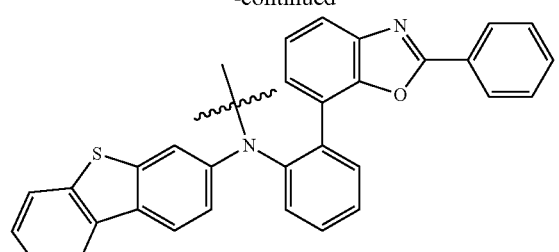
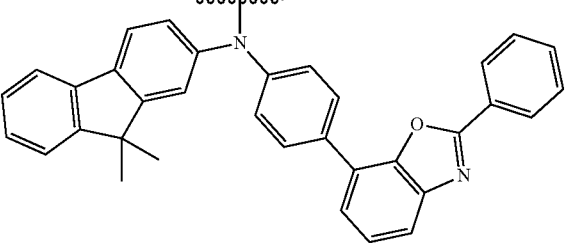
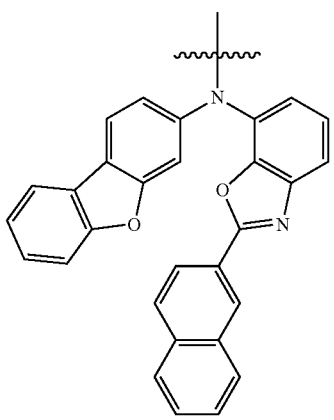
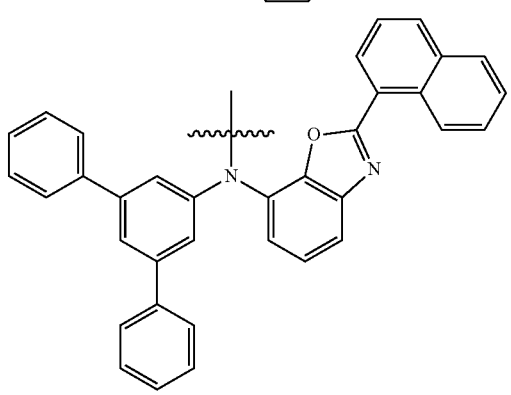
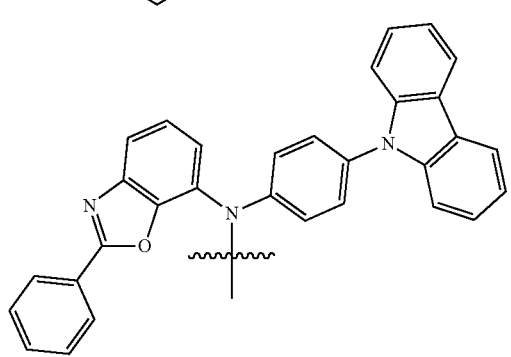

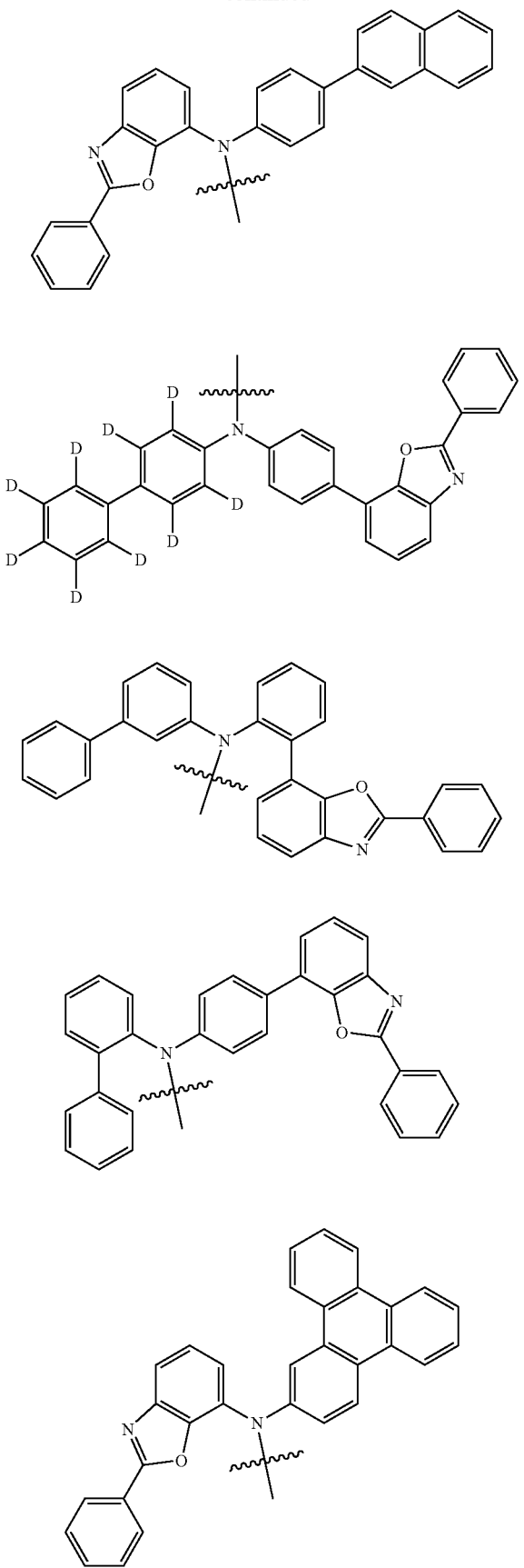
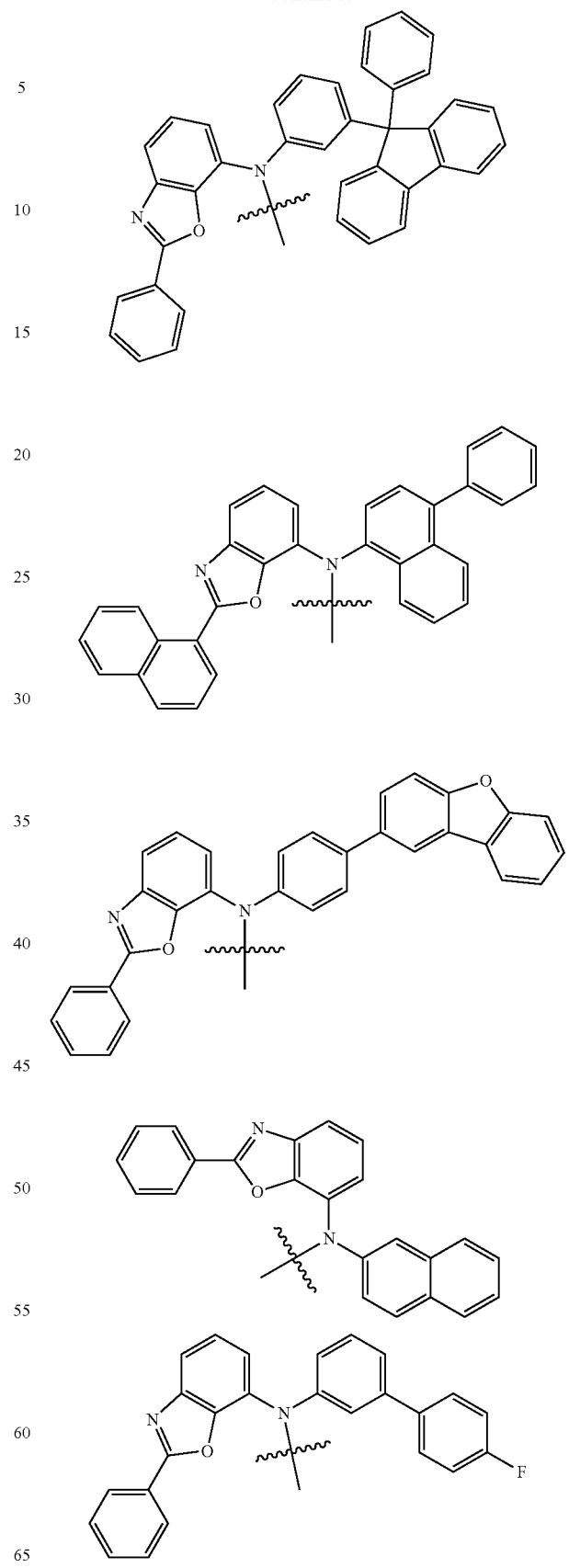

61
-continued
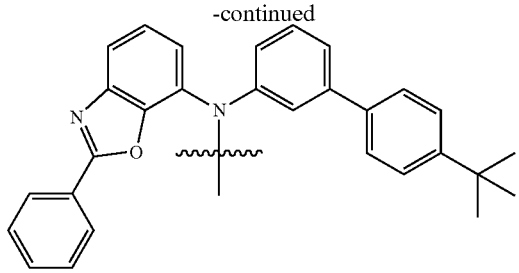
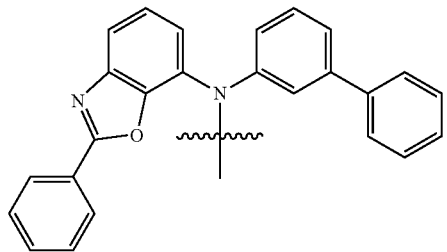
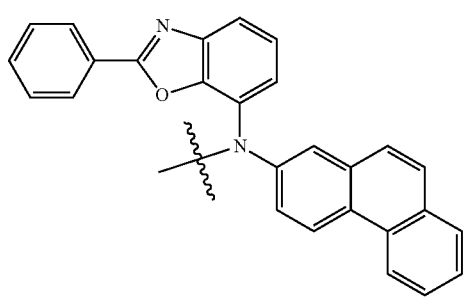
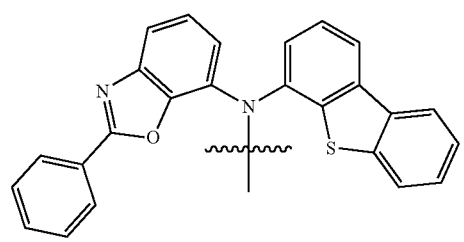
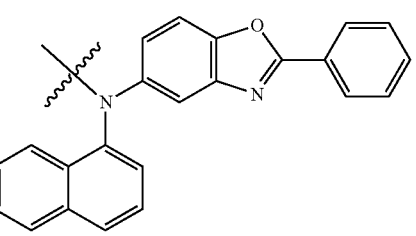
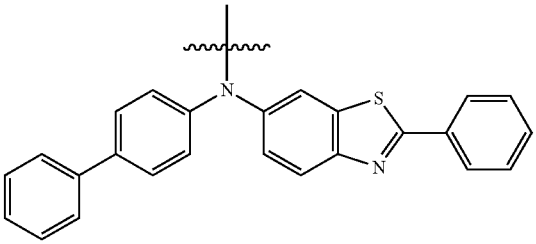
62
-continued
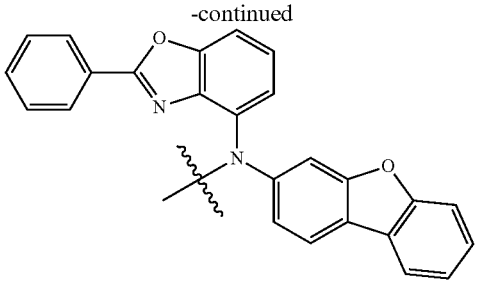
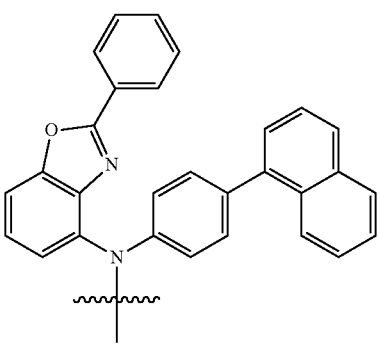
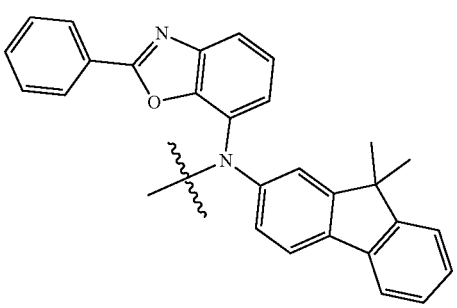
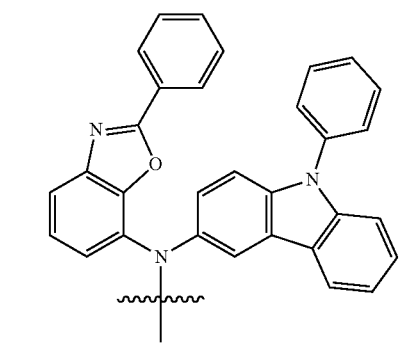
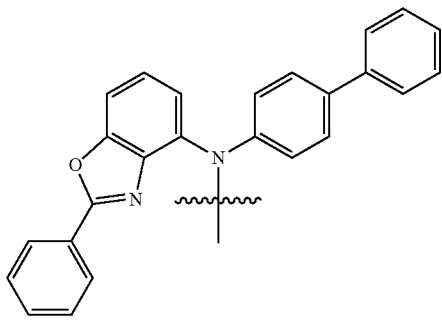

63
-continued
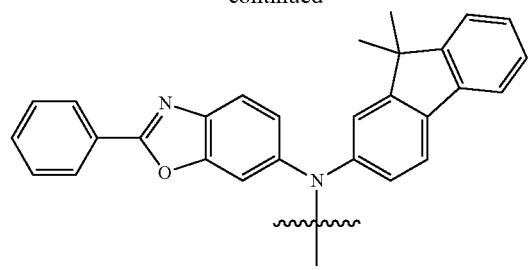
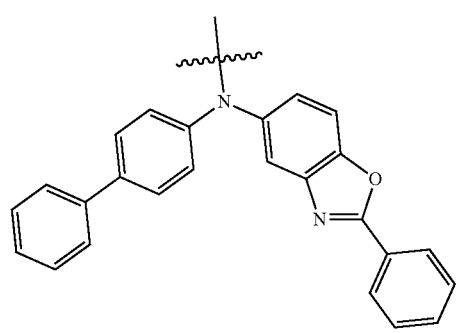
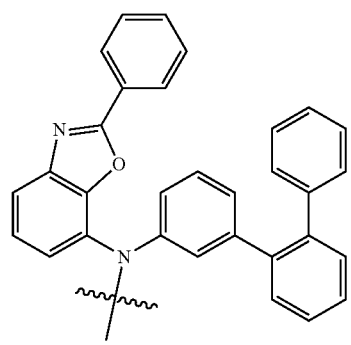
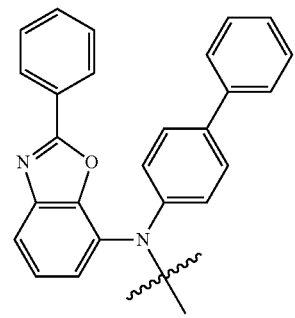
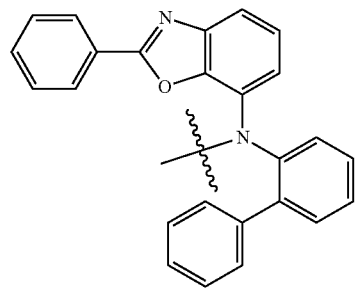
64
-continued
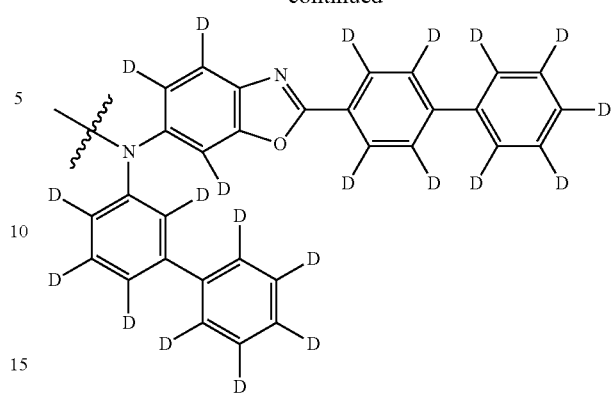
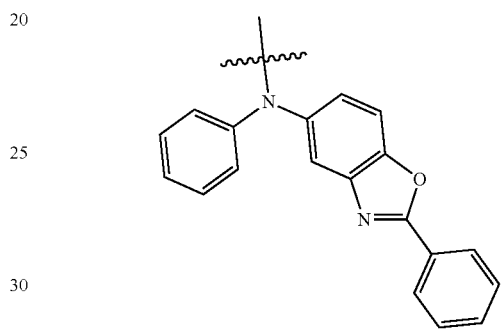
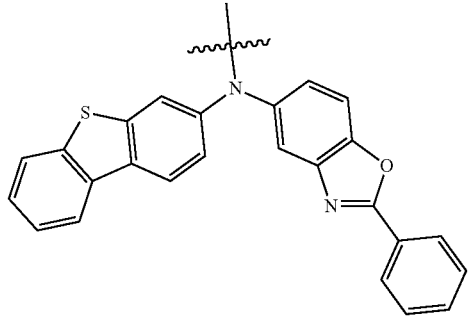
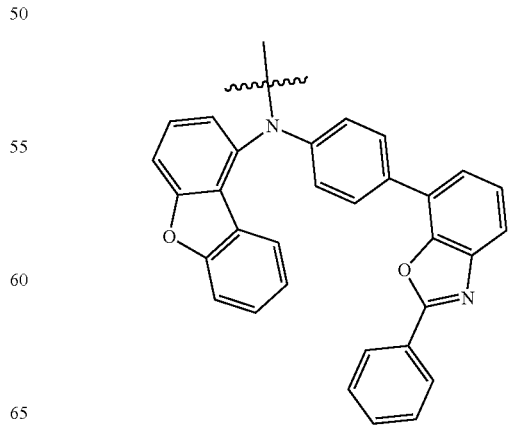

65
-continued
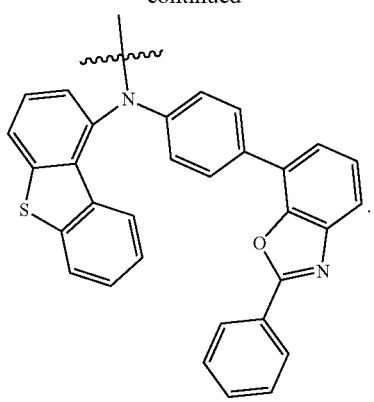
In some embodiments, the arylamine compound is selected from the group consisting of the following compounds:
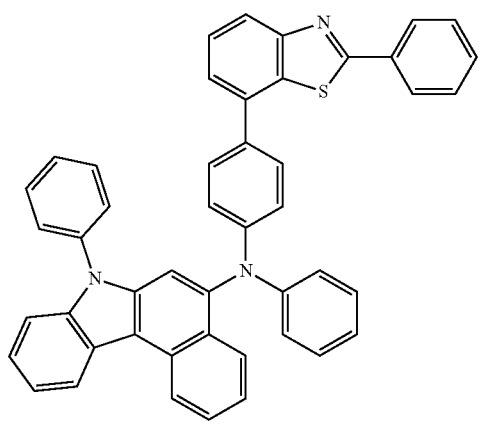
3
66
-continued
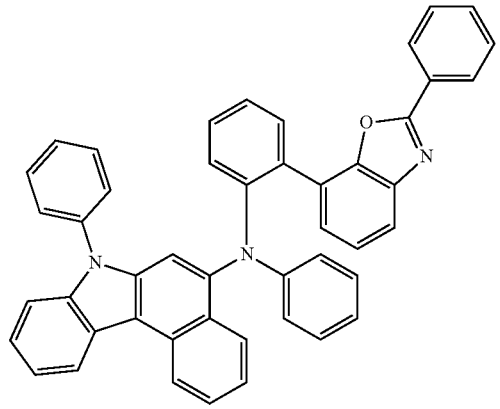
1
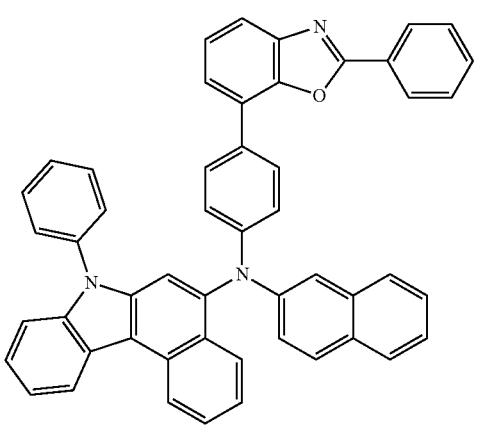
4
2
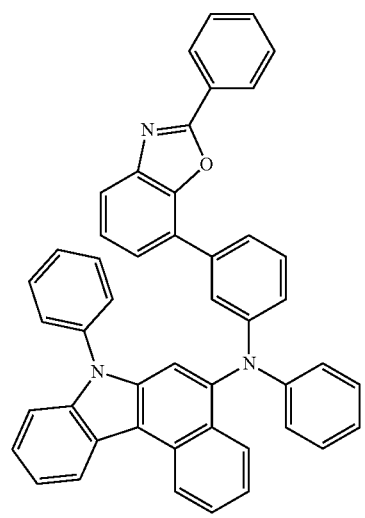
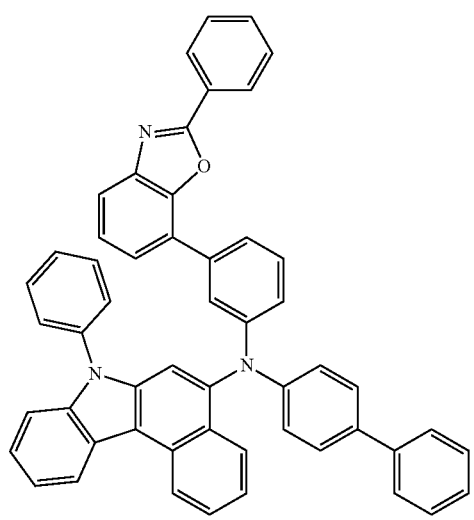
5

67
-continued
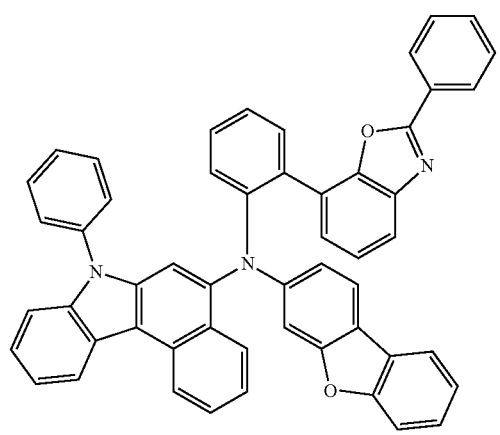
6
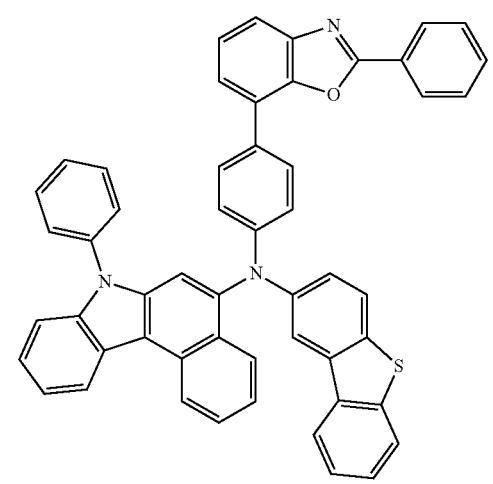
7
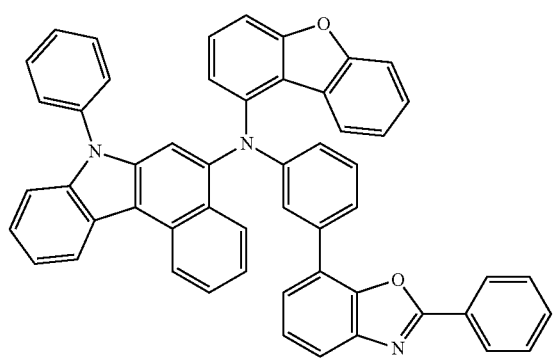
8
68
-continued
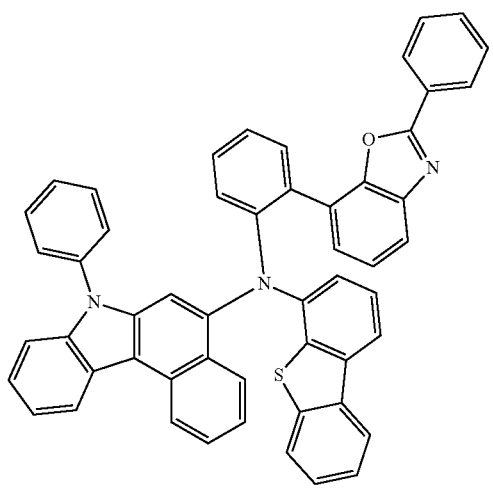
9
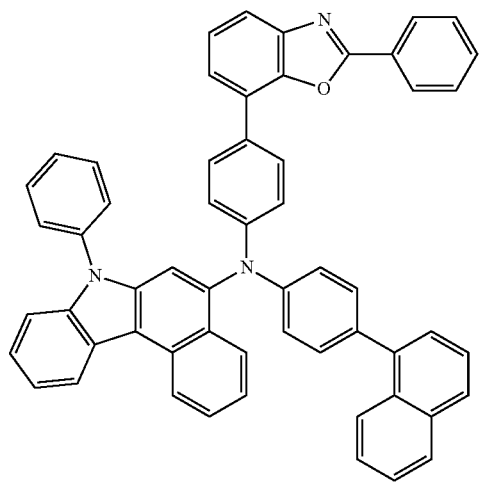
10
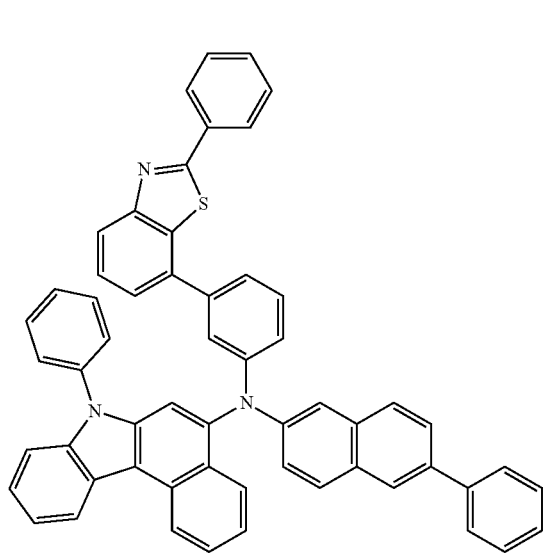
11

12
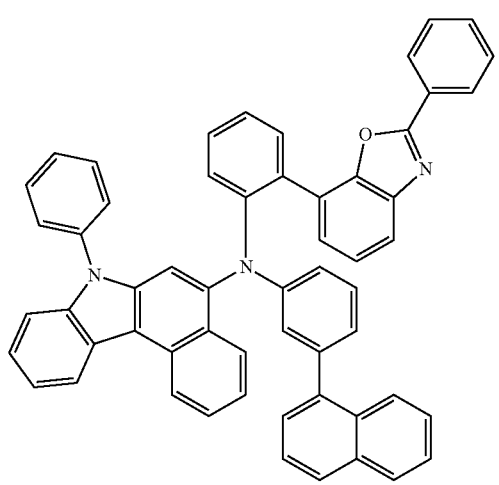
13
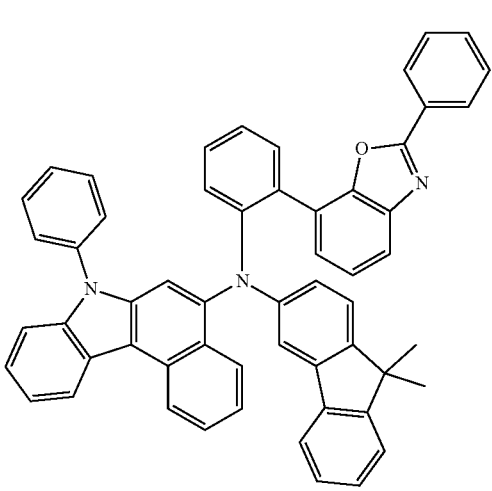
14
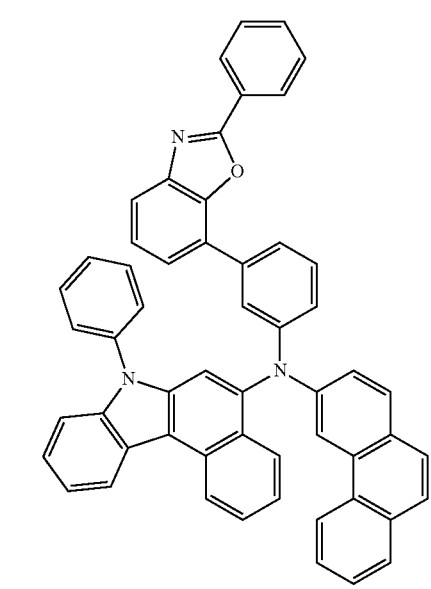
15
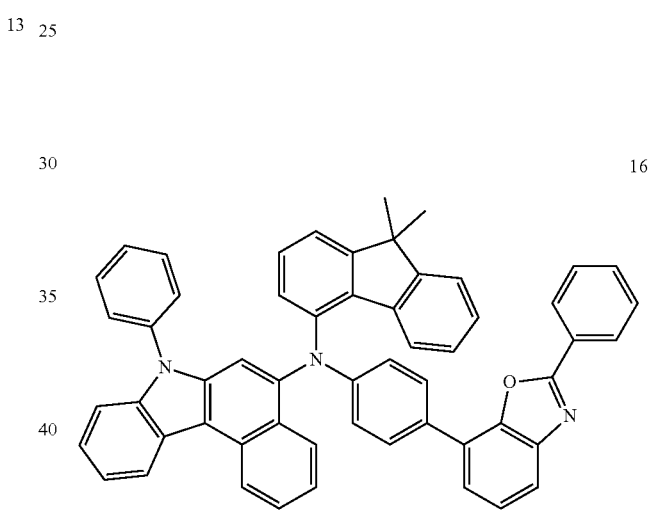
16
17
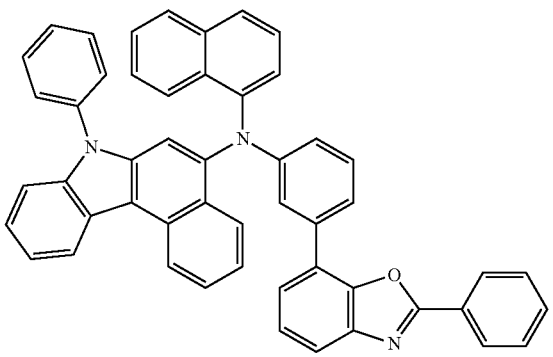

-continued
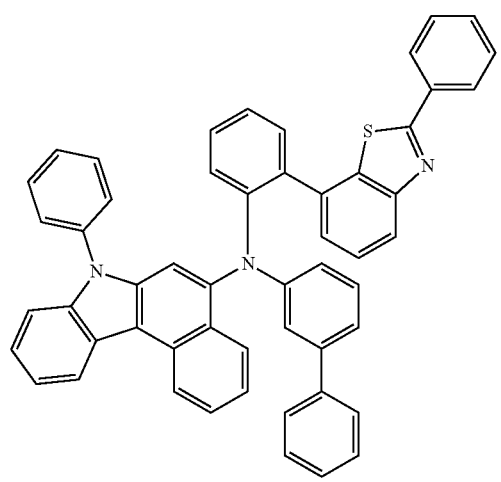
18
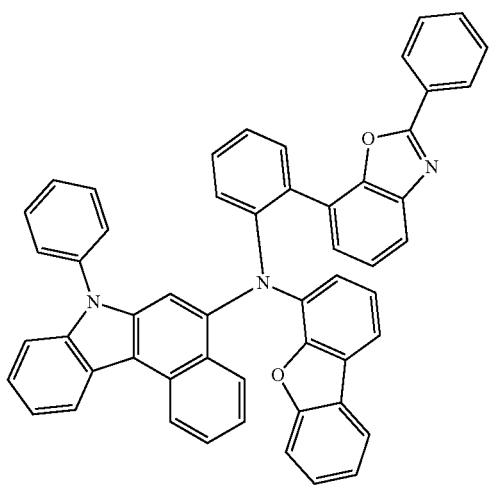
21
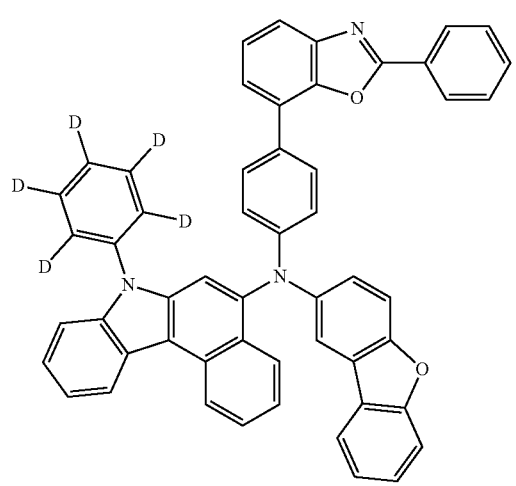
19
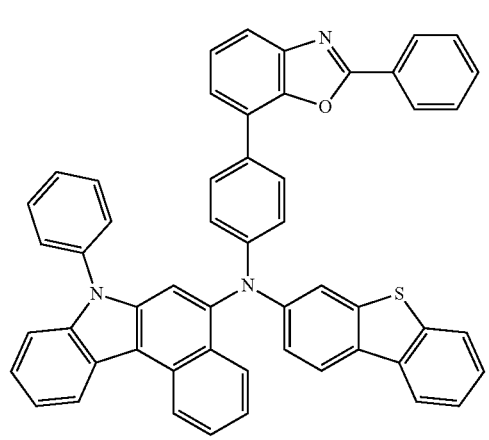
22
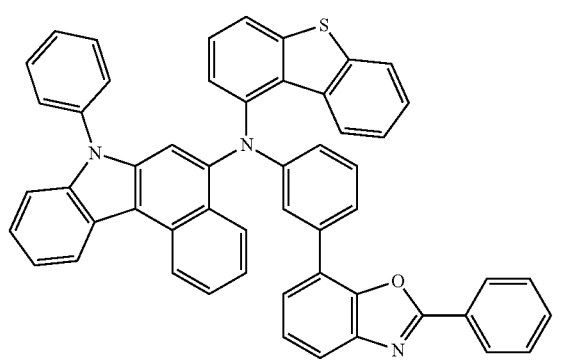
20
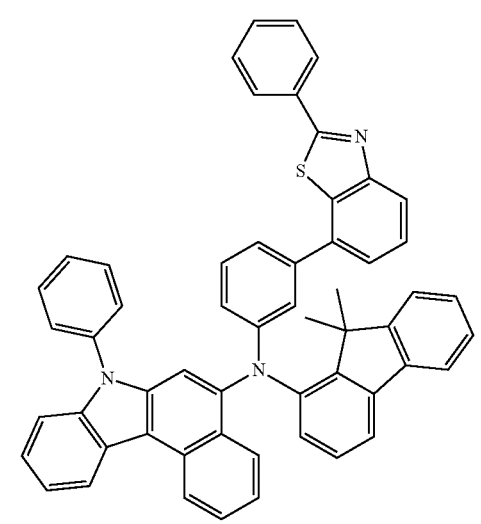
23

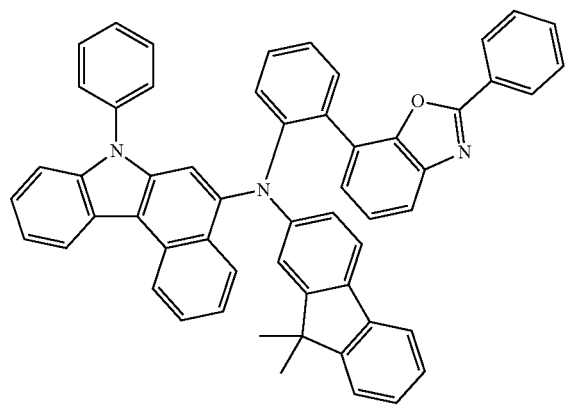
24
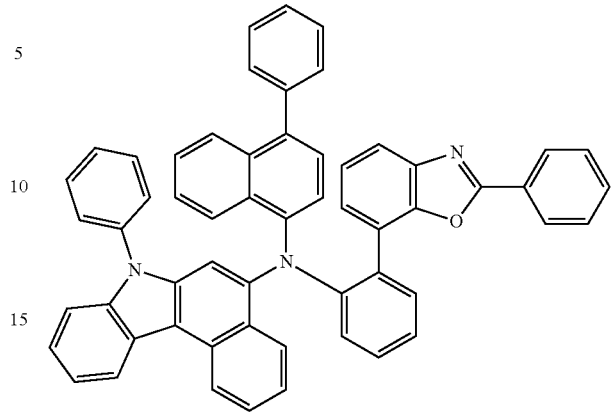
27
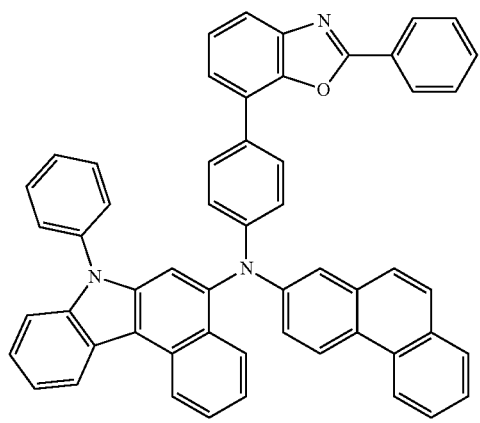
25
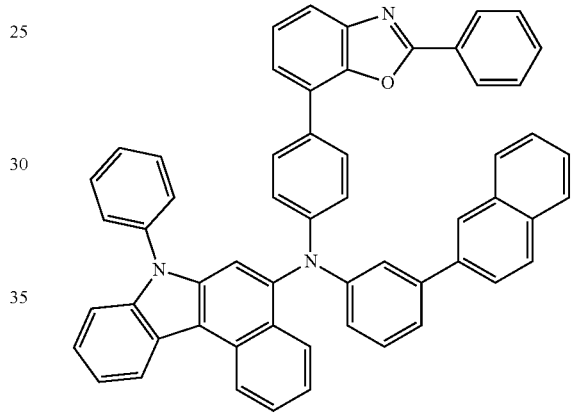
28
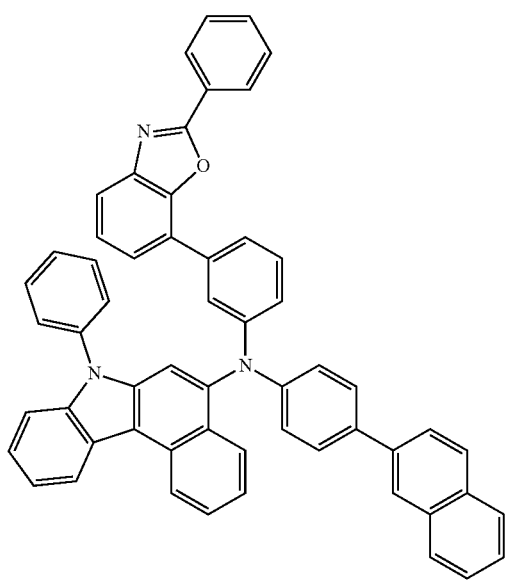
26
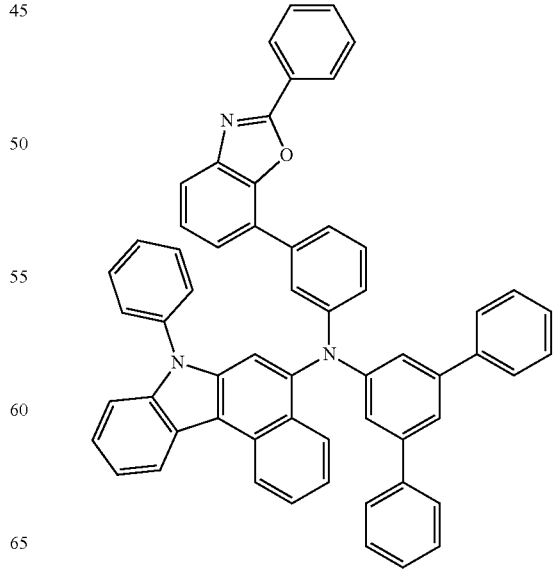
29

-continued
75
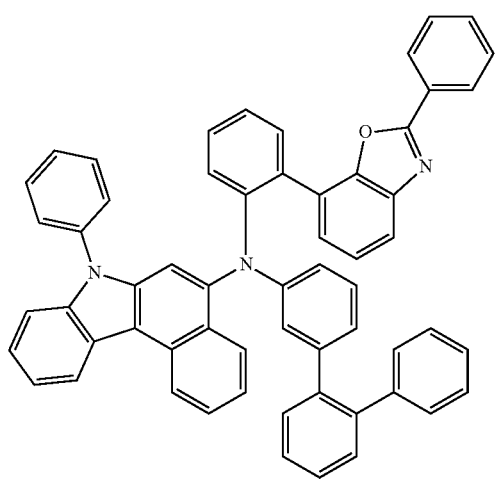
30
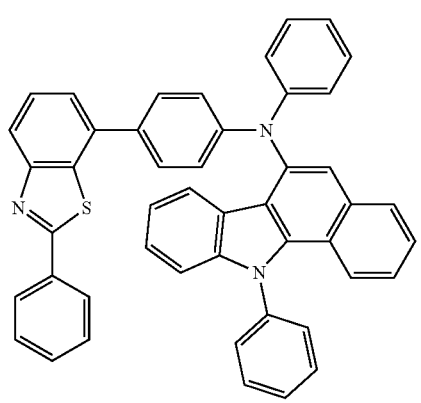
31
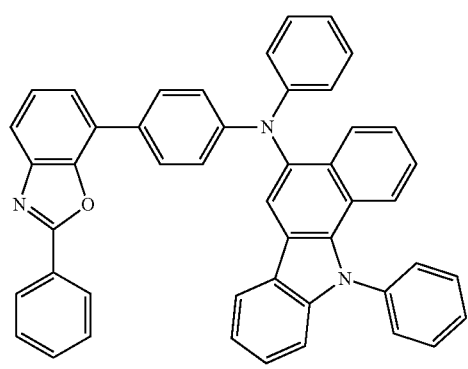
32
76
-continued
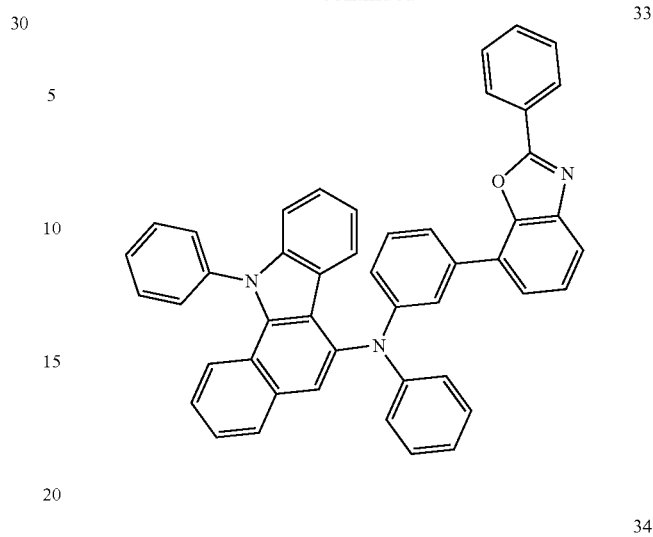
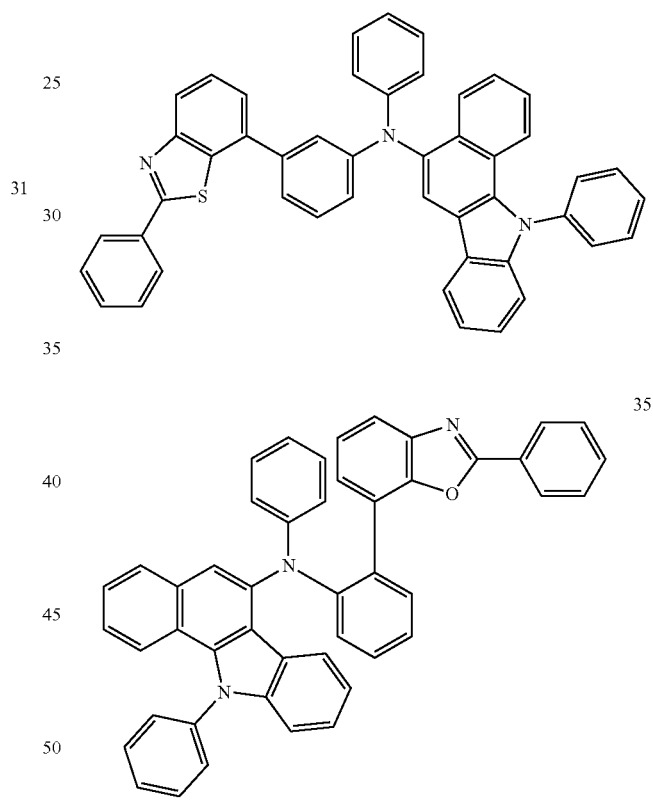
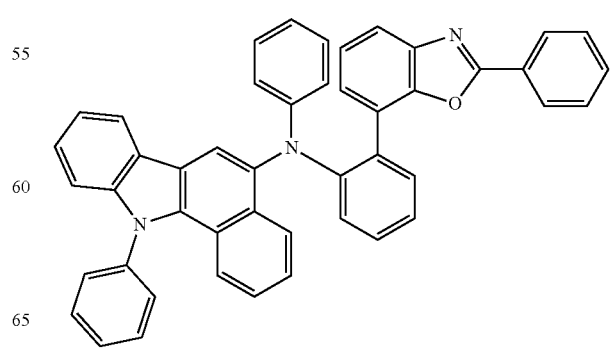

37
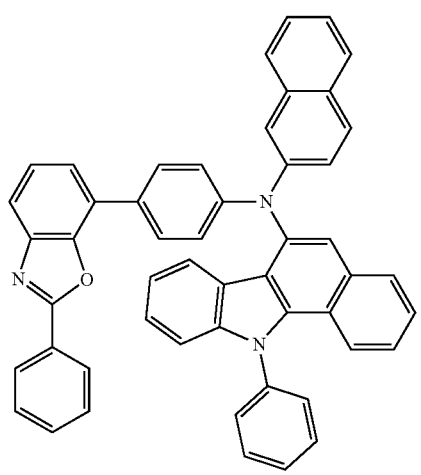
38
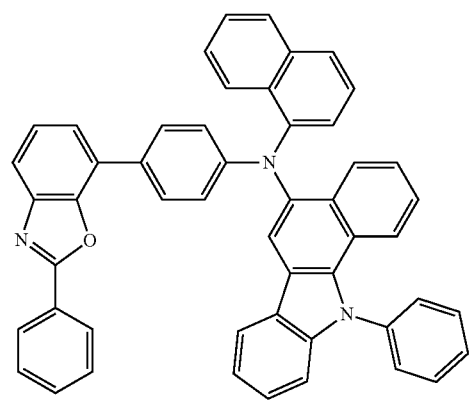
39
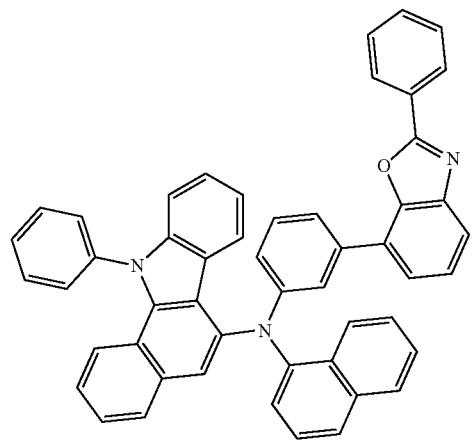
40
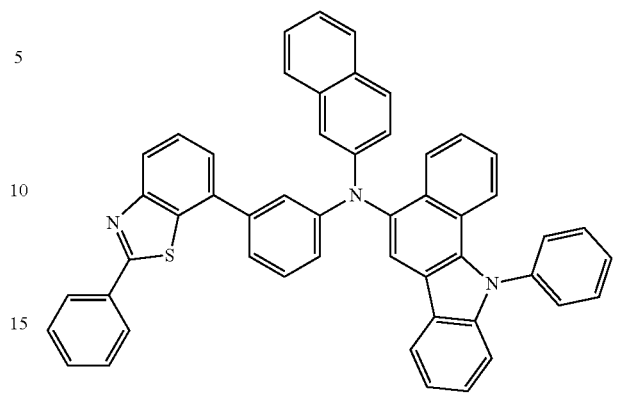
41
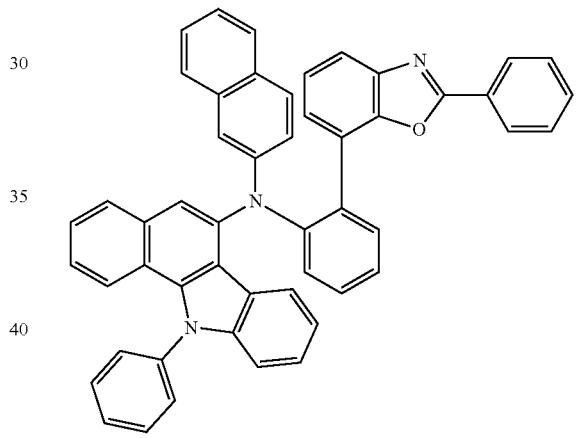
42
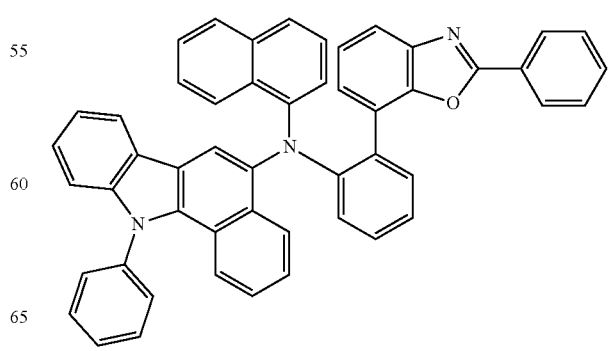

43
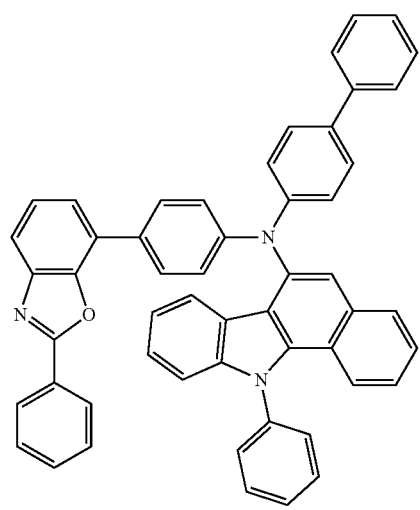
44
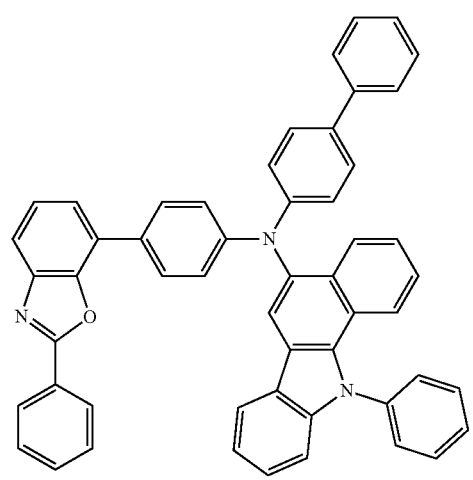
45
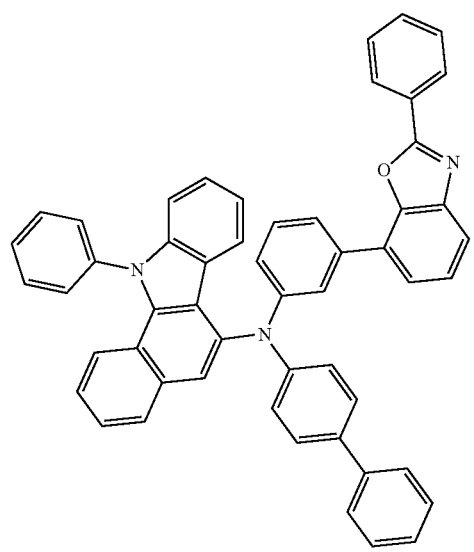
46
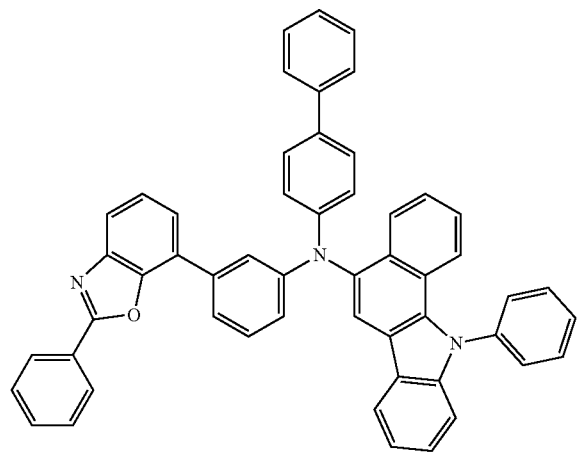
47
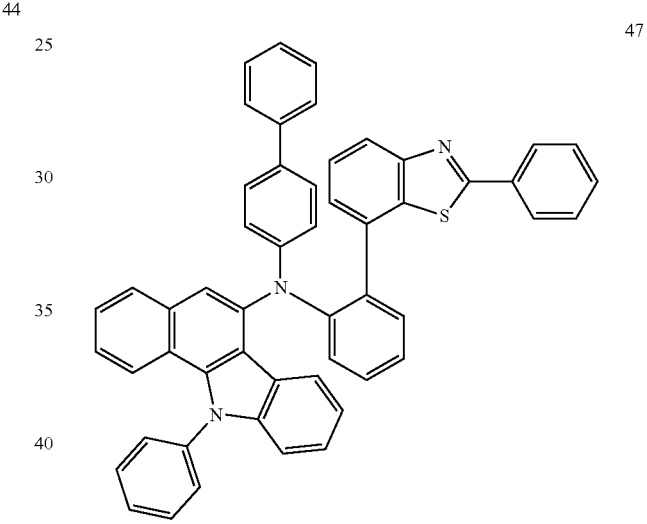
48
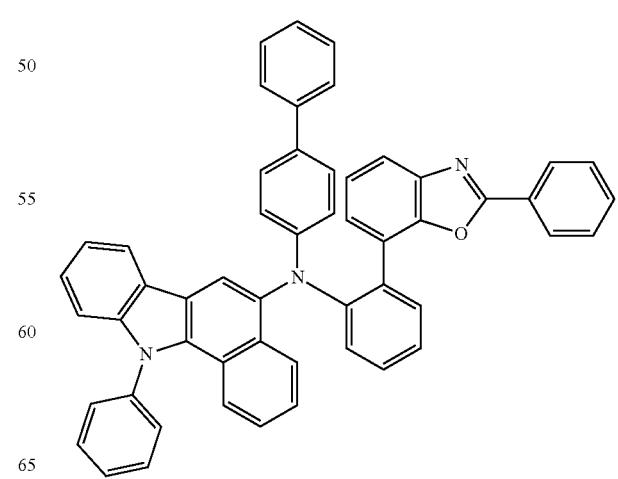

49
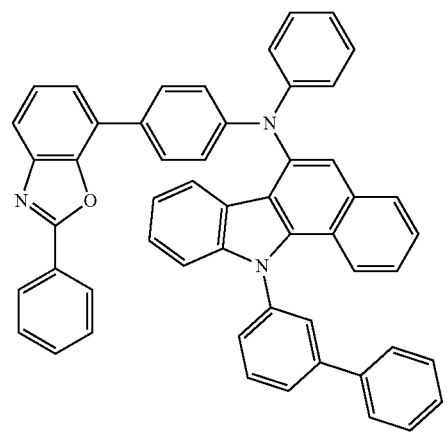
52
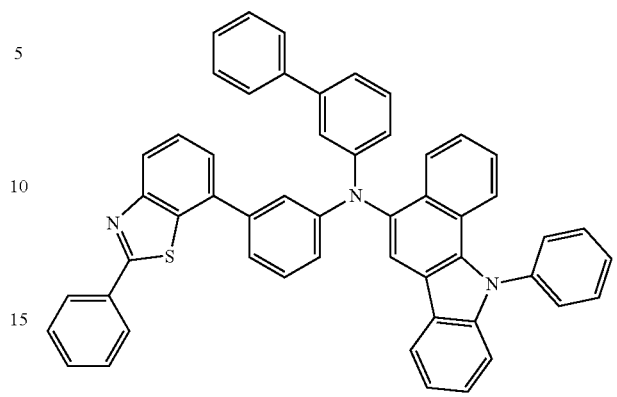
50
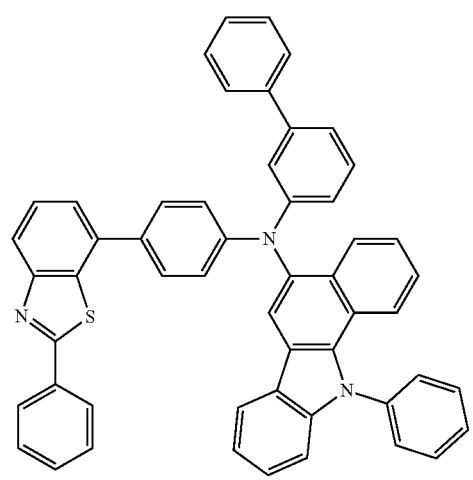
53
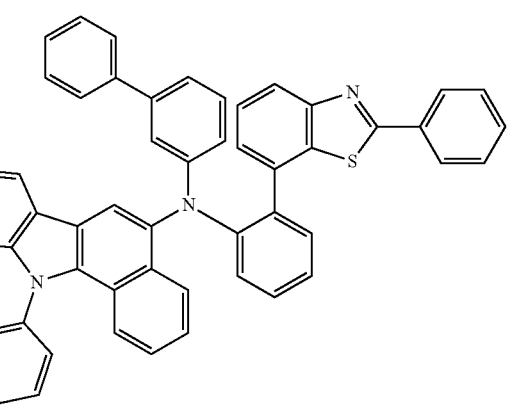
51
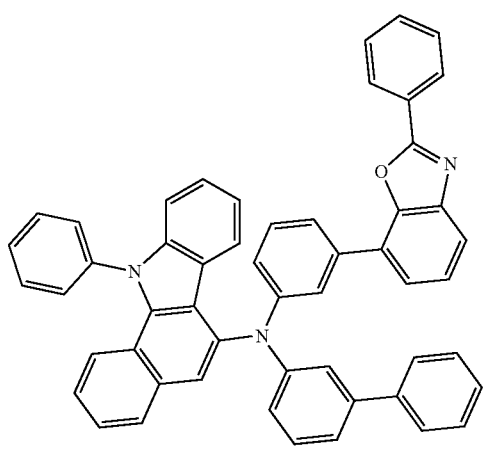
54

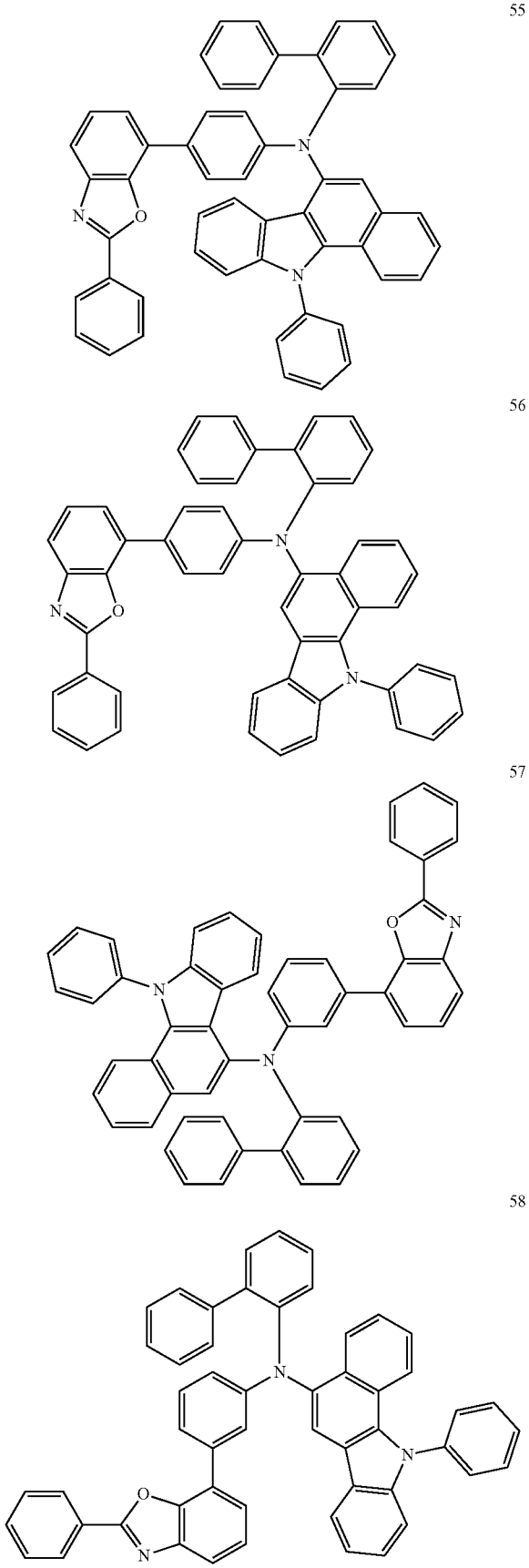
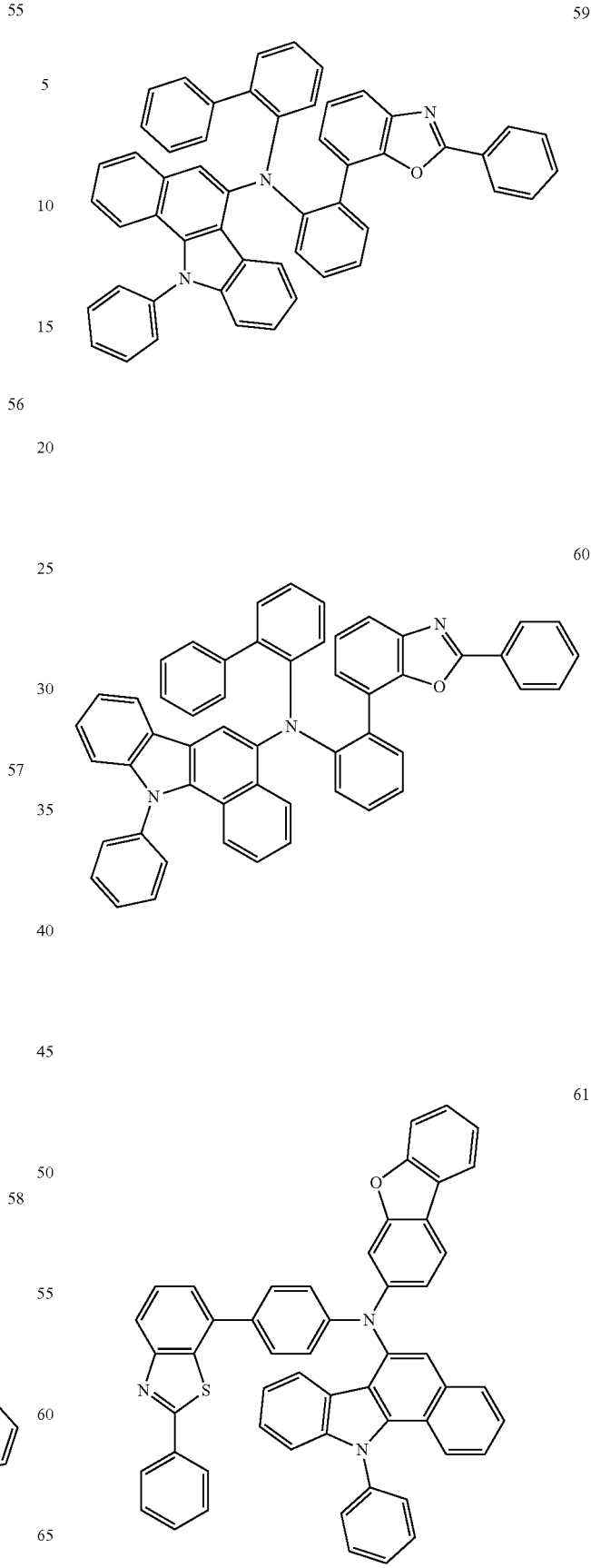

-continued
62
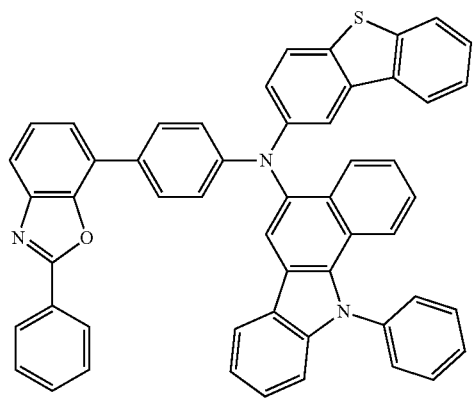
65
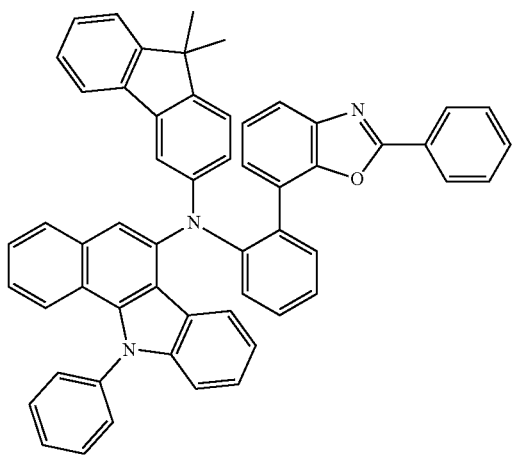
63
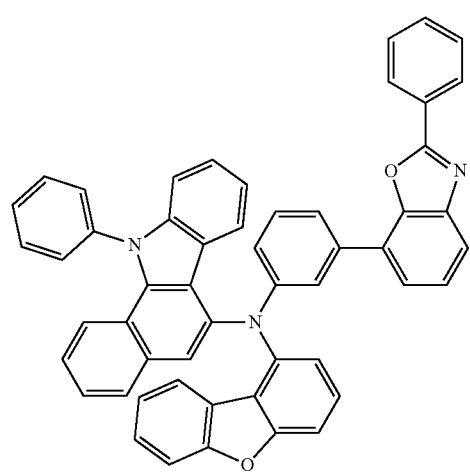
66
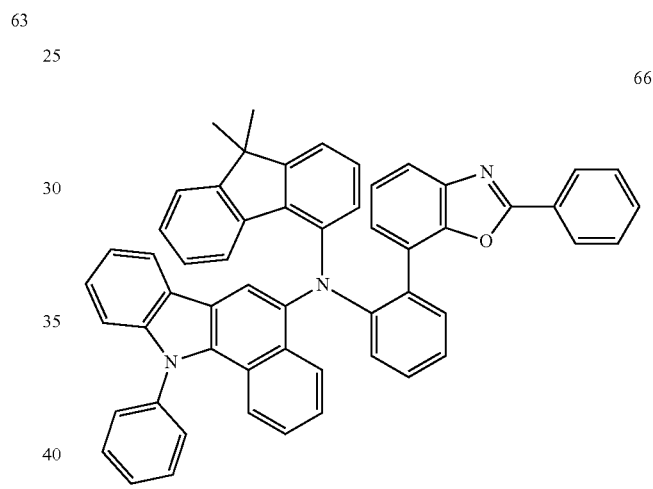
64
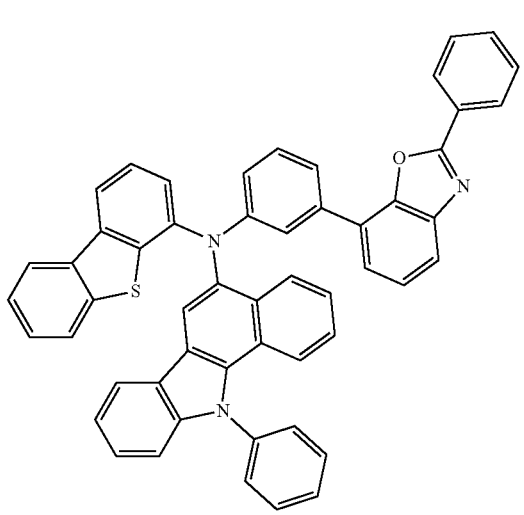
67
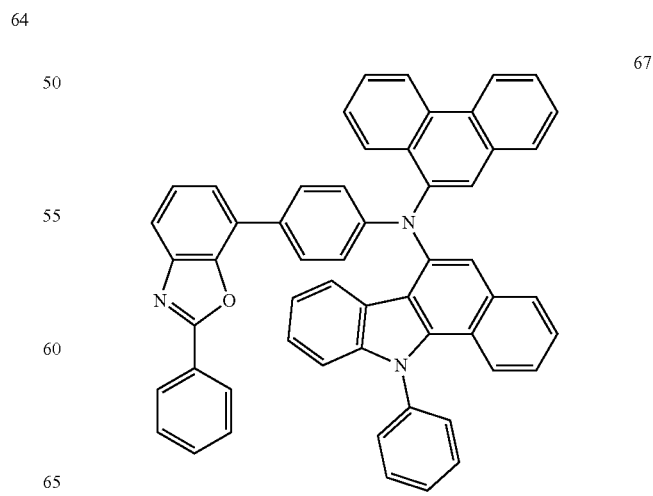

68
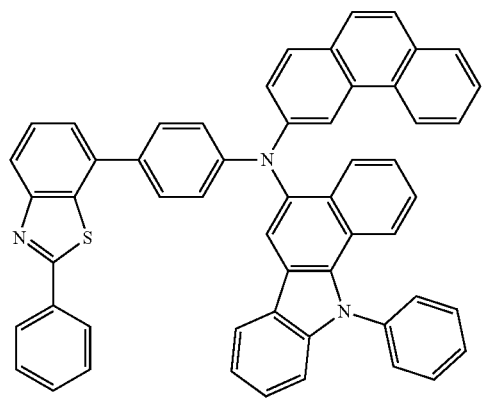
69
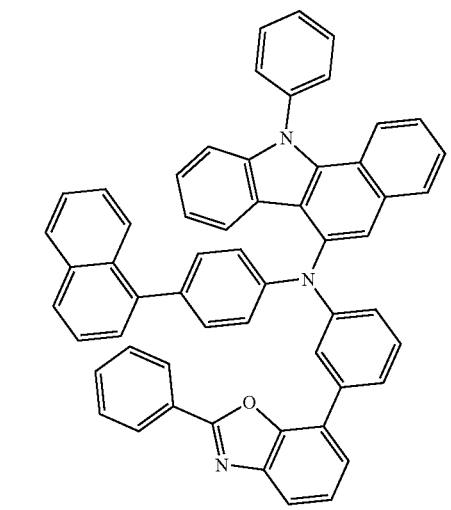
70
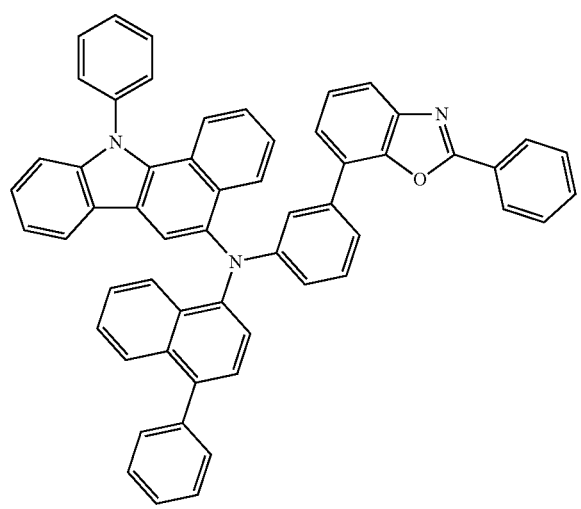
71
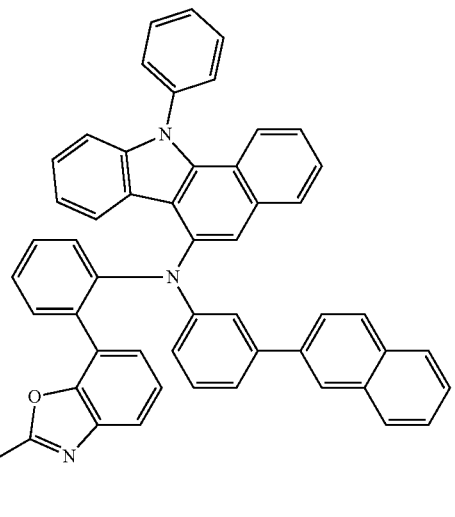
72
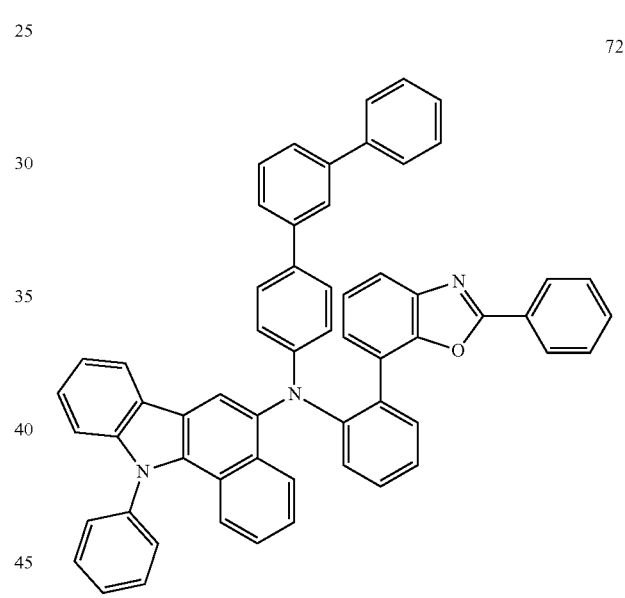
73
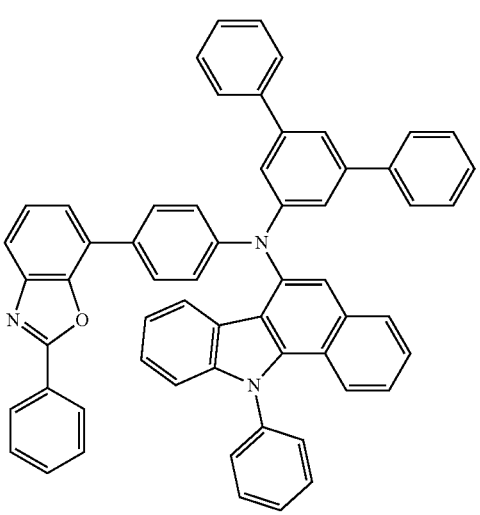

74
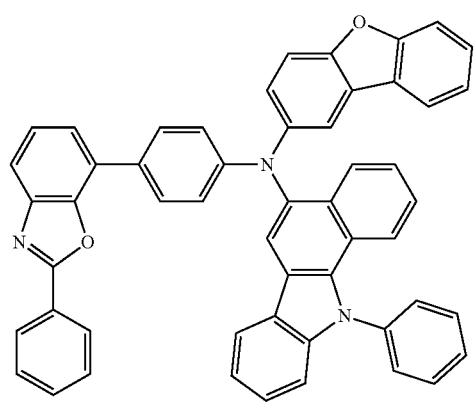
75
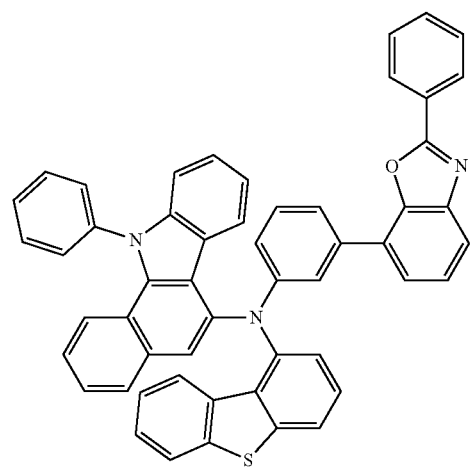
76
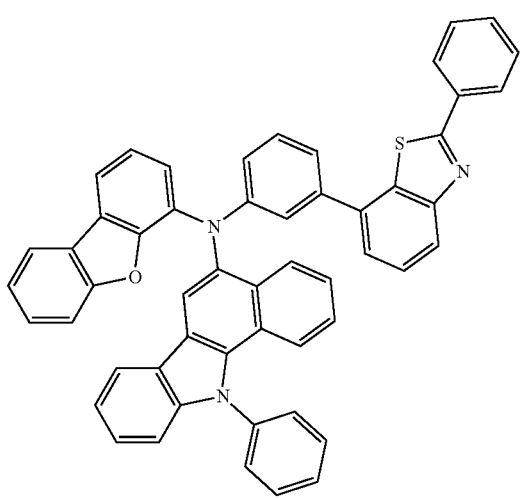
77
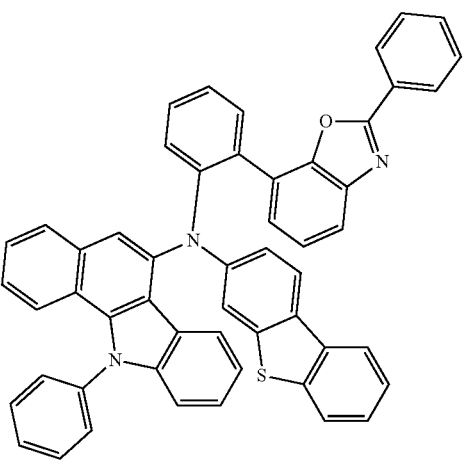
78
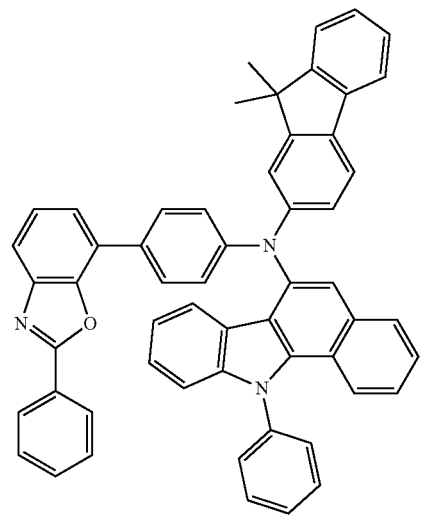
79

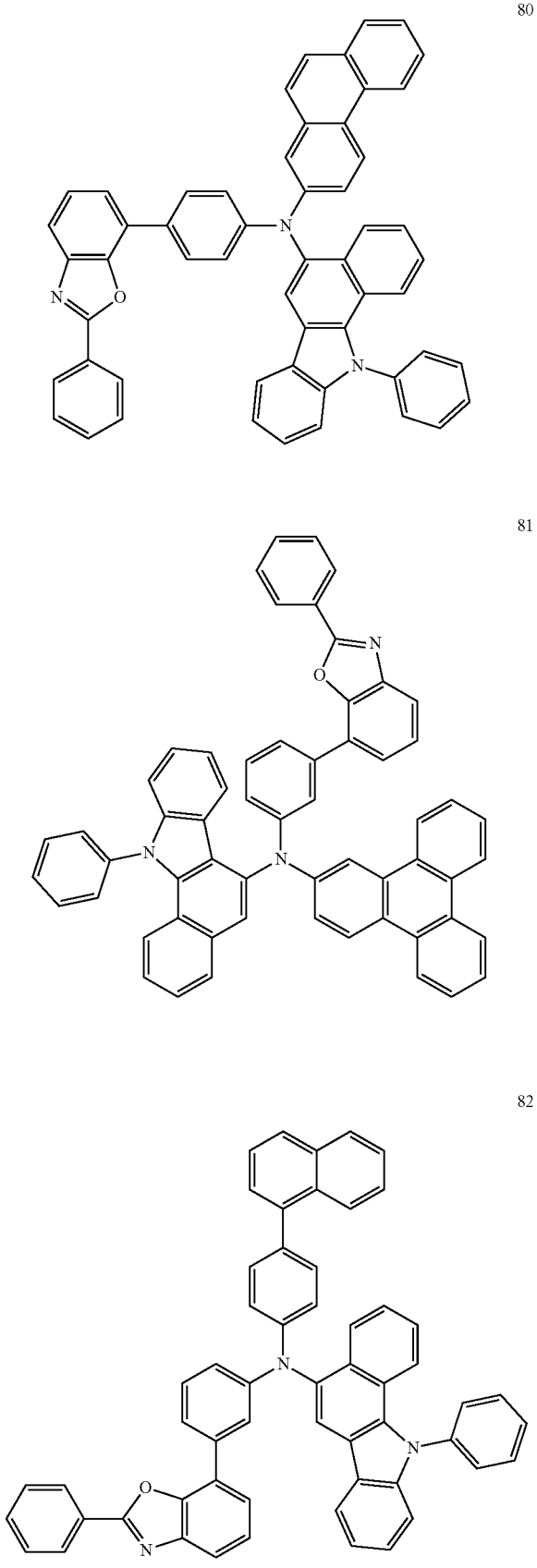
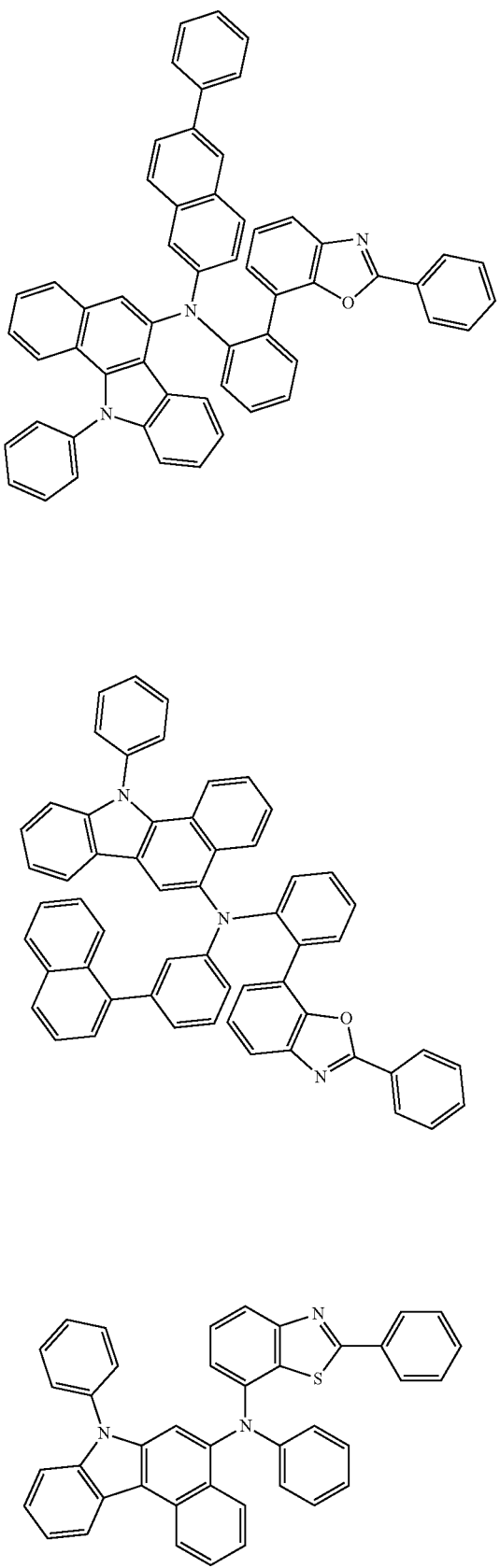

86
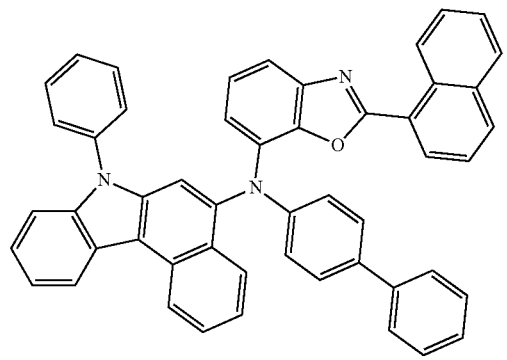
87
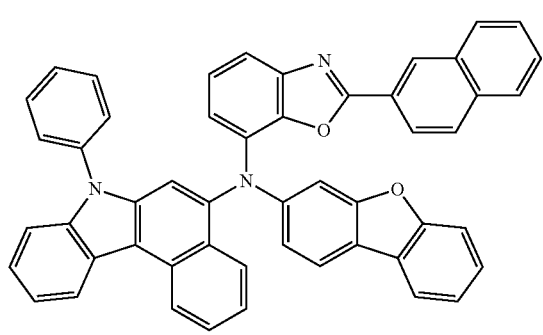
88
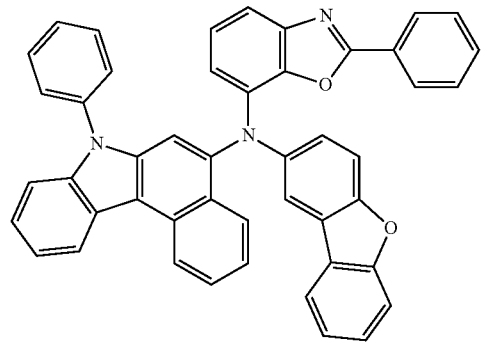
89
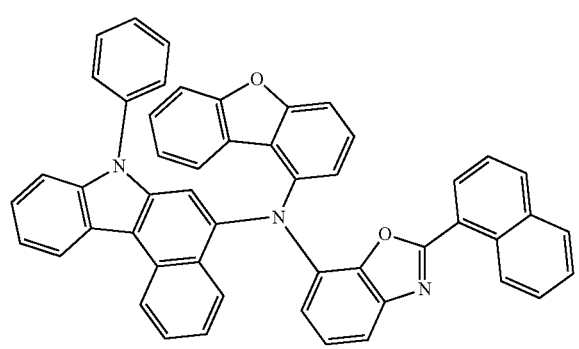
90
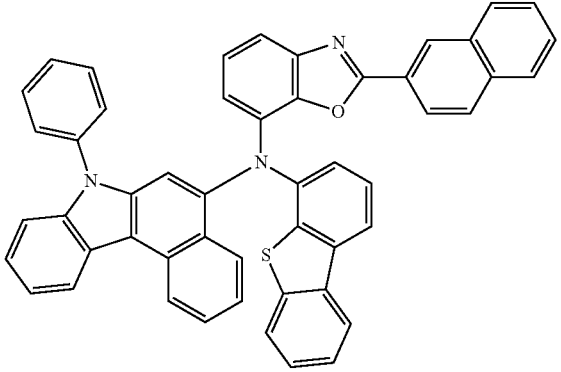
91
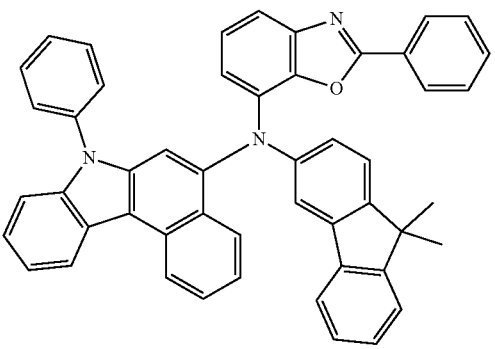
92
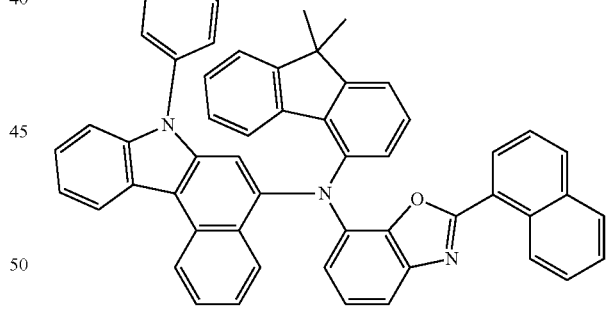
93
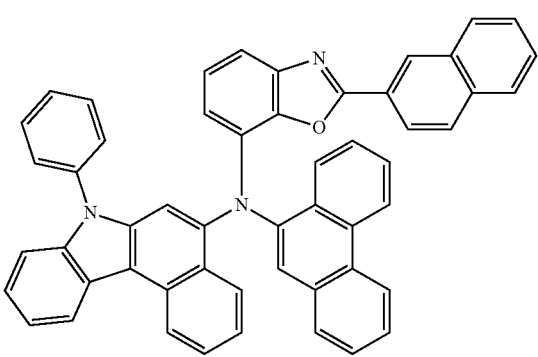

95
-continued
94
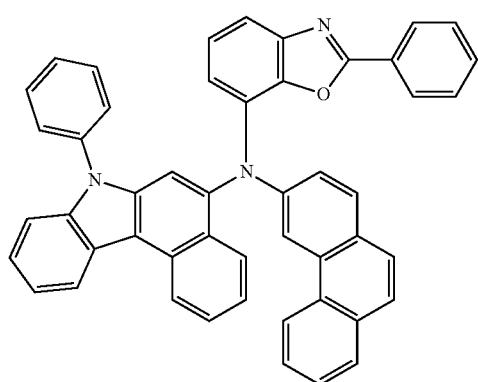
95
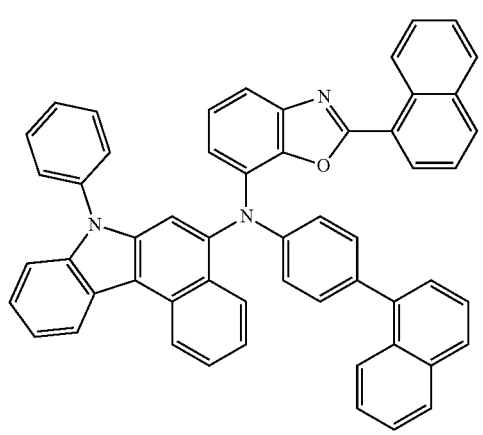
96
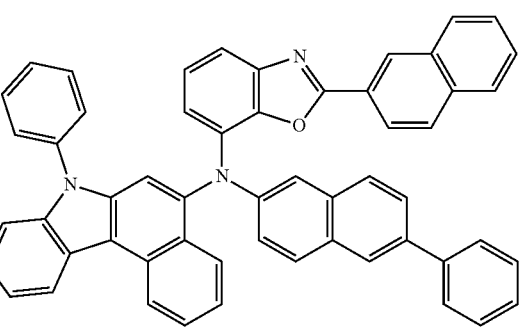
96
-continued
98
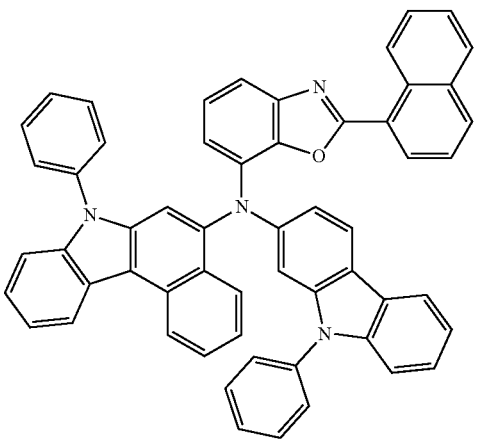
99
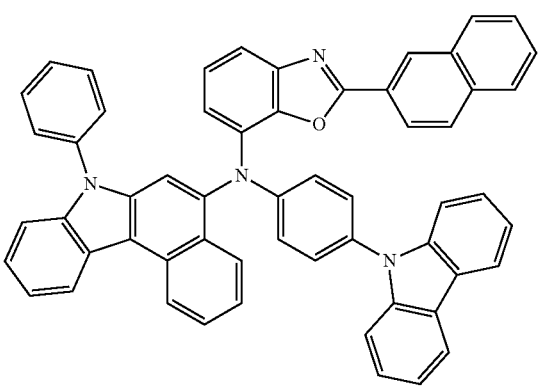
100
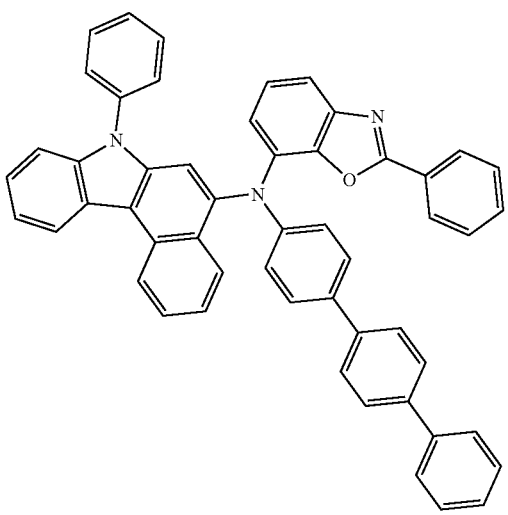
97
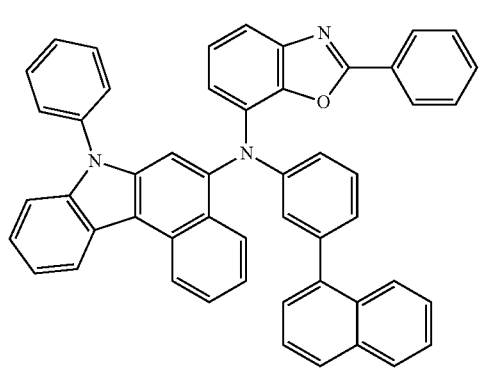

101 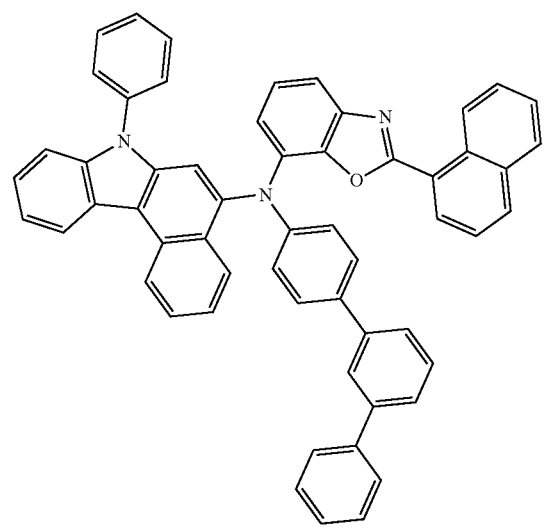
102 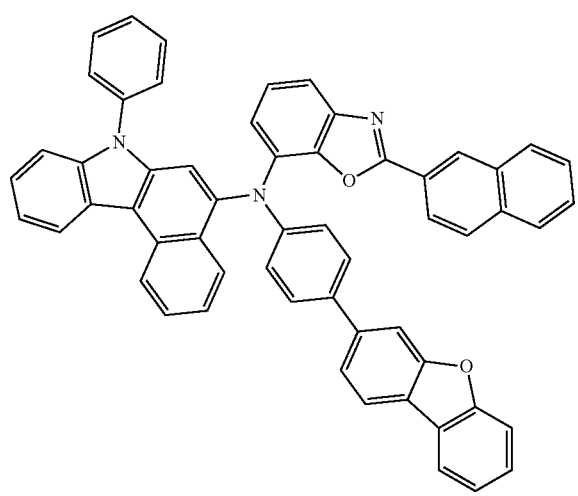
103 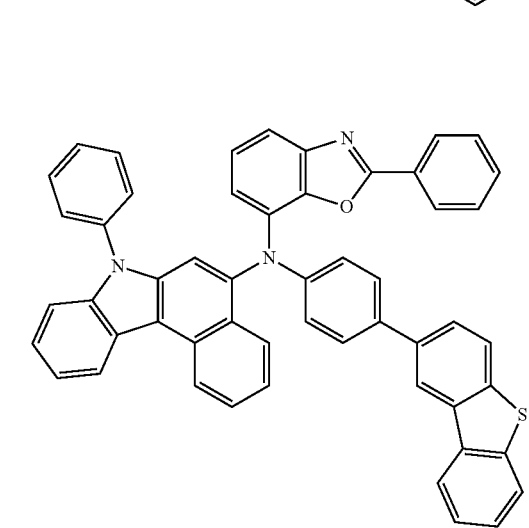
104 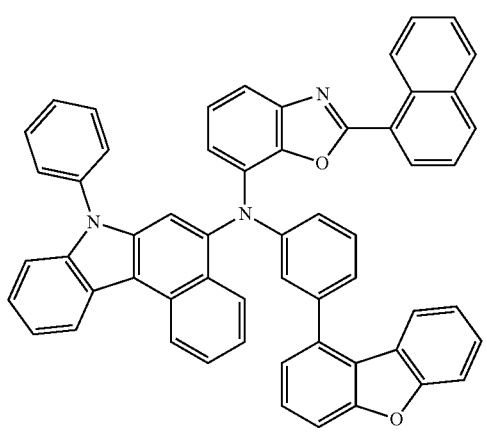
105 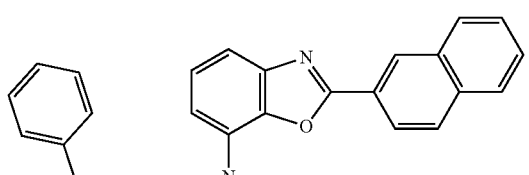
106 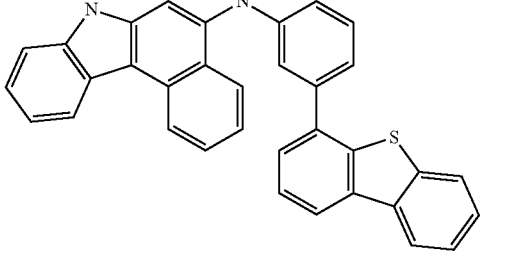
107 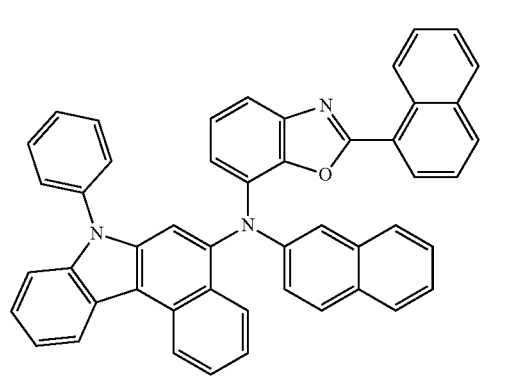

-continued
108
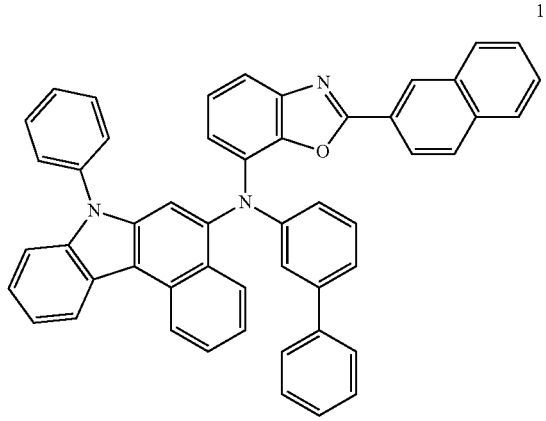
109
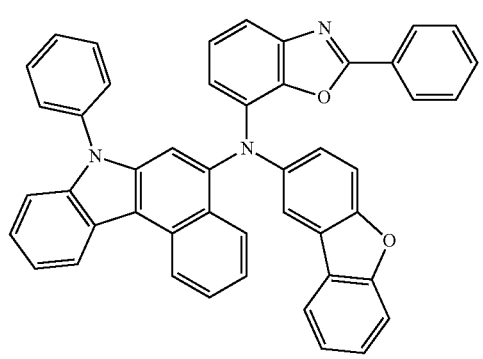
110
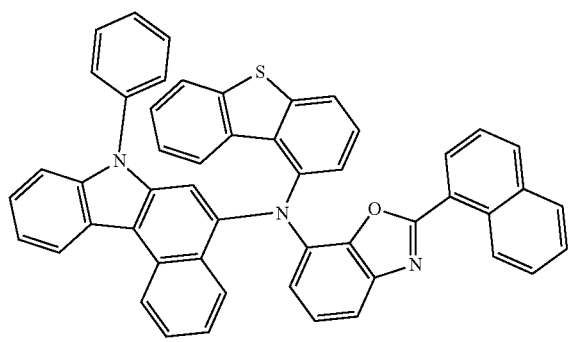
111
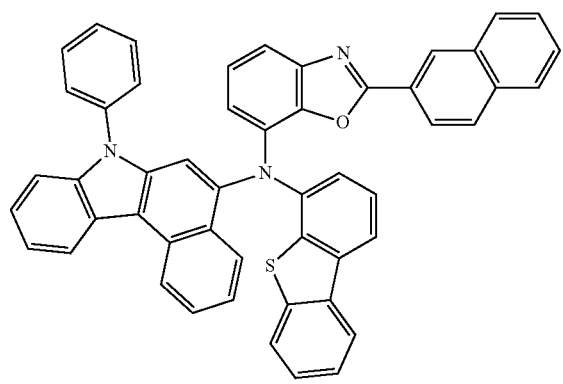
-continued
112
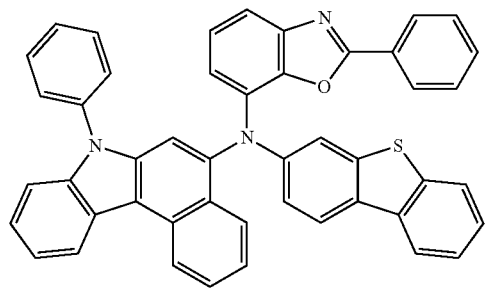
113
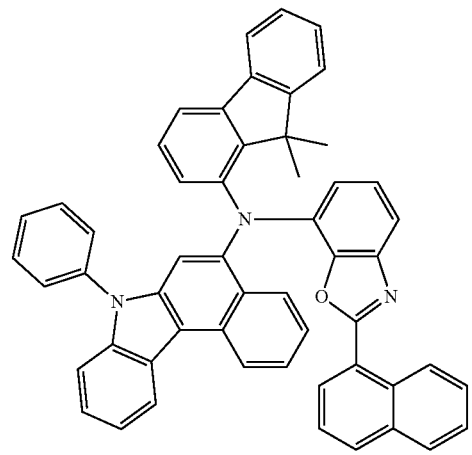
114
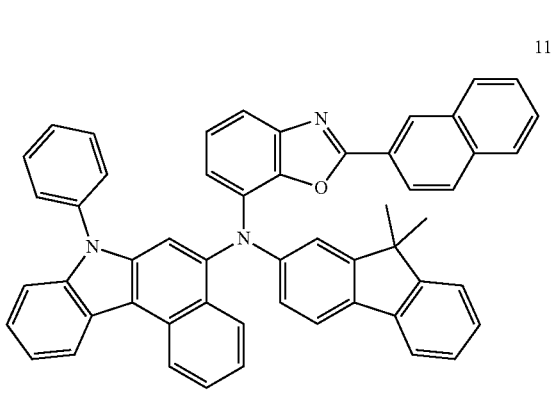
115
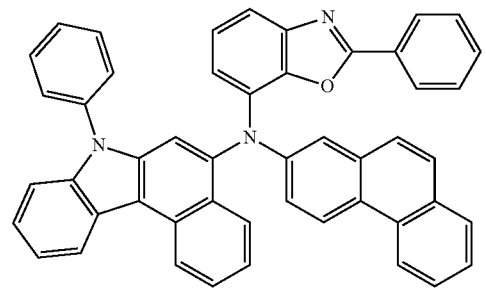

-continued
116
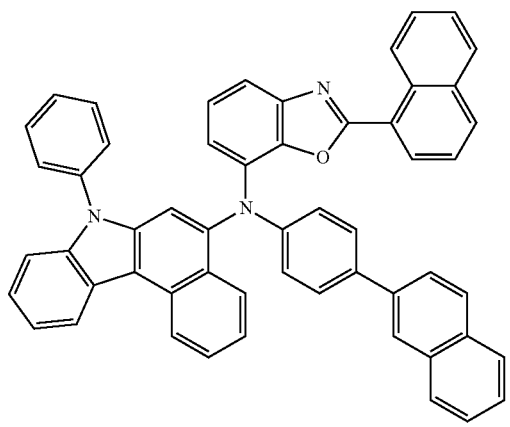
117
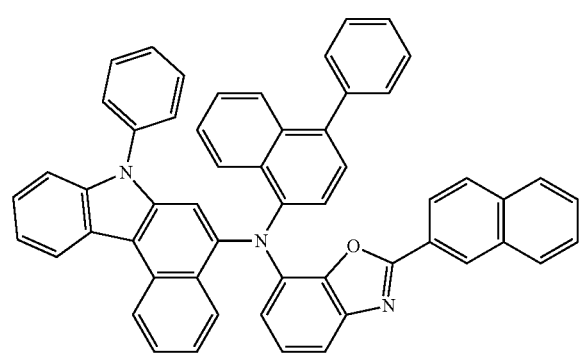
118
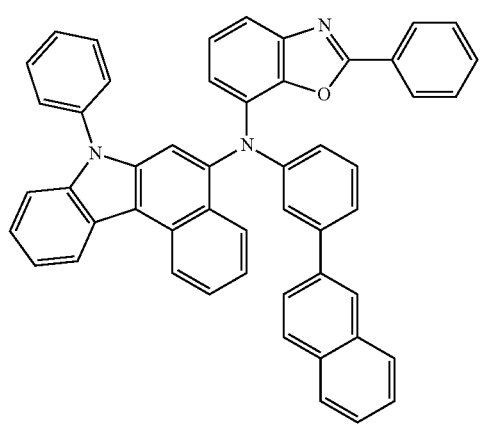
-continued
119
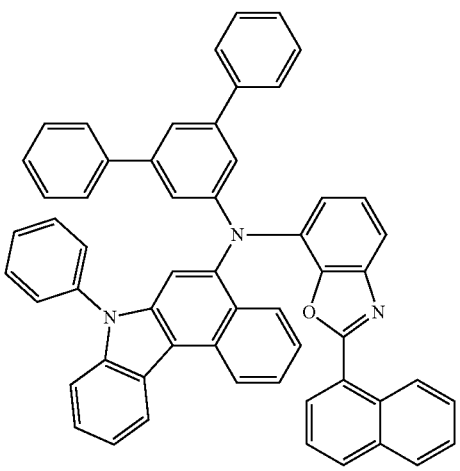
120
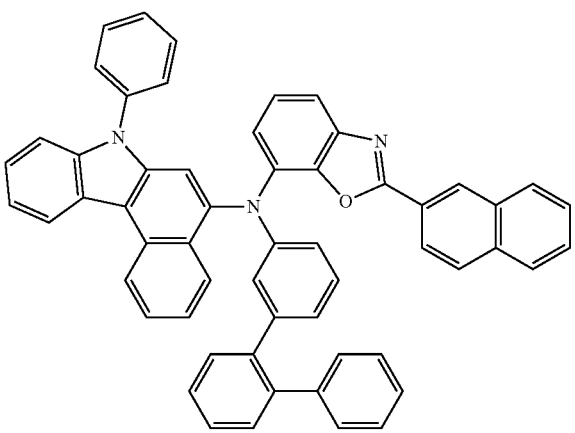
121
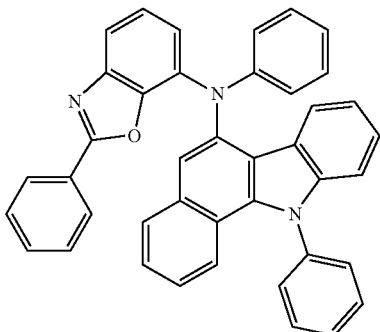
122
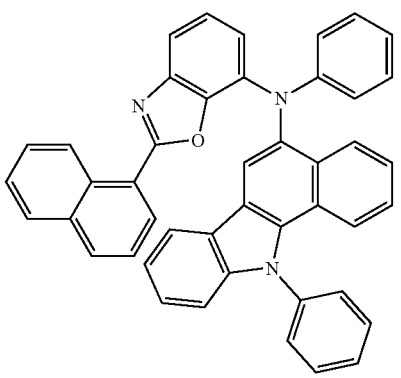

123
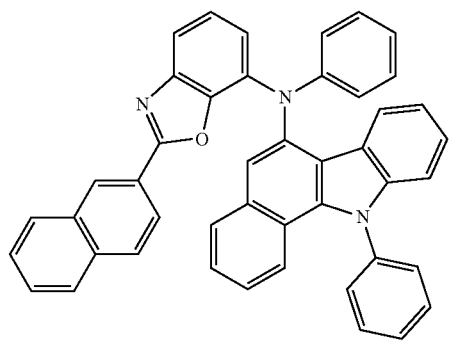
124
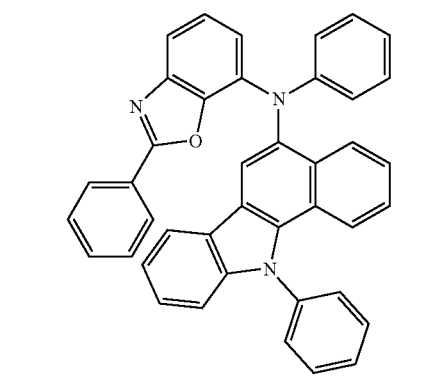
125
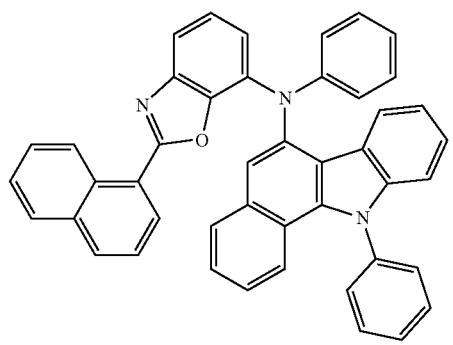
126
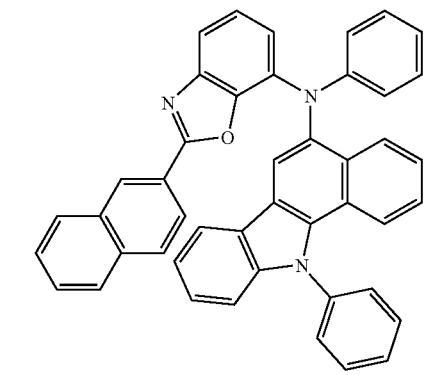
127
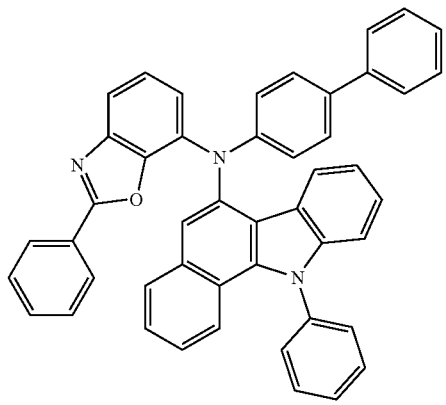
128
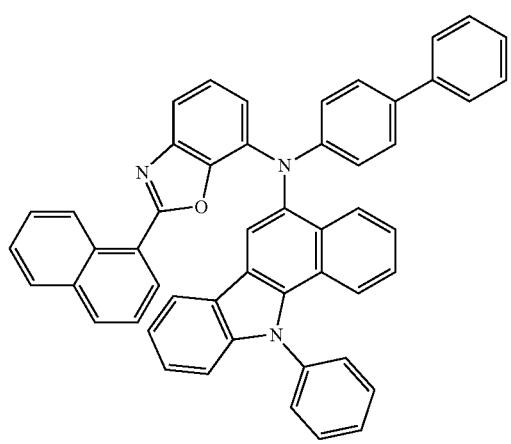
129
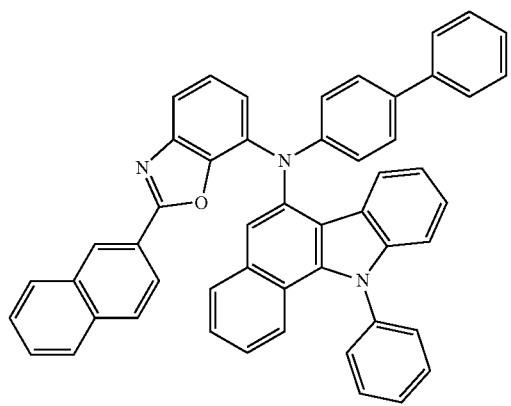

130
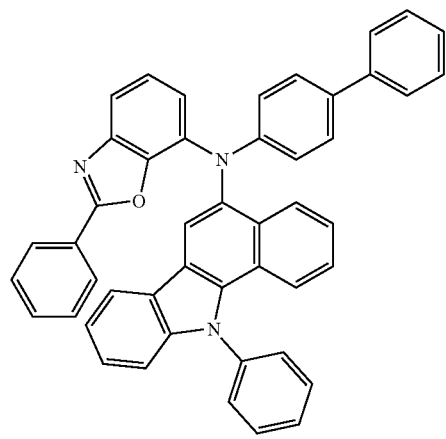
131
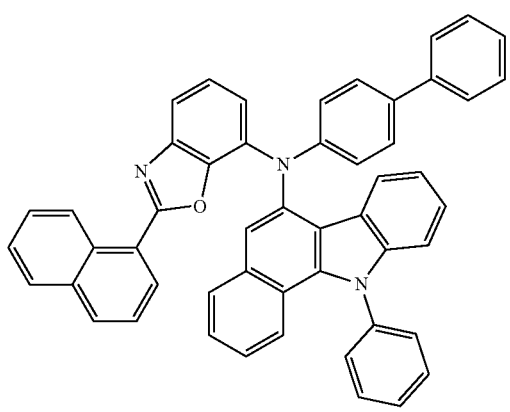
132
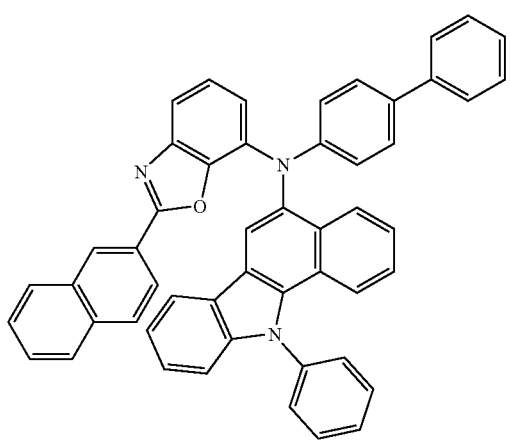
133
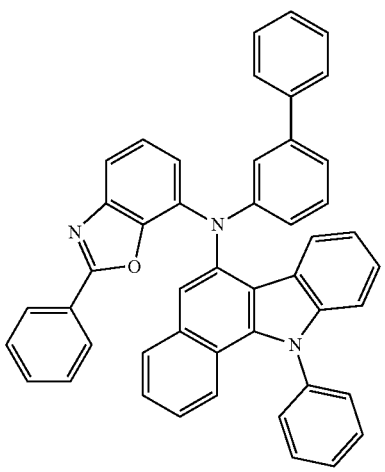
134
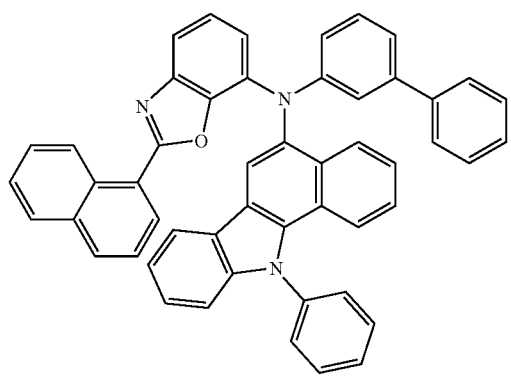
135
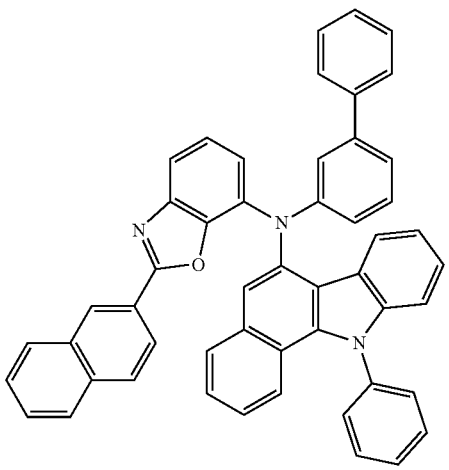

107
-continued
136
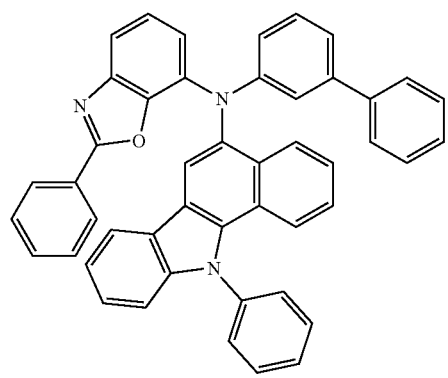
137
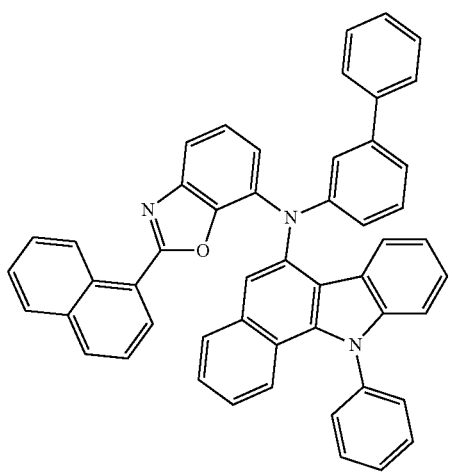
138
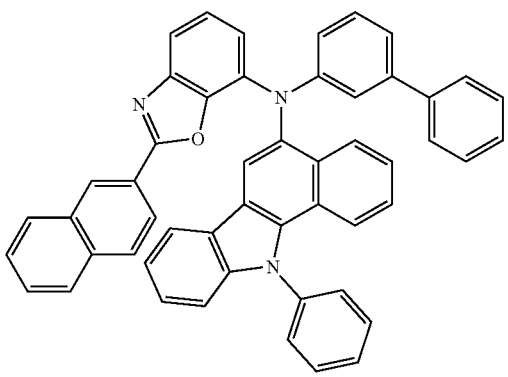
139
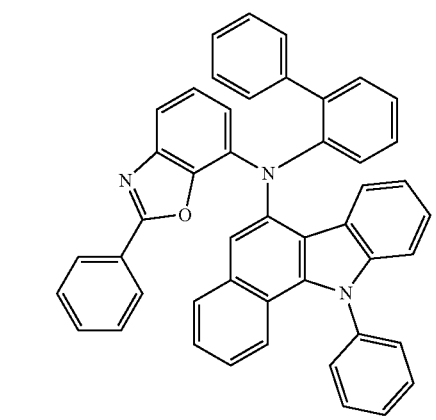
108
-continued
140
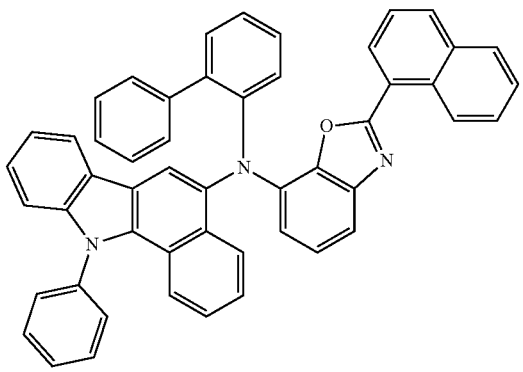
141
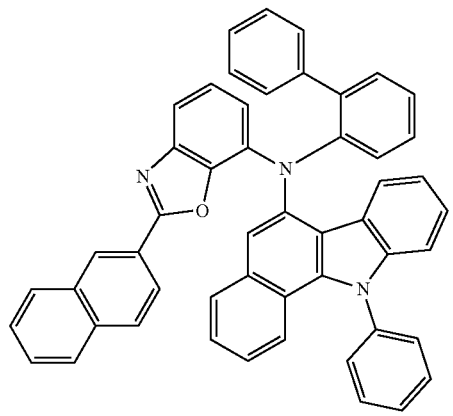
142
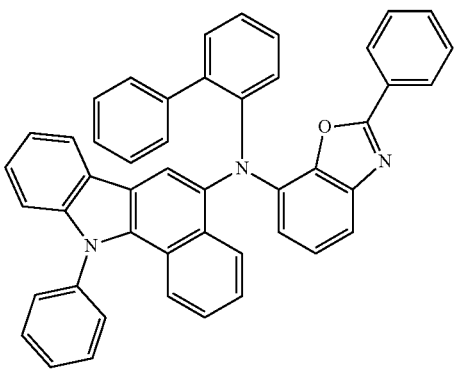
143
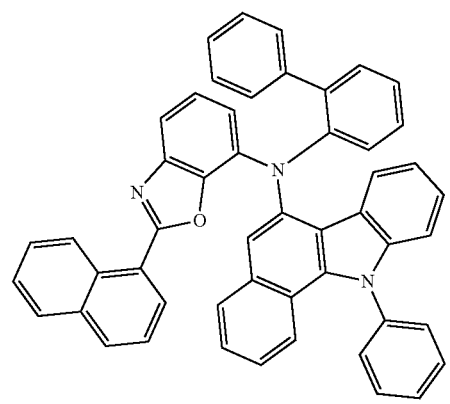

144
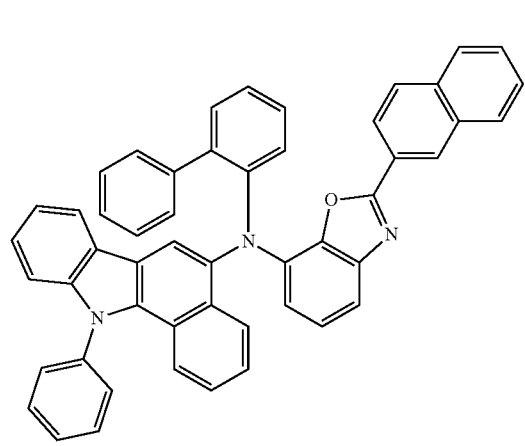
145
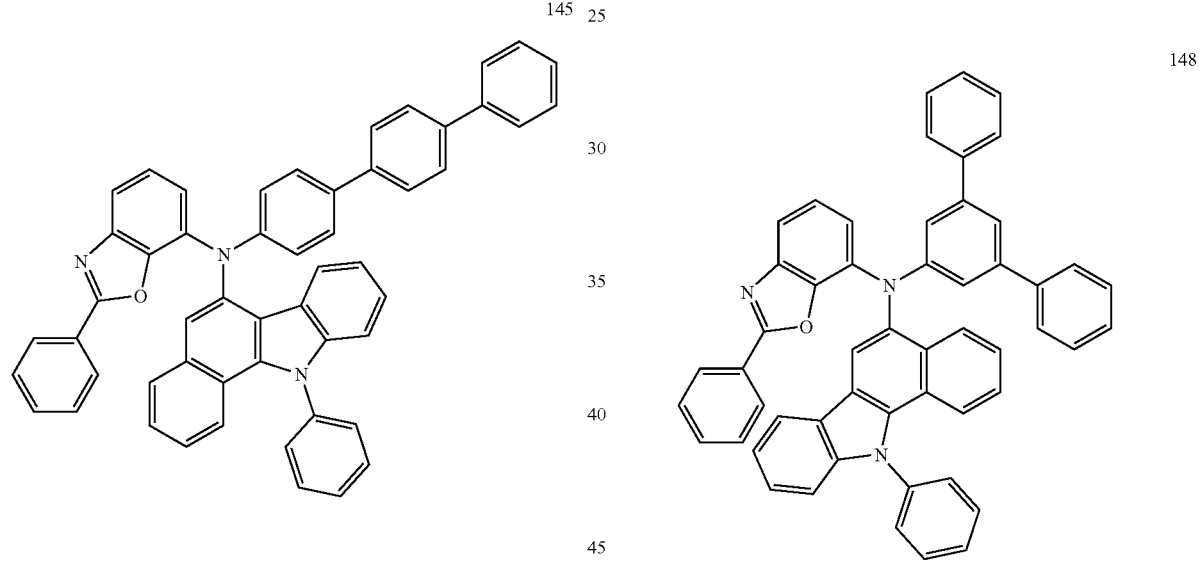
146
147
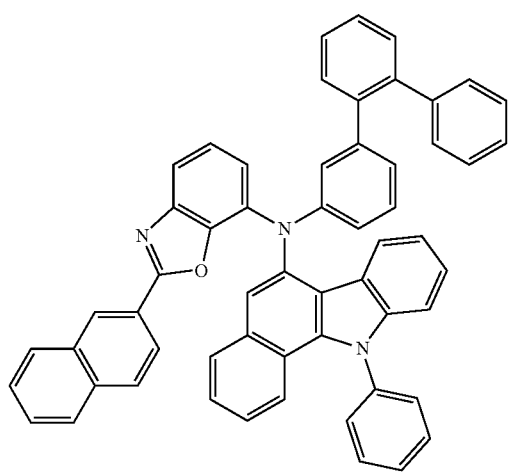
148
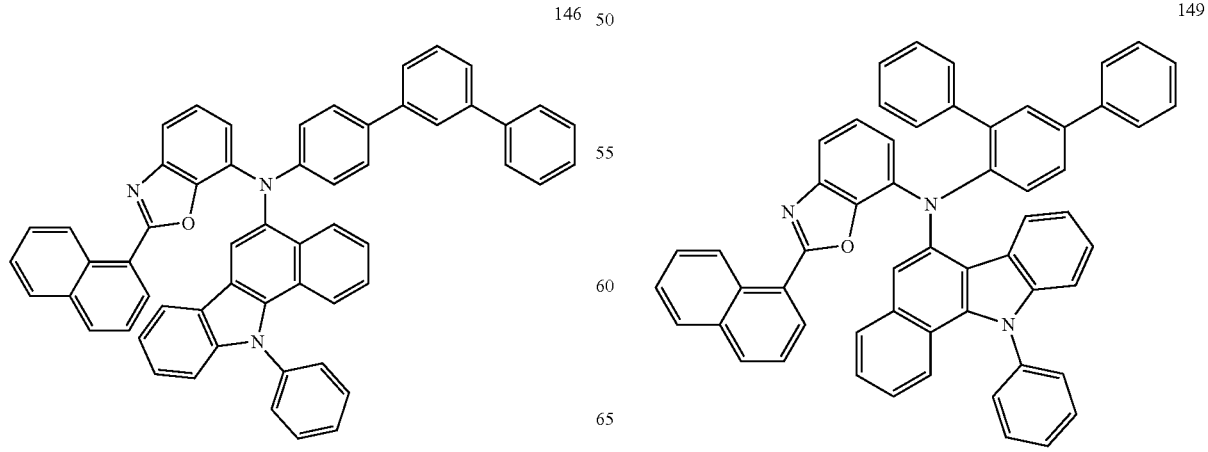
149

150
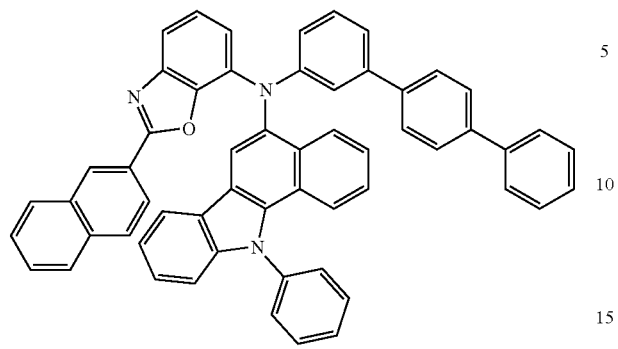
151
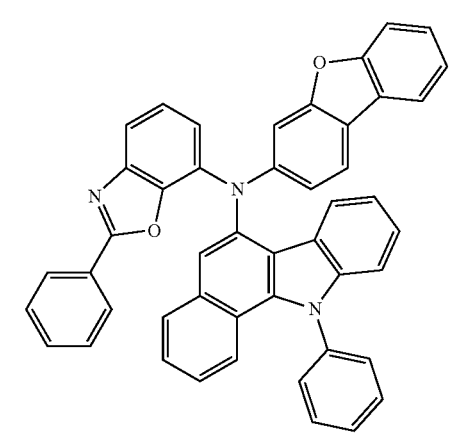
152
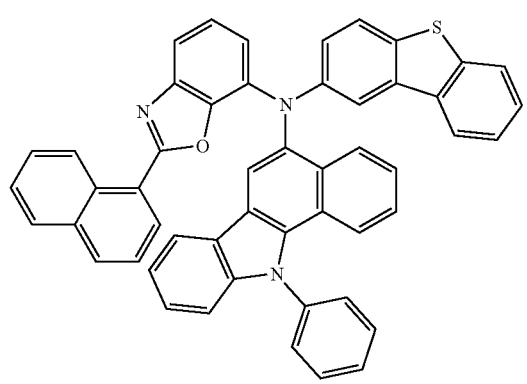
153
154
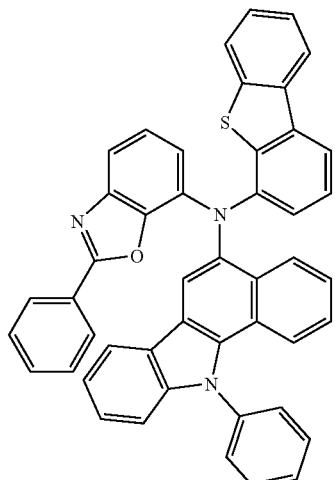
155
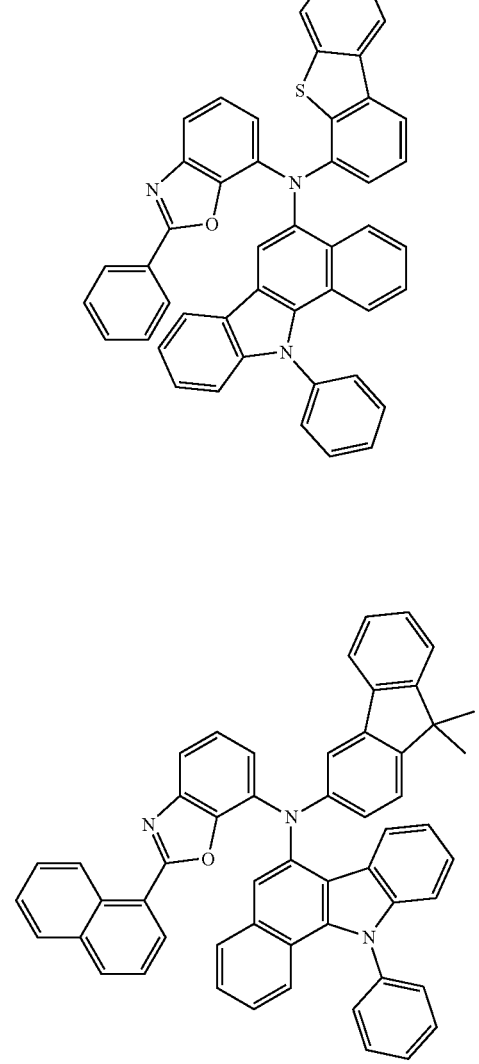
156
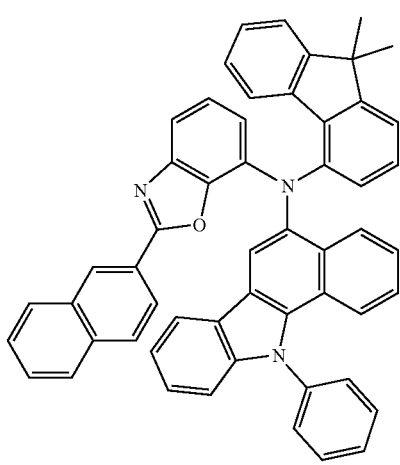

157
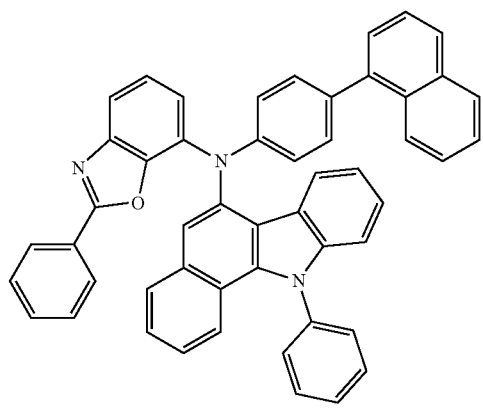
158
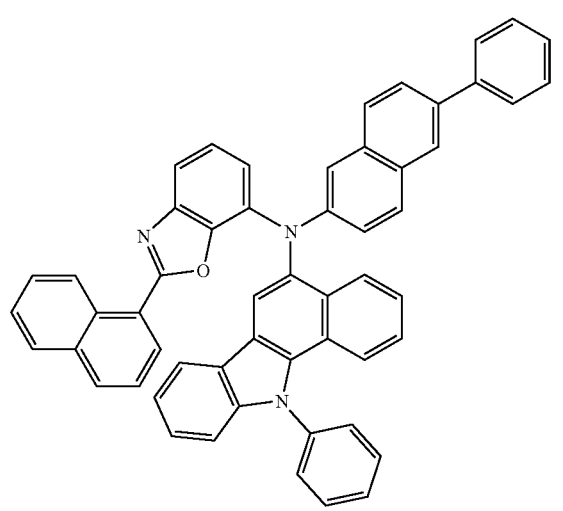
159
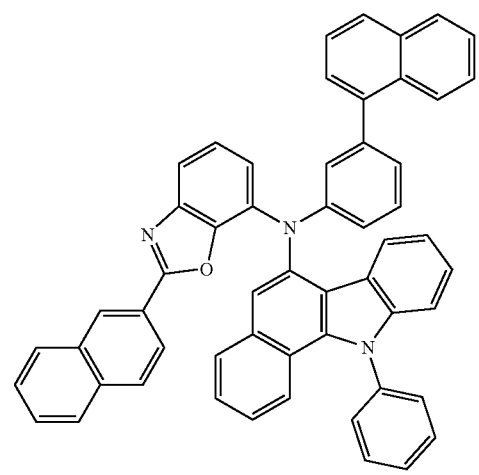
160
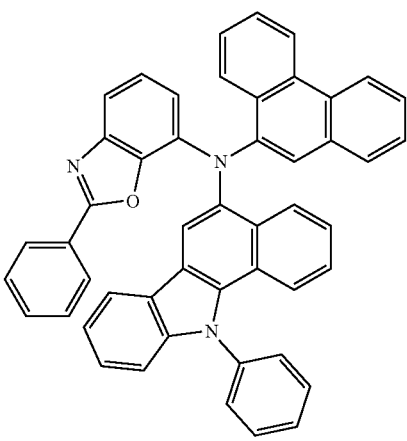
161
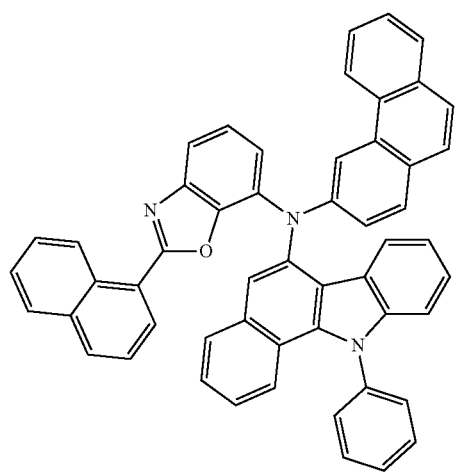
162
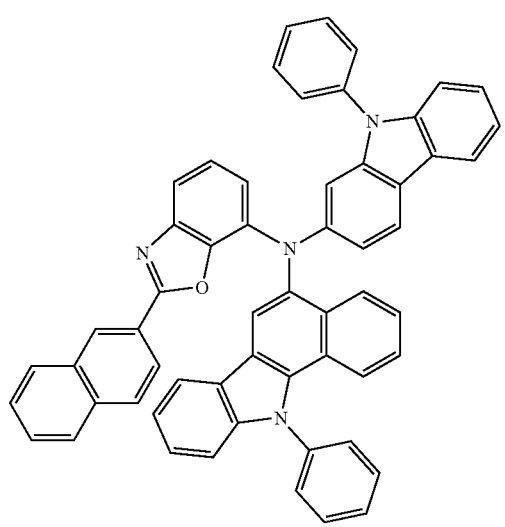

163
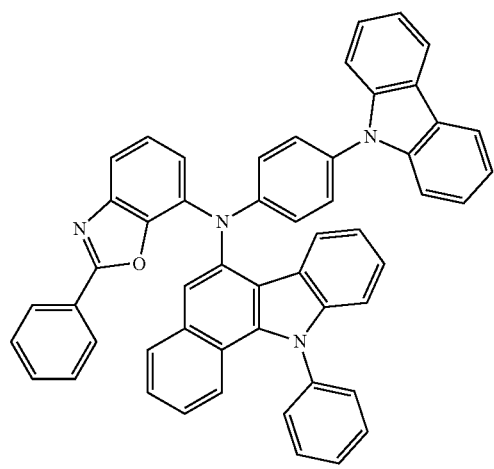
164
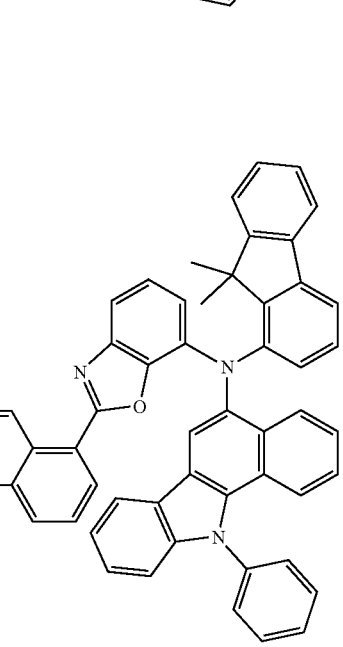
165
166
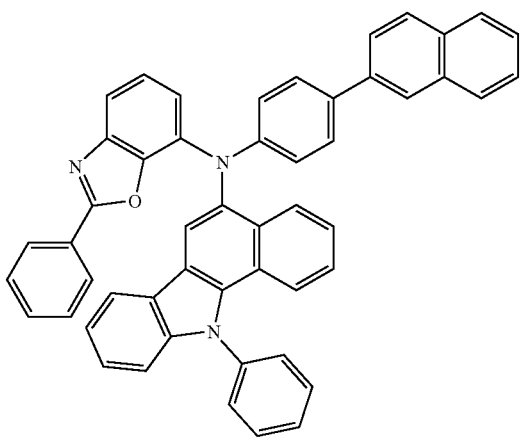
167
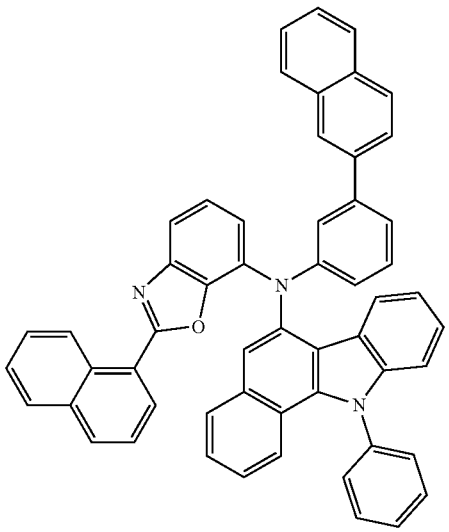
168
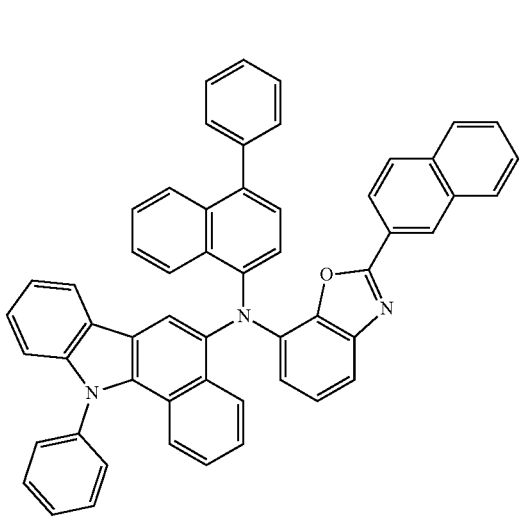

169
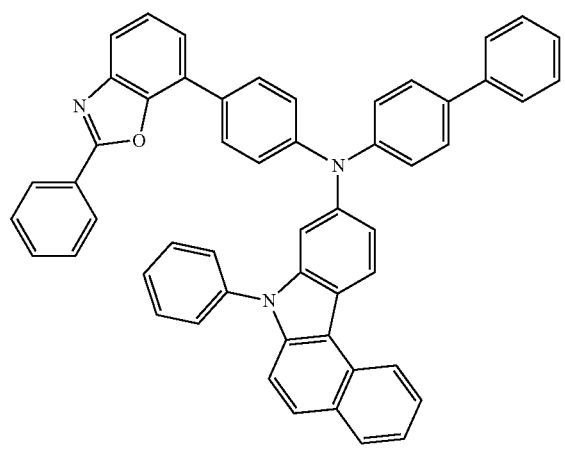
172
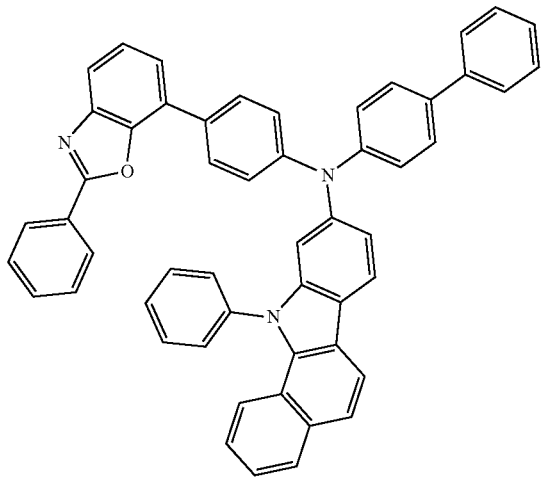
170
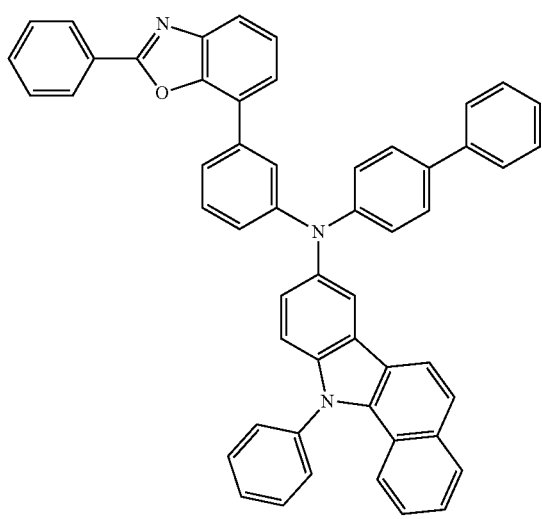
173
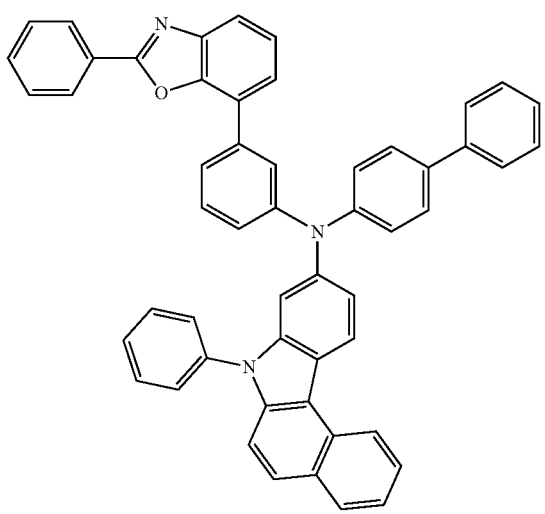
171
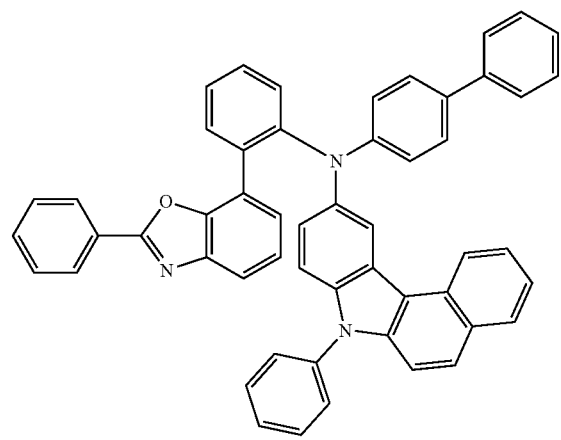
174
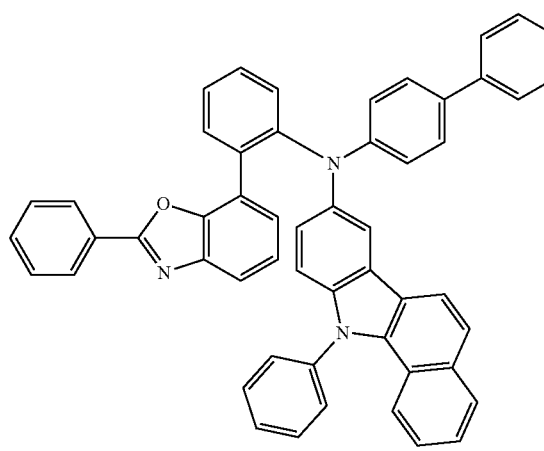

-continued
175
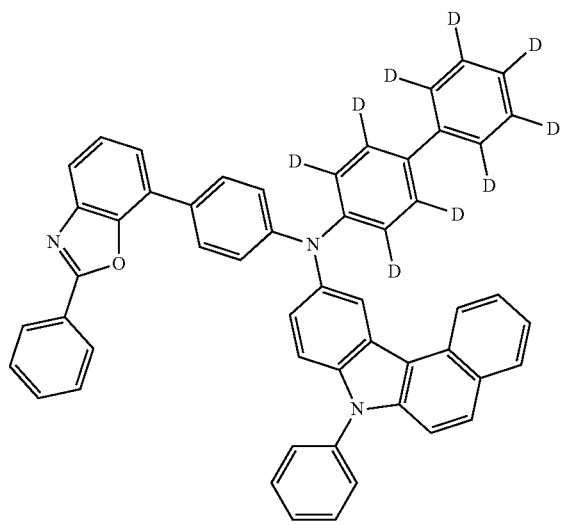
176
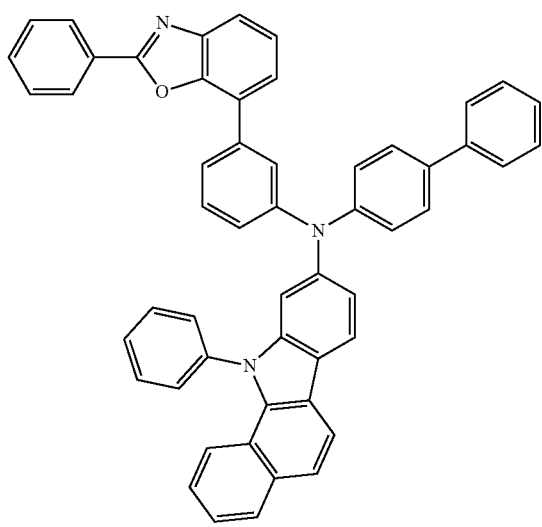
177
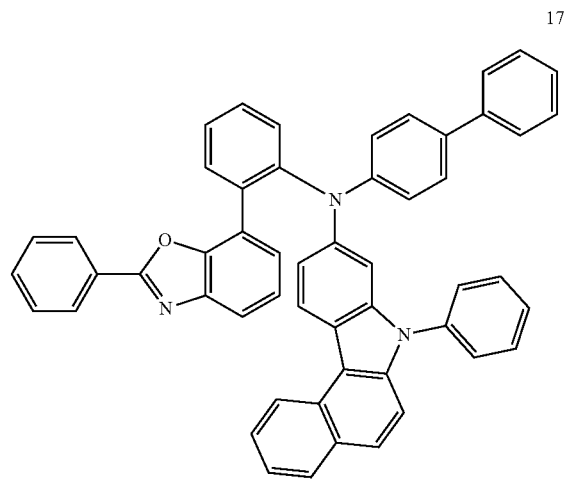
-continued
178
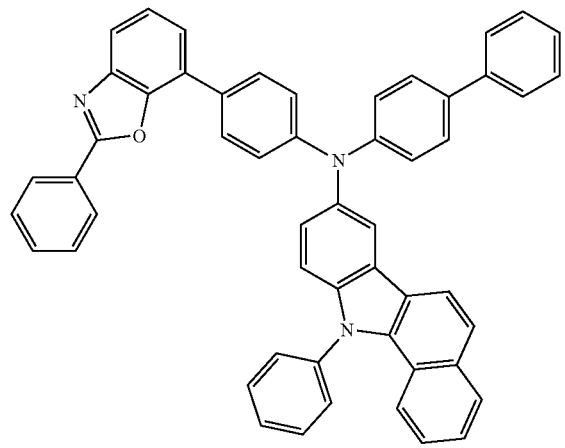
179
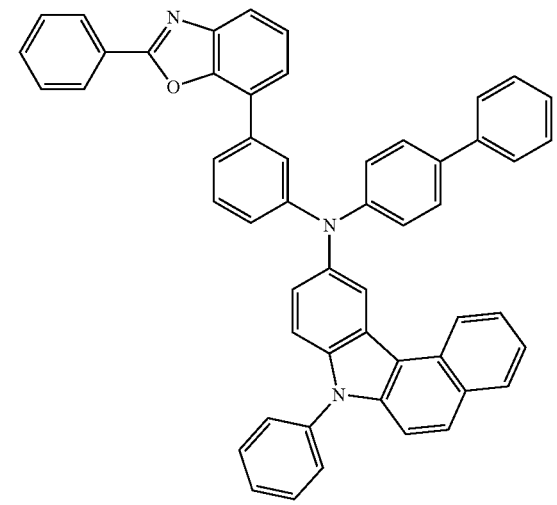
180
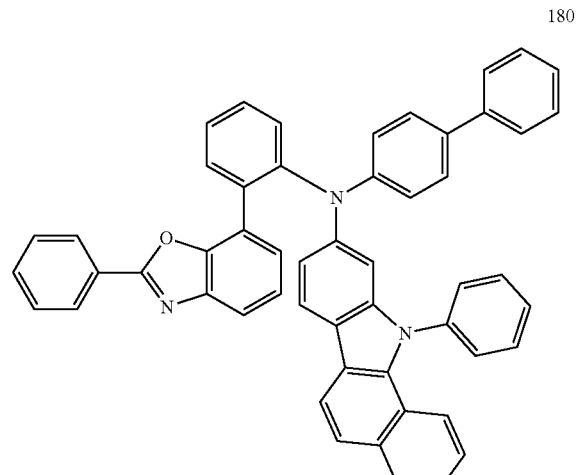

181
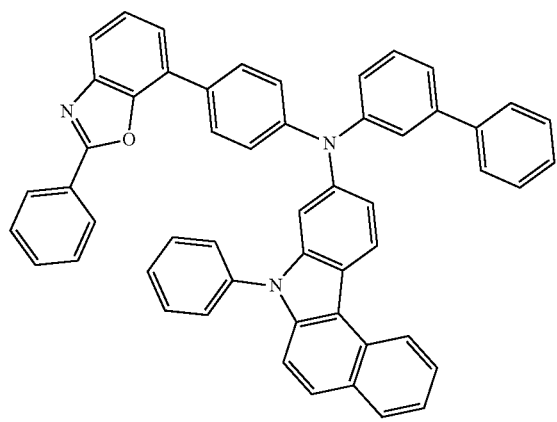
184
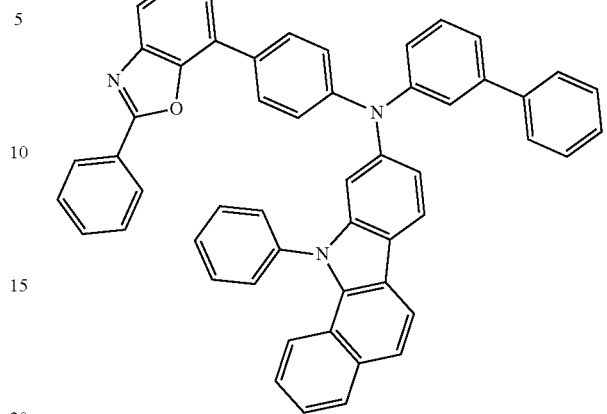
182
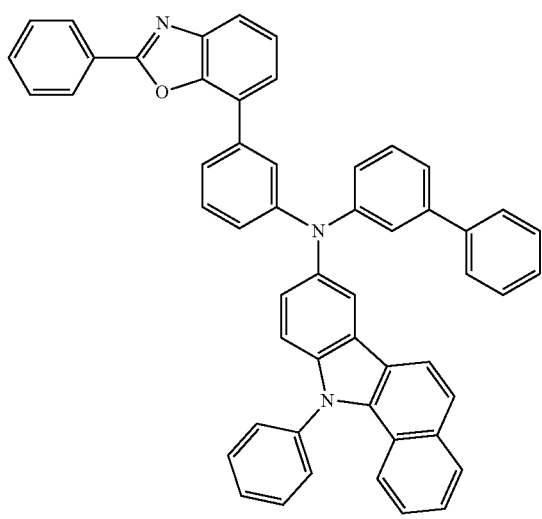
185
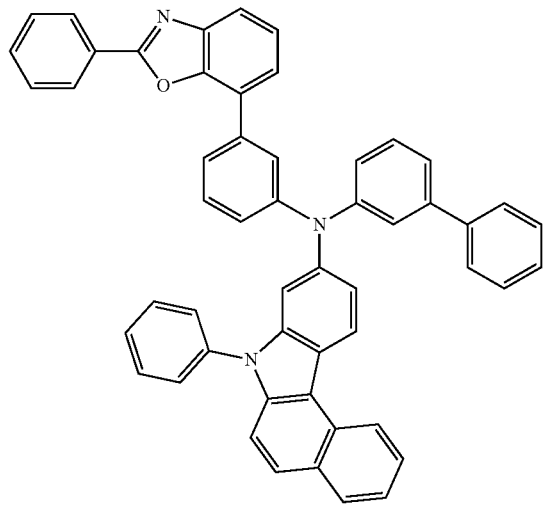
183
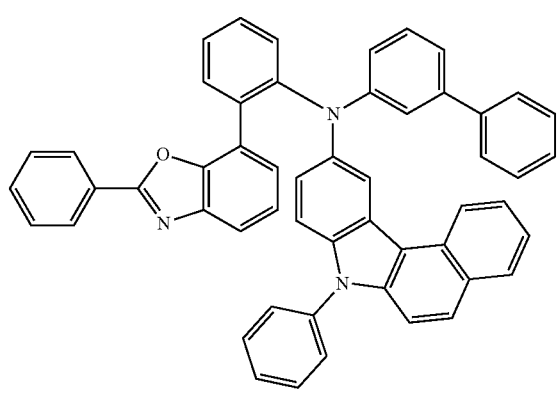
186
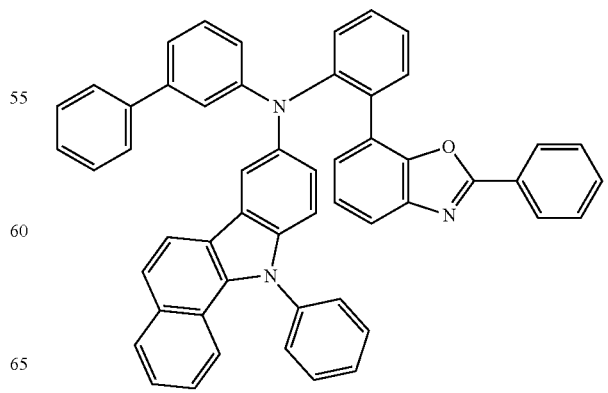

187
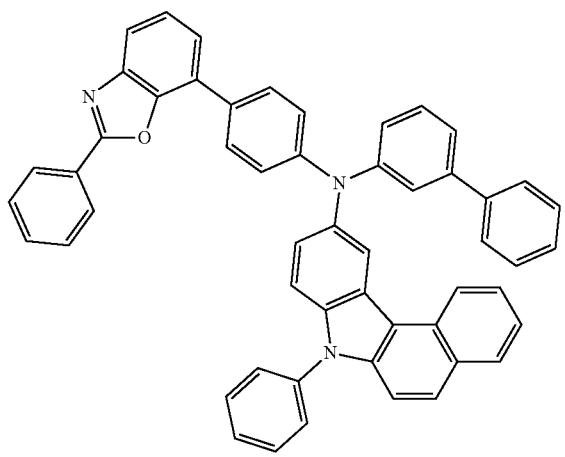
188
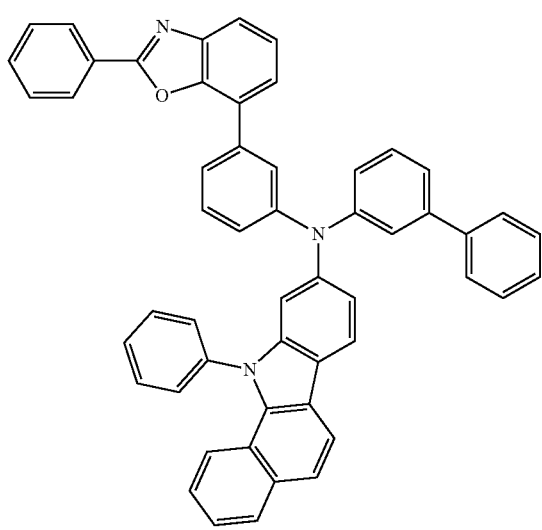
189
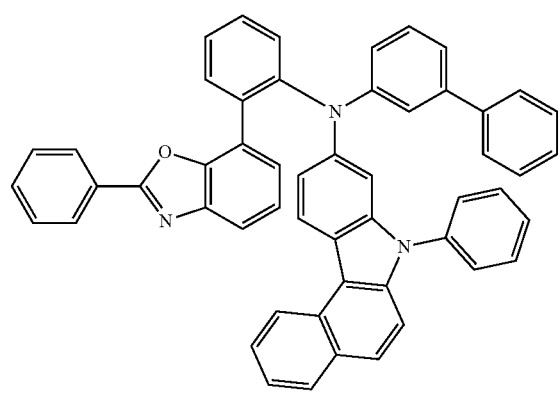
190
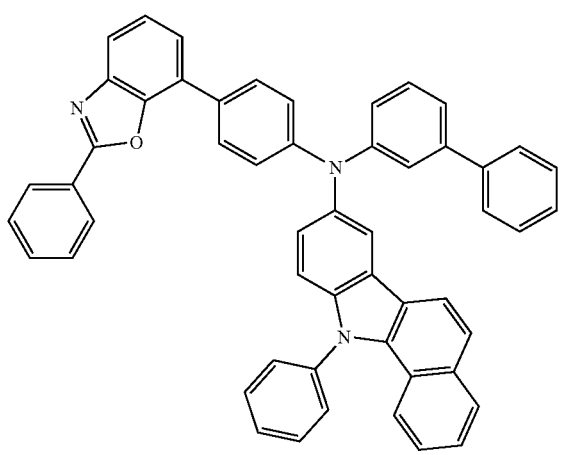
191
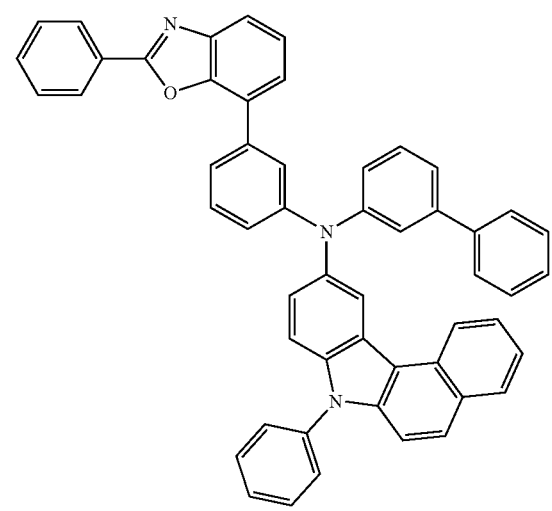
192
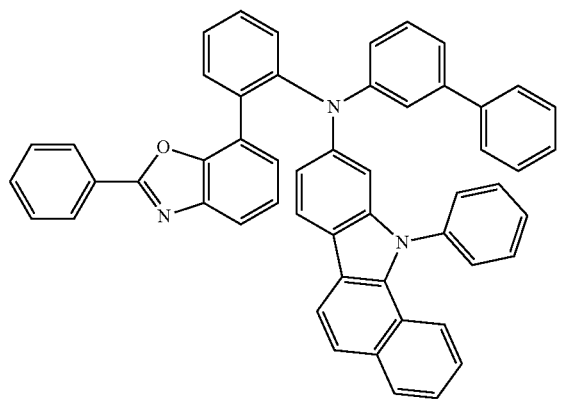

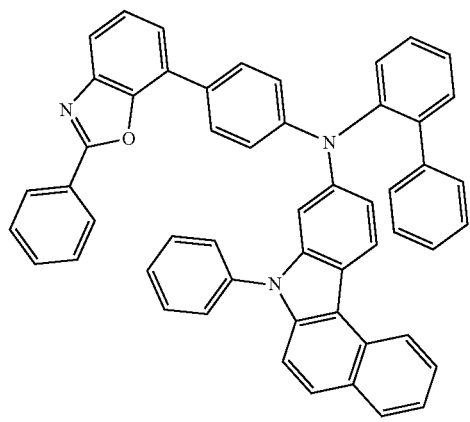
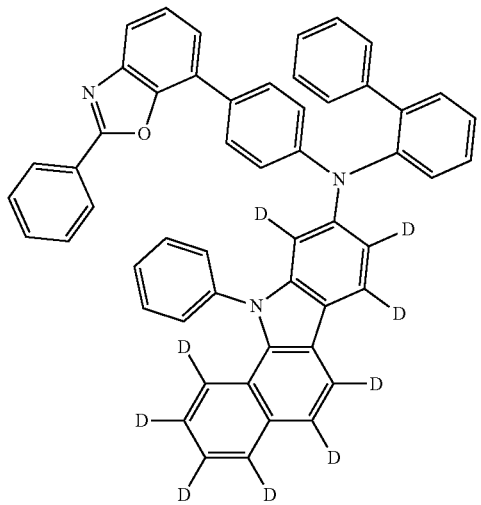
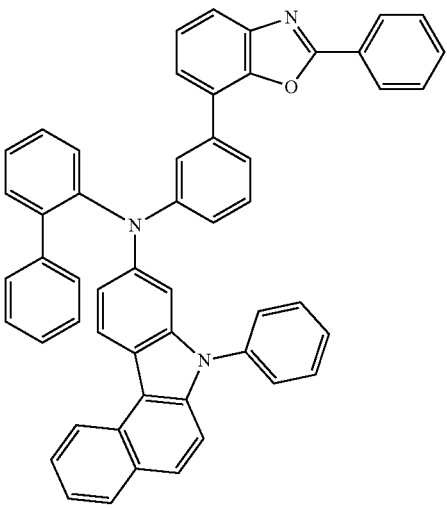
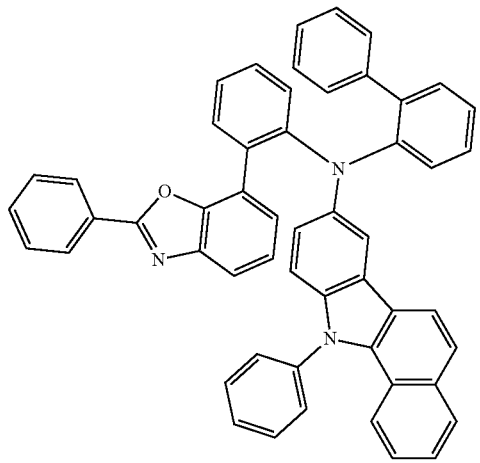

-continued
199
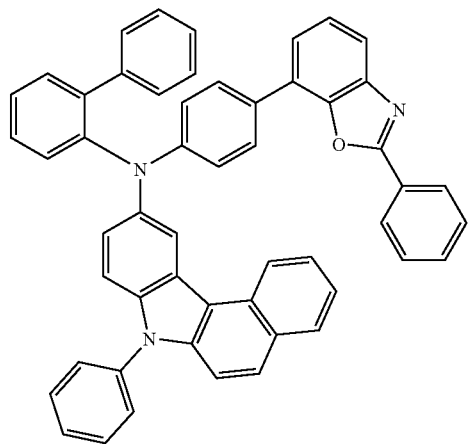
200
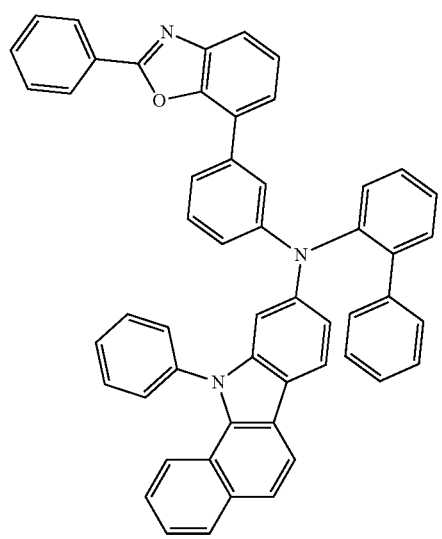
201
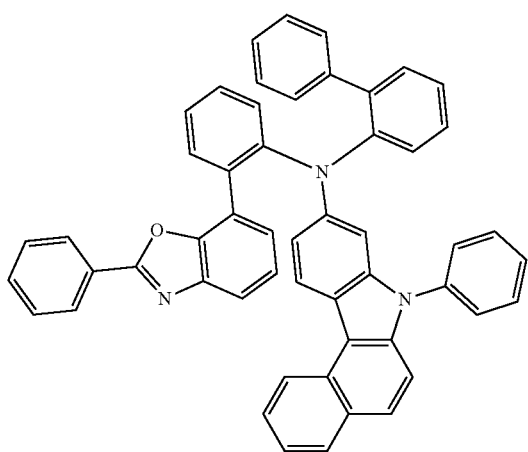
-continued
202
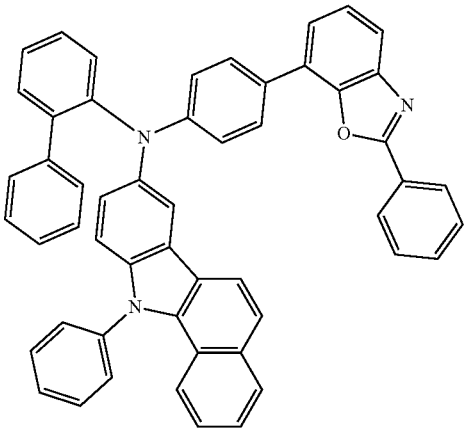
203
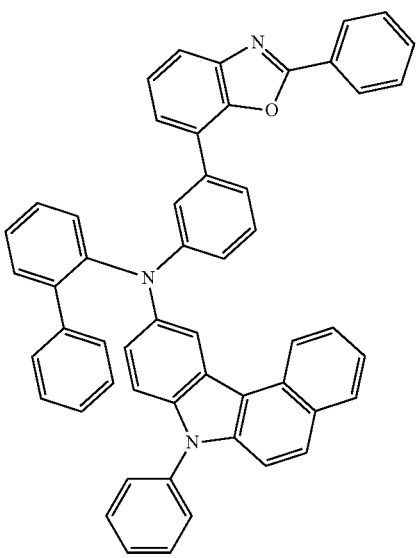
204
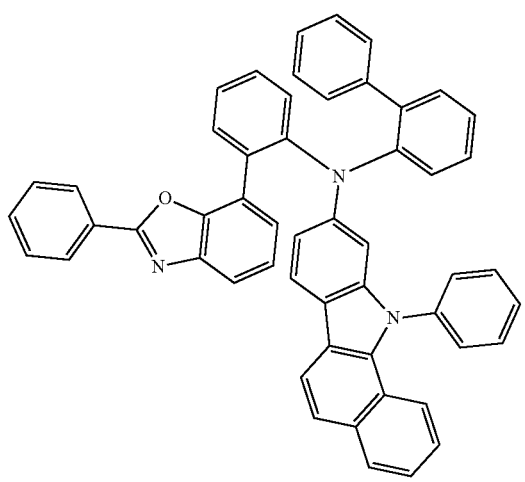

205
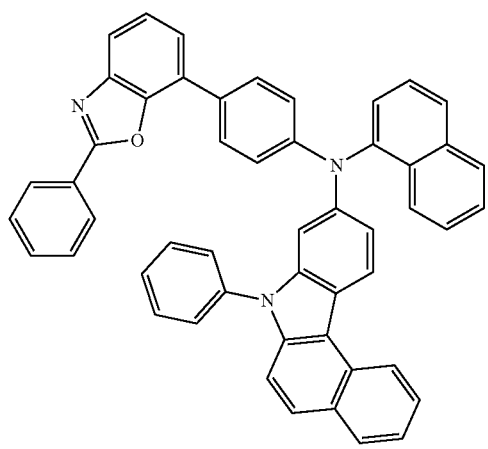
206
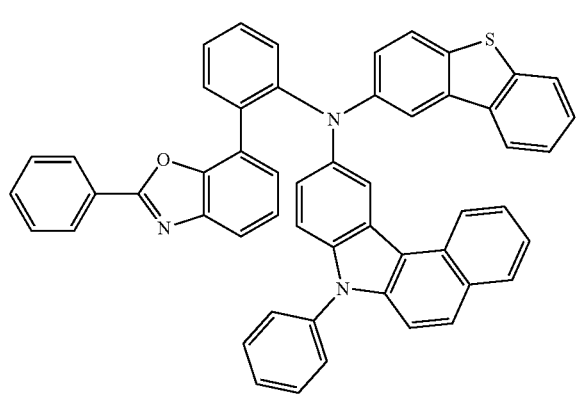
208
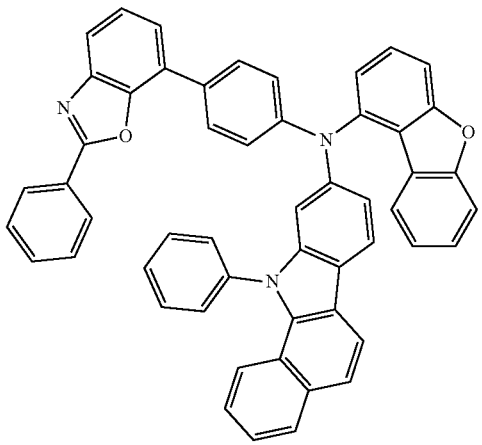
209
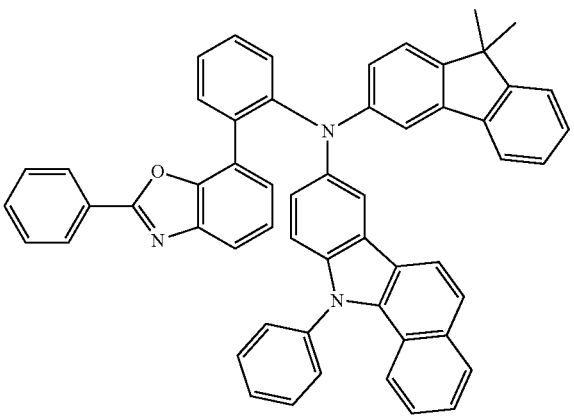
207
210

-continued
211
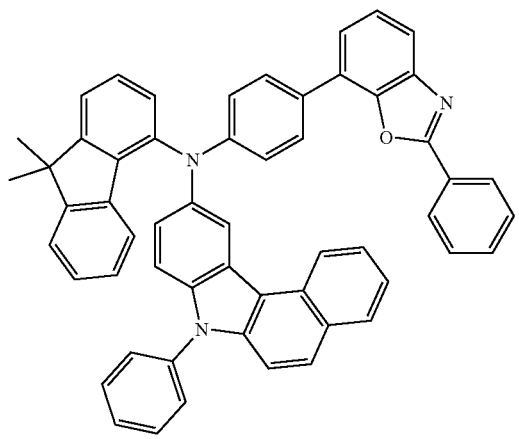
212
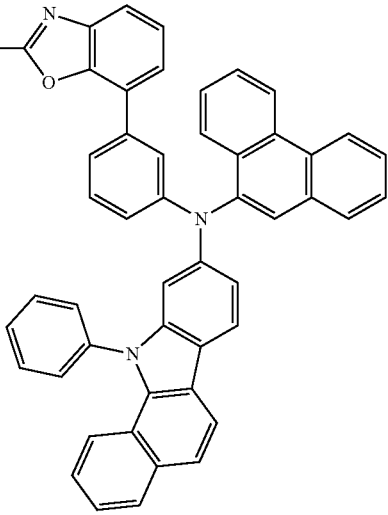
213
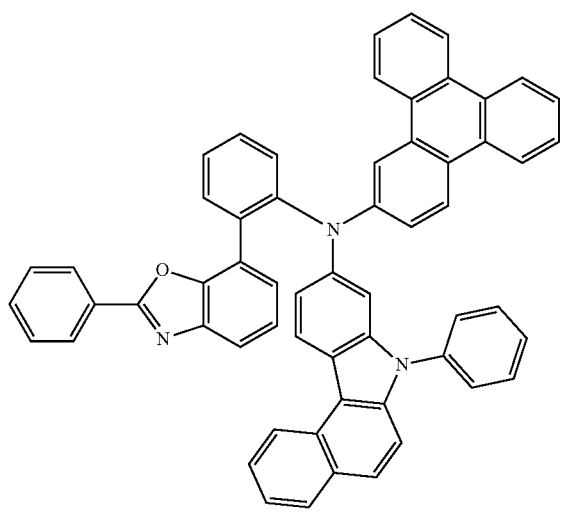
214
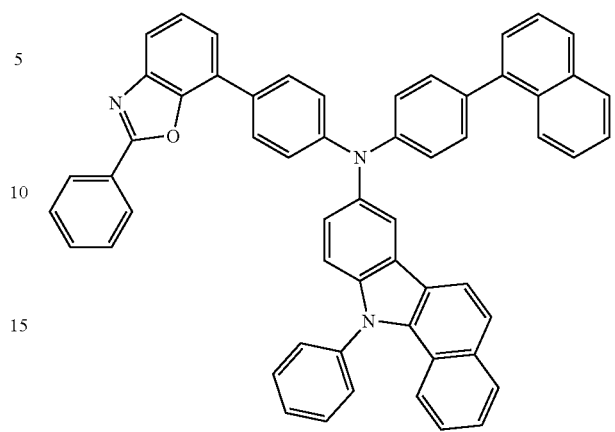
215
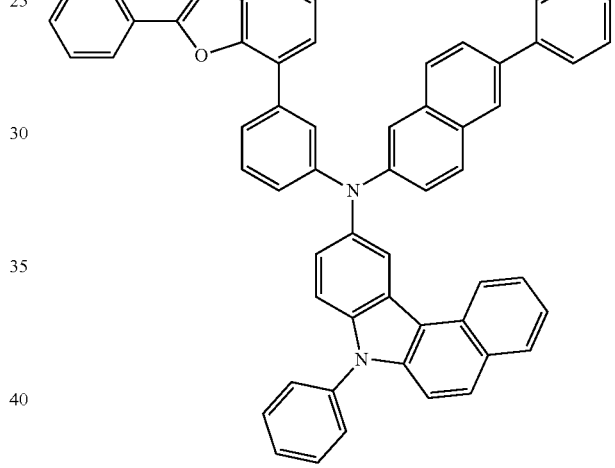
216
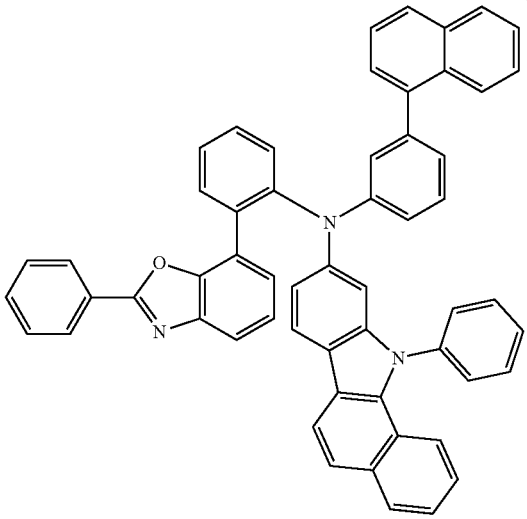

217
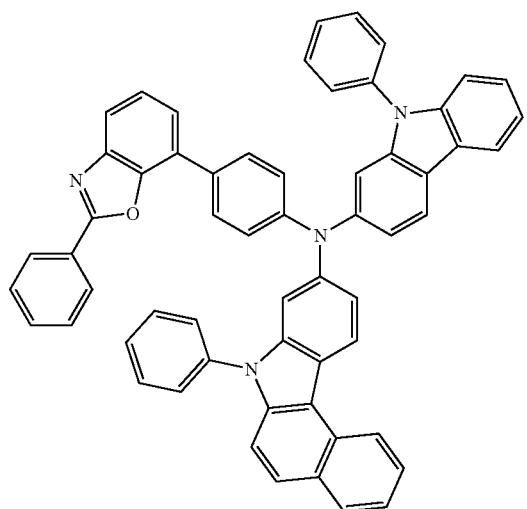
218
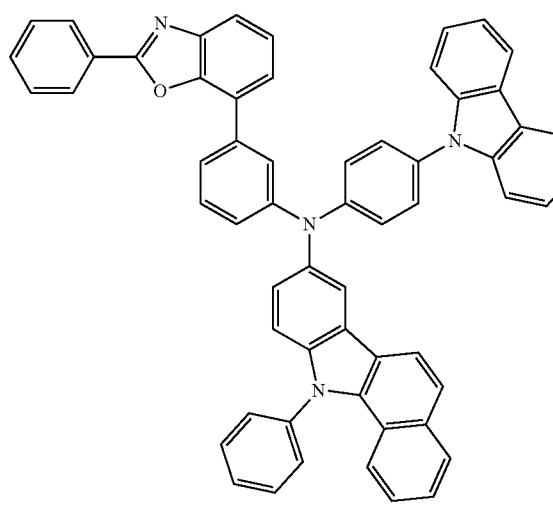
219
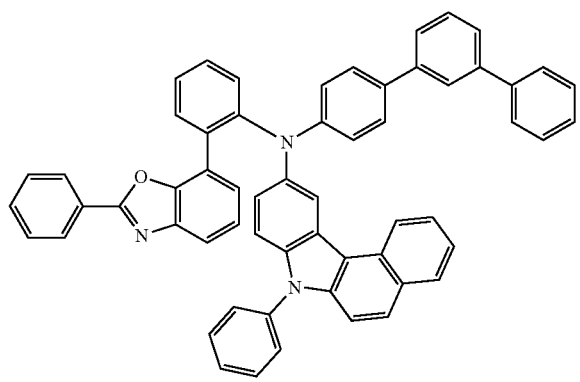
220
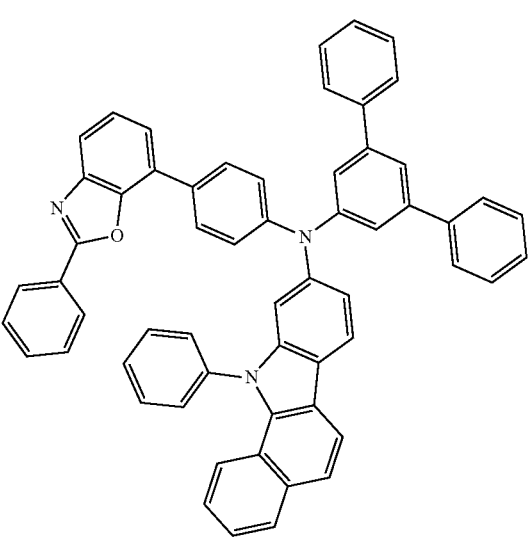
221
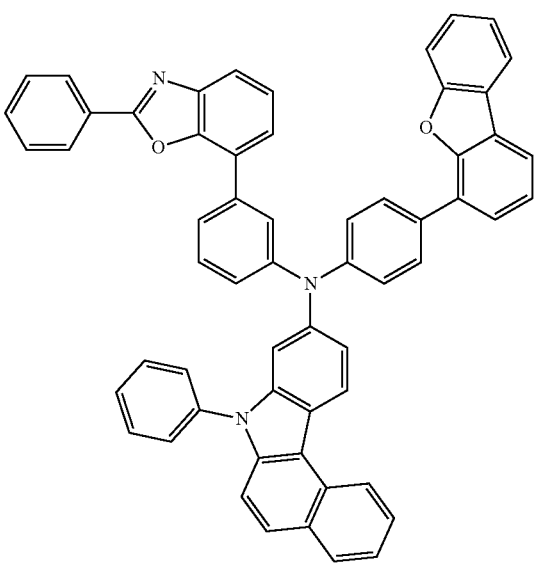

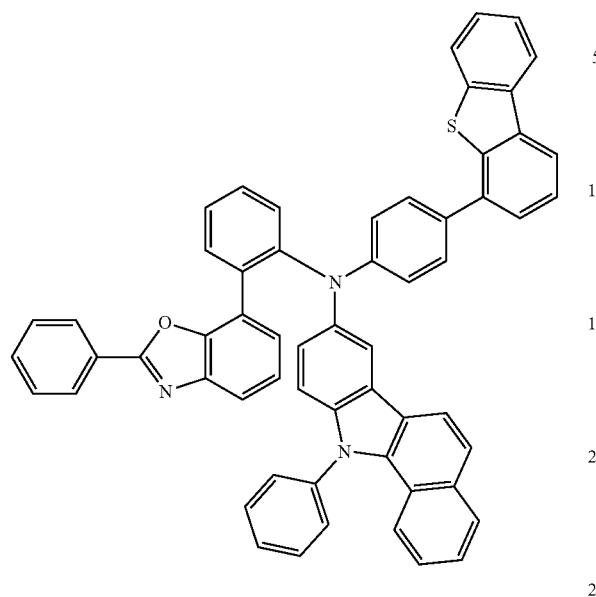
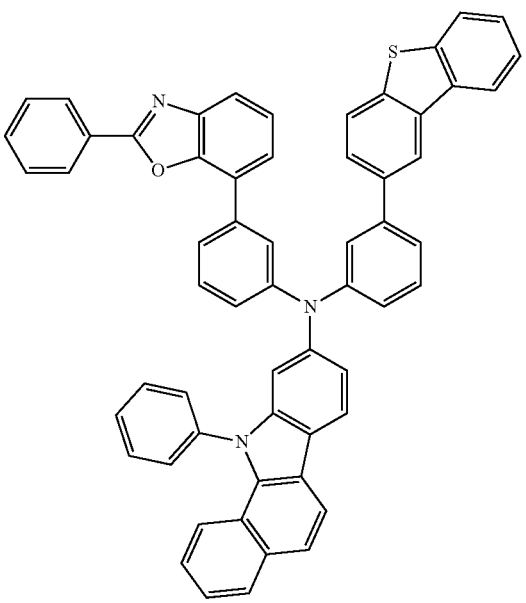
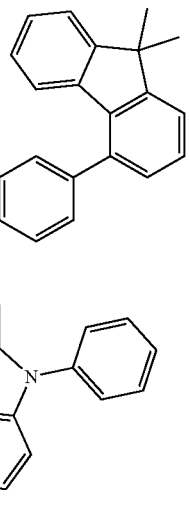
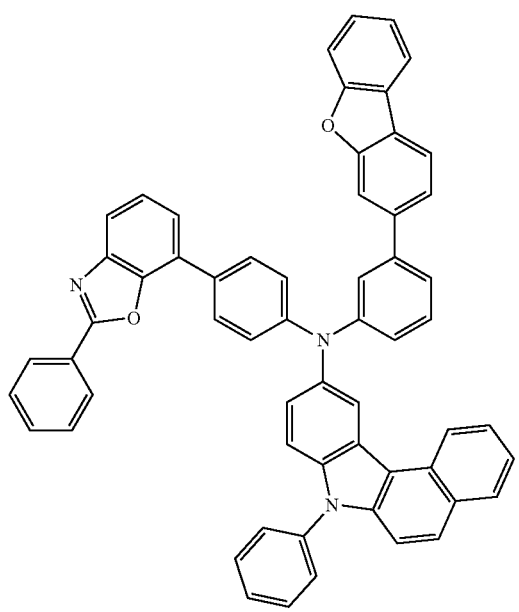
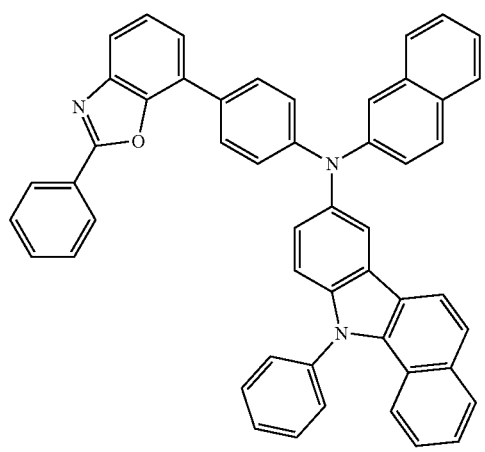

137
-continued
227
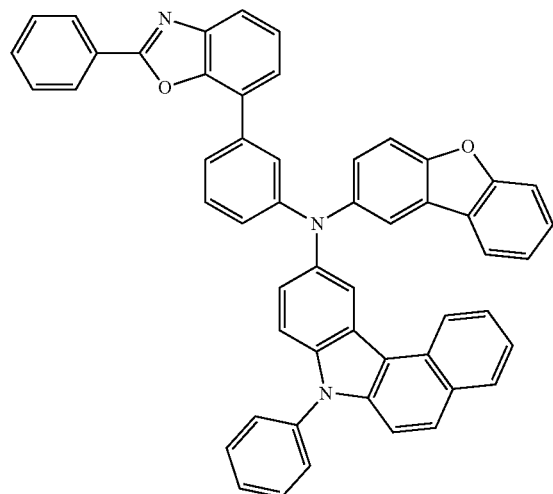
228
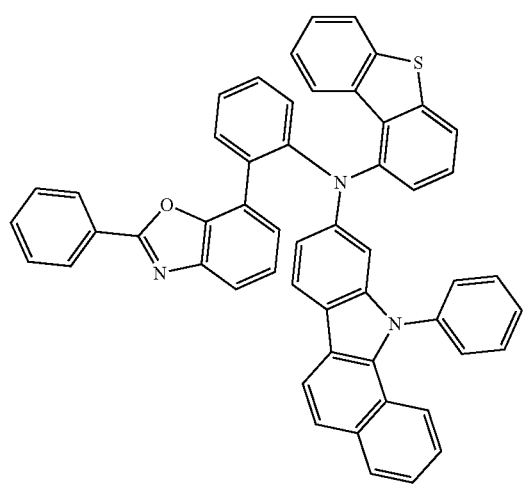
229
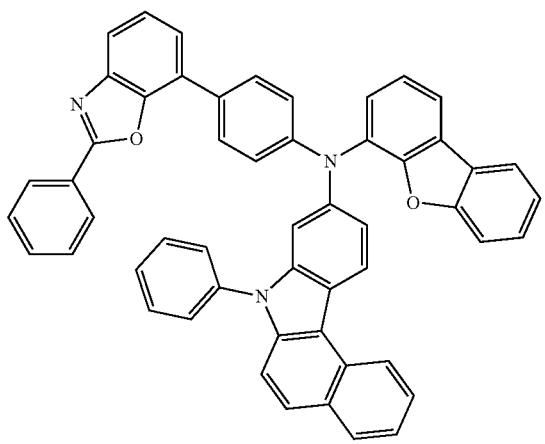
138
-continued
230
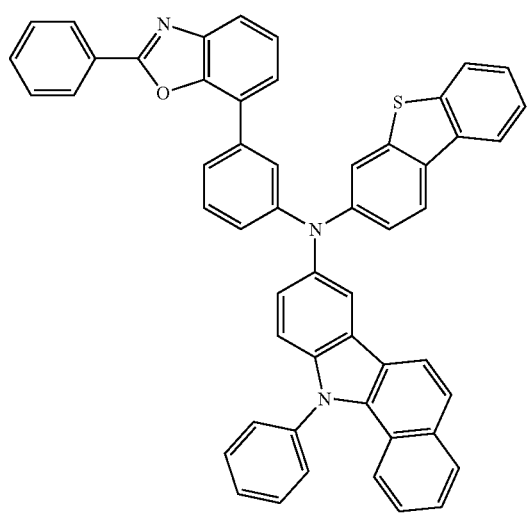
231
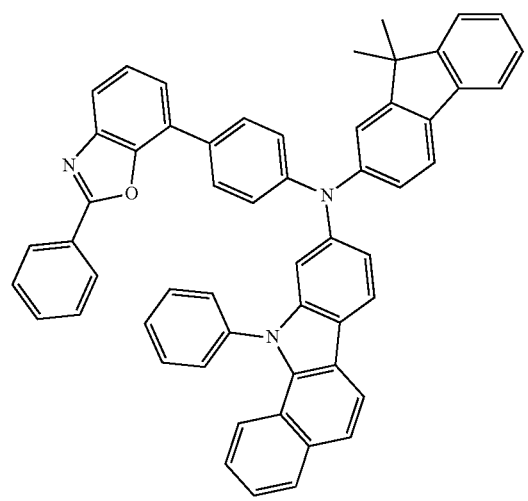
232

-continued
233
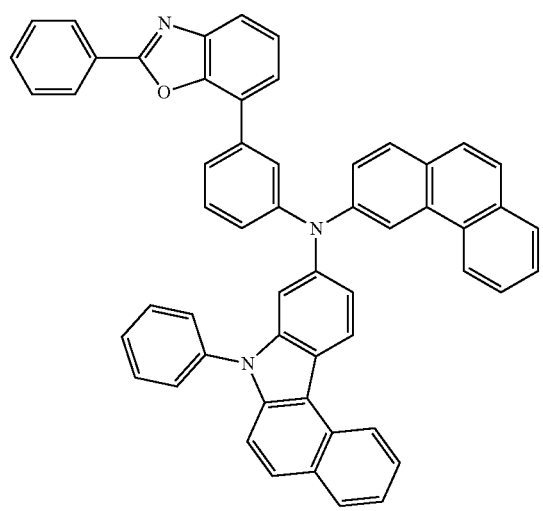
234
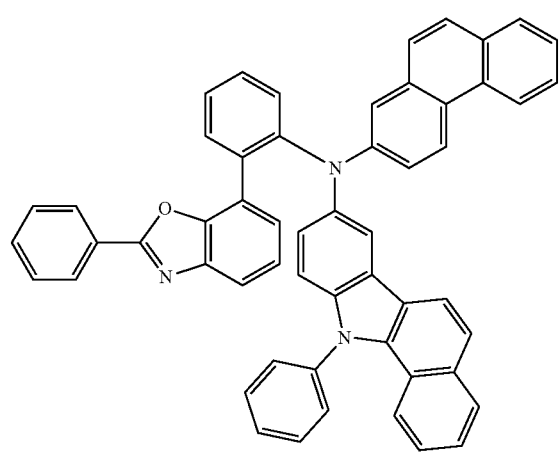
235
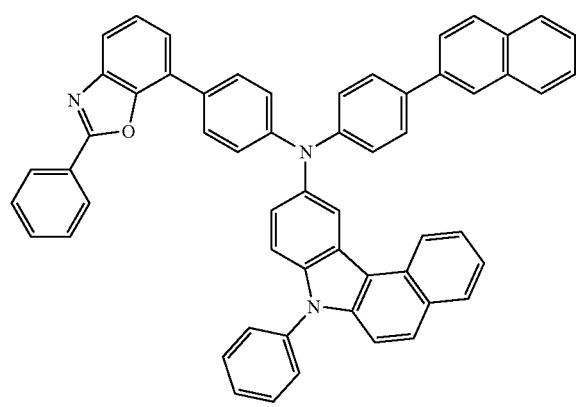
-continued
236
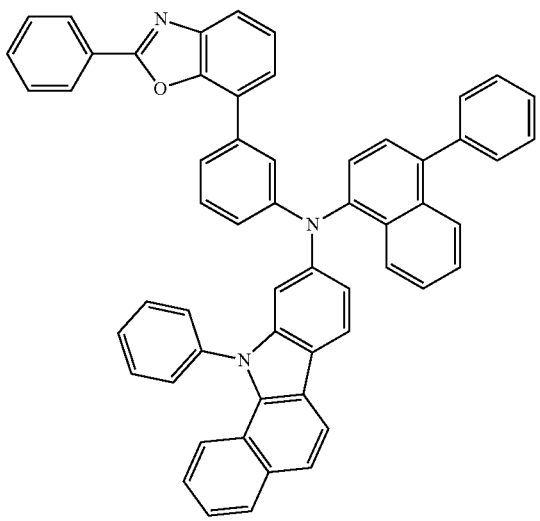
237
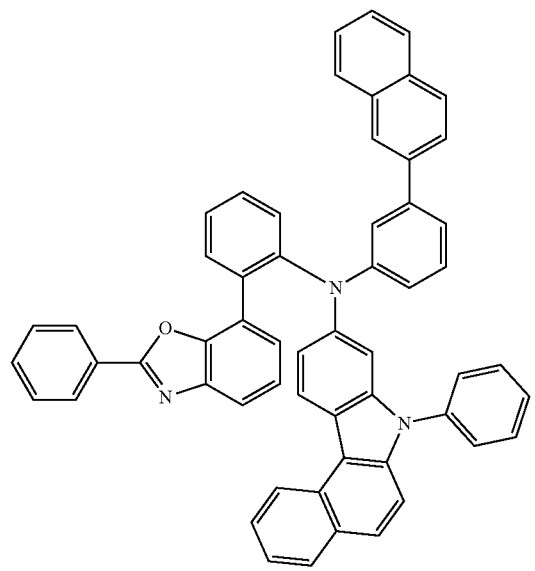
238
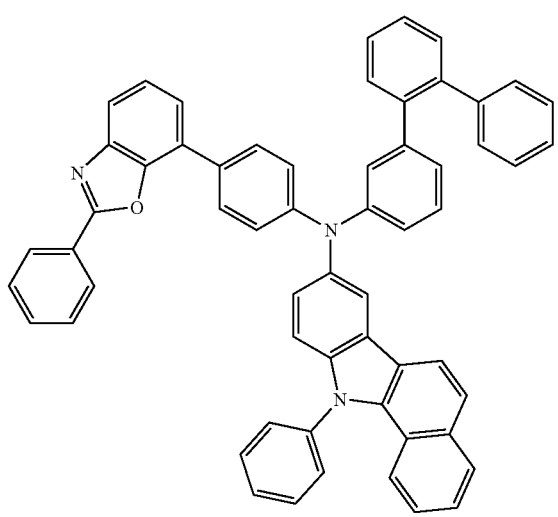

239
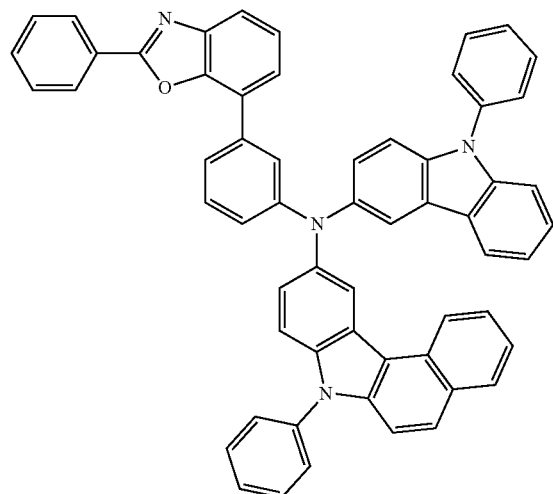
240
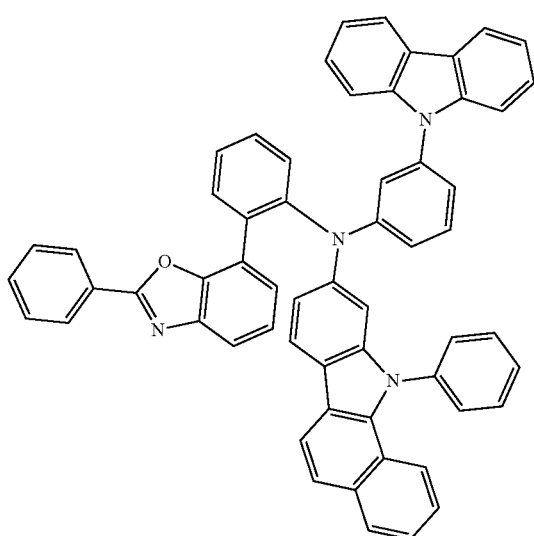
241
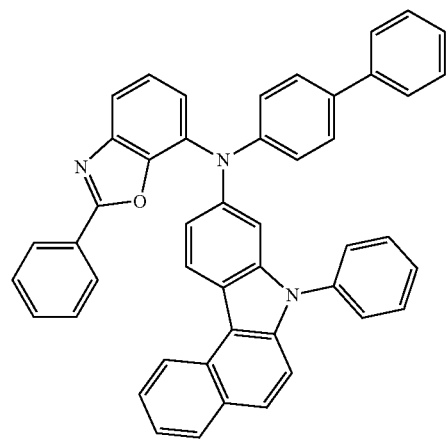
242
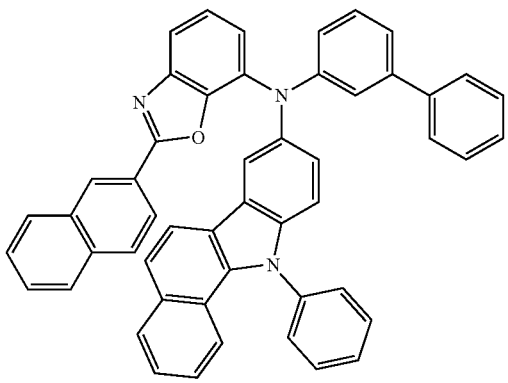
243
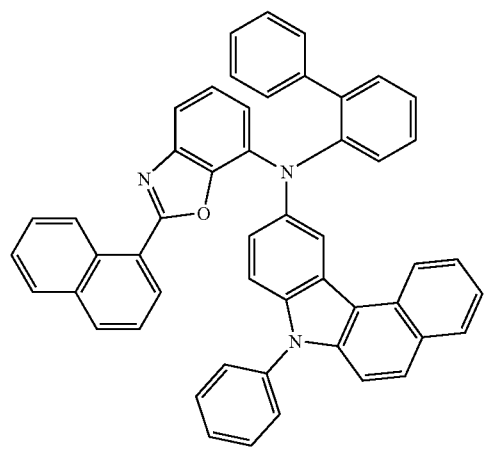
244
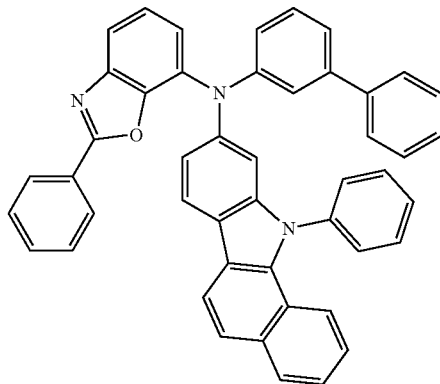

245
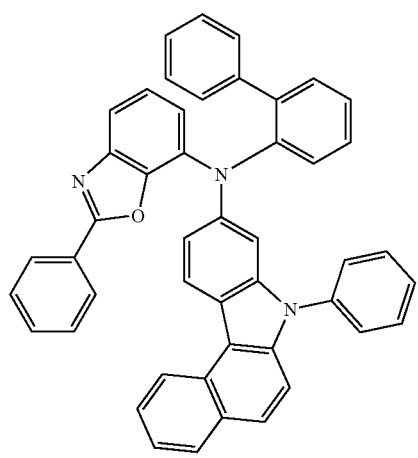
246
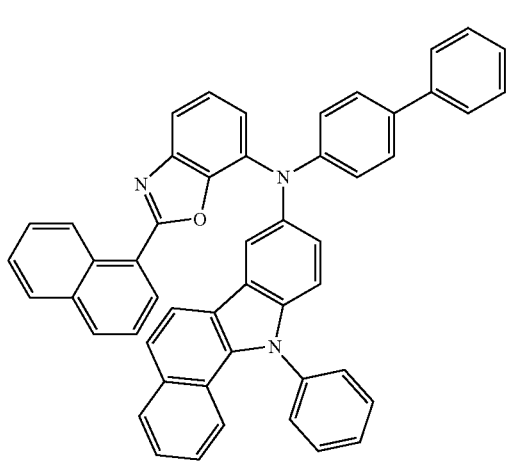
247
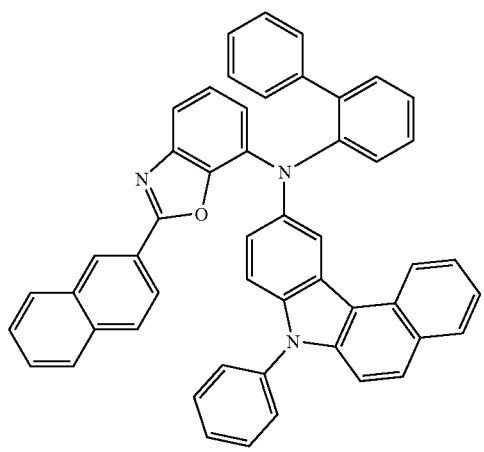
248
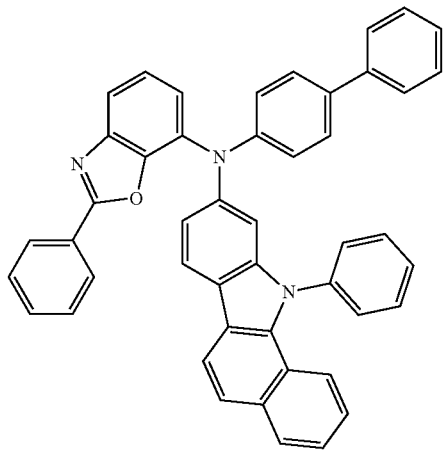
249
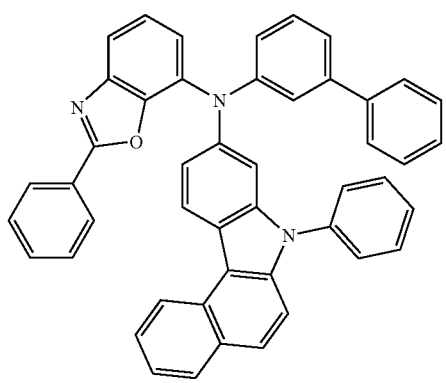
250
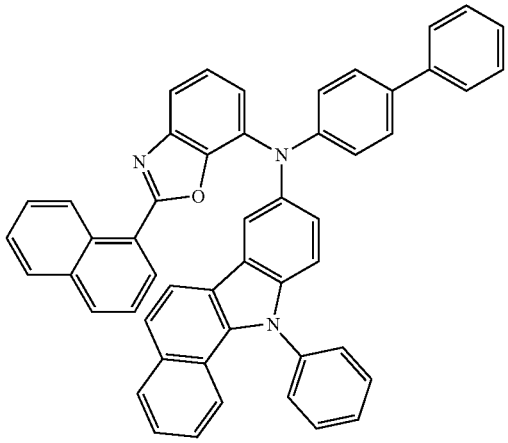

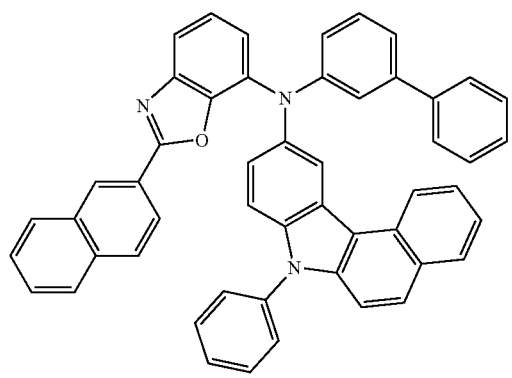
251
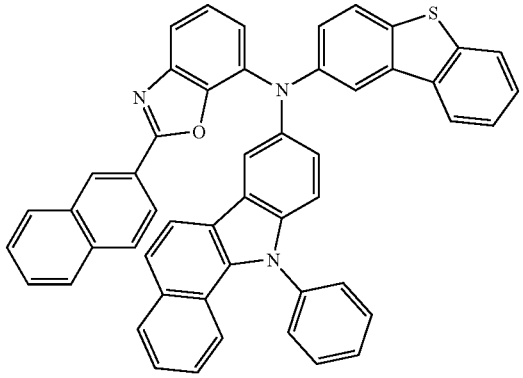
254
252
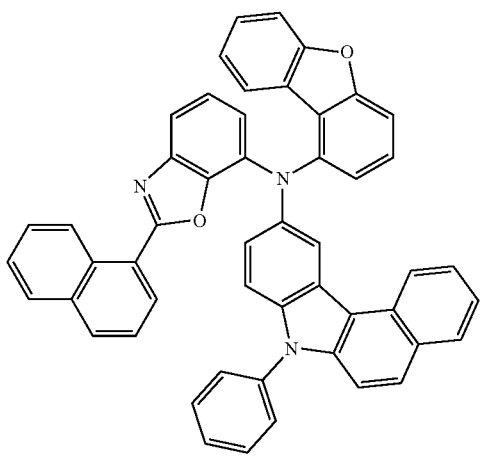
255
253
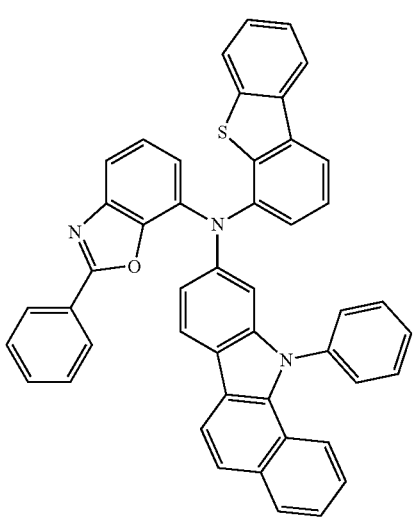
256

257 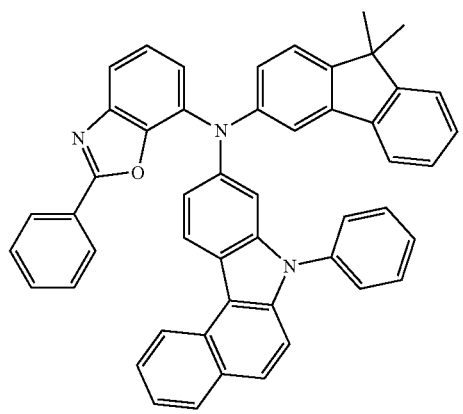
258 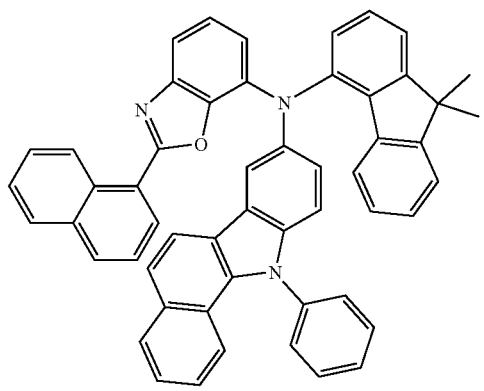
259 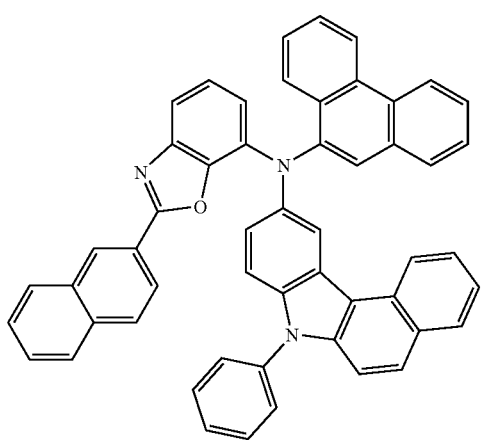
260 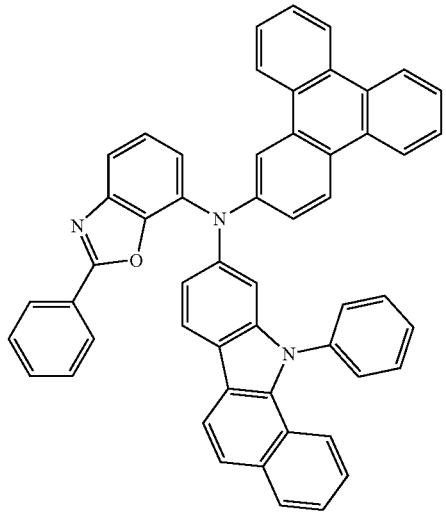
261
262 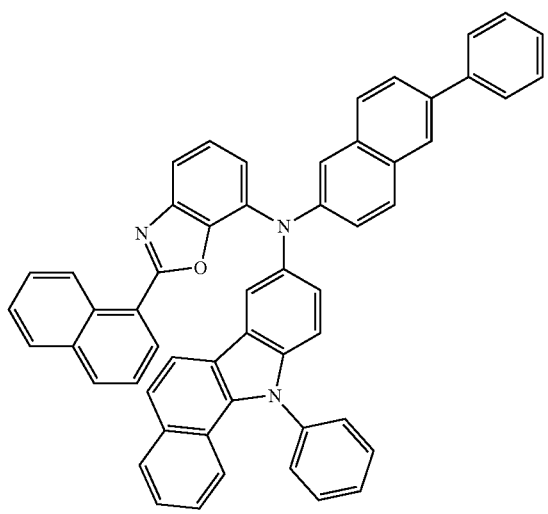

263
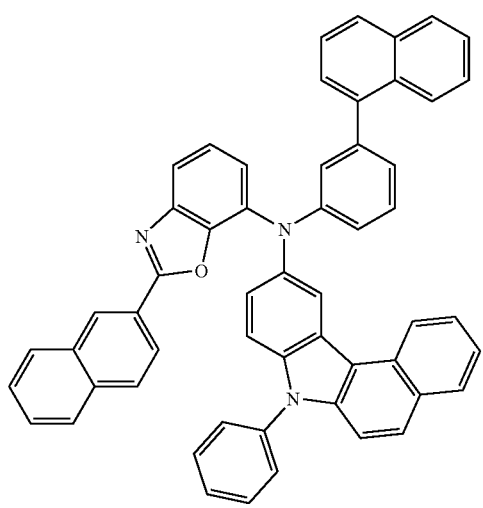
266
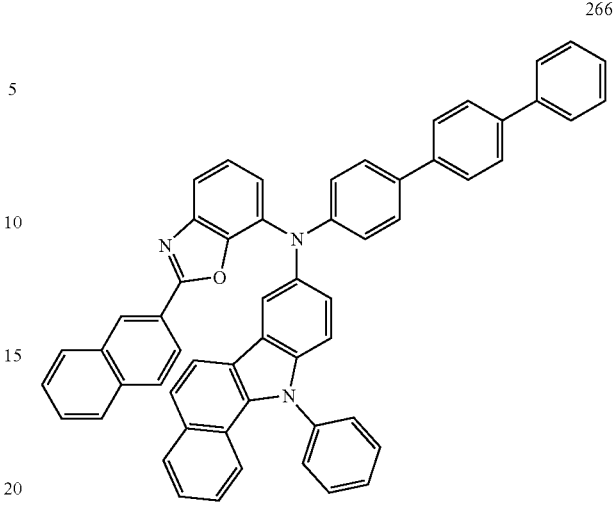
264
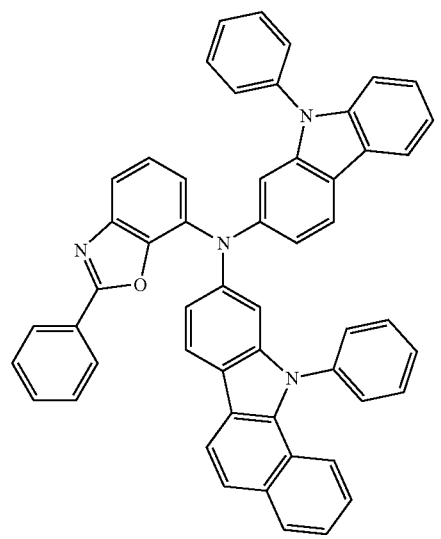
267
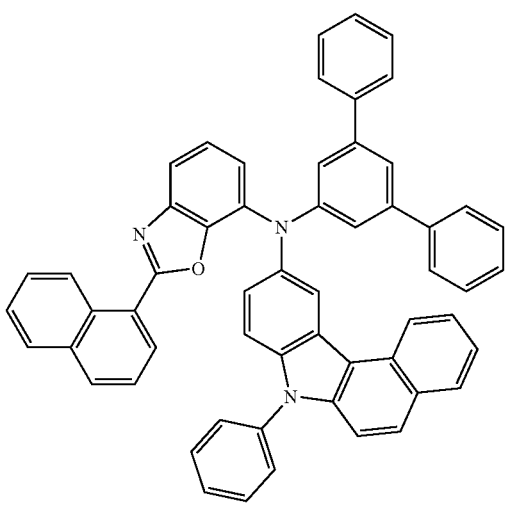
265
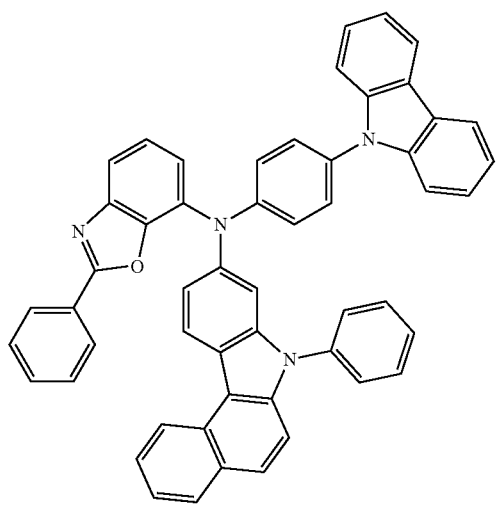
268
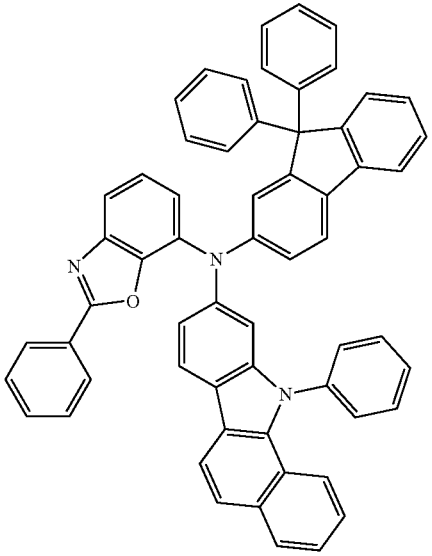

-continued
269
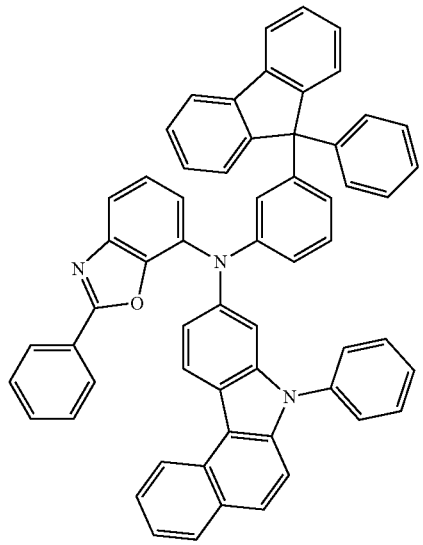
270
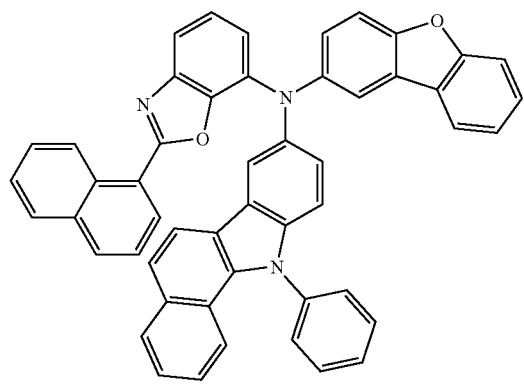
271
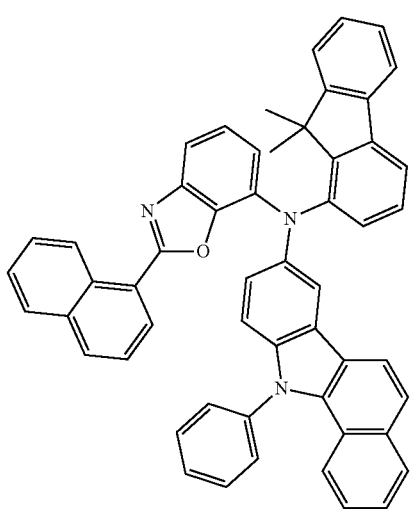
-continued
272
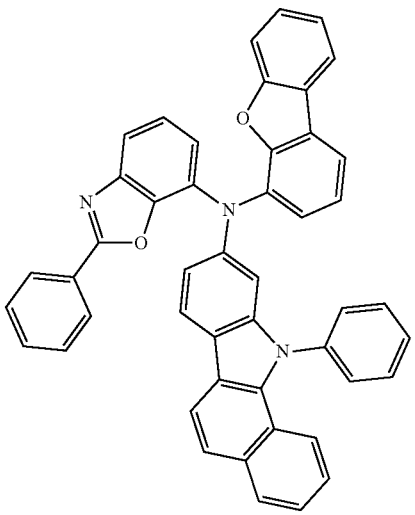
273
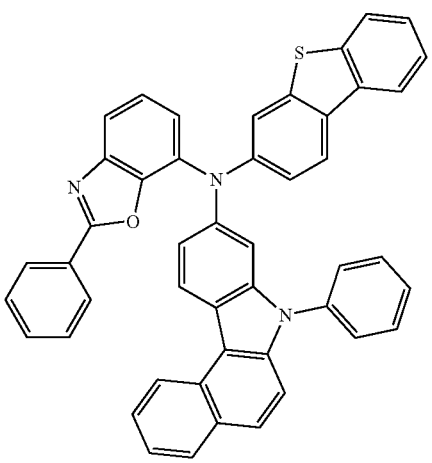
274

153
-continued
275
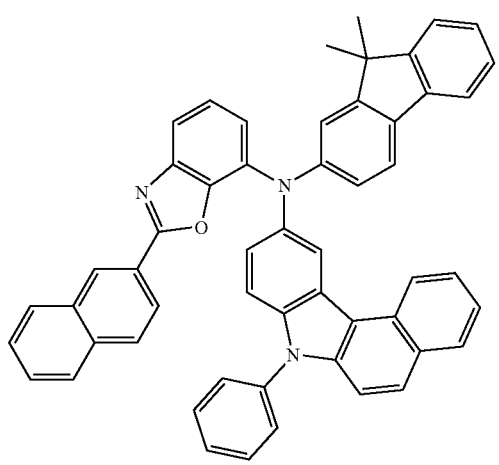
276
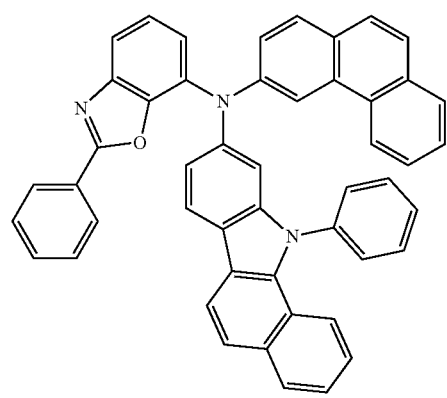
277
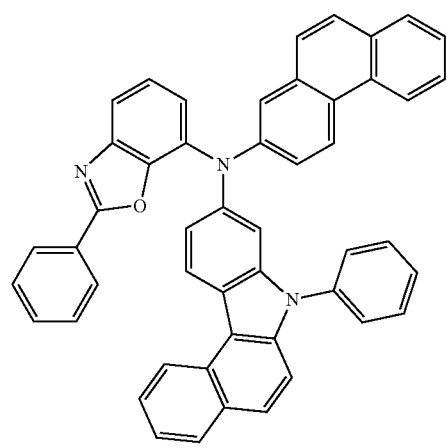
154
-continued
278
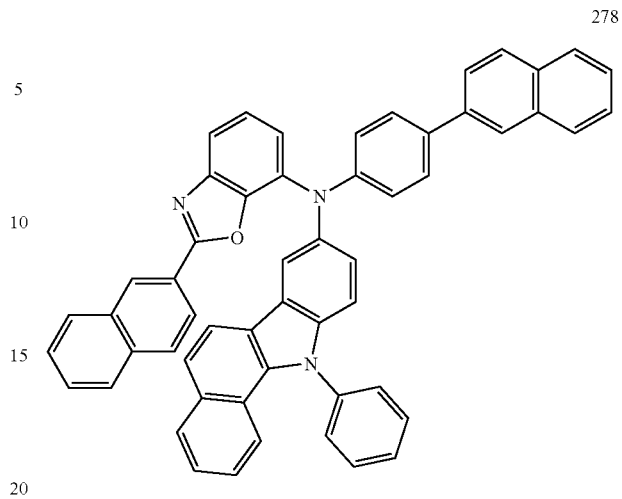
279
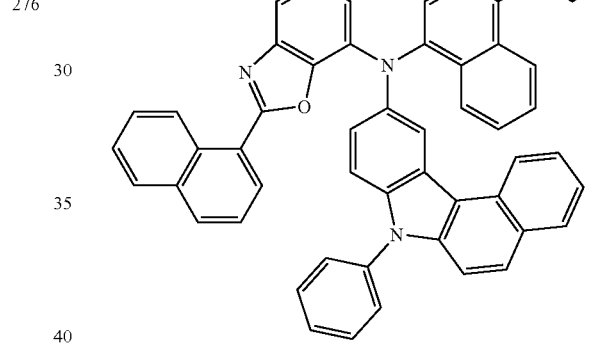
280
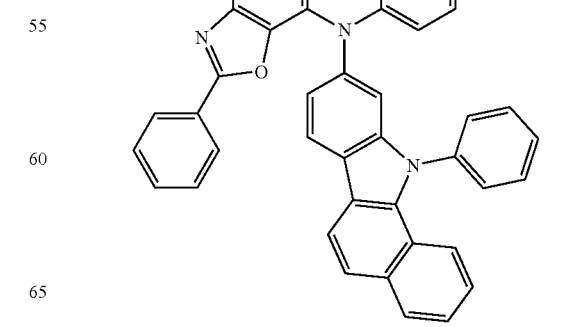

155
-continued
281
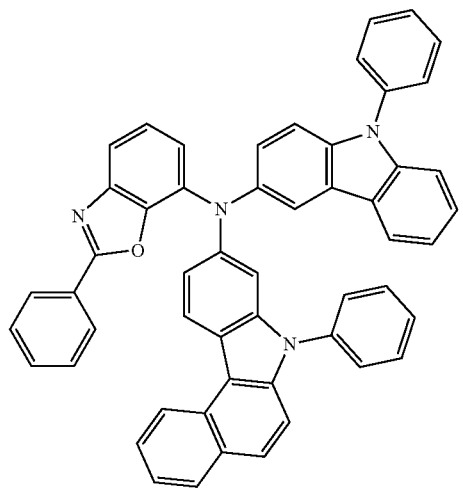
282
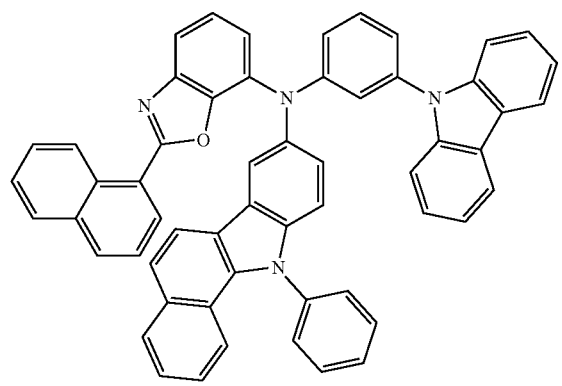
283
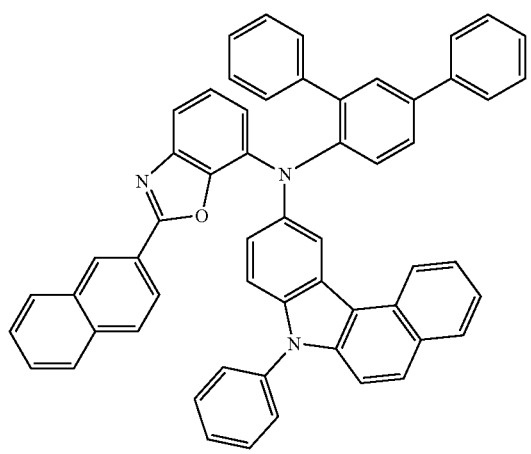
156
-continued
284
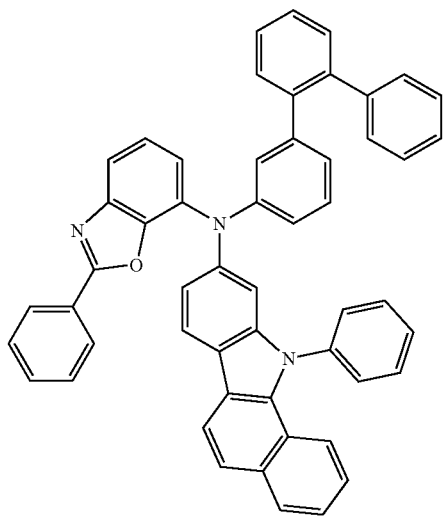
285
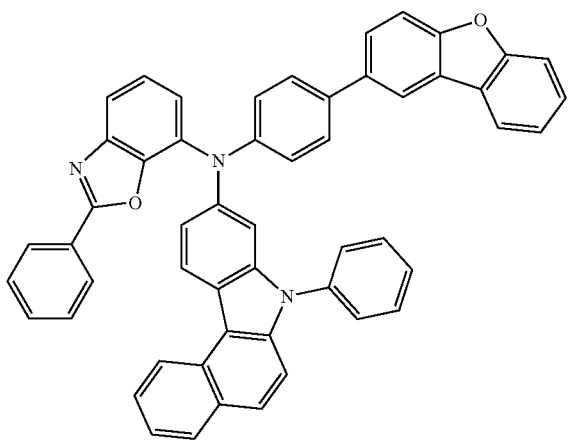
286
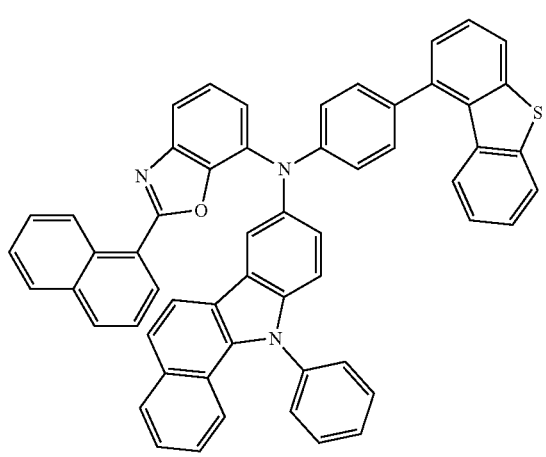

287
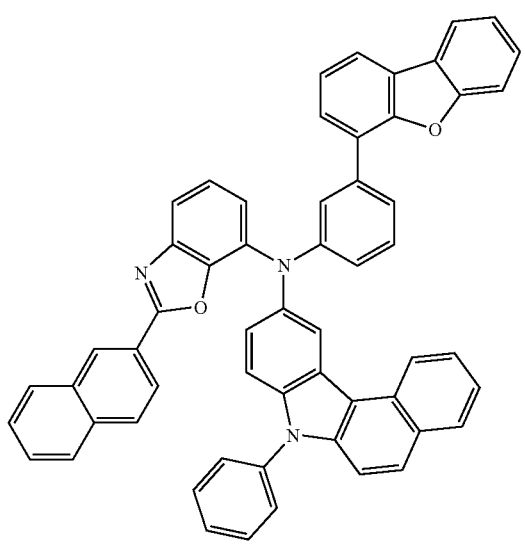
288
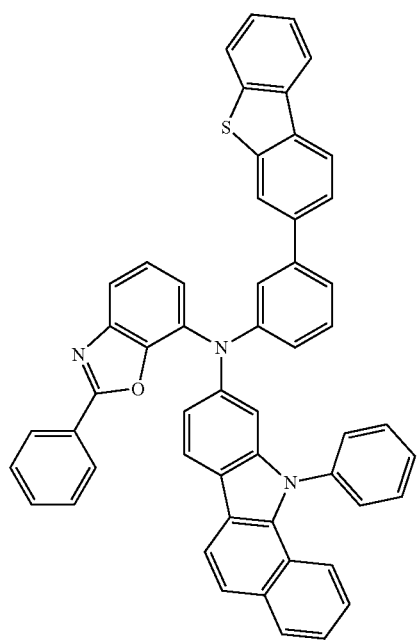
289
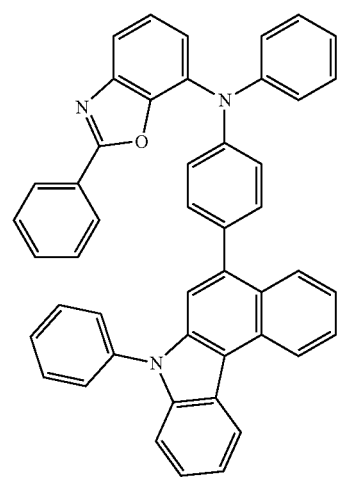
290
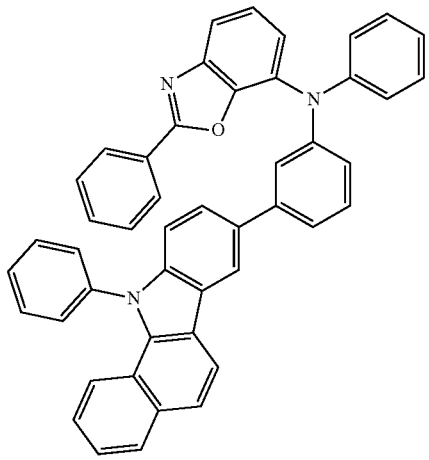
291
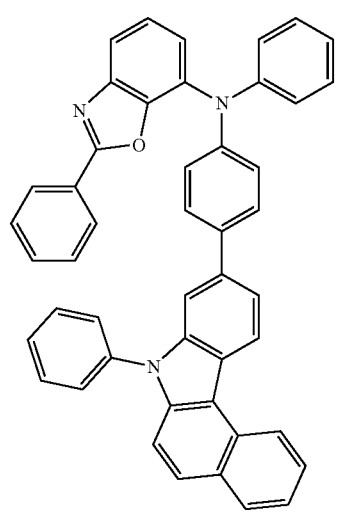
292
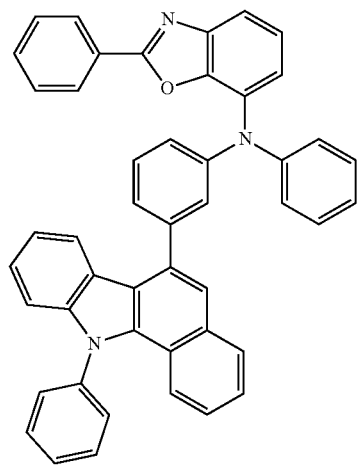

293
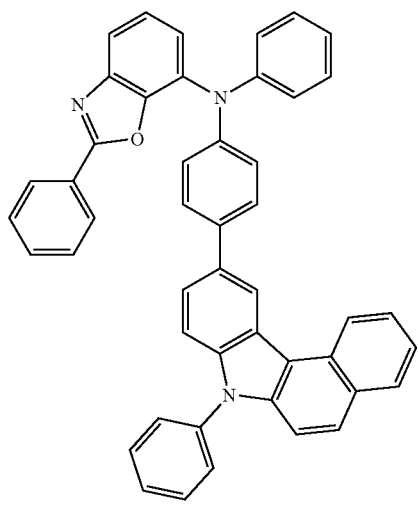
294
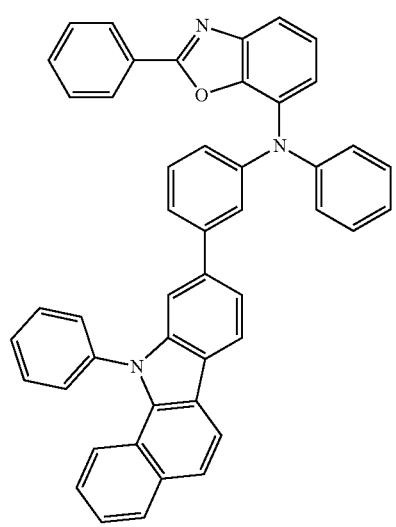
295
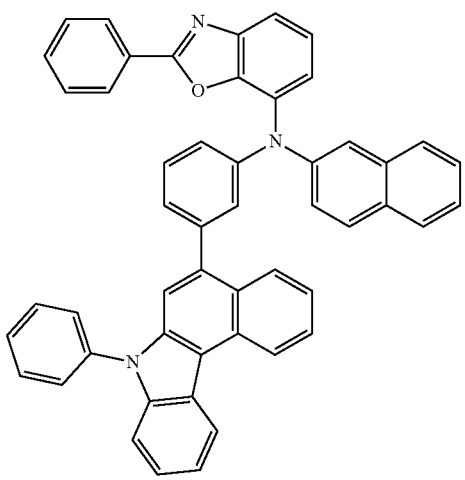
296
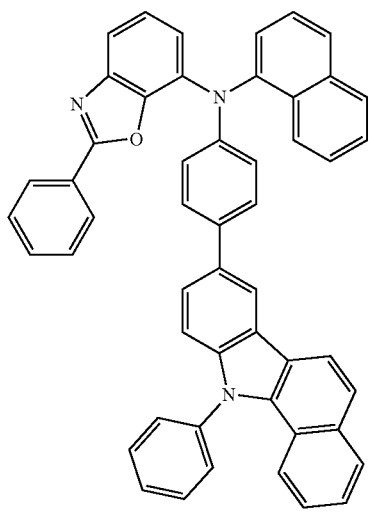
297
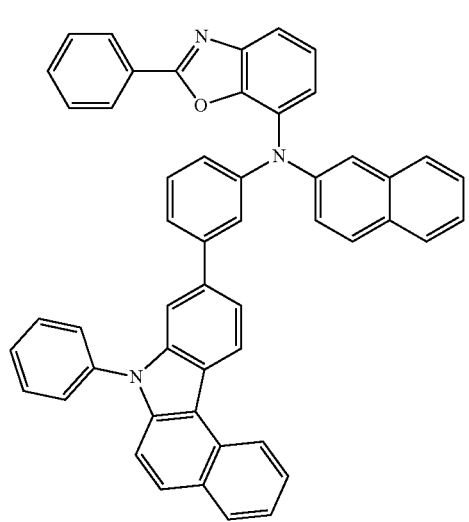
298
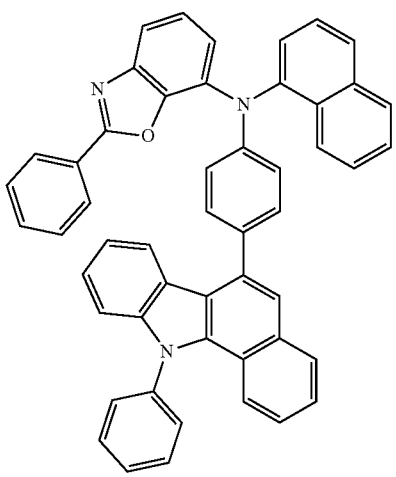

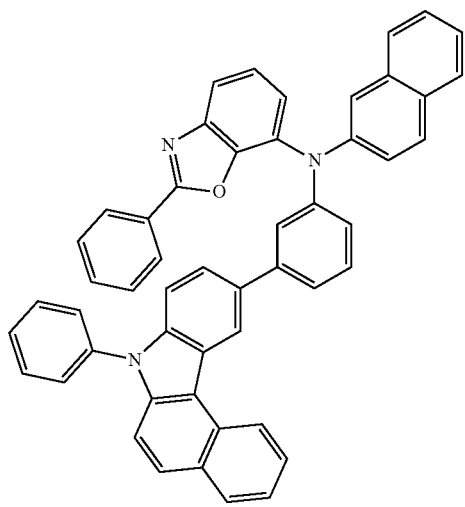
299
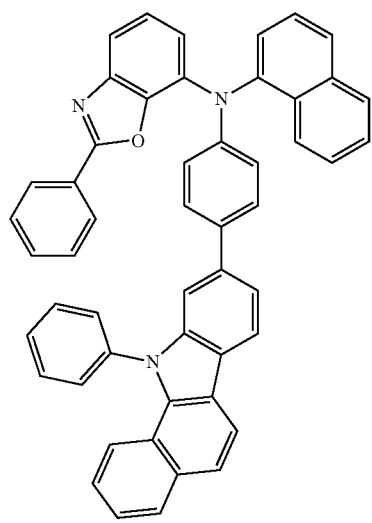
300
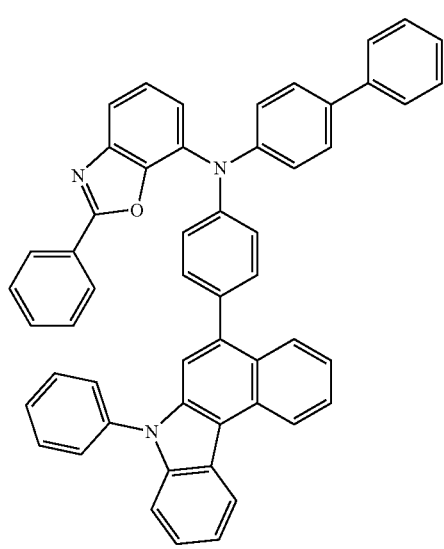
301
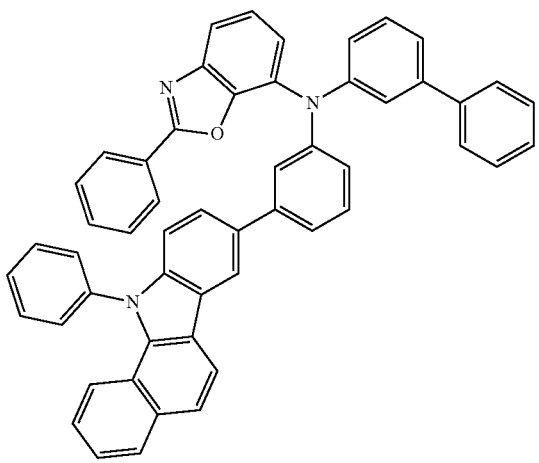
302
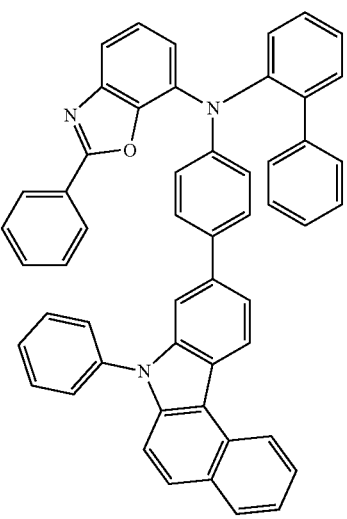
303
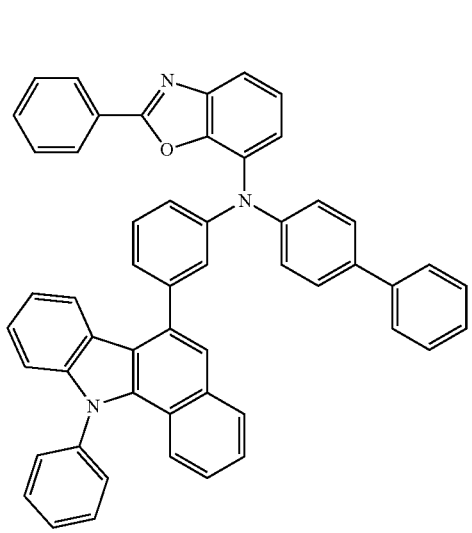
304

305
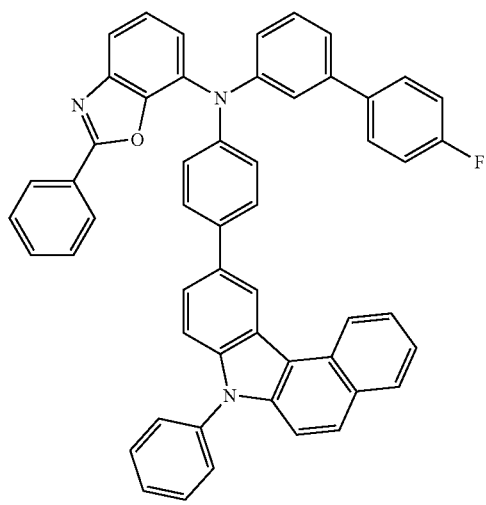
306
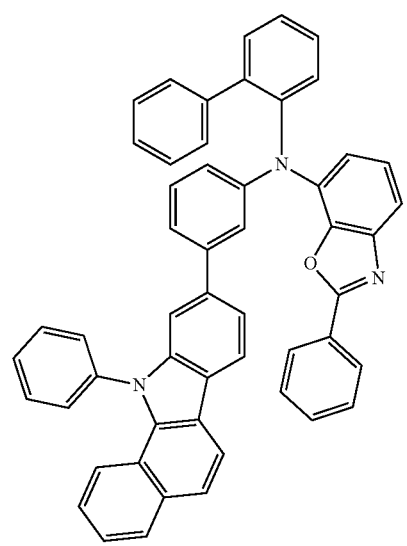
307
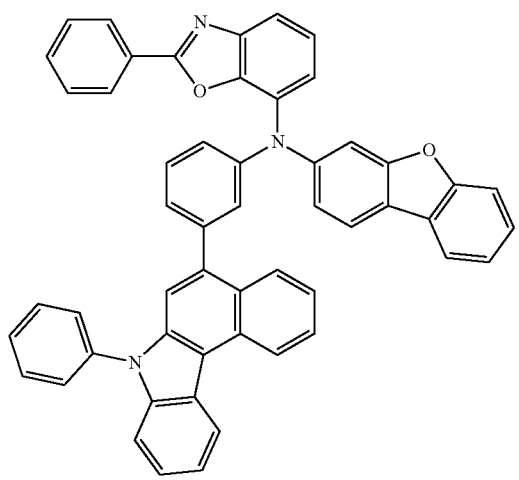
308
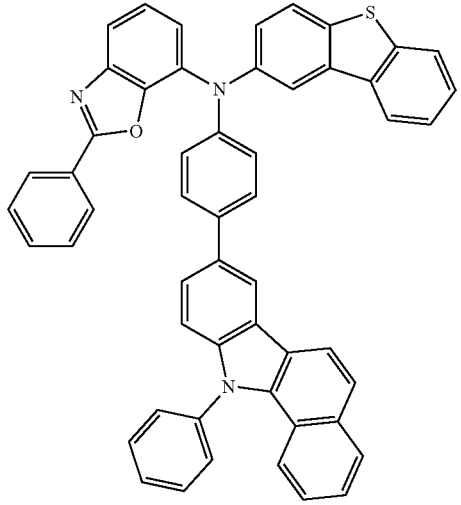
309
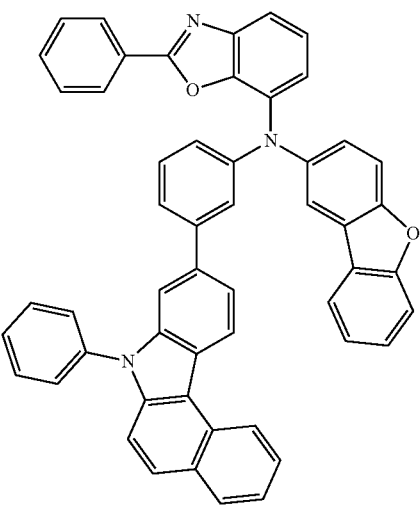
310
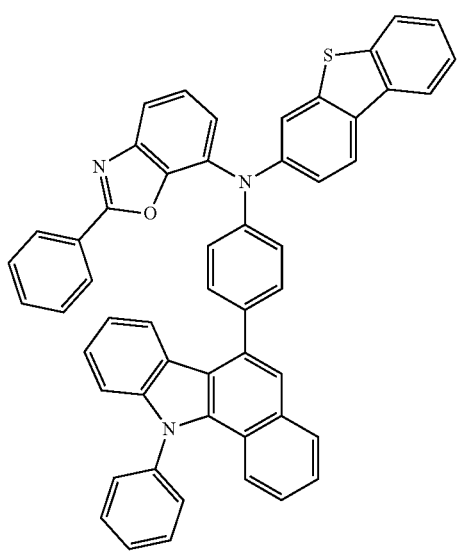

311
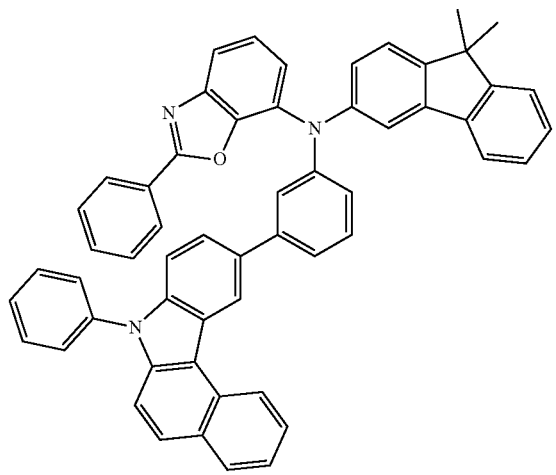
312
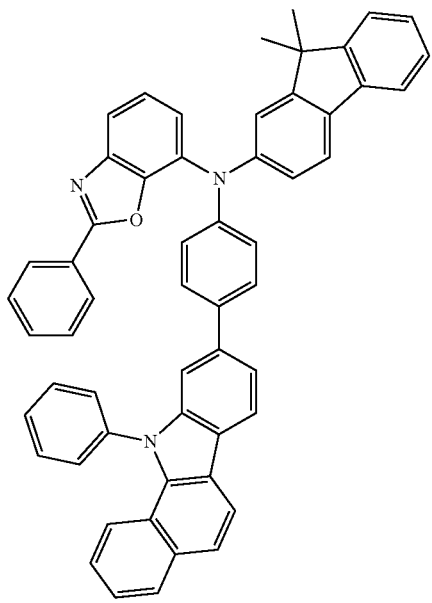
313
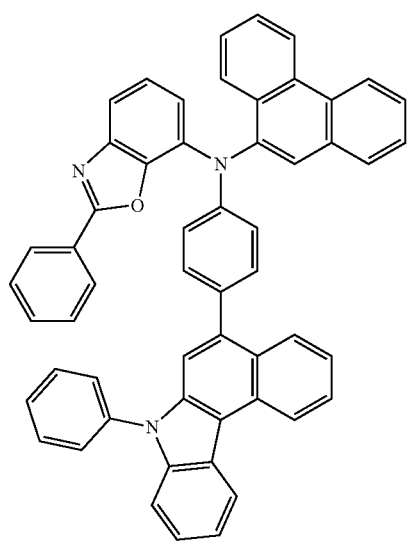
314
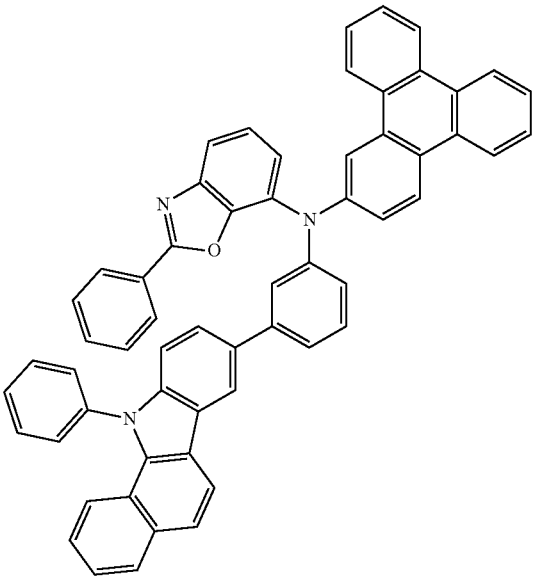
315
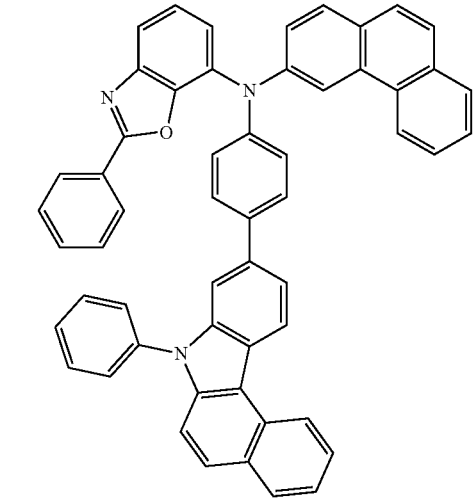
316
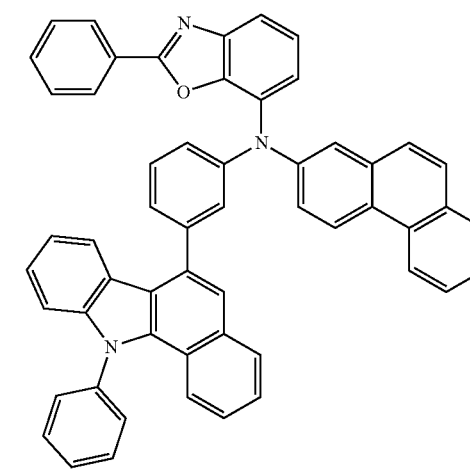

-continued
317
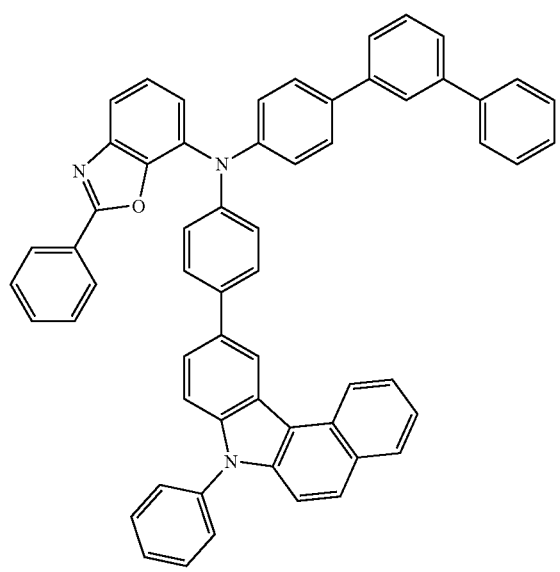
318
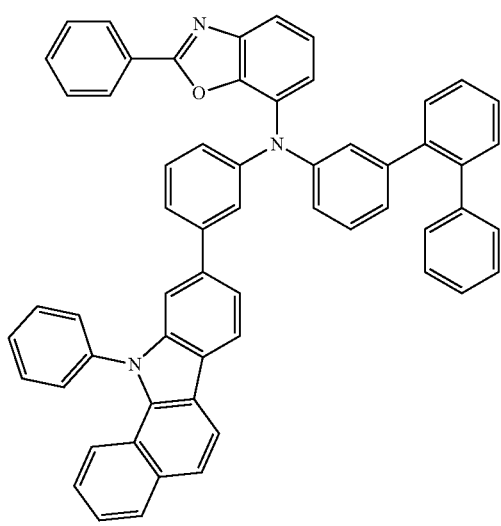
319
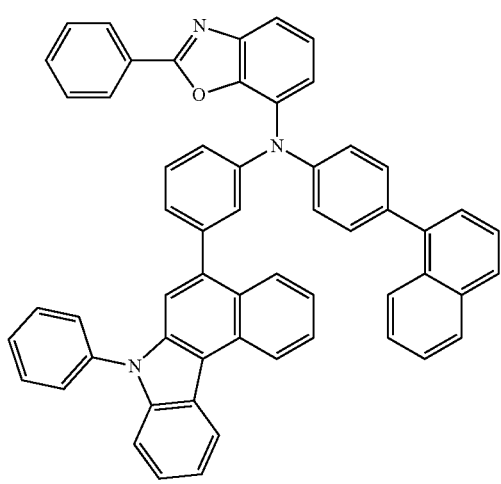
-continued
320
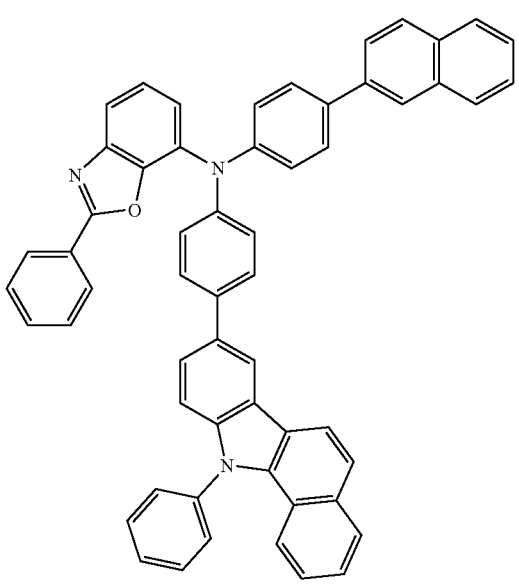
321
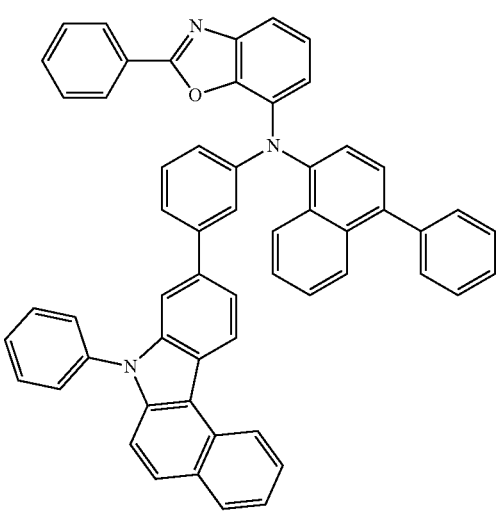
322
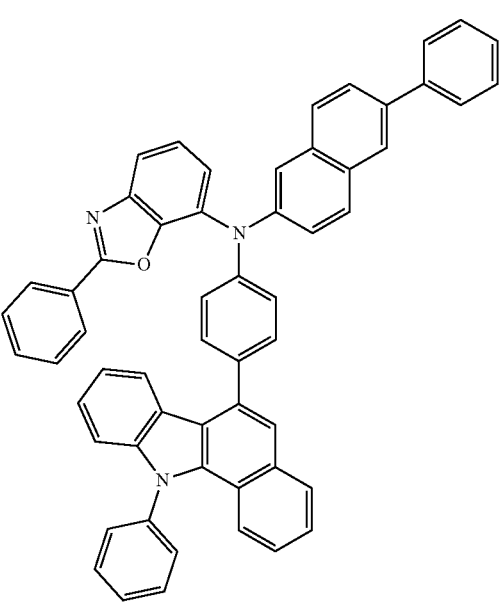

169
-continued
323
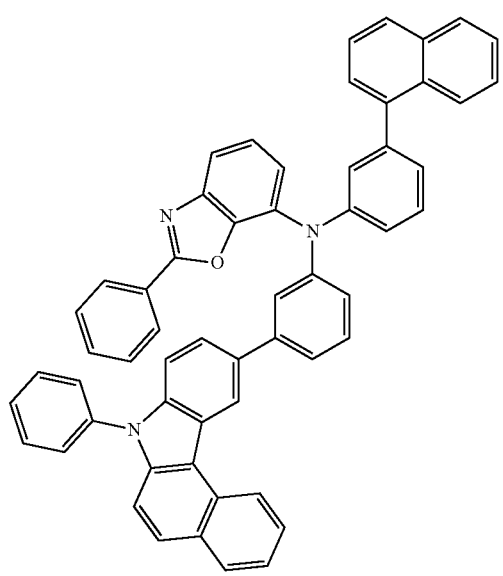
324
325
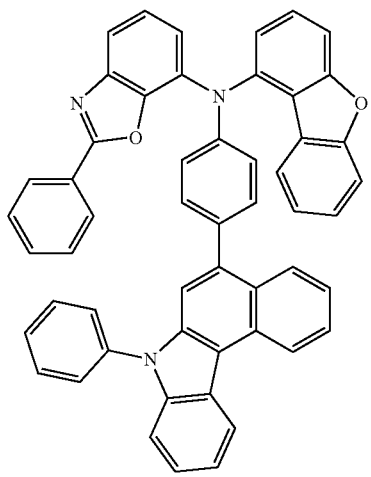
326
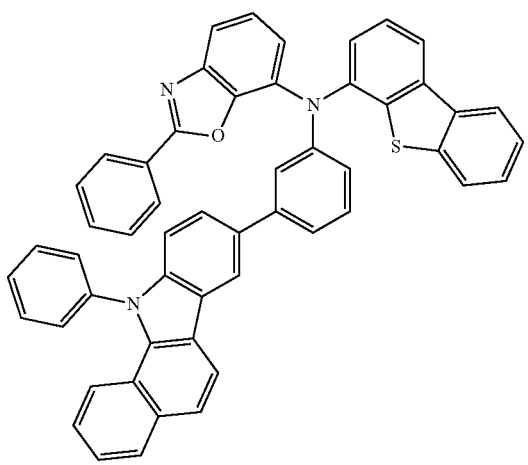
327
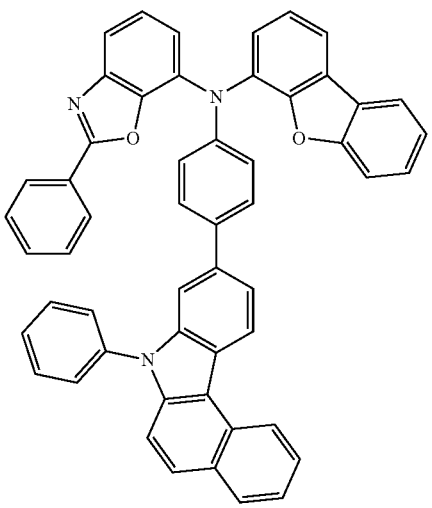
170
-continued 328
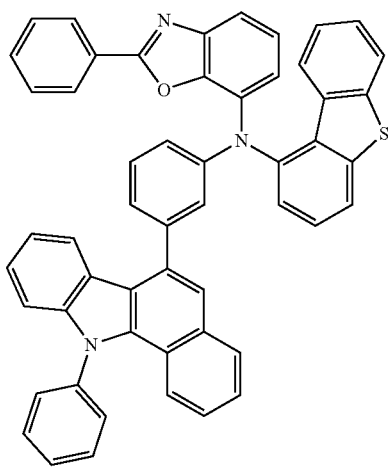
329
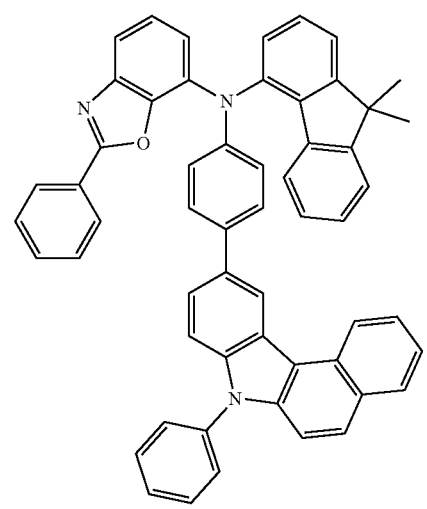
330
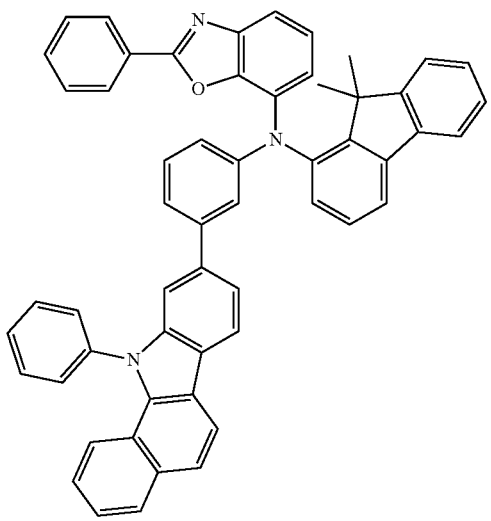
331
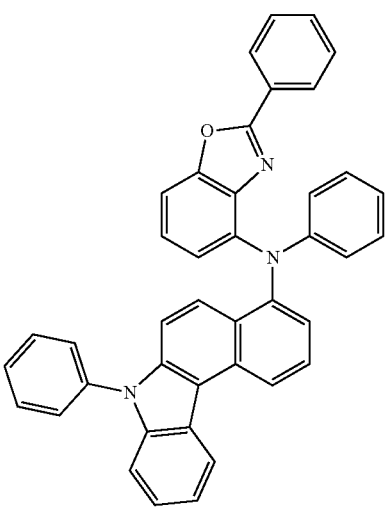
332
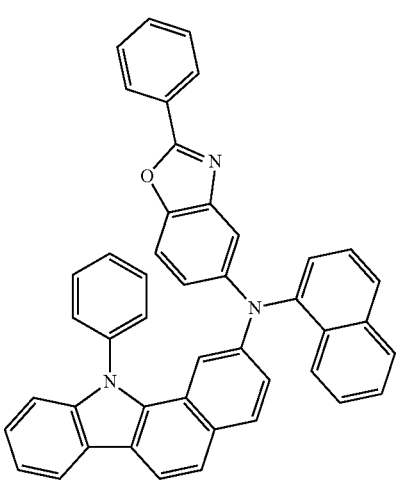
333
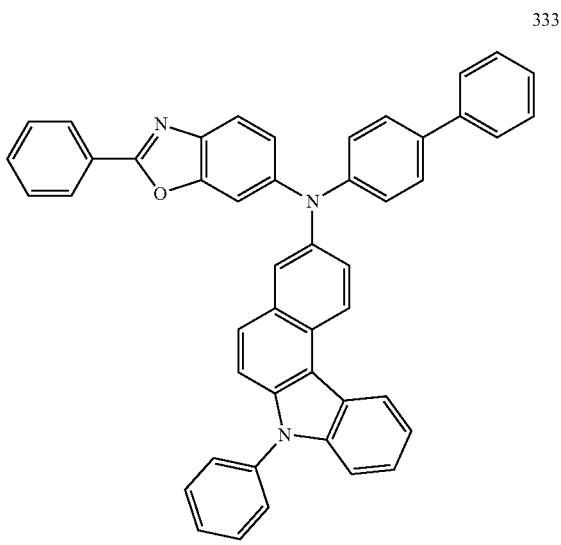

334
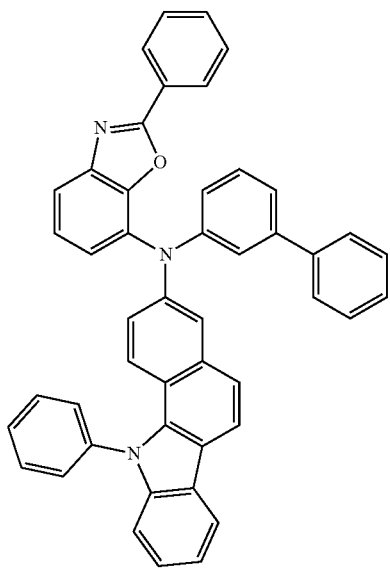
335
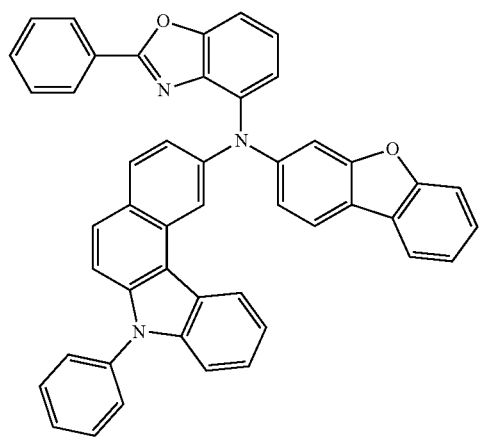
336
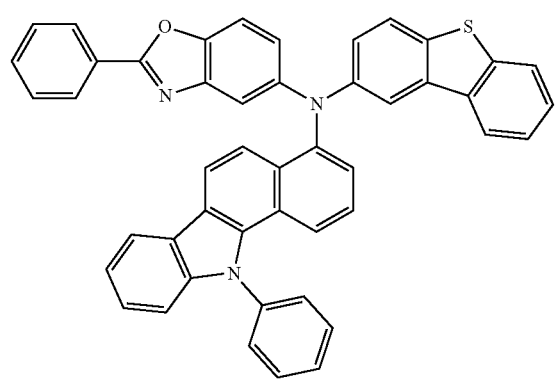
337
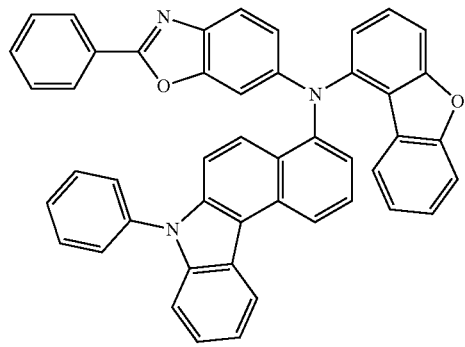
338
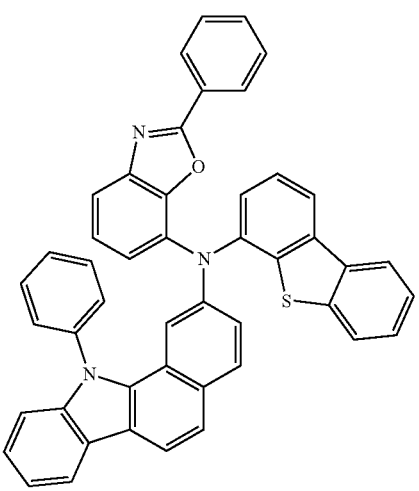
339
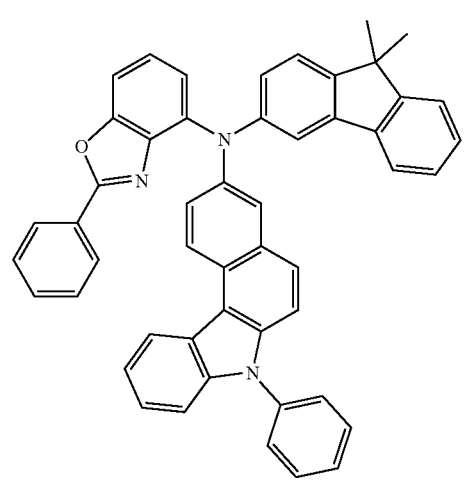

340
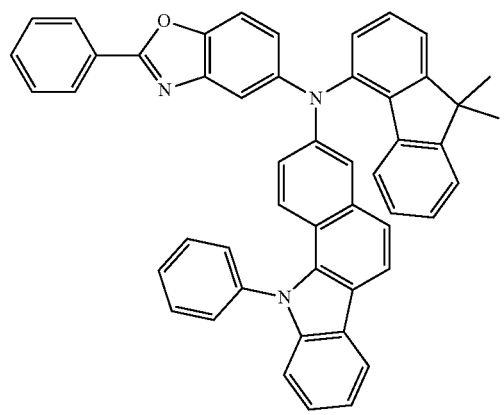
343
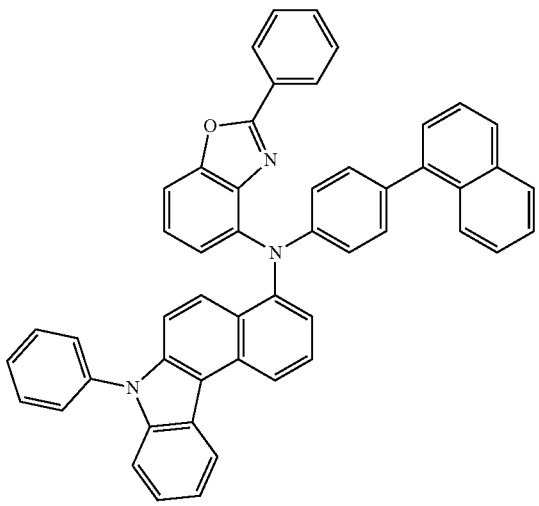
341
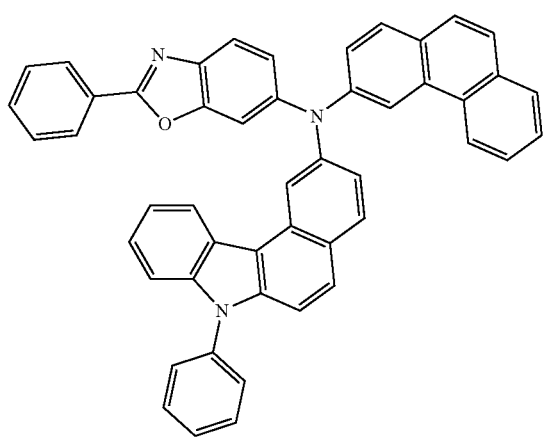
344
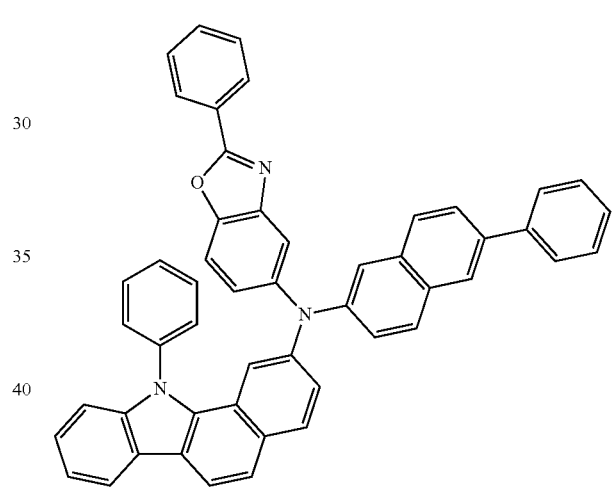
342
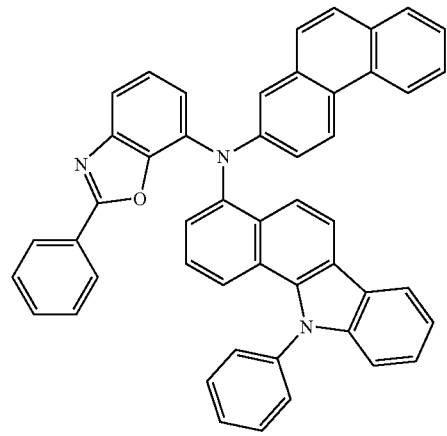
345
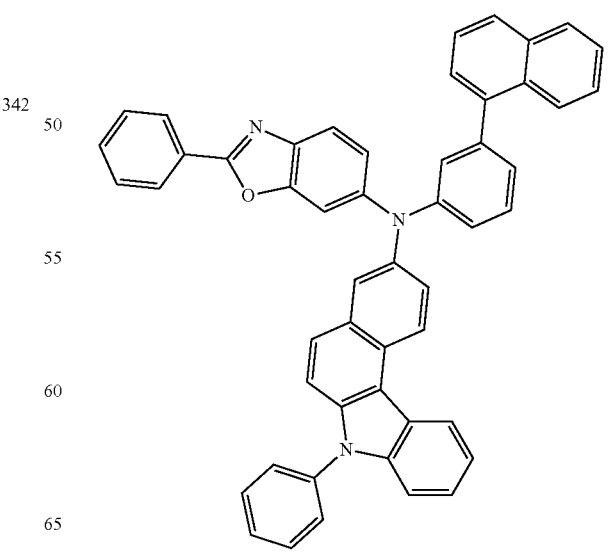

346 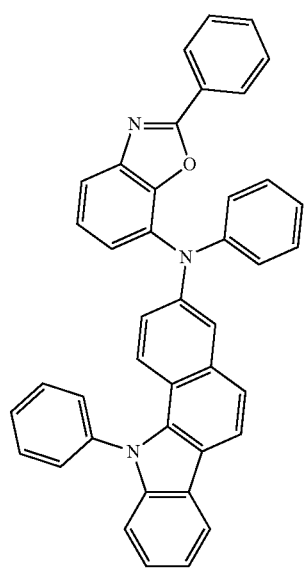
347 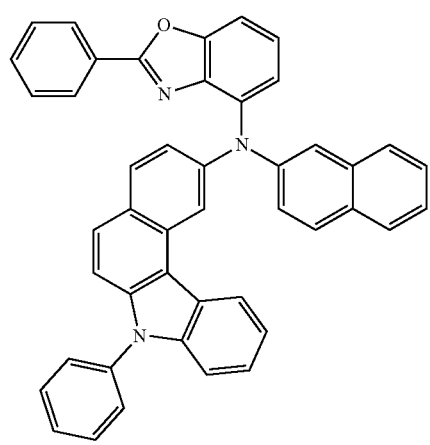
348 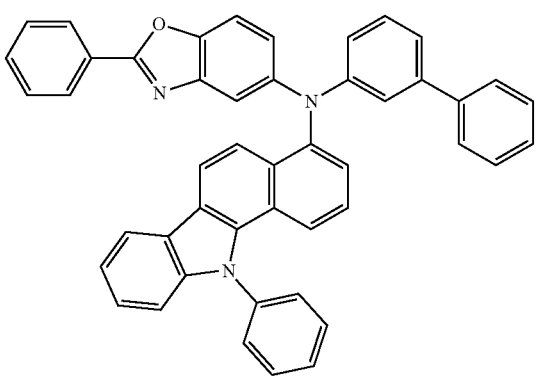
349 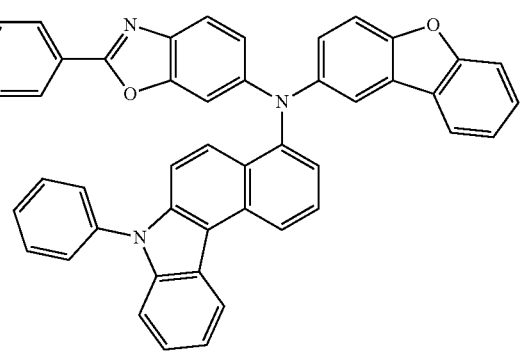
350 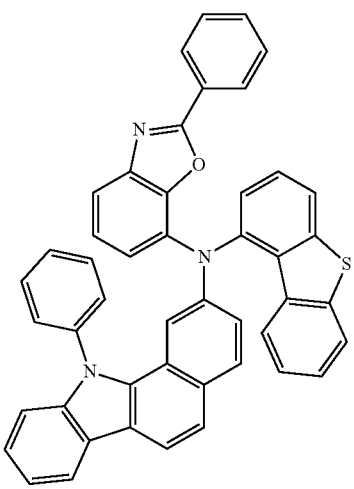
351 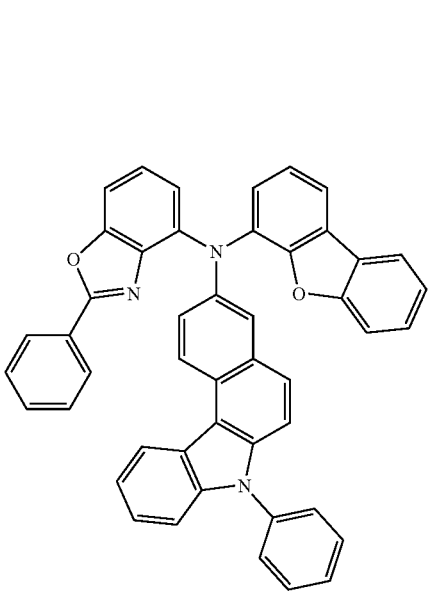

352
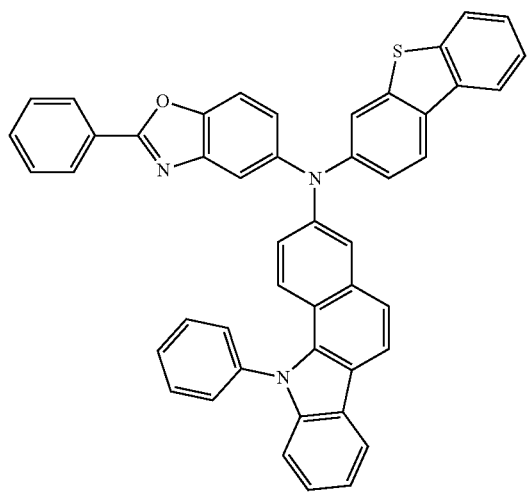
353
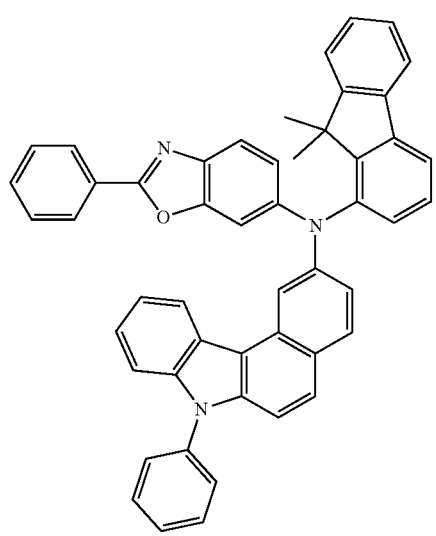
354
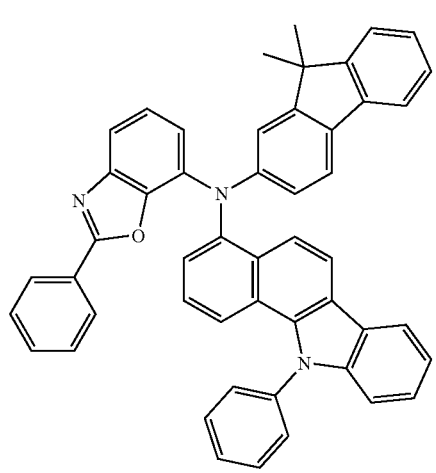
355
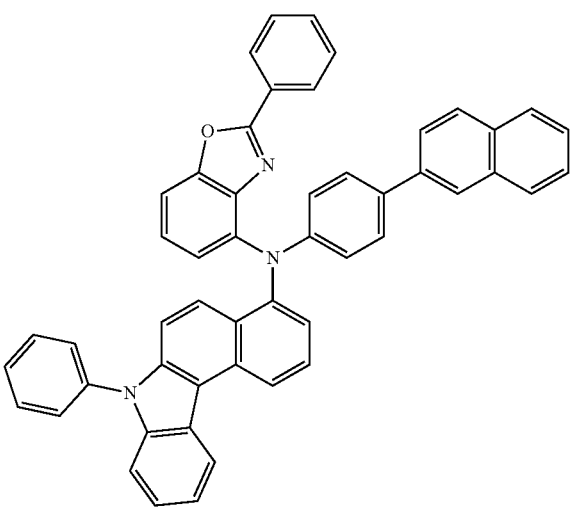
356
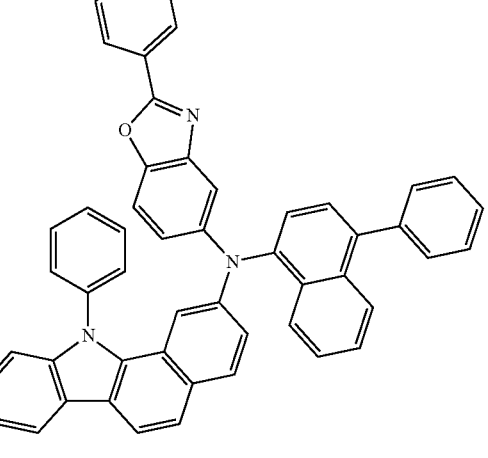
357
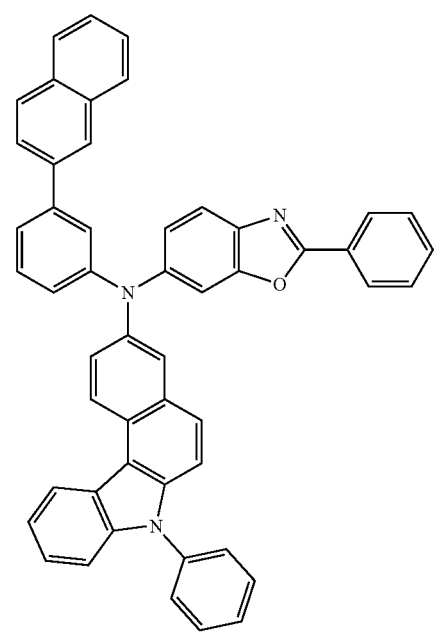

358
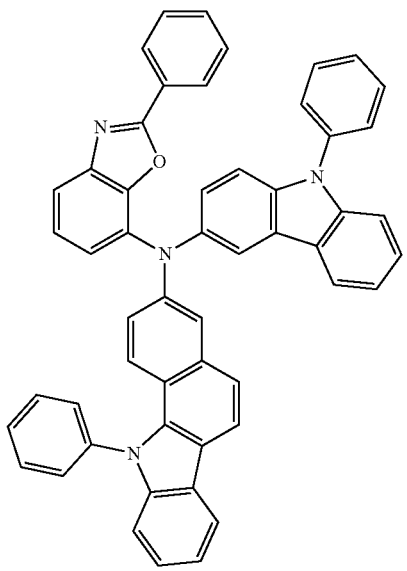
359
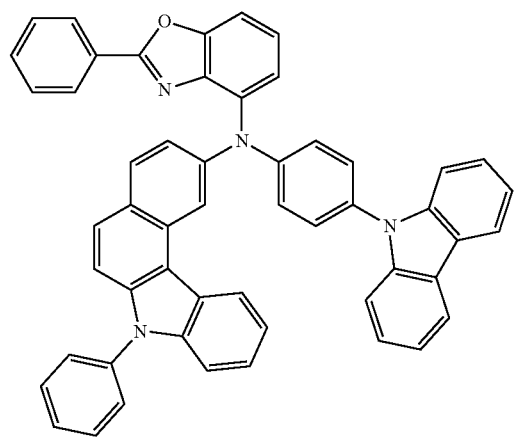
360
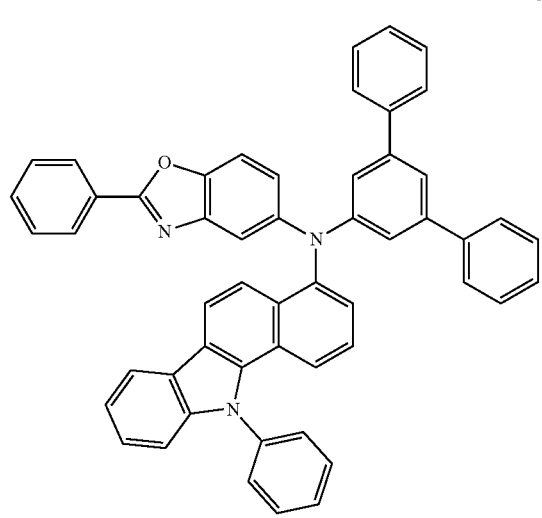
361
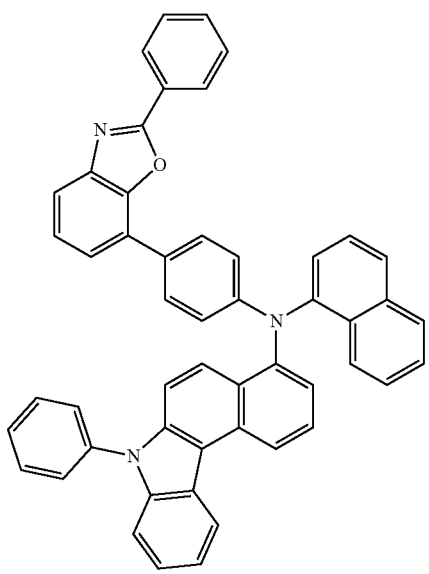
362
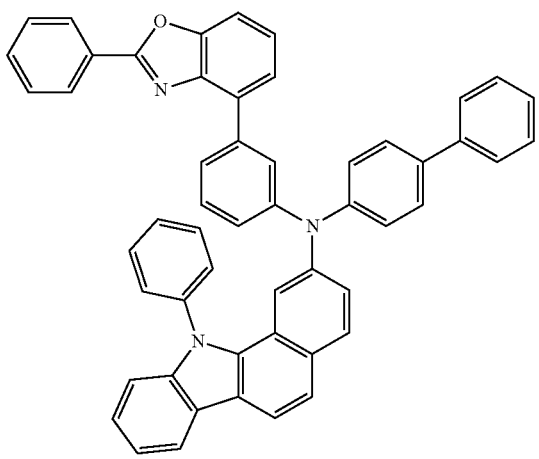
363
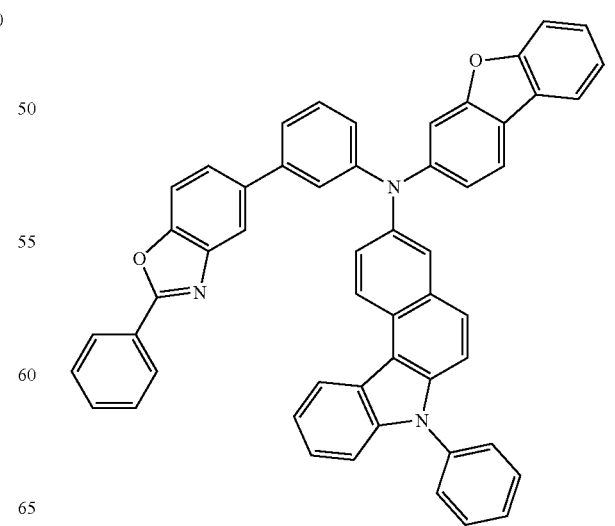

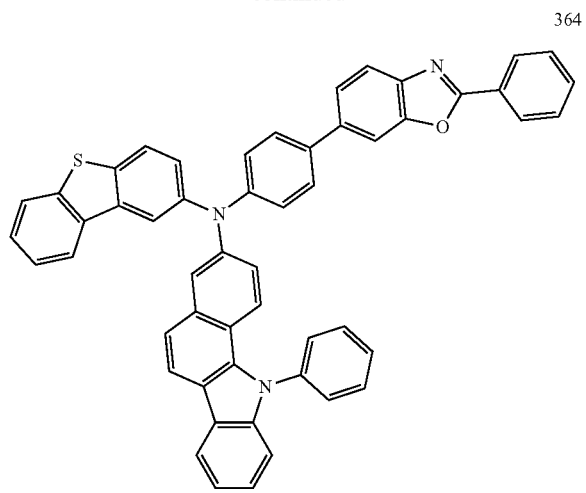
364
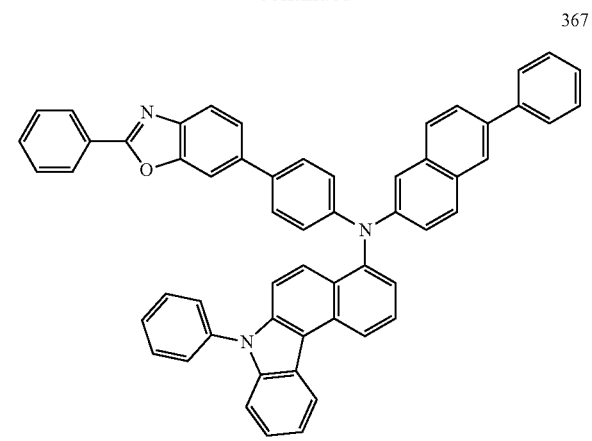
367
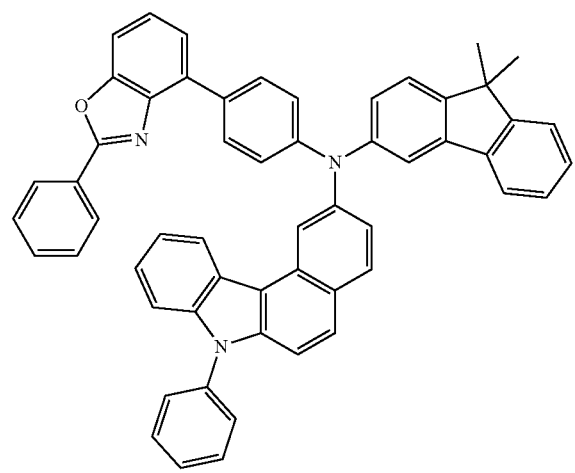
365
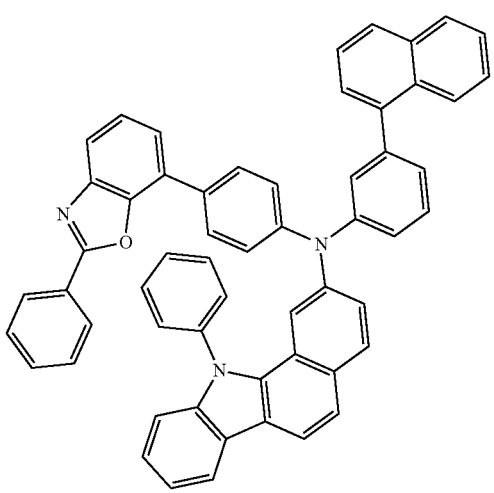
368
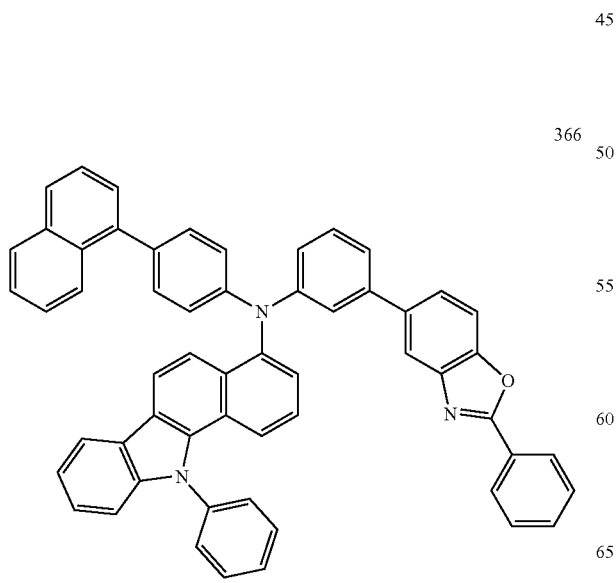
366
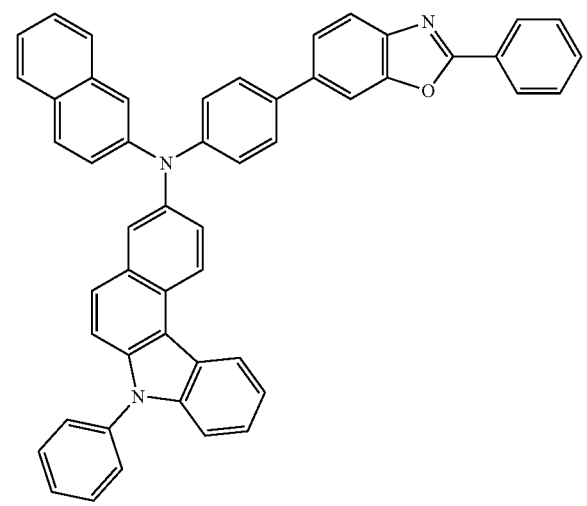
369

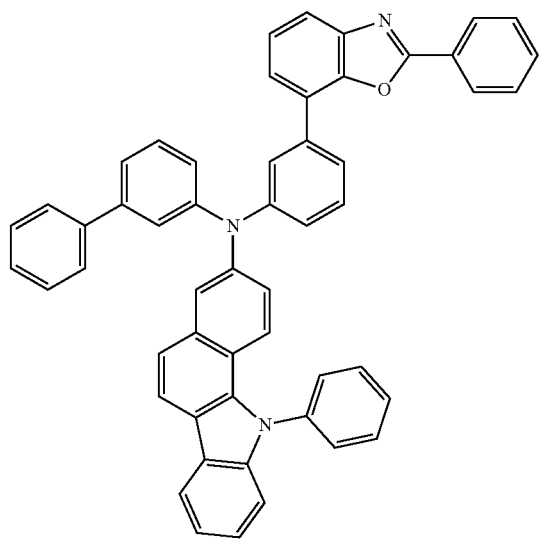
370
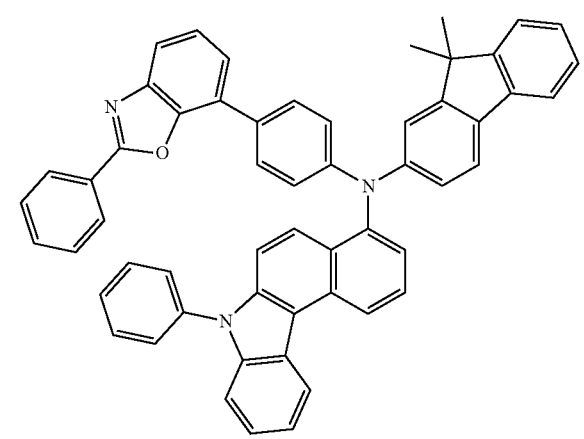
373
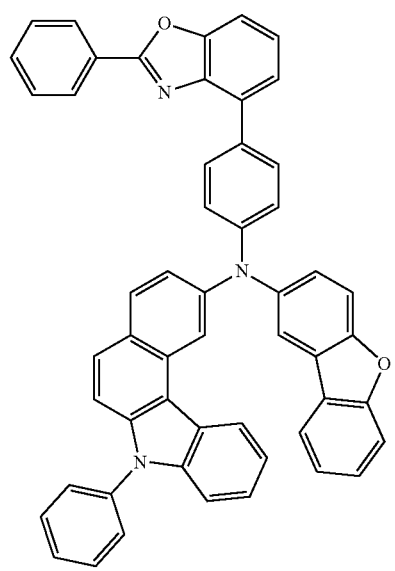
370
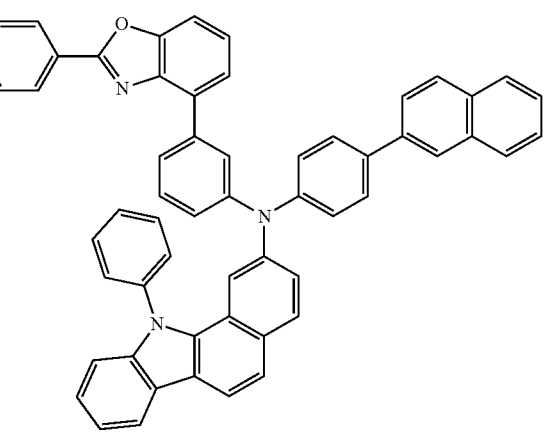
374
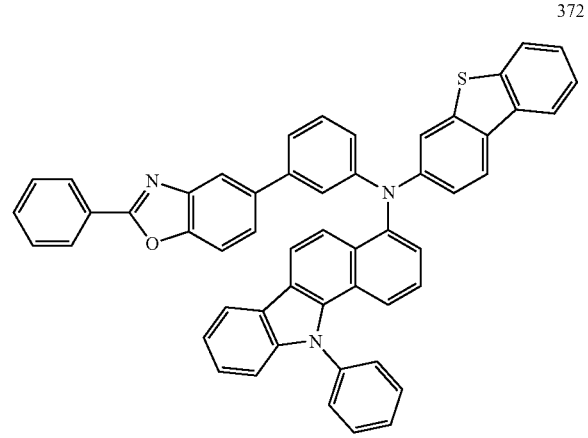
372
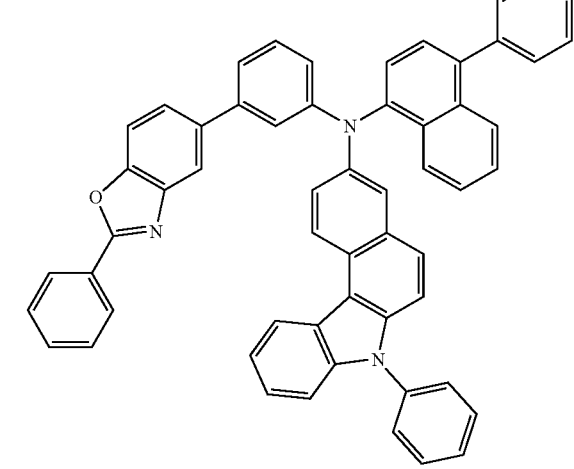
375

376
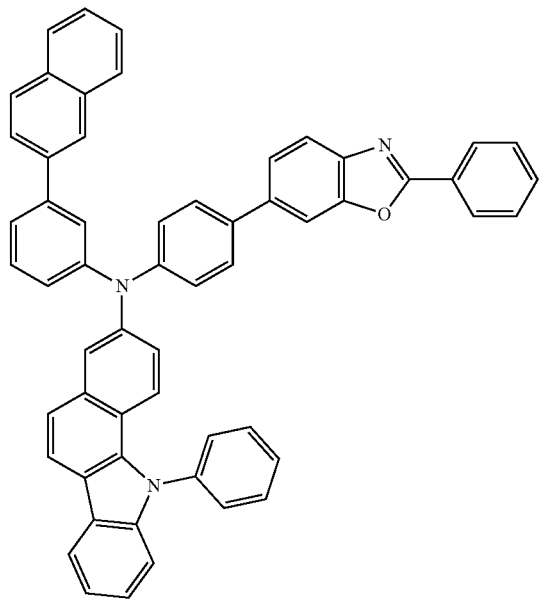
377
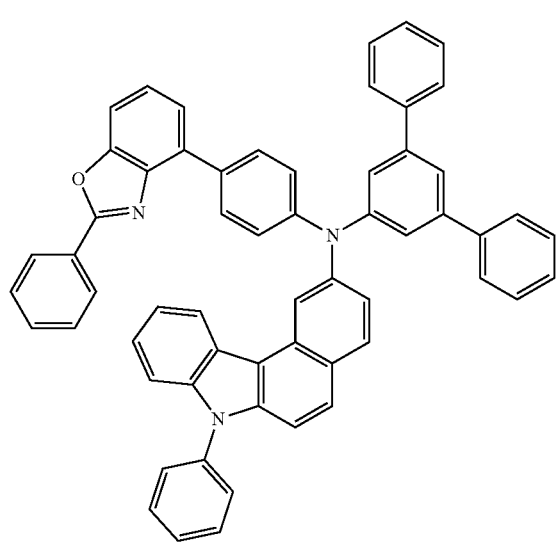
378
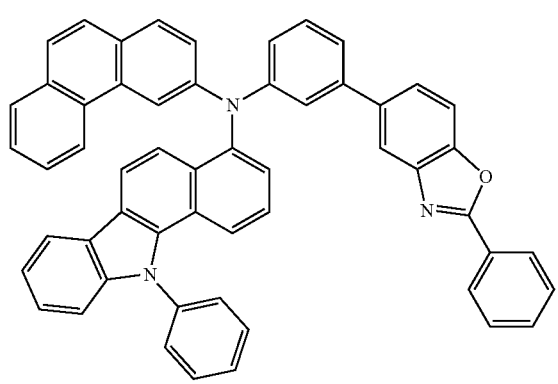
379
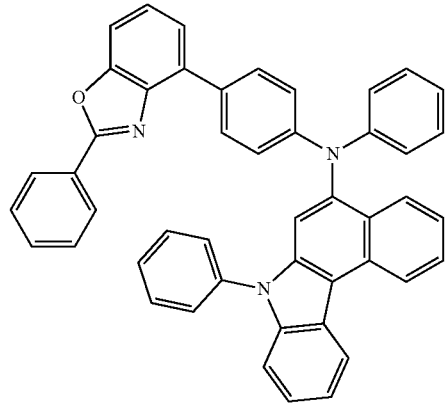
380
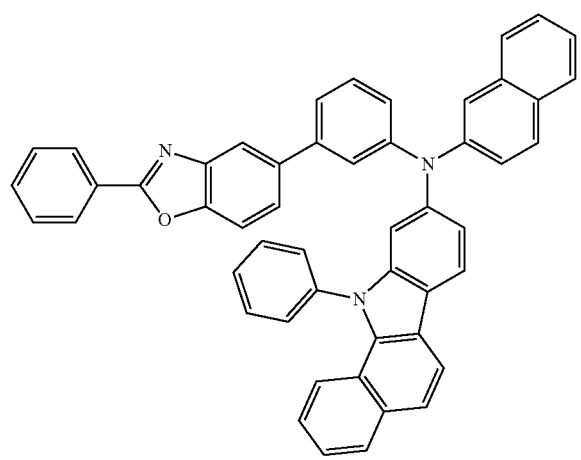
381
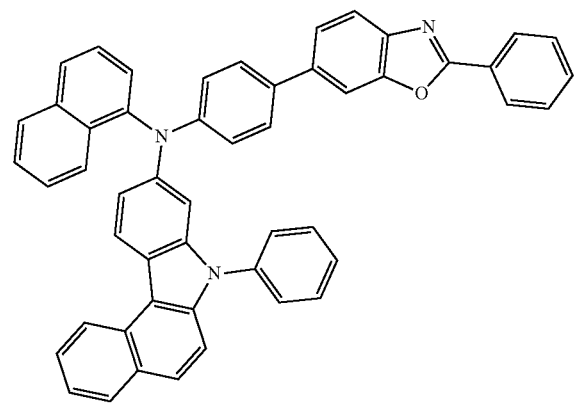

189
-continued
382
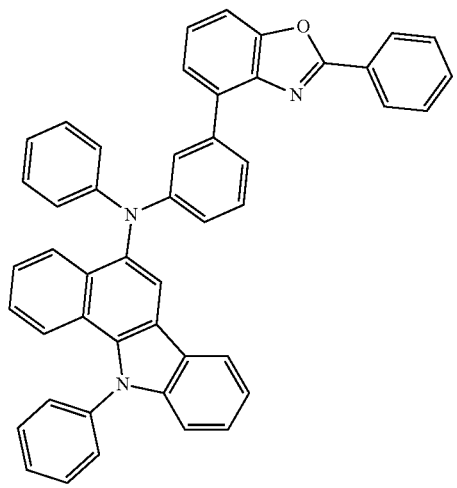
383
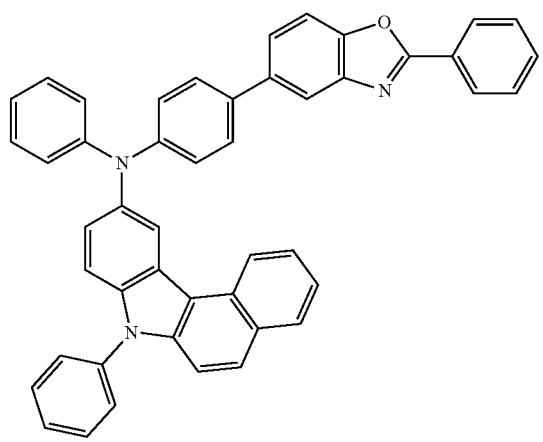
384
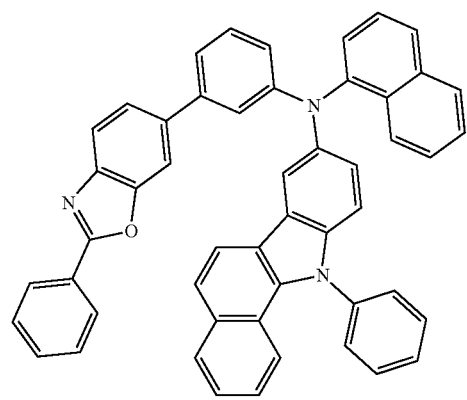
190
-continued
385
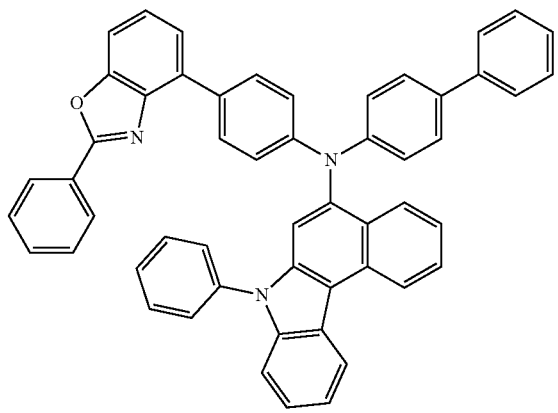
386
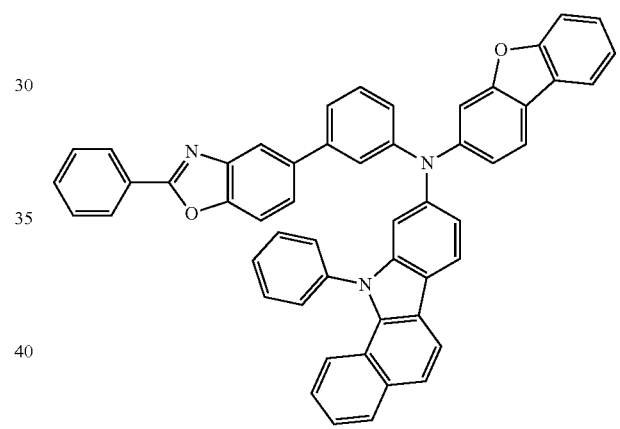
387
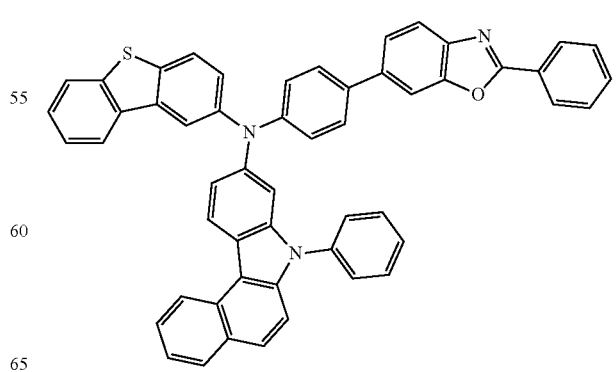

191
-continued
388
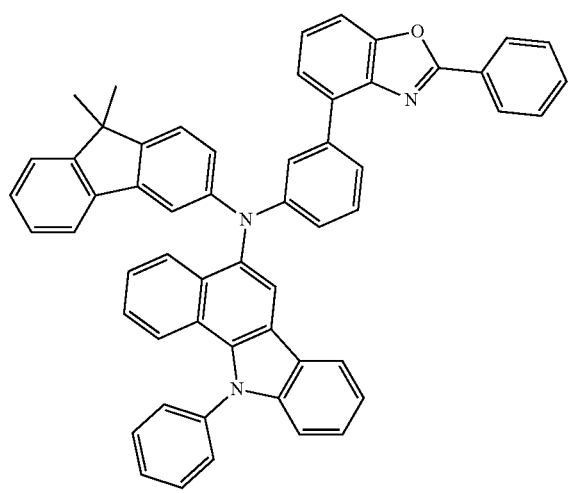
389
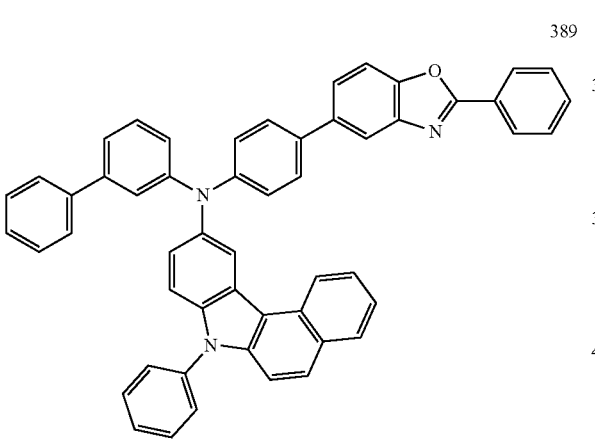
390
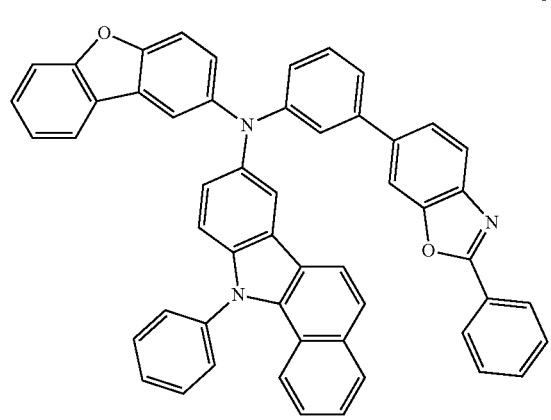
192
-continued
391
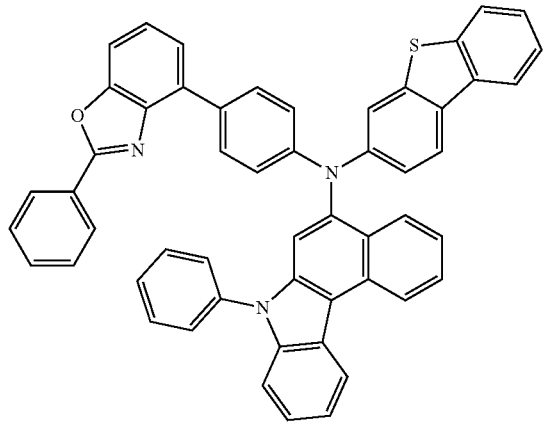
392
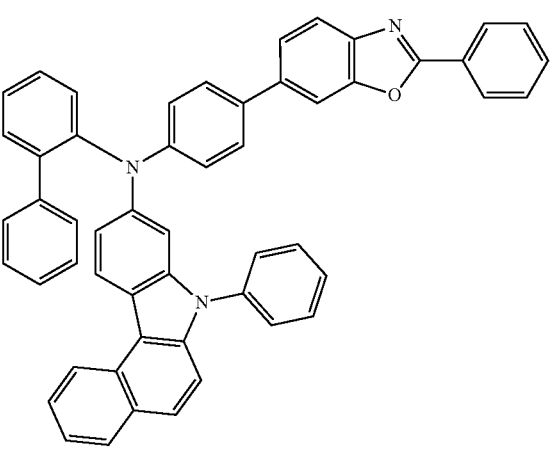
393

193
-continued
394
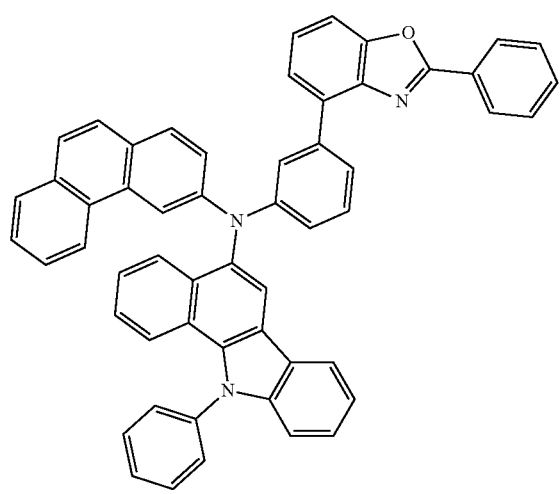
395
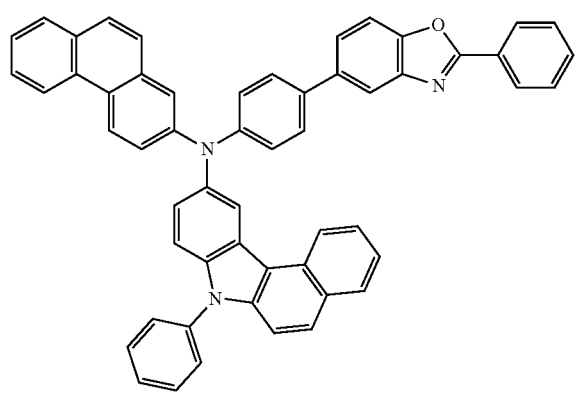
396
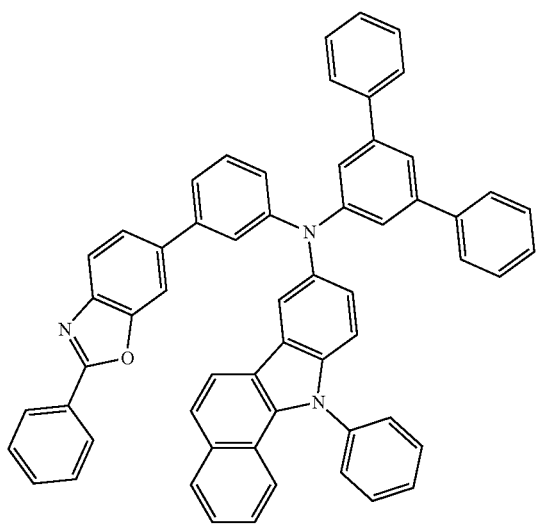
194
-continued
397
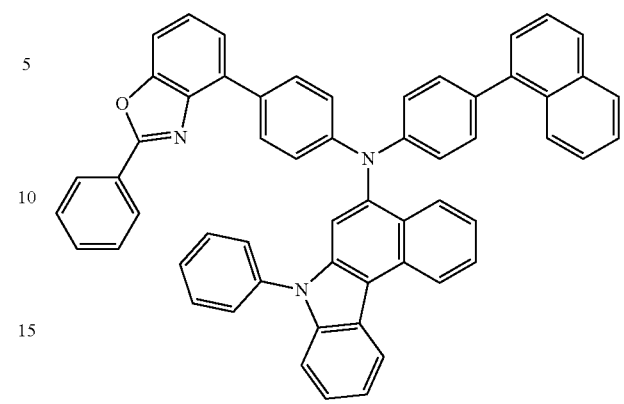
398
399
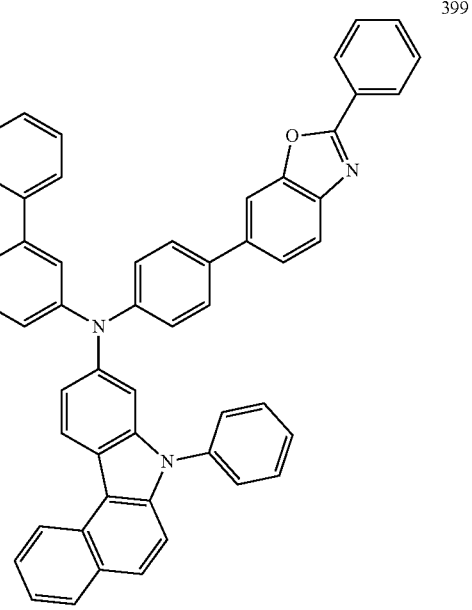

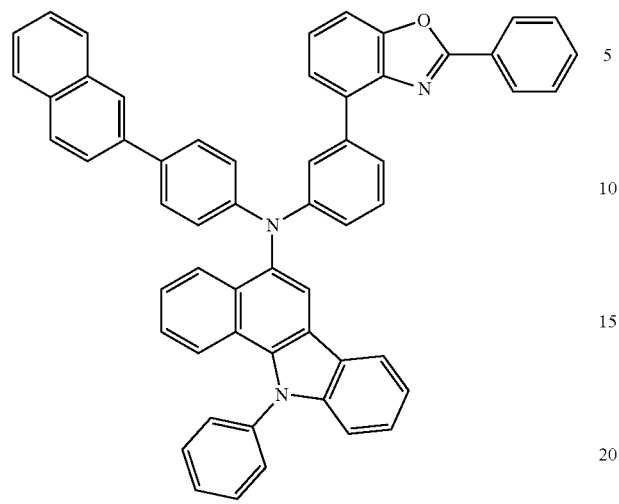
400
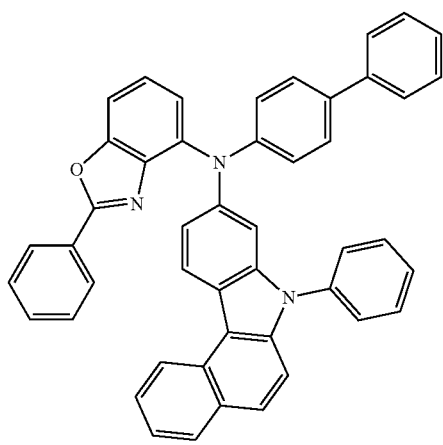
403
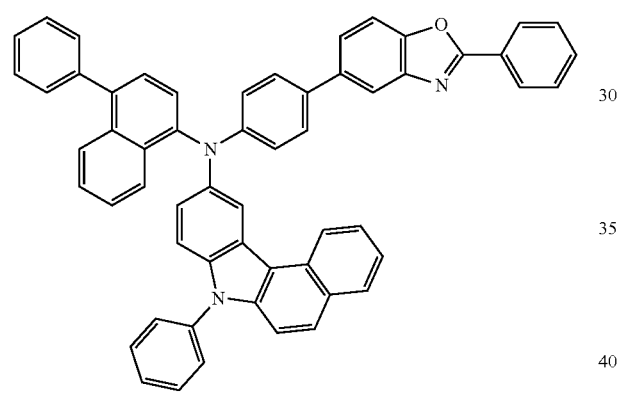
401
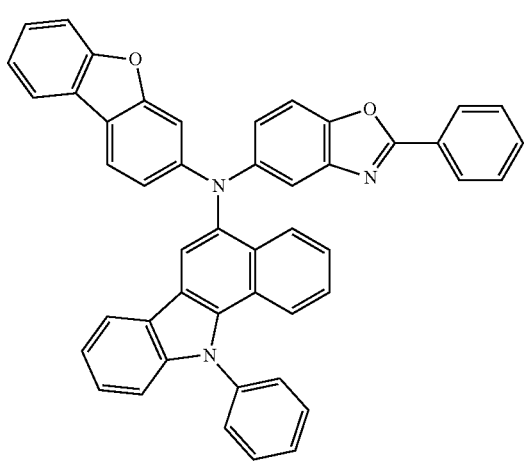
404
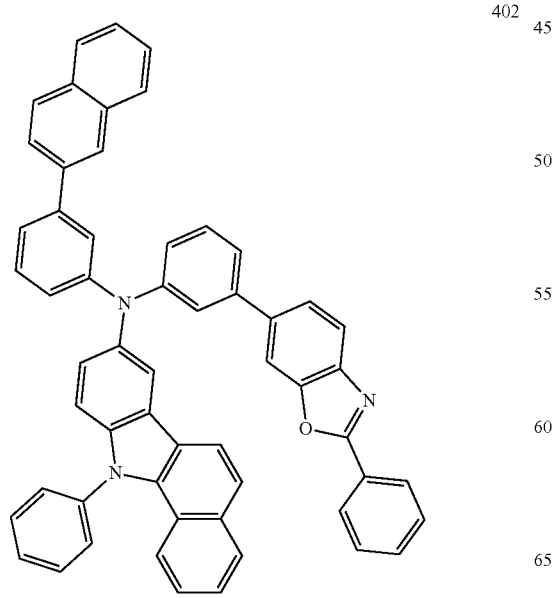
402
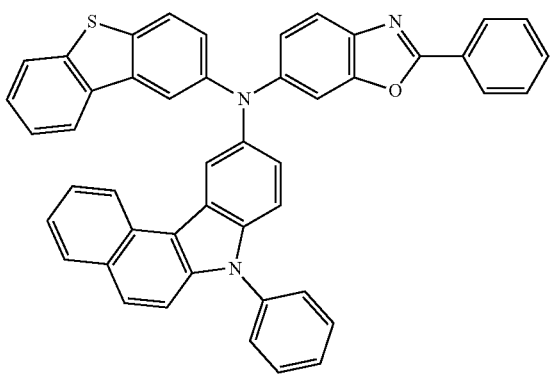
405

197
-continued
406
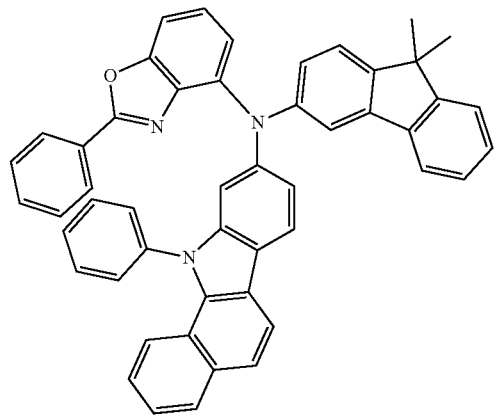
407
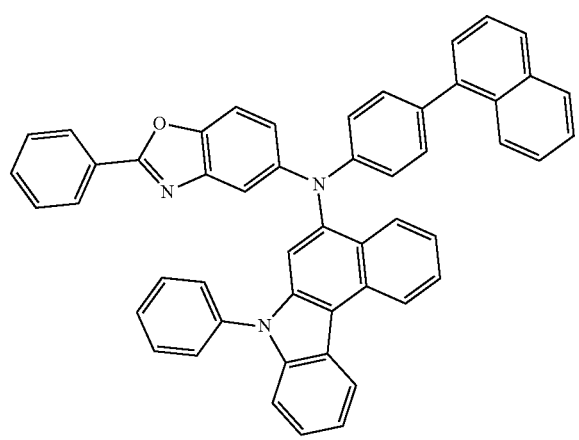
408
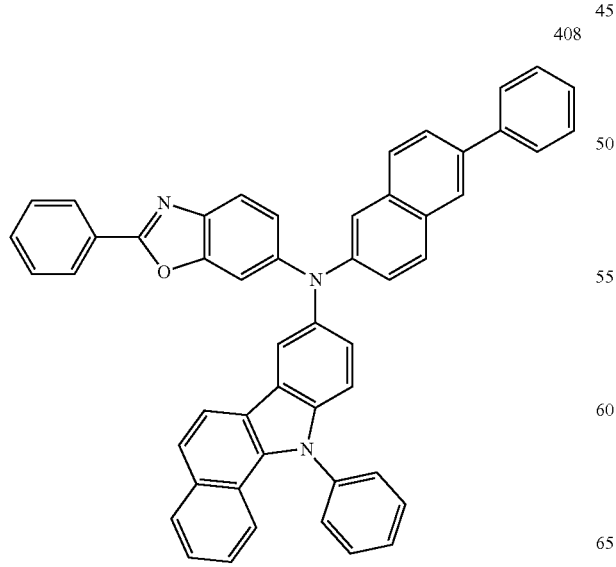
198
-continued
409
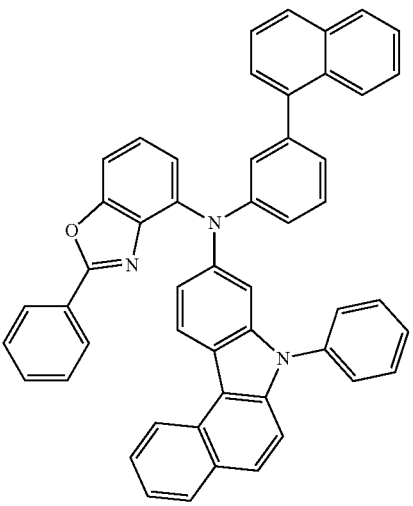
410
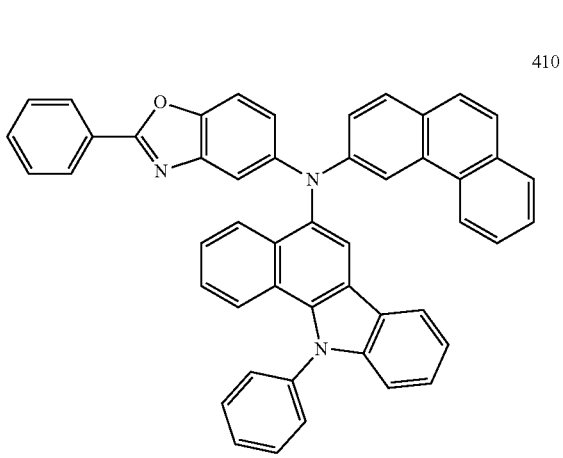
411
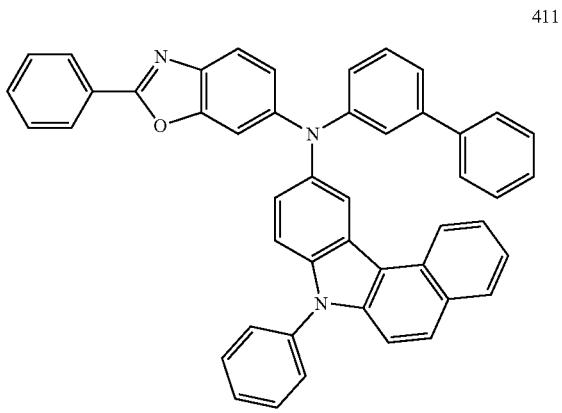

199
-continued
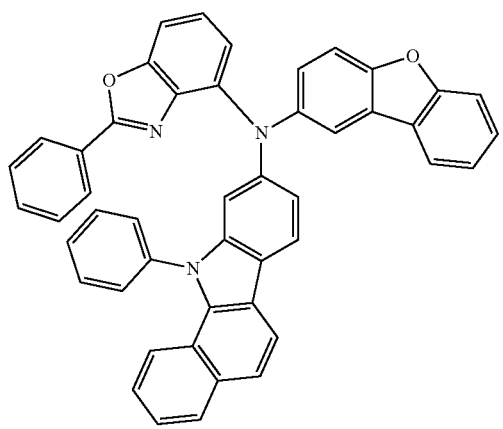
412
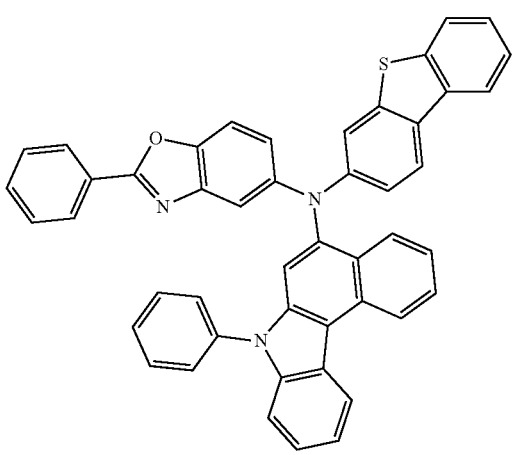
413
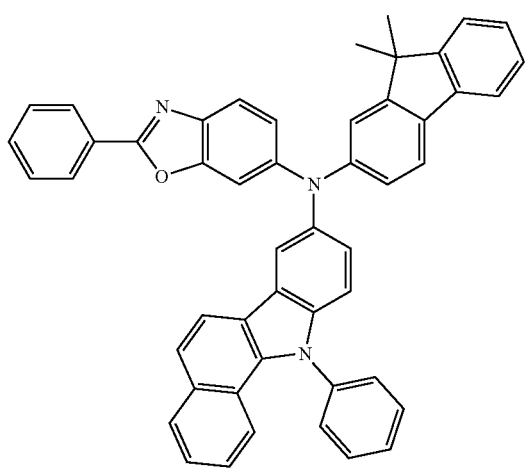
414
200
-continued
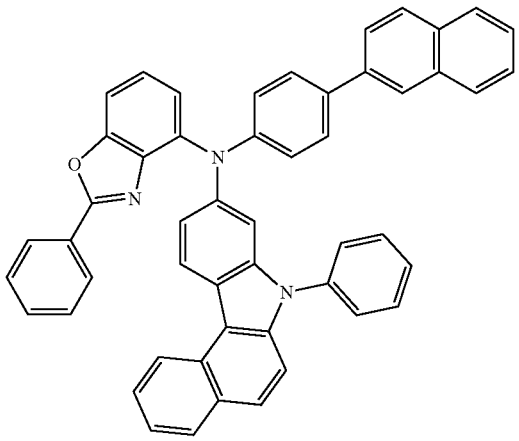
415
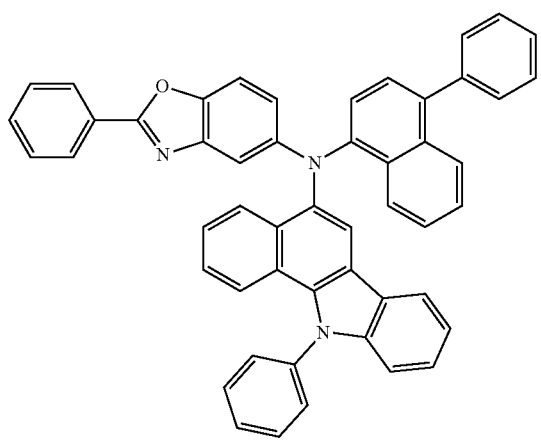
416
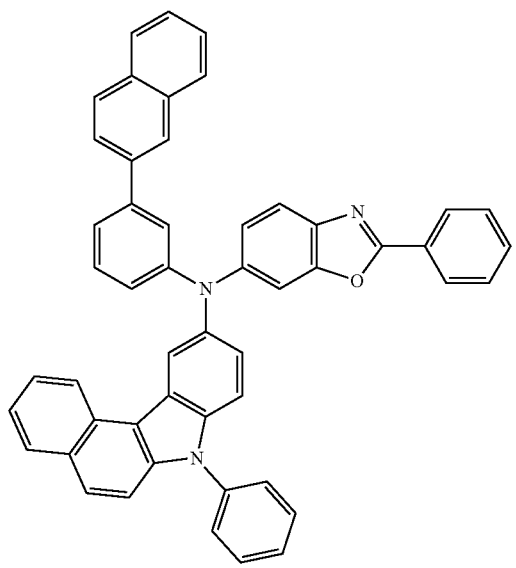
417

418
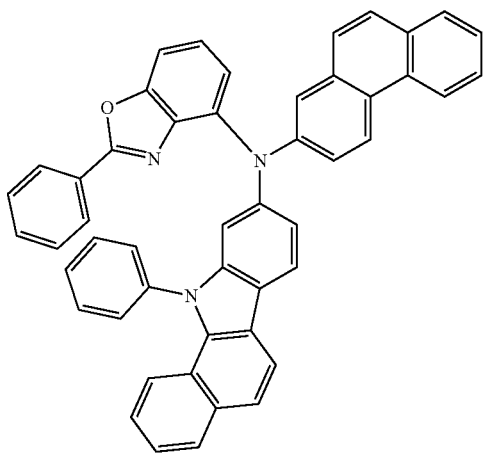
419
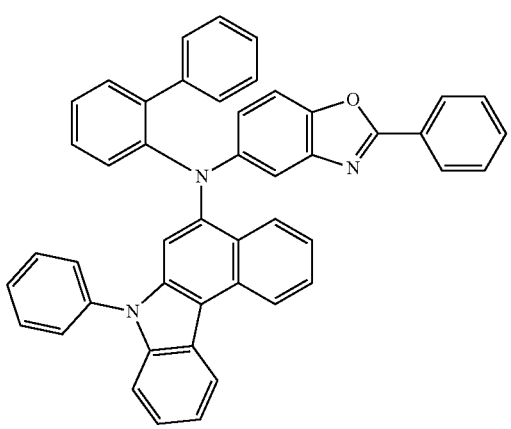
420
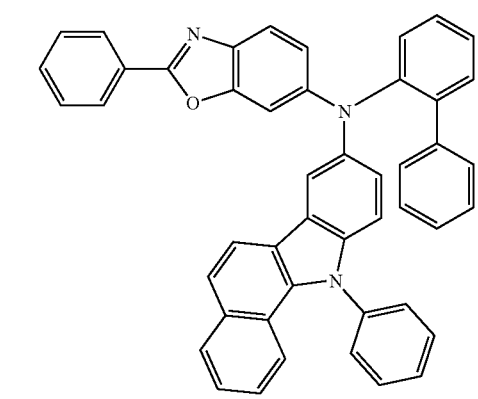
421
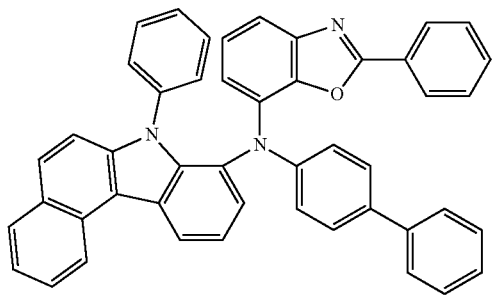
422
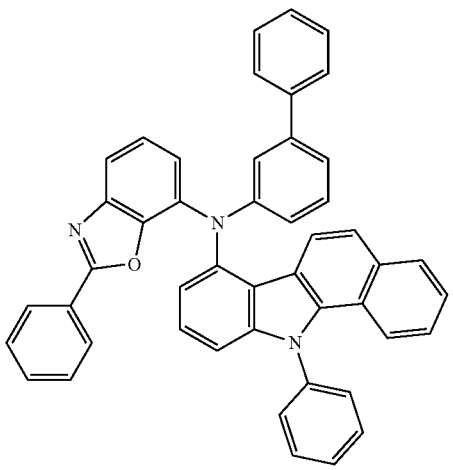
423
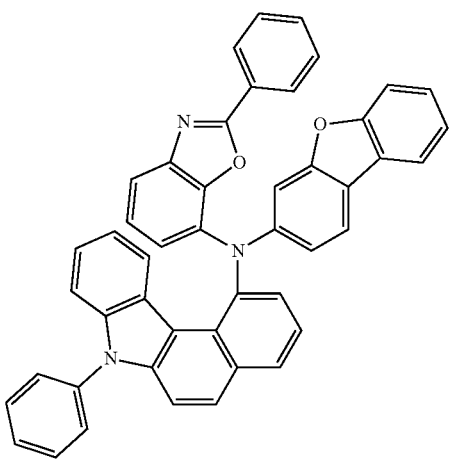
424

203
425
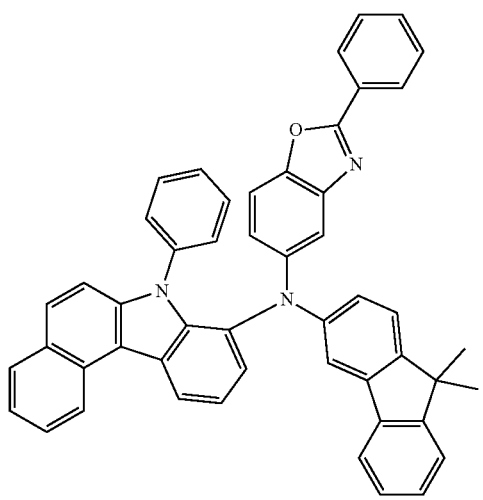
426
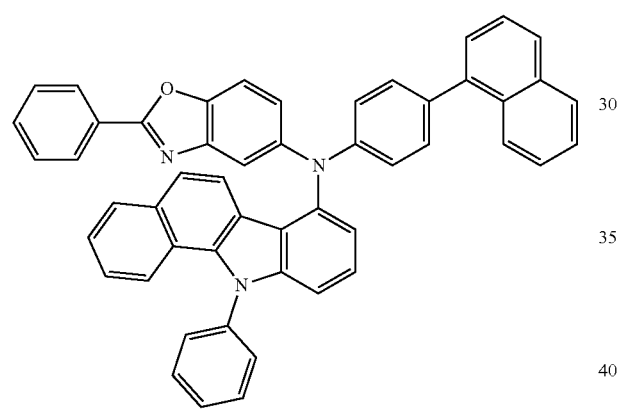
427
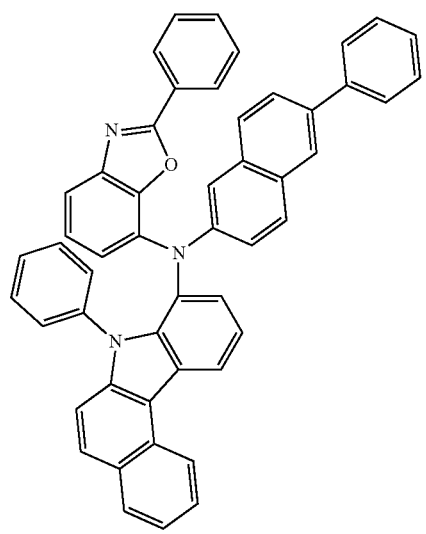
204
428
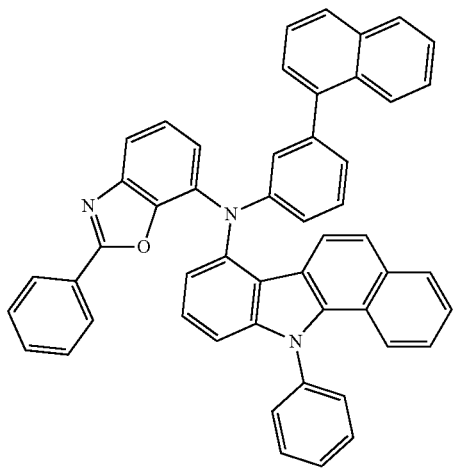
429
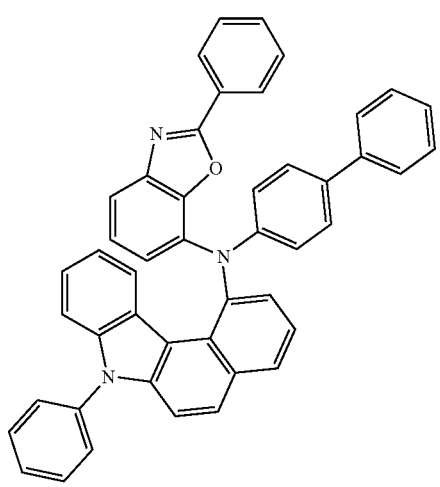
430
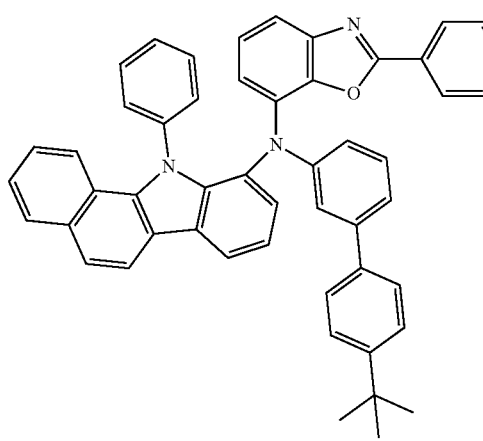

-continued
431
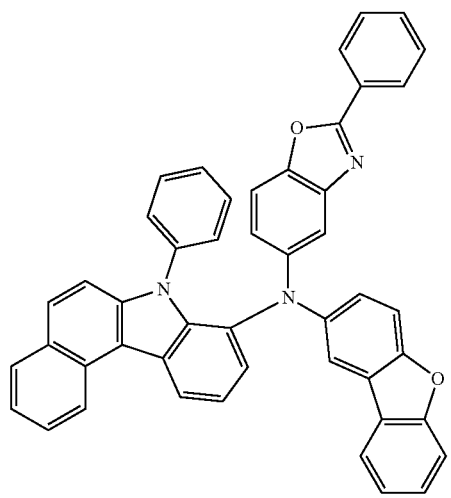
432
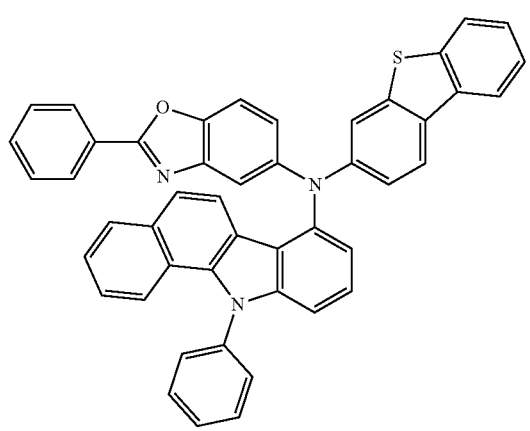
433
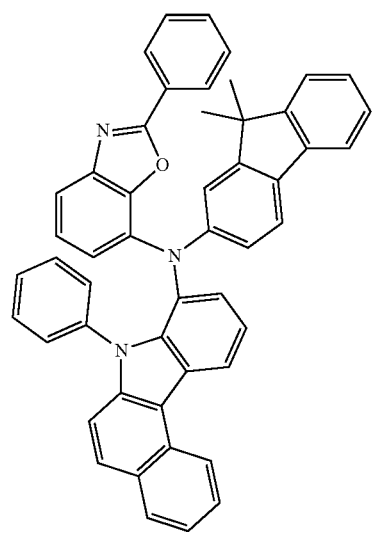
-continued
434
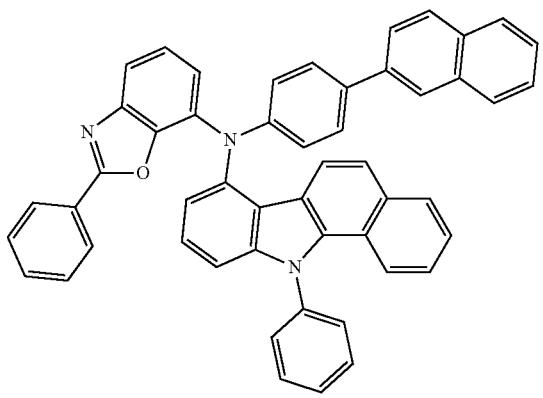
435
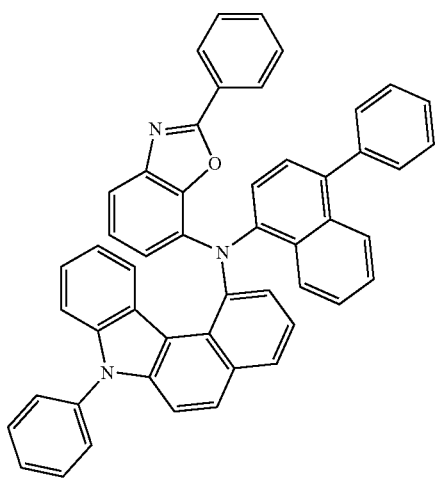
436
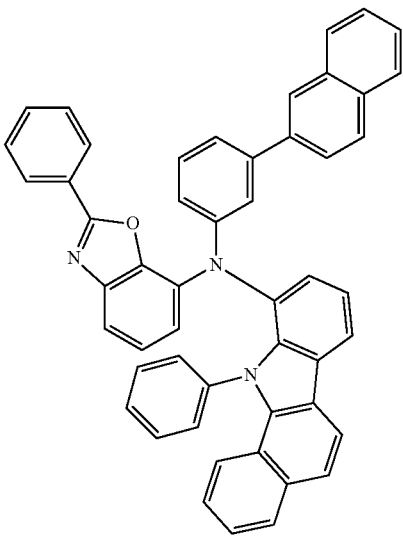

207
-continued
437
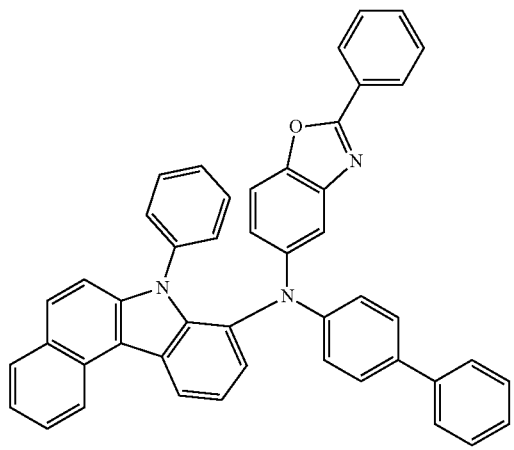
438
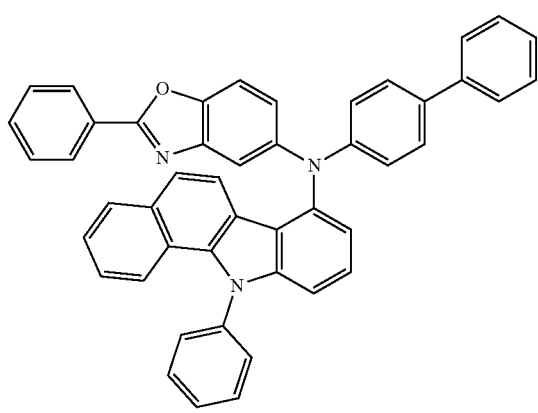
439
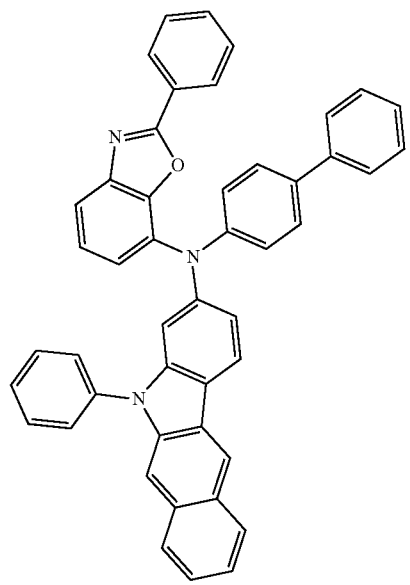
208
-continued
440
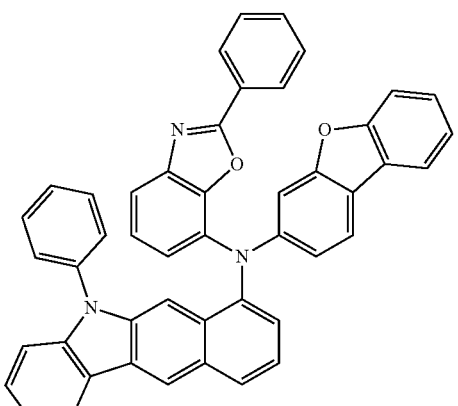
441
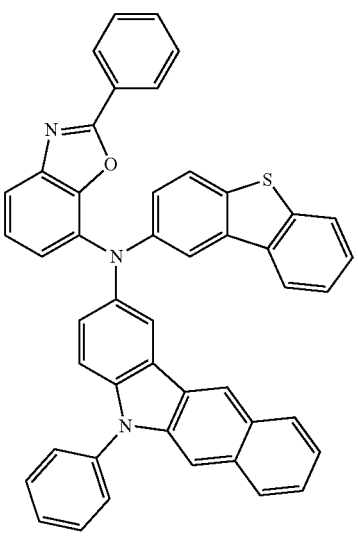
442
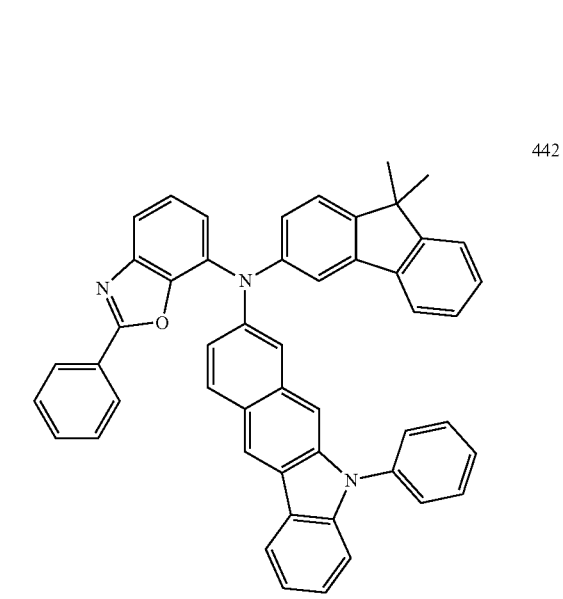

-continued
443
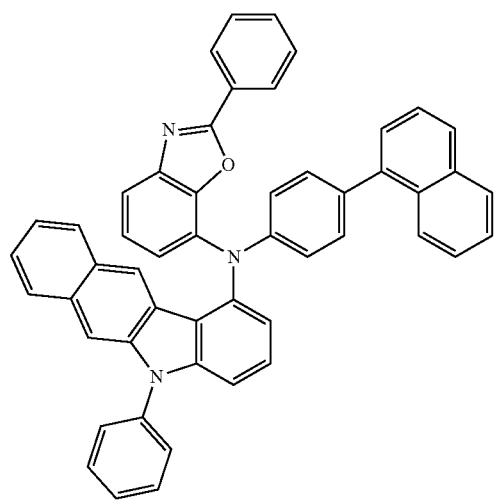
444
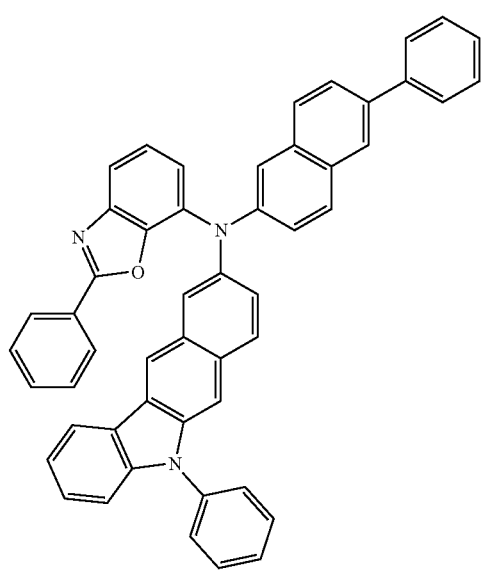
445
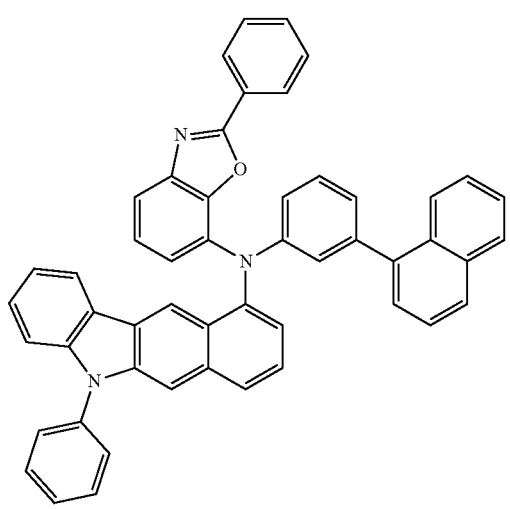
-continued
446
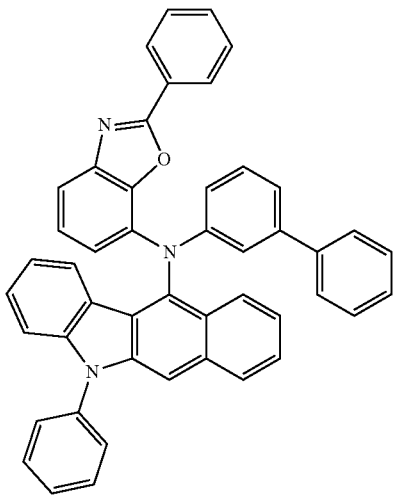
447
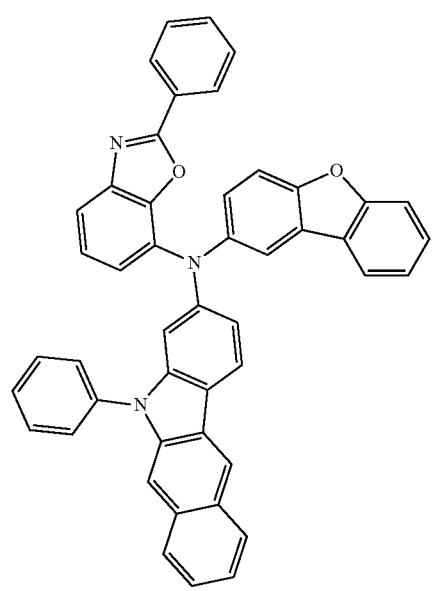
448
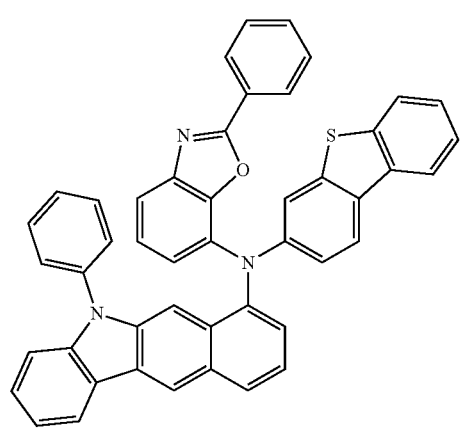

449
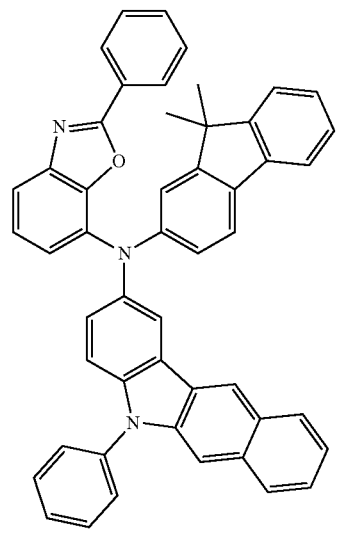
450
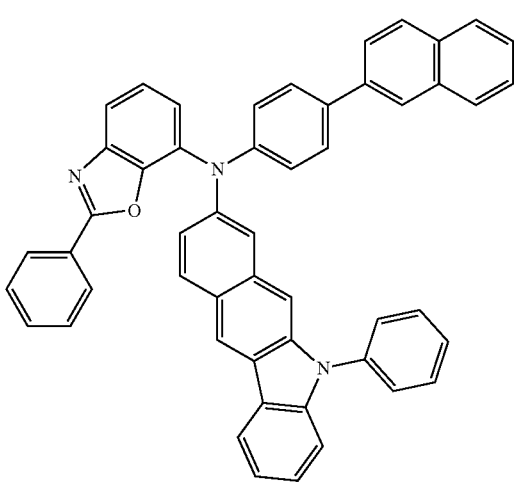
451
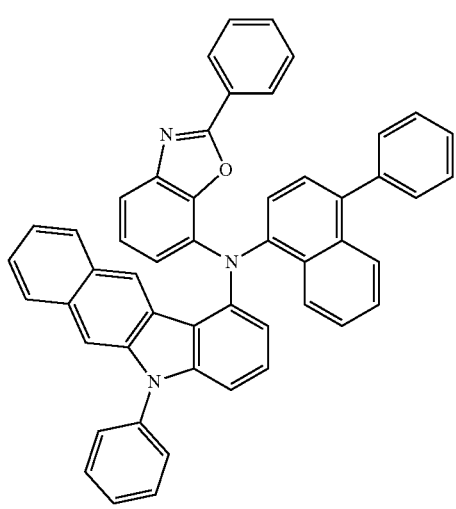
452
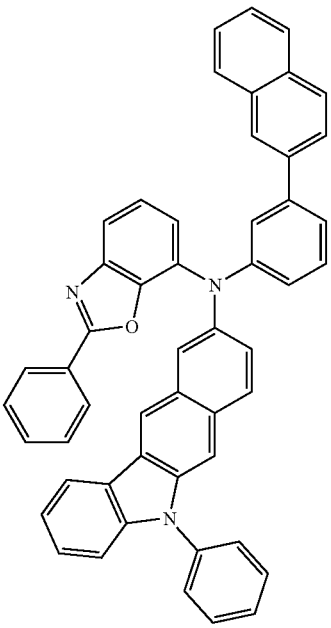
453
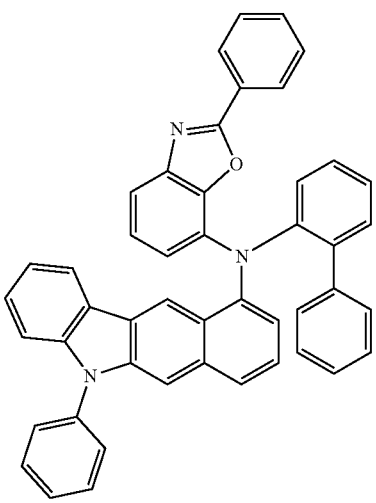
454
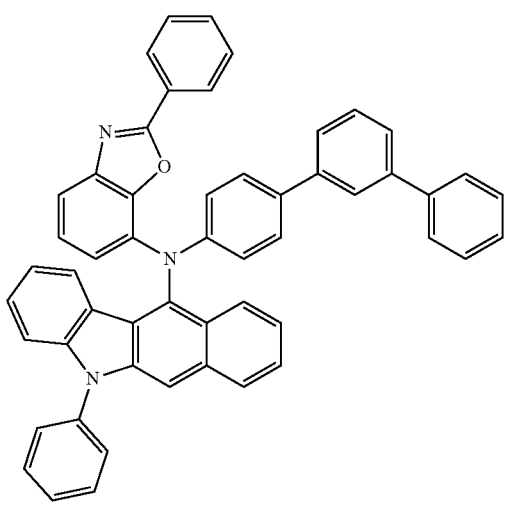

455
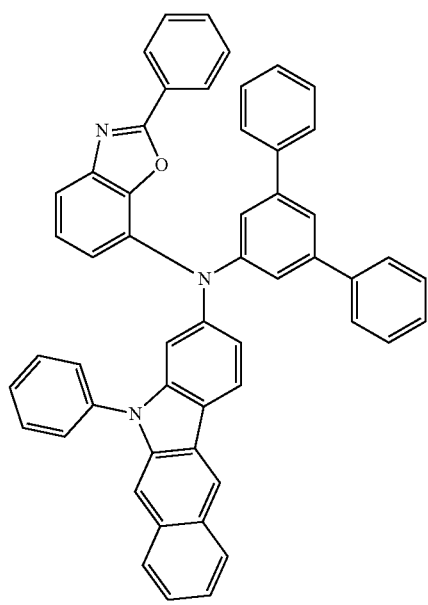
456
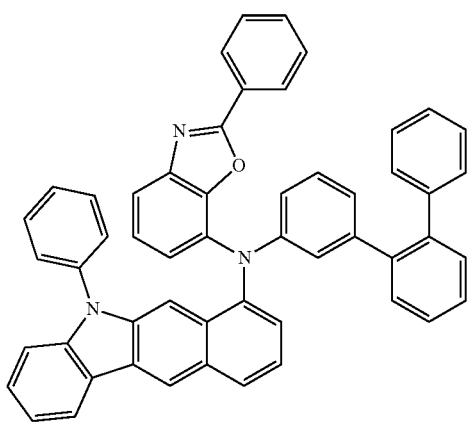
457
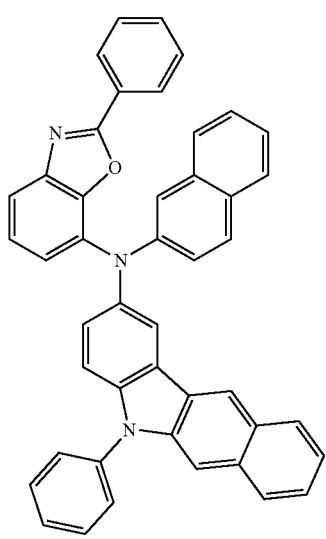
458
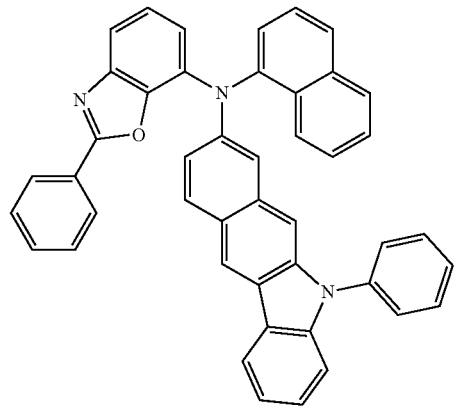
459
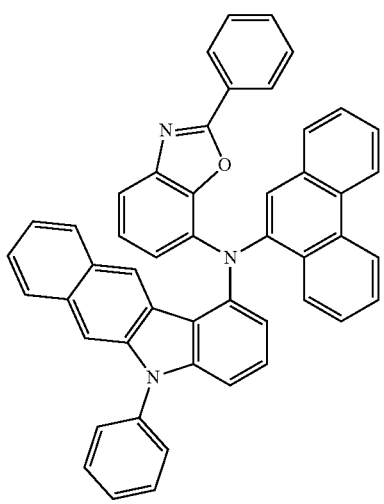
460
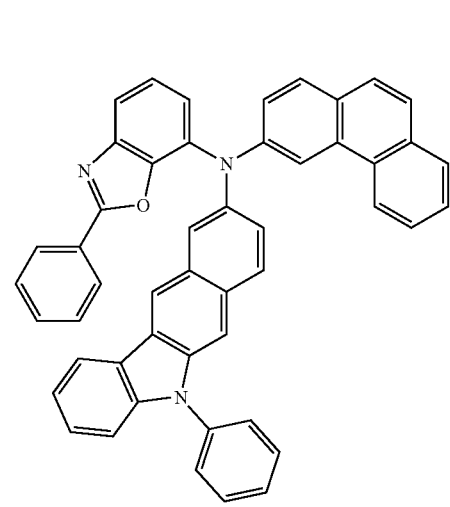

215
-continued
461
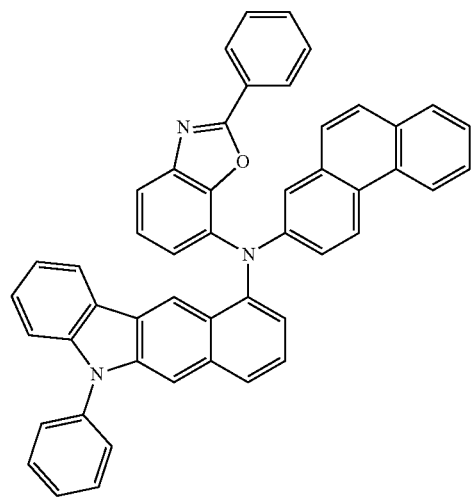
462
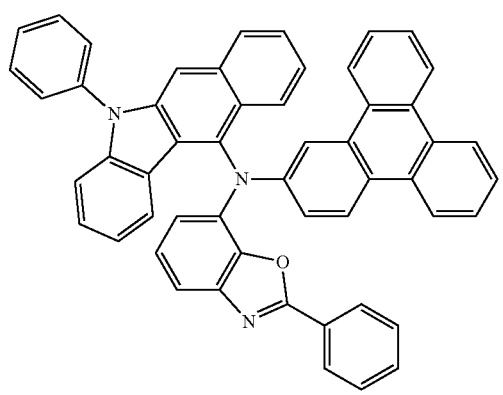
463
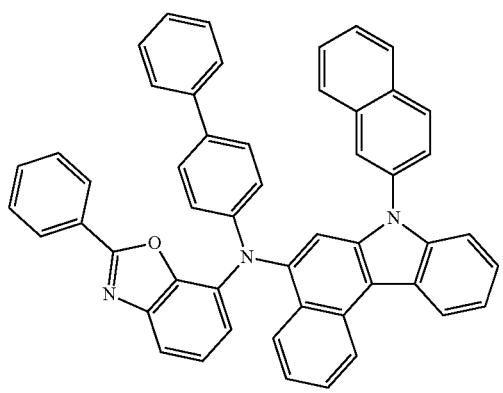
216
-continued
464
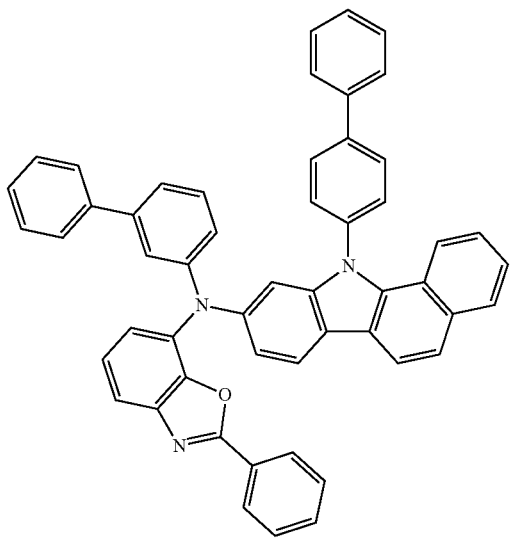
465
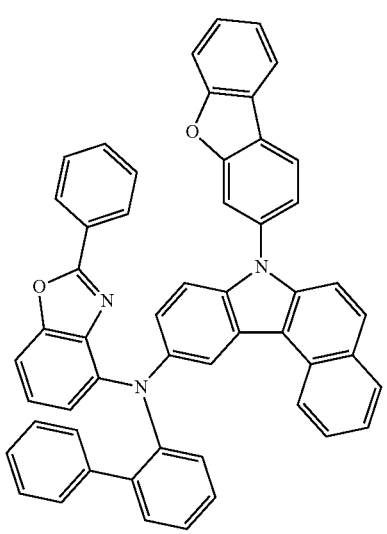
466
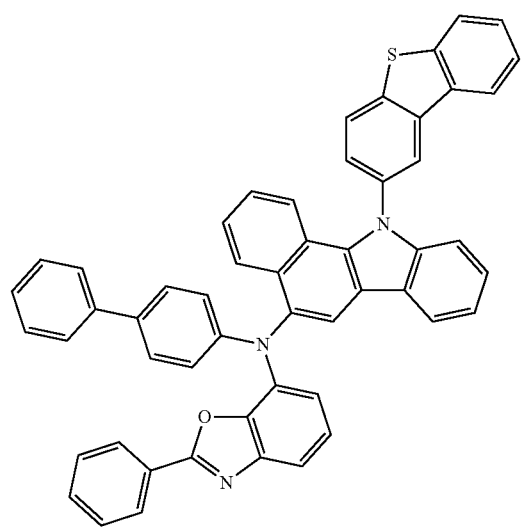

217
-continued
467
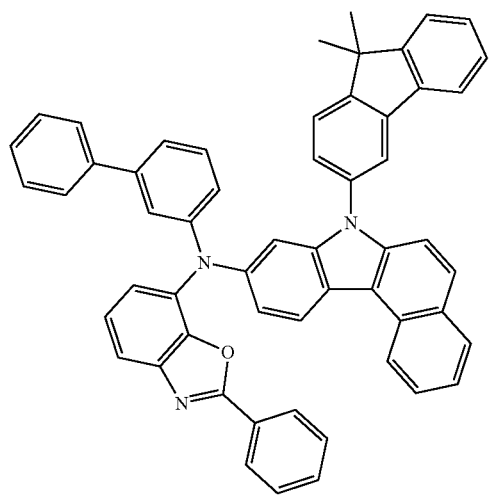
468
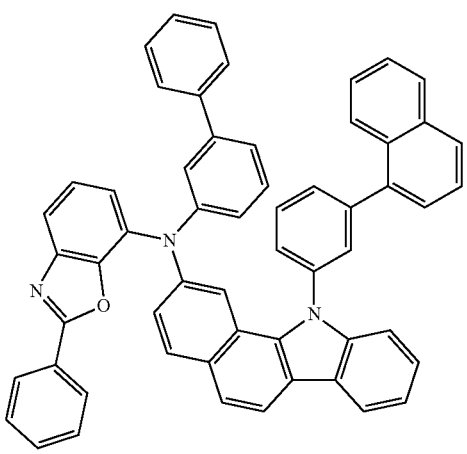
469
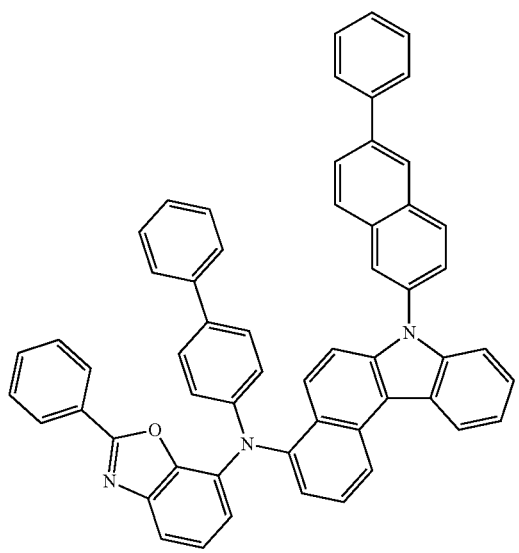
218
-continued
470
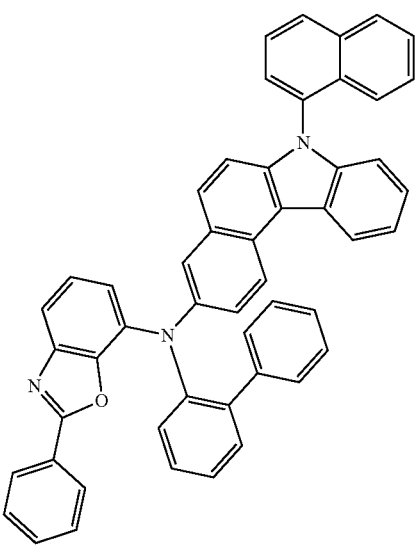
471
472
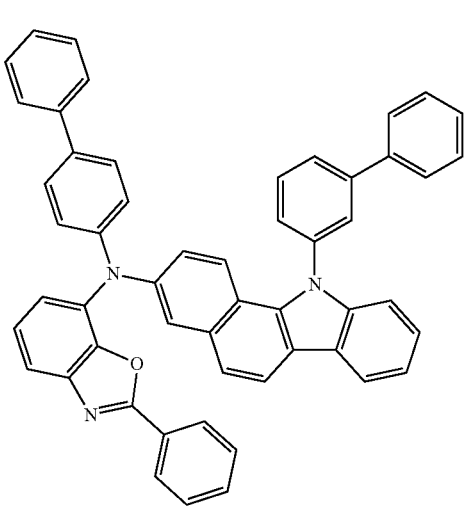

-continued
473
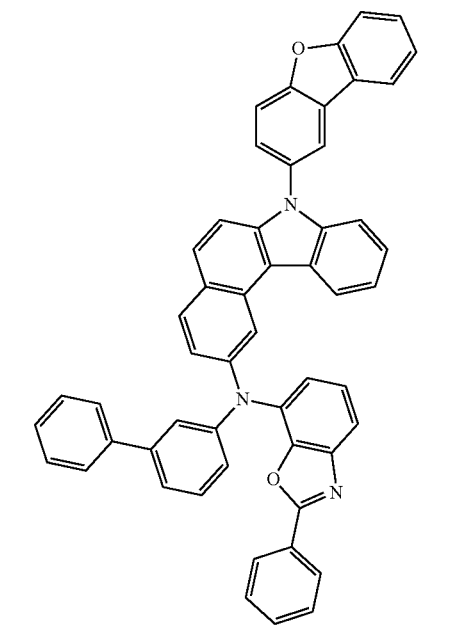
474
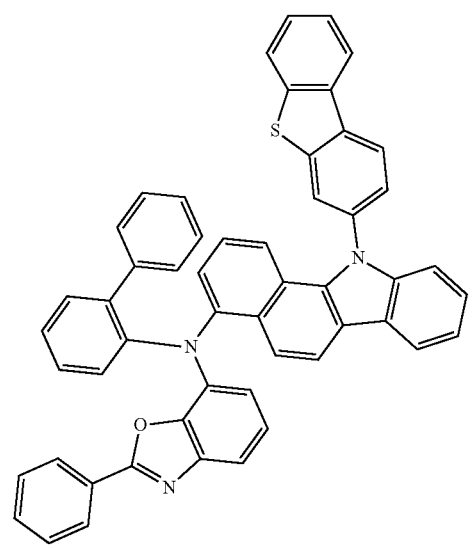
475
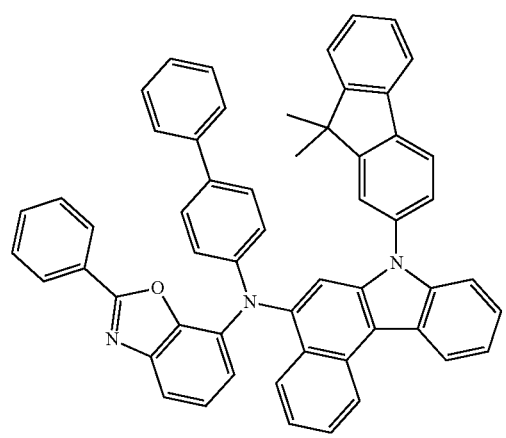
-continued
476
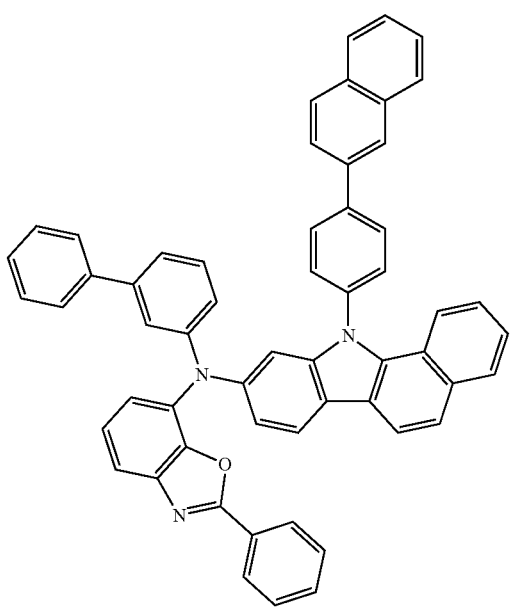
477
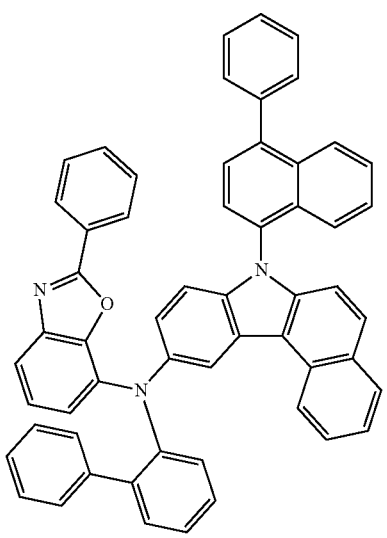
478
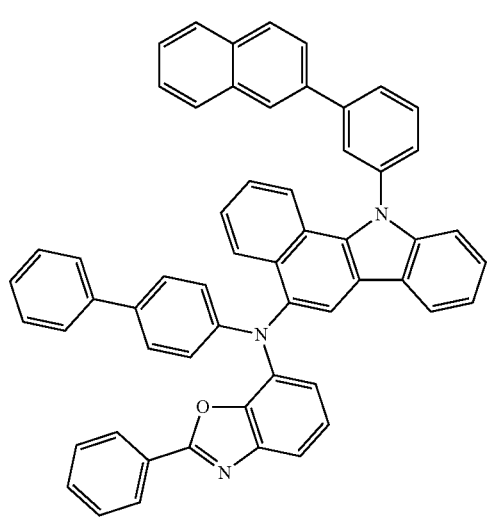

221
-continued
479
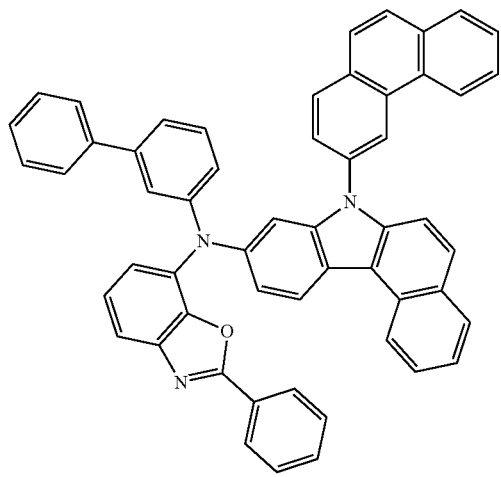
480
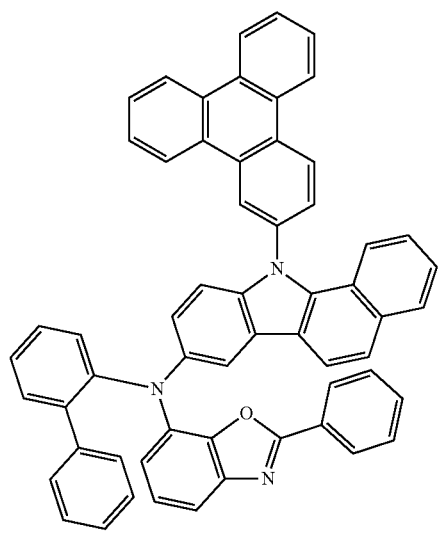
481
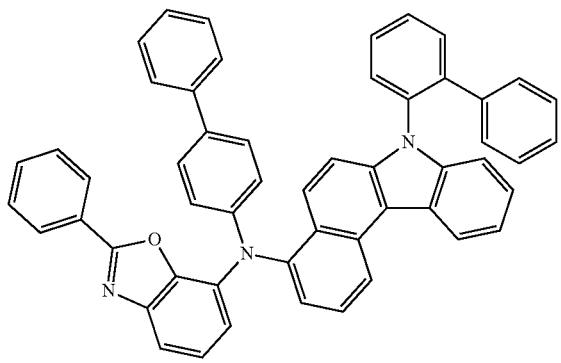
222
-continued
482
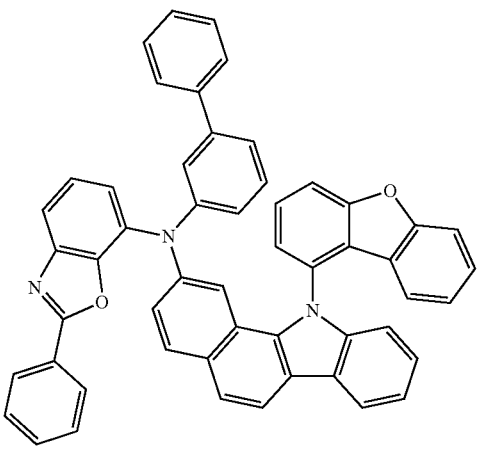
483
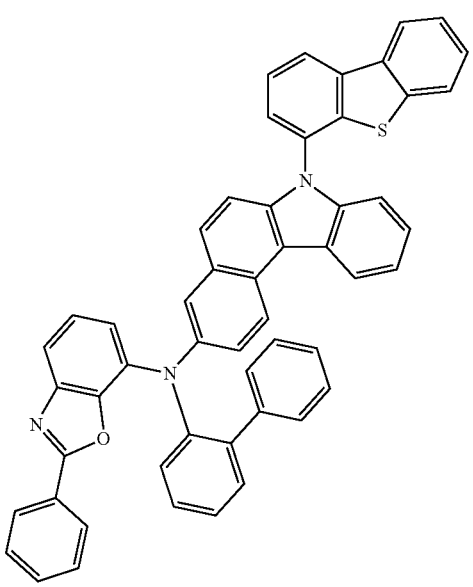
484
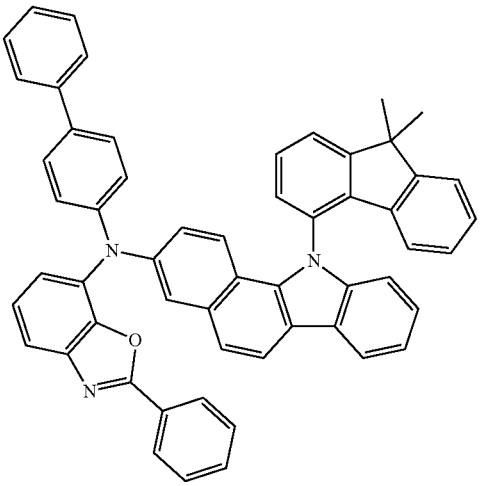

223
-continued
485
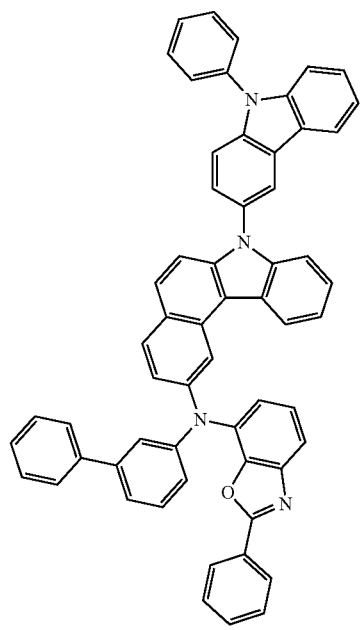
486
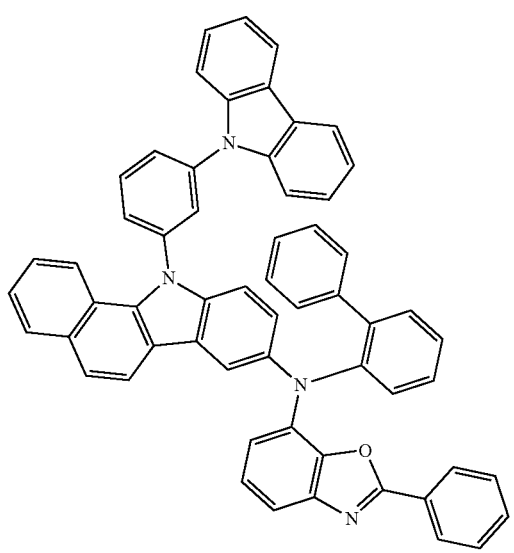
224
-continued
487
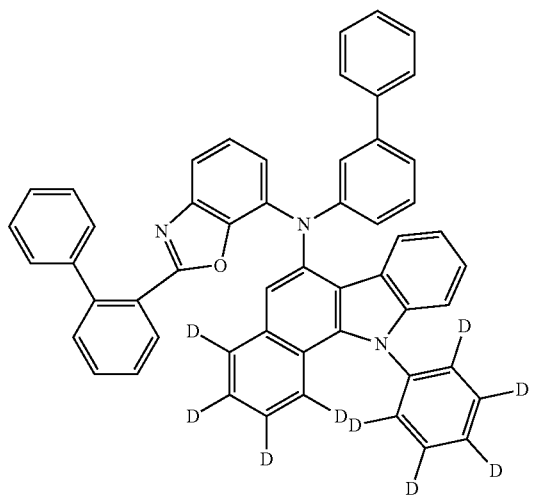
488
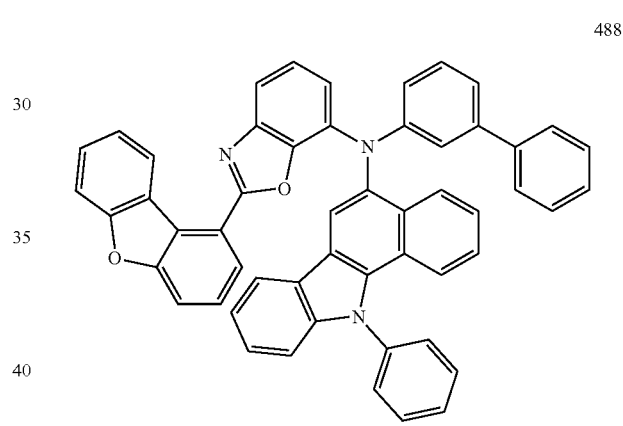
489
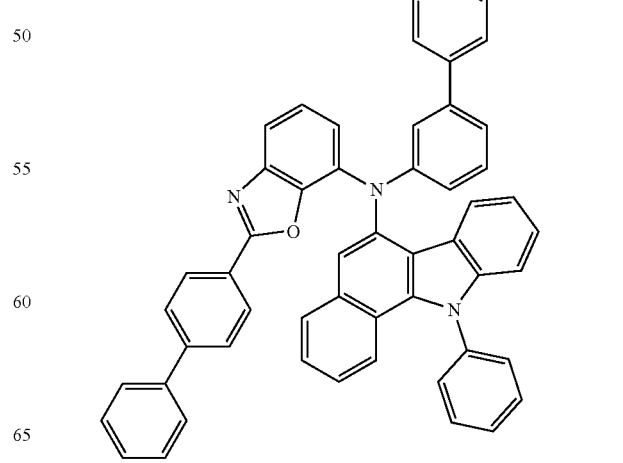

225
-continued
490
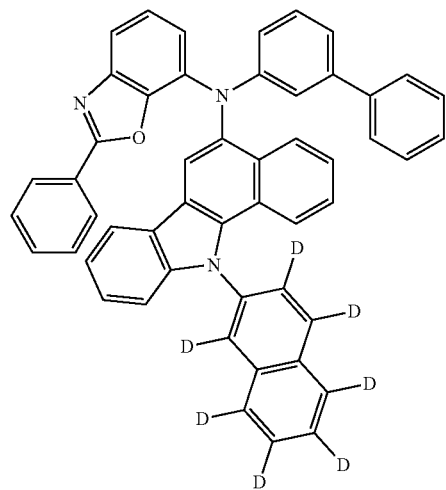
491
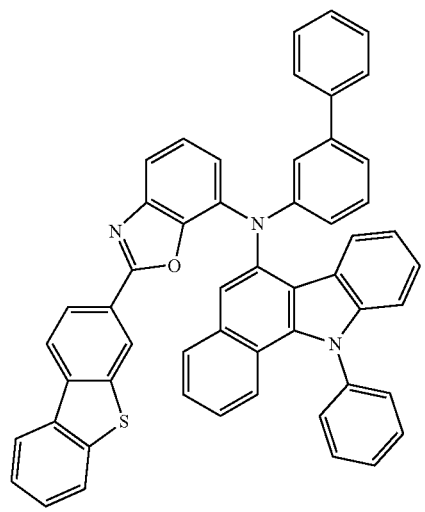
492
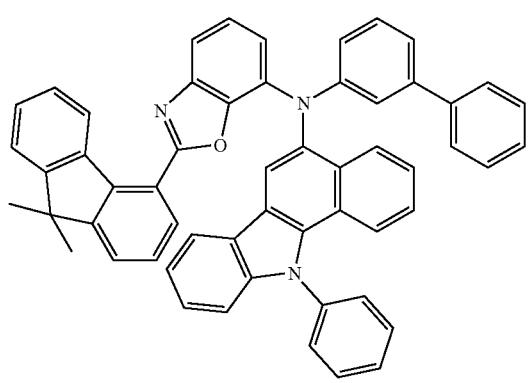
226
-continued
493
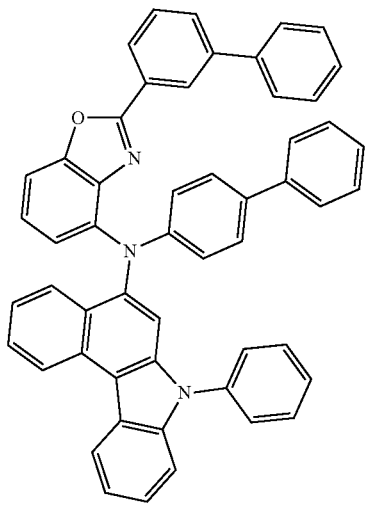
494
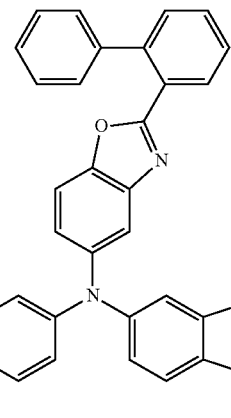
495
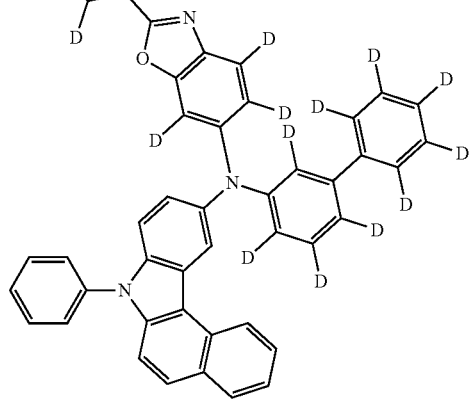

227
-continued
496
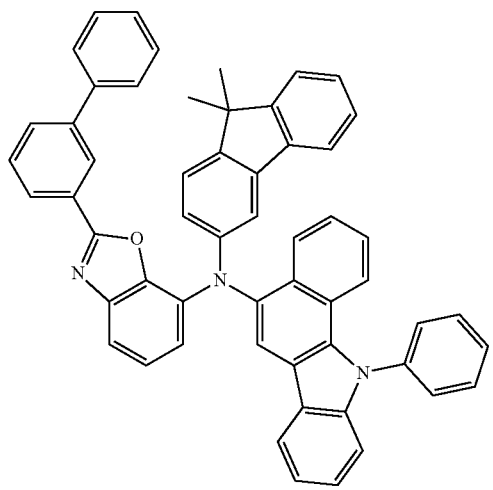
497
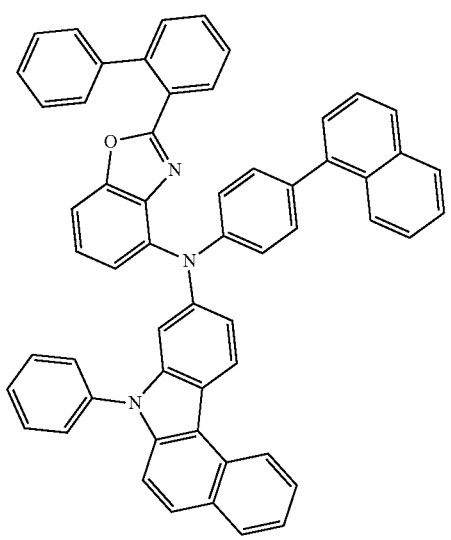
498
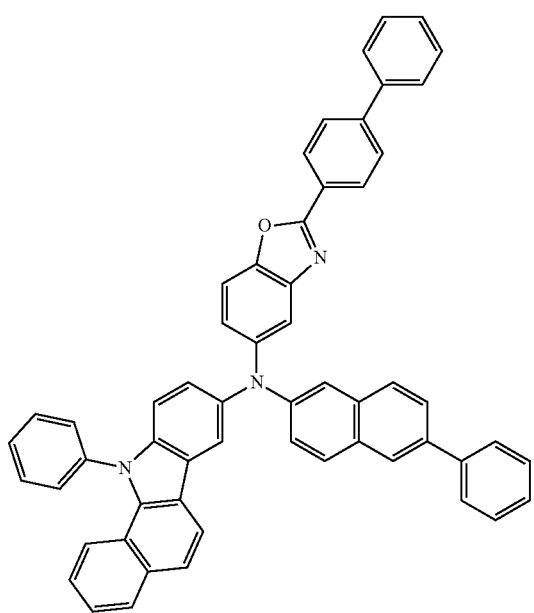
228
-continued
499
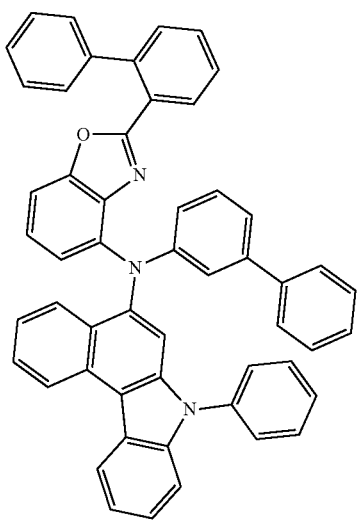
500
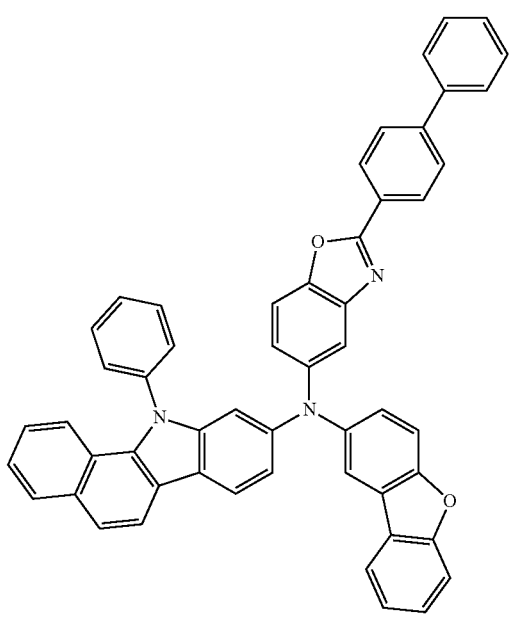

-continued
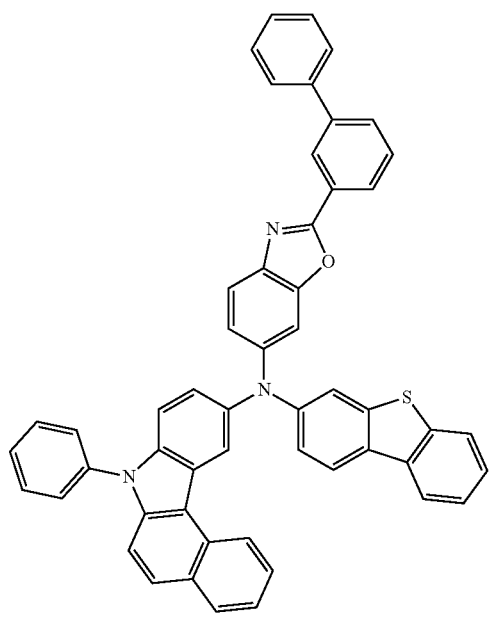
501
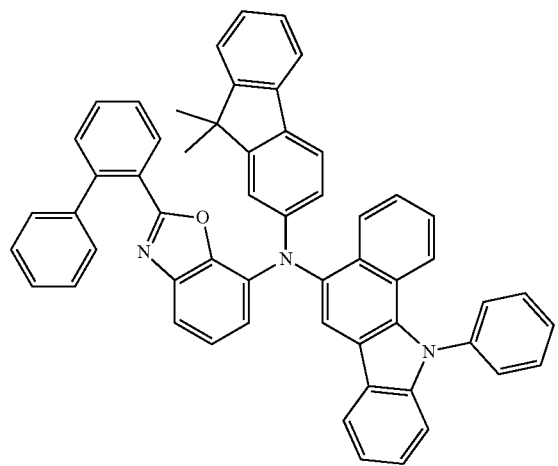
502
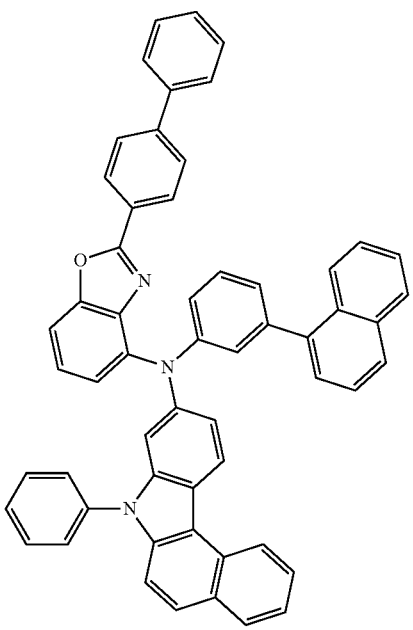
503
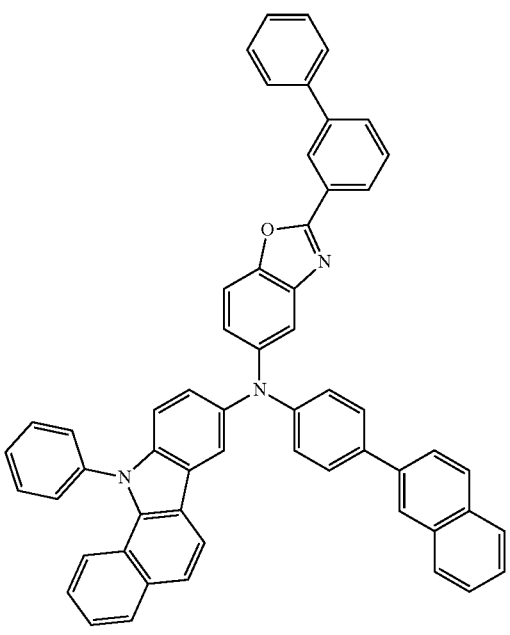
504

505

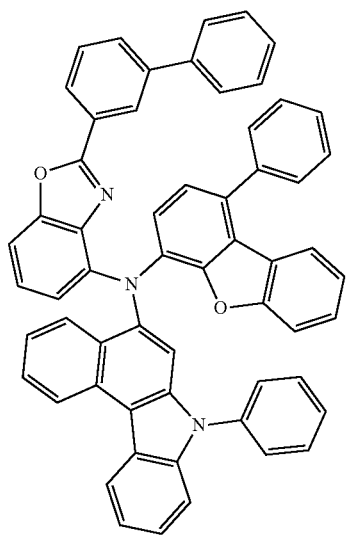

506

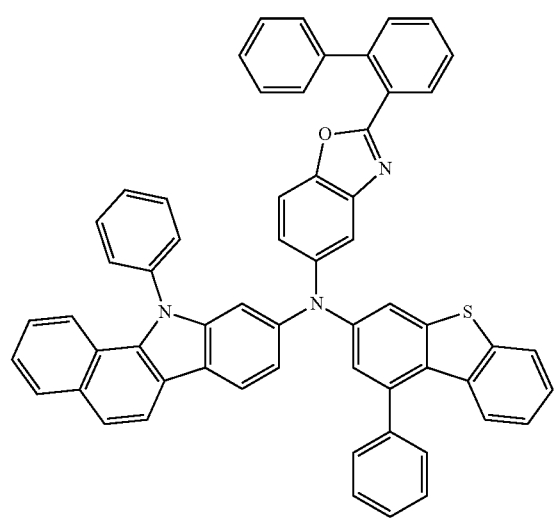

507

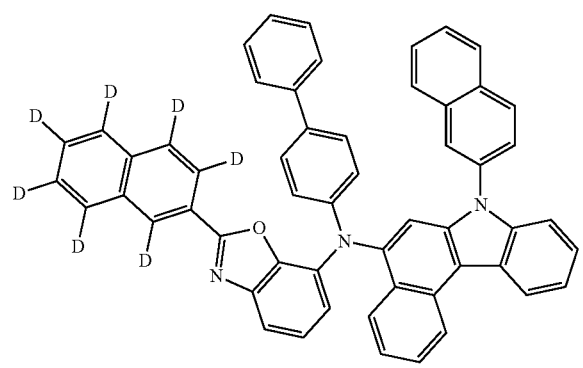

508

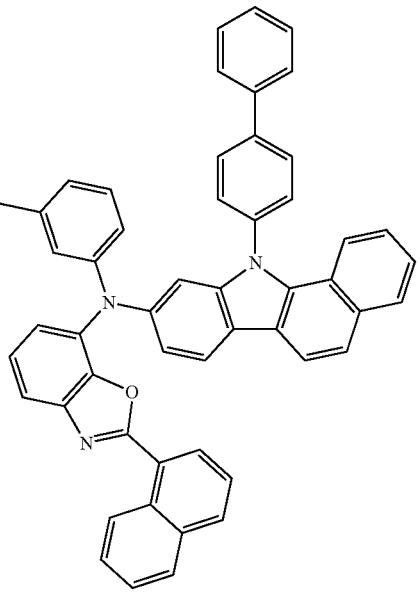

509

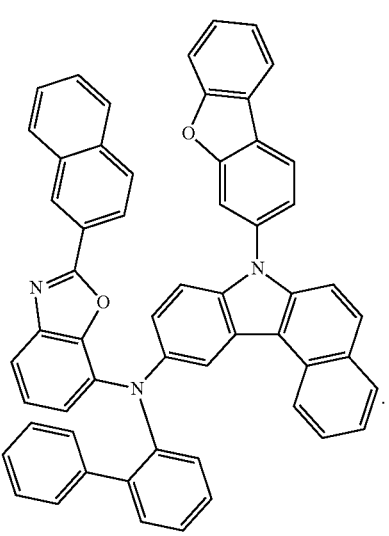

The present disclosure, in a second aspect, provides an organic electroluminescent device comprising an anode, a cathode, and a functional layer disposed between the anode and the cathode. The functional layer comprises the arylamine compound described in the first aspect of the present disclosure.

The arylamine compound provided in the present disclosure may be used to form at least one organic film layer in the functional layer so as to improve properties of the organic electroluminescent device such as luminous efficiency and service life.

Optionally, the functional layer comprises an organic light-emitting layer. The organic light-emitting layer comprises the arylamine compound. The organic light-emitting layer may be composed of the arylamine compound provided in the present disclosure, or may be composed of the arylamine compound provided in the present disclosure together with other materials.

Optionally, the functional layer further comprises a hole transport layer (also known as first hole transport layer) and a hole adjustment layer (also known as second hole transport layer). The hole transport layer is located between the anode and the organic light-emitting layer, and the hole adjustment layer is located between the hole transport layer and the organic light-emitting layer. In some embodiments, the hole adjustment layer is composed of the arylamine compound provided in the present disclosure, or composed of the arylamine compound provided in the present disclosure together with other materials.

According to a specific embodiment, the organic electroluminescent device is as shown in FIG. 1, and comprises an anode 100, a hole injection layer 310, a hole transport layer 321, a hole adjustment layer 322, an organic light-emitting layer 330, an electron transport layer 340, an electron injection layer 350, and a cathode 200 that are stacked in sequence.

In the present disclosure, the anode 100 comprises an anode material, which is preferably a high-work function material contributing to injection of holes into the functional layer. Specific examples of the anode material include, but are not limited to: metals such as nickel, platinum, vanadium, chromium, copper, zinc, gold, and alloys thereof; metal oxides such as zinc oxide, indium oxide, indium tin oxide (ITO), and indium zinc oxide (IZO); combinations of metals and oxides, such as ZnO:Al or $SnO_2$:Sb; and conductive polymers such as poly(3-methylthiophene), poly[3,4-(ethylene-1,2-dioxy)thiophene] (PEDT), polypyrrole, and polyaniline. Preferably, a transparent electrode comprising indium tin oxide (ITO) is included as the anode.

In the present disclosure, the hole transport layer and the hole adjustment layer each may comprise one or more hole transport materials. The hole transport material may be selected from carbazole polymer, carbazole-linked triarylamine compounds, or other types of compounds, which may be selected from the following compounds or any combination thereof:

HT-1

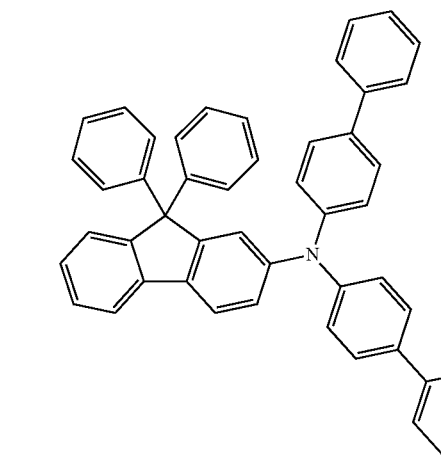

HT-2

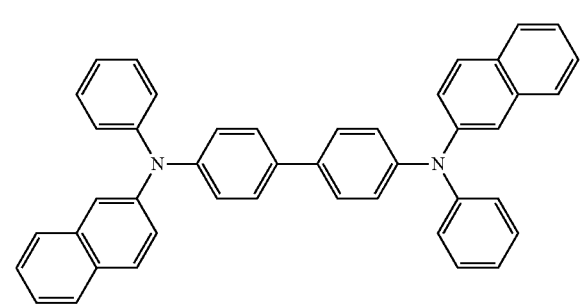

HT-3

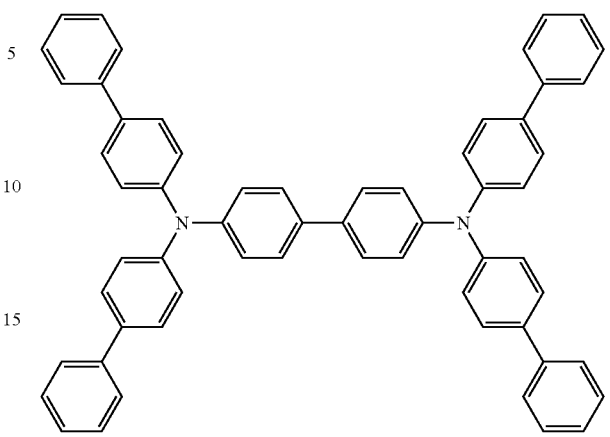

HT-4

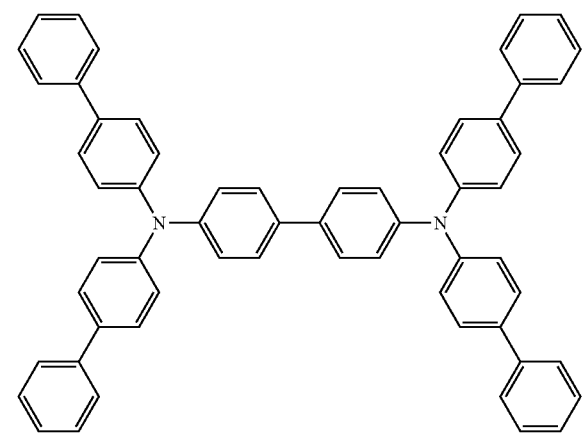

HT-5

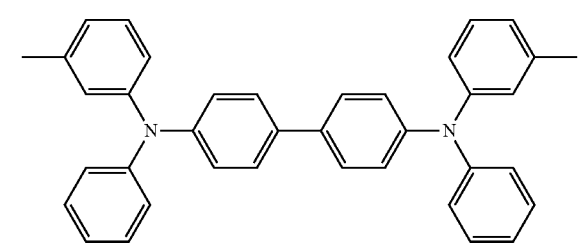

HT-6
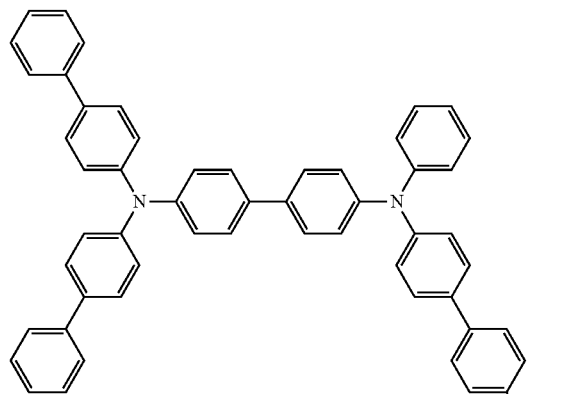
HT-9(α-NPD)
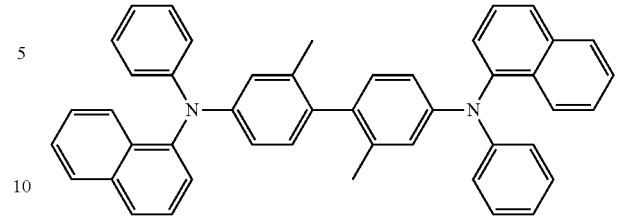
HT-10
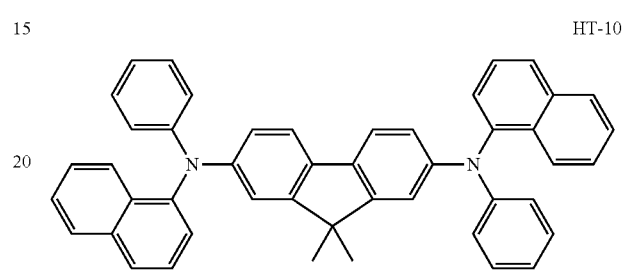
HT-7
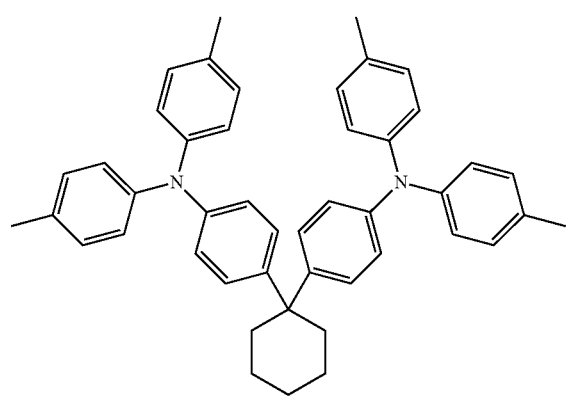
HT-11
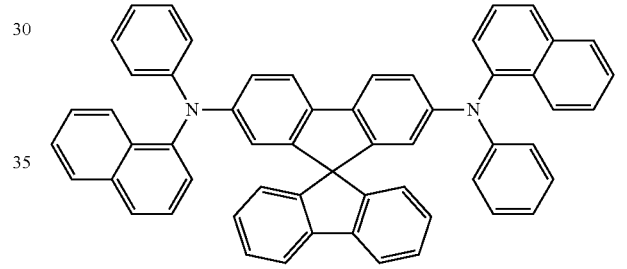
HT-8
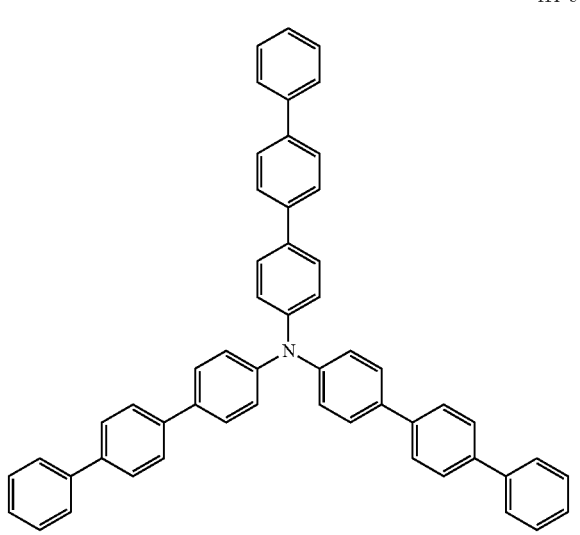
HT-12
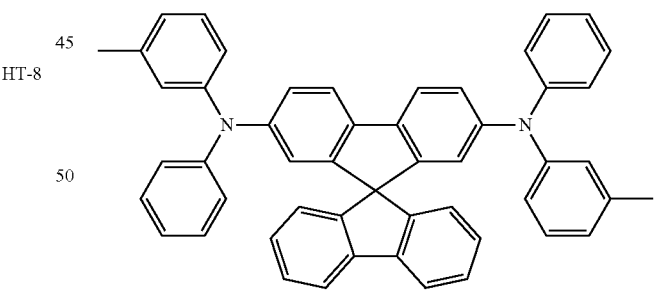
HT-13
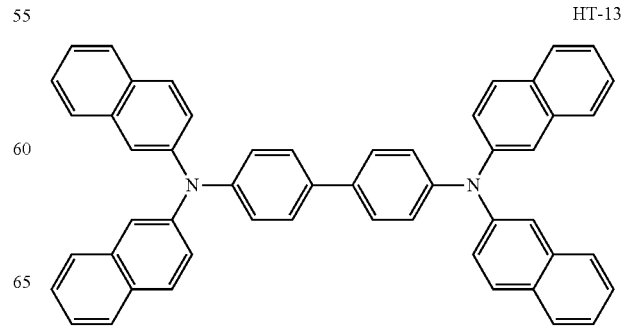

HT-14

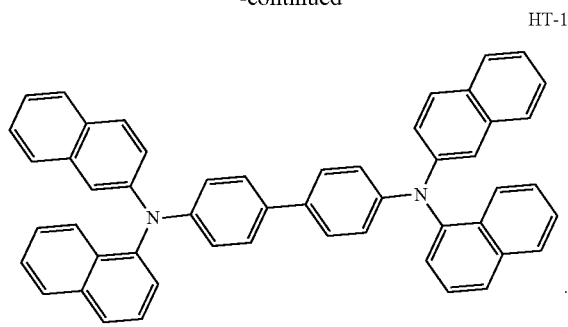

In an embodiment, the hole transport layer 321 is composed of α-NPD.

In an embodiment, the hole adjustment layer 322 is composed of HT-1.

Optionally, a hole injection layer 310 is further provided between the anode 100 and the hole transport layer 321 so as to enhance the ability to inject holes into the hole transport layer 321. The hole injection layer 310 may be composed of a material selected from benzidine derivatives, starburst arylamine compounds, phthalocyanine derivatives, and other materials, and the present disclosure is not particularly restricted in this respect. The material of the hole injection layer 310 is, for example, selected from the following compounds or any combinations thereof:

F4-TCNQ

HAT-CN m-MTDATA

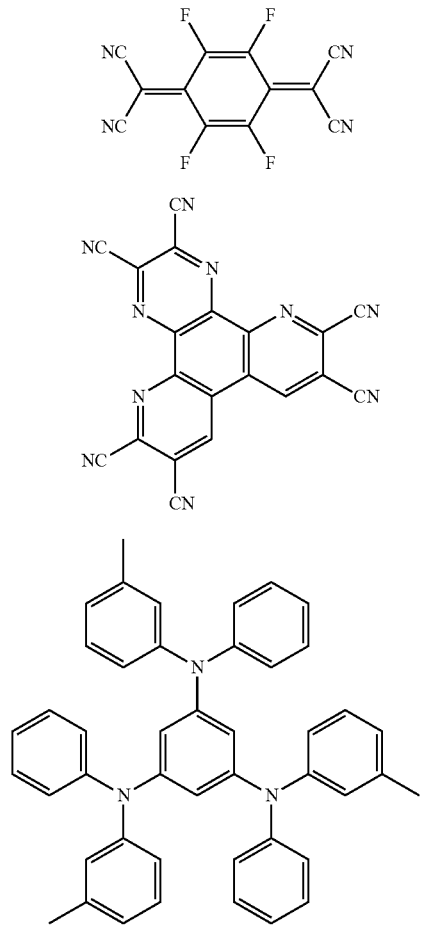

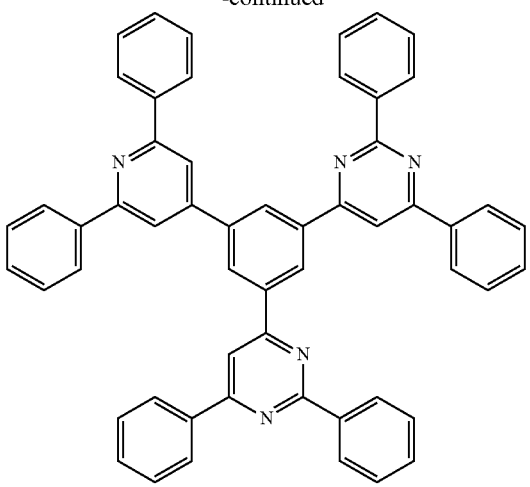

1T-NATA

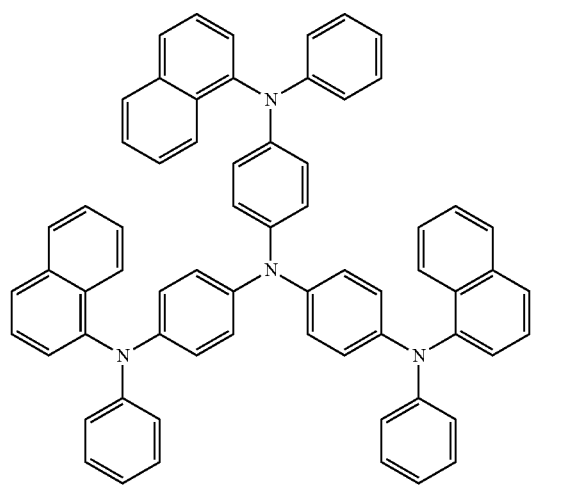

2T-NATA

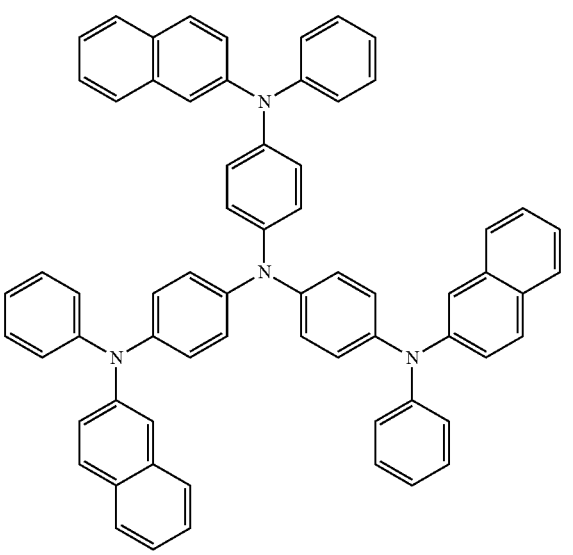

NATA

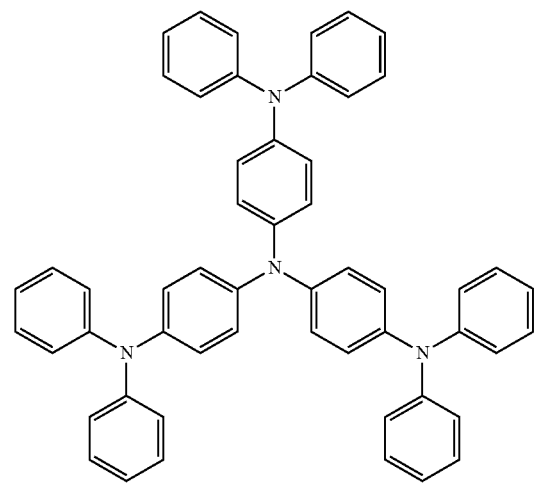

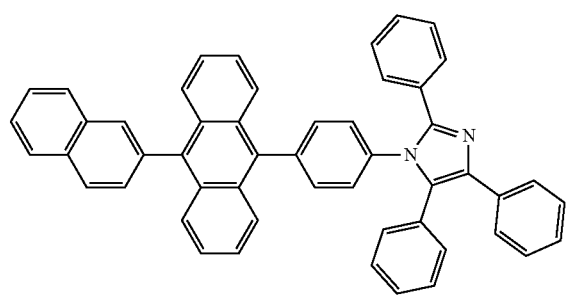

PPDN

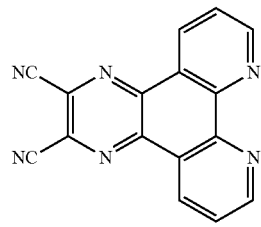

PD

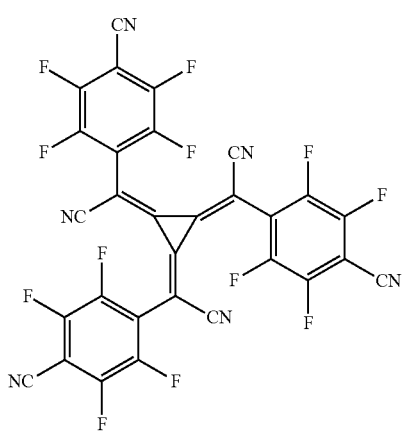

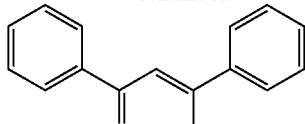

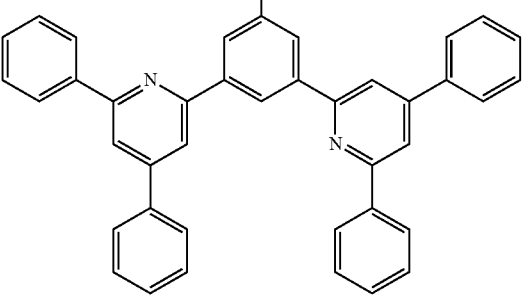

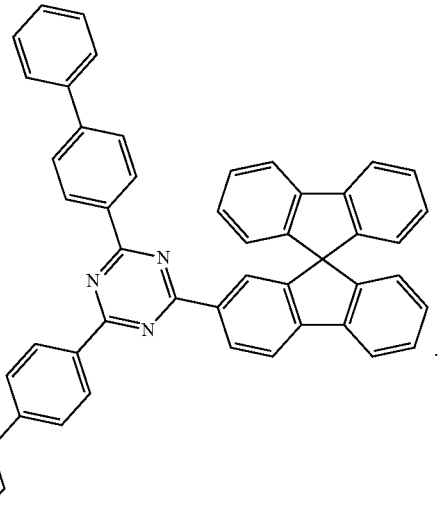

In an embodiment of the present disclosure, the hole injection layer 310 is composed of PD.

Optionally, the organic light-emitting layer 330 may be composed of a single luminescent material, or may comprise a host material and a dopant material. Optionally, the organic light-emitting layer 330 is composed of a host material and a dopant material. Holes injected into the organic light-emitting layer 330 and electrons injected into the organic light-emitting layer 330 can recombine in the organic light-emitting layer 330 to form excitons. The excitons transmit energy to the host material, and the host material transmits the energy to the dopant material, thereby enabling the dopant material to emit light.

The host material of the organic light-emitting layer 330 may include metal chelating compounds, stilbene derivatives, aromatic amine derivatives, dibenzofuran derivatives, or other types of materials. The host material of the organic light-emitting layer 330 may be one compound, or a combination of two or more compounds. Optionally, the host material comprises the arylamine compound of the present disclosure.

The dopant material of the organic light-emitting layer 330 may be a compound having a condensed aryl ring or a derivative thereof, a compound having a heteroaryl ring or a derivative thereof, an aromatic amine derivative, or other materials, and the present disclosure is not particularly restricted in this respect. The dopant material is also known as a doping material or a dopant, which can be categorized, according to its type of luminescence, as a fluorescent dopant or a phosphorescent dopant. Specific examples of the phosphorescent dopant include, but are not limited to:
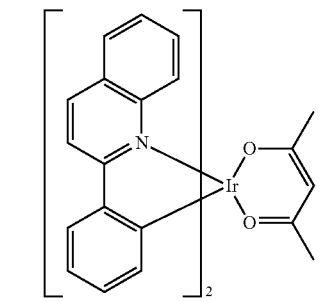
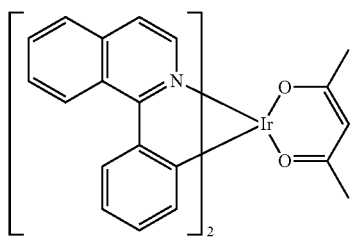
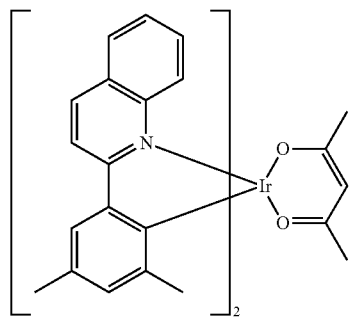
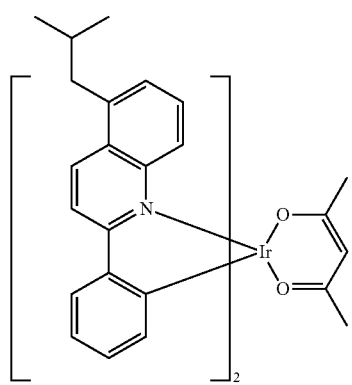
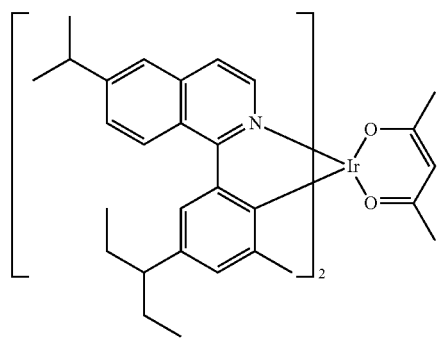
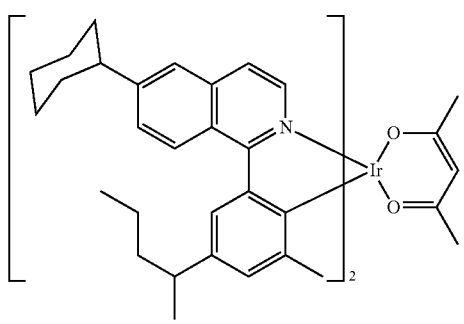
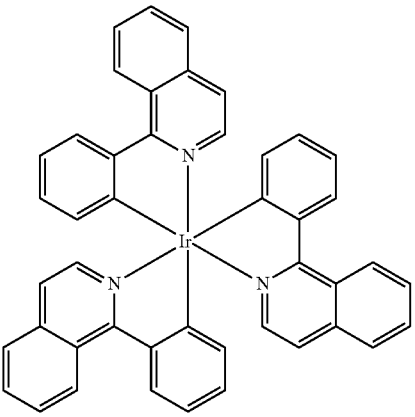
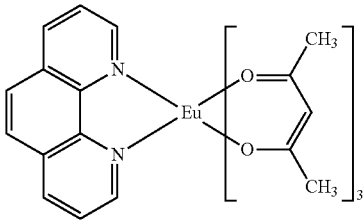
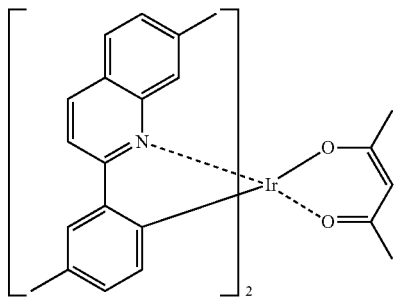

-continued
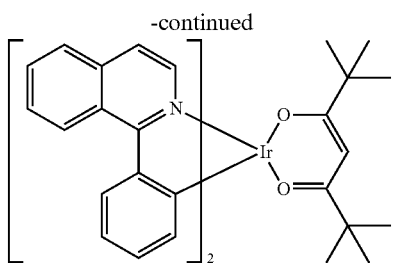
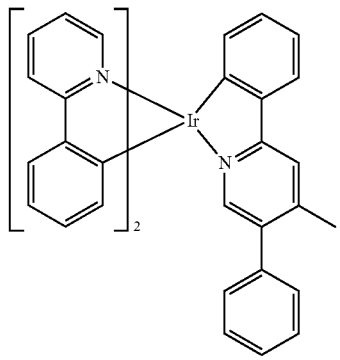
Ir(MDQ)2(acac)
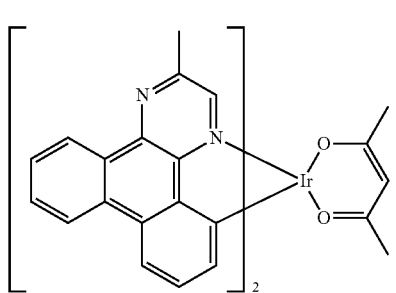
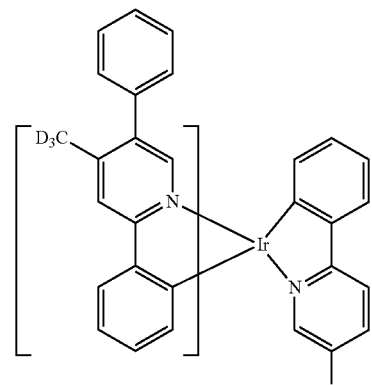
fac-Ir(ppy)3
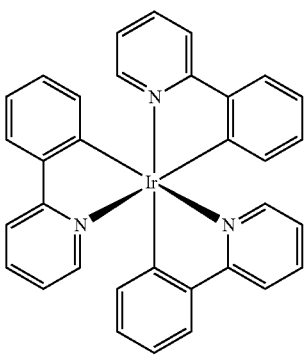
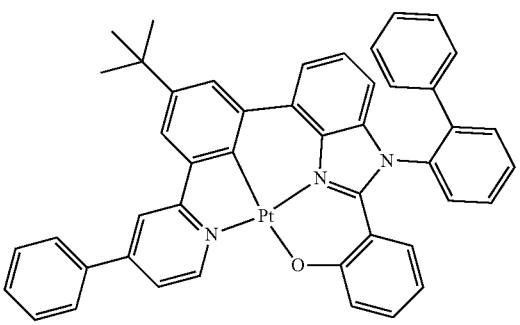
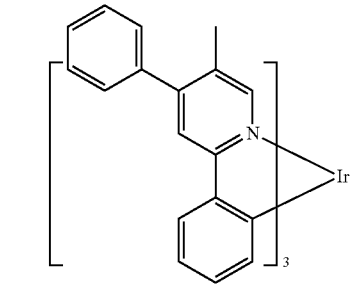
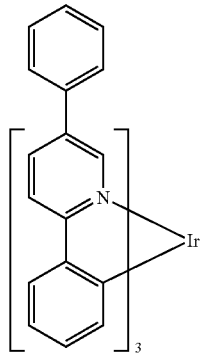
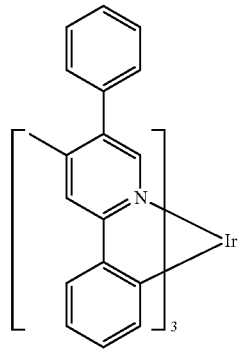
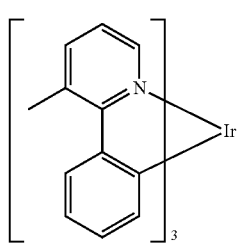

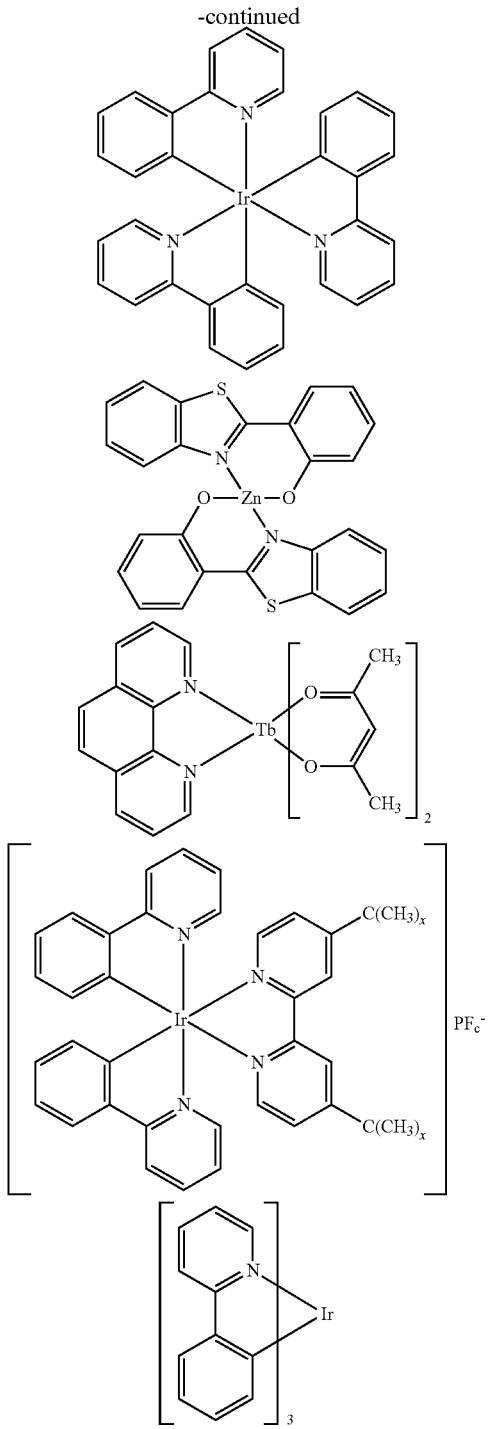

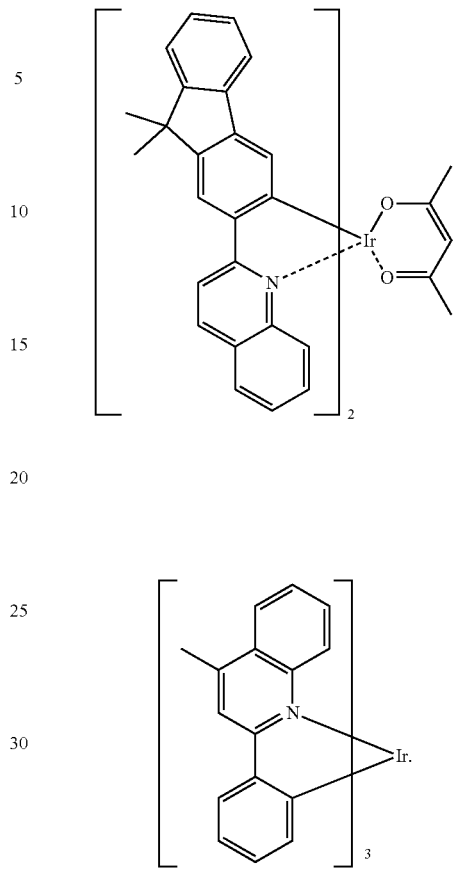

In an embodiment of the present disclosure, the organic electroluminescent device is a red light-emitting organic electroluminescent device. In a more specific embodiment, the host material of the organic light-emitting layer 330 comprises the arylamine compound of the present disclosure. The dopant material may be, for example, RD-1.

The electron transport layer 340 may be a single-layer structure or a multi-layer structure, and may comprise one or more electron transport materials. The electron transport materials may be selected from, but are not limited to, LiQ, benzimidazole derivatives, oxadiazole derivatives, quinoxaline derivatives, or other electron transport materials, which are not particularly limited in the present disclosure. The material of the electron transport layer 340 includes, but is not limited to, the following compounds:

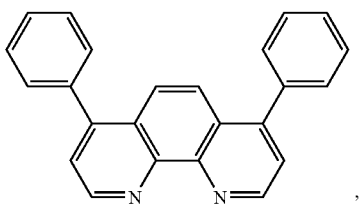

(ET-2)
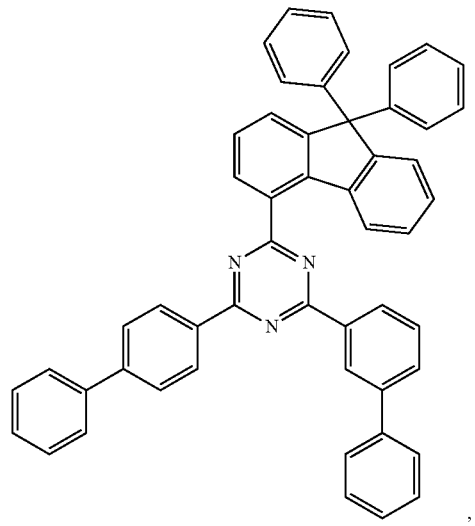,
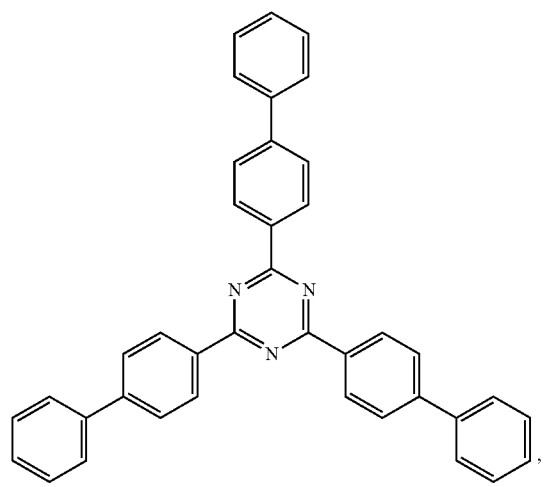,
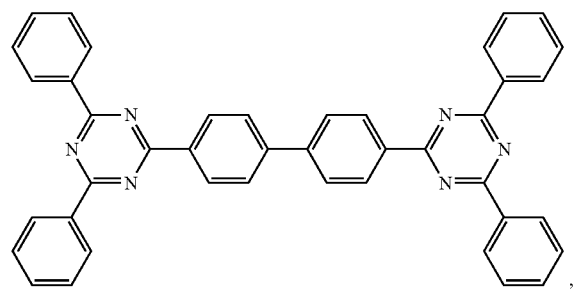,
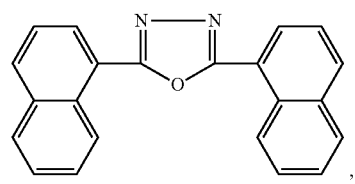,
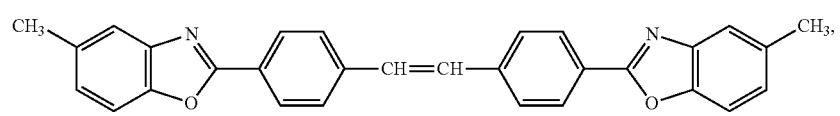

-continued

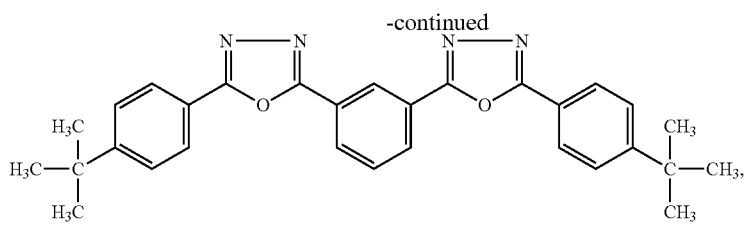

(ET-1)

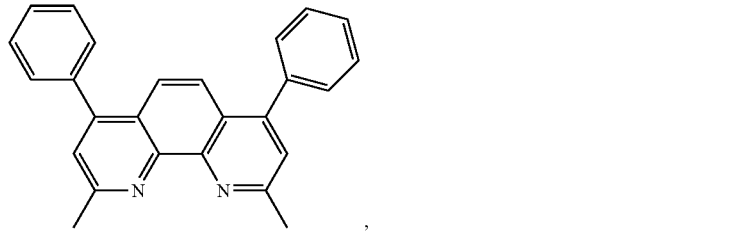

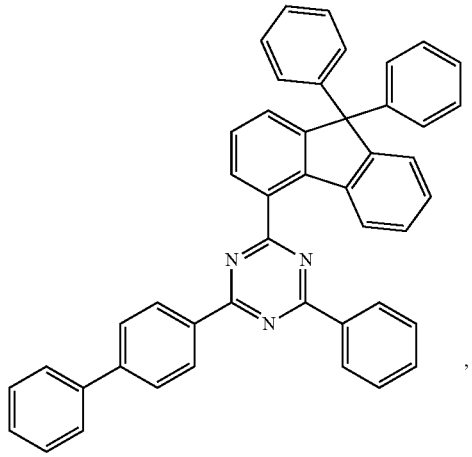

(BmPyPhB)

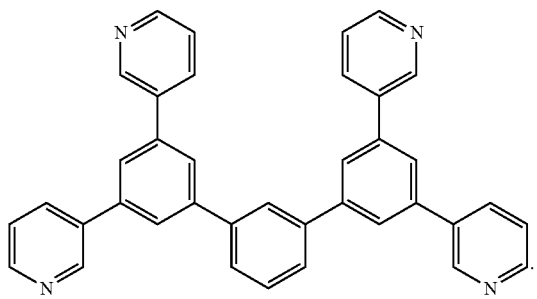

In an embodiment of the present disclosure, the electron transport layer 340 is composed of ET-1 and LiQ.

In the present disclosure, the cathode 200 comprises a cathode material, which is a low-work function material contributing to injection of electrons into the functional layer. Specific examples of the cathode material include, but are not limited to, metals such as magnesium, calcium, sodium, potassium, titanium, indium, yttrium, lithium, gadolinium, aluminum, silver, tin, lead, and alloys thereof; or multilayer materials such as LiF/Al, Liq/Al, LiO$_2$/Al, LiF/Ca, LiF/Al, and BaF$_2$/Ca. Optionally, a metal electrode comprising magnesium and silver is included as the cathode.

Optionally, an electron injection layer 350 is further provided between the cathode 200 and the electron transport layer 340 so as to enhance the ability to inject electrons into the electron transport layer 340. The electron injection layer 350 may comprise an inorganic material such as an alkali metal sulfide, an alkali metal halide, and the like, or may comprise a complex of an alkali metal and an organic compound. In an embodiment of the present disclosure, the electron injection layer 350 comprises ytterbium (Yb).

The present disclosure, in a third aspect, provides an electronic apparatus including the organic electroluminescent device described in the second aspect of the present disclosure.

Figure 2:
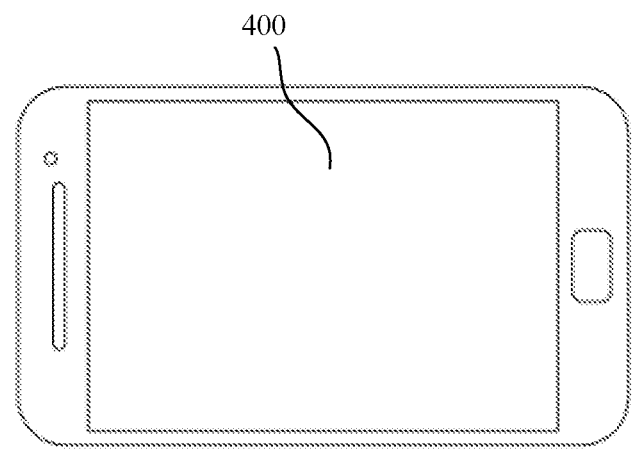
FIG. 2 is a schematic structural diagram of an electronic apparatus according to an embodiment of the present disclosure.

According to an embodiment, as shown in FIG. 2, the electronic apparatus provided is an electronic apparatus 400 including the organic electroluminescent device described above. The electronic apparatus 400 may be, for example, a display device, a lighting device, an optical communication device, or other type of electronic devices, including, but not limited to, for example, a computer screen, a mobile phone screen, a television, electronic paper, an emergency lamp, an optical module, etc.

A synthesis method of the arylamine compound of the present disclosure is described in detail below in conjunction with Synthesis Examples, but the present disclosure is not limited thereto in any way.

Synthesis Examples

Those skilled in the art should appreciate that chemical reactions described in the present disclosure may be used properly to prepare many arylamine compounds of the present disclosure, and other methods that can be used to prepare the compounds of the present disclosure are all considered to be within the scope of the present disclosure.

For example, the synthesis of those non-exemplary compounds of the present disclosure may be successfully accomplished by those skilled in the art by modifying the method, for example, by properly protecting an interfering group, by utilizing other known reagents other than those described in the present disclosure, or by making some conventional modifications to reaction conditions. Compounds for which a synthesis method is not mentioned in the present disclosure are raw material products obtained commercially.

Synthesis of Sub-a1

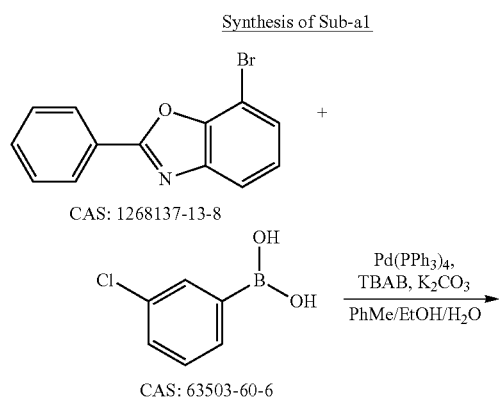

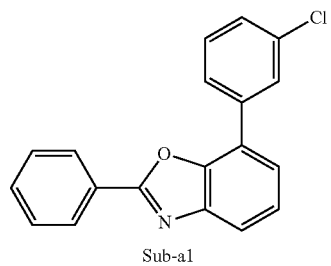

Sub-a1

7-bromo-2-phenylbenzooxazole (13.71 g, 50 mmol), 3-chlorophenylboronic acid (8.60 g, 55 mmol), tetrakis (triphenylphosphine)palladium (0.58 g, 0.5 mmol), tetrabutylammonium bromide (1.61 g, 5 mmol), anhydrous potassium carbonate (13.82 g, 100 mmol), toluene (140 mL), absolute ethanol (35 mL), and deionized water (35 mL) were sequentially added under a nitrogen atmosphere to a 500-mL three-neck flask, heated to reflux and stirred for 16 hours. After being cooled to room temperature, the reaction solution was extracted with dichloromethane (100 mL×3 times). The resulting organic phases were combined and then dried with anhydrous magnesium sulfate, followed by filtration and then distillation under reduced pressure to remove the solvent, obtaining a crude product. The crude product was purified by silica gel column chromatography with n-heptane as a mobile phase, yielding white solid Sub-a1 (12.53 g, yield 82%).

Sub-a2 to Sub-a7 were synthesized respectively following the synthesis method of Sub-a1, except that 7-bromo-2-phenylbenzooxazole was replaced with a corresponding reactant A shown in Table 1, and that 3-chlorophenylboronic acid was replaced with a corresponding reactant B.

TABLE 1

Synthesis of Sub-a2 to Sub-a7

| Sub-a | Reactant A | Reactant B | Structure of Sub-a | Yield (%) |
|---|---|---|---|---|
| Sub-a2 | CAS: 1268137-13-8 | CAS: 1679-18-1 | | 74 |
| Sub-a3 | CAS: 1268137-13-8 | CAS: 3900-89-8 | | 74 |

TABLE 1-continued
Synthesis of Sub-a2 to Sub-a7
| Sub-a | Reactant A | Reactant B | Structure of Sub-a | Yield (%) |
|---|---|---|---|---|
| Sub-a4 | 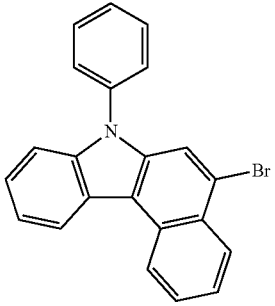 [SMILES: Brc1cc2c(c3ccccc13)c1ccccc1n2-c1ccccc1]<br>CAS: 1247092-44-9 | 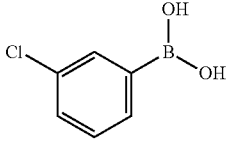<br>CAS: 63503-60-6 | 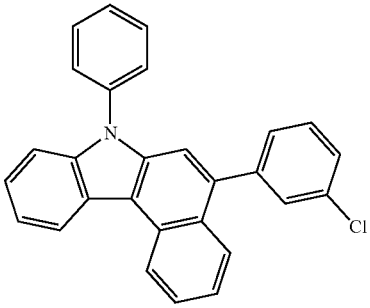 [SMILES: Clc1cccc(-c2cc3c(c4ccccc24)c2ccccc2n3-c2ccccc2)c1] | 76 |
| Sub-a5 | 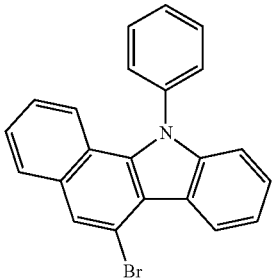 [SMILES: Brc1cc2ccccc2c2c1c1ccccc1n2-c1ccccc1]<br>CAS: 1627726-68-4 | 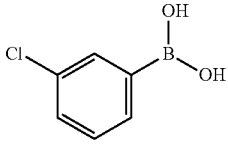<br>CAS: 63503-60-6 | 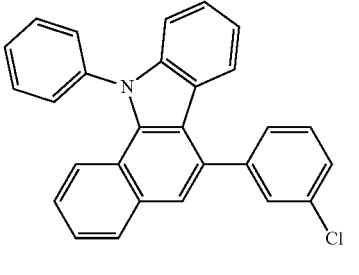 [SMILES: Clc1cccc(-c2cc3ccccc3c3c2c2ccccc2n3-c2ccccc2)c1] | 73 |
| Sub-a6 | 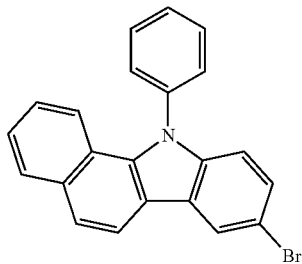 [SMILES: Brc1ccc2c(c1)c1ccc3ccccc3c1n2-c1ccccc1]<br>CAS: 1210470-49-7 | 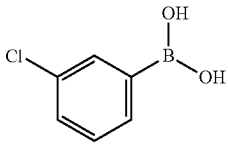<br>CAS: 63503-60-6 | 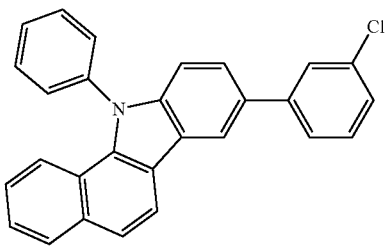 [SMILES: Clc1cccc(-c2ccc3c(c2)c2ccc4ccccc4c2n3-c2ccccc2)c1] | 79 |
| Sub-a7 | 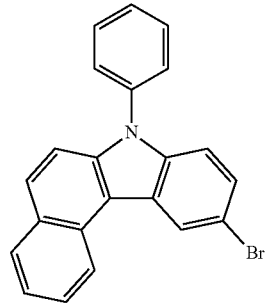 [SMILES: Brc1ccc2c(c1)c1c3ccccc3ccc1n2-c1ccccc1]<br>CAS: 1210469-11-6 | 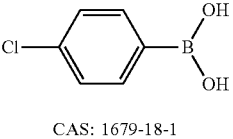<br>CAS: 1679-18-1 | 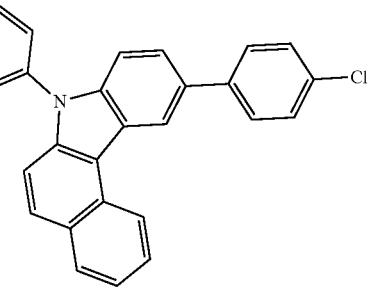 | 72 |

Synthesis of Sub-b1

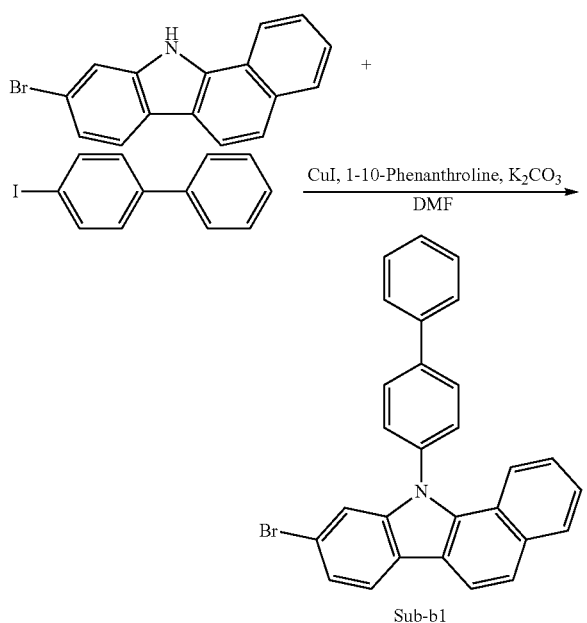

9-bromo-11H-benzo[A]carbazole (14.81 g, 50 mmol), 4-iodobiphenyl (16.81 g, 60 mmol), cuprous iodide (1.90 g, 10 mmol), 18-crown-6 (1.32 g, 5 mmol), 1,10-phenanthroline (3.96 g, 20 mmol), potassium carbonate (15.20 g, 110 mmol), and N,N-dimethylformamide (150 mL) were added sequentially under a nitrogen atmosphere to a 250-mL three-neck flask, and heated to reflux and stirred overnight. After being cooled to room temperature, the reaction solution was poured into 250 mL of deionized water, and then filtered. The filter cake was collected, dissolved in dichloromethane, and dried with anhydrous sodium sulfate, followed by filtration and then distillation under reduced pressure to remove the solvent, obtaining a crude product. The crude product was purified by silica gel column chromatography with n-heptane/dichloromethane as a mobile phase, yielding white solid Sub-b1 (18.45 g, yield 65%).

Sub-b2 to Sub-b9 were synthesized respectively following the synthesis method of Sub-b1, except that 9-bromo-11H-benzo[A]carbazole was replaced with a corresponding reactant C shown in Table 2, and that 4-iodobiphenyl was replaced with a corresponding reactant D.

TABLE 2

Synthesis of Sub-b2 to Sub-b9

| Sub-b | Reactant C | Reactant D | Structure of Sub-b | Yield (%) |
|---|---|---|---|---|
| Sub-b2 | CAS: 131409-18-2 | CAS: 612-55-5 | | 61 |
| Sub-b3 | CAS: 1698-16-4 | CAS: 5896-29-7 | | 62 |

TABLE 2-continued
Synthesis of Sub-b2 to Sub-b9
| Sub-b | Reactant C | Reactant D | Structure of Sub-b | Yield (%) |
|---|---|---|---|---|
| Sub-b4 | 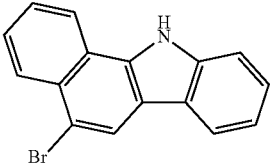 [SMILES: Brc1cc2c3ccccc3[nH]c2c2ccccc12]<br>CAS: 111181-01-2 | 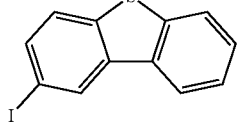<br>CAS: 177586-41-3 | 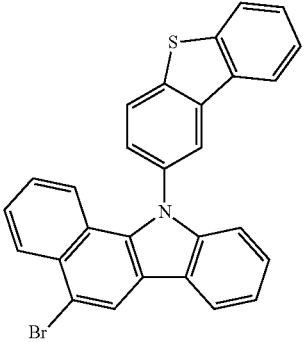 [SMILES: Brc1cc2c3ccccc3n(-c3ccc4sc5ccccc5c4c3)c2c2ccccc12] | 56 |
| Sub-b5 | 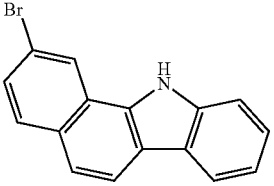 [SMILES: Brc1ccc2ccc3c4ccccc4[nH]c3c2c1]<br>CAS: 103569-04-6 | 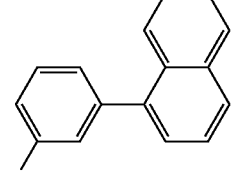<br>CAS: 1001337-34-3 | 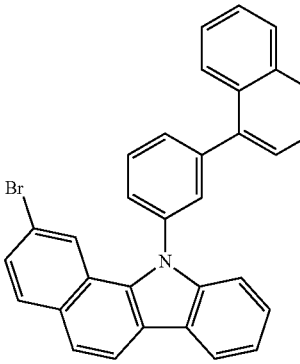 | 59 |
| Sub-b6 | 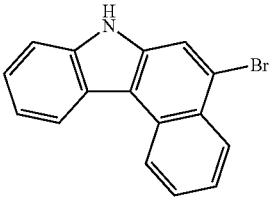 [SMILES: Brc1cc2[nH]c3ccccc3c2c2ccccc12]<br>CAS: 131409-18-2 | 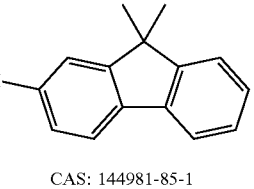<br>CAS: 144981-85-1 | 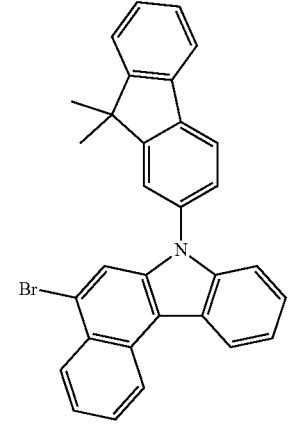 [SMILES: CC1(C)c2ccccc2-c2ccc(-n3c4ccccc4c4c5ccccc5c(Br)cc43)cc21] | 57 |
| Sub-b7 | 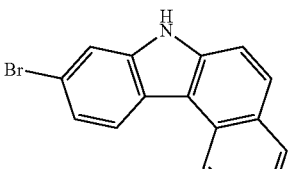<br>CAS: 1357572-66-7 | 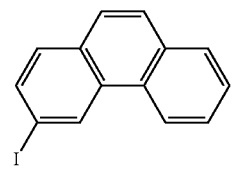 [SMILES: Ic1ccc2ccc3ccccc3c2c1]<br>CAS: 33240-31-2 | 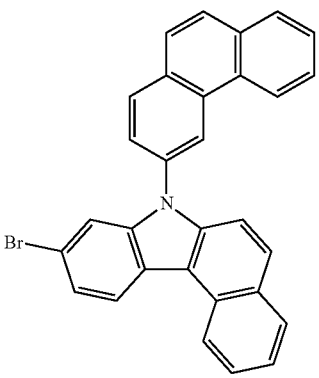 [SMILES: Brc1ccc2c3c4ccccc4ccc3n(-c3ccc4ccc5ccccc5c4c3)c2c1] | |

TABLE 2-continued

Synthesis of Sub-b2 to Sub-b9

| Sub-b | Reactant C | Reactant D | Structure of Sub-b | Yield (%) |
|---|---|---|---|---|
| Sub-b8 | CAS: 21064-34-6 | CAS: 870119-42-9 | | 60 |
| Sub-b9 | CAS: 131409-18-2 | CAS: 7379-67-1 | | 62 |

Synthesis of Sub-b10

RM-1 (CAS: 1374003-98-1, 9.31 g, 25 mmol) and 200 mL of benzene-D6 were added under a nitrogen atmosphere to a 100-mL three-neck flask, and heated to 60° C., followed by addition of trifluoromethanesulfonic acid (22.51 g, 150 mmol), and heating to boil for a reaction under stirring for 24 hours. After the reaction solution was cooled to room temperature, 50 mL of deuteroxide was added, followed by stirring for 10 minutes, and then addition of a saturated aqueous solution of $K_3PO_4$ to neutralize the reaction solution. The resulting organic layers (50 mL×3 times) were extracted with dichloromethane. The organic phases were combined and then dried with anhydrous sodium sulfate, followed by filtration and then distillation under reduced pressure to remove the solvent, obtaining a crude product. The crude product was purified by silica gel column chromatography using n-heptane/dichloromethane as a mobile phase, yielding white solid Sub-b10 (6.10 g, yield 64%).

Sub-b11 was synthesized following the synthesis method of Sub-b10, except that RM-1 was replaced with reactant E shown in Table 2.

TABLE 2 continued: Synthesis of Sub-b11

| Sub-b | Reactant E | Sub-b | Yield (%) |
|---|---|---|---|
| Sub-b11 | 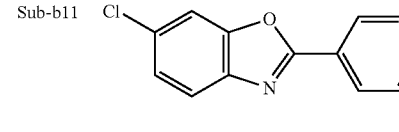 CAS: 2415099-58-8 | 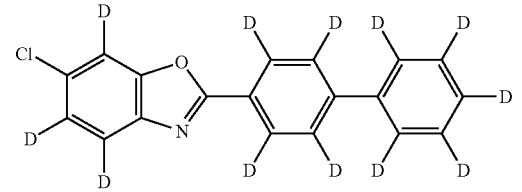 [SMILES: [2H]c1c([2H])c([2H])c(-c2c([2H])c([2H])c(-c3nc4c([2H])c([2H])c(Cl)c([2H])c4o3)c([2H])c2[2H])c([2H])c1[2H]] | 53 |

Synthesis of Sub-c1

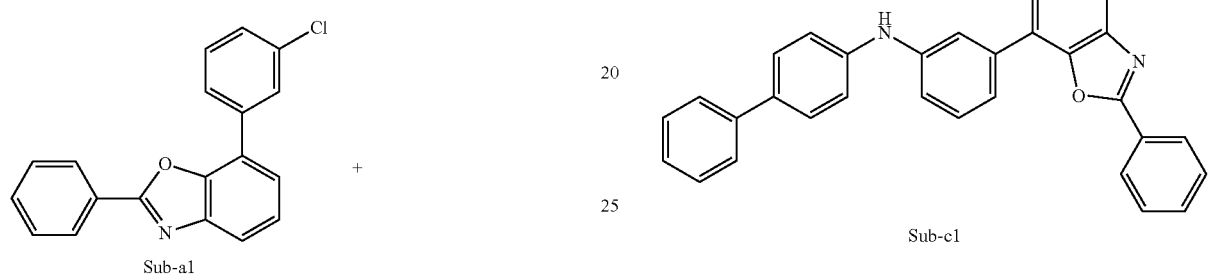

Sub-a1 (15.28 g, 50 mmol), 4-benzidine((8.46 g, 50 mmol), tris(dibenzylideneacetonyl)bis-palladium (0.916 g, 1 mmol), 2-dicyclohexylphosphino-2',4',6' triisopropylbiphenyl (XPhos, 0.95 g, 2 mmol), sodium tert-butoxide (9.61 g, 100 mmol), and toluene (150 mL) were sequentially added under a nitrogen atmosphere to a 250-mL three-neck flask, heated to reflux and stirred overnight. After being cooled to room temperature, the reaction solution was poured into 250 mL of deionized water, stirred thoroughly for 30 minutes, and filtered. The resulting filter cake was rinsed with deionized water to neutral, and then rinsed with absolute ethanol (100 mL). The filter cake was collected and recrystallized with toluene, obtaining gray-green solid Sub-c1 (17.10 g; yield 78%).

Sub-c2 to Sub-c37 were synthesized respectively following the synthesis method of Sub-c1, except that Sub-a1 was replaced with a corresponding reactant F shown in Table 3, and that 4-benzidine was replaced with a corresponding reactant G.

TABLE 3

Synthesis of Sub-c2 to Sub-c37

| Sub-c | Reactant F | Reactant G | Structure of Sub-c | Yield (%) |
|---|---|---|---|---|
| Sub-c2 | 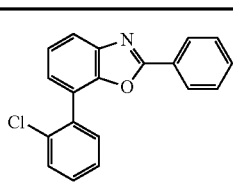 | 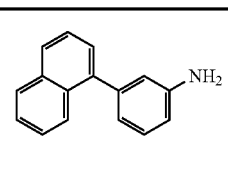 CAS: 728919-25-3 | 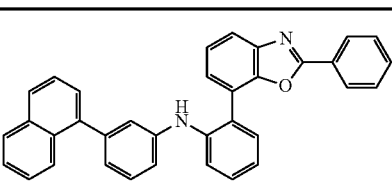 | 61 |

TABLE 3-continued
Synthesis of Sub-c2 to Sub-c37
| Sub-c | Reactant F | Reactant G | Structure of Sub-c | Yield (%) |
|---|---|---|---|---|
| Sub-c3 | 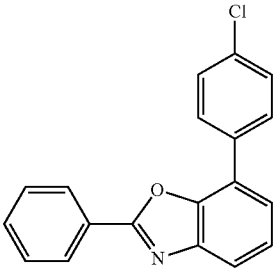 [SMILES: Clc1ccc(-c2cccc3nc(-c4ccccc4)oc23)cc1] | 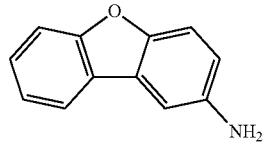<br>CAS: 3693-22-9 | 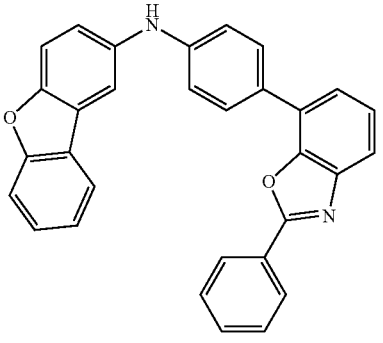 [SMILES: c1ccc(-c2nc3cccc(-c4ccc(Nc5ccc6oc7ccccc7c6c5)cc4)c3o2)cc1] | 71 |
| Sub-c4 | 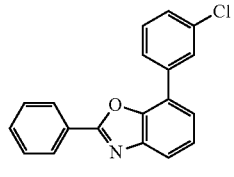 [SMILES: Clc1cccc(-c2cccc3nc(-c4ccccc4)oc23)c1] | 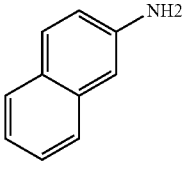 [SMILES: Nc1ccc2ccccc2c1]<br>CAS: 91-59-8 | 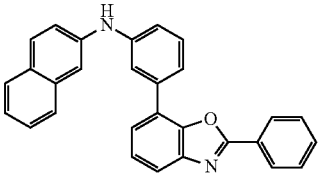 [SMILES: c1ccc(-c2nc3cccc(-c4cccc(Nc5ccc6ccccc6c5)c4)c3o2)cc1] | 60 |
| Sub-c5 | 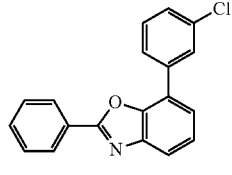 [SMILES: Clc1cccc(-c2cccc3nc(-c4ccccc4)oc23)c1] | 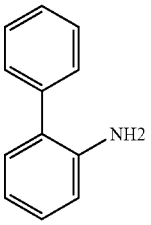<br>CAS: 90-41-5 | 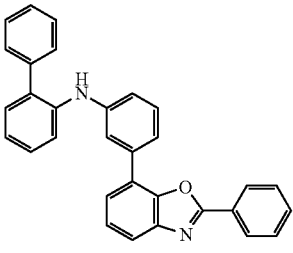 [SMILES: c1ccc(-c2nc3cccc(-c4cccc(Nc5ccccc5-c5ccccc5)c4)c3o2)cc1] | 62 |
| Sub-c6 | 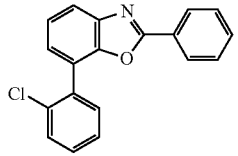 [SMILES: Clc1ccccc1-c1cccc2nc(-c3ccccc3)oc12] | 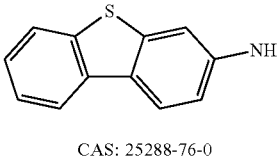<br>CAS: 25288-76-0 | 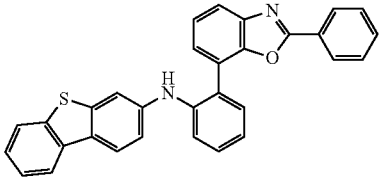 [SMILES: c1ccc(-c2nc3cccc(-c4ccccc4Nc4ccc5c(c4)sc4ccccc45)c3o2)cc1] | 61 |
| Sub-c7 | 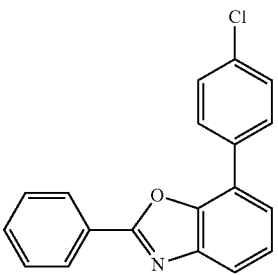 [SMILES: Clc1ccc(-c2cccc3nc(-c4ccccc4)oc23)cc1] | 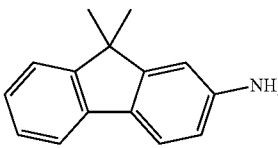<br>CAS: 108714-73-4 | 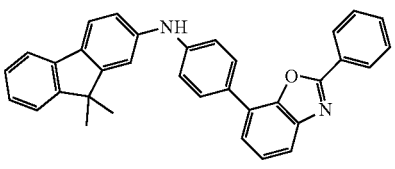 [SMILES: CC1(C)c2ccccc2-c2ccc(Nc3ccc(-c4cccc5nc(-c6ccccc6)oc45)cc3)cc21] | 64 |

TABLE 3-continued

Synthesis of Sub-c2 to Sub-c37

| Sub-c | Reactant F | Reactant G | Structure of Sub-c | Yield (%) |
|---|---|---|---|---|
| Sub-c8 | CAS: 2749511-90-6 | CAS: 4106-66-5 | | 73 |
| Sub-c9 | CAS: 2415412-21-2 | CAS: 63006-66-6 | | 69 |
| Sub-c10 | CAS: 1268137-13-8 | CAS: 52708-37-9 | | 61 |
| Sub-c11 | CAS: 1268137-13-8 | CAS: 209848-36-2 | | 74 |
| Sub-c12 | | CAS: 344298-96-0 | | 74 |

TABLE 3-continued
Synthesis of Sub-c2 to Sub-c37
| Sub-c | Reactant F | Reactant G | Structure of Sub-c | Yield (%) |
|---|---|---|---|---|
| Sub-c13 | 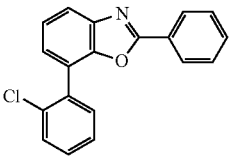 [SMILES: Clc1ccccc1-c1cccc2nc(-c3ccccc3)oc12] | 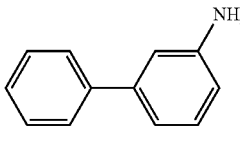<br>CAS: 2243-47-2 | 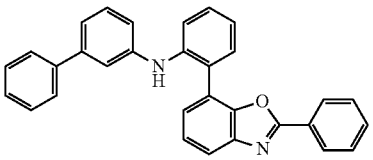 [SMILES: c1ccc(-c2cccc(Nc3ccccc3-c3cccc4nc(-c5ccccc5)oc34)c2)cc1] | 59 |
| Sub-c14 | 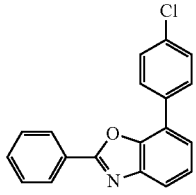 [SMILES: Clc1ccc(-c2cccc3nc(-c4ccccc4)oc23)cc1] | 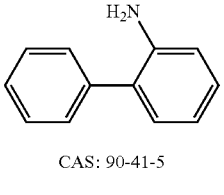<br>CAS: 90-41-5 | 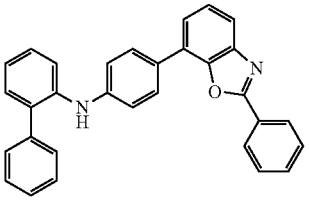 [SMILES: c1ccc(-c2nc3cccc(-c4ccc(Nc5ccccc5-c5ccccc5)cc4)c3o2)cc1] | 65 |
| Sub-c15 | 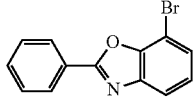 [SMILES: Brc1cccc2nc(-c3ccccc3)oc12]<br>CAS: 1268137-13-8 | 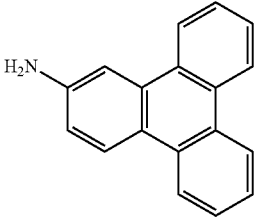 [SMILES: Nc1ccc2c3ccccc3c3ccccc3c2c1]<br>CAS: 17169-81-2 | 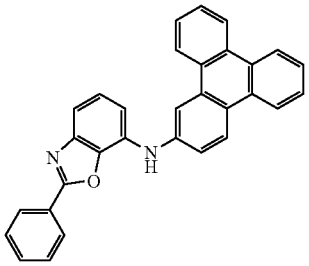 [SMILES: c1ccc(-c2nc3cccc(Nc4ccc5c6ccccc6c6ccccc6c5c4)c3o2)cc1] | 65 |
| Sub-c16 | 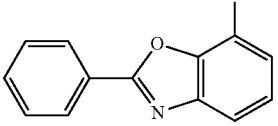<br>CAS: 1268137-13-8 | 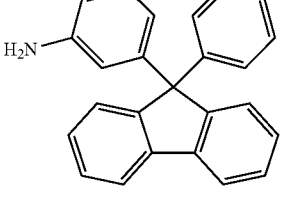<br>CAS: 2452270-61-8 | 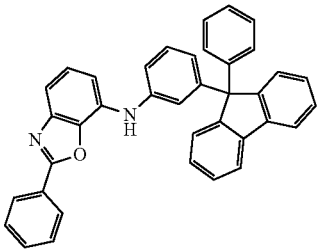 [SMILES: c1ccc(-c2nc3cccc(Nc4cccc(C5(c6ccccc6)c6ccccc6-c6ccccc65)c4)c3o2)cc1] | 72 |
| Sub-c17 | 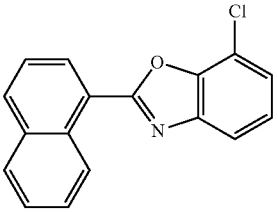 [SMILES: Clc1cccc2nc(-c3cccc4ccccc34)oc12]<br>CAS: 2415412-21-2 | 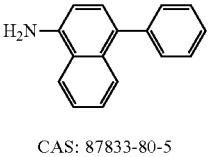<br>CAS: 87833-80-5 | 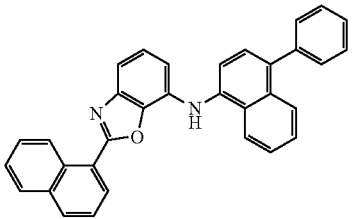 [SMILES: c1ccc(-c2ccc(Nc3cccc4nc(-c5cccc6ccccc56)oc34)c3ccccc23)cc1] | 74 |
| Sub-c18 | 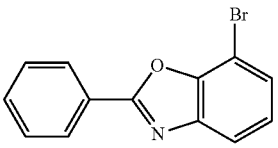 [SMILES: Brc1cccc2nc(-c3ccccc3)oc12]<br>CAS: 1268137-13-8 | 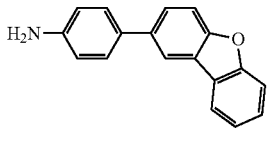 [SMILES: Nc1ccc(-c2ccc3oc4ccccc4c3c2)cc1]<br>CAS: 1178274-17-3 | 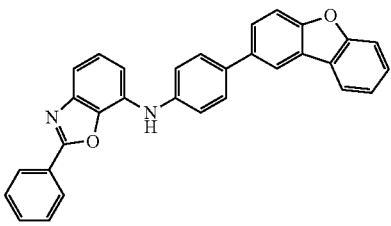 [SMILES: c1ccc(-c2nc3cccc(Nc4ccc(-c5ccc6oc7ccccc7c6c5)cc4)c3o2)cc1] | 66 |

TABLE 3-continued
Synthesis of Sub-c2 to Sub-c37
| Sub-c | Reactant F | Reactant G | Structure of Sub-c | Yield (%) |
|---|---|---|---|---|
| Sub-c19 | 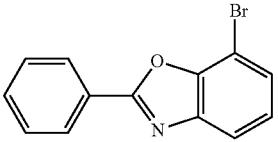 [SMILES: Brc1cccc2nc(-c3ccccc3)oc12]<br>CAS: 1268137-13-8 | 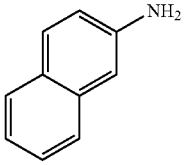 [SMILES: Nc1ccc2ccccc2c1]<br>CAS: 91-59-8 | 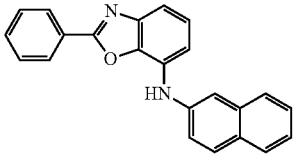 [SMILES: c1ccc(-c2nc3cccc(Nc4ccc5ccccc5c4)c3o2)cc1] | 67 |
| Sub-c20 | 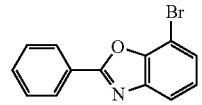 [SMILES: Brc1cccc2nc(-c3ccccc3)oc12]<br>CAS: 1268137-13-8 | 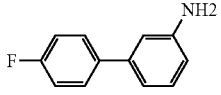<br>CAS: 10540-45-1 | 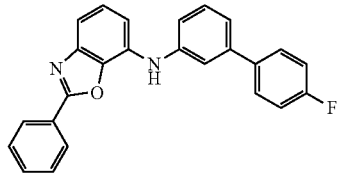 [SMILES: Fc1ccc(-c2cccc(Nc3cccc4nc(-c5ccccc5)oc34)c2)cc1] | 69 |
| Sub-c21 | 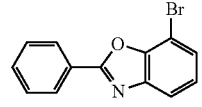 [SMILES: Brc1cccc2nc(-c3ccccc3)oc12]<br>CAS: 1268137-13-8 | 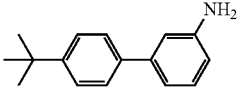<br>CAS: 893738-00-6 | 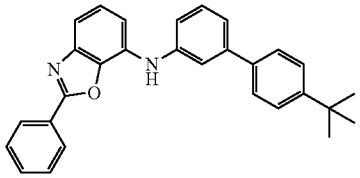 [SMILES: CC(C)(C)c1ccc(-c2cccc(Nc3cccc4nc(-c5ccccc5)oc34)c2)cc1] | 72 |
| Sub-c22 | 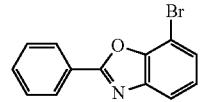 [SMILES: Brc1cccc2nc(-c3ccccc3)oc12]<br>CAS: 1268137-13-8 | 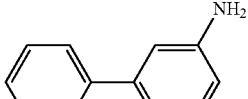<br>CAS: 2243-47-2 | 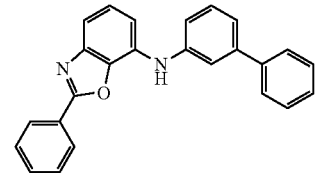 [SMILES: c1ccc(-c2cccc(Nc3cccc4nc(-c5ccccc5)oc34)c2)cc1] | 63 |
| Sub-c23 | 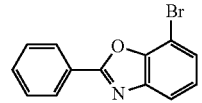 [SMILES: Brc1cccc2nc(-c3ccccc3)oc12]<br>CAS: 1268137-13-8 | 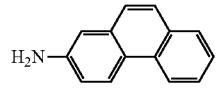<br>CAS: 3366-65-2 | 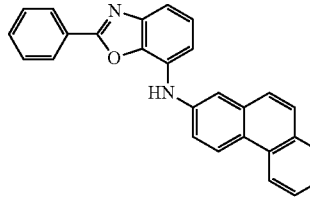 | 70 |
| Sub-c24 | 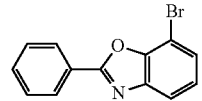 [SMILES: Brc1cccc2nc(-c3ccccc3)oc12]<br>CAS: 1268137-13-8 | 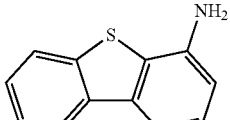<br>CAS: 72433-66-0 | 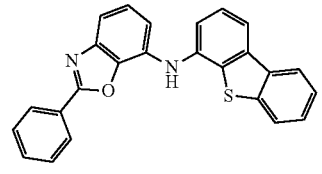 [SMILES: c1ccc(-c2nc3cccc(Nc4cccc5c4sc4ccccc45)c3o2)cc1] | 66 |
| Sub-c25 | 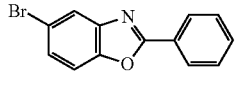<br>CAS: 69918-19-0 | 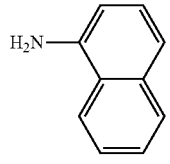<br>CAS: 134-32-7 | 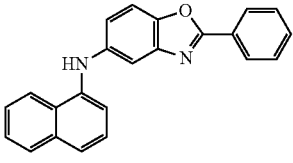 [SMILES: c1ccc(-c2nc3cc(Nc4cccc5ccccc45)ccc3o2)cc1] | 61 |
| Sub-c26 | 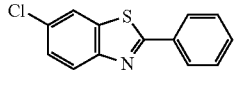 [SMILES: Clc1ccc2nc(-c3ccccc3)sc2c1]<br>CAS: 7466-32-2 | 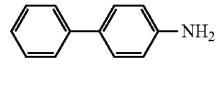<br>CAS: 92-67-1 | 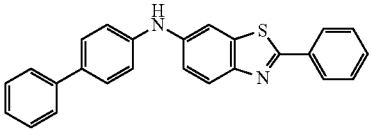 [SMILES: c1ccc(-c2ccc(Nc3ccc4nc(-c5ccccc5)sc4c3)cc2)cc1] | 67 |

TABLE 3-continued
Synthesis of Sub-c2 to Sub-c37
| Sub-c | Reactant F | Reactant G | Structure of Sub-c | Yield (%) |
|---|---|---|---|---|
| Sub-c27 | 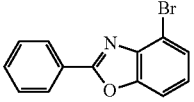 [SMILES: Brc1cccc2oc(-c3ccccc3)nc12]<br>CAS: 1792993-81-7 | 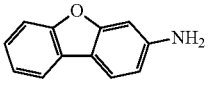<br>CAS: 4106-66-5 | 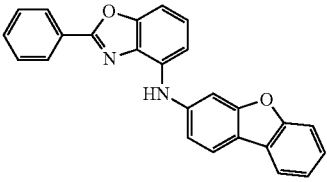 [SMILES: c1ccc(-c2nc3c(Nc4ccc5c(c4)oc4ccccc45)cccc3o2)cc1] | 71 |
| Sub-c28 | 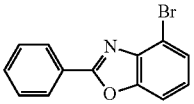 [SMILES: Brc1cccc2oc(-c3ccccc3)nc12]<br>CAS: 1792993-81-7 | 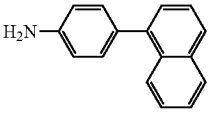 [SMILES: Nc1ccc(-c2cccc3ccccc23)cc1]<br>CAS: 125404-00-4 | 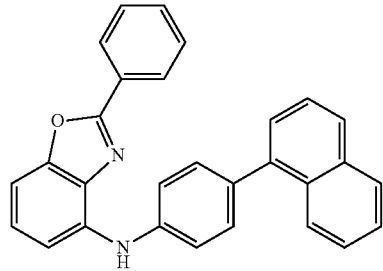 [SMILES: c1ccc(-c2nc3c(Nc4ccc(-c5cccc6ccccc56)cc4)cccc3o2)cc1] | 64 |
| Sub-c29 | 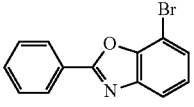 [SMILES: Brc1cccc2nc(-c3ccccc3)oc12]<br>CAS: 1268137-13-8 | 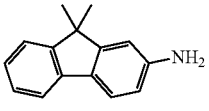<br>CAS: 108714-73-4 | 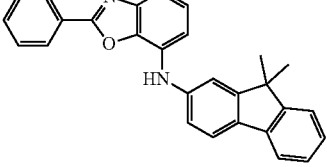 | 65 |
| Sub-c30 | 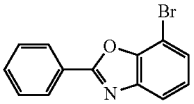 [SMILES: Brc1cccc2nc(-c3ccccc3)oc12]<br>CAS: 1268137-13-8 | 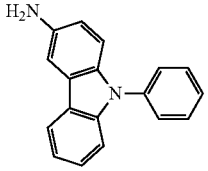 [SMILES: Nc1ccc2c(c1)c1ccccc1n2-c1ccccc1]<br>CAS: 1318253-36-9 | 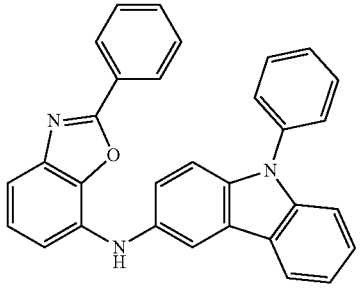 [SMILES: c1ccc(-c2nc3cccc(Nc4ccc5c(c4)c4ccccc4n5-c4ccccc4)c3o2)cc1] | 73 |
| Sub-c31 | 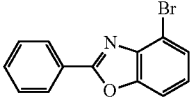 [SMILES: Brc1cccc2oc(-c3ccccc3)nc12]<br>CAS: 1792993-81-7 | 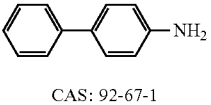<br>CAS: 92-67-1 | 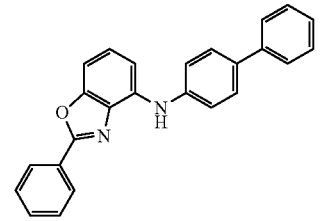 [SMILES: c1ccc(-c2ccc(Nc3cccc4oc(-c5ccccc5)nc34)cc2)cc1] | 67 |
| Sub-c32 | 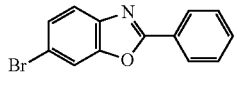<br>CAS: 537025-33-5 | 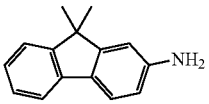<br>CAS: 108714-73-4 | 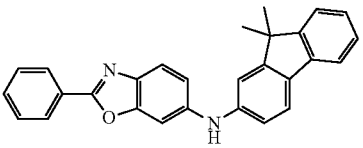 [SMILES: CC1(C)c2ccccc2-c2ccc(Nc3ccc4nc(-c5ccccc5)oc4c3)cc21] | 65 |

TABLE 3-continued
Synthesis of Sub-c2 to Sub-c37
| Sub-c | Reactant F | Reactant G | Structure of Sub-c | Yield (%) |
|---|---|---|---|---|
| Sub-c33 | 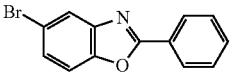 CAS: 69918-19-0 | 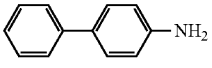 CAS: 92-67-1 | 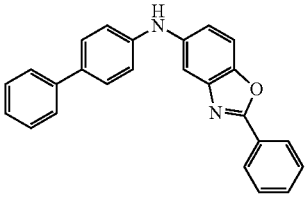 [SMILES: c1ccc(-c2ccc(Nc3ccc4oc(-c5ccccc5)nc4c3)cc2)cc1] | 65 |
| Sub-c34 | 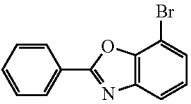 [SMILES: Brc1cccc2nc(-c3ccccc3)oc12] CAS: 1268137-13-8 | 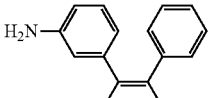 CAS: 7138-08-1 | 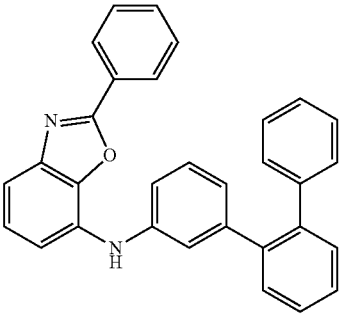 [SMILES: c1ccc(-c2nc3cccc(Nc4cccc(-c5ccccc5-c5ccccc5)c4)c3o2)cc1] | 69 |
| Sub-c35 | 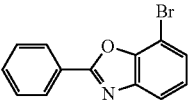 [SMILES: Brc1cccc2nc(-c3ccccc3)oc12] CAS: 1268137-13-8 | 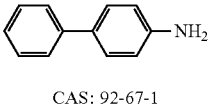 CAS: 92-67-1 | 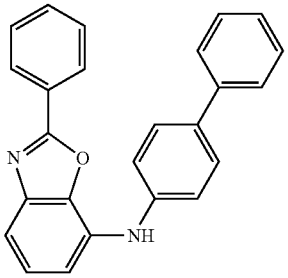 [SMILES: c1ccc(-c2ccc(Nc3cccc4nc(-c5ccccc5)oc34)cc2)cc1] | 62 |
| Sub-c36 | 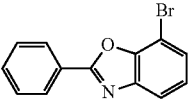 [SMILES: Brc1cccc2nc(-c3ccccc3)oc12] CAS: 1268137-13-8 | 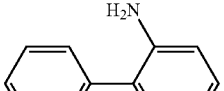 CAS: 90-41-5 | 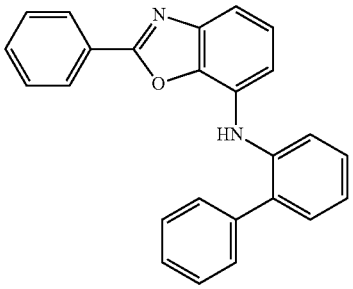 [SMILES: c1ccc(-c2nc3cccc(Nc4ccccc4-c4ccccc4)c3o2)cc1] | 60 |
| Sub-c37 | 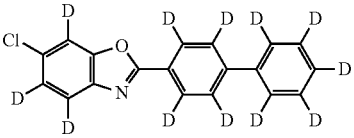 [SMILES: [2H]c1c([2H])c([2H])c(-c2c([2H])c([2H])c(-c3nc4c([2H])c([2H])c(Cl)c([2H])c4o3)c([2H])c2[2H])c([2H])c1[2H]] Sub-b11 | 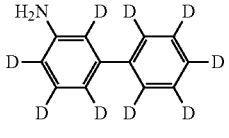 1020718-93-7 | 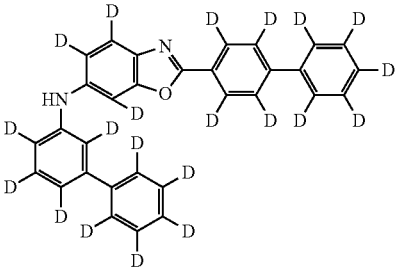 [SMILES: [2H]c1c([2H])c([2H])c(-c2c([2H])c([2H])c(-c3nc4c([2H])c([2H])c(Nc5c([2H])c([2H])c([2H])c(-c6c([2H])c([2H])c([2H])c([2H])c6[2H])c5[2H])c([2H])c4o3)c([2H])c2[2H])c([2H])c1[2H]] | 66 |

Synthesis of Compound 5

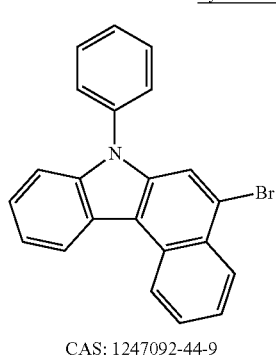

CAS: 1247092-44-9

+

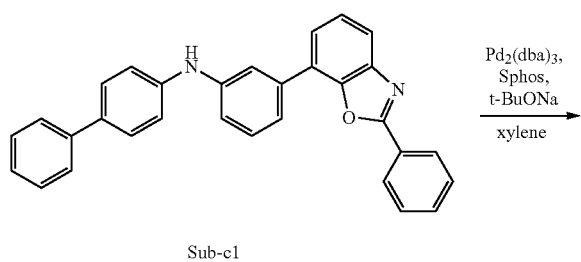

Sub-c1

→ (Pd₂(dba)₃, Sphos, t-BuONa, xylene)

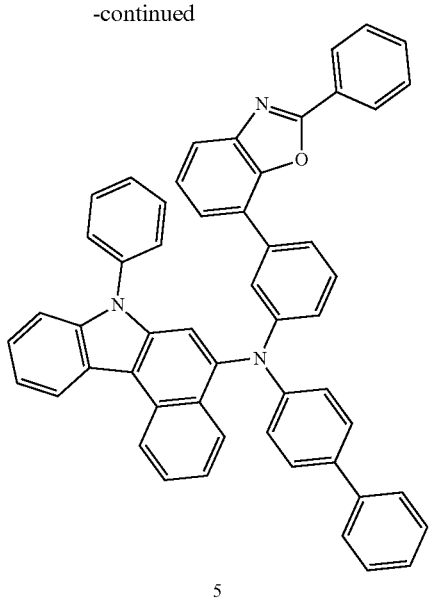

5

Sub-c1 (10.96 g, 25 mmol), 5-bromo-7-phenyl-7H-benzo[c]carbazole (10.24 g, 27.5 mmol), tris(dibenzylideneacetonyl)bis-palladium (0.46 g, 0.5 mmol), 2-biscyclohexylphosphino-2',6'-dimethoxybiphenyl (Sphos, 0.41 g, 1 mmol), sodium tert-butoxide (4.80 g, 50 mmol), and xylene (100 mL) were sequentially added under a nitrogen atmosphere to a 250-mL three-neck flask, heated to reflux and stirred overnight. After being cooled to room temperature, the reaction solution was extracted with dichloromethane (100 mL×3 times). The resulting organic phases were combined and then dried with anhydrous magnesium sulfate, followed by filtration and distillation under reduced pressure to remove the solvent, obtaining a crude product. The crude product was purified by silica gel column chromatography with n-heptane as a mobile phase, yielding white solid Compound 5 (11.50 g, yield 63%), m/z=730.3[M+H]⁺. Compounds of the present disclosure shown in Table 4 were synthesized respectively following the synthesis method of Compound 5, except that Sub-c1 was replaced with a corresponding reactant H shown in Table 4, and that 5-bromo-7-phenyl-7H-benzo[c]carbazole was replaced with a corresponding reactant J.

TABLE 4

Synthesis of compounds of the present disclosure

| Reactant H | Reactant J | Compound and its Structure | m/z ([M + H]+) | Yield (%) |
|---|---|---|---|---|
| (structure, CAS: 1247092-44-9) | (structure) | (structure, 12) | 780.3 | 65 |

TABLE 4-continued
Synthesis of compounds of the present disclosure
| Reactant H | Reactant J | Compound and its Structure | m/z ([M + H]+) | Yield (%) |
|---|---|---|---|---|
| 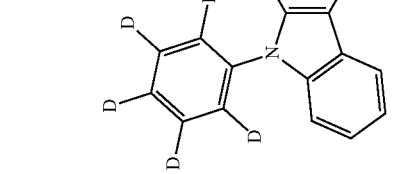 | 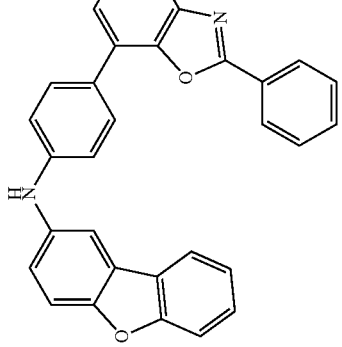 | 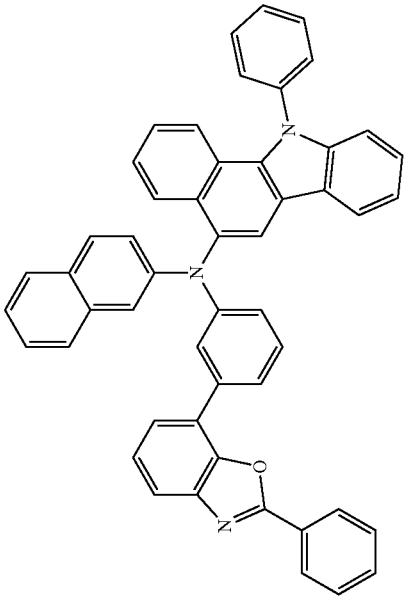 19 | 749.3 | 65 |
| 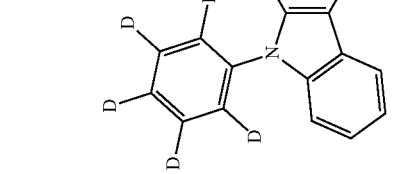 CAS: 1210469-09-2 | 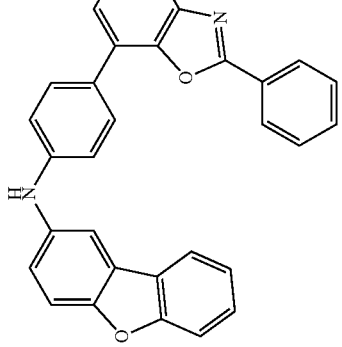 | 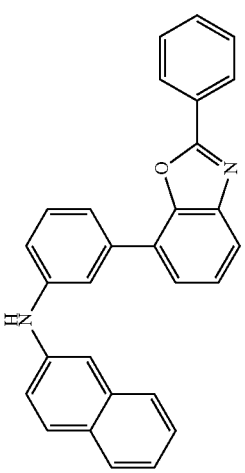 40 | 704.3 | 63 |

TABLE 4-continued
Synthesis of compounds of the present disclosure
| Reactant H | Reactant J | Compound and its Structure | m/z ([M + H]+) | Yield (%) |
|---|---|---|---|---|
| 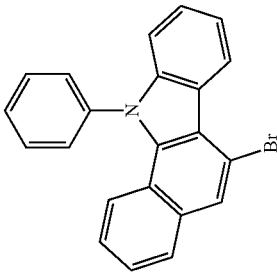 CAS: 1627726-68-4 | 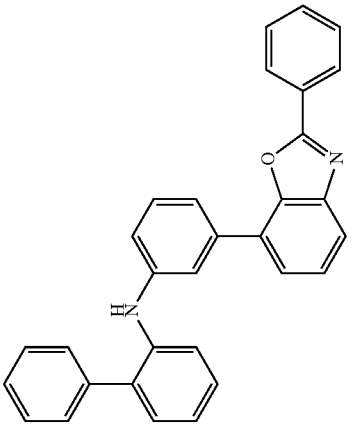 | 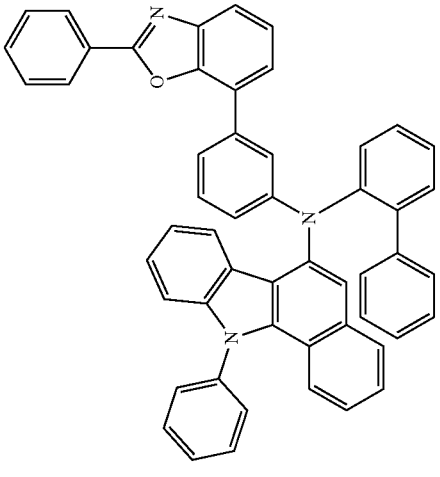 57 | 730.3 | 55 |
| 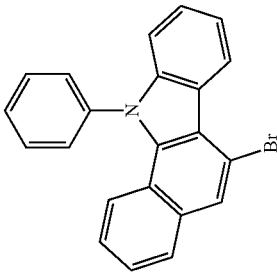 CAS: 1627726-68-4 | 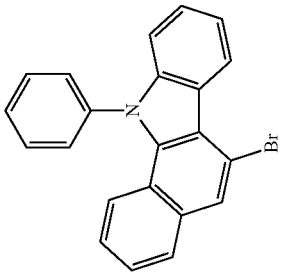 | 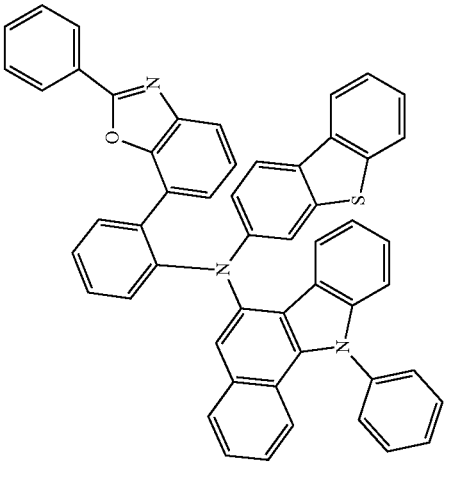 77 | 760.2 | 59 |

TABLE 4-continued

Synthesis of compounds of the present disclosure

| Reactant H | Reactant J | Compound and its Structure | m/z ([M + H]+) | Yield (%) |
|---|---|---|---|---|
| CAS: 1627726-68-4 | | 79 | 770.3 | 53 |
| CAS: 1247092-44-9 | | 87 | 718.2 | 56 |

TABLE 4-continued
Synthesis of compounds of the present disclosure
| Reactant H | Reactant J | Compound and its Structure | m/z ([M + H]+) | Yield (%) |
|---|---|---|---|---|
| 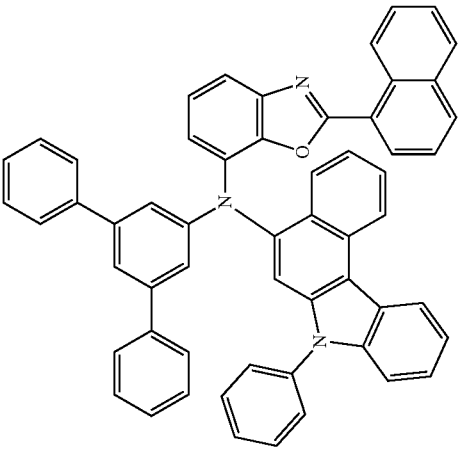<br>CAS: 1247092-44-9 | 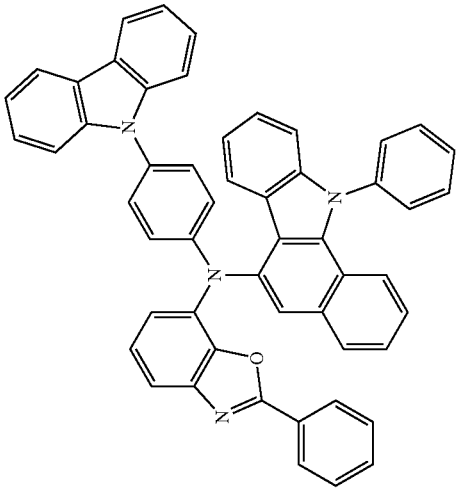 | 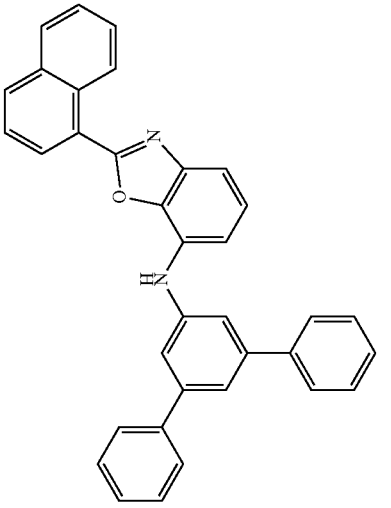<br>119 | 780.3 | 62 |
| 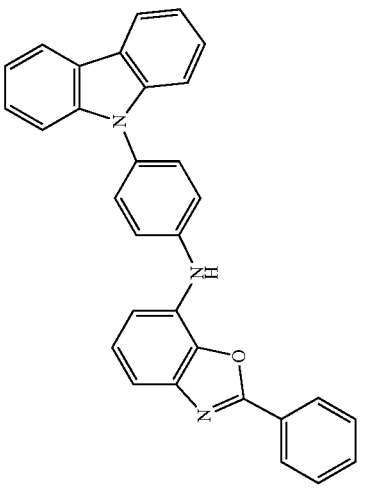<br>CAS: 1627726-68-4 | 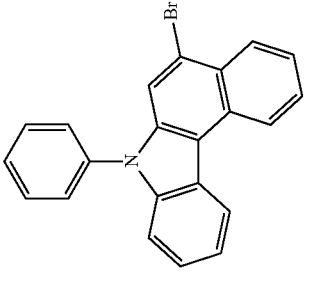 | 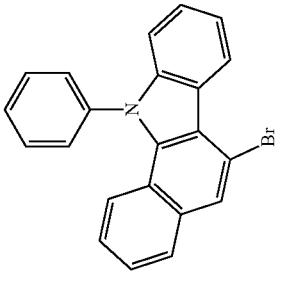 | 743.3 | 52 |

TABLE 4-continued
Synthesis of compounds of the present disclosure
| Reactant H | Reactant J | Compound and its Structure | m/z ([M + H]+) | Yield (%) |
|---|---|---|---|---|
| 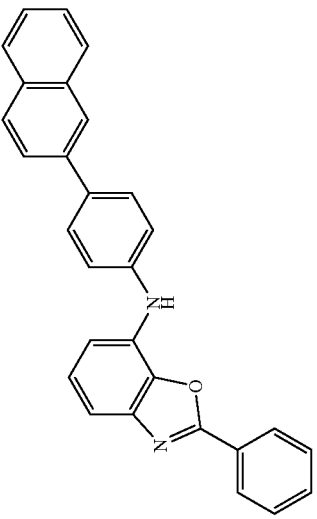 CAS: 1210469-09-2 | 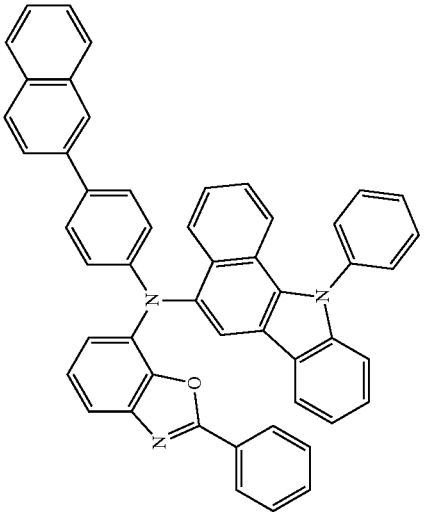 | 163 166 | 704.3 | 58 |

TABLE 4-continued

Synthesis of compounds of the present disclosure

| Reactant H | Reactant J | Compound and its Structure | m/z ([M + H]+) | Yield (%) |
|---|---|---|---|---|
| CAS: 1357572-67-8 | | 173 | 730.3 | 63 |

TABLE 4-continued
Synthesis of compounds of the present disclosure
| Reactant H | Reactant J | Compound and its Structure | m/z ([M + H]+) | Yield (%) |
|---|---|---|---|---|
| 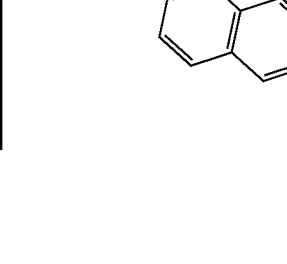 CAS: 1210469-11-6 | 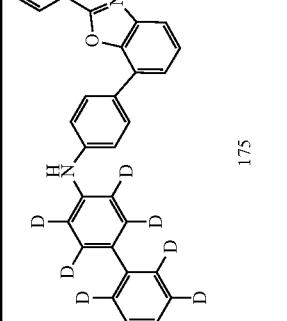 175 | 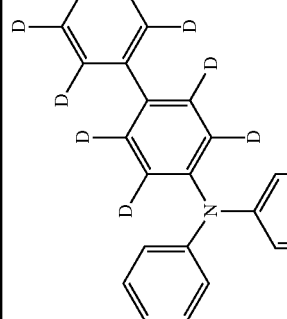 175 | 739.3 | 64 |
| 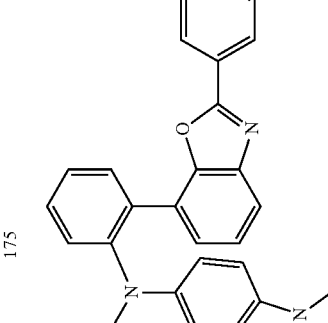 CAS: 1210470-49-7 | 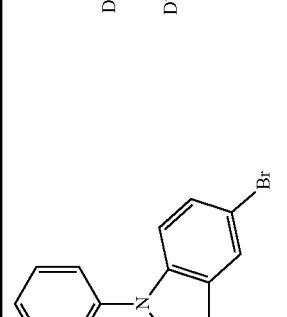 | 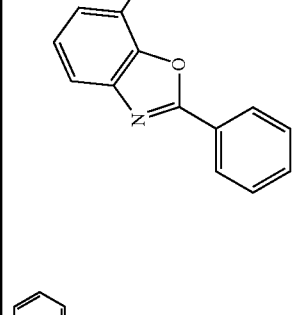 186 | 730.3 | 58 |

TABLE 4-continued

Synthesis of compounds of the present disclosure

| Reactant H | Reactant J | Compound and its Structure | m/z ([M + H]+) | Yield (%) |
|---|---|---|---|---|
| | | 196 | 739.3 | 53 |

TABLE 4-continued

Synthesis of compounds of the present disclosure

| Reactant H | Reactant J | Compound and its Structure | m/z ([M + H]+) | Yield (%) |
|---|---|---|---|---|
| CAS: 1374003-98-1 | | 260 | 728.3 | 64 |

TABLE 4-continued
Synthesis of compounds of the present disclosure
| Reactant H | Reactant J | Compound and its Structure | m/z ([M + H]+) | Yield (%) |
|---|---|---|---|---|
| 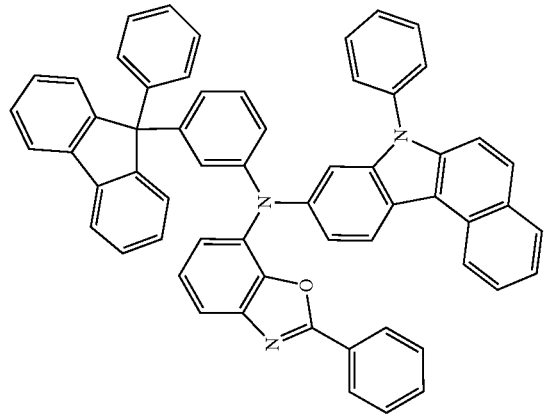 CAS: 1357572-67-8 | 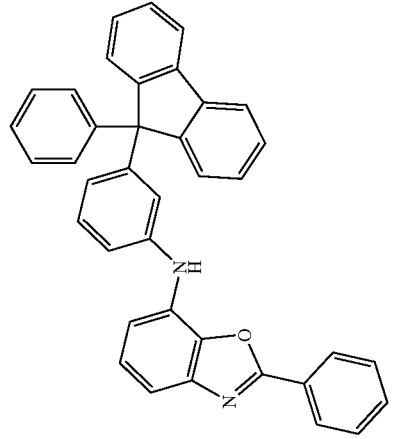 | 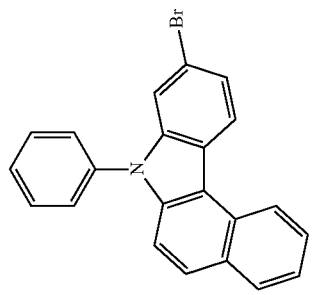 269 | 818.3 | 53 |

TABLE 4-continued

Synthesis of compounds of the present disclosure

| Reactant H | Reactant J | Compound and its Structure | m/z ([M + H]+) | Yield (%) |
|---|---|---|---|---|
| CAS: 1210469-11-6 | | 279 | 754.3 | 50 |
| CAS: 1357572-67-8 | | 285 | 744.3 | 64 |

TABLE 4-continued
Synthesis of compounds of the present disclosure
| Reactant H | Reactant J | Compound and its Structure | m/z ([M + H]⁺) | Yield (%) |
|---|---|---|---|---|
| 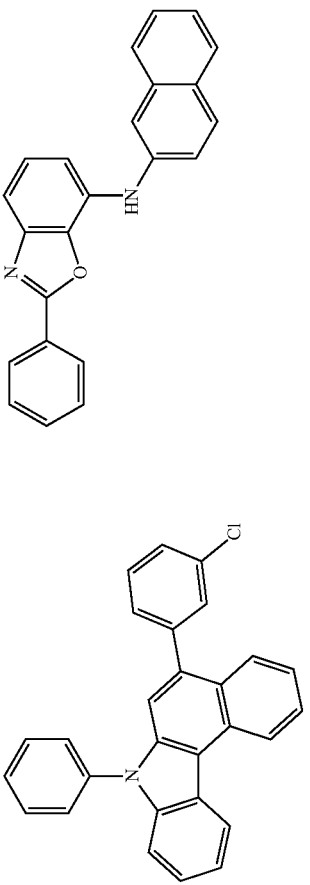 | 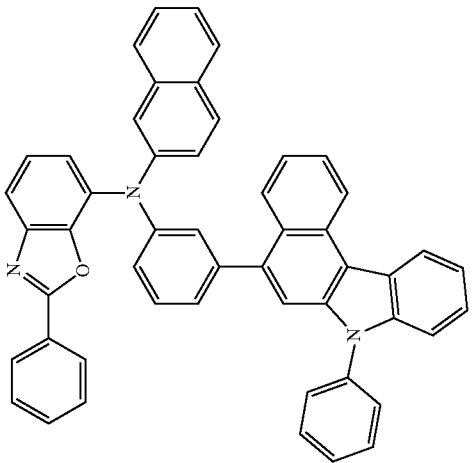 | 295 | 704.3 | 63 |

TABLE 4-continued

Synthesis of compounds of the present disclosure

| Reactant H | Reactant J | Compound and its Structure | m/z ([M + H]+) | Yield (%) |
|---|---|---|---|---|
| | | 305 | 748.3 | 59 |

TABLE 4-continued

Synthesis of compounds of the present disclosure

| Reactant H | Reactant J | Compound and its Structure | m/z ([M + H]+) | Yield (%) |
|---|---|---|---|---|
| | | | 754.3 | 60 |
| | | 316 | 760.2 | 62 |

TABLE 4-continued
Synthesis of compounds of the present disclosure
| Reactant H | Reactant J | Compound and its Structure | m/z ([M + H]+) | Yield (%) |
|---|---|---|---|---|
| 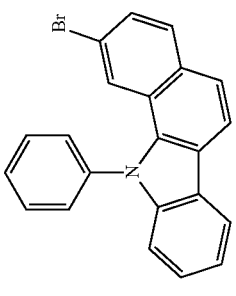<br>CAS: 1614244-24-4 | 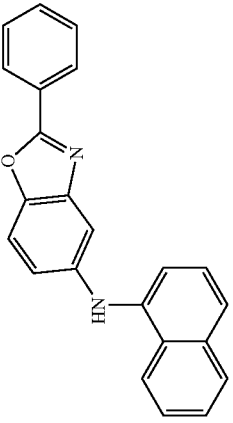 | 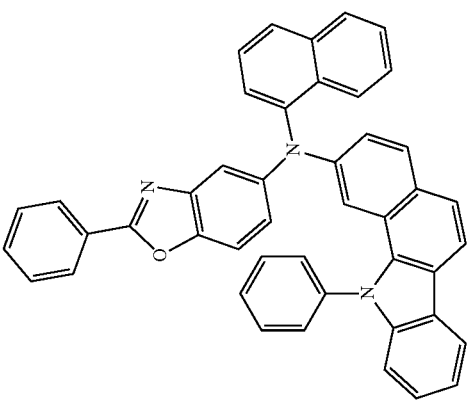<br>326 332 | 628.2 | 56 |

TABLE 4-continued

Synthesis of compounds of the present disclosure

| Reactant H | Reactant J | Compound and its Structure | m/z ([M + H]+) | Yield (%) |
|---|---|---|---|---|
| CAS:1884145-09-8 | | 333 | 670.2 | 57 |
| CAS: 2763492-42-6 | | | 668.2 | 62 |

TABLE 4-continued
Synthesis of compounds of the present disclosure
| Reactant H | Reactant J | Compound and its Structure | m/z ([M + H]+) | Yield (%) |
|---|---|---|---|---|
| 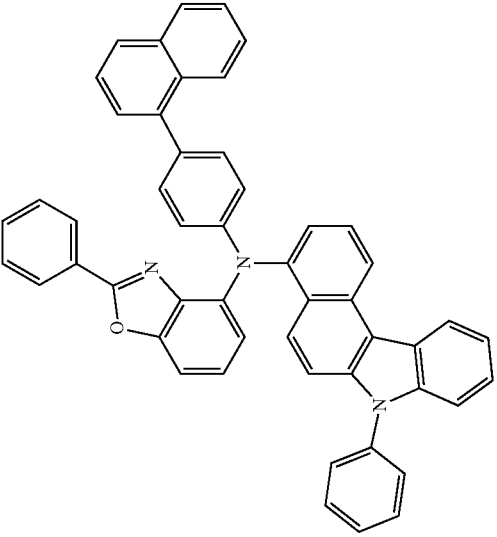<br>CAS: 2217624-12-7 | 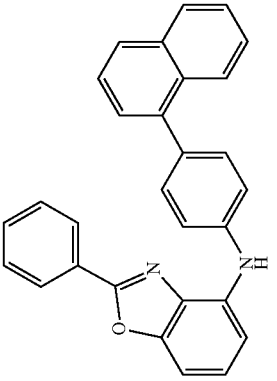 | 335<br>343 | 704.3 | 56 |

TABLE 4-continued

Synthesis of compounds of the present disclosure

| Reactant H | Reactant J | Compound and its Structure | m/z ([M + H]+) | Yield (%) |
|---|---|---|---|---|
| CAS: 2377767-81-0 | | 358 | 743.3 | 60 |

TABLE 4-continued
Synthesis of compounds of the present disclosure
| Reactant H | Reactant J | Compound and its Structure | m/z ([M + H]+) | Yield (%) |
|---|---|---|---|---|
| 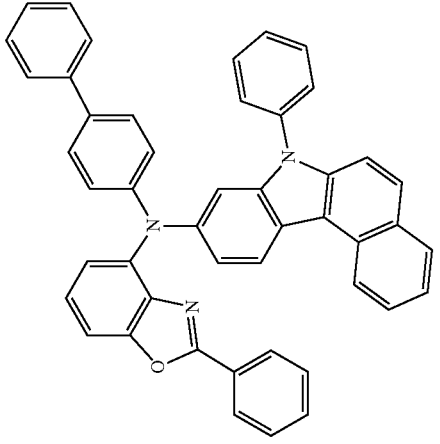<br>CAS: 1357572-67-8 | 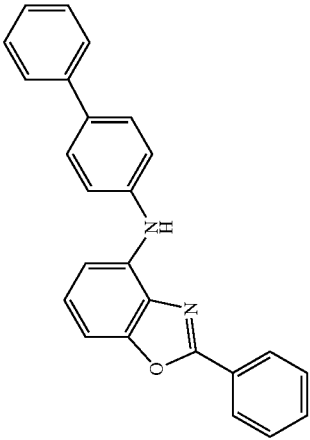 | 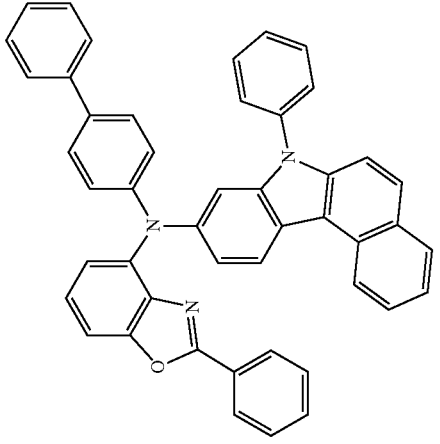<br>403 | 654.3 | 62 |
| 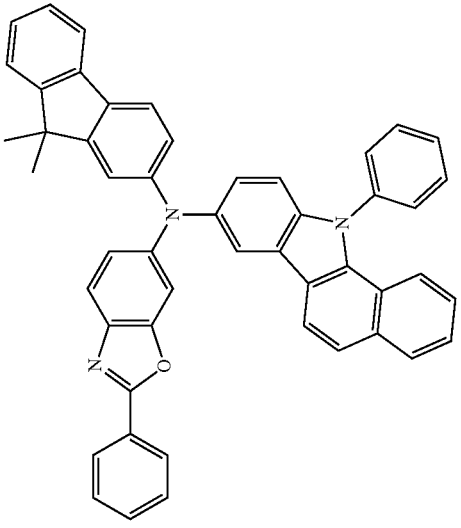<br>CAS: 1210470-49-7 | 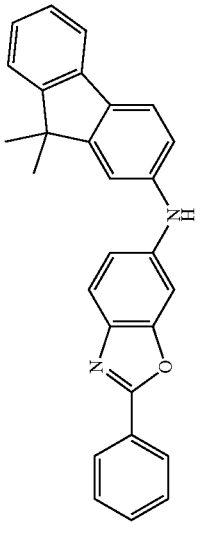 | 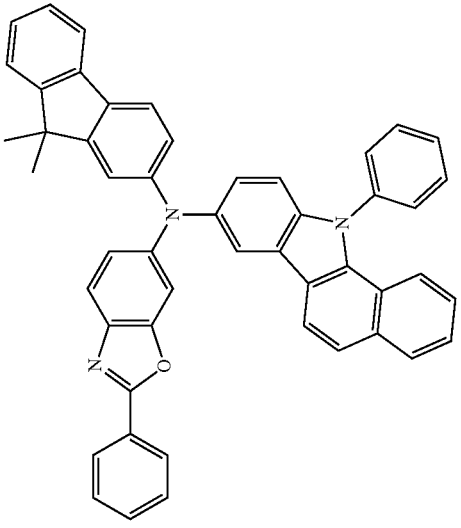<br>414 | 694.3 | 64 |

TABLE 4-continued

Synthesis of compounds of the present disclosure

| Reactant H | Reactant J | Compound and its Structure | m/z ([M + H]+) | Yield (%) |
|---|---|---|---|---|
| CAS: 1686100-20-8 | | 430 | 710.3 | 44 |
| CAS: 1686100-27-5 | | 434 | 704.3 | 48 |

TABLE 4-continued

Synthesis of compounds of the present disclosure

| Reactant H | Reactant J | Compound and its Structure | m/z ([M + H]+) | Yield (%) |
|---|---|---|---|---|
| (structure shown) CAS: 1686100-19-5 | (structure shown) | 437 | 654.3 | 65 |

TABLE 4-continued
Synthesis of compounds of the present disclosure
| Reactant H | Reactant J | Compound and its Structure | m/z ([M + H]+) | Yield (%) |
|---|---|---|---|---|
| 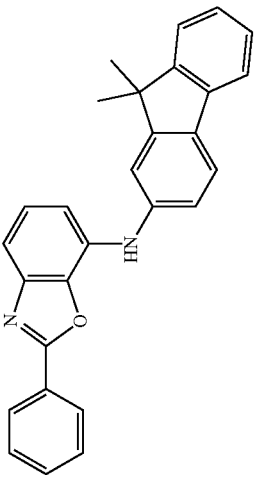 CAS: 1268271-78-8 | 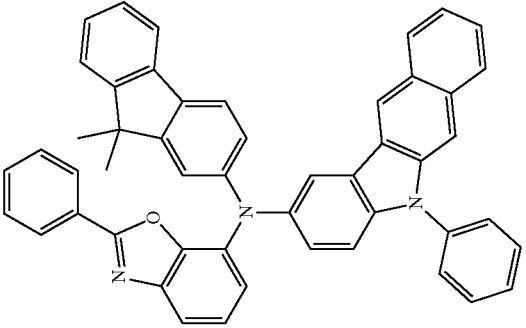 | 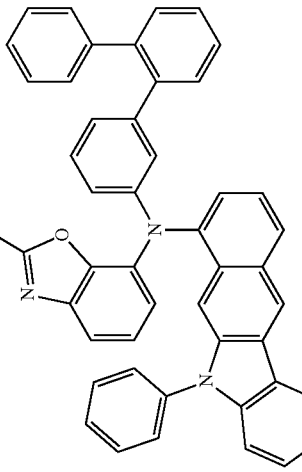 | 694.3 | 62 |
| 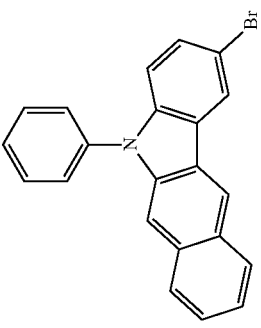 CAS: 2641978-60-9 | | 449 | 730.3 | 64 |

TABLE 4-continued
Synthesis of compounds of the present disclosure
| Reactant H | Reactant J | Compound and its Structure | m/z ([M + H]+) | Yield (%) |
|---|---|---|---|---|
| 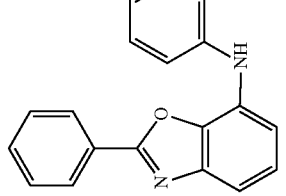 | 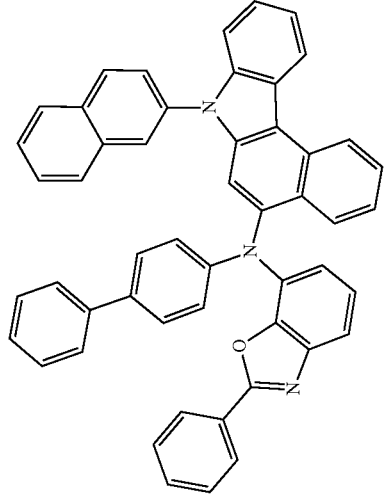 | 456 463 | 704.3 | 50 |

TABLE 4-continued

Synthesis of compounds of the present disclosure

| Reactant H | Reactant J | Compound and its Structure | m/z ([M + H]+) | Yield (%) |
|---|---|---|---|---|
| | | 464 | 730.3 | 56 |

TABLE 4-continued
Synthesis of compounds of the present disclosure
| Reactant H | Reactant J | Compound and its Structure | m/z ([M + H]+) | Yield (%) |
|---|---|---|---|---|
| 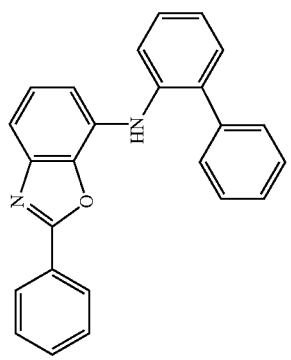 | 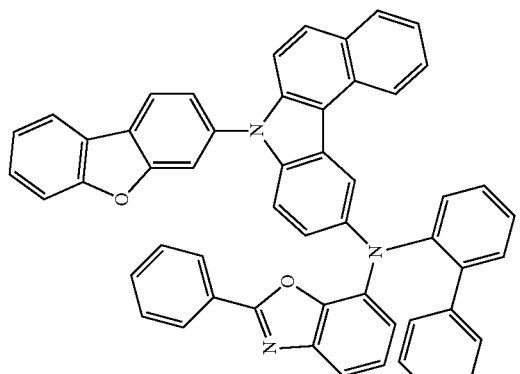 | 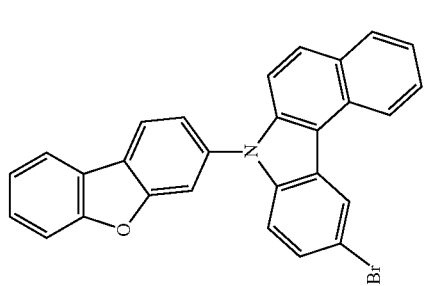 465 | 744.3 | 60 |
| 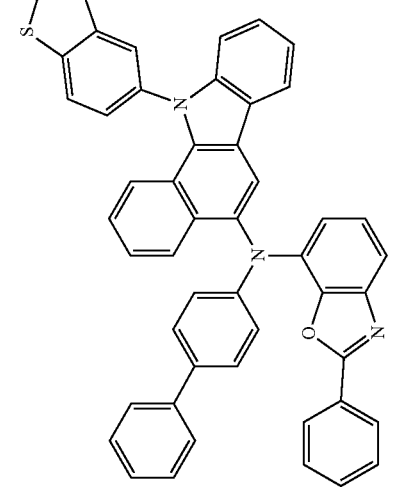 | | 466 | 760.2 | 58 |

TABLE 4-continued
Synthesis of compounds of the present disclosure
| Reactant H | Reactant J | Compound and its Structure | | m/z ([M + H]+) | Yield (%) |
|---|---|---|---|---|---|
| 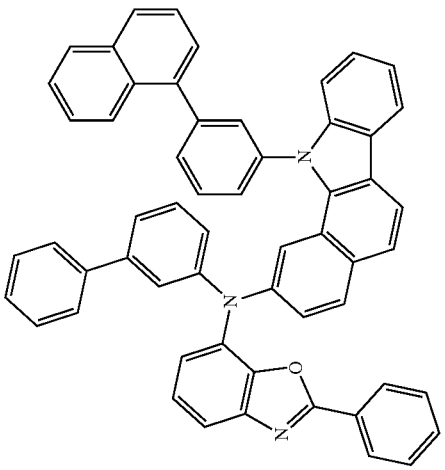 | 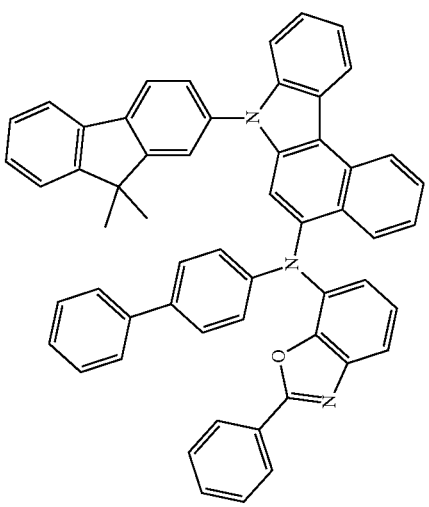 | 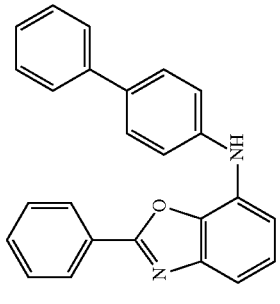 | 470 | 780.3 | 61 |
| | | 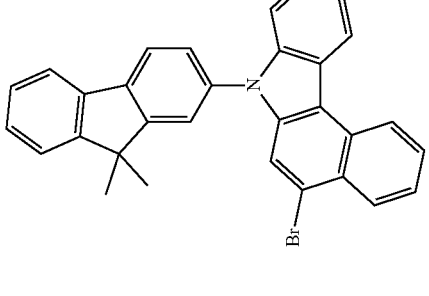 | 475 | 770.3 | 56 |

TABLE 4-continued
Synthesis of compounds of the present disclosure
| Reactant H | Reactant J | Compound and its Structure | m/z ([M + H]+) | Yield (%) |
|---|---|---|---|---|
| 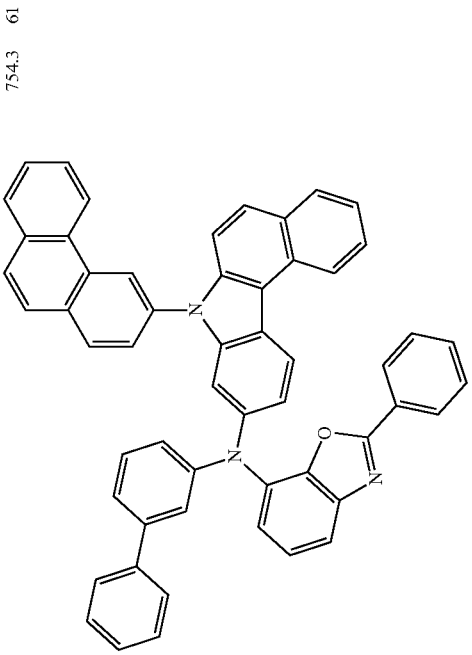 | 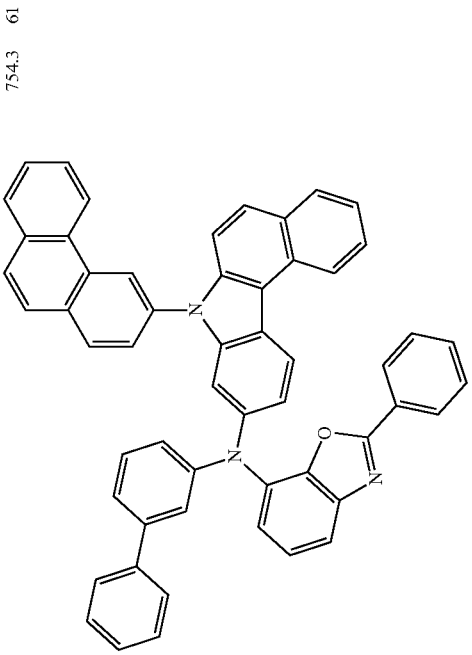 | 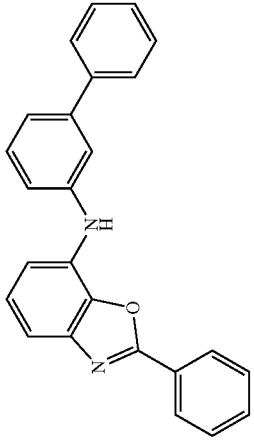 479 | 754.3 | 61 |

TABLE 4-continued
Synthesis of compounds of the present disclosure
| Reactant H | Reactant J | Compound and its Structure | m/z ([M + H]+) | Yield (%) |
|---|---|---|---|---|
| 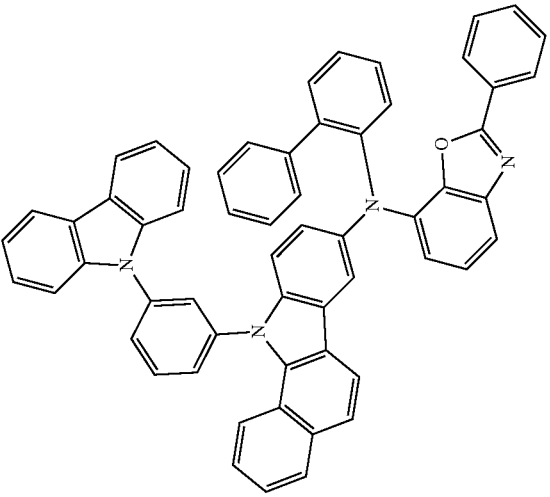 | 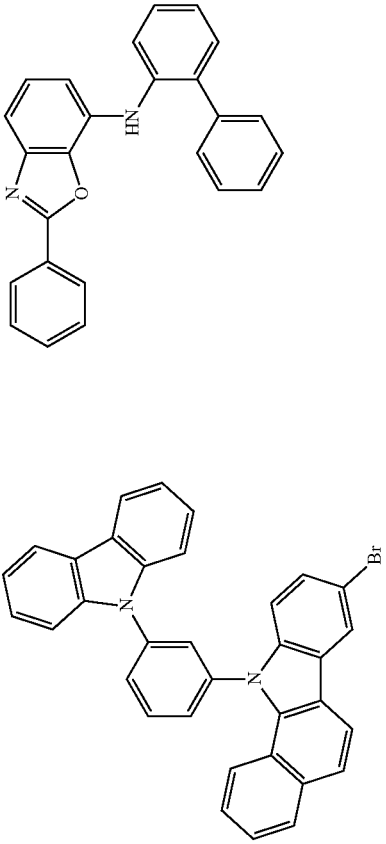 | 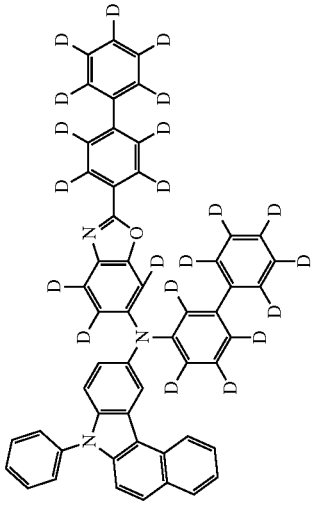 486 | 819.3 751.4 | 59 61 |

TABLE 4-continued

Synthesis of compounds of the present disclosure

| Reactant H | Reactant J | Compound and its Structure | m/z ([M + H]+) | Yield (%) |
|---|---|---|---|---|
| | | 495 | | |

1H-NMR NMR Data of Compounds:

| Compound | (400 MHZ, CD$_2$Cl$_2$) δ ppm |
|---|---|
| Compound 166 | 8.66 (d, 1H), 8.23 (d, 2H), 7.99 (d, 1H), 7.88-7.82 (m, 4H), 7.75-7.69 (m, 2H), 7.64 (t, 1H), 7.57 (t, 2H), 7.54-7.27 (m, 16H), 7.12 (t, 1H), 6.53 (d, 2H), 6.16 (d, 1H) |
| Compound 173 | 8.24-8.20 (m, 3H), 8.04 (d, 1H), 7.97 (d, 1H), 7.82 (d, 1H), 7.65-7.48 (m, 13H), 7.46 (d, 2H), 7.44-7.34 (m, 7H), 7.28 (d, 1H), 7.22 (s, 1H), 6.72-6.63 (m, 4H), 6.30 (d, 1H) |

Fabrication and Evaluation of Organic Electroluminescent Devices

Example 1: Fabrication of a Red Light-Emitting Organic Electroluminescent Device First, anode pretreatment was performed by the following processes. A surface of an ITO/Ag/ITO substrate, with thicknesses of ITO/Ag/ITO being 100 Å, 1000 Å, and 100 Å, respectively, was treated using ultraviolet ozone and O$_2$:N$_2$ plasma to increase the work function of the anode, and then cleaned with an organic solvent to remove impurities and oil on the ITO substrate.

Compound PD was deposited by vacuum evaporation on the experimental substrate (anode) to form a hole injection layer (HIL) with a thickness of 100 Å, and then α-NPD was deposited by vacuum evaporation on the hole injection layer to form a hole transport layer with a thickness of 1080 Å.

Compound HT-1 was deposited by vacuum evaporation on the hole transport layer to form a hole adjustment layer with a thickness of 690 Å.

Next, Compound 5, Compound RH—N, and Compound RD-1 were co-deposited by evaporation on the hole adjustment layer in a mass ratio of 49%: 49%: 2% to form a red light-emitting layer (EML) with a thickness of 400 Å.

Compound ET-1 and Compound LiQ were mixed in a 1:1 weight ratio and deposited by evaporation on the light-emitting layer to form an electron transport layer (ETL) with a thickness of 350 Å; Yb was deposited by evaporation on the electron transport layer to form an electron injection layer (EIL) with a thickness of 10 Å; and then magnesium (Mg) and silver (Ag) were mixed in a rate ratio of 1:9, and deposited by vacuum evaporation on the electron injection layer to form a cathode with a thickness of 130 Å.

Further, Compound CP-1 was deposited by vacuum evaporation on the above cathode to form a capping layer with a thickness of 820 Å, completing the fabrication of a red organic electroluminescent device.

Examples 2 to 44

Organic electroluminescent devices were fabricated respectively by the same method as used in Example 1, except that Compound 5 in Example 1 was replaced with a corresponding Compound X shown in the following Table 5 when a light-emitting layer was formed.

Comparative Examples 1 to 4

Organic electroluminescent devices were fabricated respectively by the same method as used in Example 1, except that Compound 5 in Example 1 was replaced with a corresponding one of Compound A, Compound B, Compound C, and Compound D when a light-emitting layer was formed.

Structures of the compounds used in the Examples and Comparative Examples are as follows:

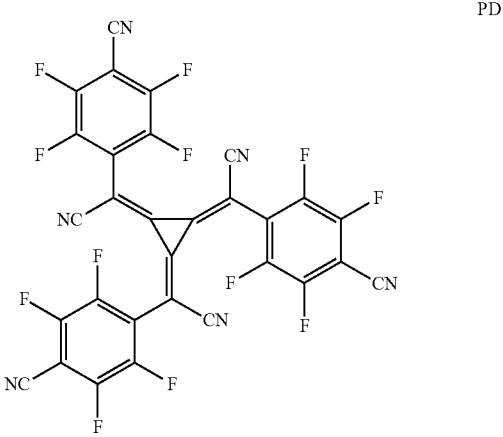

PD

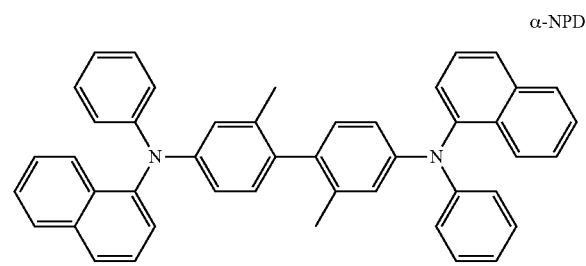

α-NPD

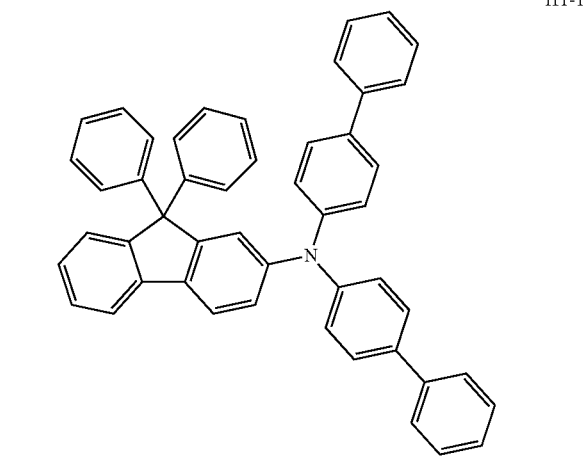

HT-1

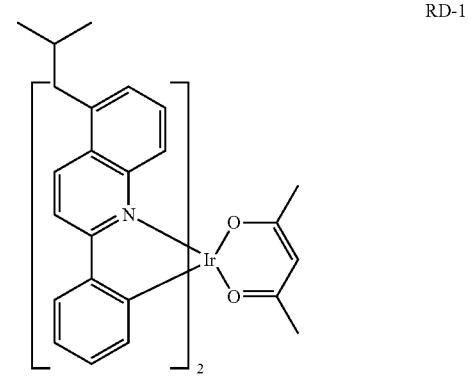

RD-1

ET-1
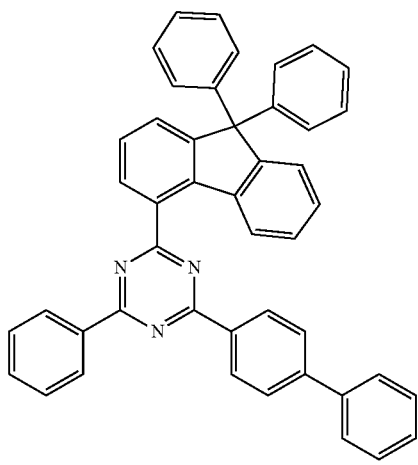
Compound A
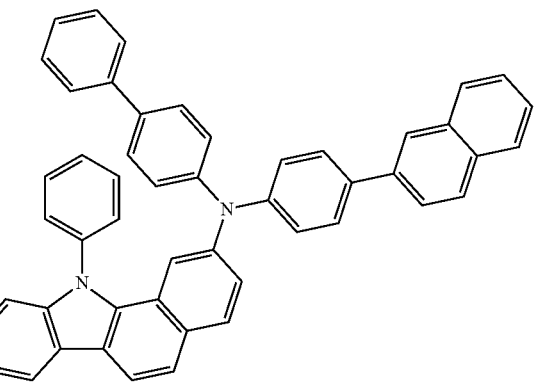
LiQ
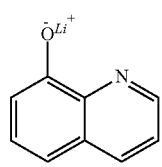
CP-1
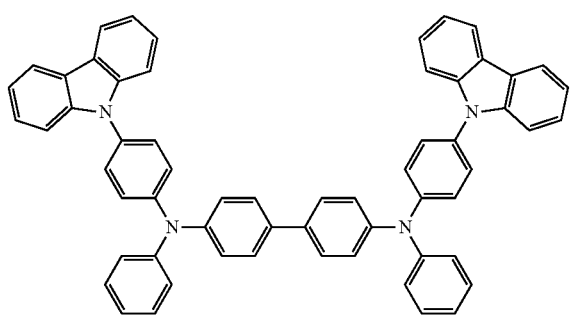
Compound B
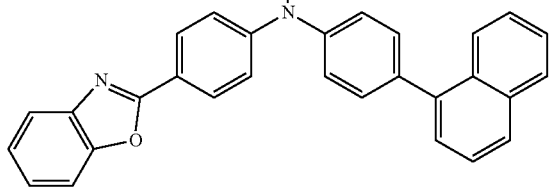
RH-N
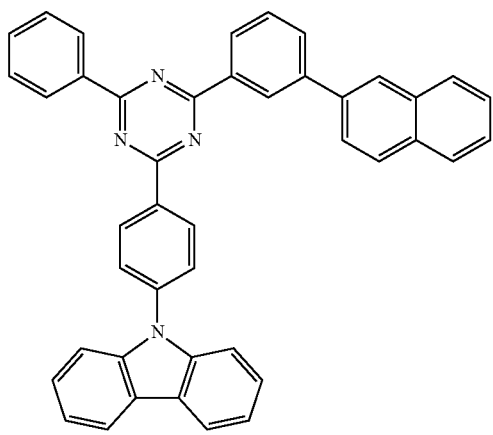
Compound C
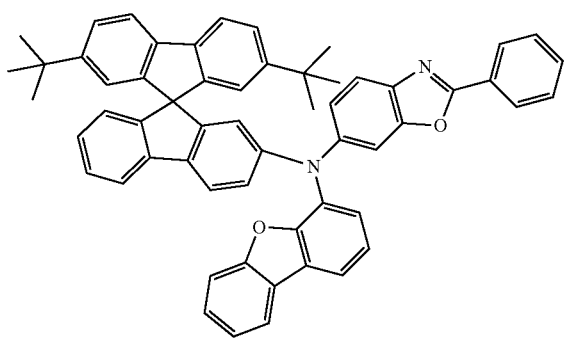

-continued

Compound D

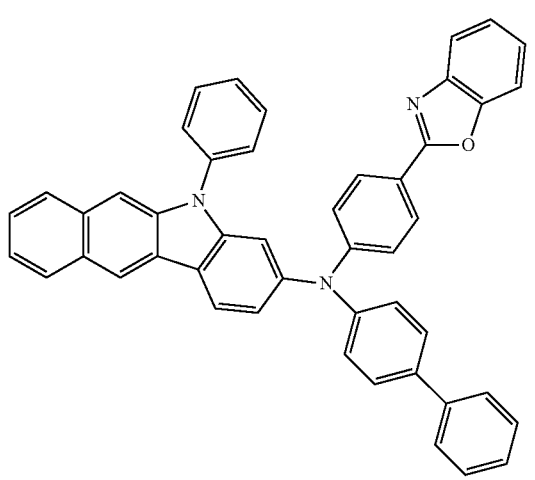

The red organic electroluminescent devices fabricated in Examples 1 to 44 and Comparative Examples 1 to 4 were tested for their performance. Specifically, the IVL characteristics of the devices were tested under the condition of 10 mA/cm$^2$, and the T$_{95}$ lifetime of the devices was tested under the condition of 20 mA/cm$^2$. Test results are shown in Table 5.

TABLE 5

| No. | Compound X in light-emitting layer | Operating voltage (V) | Cd/A | CIEx | CIEy | T$_{95}$(h)@ 20 mA/cm$^2$ |
|---|---|---|---|---|---|---|
| Example 1 | Compound 5 | 3.42 | 59.6 | 0.680 | 0.320 | 430 |
| Example 2 | Compound 12 | 3.44 | 59.3 | 0.680 | 0.320 | 423 |
| Example 3 | Compound 19 | 3.46 | 59.5 | 0.680 | 0.320 | 435 |
| Example 4 | Compound 40 | 3.44 | 59.8 | 0.680 | 0.320 | 426 |
| Example 5 | Compound 57 | 3.45 | 59.7 | 0.680 | 0.320 | 436 |
| Example 6 | Compound 77 | 3.44 | 59.0 | 0.680 | 0.320 | 431 |
| Example 7 | Compound 79 | 3.44 | 59.8 | 0.680 | 0.320 | 429 |
| Example 8 | Compound 87 | 3.46 | 56.3 | 0.680 | 0.320 | 480 |
| Example 9 | Compound 119 | 3.46 | 56.7 | 0.680 | 0.320 | 481 |
| Example 10 | Compound 163 | 3.43 | 56.5 | 0.680 | 0.320 | 469 |
| Example 11 | Compound 166 | 3.44 | 56.6 | 0.680 | 0.320 | 468 |
| Example 12 | Compound 173 | 3.43 | 59.7 | 0.680 | 0.320 | 432 |
| Example 13 | Compound 175 | 3.44 | 58.7 | 0.680 | 0.320 | 434 |
| Example 14 | Compound 186 | 3.45 | 59.4 | 0.680 | 0.320 | 428 |
| Example 15 | Compound 196 | 3.42 | 60.3 | 0.680 | 0.320 | 431 |
| Example 16 | Compound 260 | 3.46 | 56.2 | 0.680 | 0.320 | 472 |
| Example 17 | Compound 269 | 3.44 | 56.3 | 0.680 | 0.320 | 484 |
| Example 18 | Compound 279 | 3.46 | 56.0 | 0.680 | 0.320 | 476 |
| Example 19 | Compound 285 | 3.46 | 56.5 | 0.680 | 0.320 | 466 |
| Example 20 | Compound 295 | 3.45 | 59.1 | 0.680 | 0.320 | 425 |
| Example 21 | Compound 305 | 3.43 | 59.0 | 0.680 | 0.320 | 436 |
| Example 22 | Compound 316 | 3.42 | 60.4 | 0.680 | 0.320 | 435 |
| Example 23 | Compound 326 | 3.43 | 59.3 | 0.680 | 0.320 | 430 |
| Example 24 | Compound 332 | 3.43 | 56.2 | 0.680 | 0.320 | 474 |
| Example 25 | Compound 333 | 3.44 | 56.0 | 0.680 | 0.320 | 477 |
| Example 26 | Compound 335 | 3.43 | 56.1 | 0.680 | 0.320 | 483 |
| Example 27 | Compound 343 | 3.45 | 55.7 | 0.680 | 0.320 | 469 |
| Example 28 | Compound 358 | 3.45 | 56.4 | 0.680 | 0.320 | 466 |
| Example 29 | Compound 403 | 3.46 | 56.8 | 0.680 | 0.320 | 467 |
| Example 30 | Compound 414 | 3.44 | 56.3 | 0.680 | 0.320 | 473 |
| Example 31 | Compound 430 | 3.43 | 55.8 | 0.680 | 0.320 | 476 |
| Example 32 | Compound 434 | 3.43 | 55.6 | 0.680 | 0.320 | 479 |
| Example 33 | Compound 437 | 3.45 | 55.7 | 0.680 | 0.320 | 478 |
| Example 34 | Compound 449 | 3.66 | 56.8 | 0.680 | 0.320 | 427 |
| Example 35 | Compound 456 | 3.66 | 56.2 | 0.680 | 0.320 | 422 |
| Example 36 | Compound 463 | 3.43 | 56.1 | 0.680 | 0.320 | 474 |
| Example 37 | Compound 464 | 3.46 | 56.6 | 0.680 | 0.320 | 465 |
| Example 38 | Compound 465 | 3.44 | 56.6 | 0.680 | 0.320 | 475 |
| Example 39 | Compound 466 | 3.44 | 56.1 | 0.680 | 0.320 | 465 |
| Example 40 | Compound 470 | 3.43 | 56.3 | 0.680 | 0.320 | 485 |
| Example 41 | Compound 475 | 3.46 | 56.0 | 0.680 | 0.320 | 479 |
| Example 42 | Compound 479 | 3.42 | 56.8 | 0.680 | 0.320 | 480 |
| Example 43 | Compound 486 | 3.43 | 55.8 | 0.680 | 0.320 | 463 |
| Example 44 | Compound 495 | 3.43 | 56.8 | 0.680 | 0.320 | 493 |
| Comparative Example 1 | Compound A | 3.76 | 49.8 | 0.680 | 0.320 | 352 |
| Comparative Example 2 | Compound B | 3.77 | 47.1 | 0.680 | 0.320 | 362 |
| Comparative Example 3 | Compound C | 3.78 | 45.5 | 0.680 | 0.320 | 360 |
| Comparative Example 4 | Compound D | 3.88 | 48.5 | 0.680 | 0.320 | 371 |

As can be seen from the above Table 5, compared with Comparative Examples 1 to 4, the Examples, in which the compounds of the present disclosure are used as the host material of the red organic electroluminescent devices, the operating voltage is decreased by at least 0.1V, and the efficiency is increased by at least 11.6%, and the service life is increased by at least 15.13%.

The structure of each of the arylamine compounds of the present disclosure includes benzocarbazolyl and benzoxazolyl or benzothiazolyl groups. The benzocarbazolyl group has an excellent hole transport property, and the benzoxazolyl or benzothiazolyl group has a relatively large conjugation plane, which is conducive to intermolecular accumulation and can further improve hole mobility in the compounds of the present disclosure. A triarylamine compound, when used as a hole transport-type host material, can be oxidized to form free radical cations. The benzoxazolyl or benzothiazolyl group linked, directly or indirectly via a benzene ring, to the nitrogen atoms of the arylamine can stabilize theses free radical cations and improve the electrochemical stability of the compounds. Therefore, the compounds of the present disclosure, when used as a hole transport-type host material in a mixed-type host material, can significantly improve the efficiency of a device and significantly prolong service life thereof.

The above describes in detail the preferred embodiments of the present disclosure with reference to the accompanying drawings. The present disclosure, however, is not limited to those specific details provided in the above embodiments. A variety of simple variations may be made to the technical solutions of the present disclosure within the scope of the technical conception of the present disclosure, and all such simple variations are within the protection scope of the present disclosure.

The invention claimed is:

1. An arylamine compound, having a structure shown in Formula 1;

Formula 1

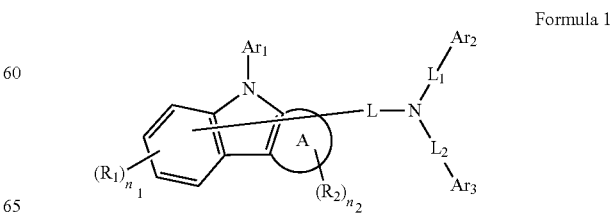

wherein:

ring A is a naphthalene ring;

L, L₁, and L₂ are identical or different, and are each independently selected from the group consisting of single bond, substituted or unsubstituted phenylene, substituted or unsubstituted naphthylene, and substituted or unsubstituted biphenylene;

the substituents in L, L₁, and L₂ are each independently selected from the group consisting of deuterium, fluorine, cyano, trimethylsilyl, trideuteromethyl, trifluoromethyl, methyl, ethyl, isopropyl and tert-butyl;

Ar₂ is a group shown in Formula 2;

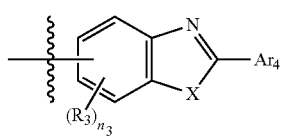

Formula 2

X is selected from O or S;

Ar₁ and Ar₃ are each independently selected from substituted or unsubstituted group W, wherein the unsubstituted group W is selected from the group consisting of the following groups:

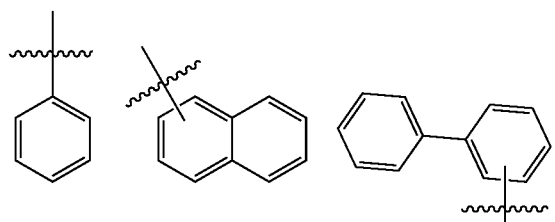

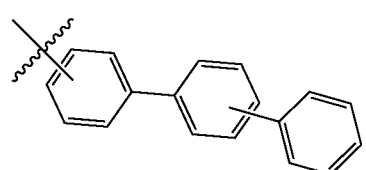

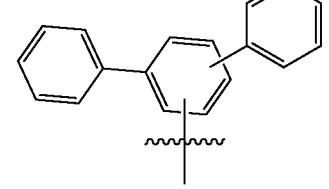

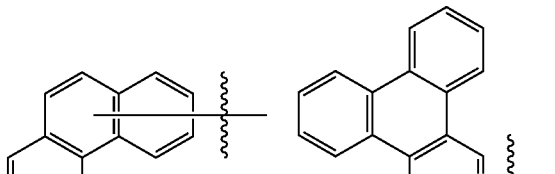

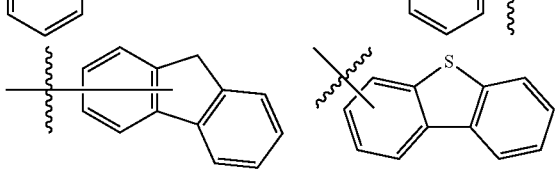

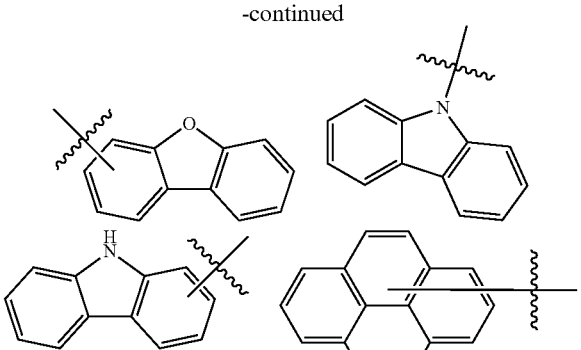

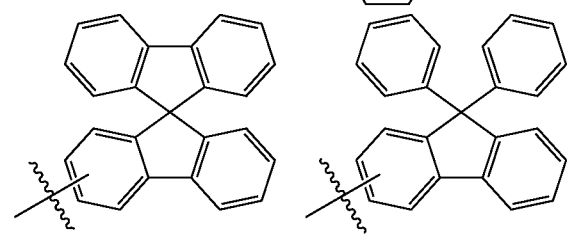

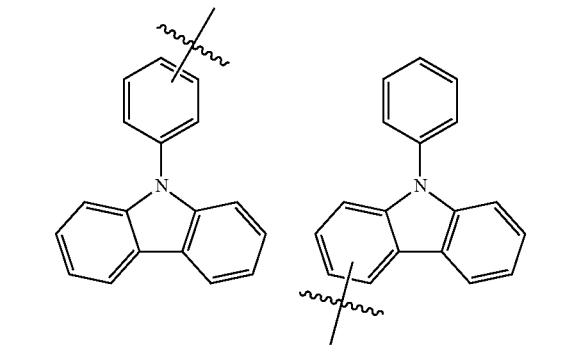

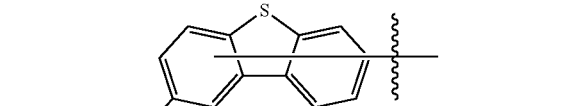

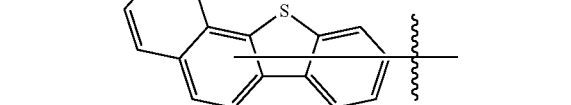

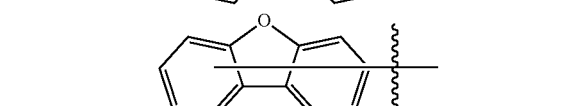

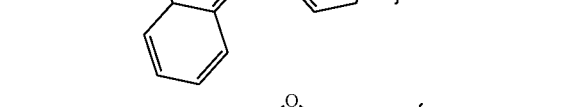

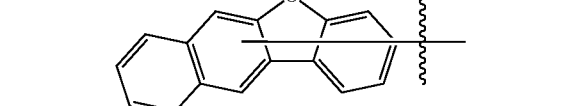

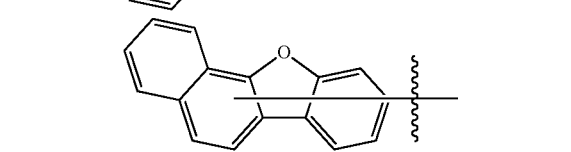

-continued

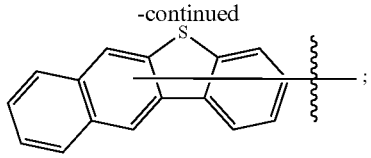

the substituted group W each has one or more substituents, the substituents being each independently selected from the group consisting of deuterium, fluorine, cyano, trimethylsilyl, trifluoromethyl, methyl, ethyl, isopropyl, tert-butyl, phenyl and naphthyl, wherein when the number of the substituents in group W is greater than 1, the substituents are identical or different;

$Ar_4$ is selected from the group consisting of substituted or unsubstituted phenyl, substituted or unsubstituted naphthyl, substituted or unsubstituted biphenyl, substituted or unsubstituted terphenyl, substituted or unsubstituted fluorenyl, and substituted or unsubstituted phenanthryl;

the substituents in $Ar_4$ are each independently selected from the group consisting of deuterium, fluorine, cyano, trimethylsilyl, triphenylsilyl, trideuteromethyl, trifluoromethyl, methyl, ethyl, isopropyl, tert-butyl and phenyl; and each $R_1$, each $R_2$, each $R_3$ is independently selected from the group consisting of deuterium, cyano, fluorine, trideuteromethyl, trimethylsilyl, methyl, ethyl, isopropyl and tert-butyl; $n_1$ is selected from 0, 1, 2, 3, or 4; $n_2$ is selected from 0, 1, 2, 3, 4, 5, or 6; $n_3$ is selected from 0, 1, 2, or 3.

2. The arylamine compound according to claim 1, wherein $Ar_2$ is selected from the following groups:

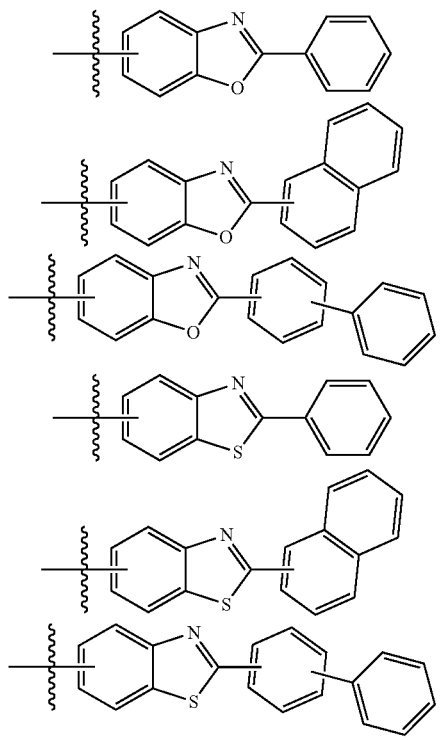

-continued

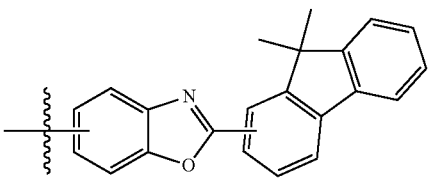

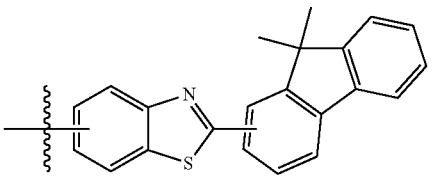

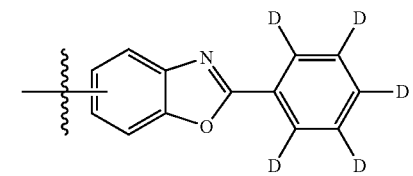

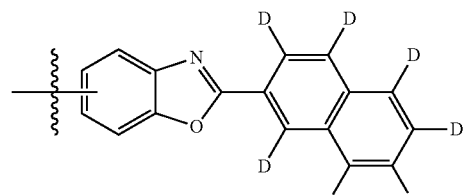

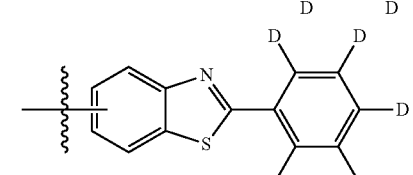

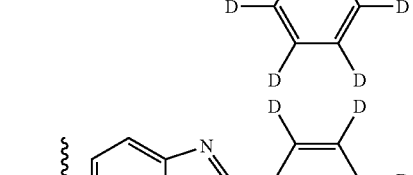

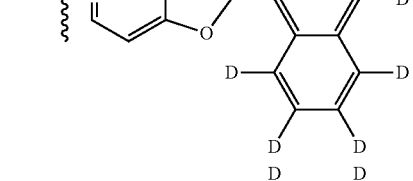

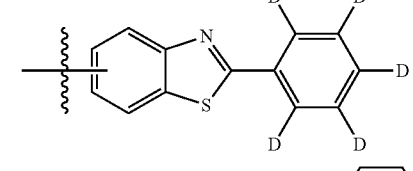

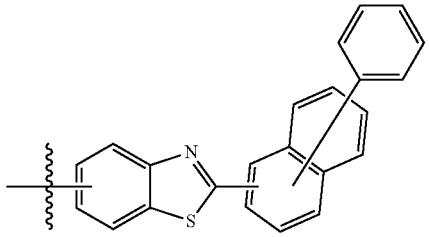

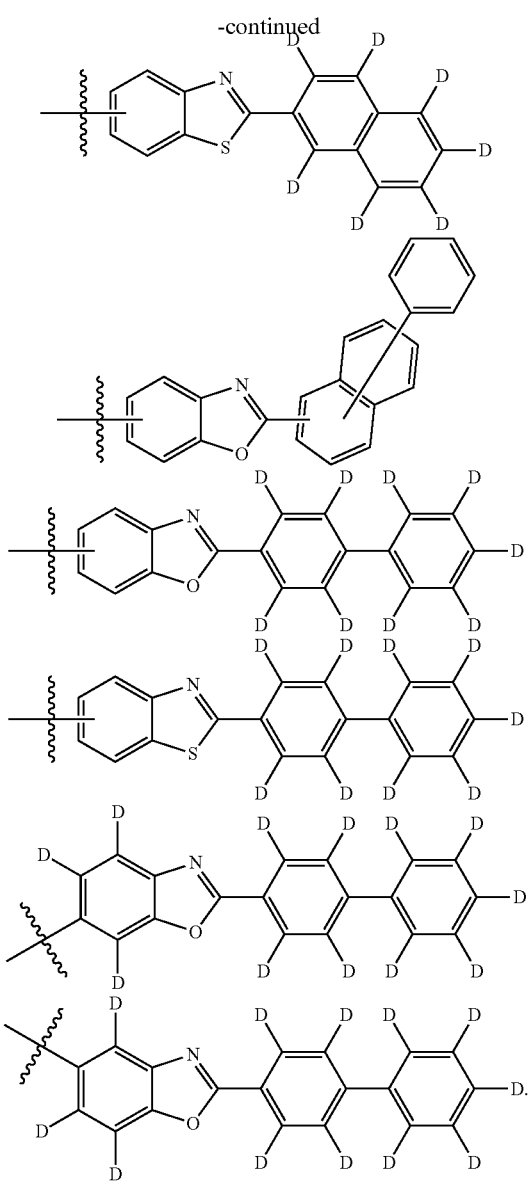
3. The arylamine compound according to claim 1, wherein
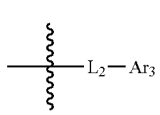
is selected from the following groups:
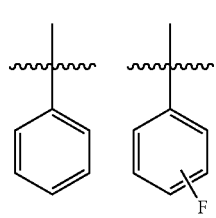
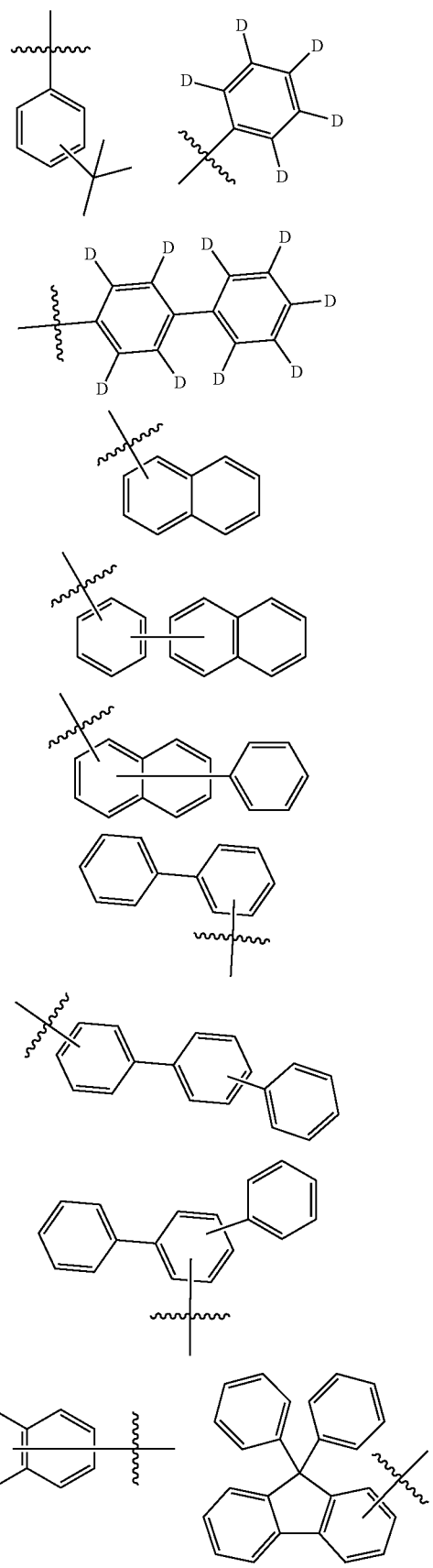
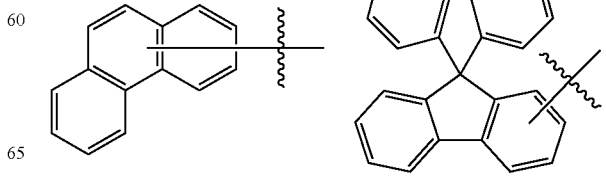

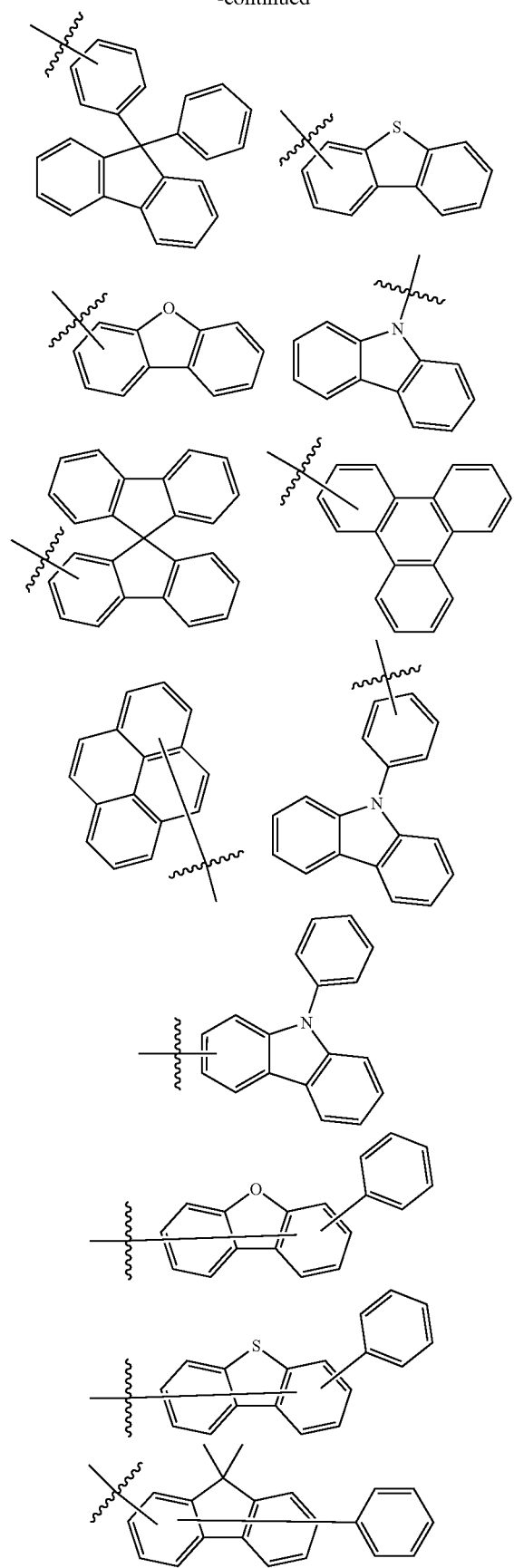
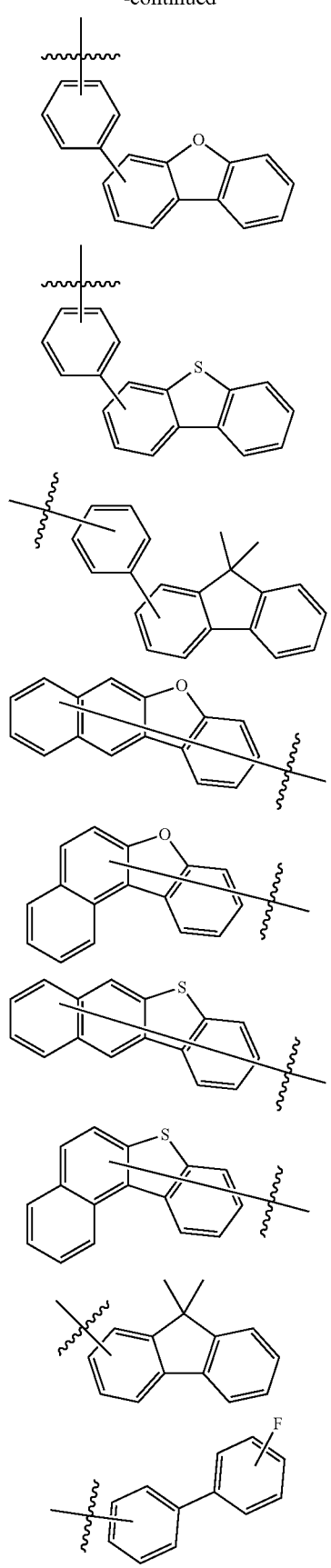

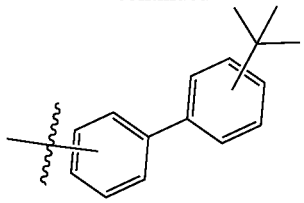
4. The arylamine compound according to claim 1, wherein
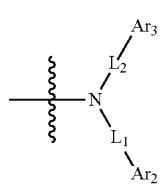
is selected from the following groups:
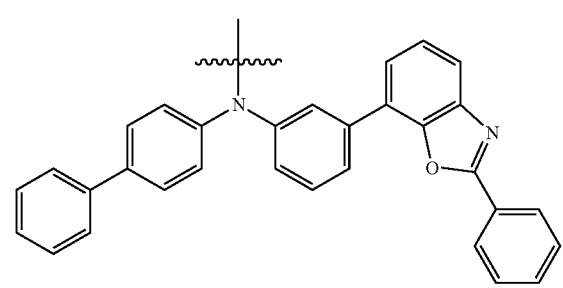
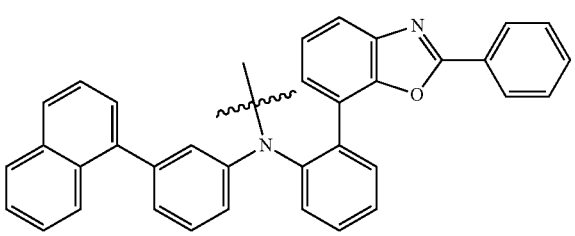 [SMILES: c1ccc(-c2nc3cccc(-c4ccccc4Nc4cccc(-c5cccc6ccccc56)c4)c3o2)cc1]
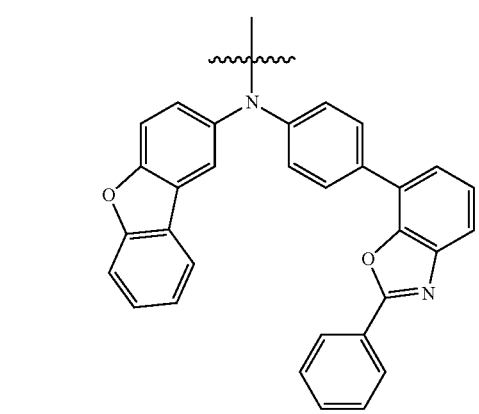
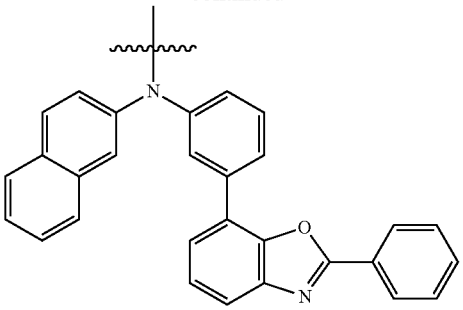
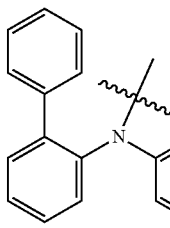
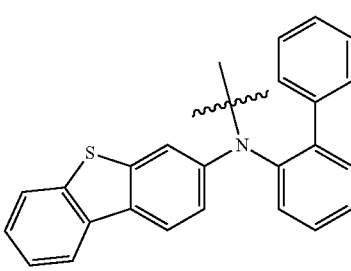
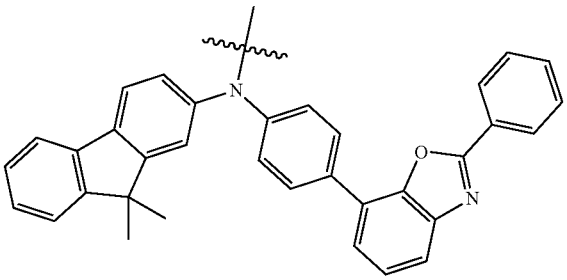
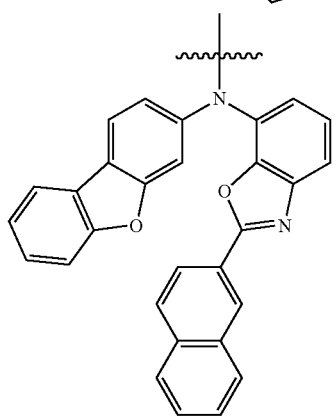

353
-continued
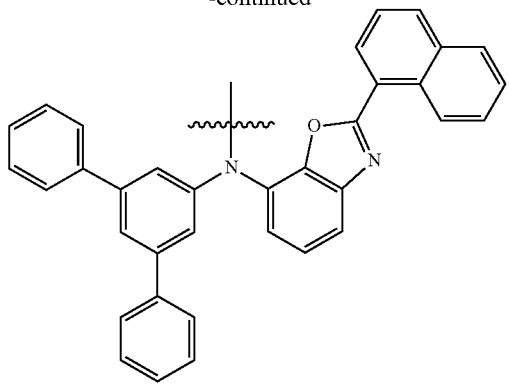
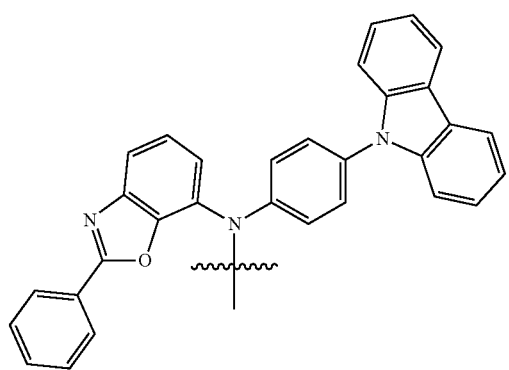
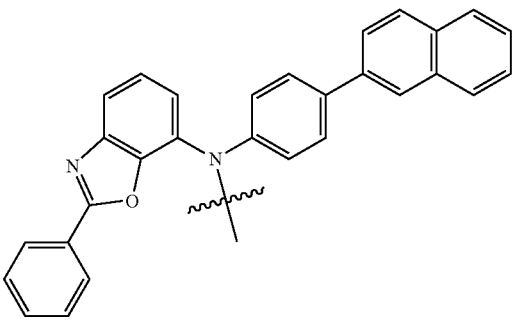
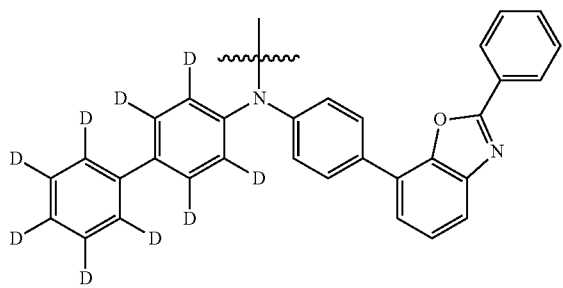
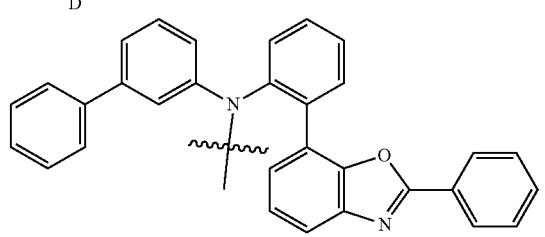
354
-continued
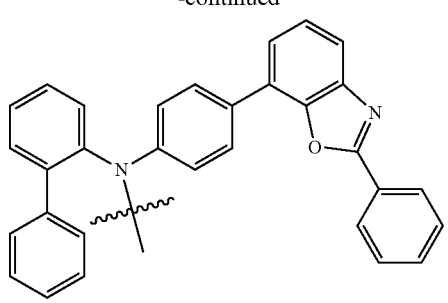
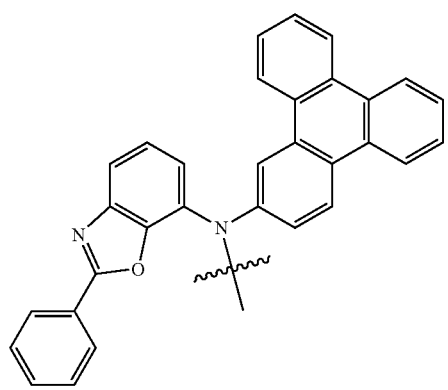
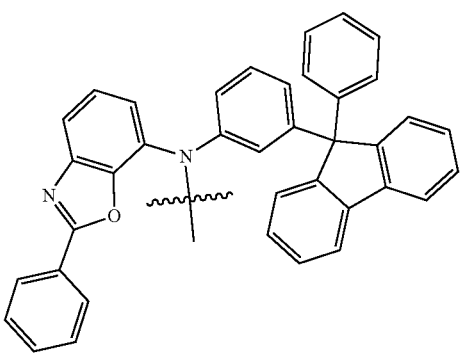
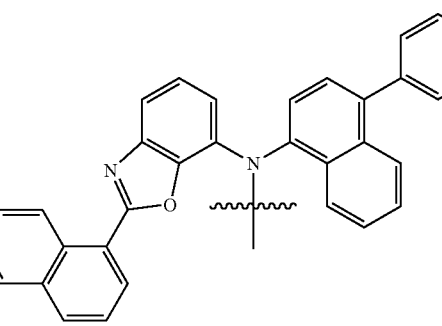
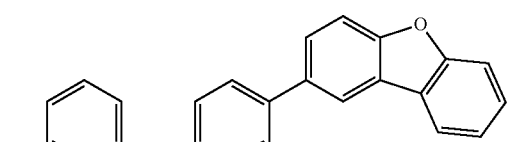

355
-continued
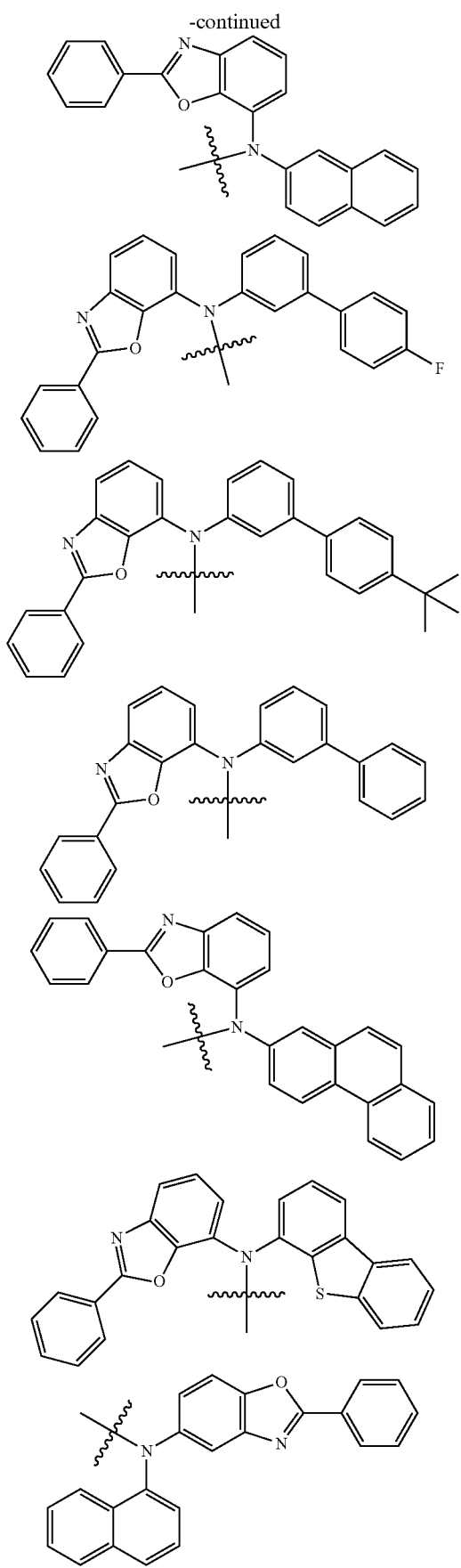
356
-continued
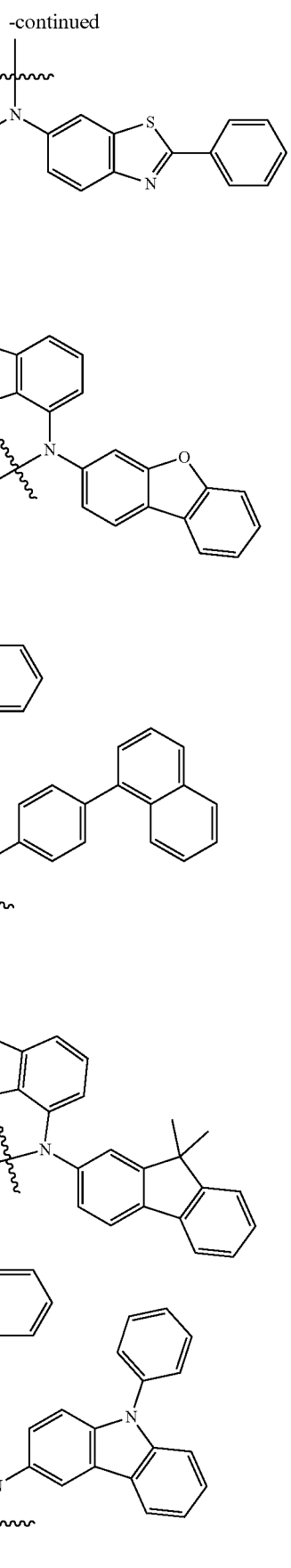

357
-continued
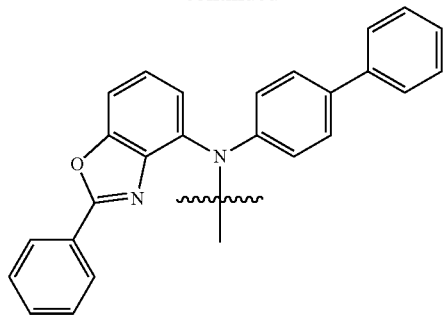
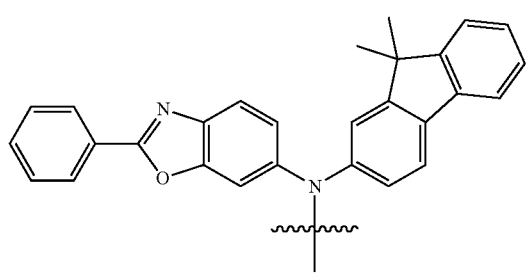
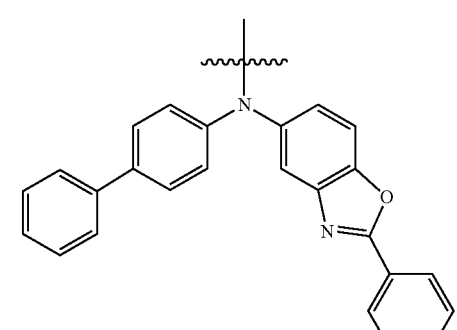
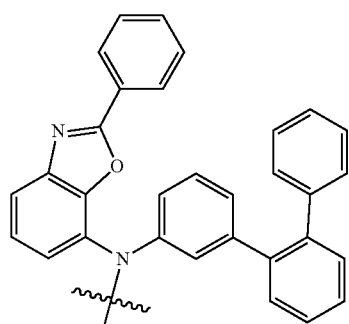
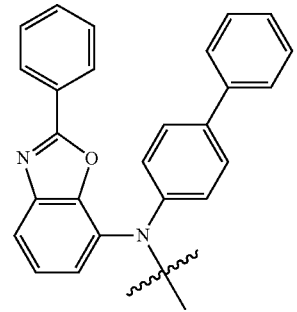
358
-continued
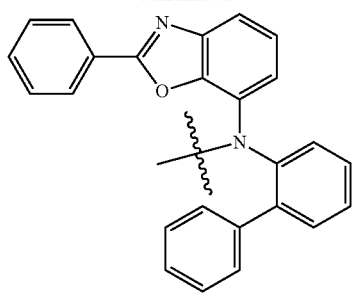
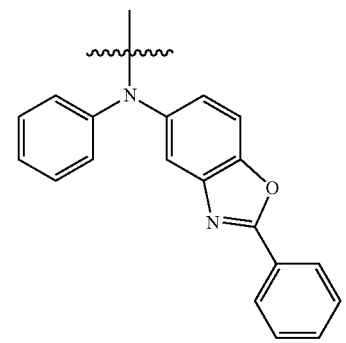
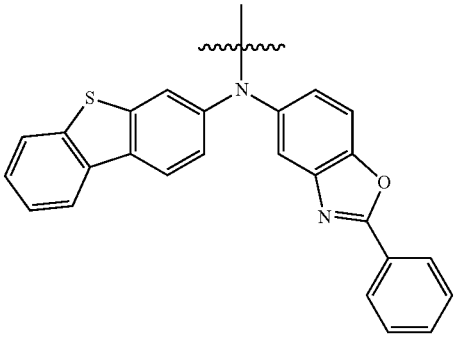

359
-continued
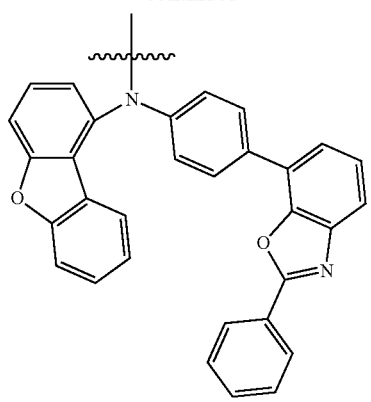
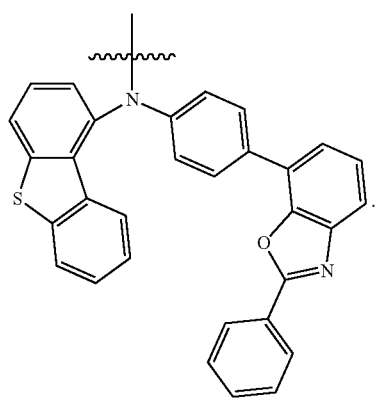
5. The arylamine compound according to claim 1, wherein the arylamine compound is selected from the group consisting of the following compounds:
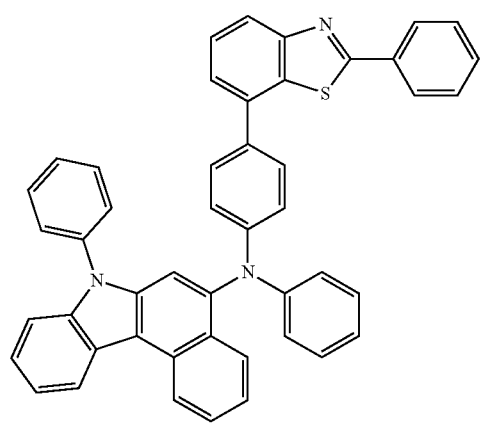
1
360
-continued
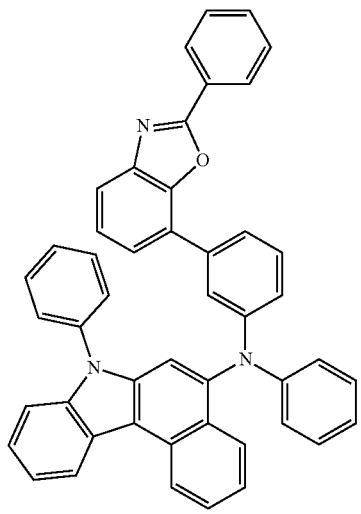
2
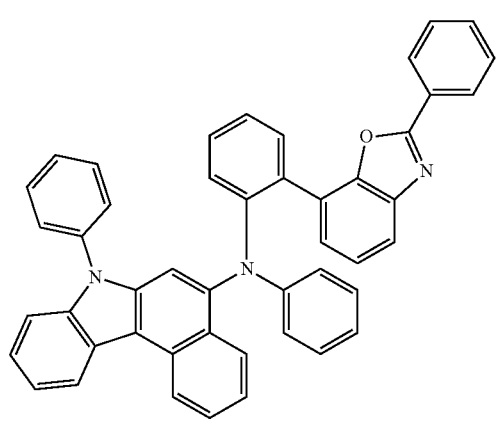
3
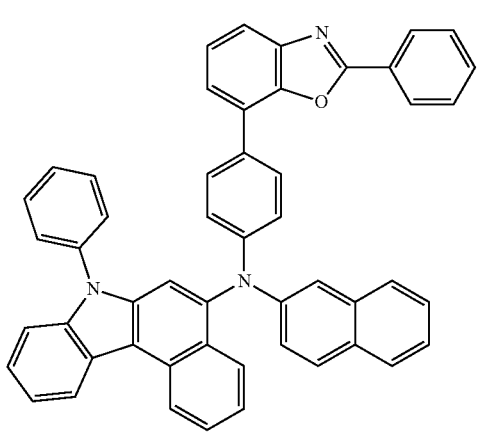
4

-continued
5
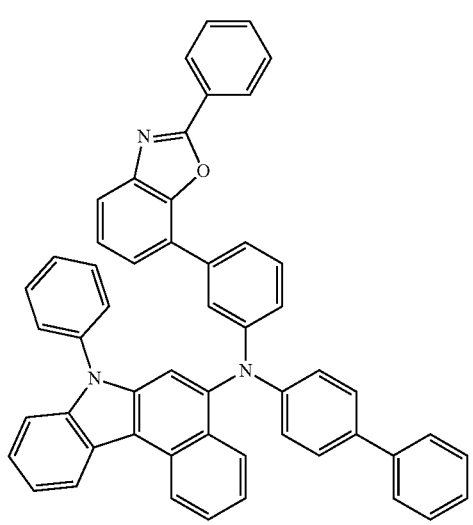
6
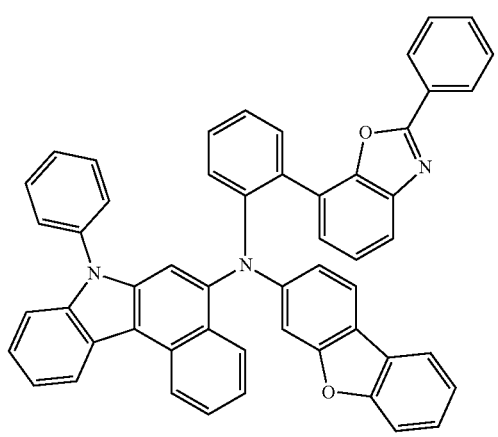
7
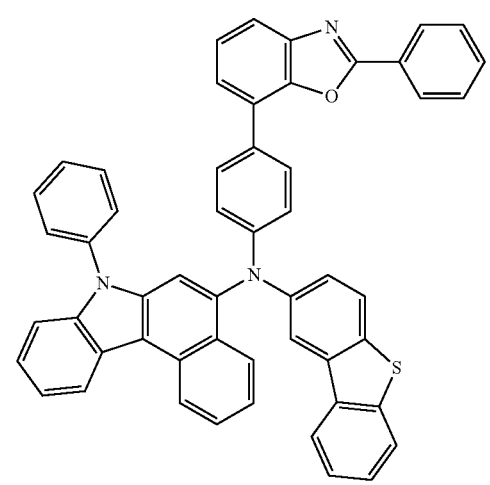
-continued
8
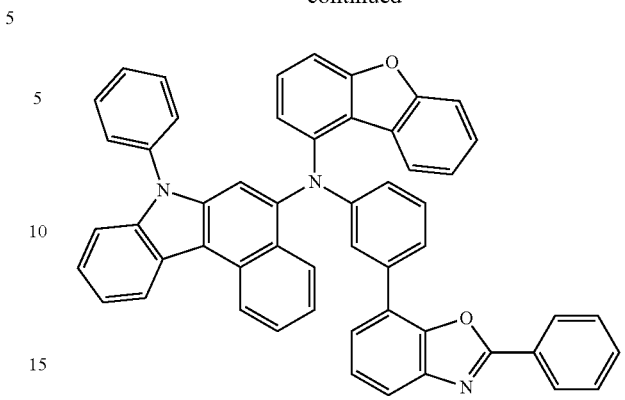
9
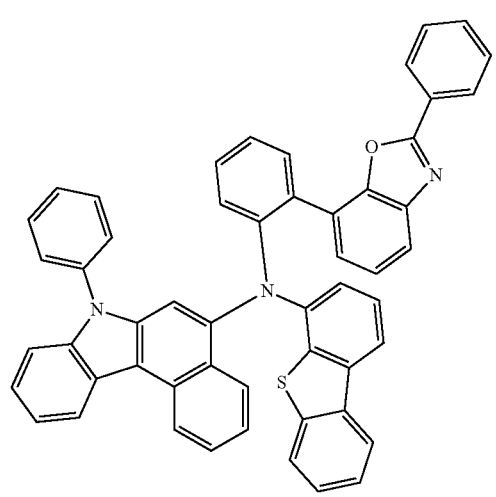
10
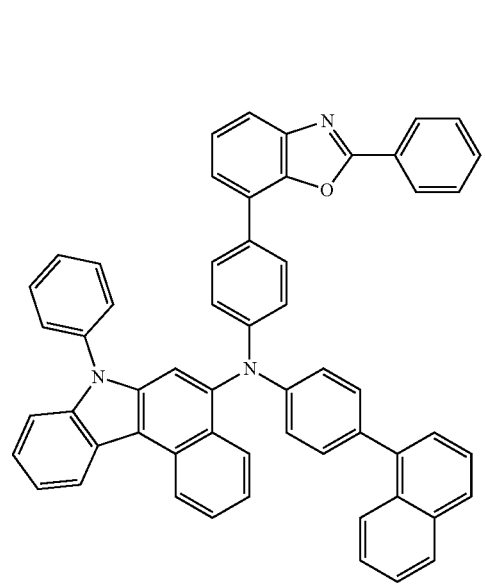

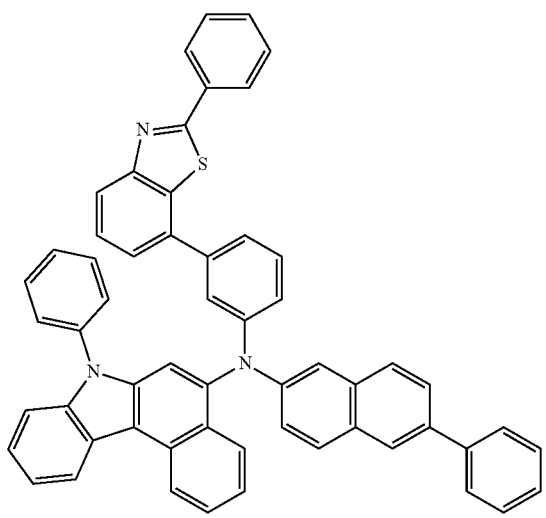
11
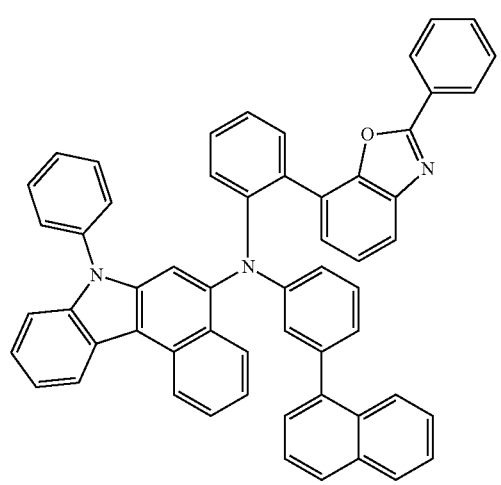 [SMILES: c1ccc(-c2nc3cccc(-c4ccccc4N(c4cccc(-c5cccc6ccccc56)c4)c4cc5c(c6ccccc46)c4ccccc4n5-c4ccccc4)c3o2)cc1]
12
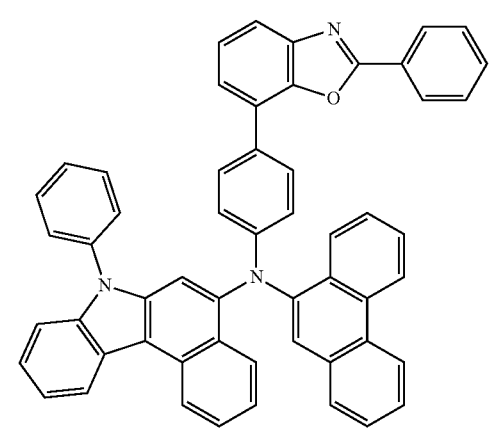
13
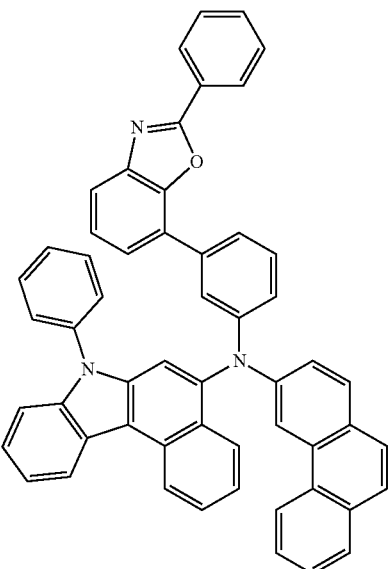
14
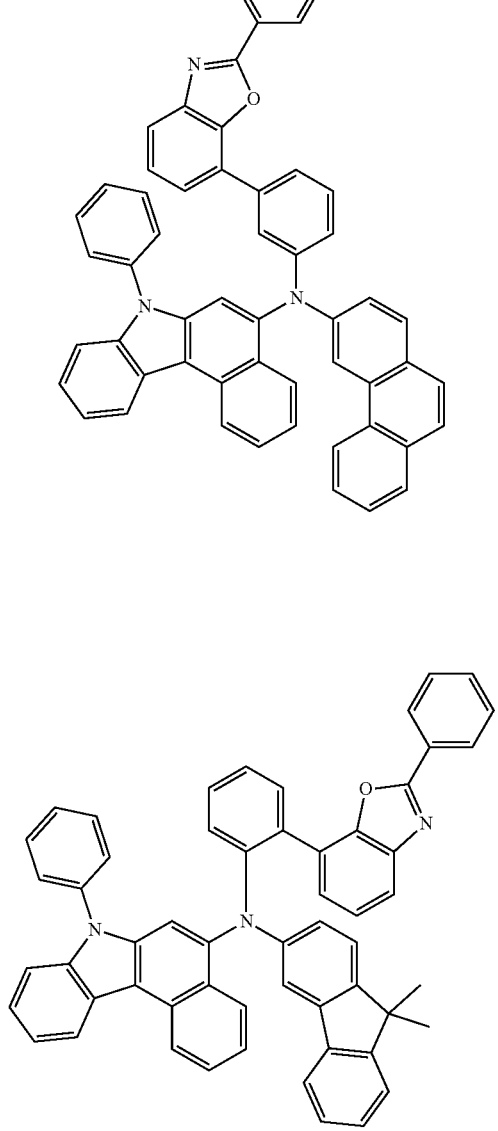
15
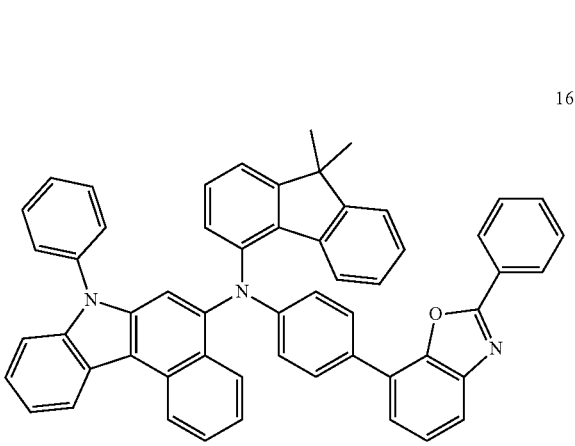
16

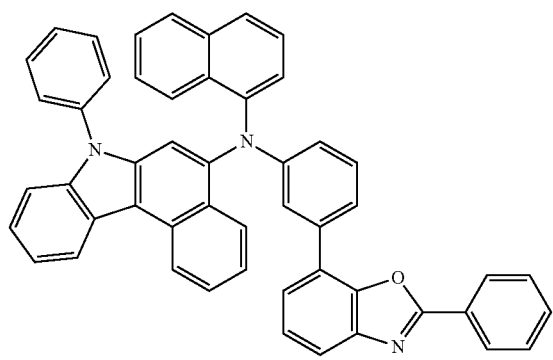
17
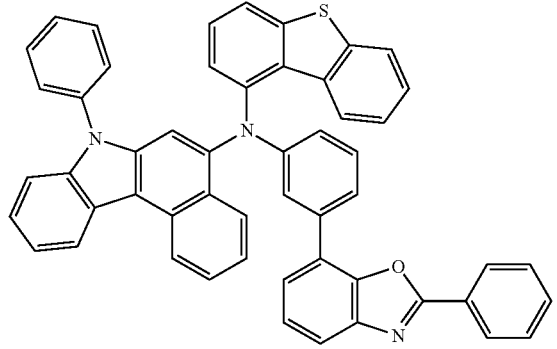
20
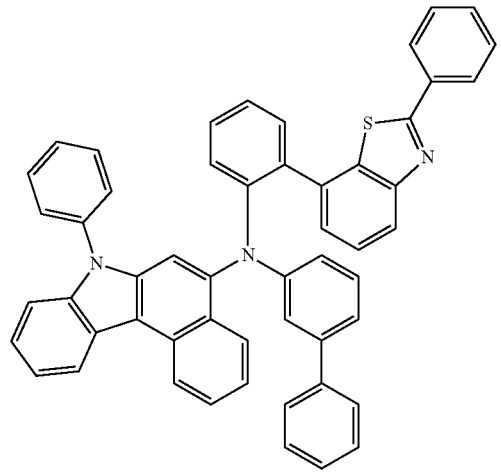
18
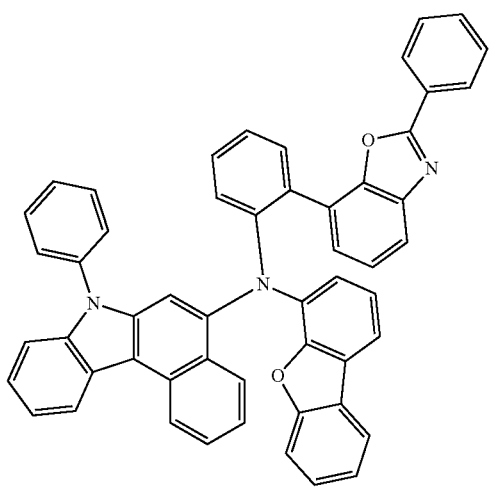
21
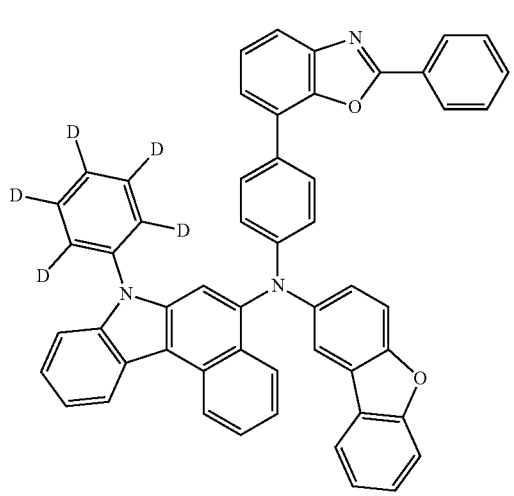 [SMILES: [2H]c1c([2H])c([2H])c(-n2c3ccccc3c3c4ccccc4c(N(c4ccc(-c5cccc6nc(-c7ccccc7)oc56)cc4)c4ccc5oc6ccccc6c5c4)cc32)c([2H])c1[2H]]
19
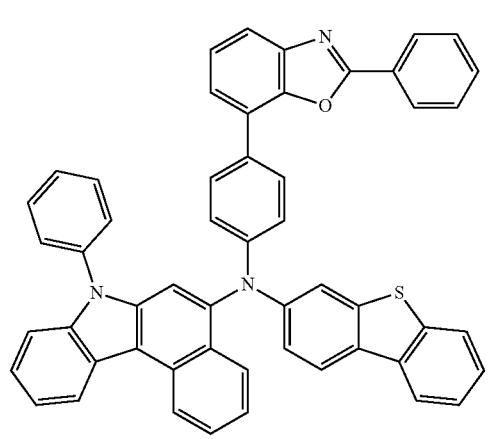
22

23
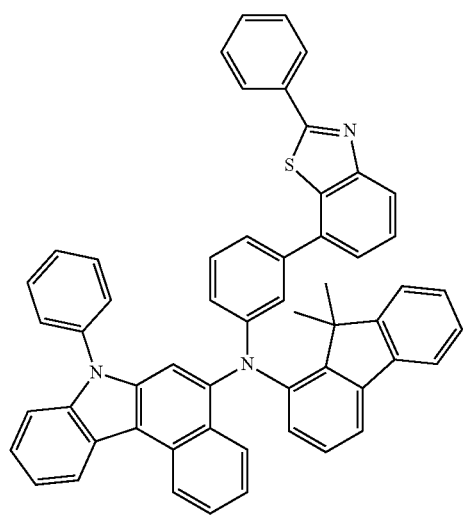
24
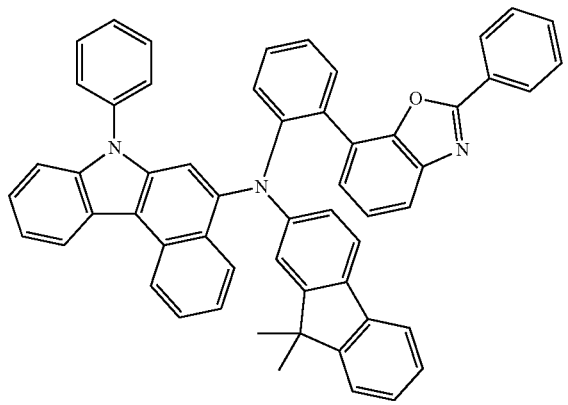
25
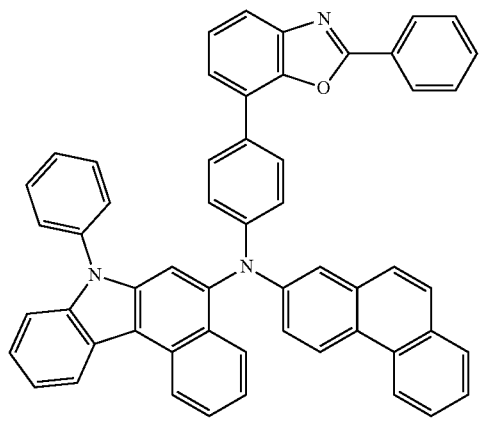
26
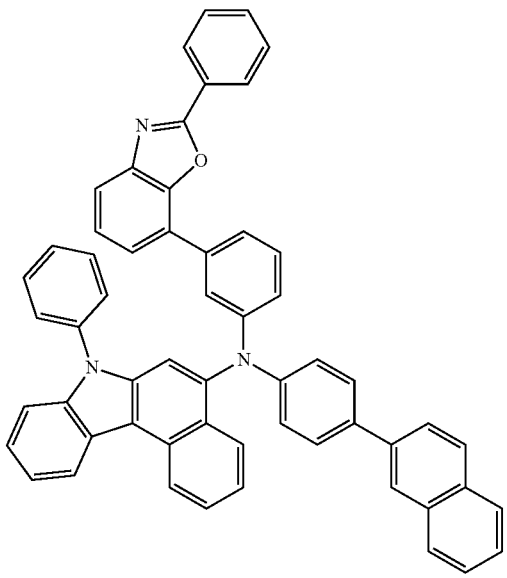
27
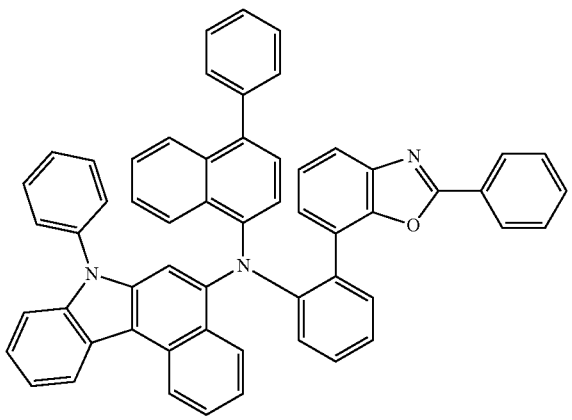
28
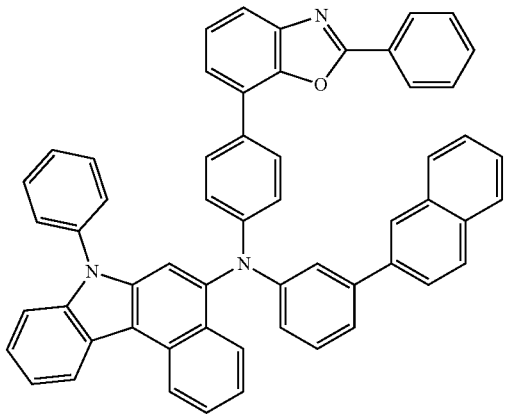

-continued
29
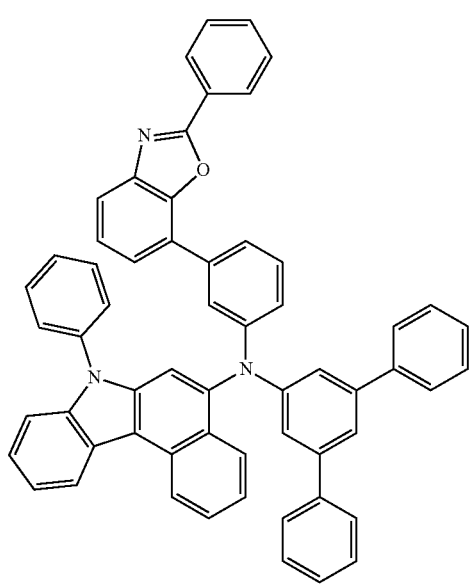
30
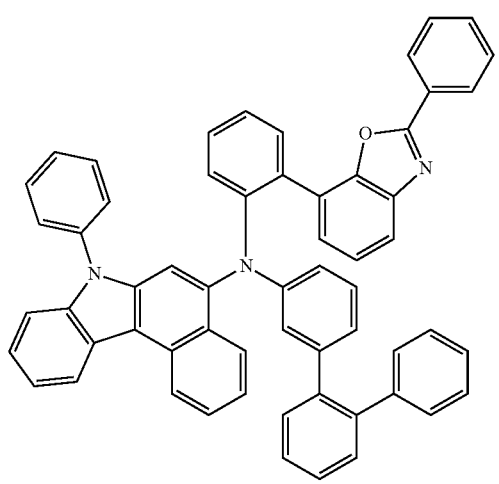
31
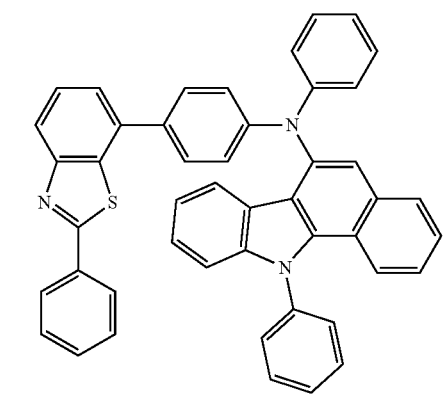
-continued
32
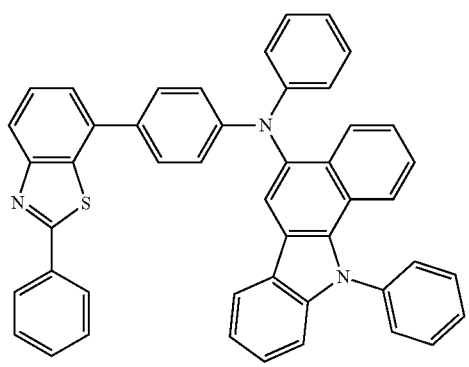
33
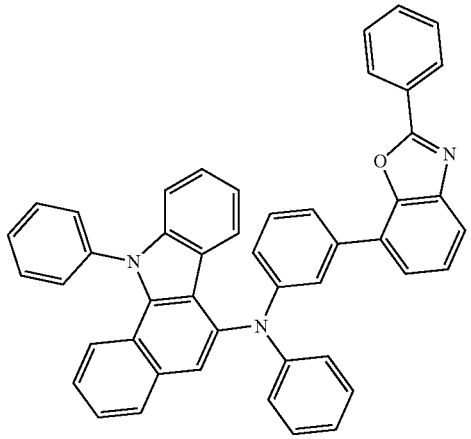
34
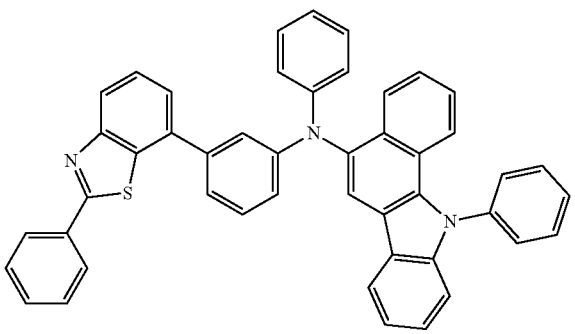
35
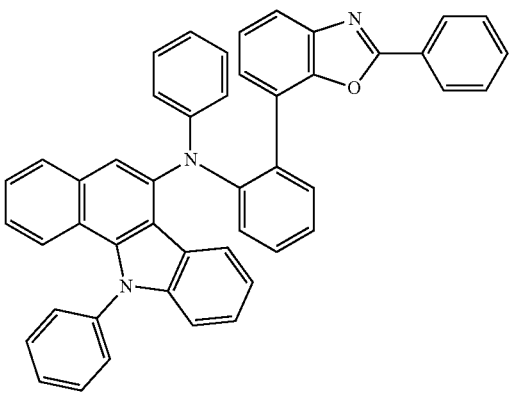

-continued
36
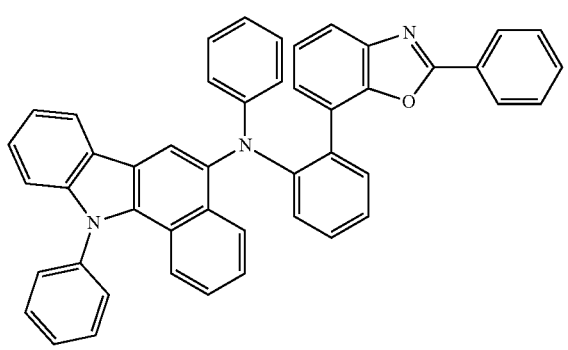
37
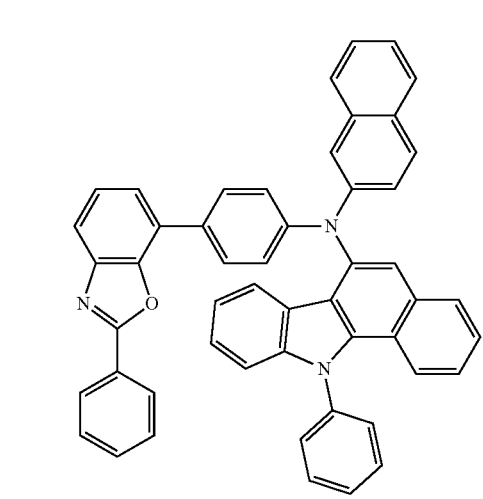
38
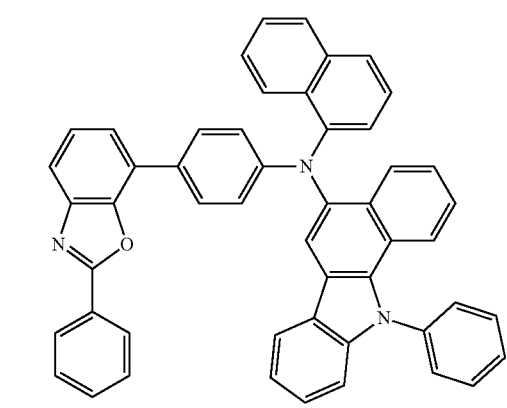
-continued
39
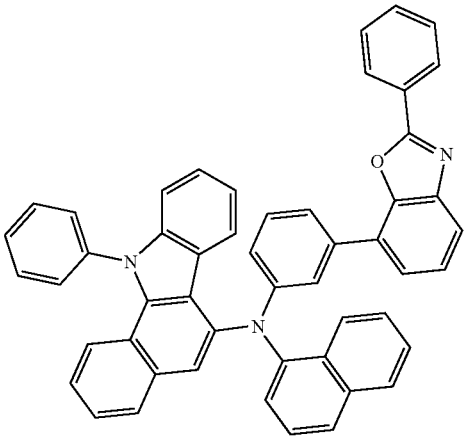
40
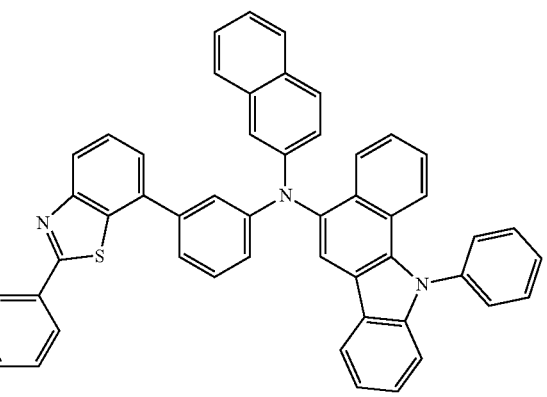
41
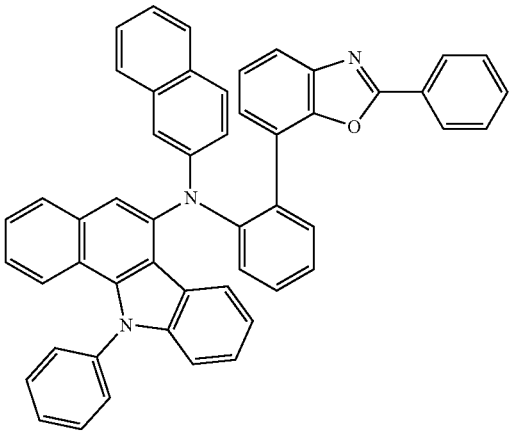
42

43
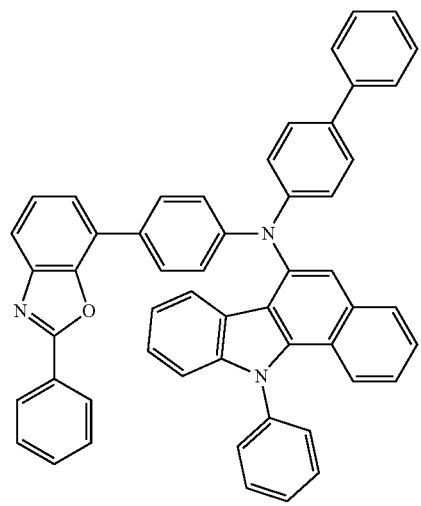
44
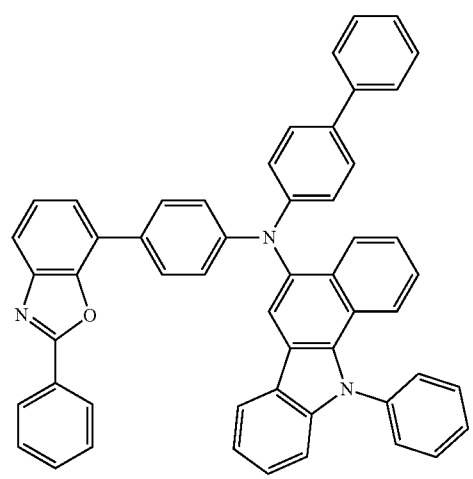
45
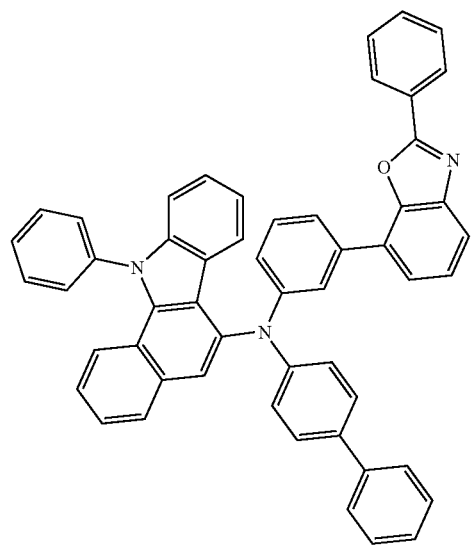
46
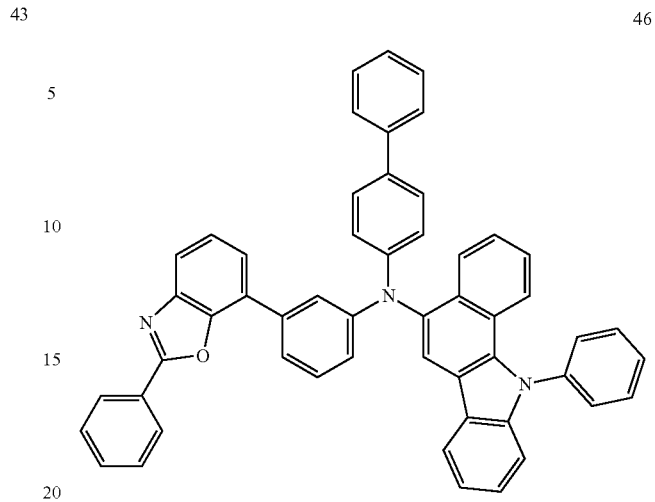
47
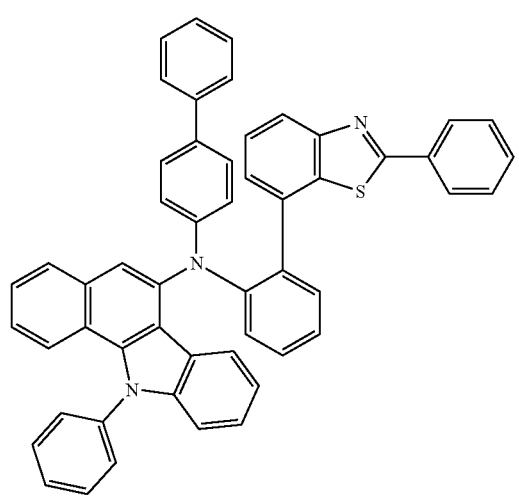
48
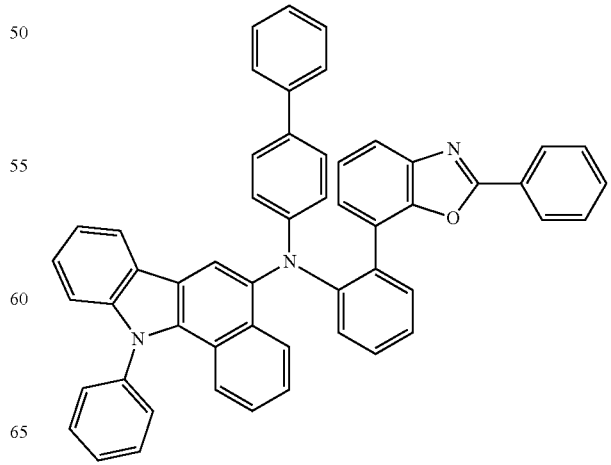

-continued
49
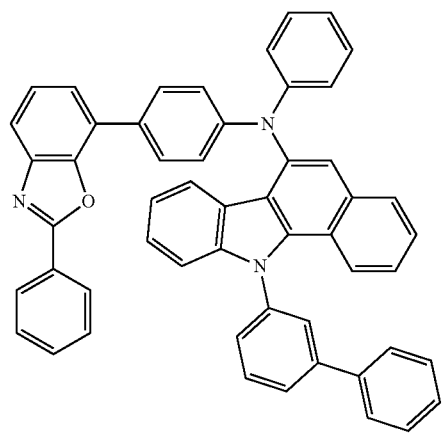
50
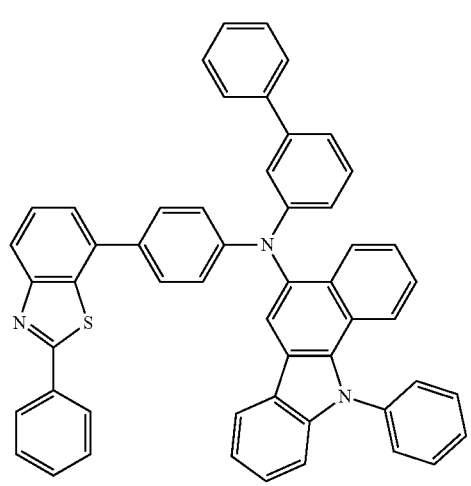
52
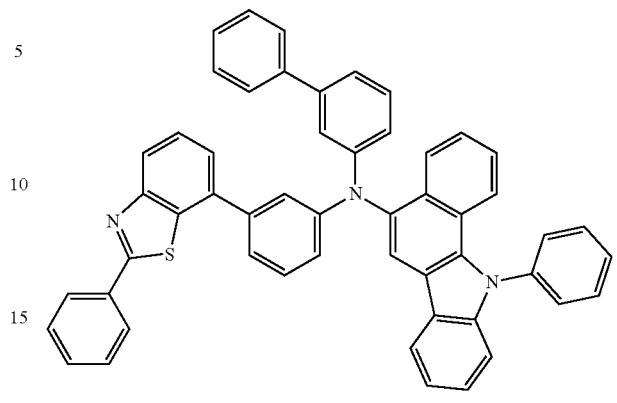
53
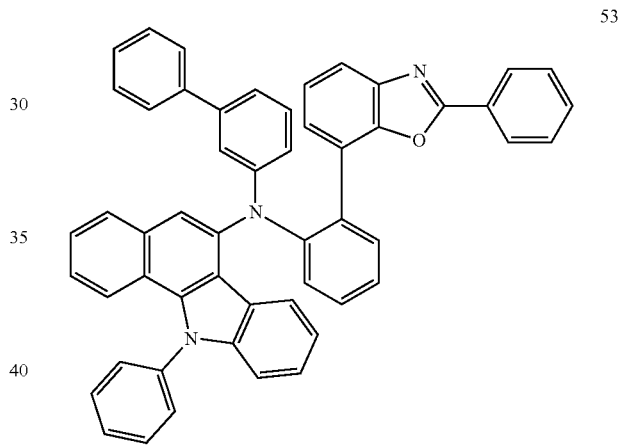
51
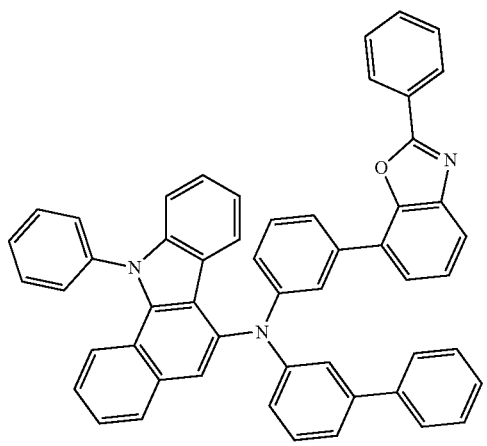
54
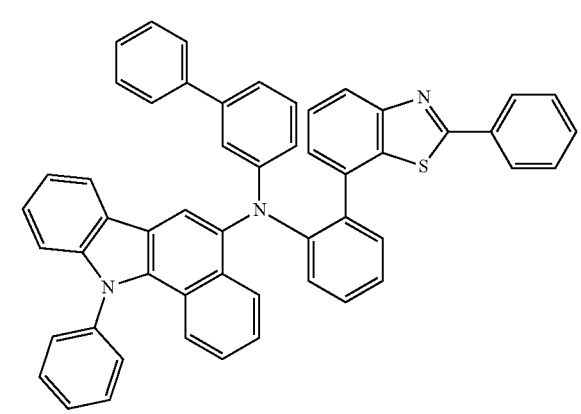

377
-continued
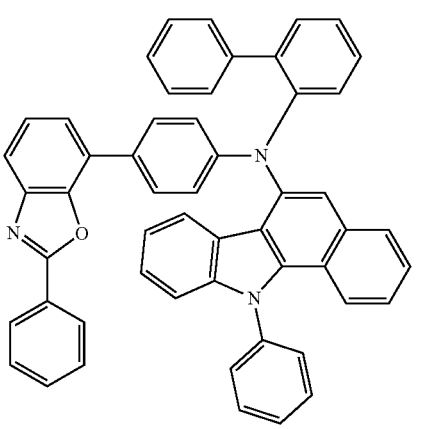
55
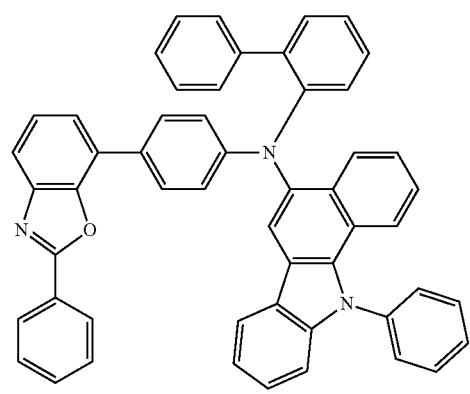
56
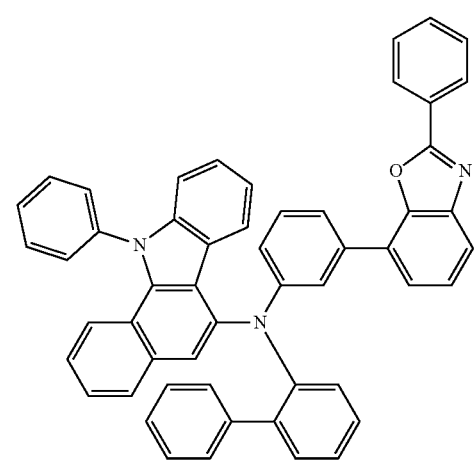
57
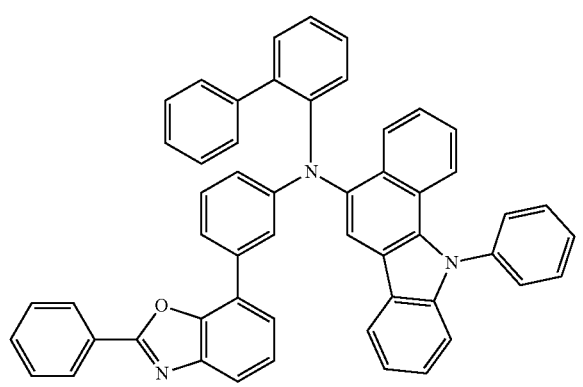
58
378
-continued
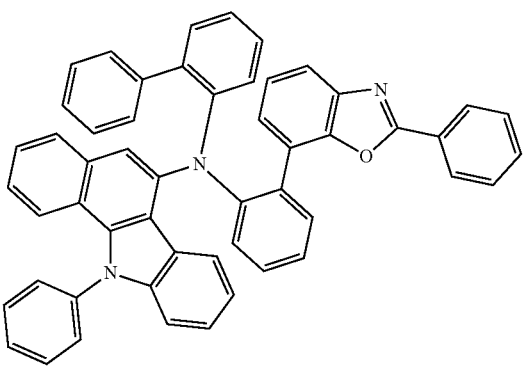
59
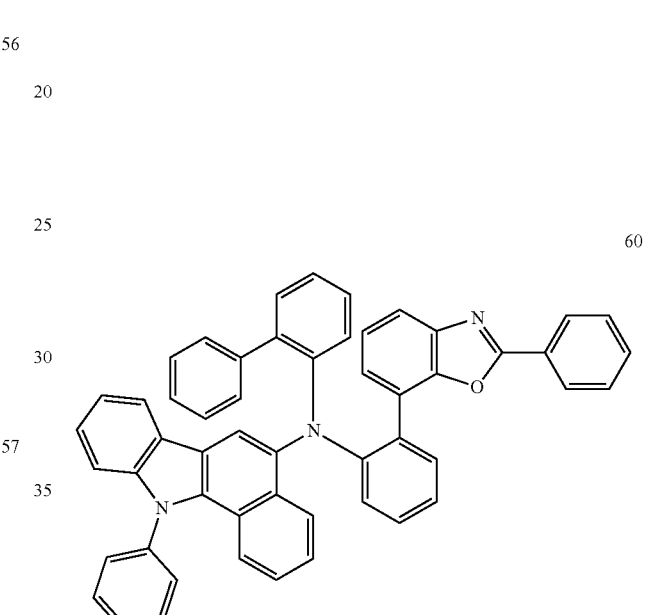
60
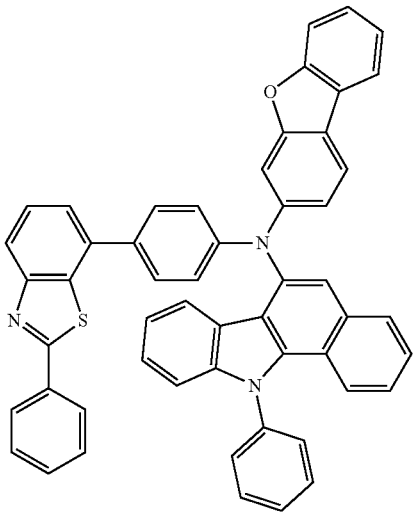
61

62
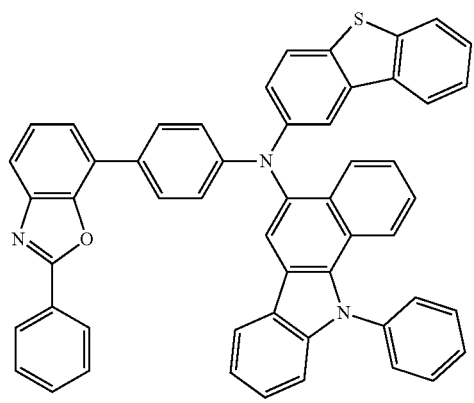
65
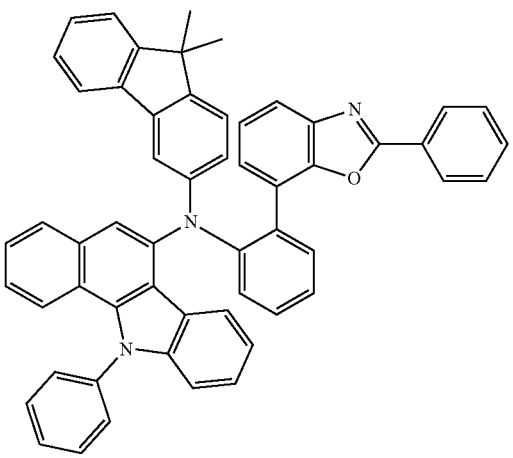
63
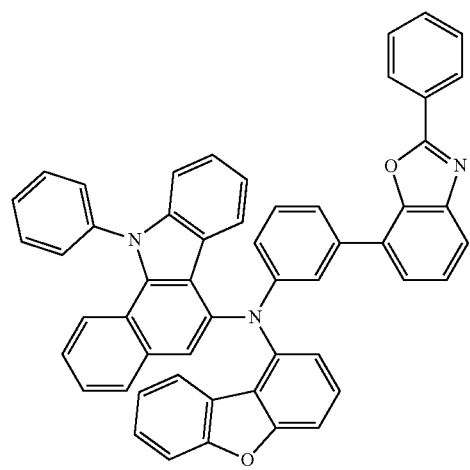
66
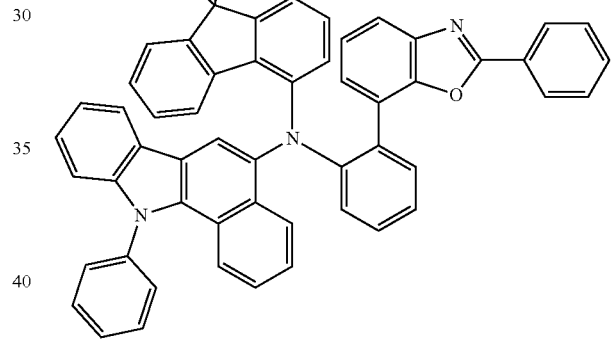
64
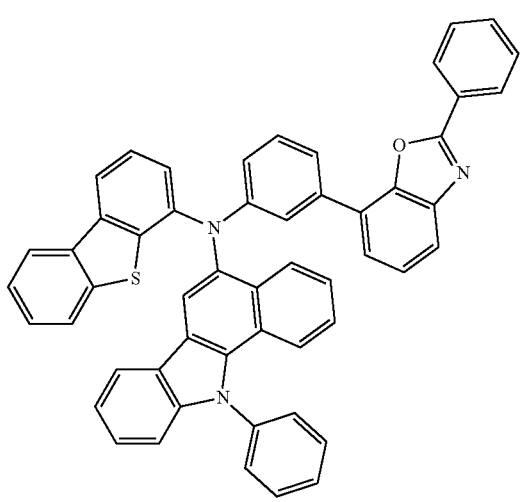
67
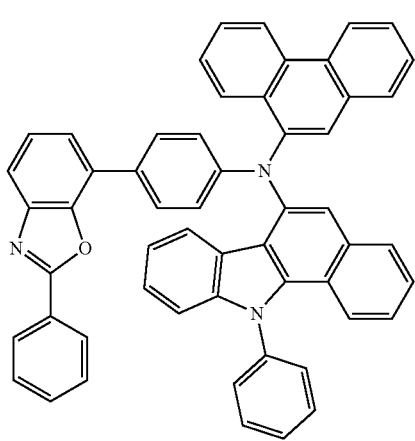

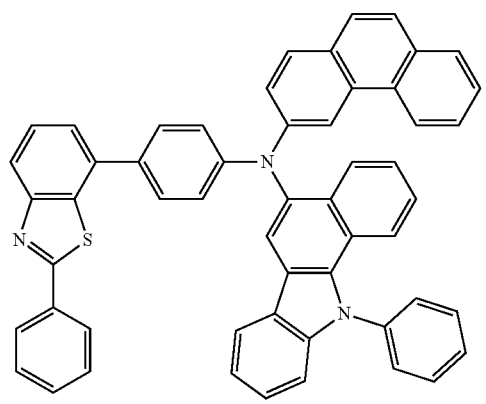
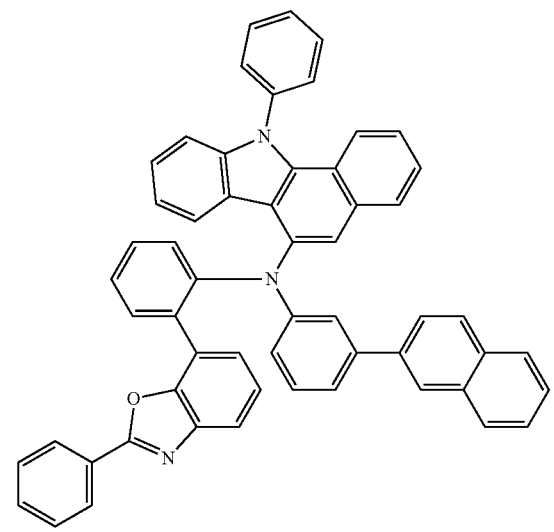
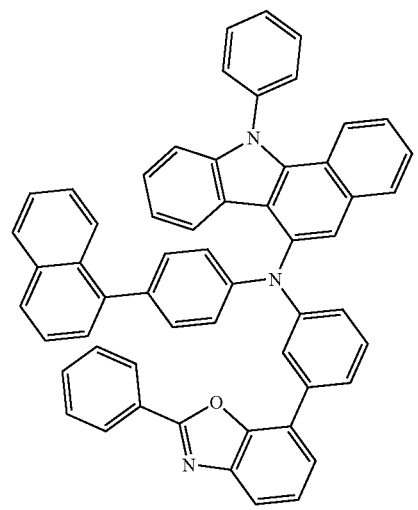
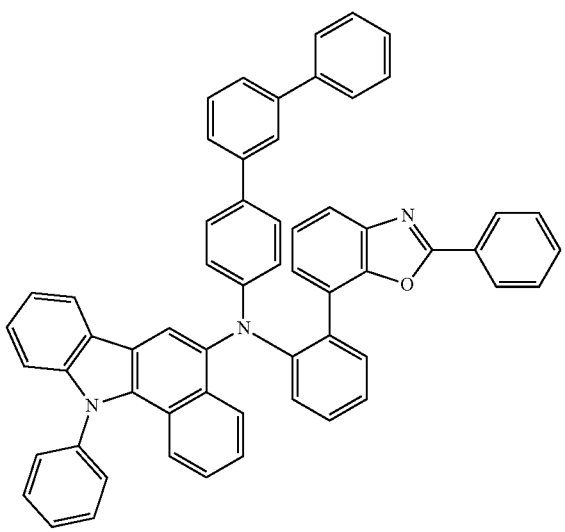
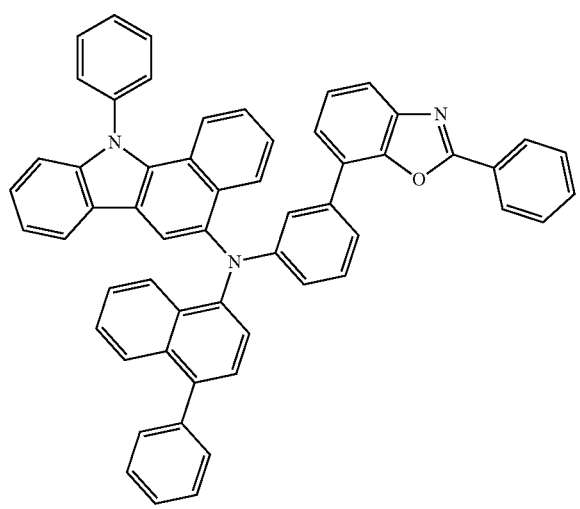
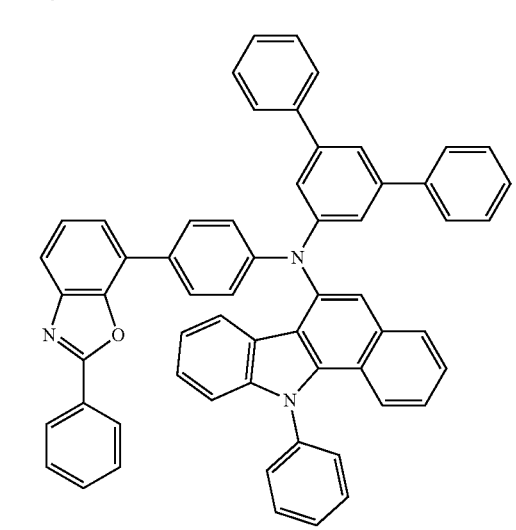

-continued
74
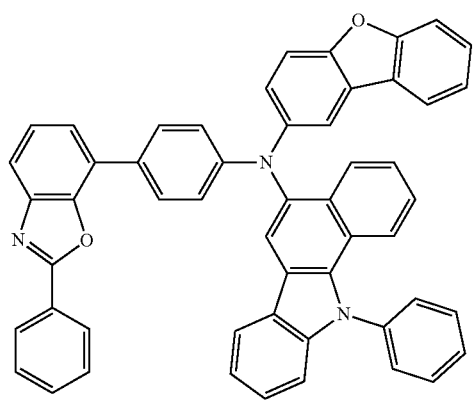
75
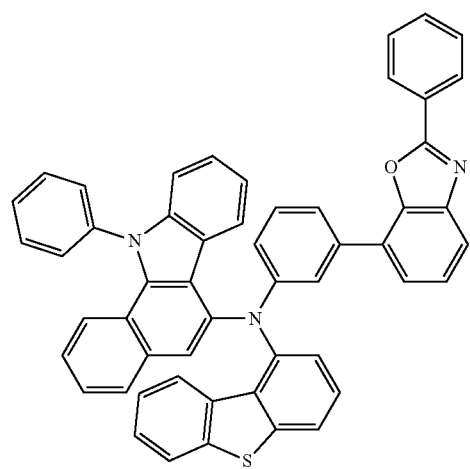
76
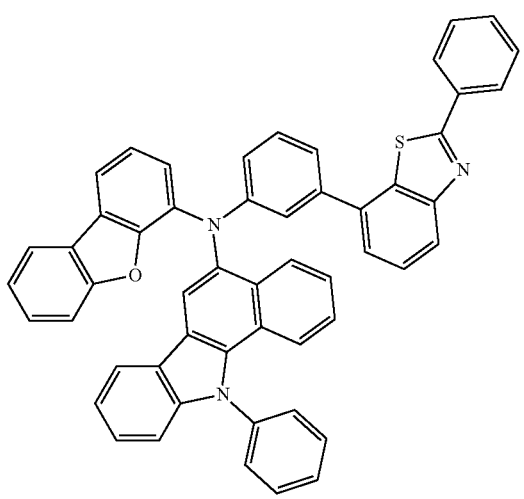
-continued
77
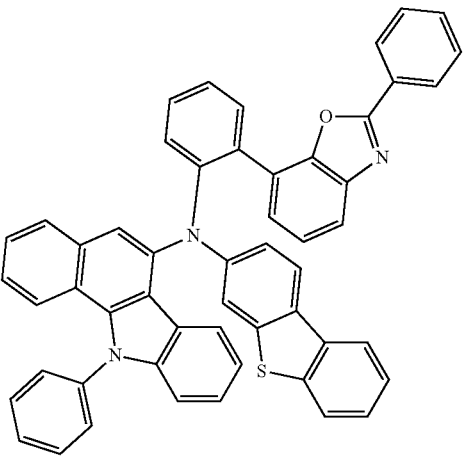
78
79
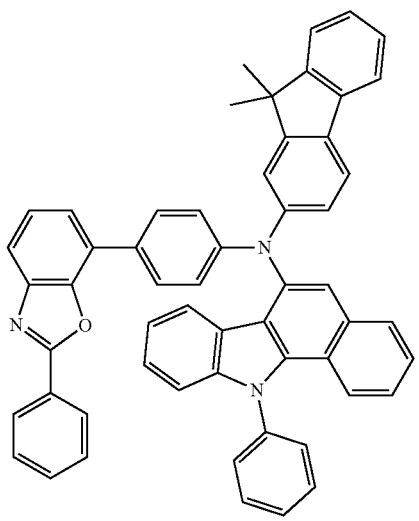 [SMILES: CC1(C)c2ccccc2-c2ccc(N(c3ccc(-c4cccc5nc(-c6ccccc6)oc45)cc3)c3cc4ccccc4c4c3c3ccccc3n4-c3ccccc3)cc21]

385
-continued
80
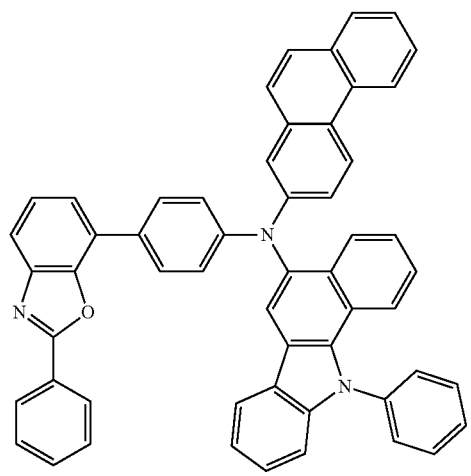
81
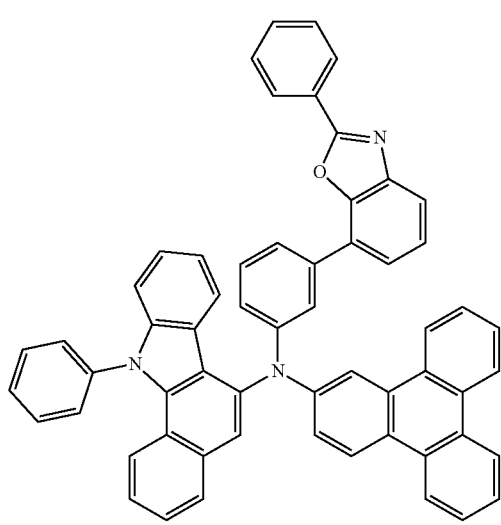
82
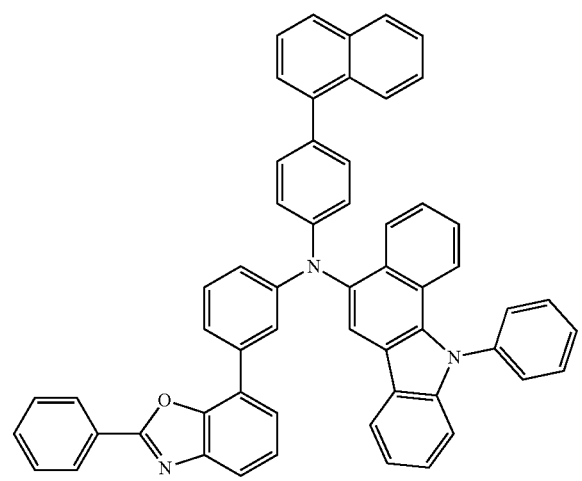
386
-continued
83
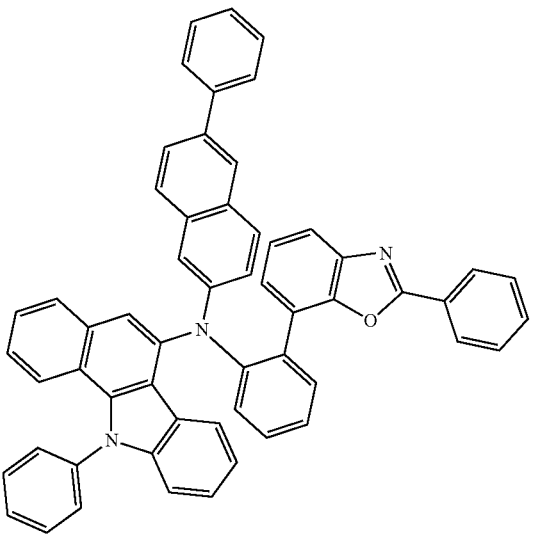
84
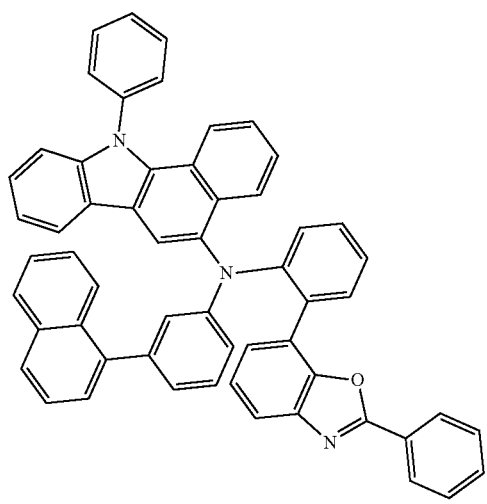
85
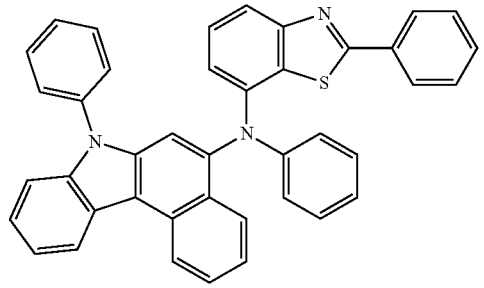

86
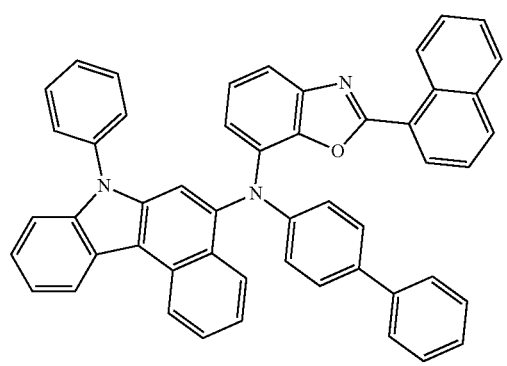
87
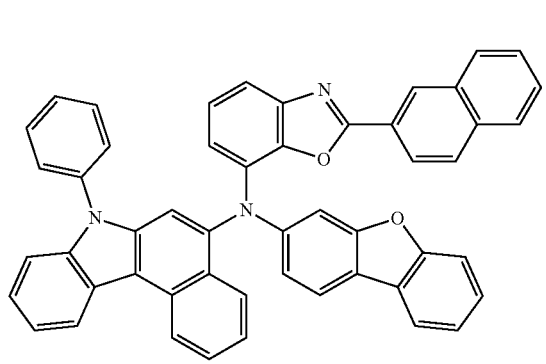 [SMILES: c1ccc(-n2c3ccccc3c3c4ccccc4c(N(c4ccc5c(c4)oc4ccccc45)c4cccc5nc(-c6ccc7ccccc7c6)oc45)cc32)cc1]
88
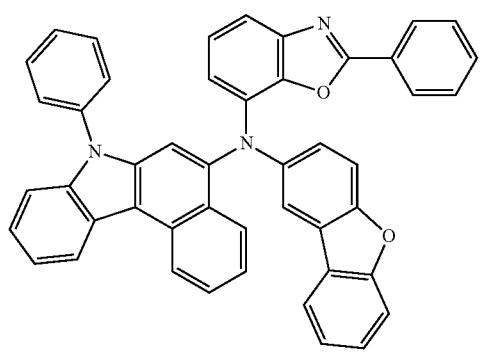
89
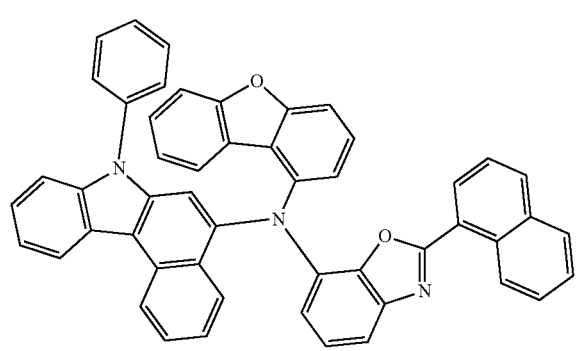
90
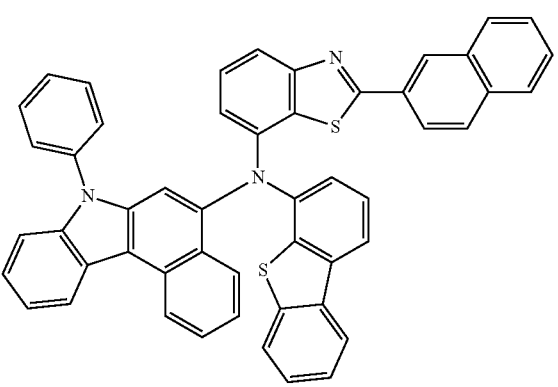
91
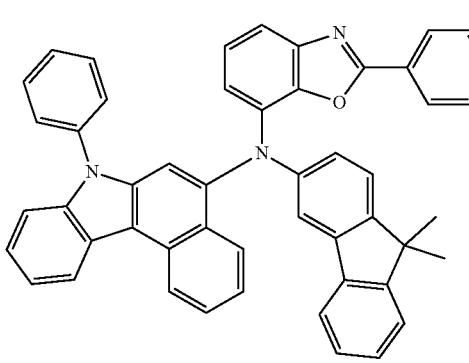
92
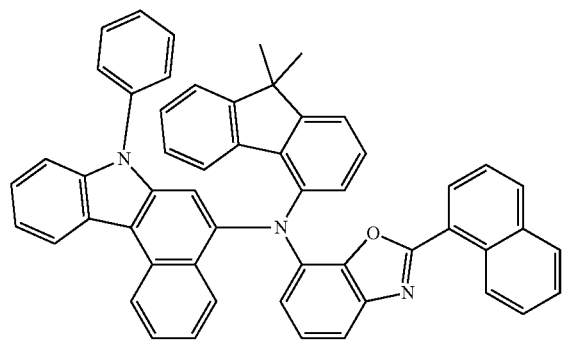
93
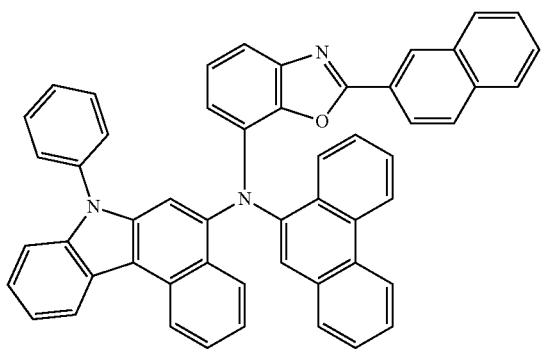

94
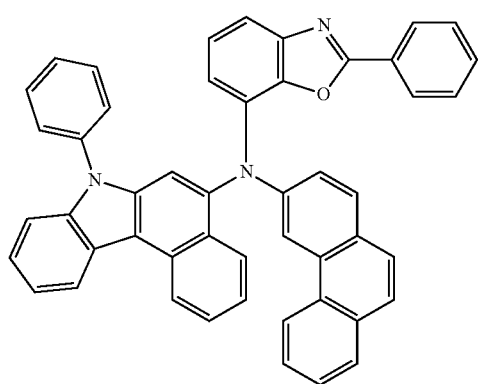
95
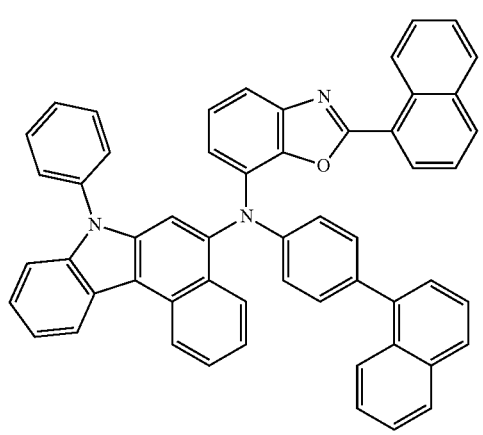
96
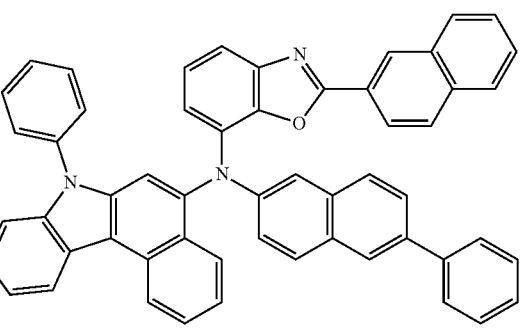
97
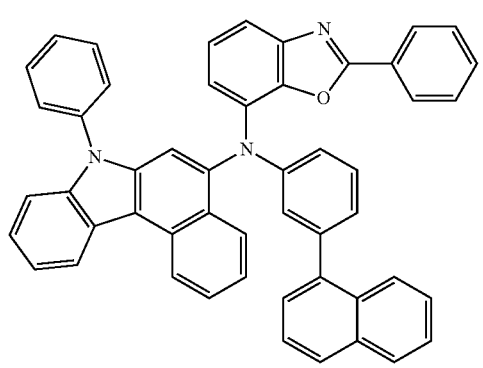
98
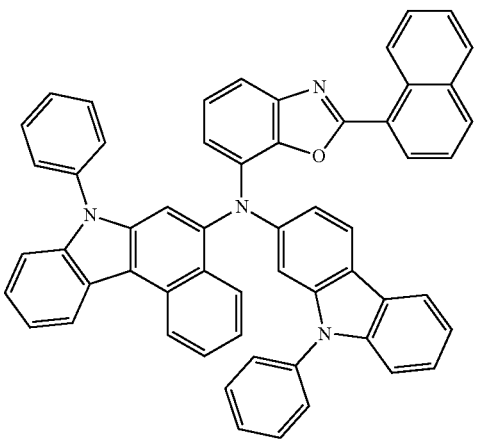
99
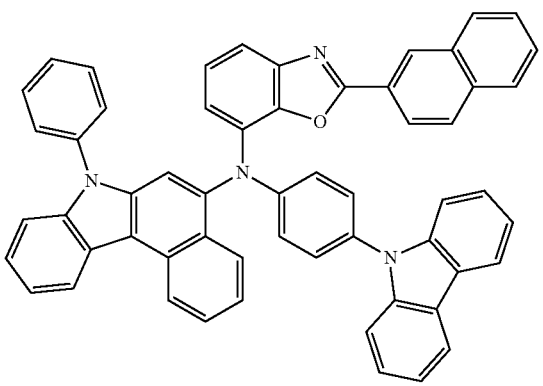
100
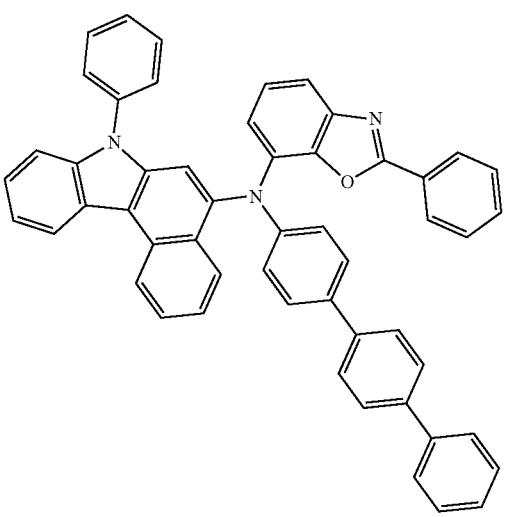

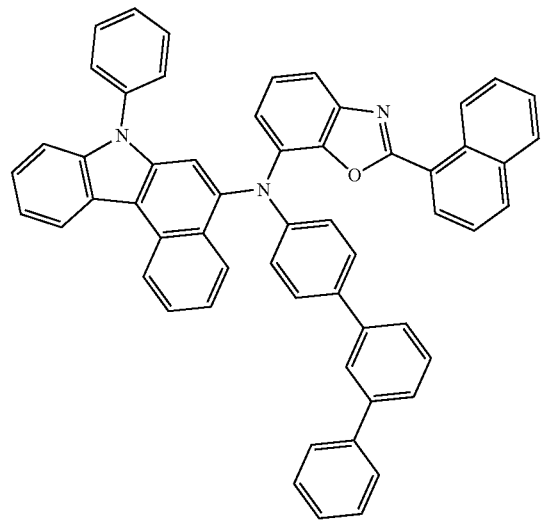
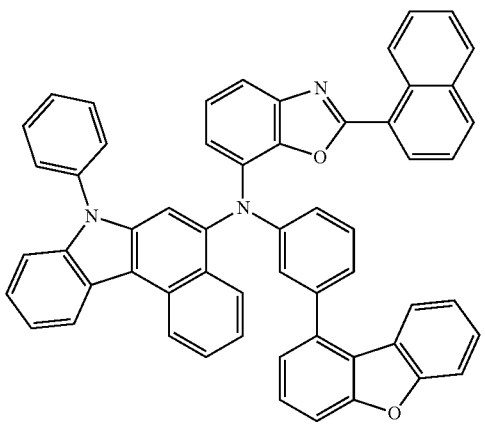
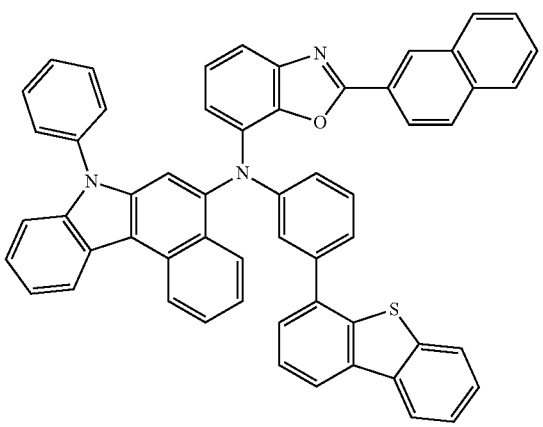
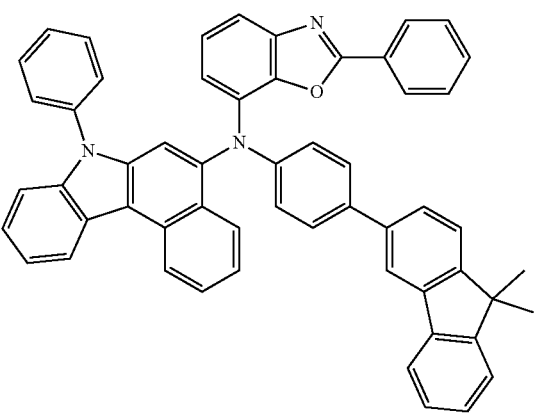
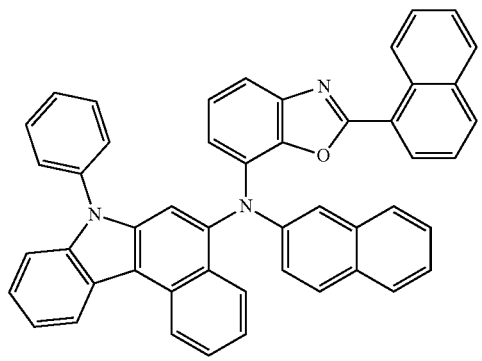

108 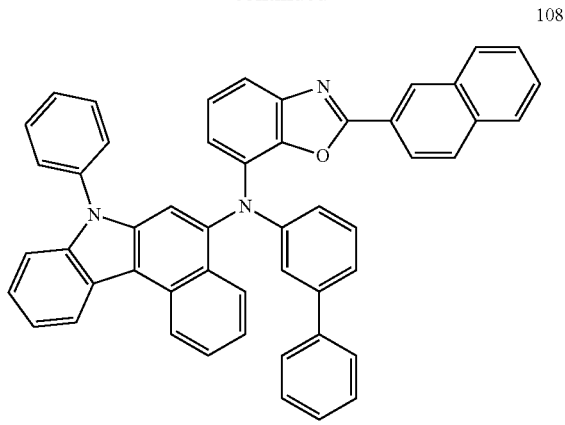
109 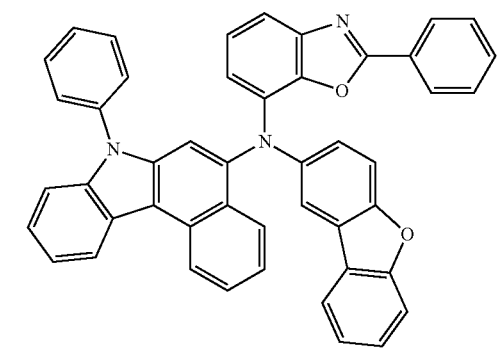
110 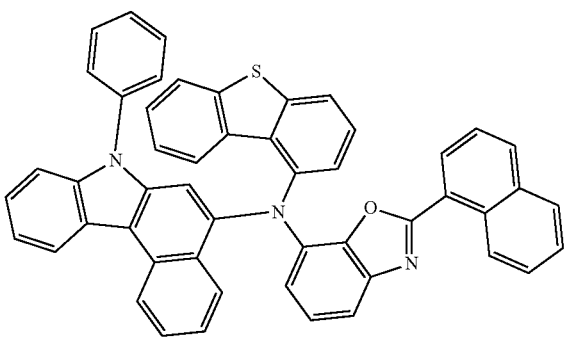
111 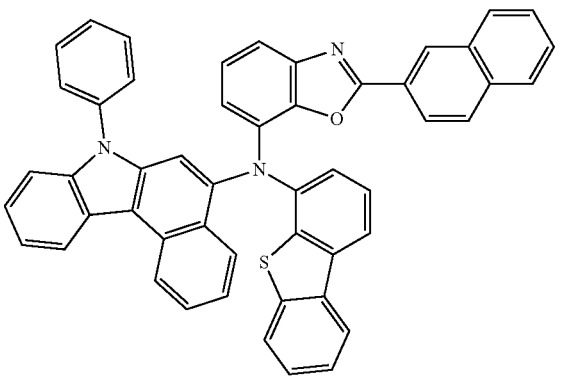
112 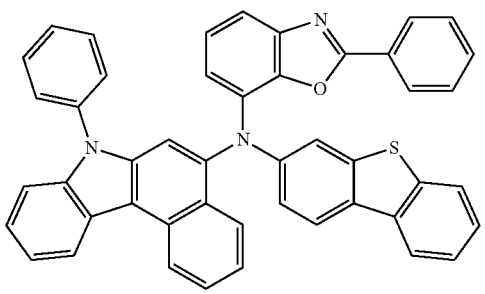
113 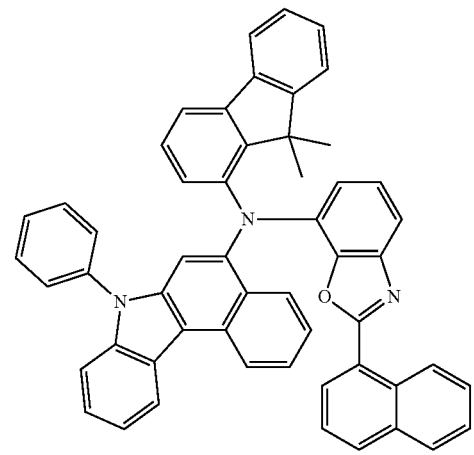
114 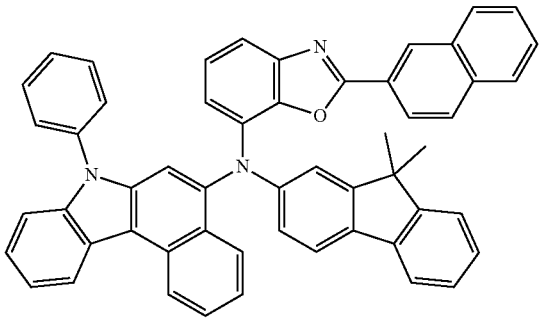
115 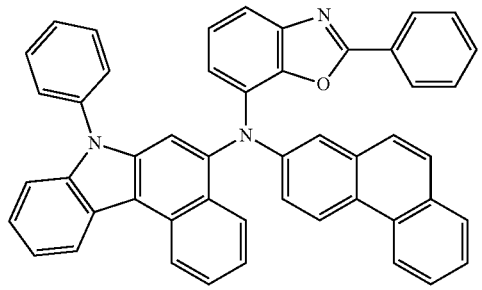

116
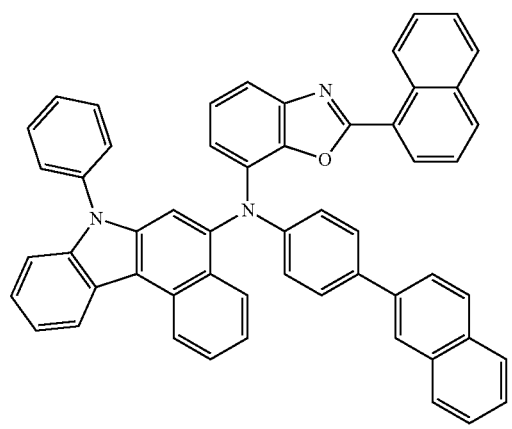
117
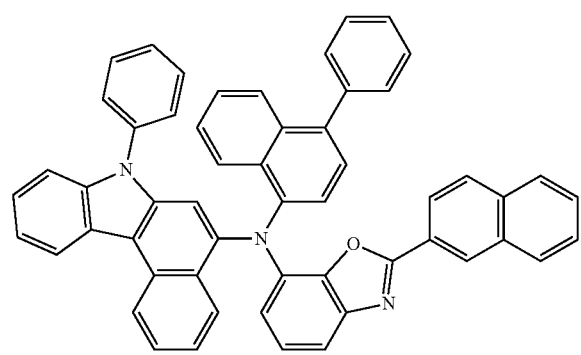
118
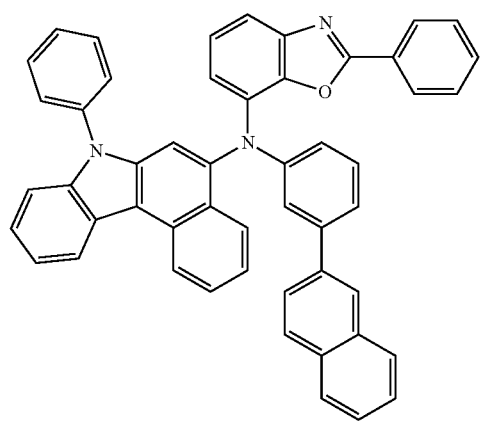
119
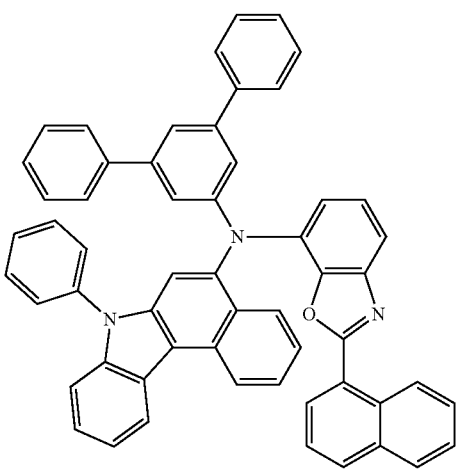
120
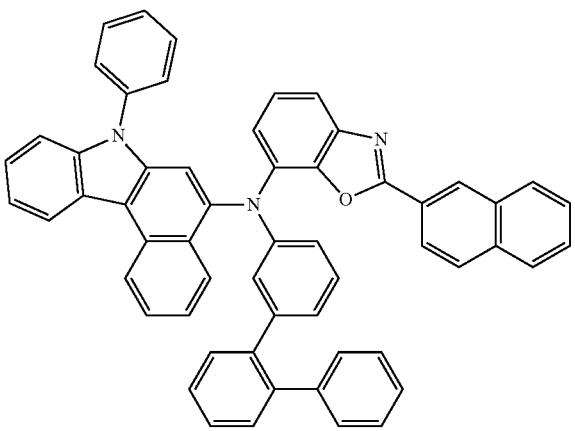
121
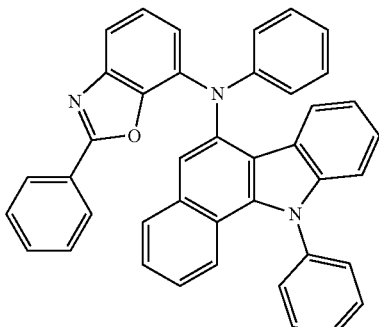
122
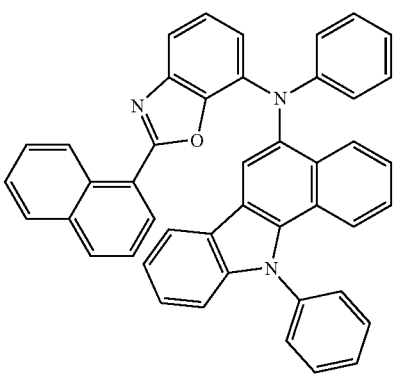

397
-continued
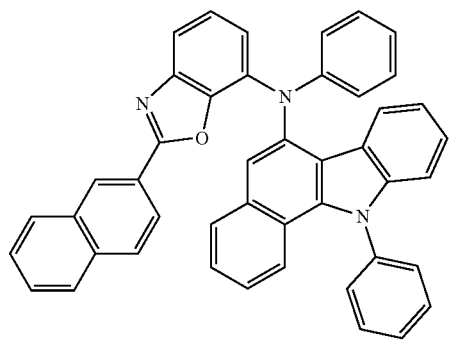
123
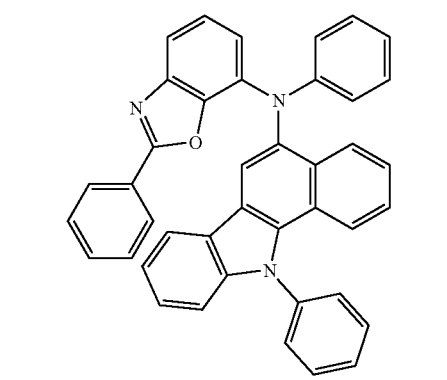
124
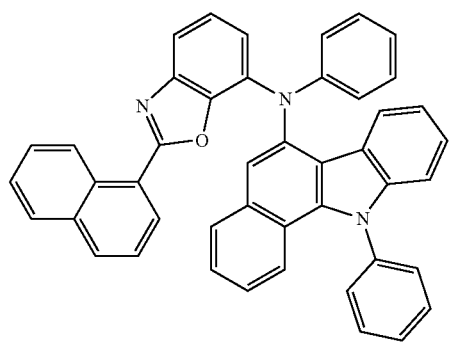
125
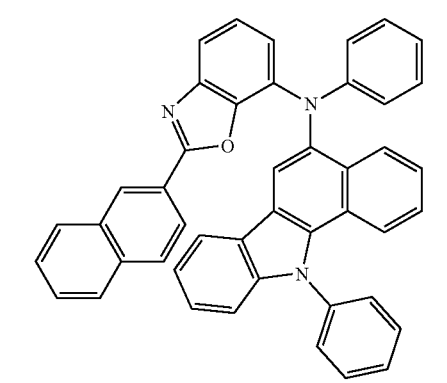
126
398
-continued
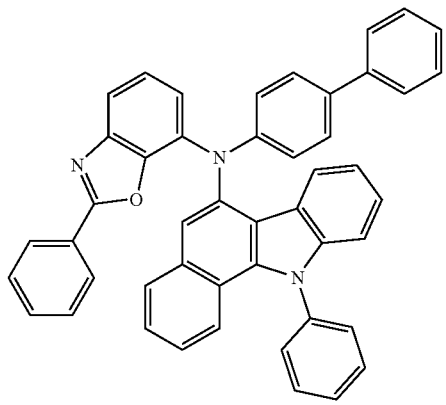
127
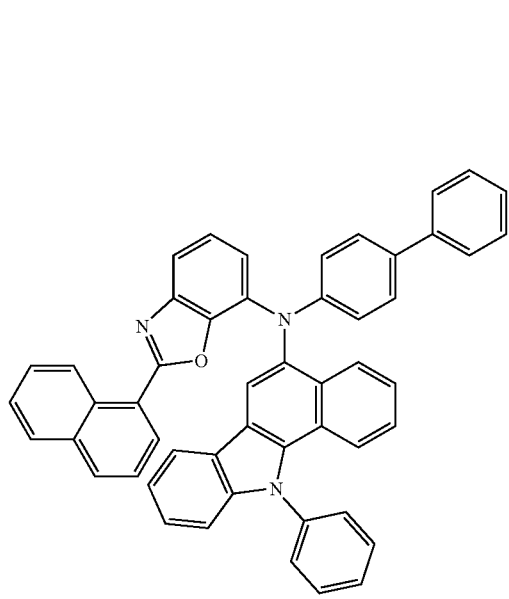
128
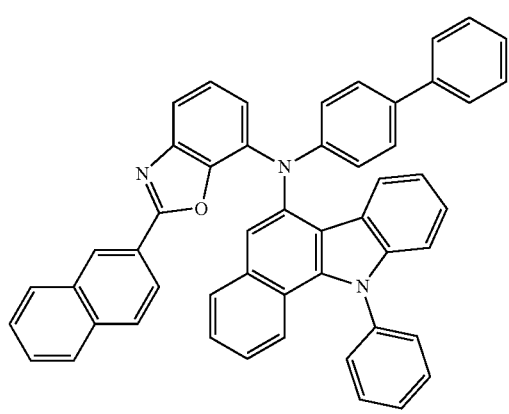
129

130
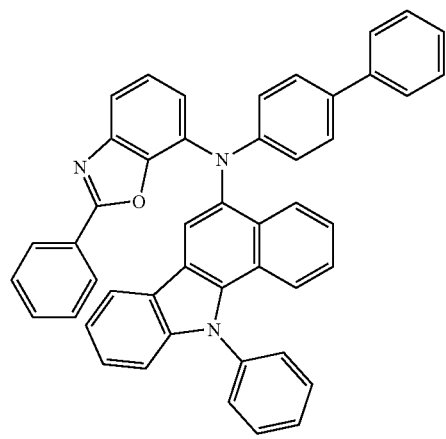
131
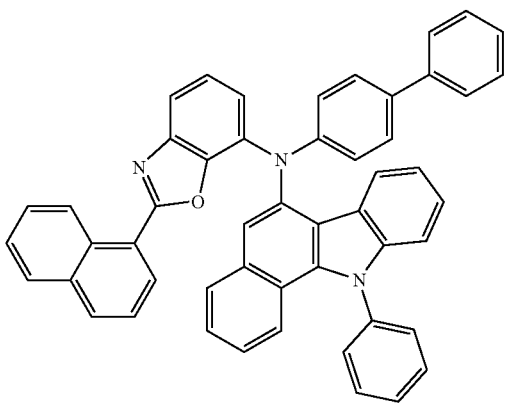
132
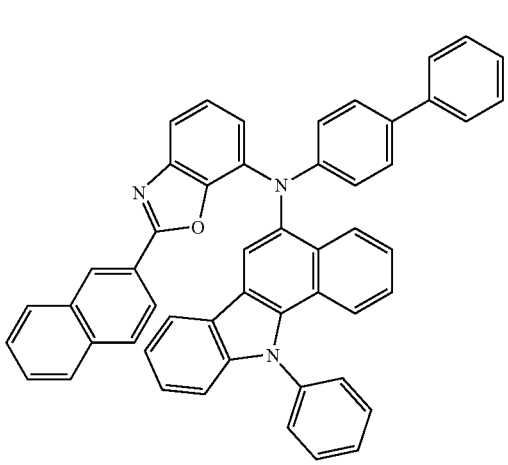
133
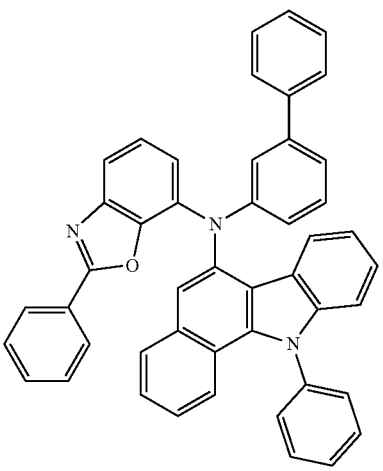
134
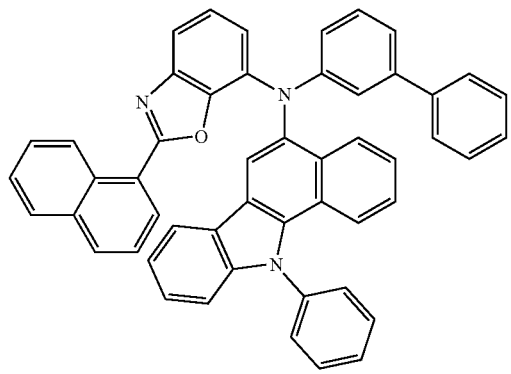
135
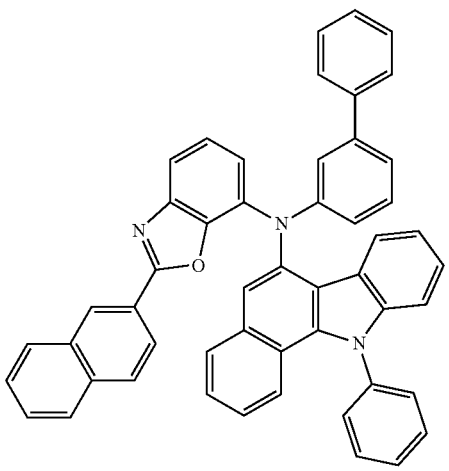

136
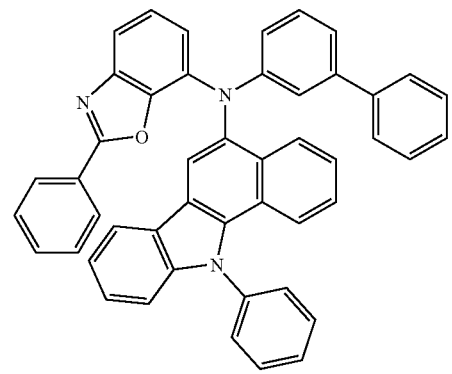
137
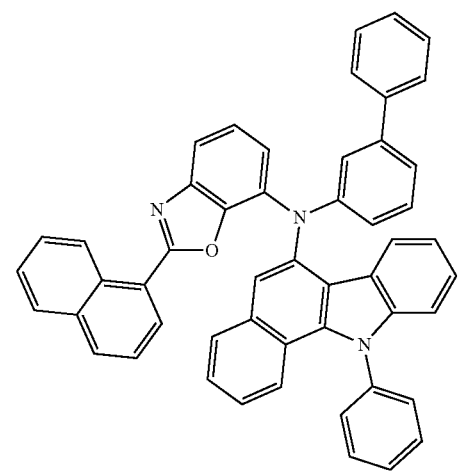
138
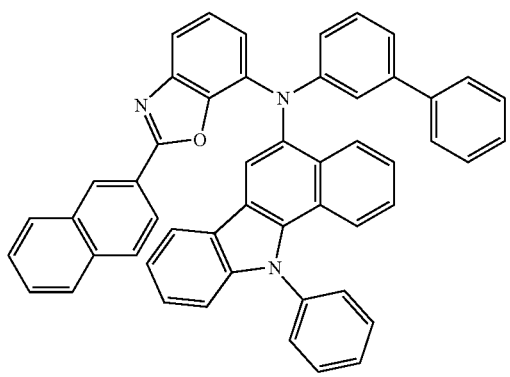
139
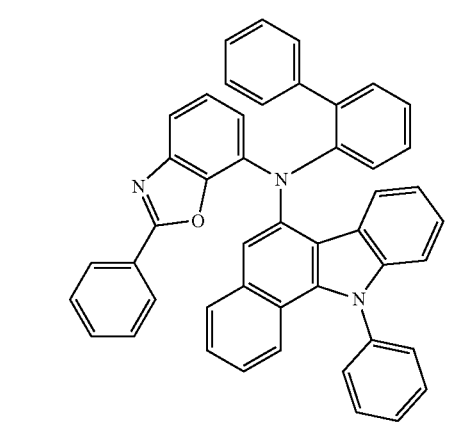
140
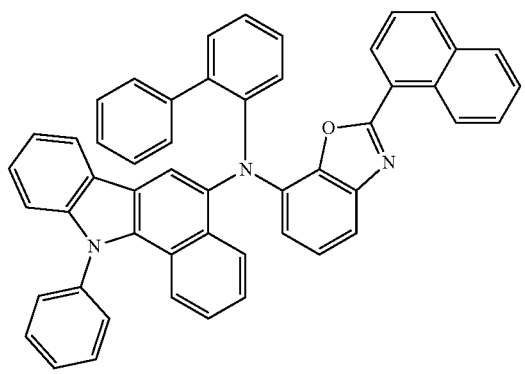
141
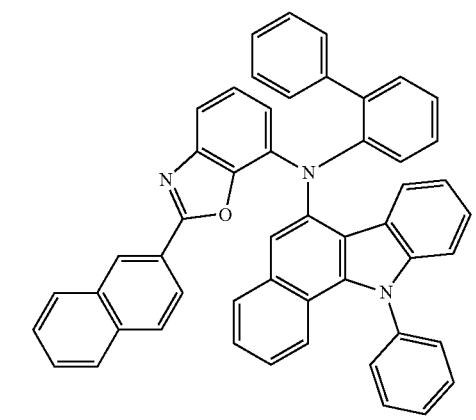
142
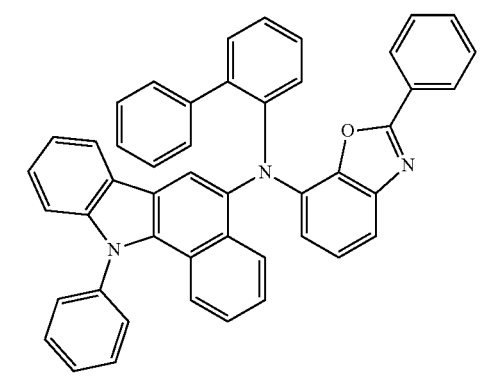
143
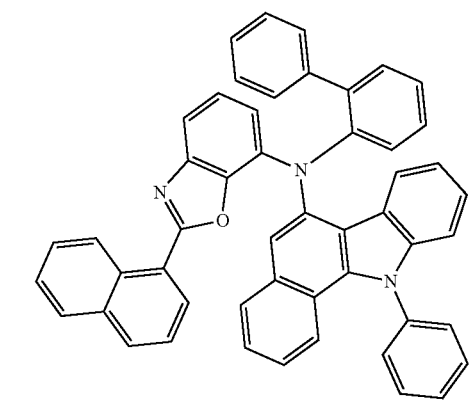

403
-continued
144
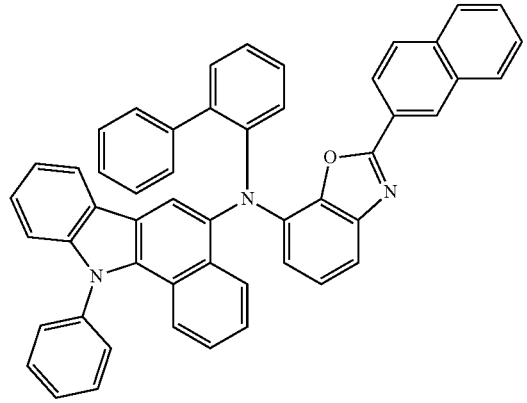
145
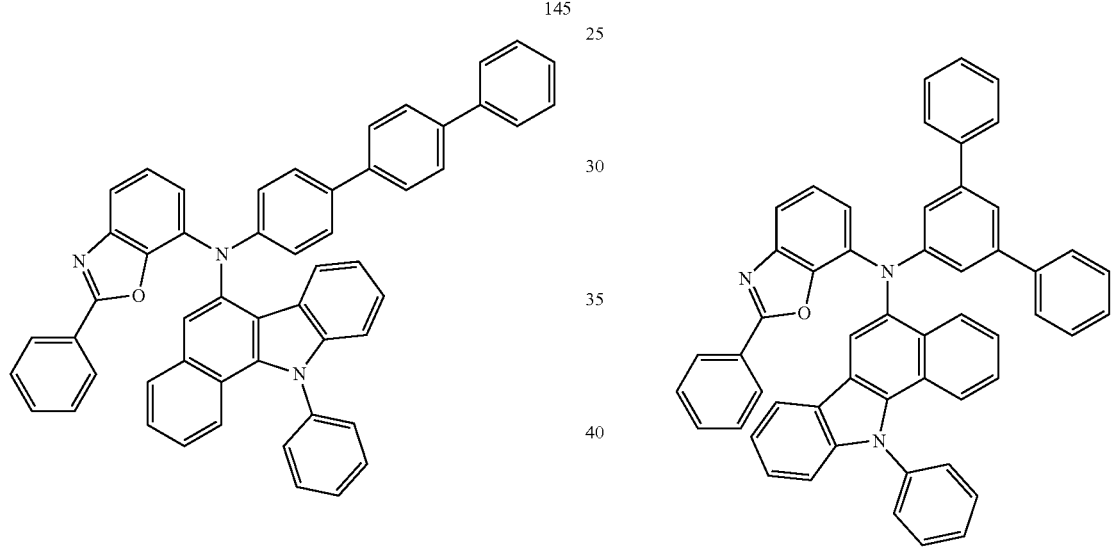
146
404
-continued
147
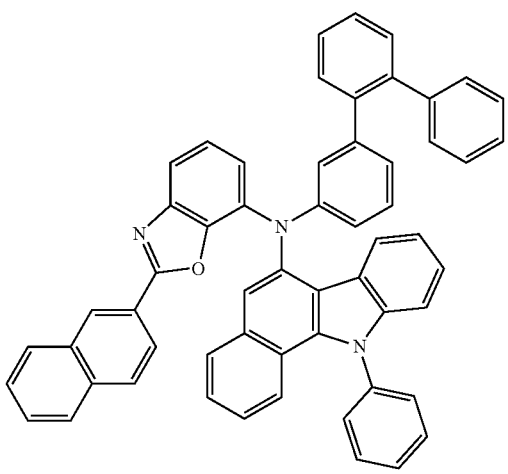
148
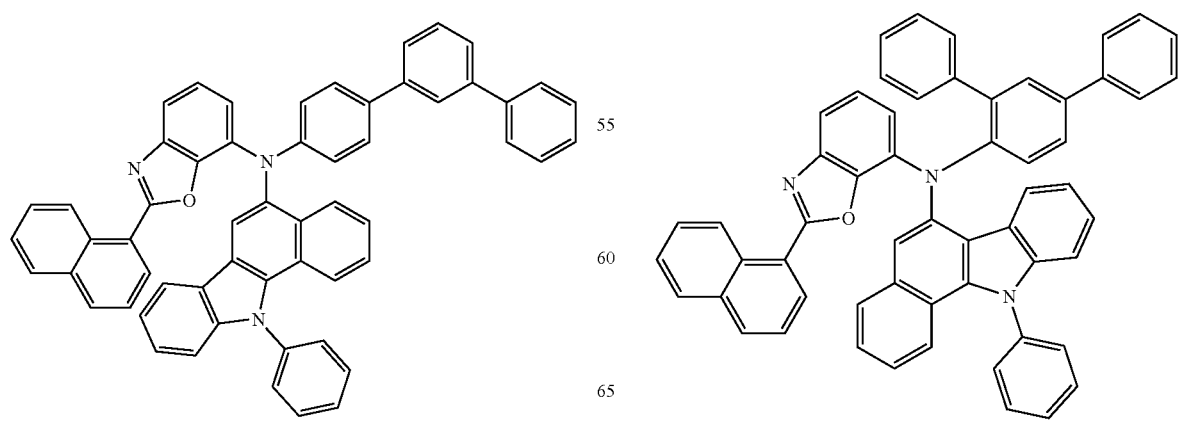
149

405
-continued
150
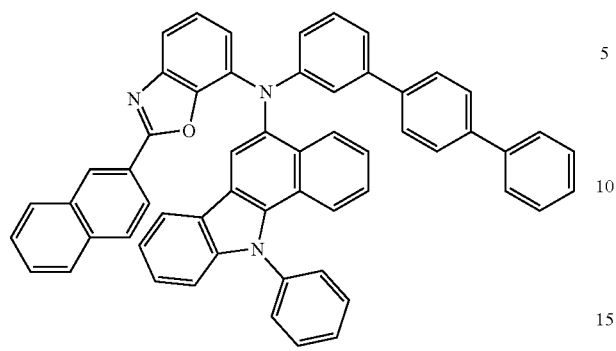
151
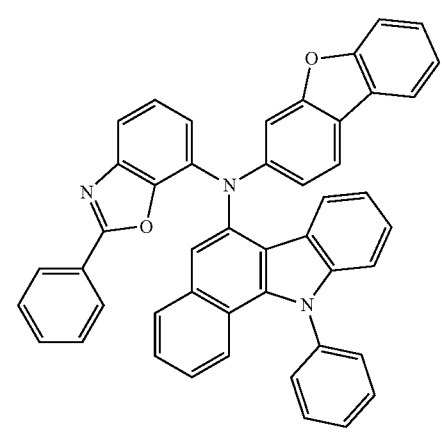
152
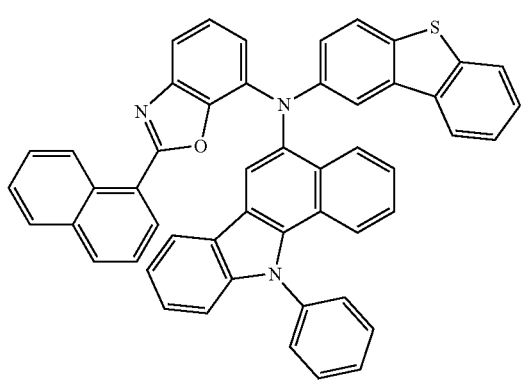
153
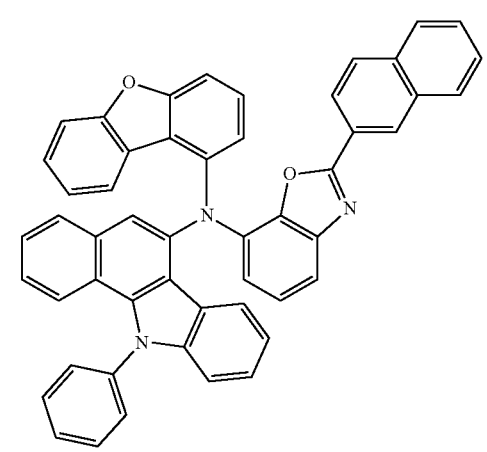
406
-continued
154
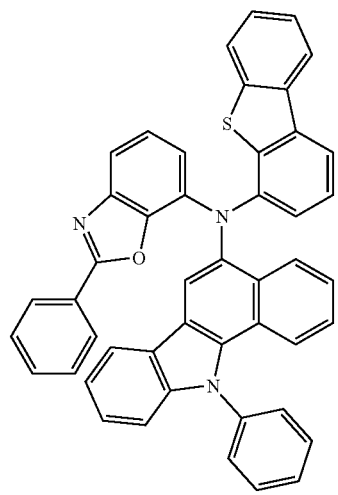
155
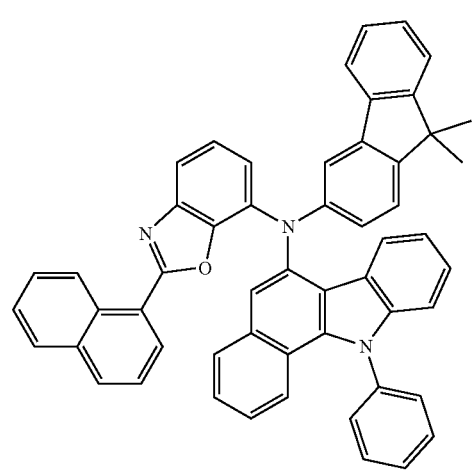
156
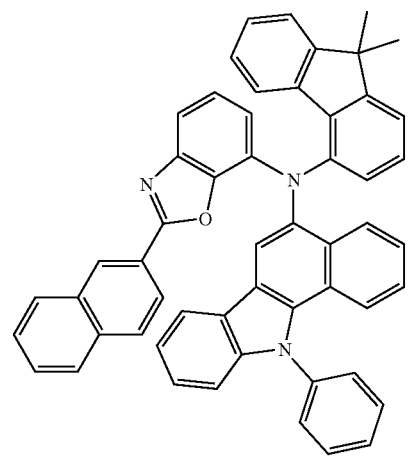

157
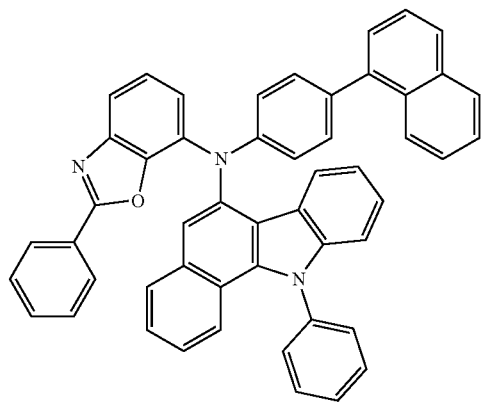
158
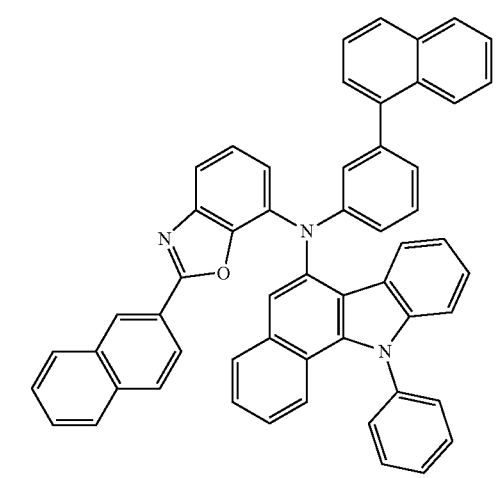
160
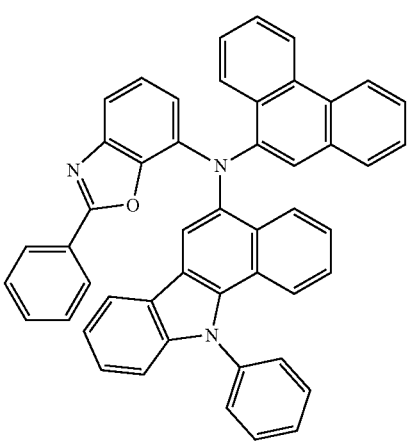
161
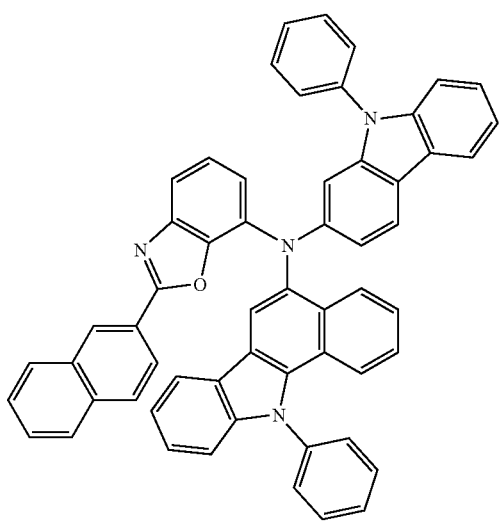
159
162

163
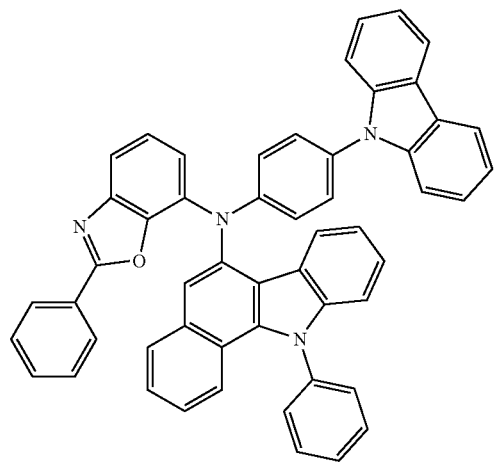 [SMILES: c1ccc(-c2nc3cccc(N(c4ccc(-n5c6ccccc6c6ccccc65)cc4)c4cc5ccccc5c5c4c4ccccc4n5-c4ccccc4)c3o2)cc1]
166
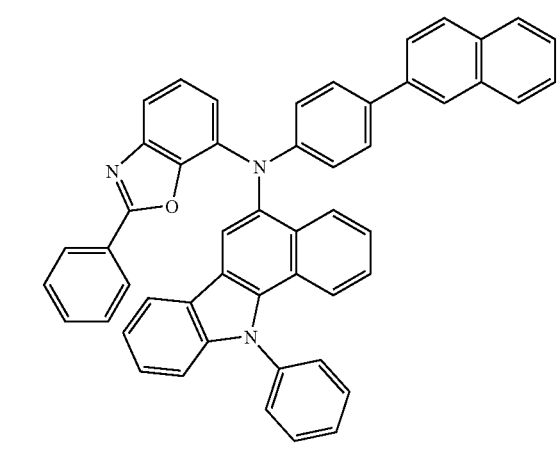
164
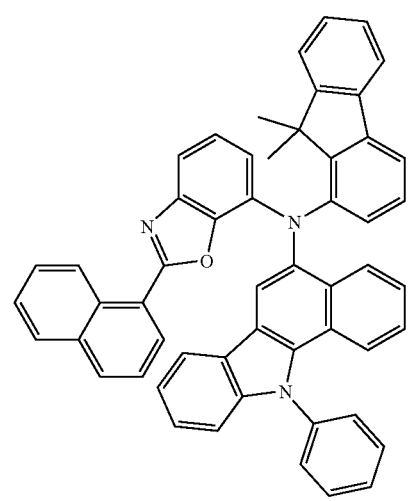
167
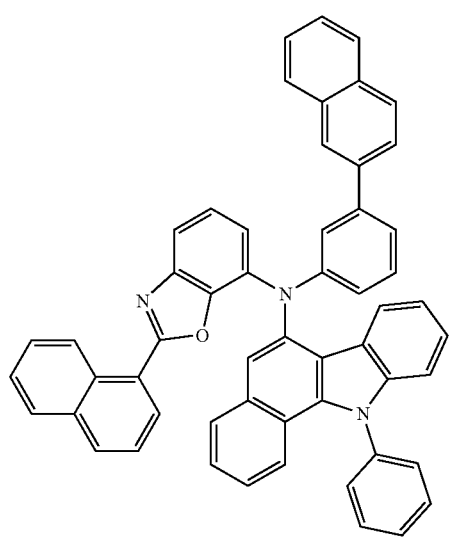
165
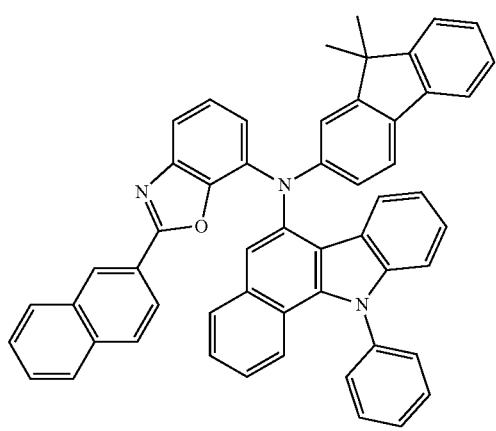
168
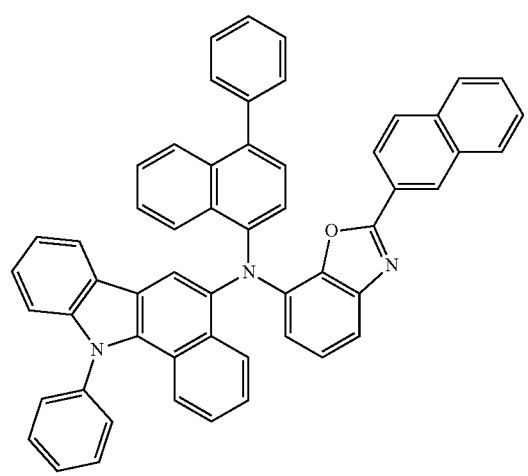

-continued
169
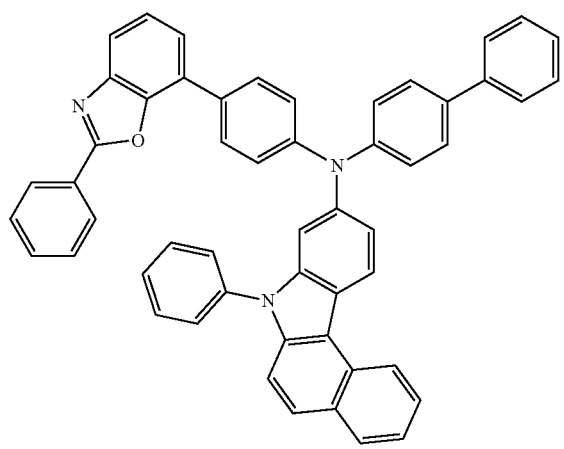
170
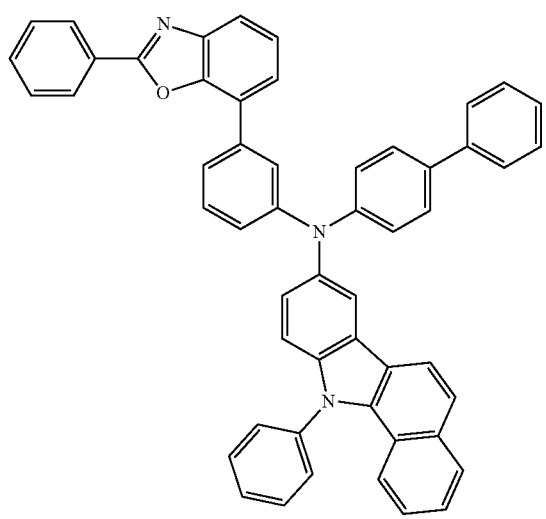
171
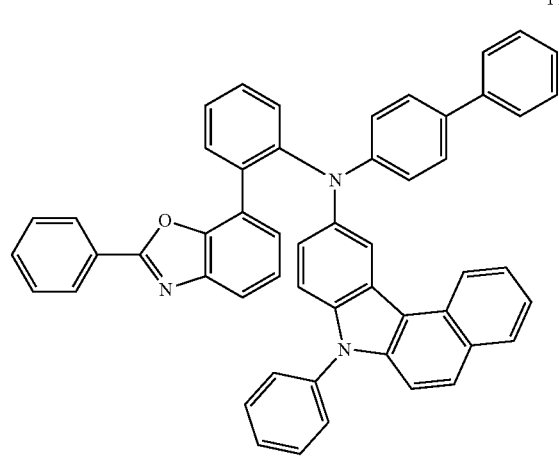
-continued
172
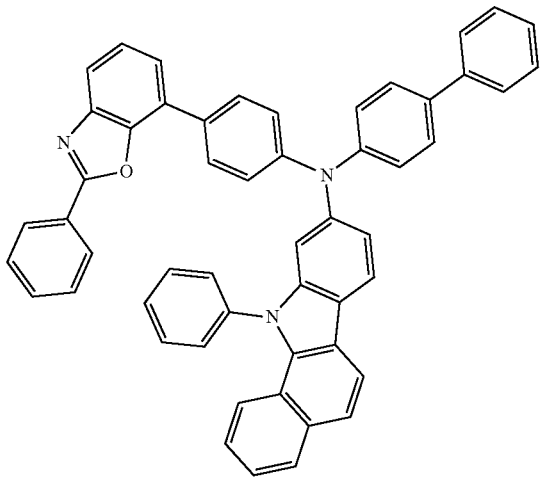
173
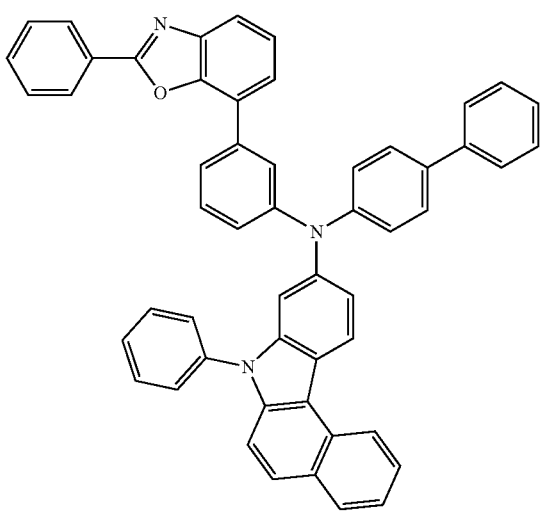
174
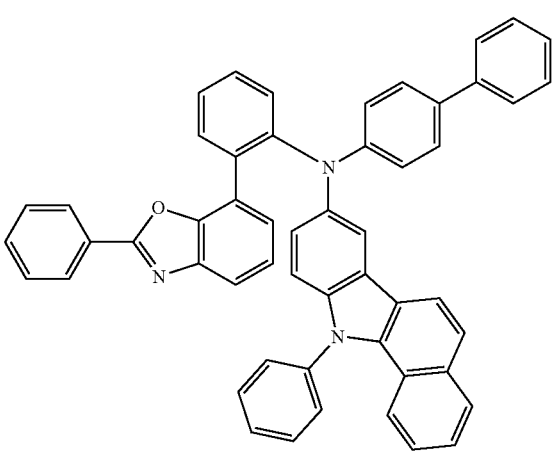

413
-continued
175
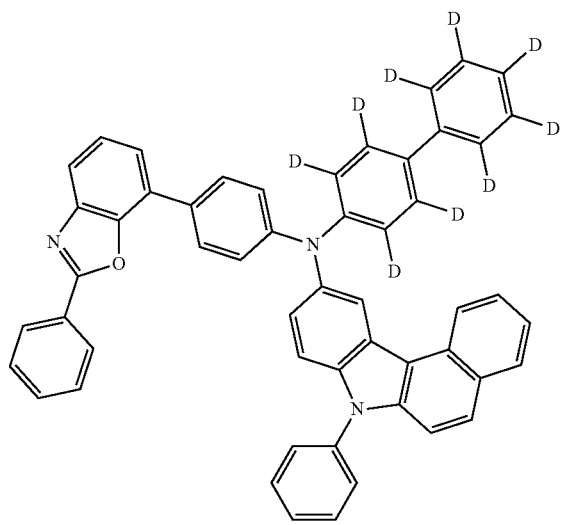
176
414
-continued
178
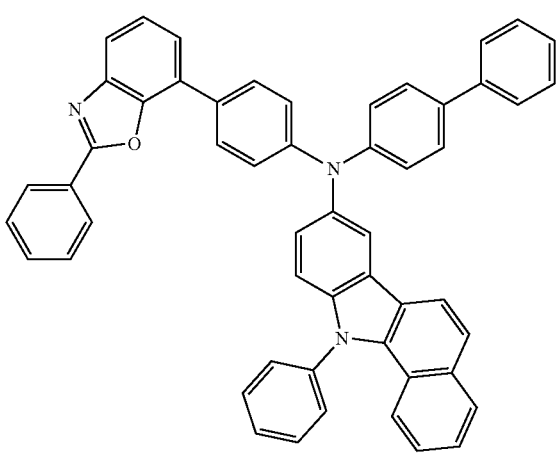
179
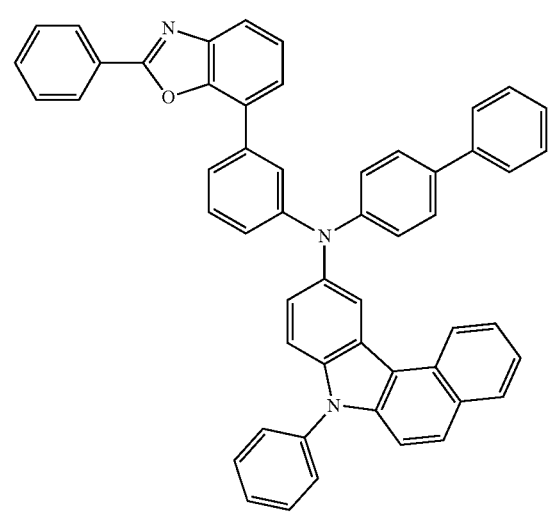
177
180
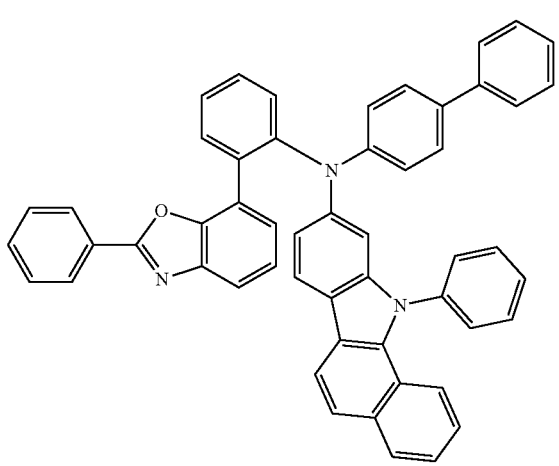

415
-continued
181
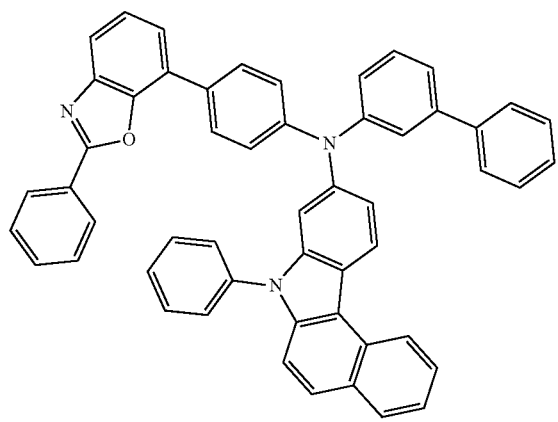
182
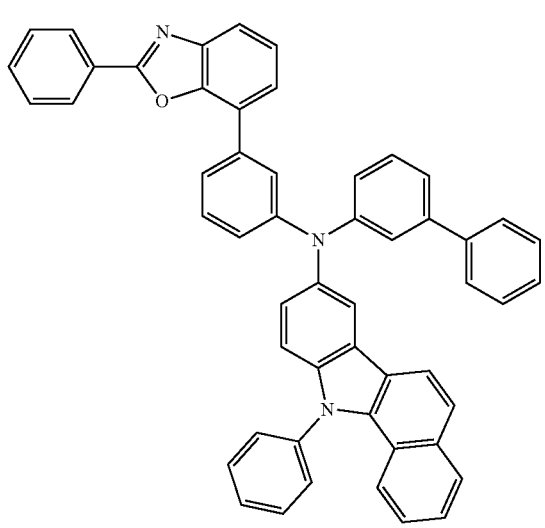
183
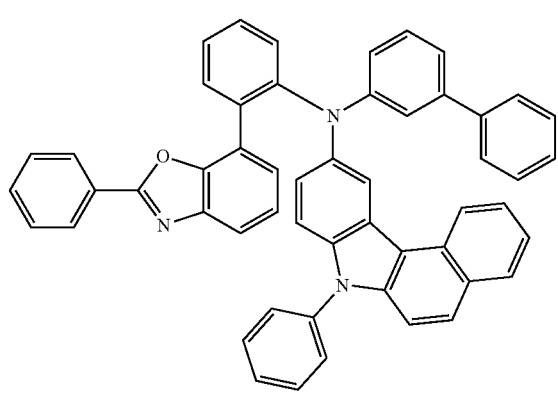
416
-continued
184
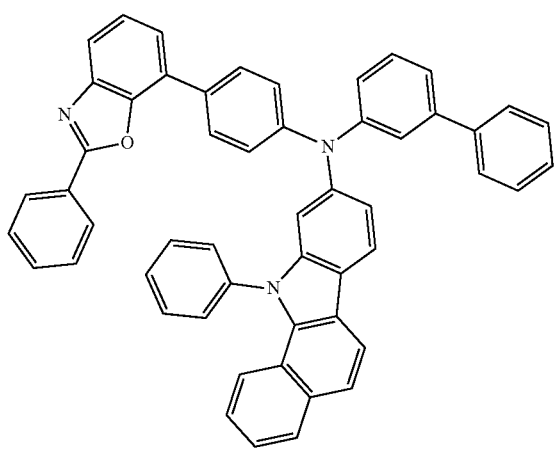
185
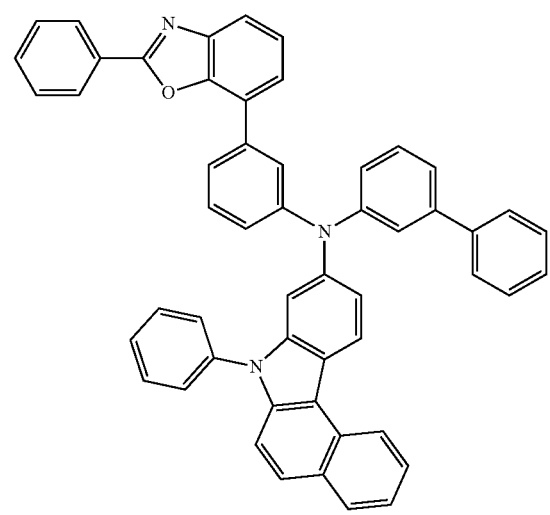
186
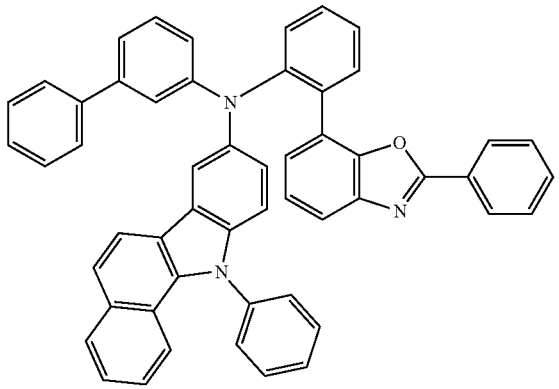

187
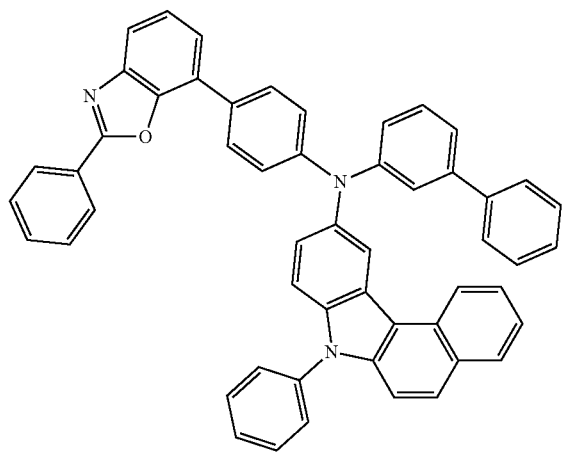
190
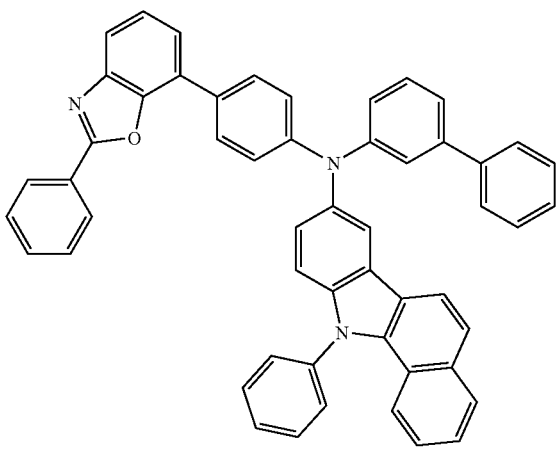
188
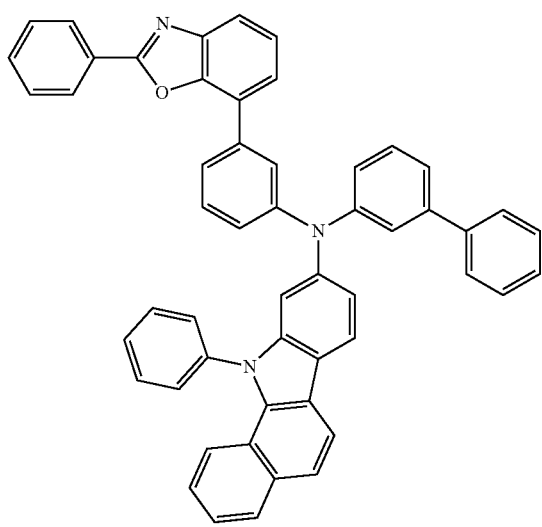
191
189
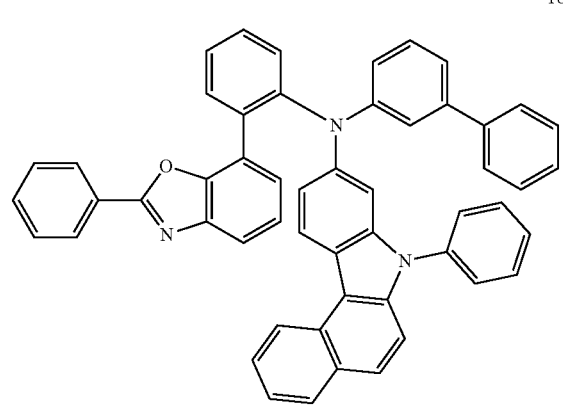
192
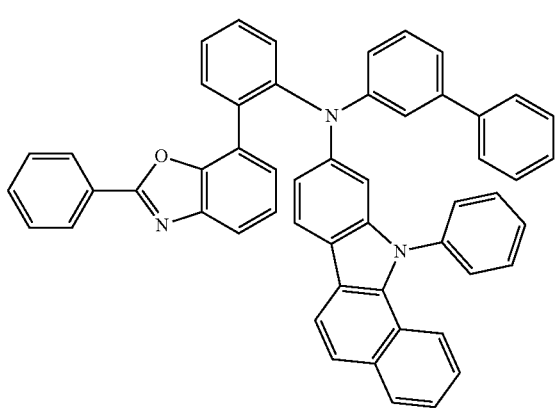

419
-continued
193
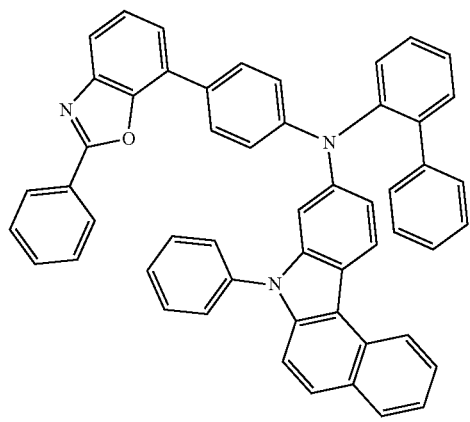
194
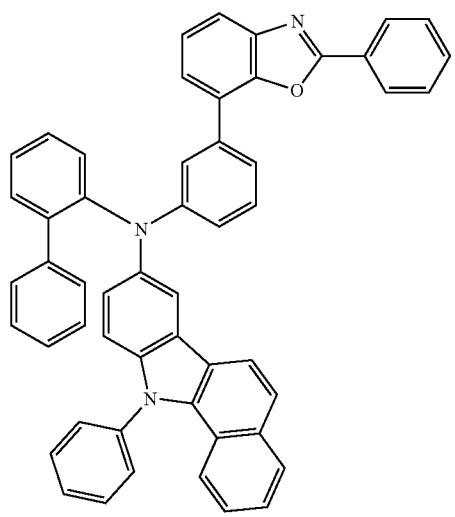
195
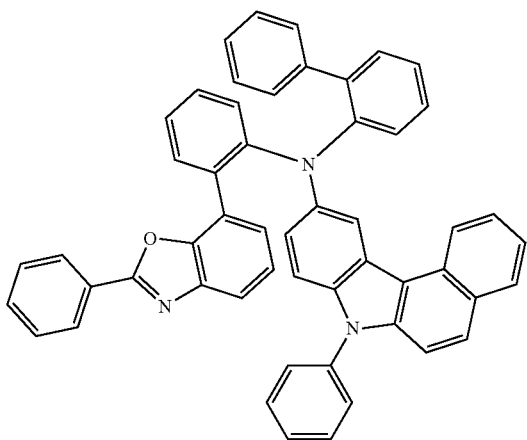
420
-continued
196
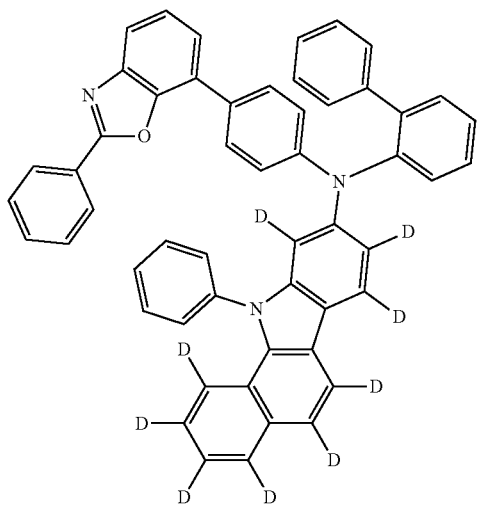
197
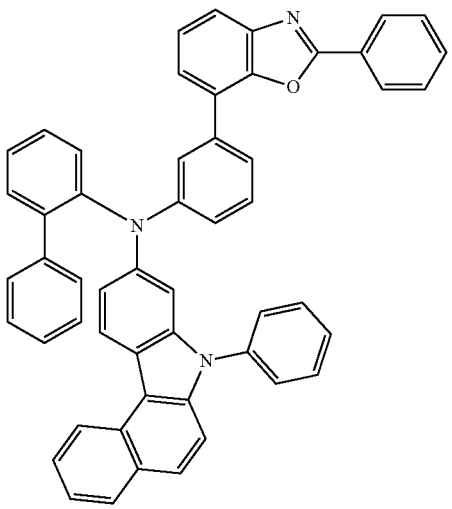
198
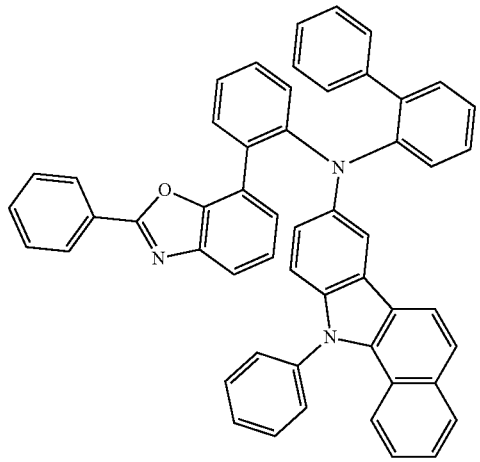

421
-continued
199
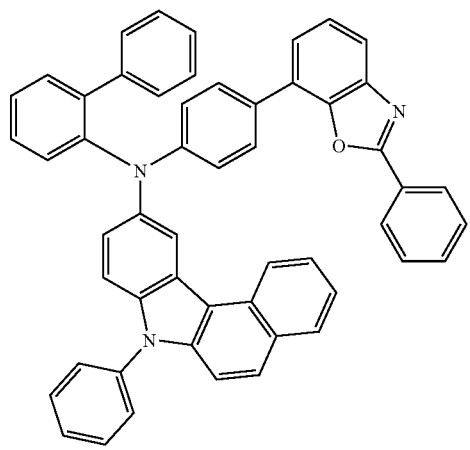
200
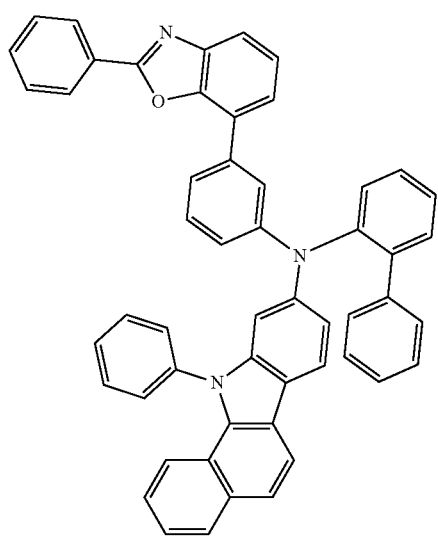
201
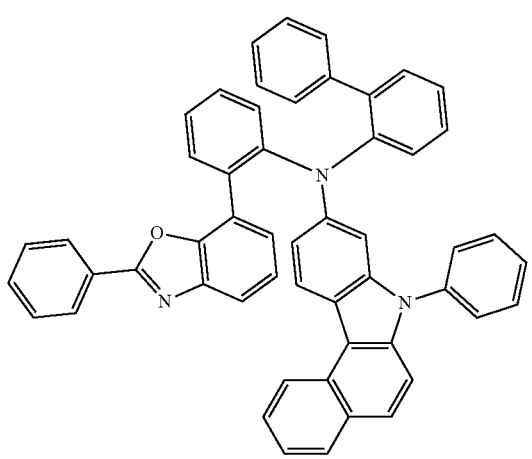
422
-continued
202
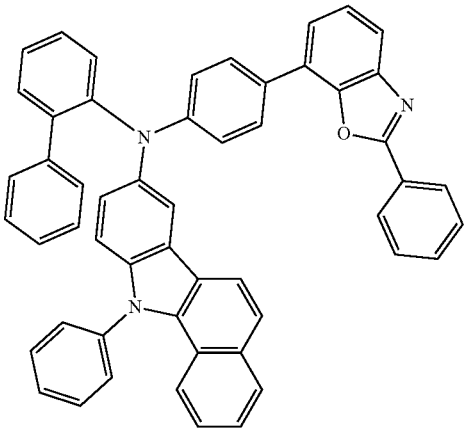
203
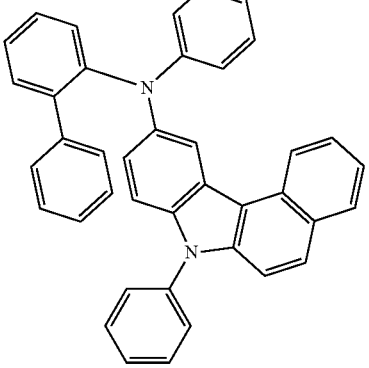
204
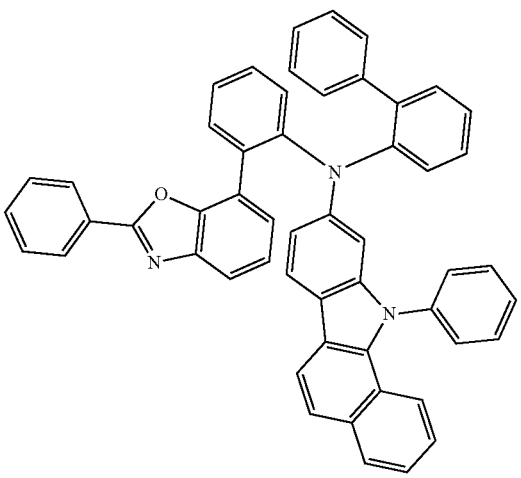

423
-continued
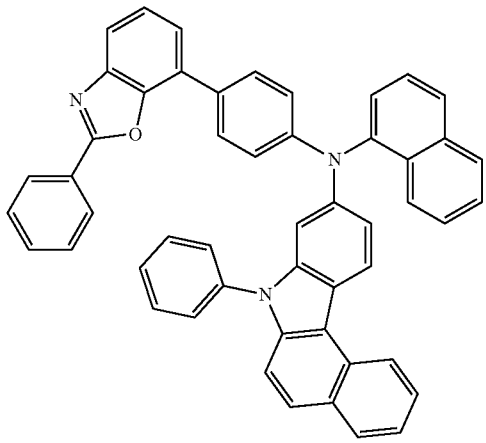
205
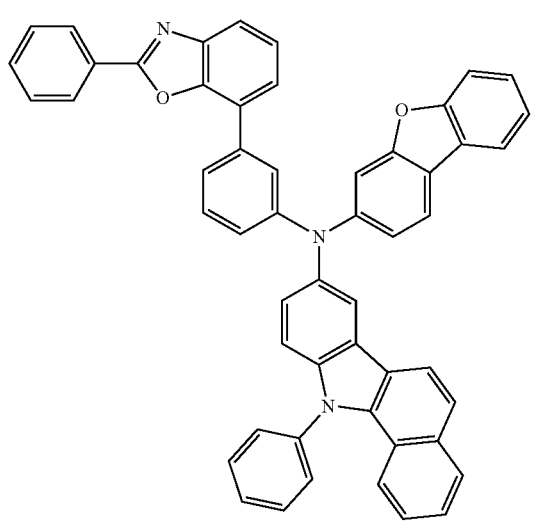
206
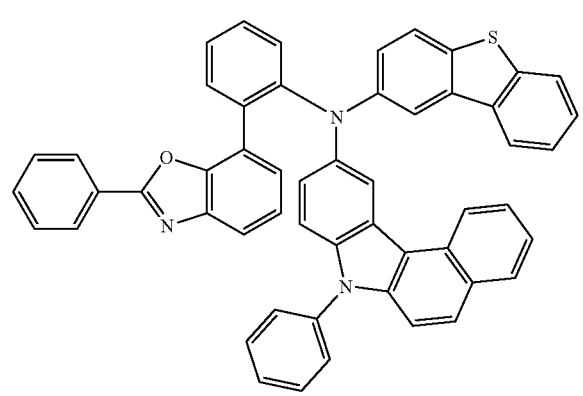
207
424
-continued
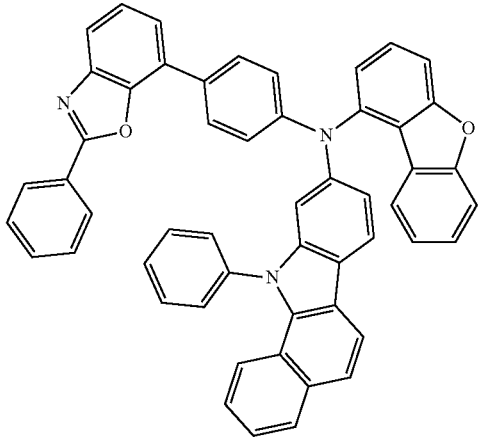
208
209
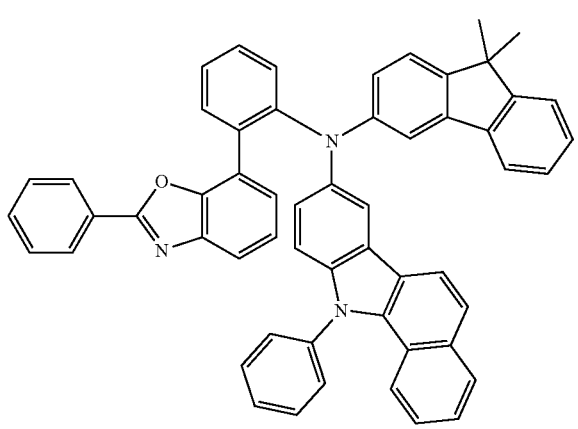
210

425
-continued
211
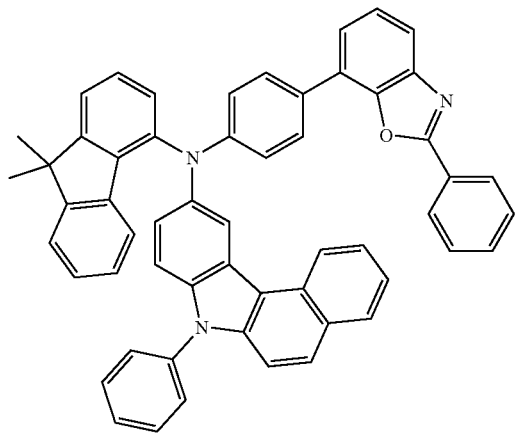
212
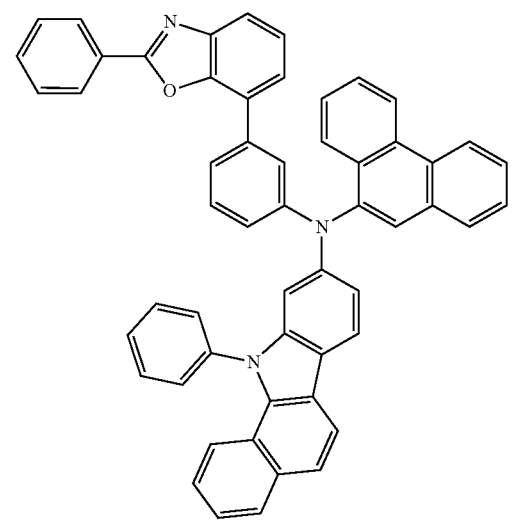
213
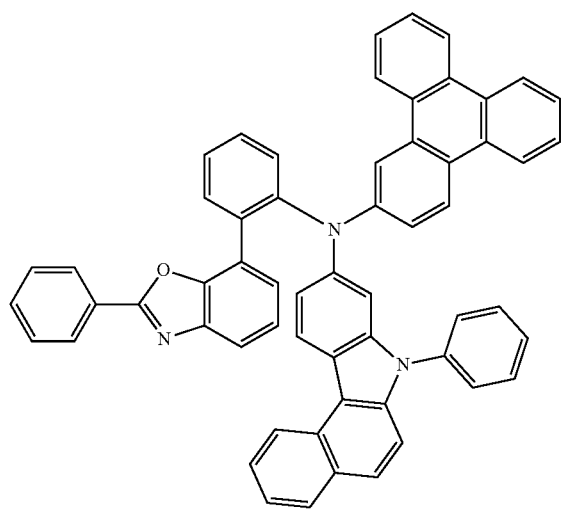
426
-continued
214
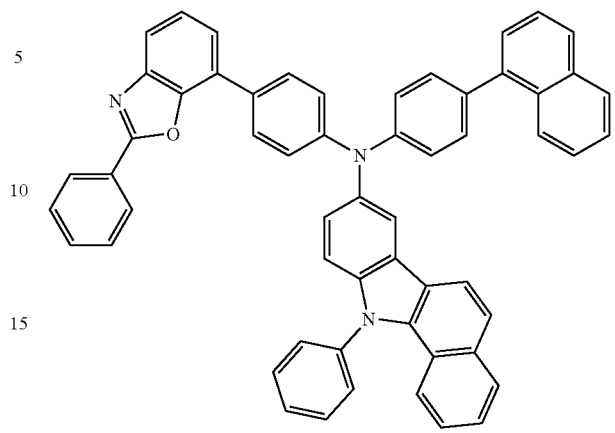
215
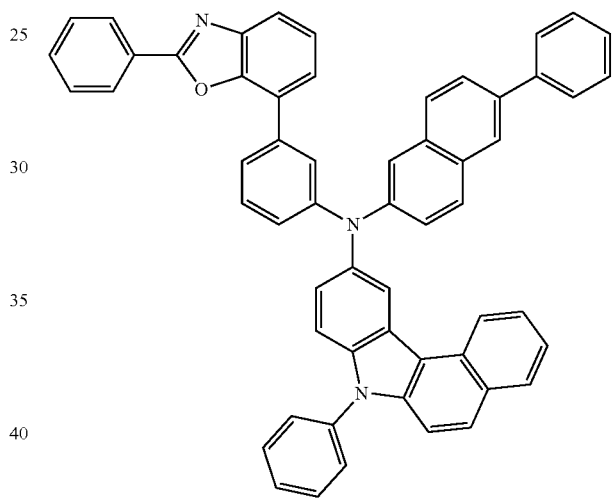
216
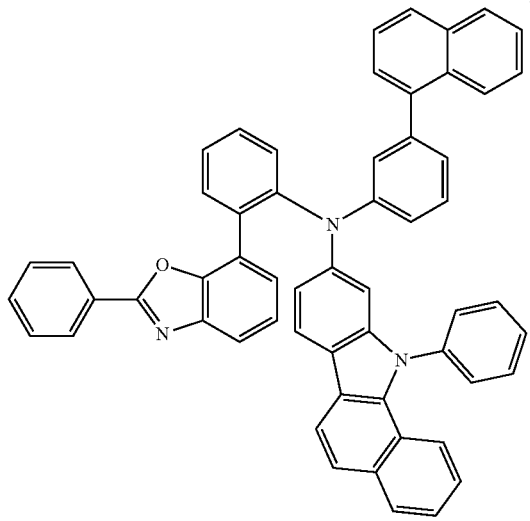

-continued
217
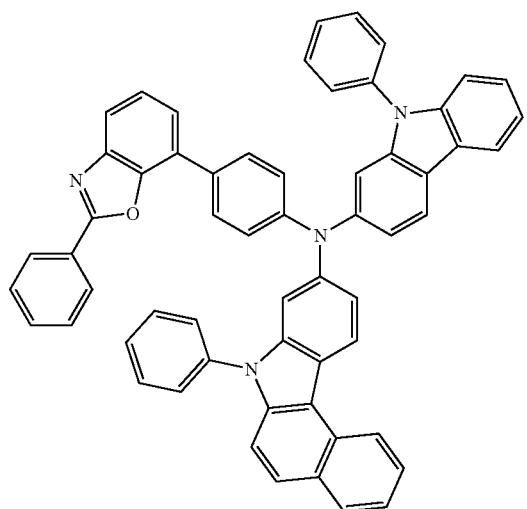
218
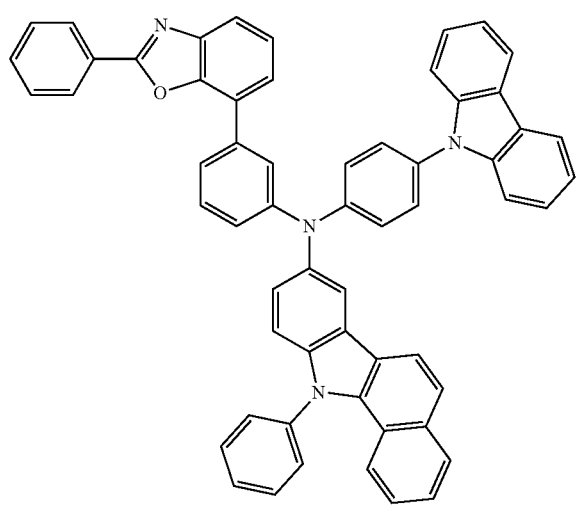
219
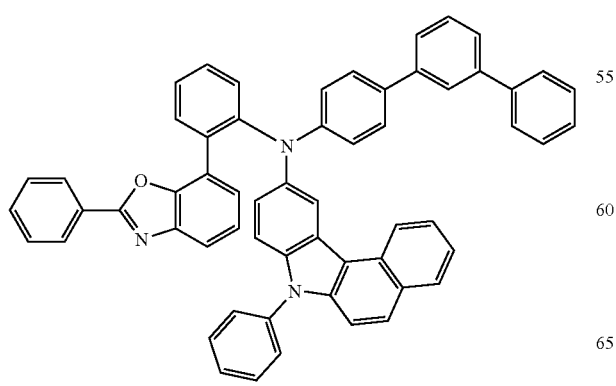
-continued
220
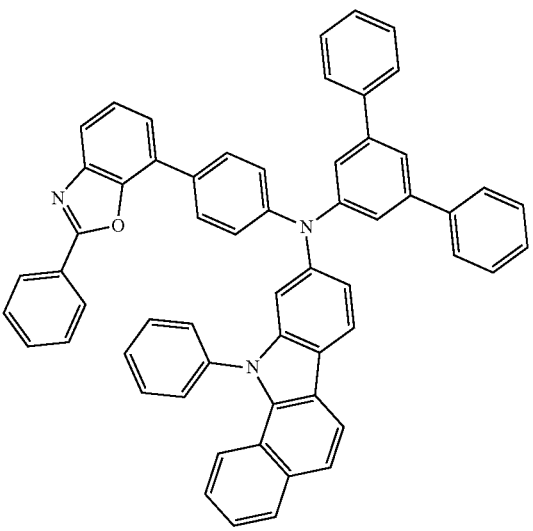
221
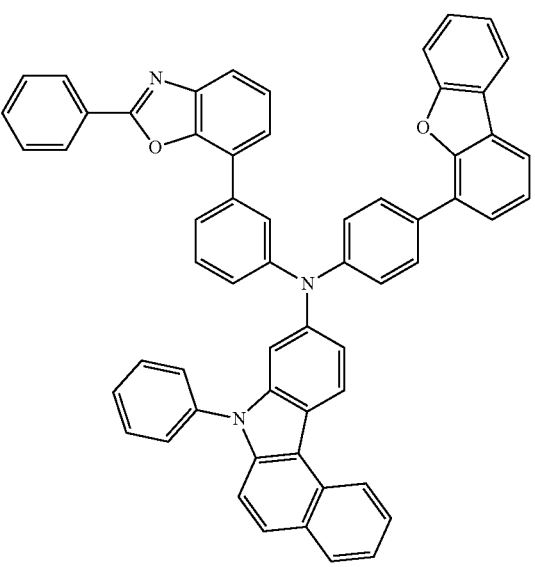

429
-continued
222
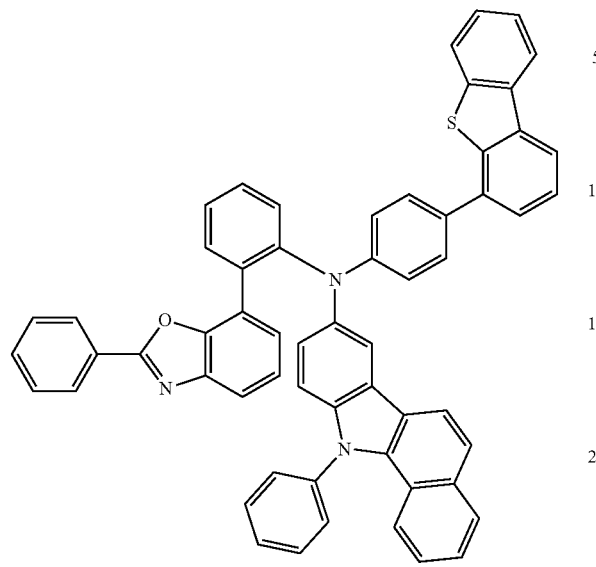
223
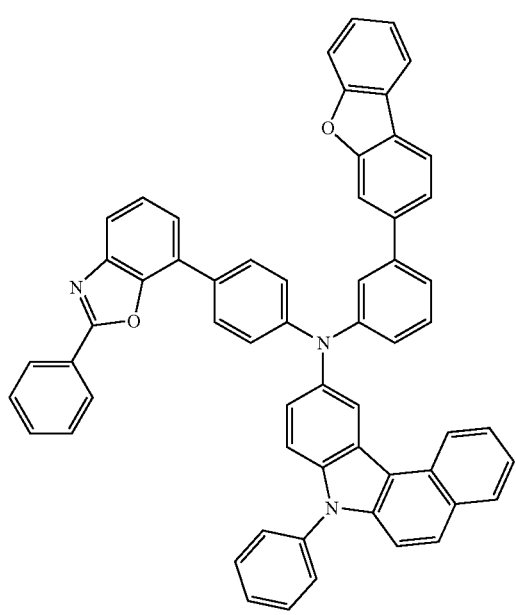
430
-continued
224
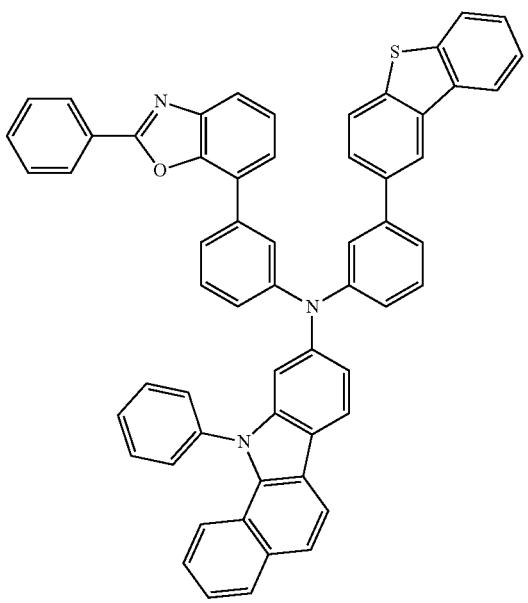
225
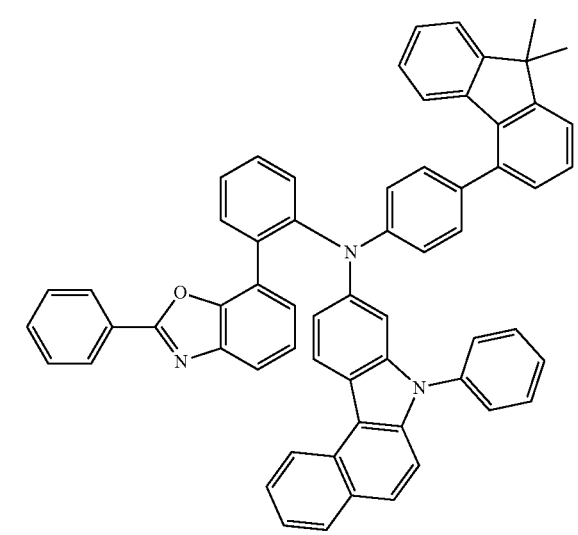
226

431
-continued
432
-continued
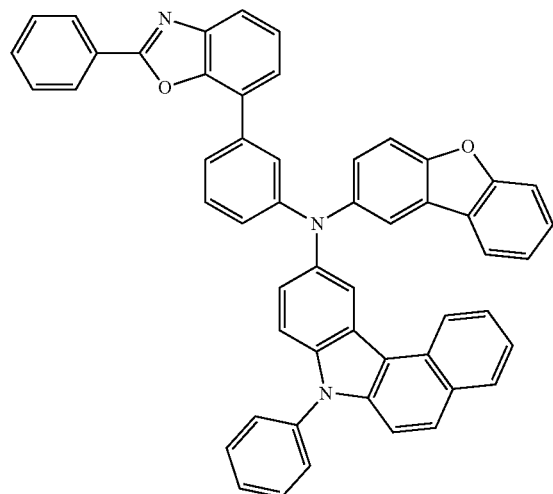
227
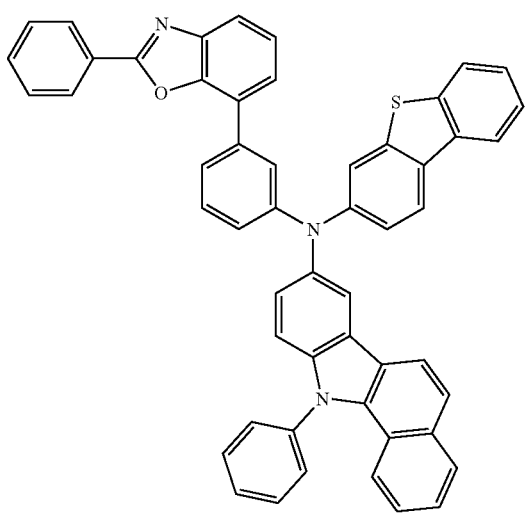
230
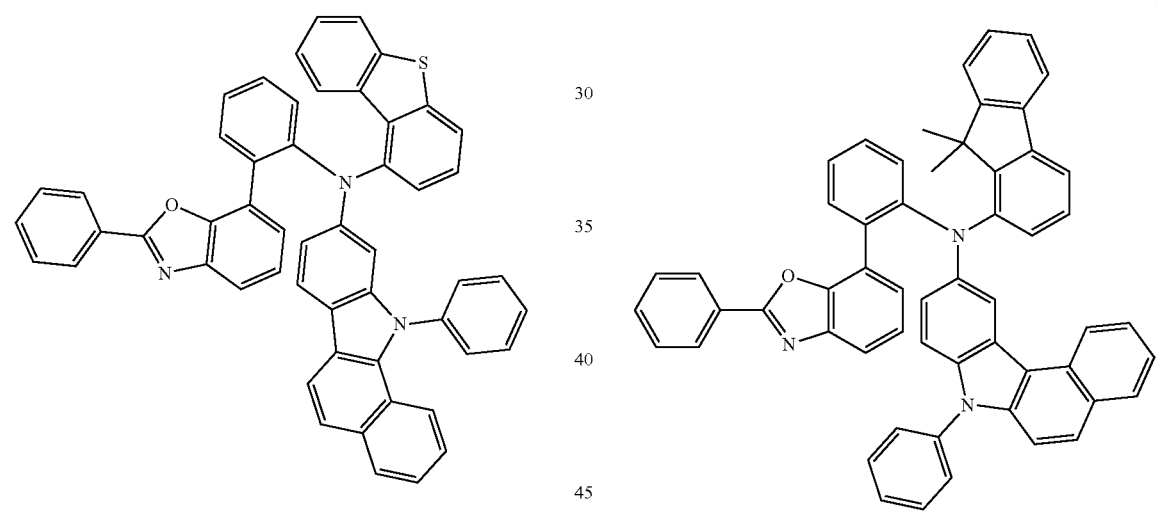
228
231
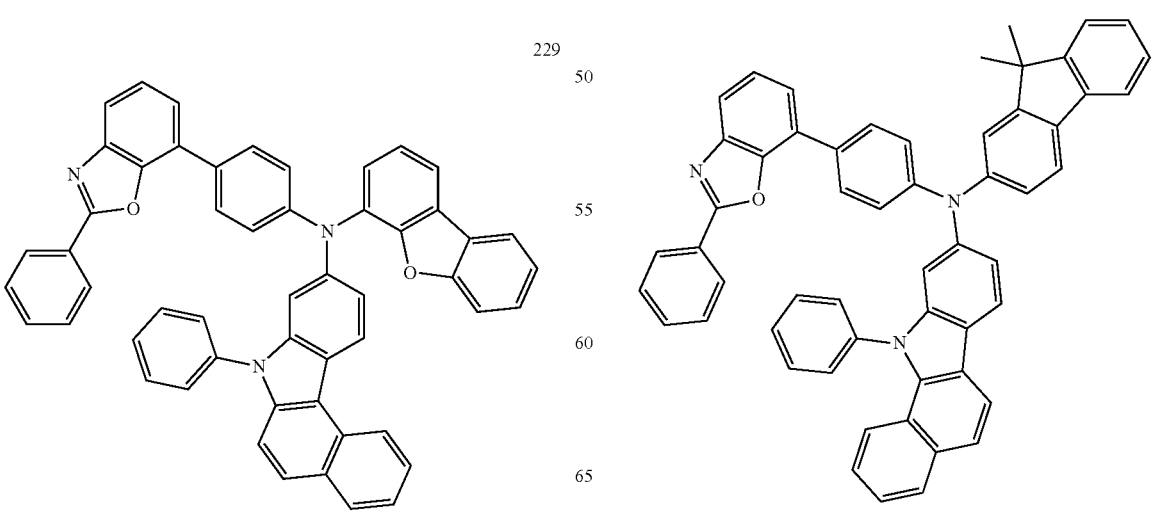
229
232

433
-continued
233
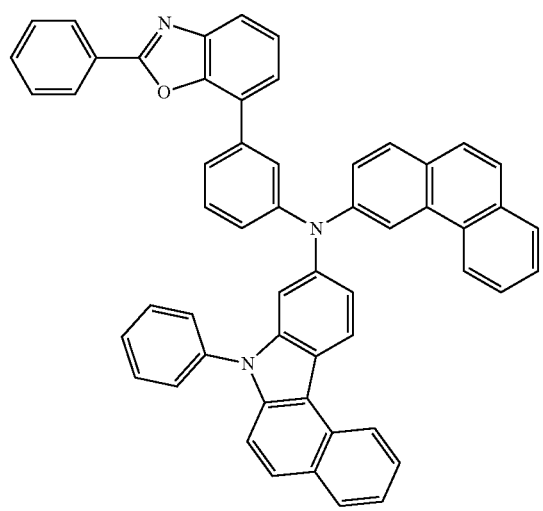
234
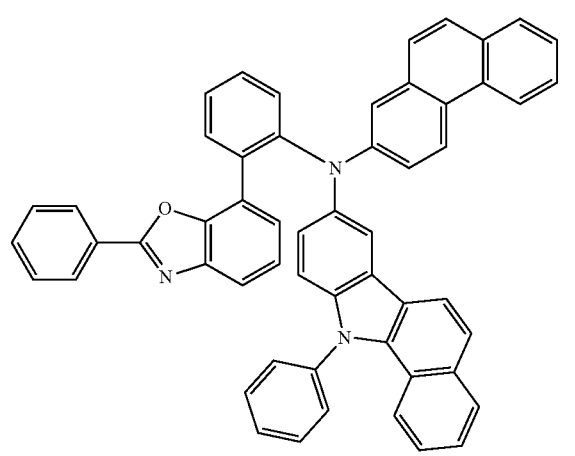
235
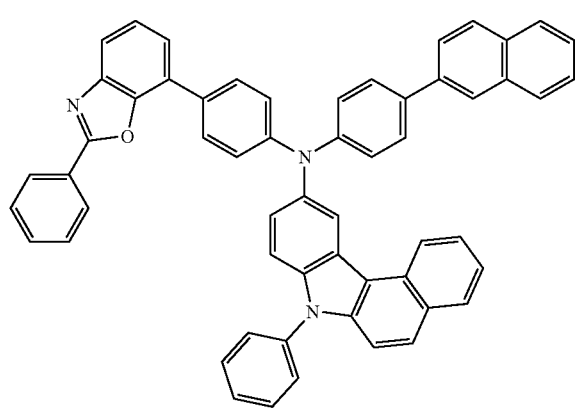
434
-continued
236
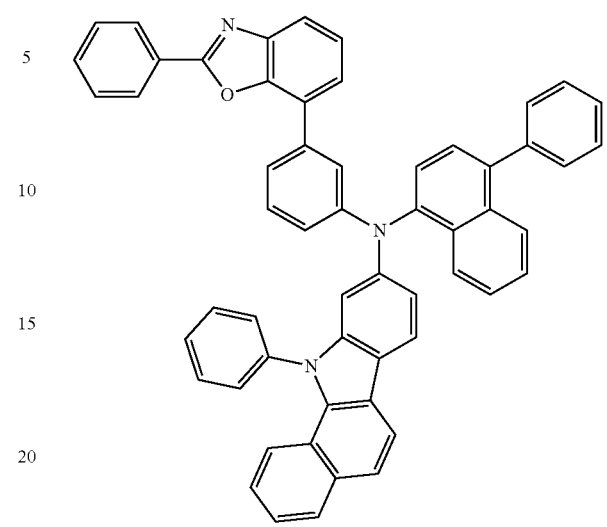
237
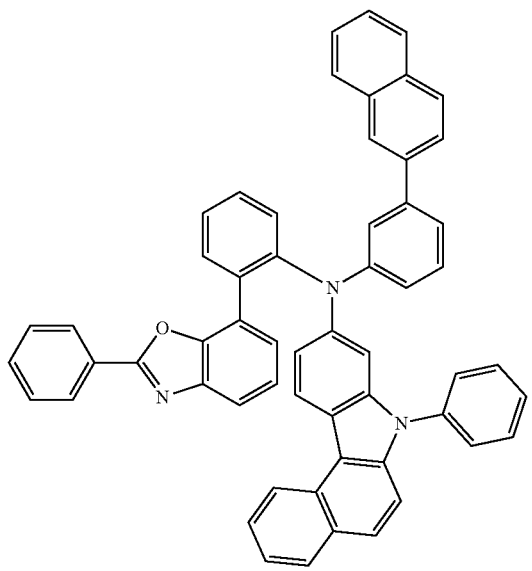
238
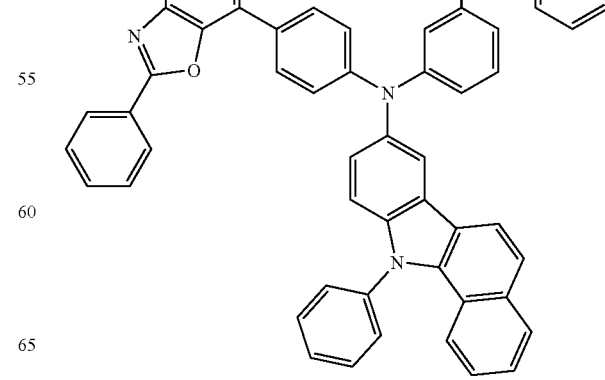

435
-continued
239
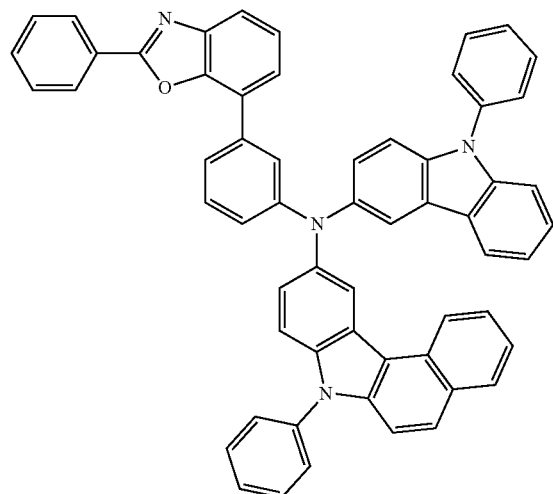
240
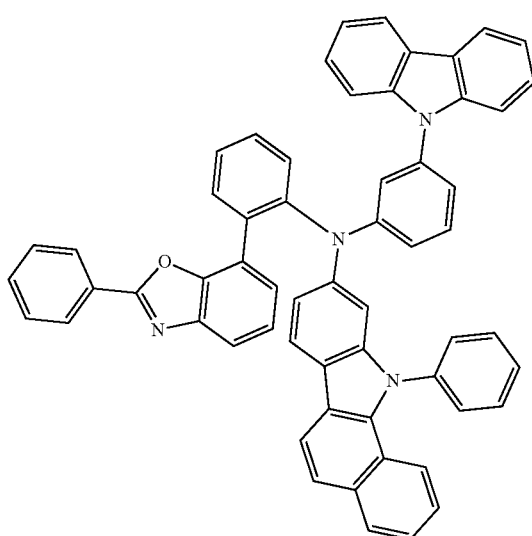
241
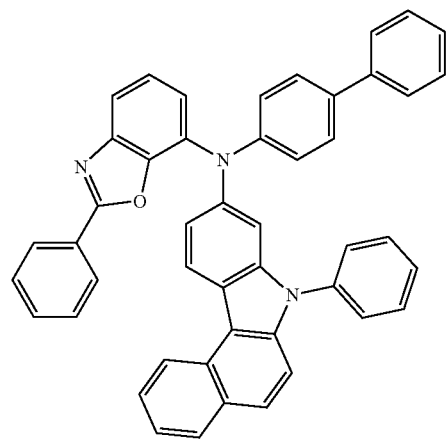
436
-continued
242
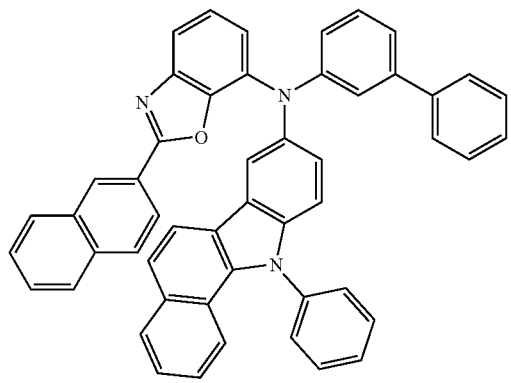
243
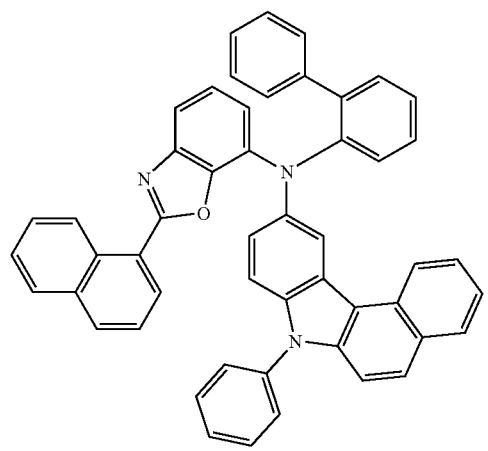
244
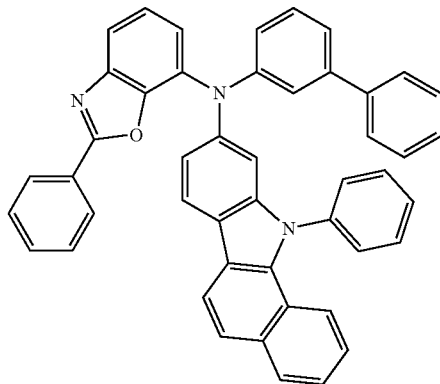

| 437 -continued | 438 -continued |
|---|---|
| 245 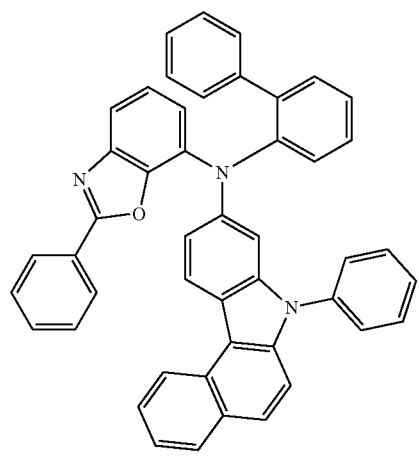 | 248 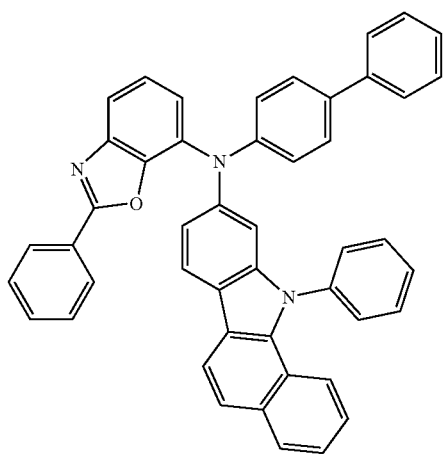 |
| 246 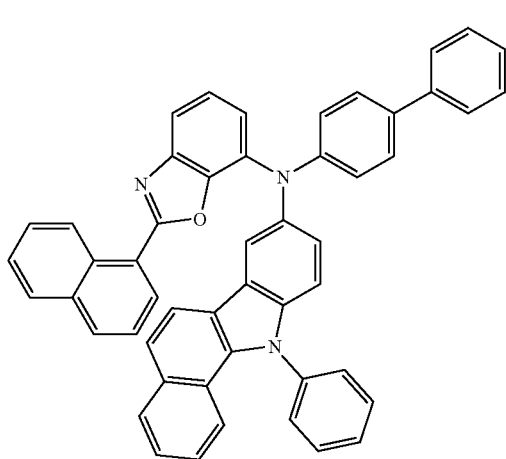 | 249 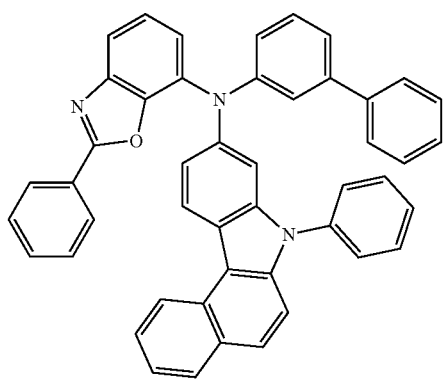 |
| | 250 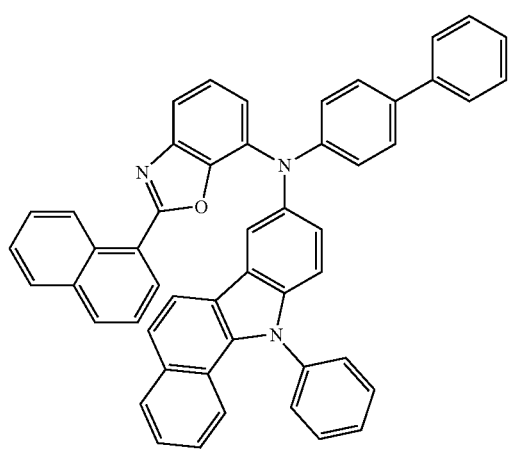 |
| 247 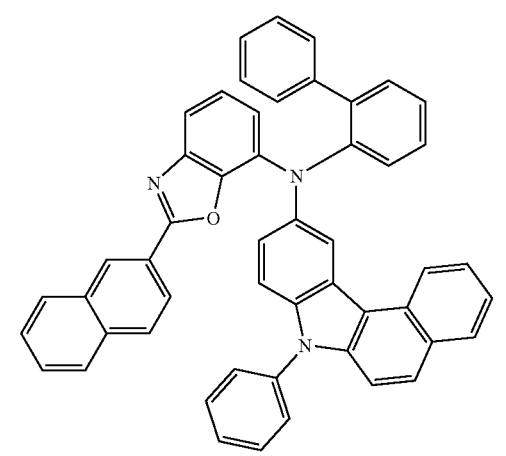 | 251 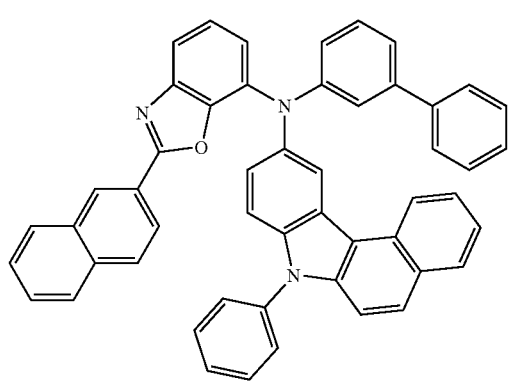 |

439
-continued
252
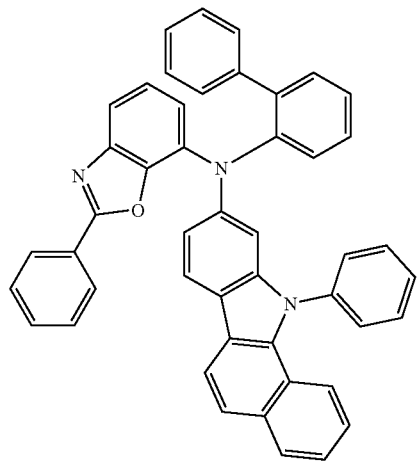
253
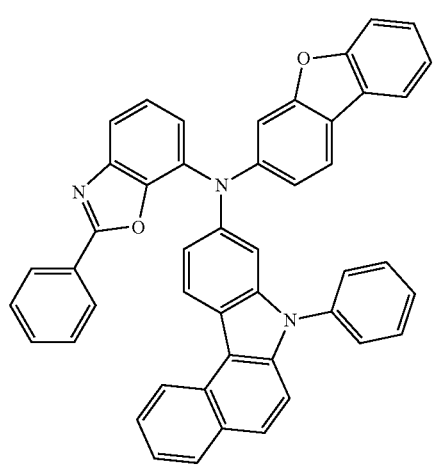
254
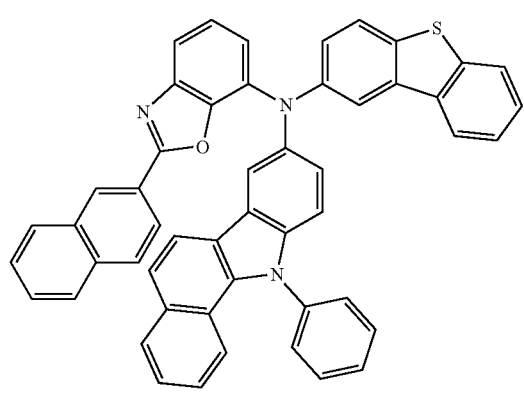
440
-continued
255
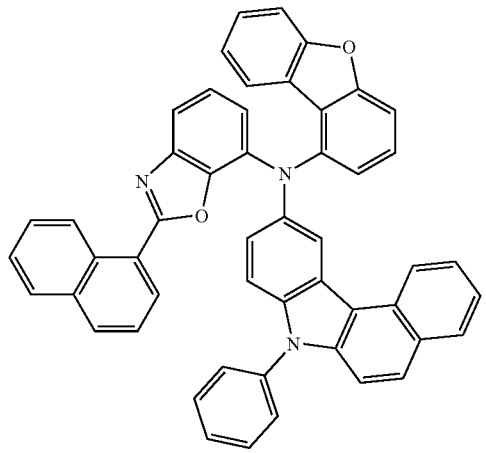
256
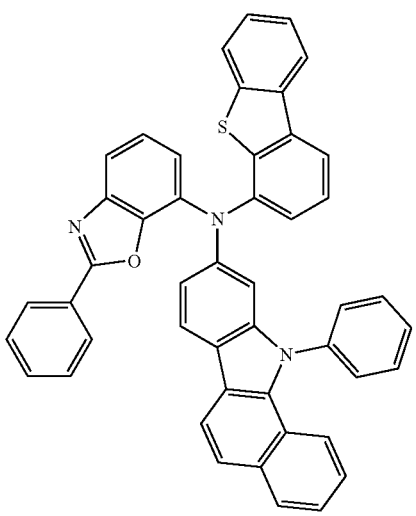
257
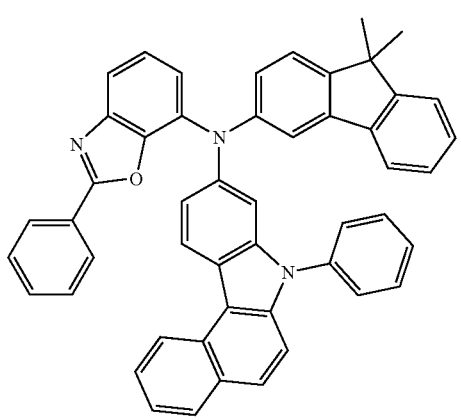

258
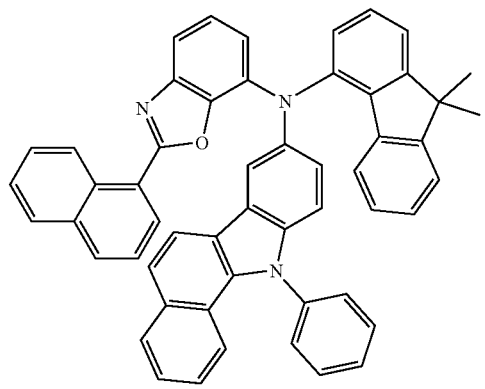
259
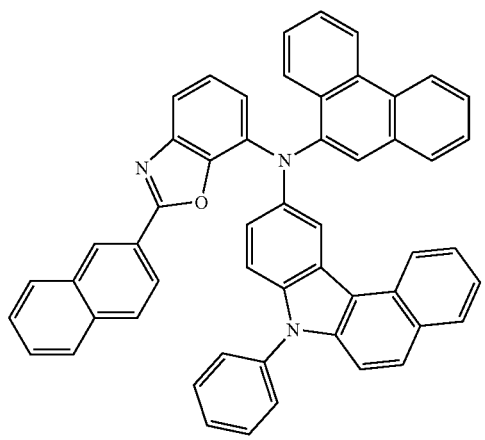
260
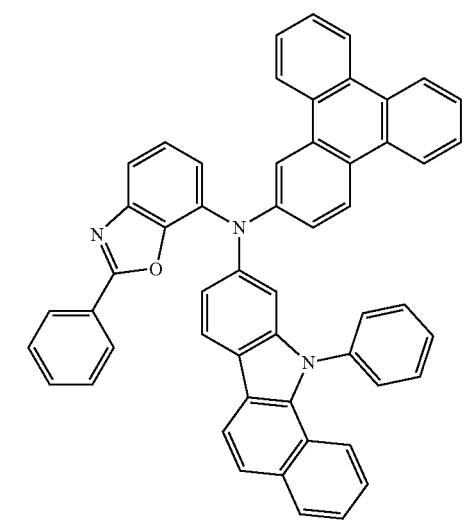
261
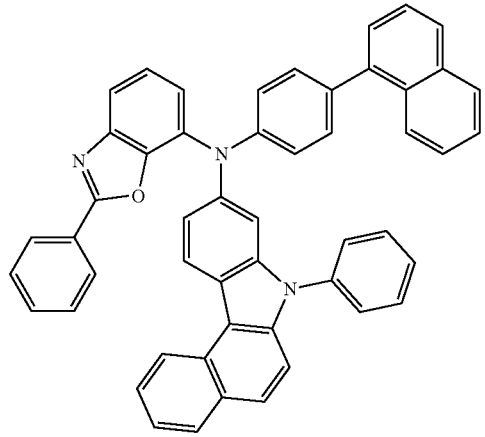
262
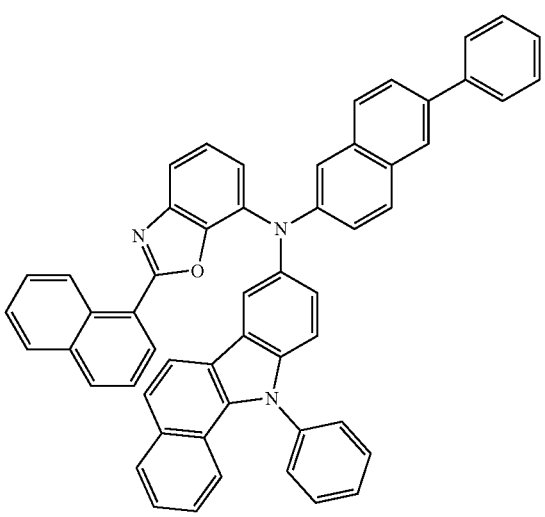
263
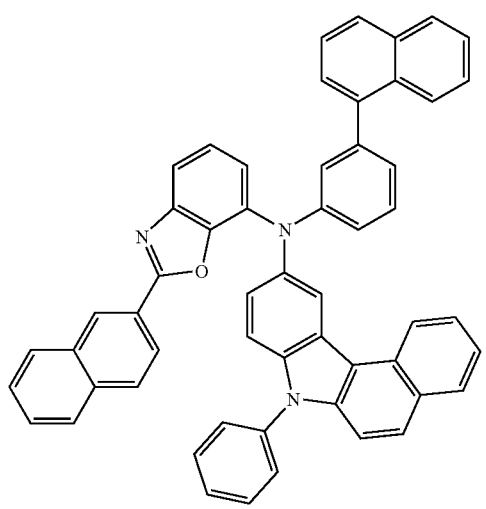

264
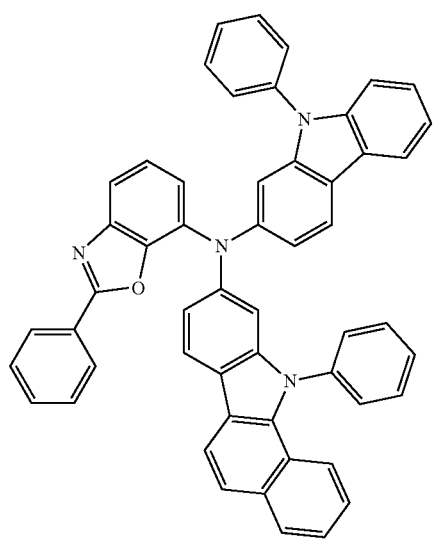
265
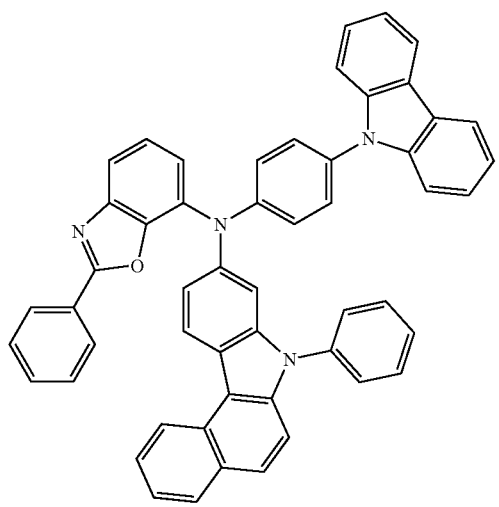
266
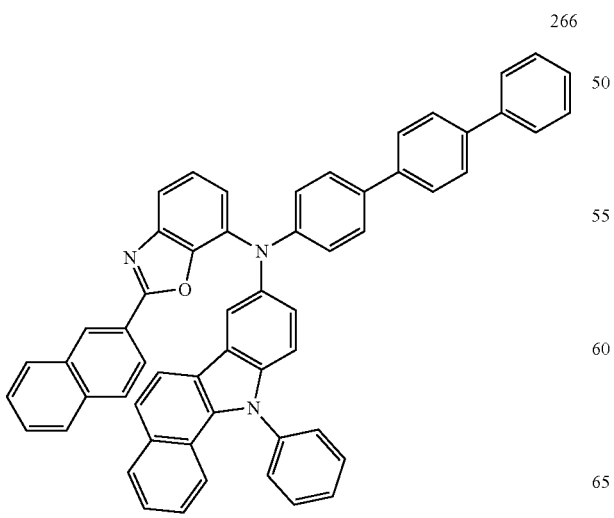
267
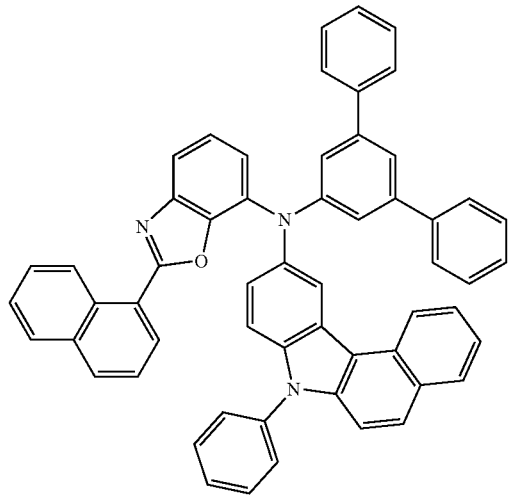
268
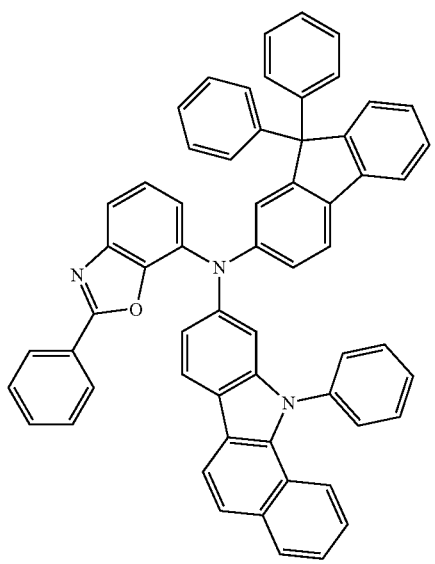
269
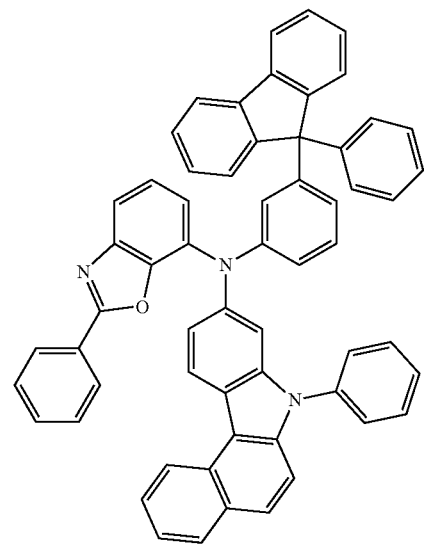

270
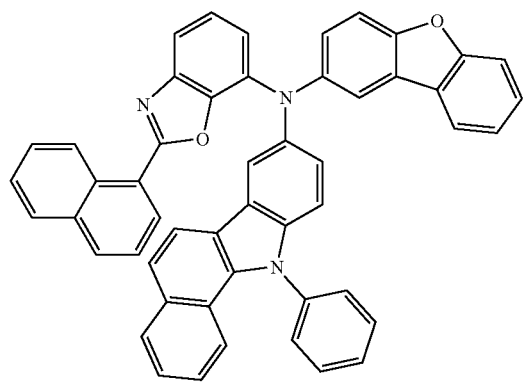
271
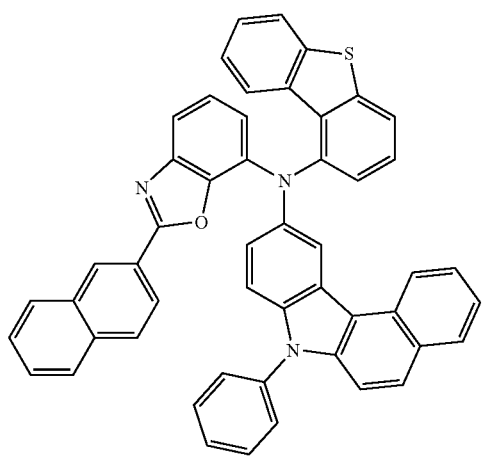
272
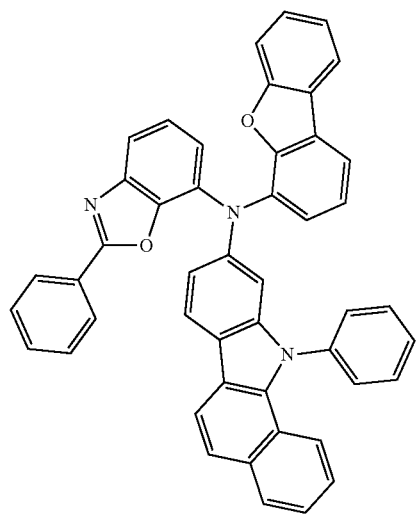
273
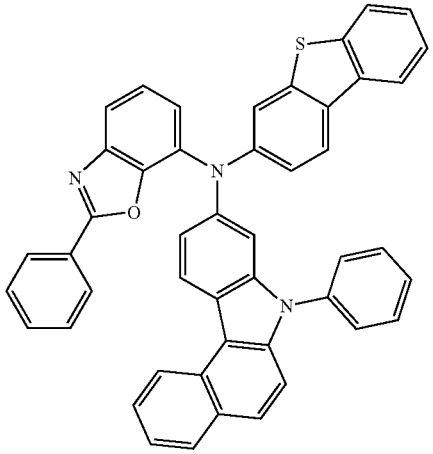
274
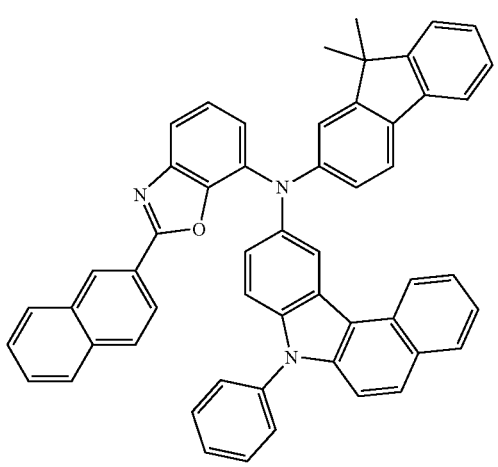
275

276
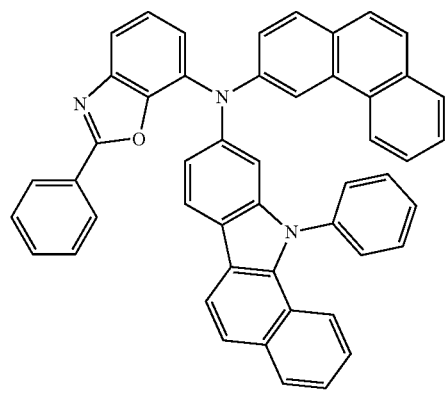
277
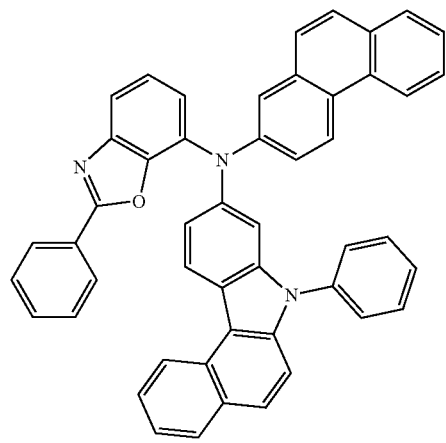
278
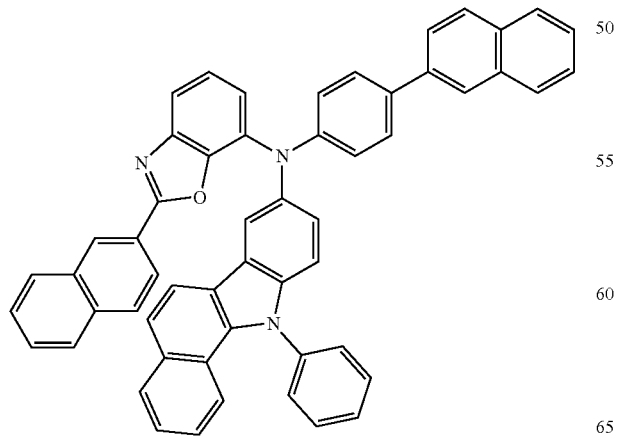
279
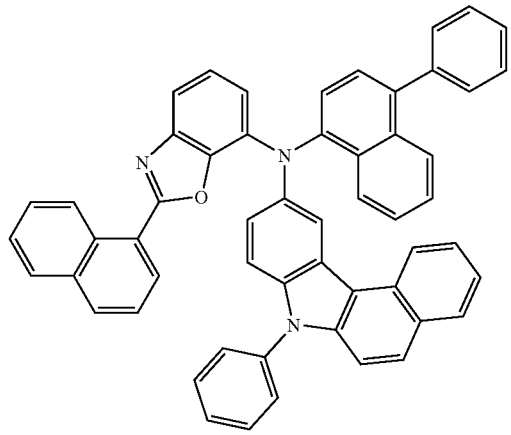 [SMILES: c1ccc(-c2ccc(N(c3ccc4c(c3)c3c5ccccc5ccc3n4-c3ccccc3)c3cccc4nc(-c5cccc6ccccc56)oc34)c3ccccc23)cc1]
280
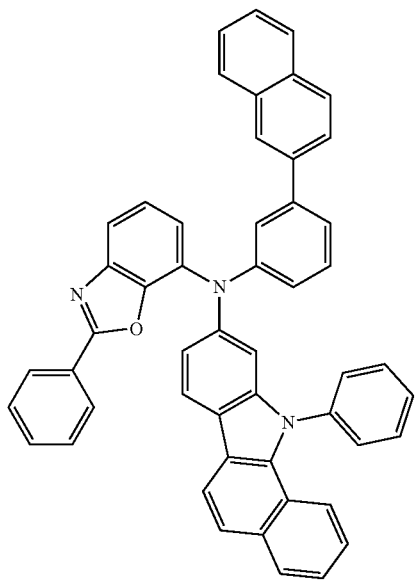
281
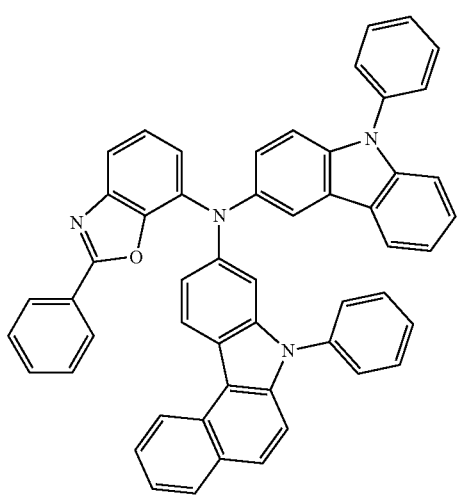

282
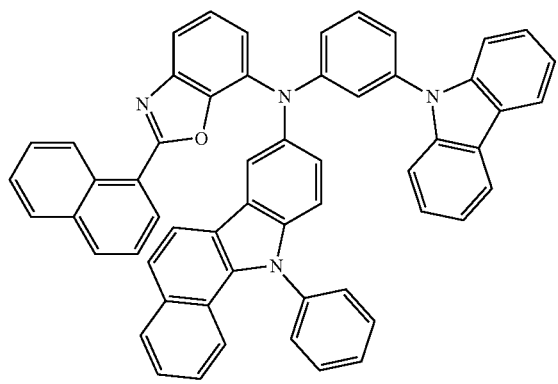
285
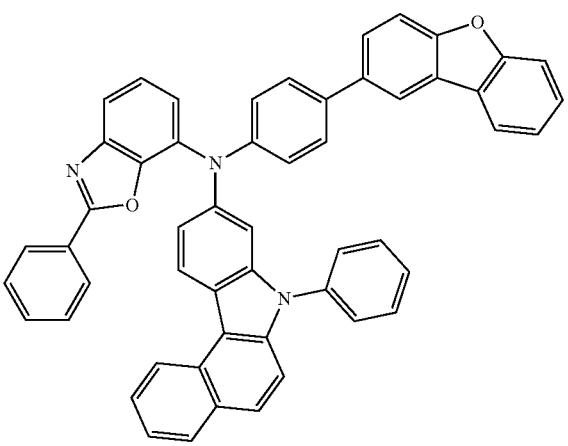 [SMILES: c1ccc(-c2nc3cccc(N(c4ccc(-c5ccc6oc7ccccc7c6c5)cc4)c4ccc5c6c7ccccc7ccc6n(-c6ccccc6)c5c4)c3o2)cc1]
283
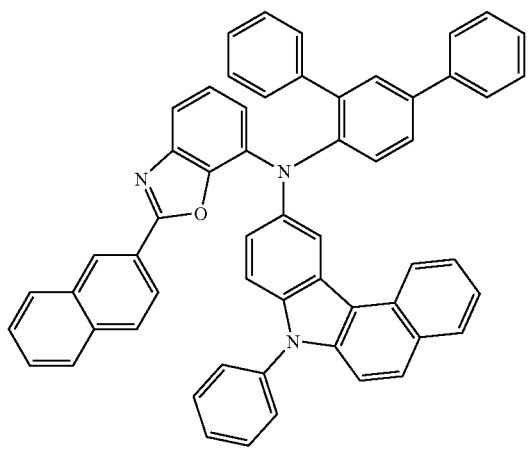
286
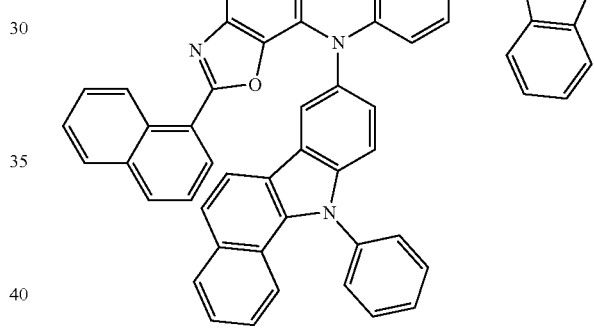
284
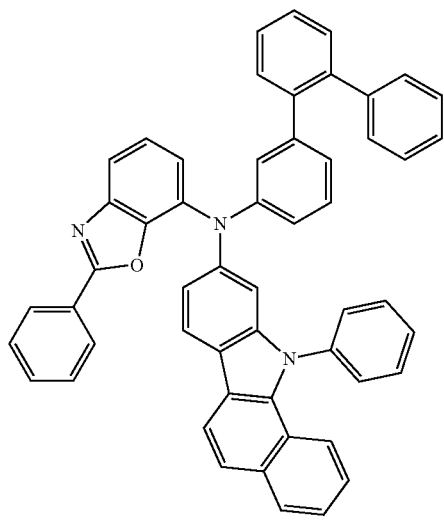
287
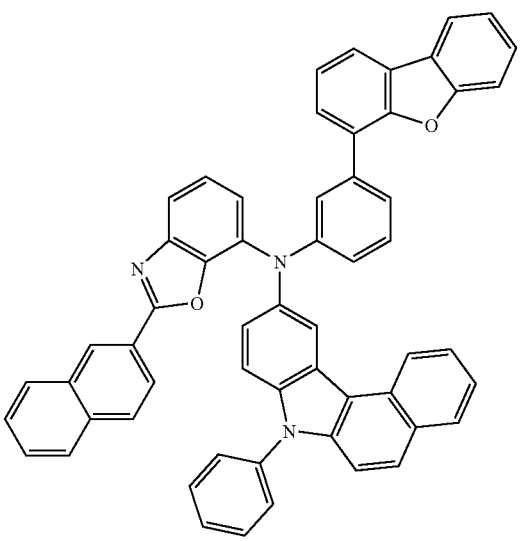

451
-continued
288
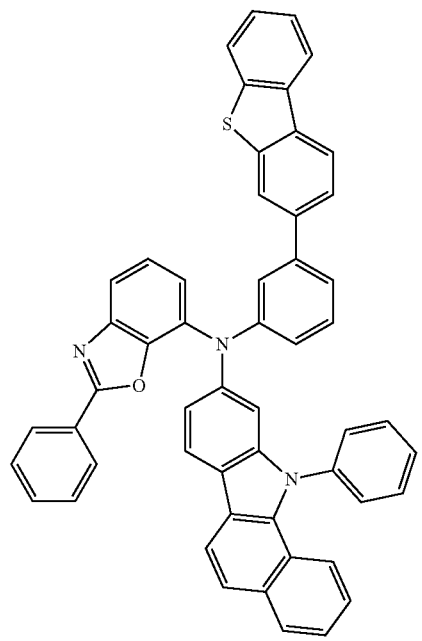
289
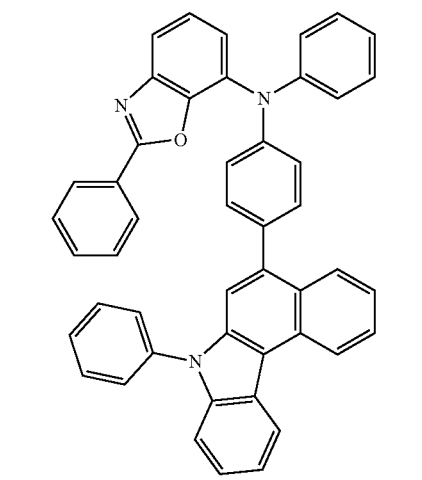
290
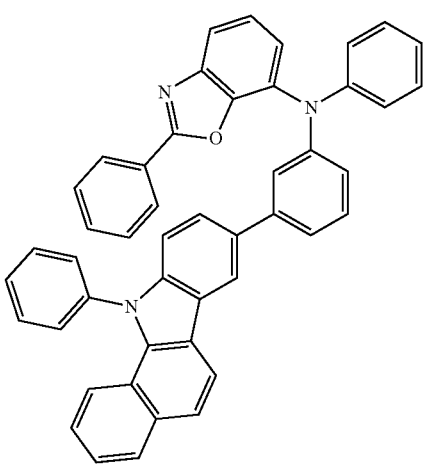
452
-continued
291
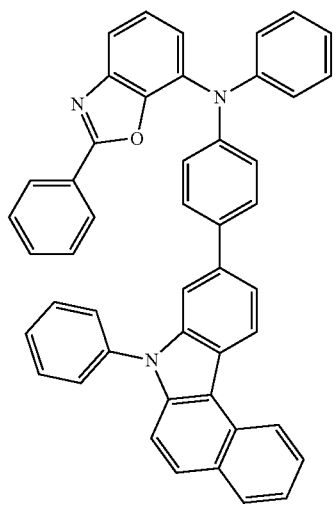
292
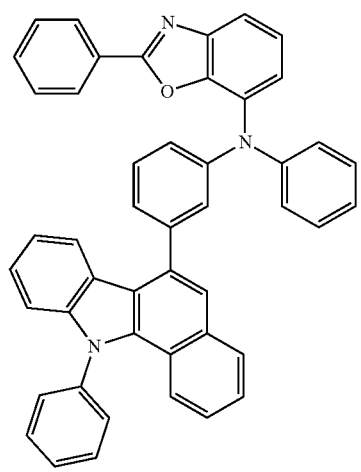
293
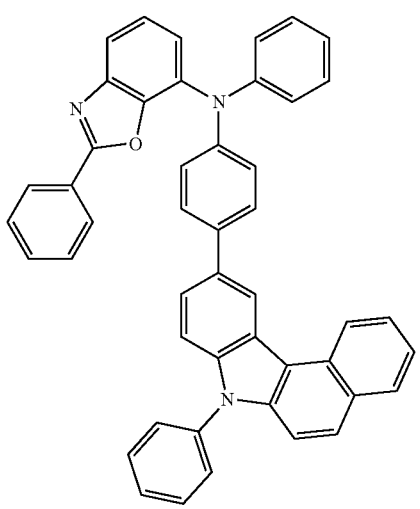

| 453 -continued | 454 -continued |
|---|---|
| 294 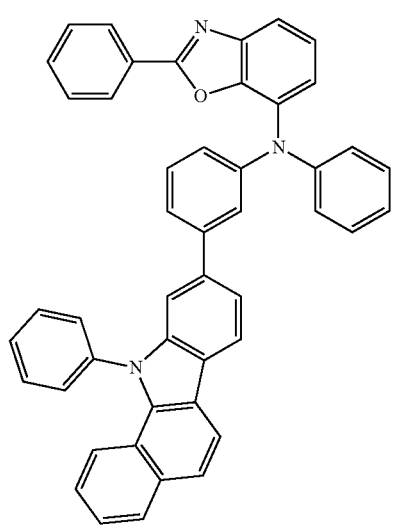 | 297 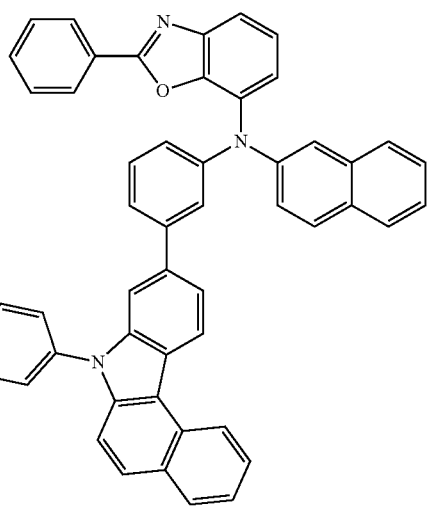 |
| 295 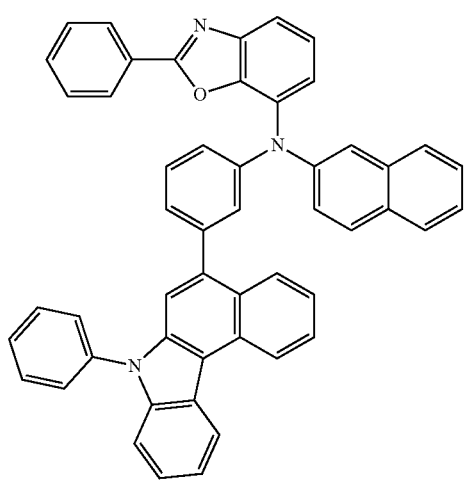 [SMILES: c1ccc(-c2nc3cccc(N(c4cccc(-c5cc6c(c7ccccc57)c5ccccc5n6-c5ccccc5)c4)c4ccc5ccccc5c4)c3o2)cc1] | 298 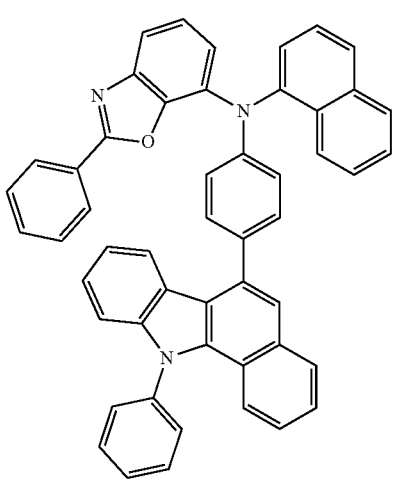 |
| 296 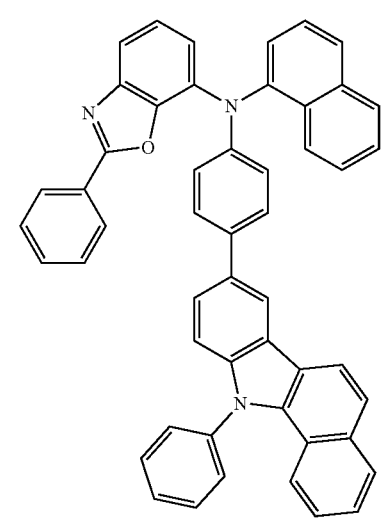 | 299 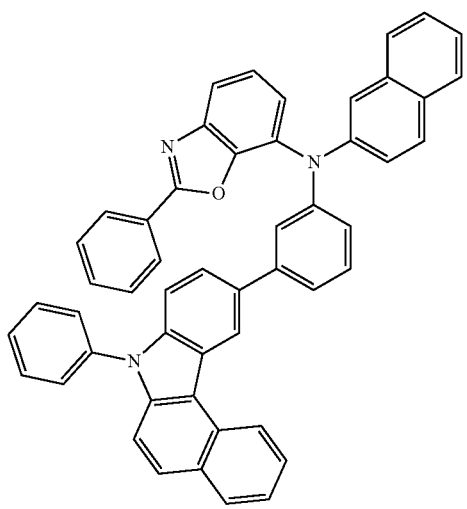 |

300
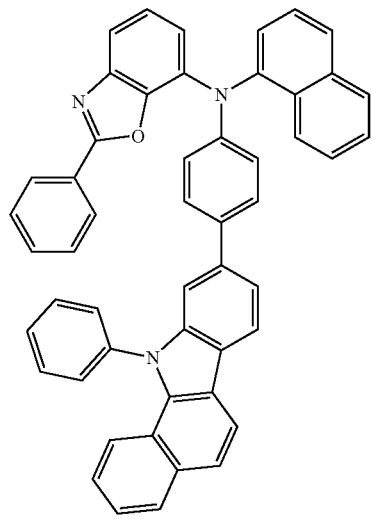
301
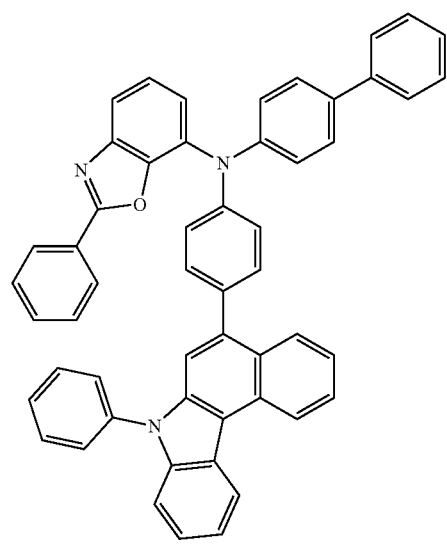
302
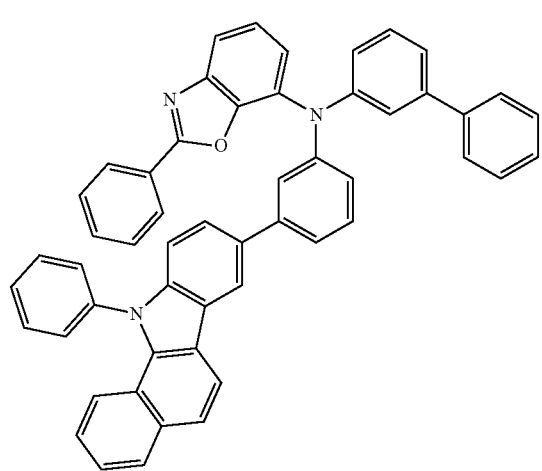
303
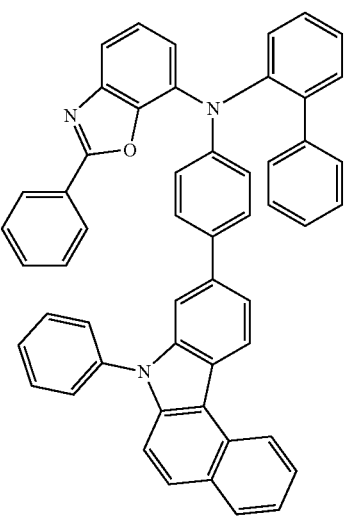
304
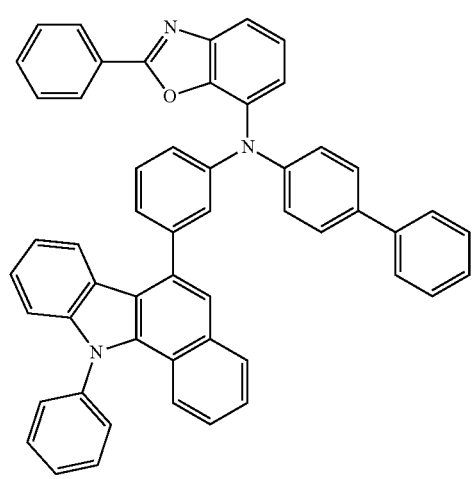
305
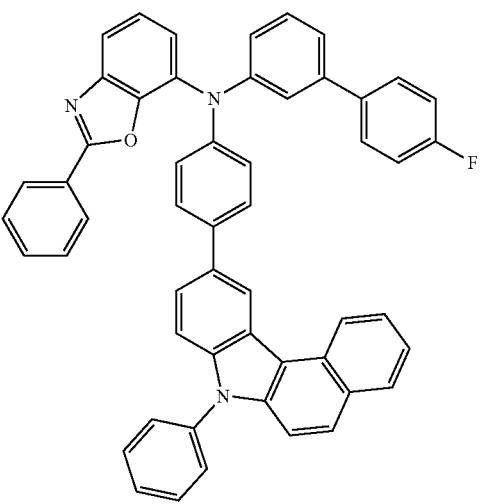 [SMILES: Fc1ccc(-c2cccc(N(c3ccc(-c4ccc5c(c4)c4c6ccccc6ccc4n5-c4ccccc4)cc3)c3cccc4nc(-c5ccccc5)oc34)c2)cc1]

-continued
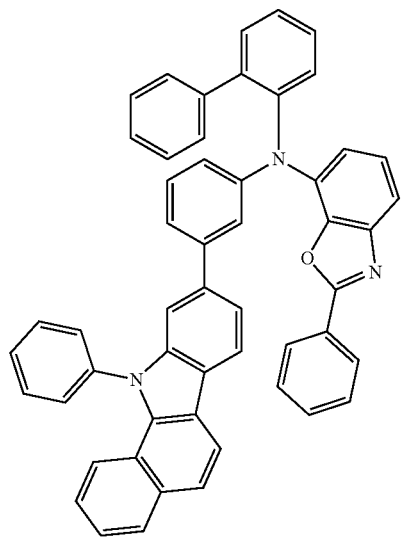
306
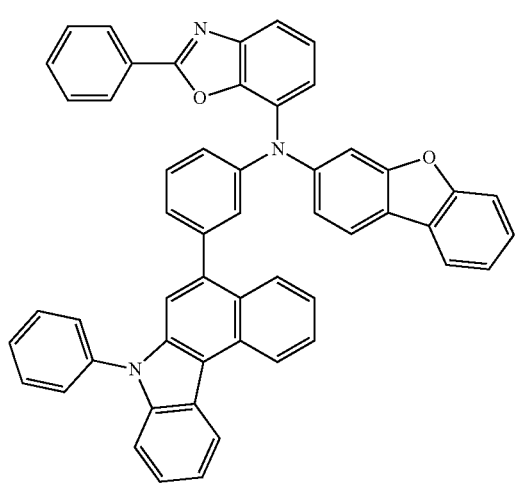
307
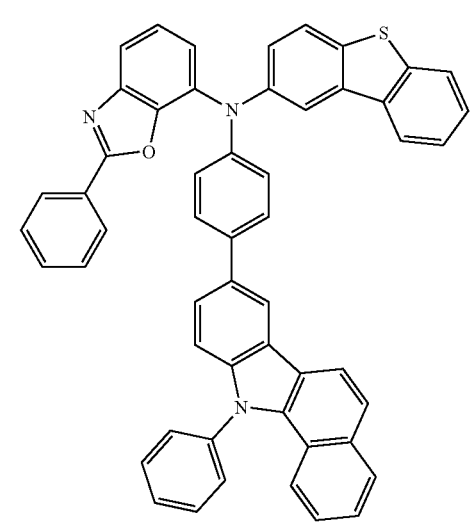
308
-continued
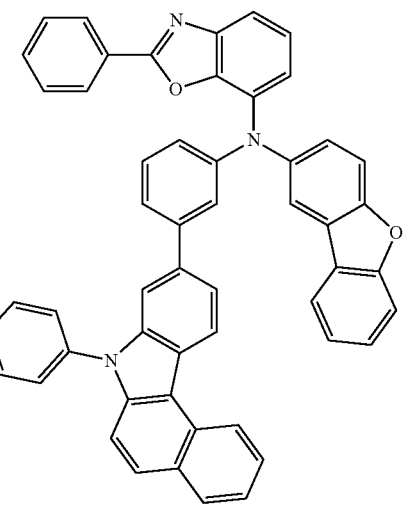
309
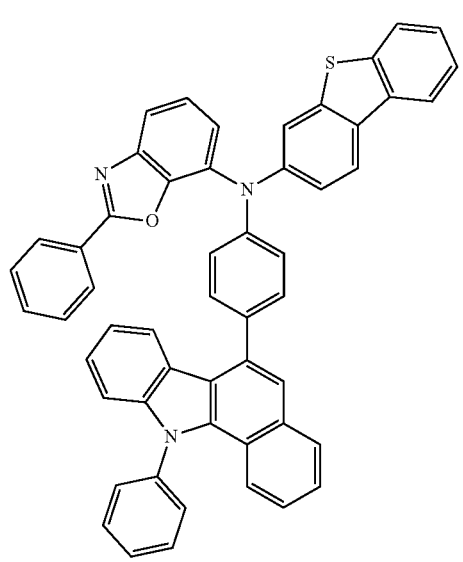
310
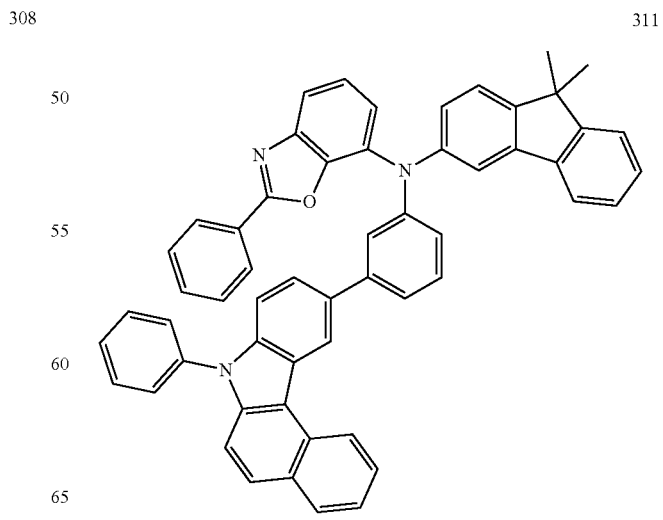
311

459
-continued
460
-continued
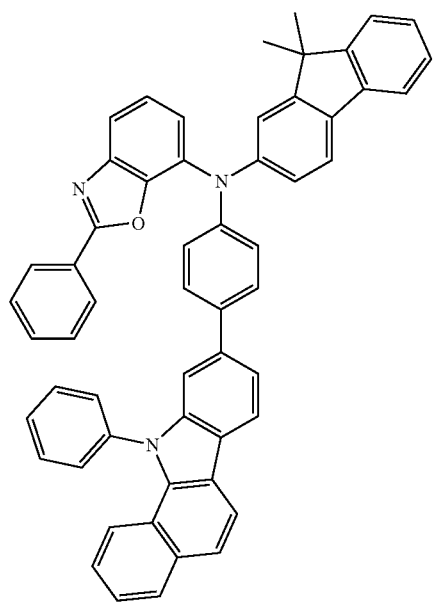
312
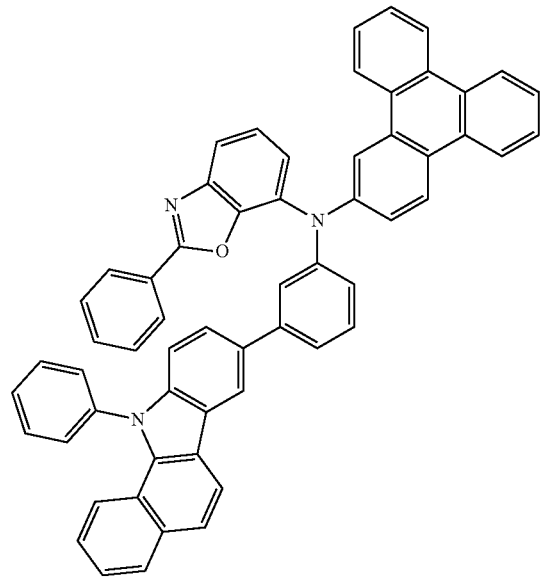
314
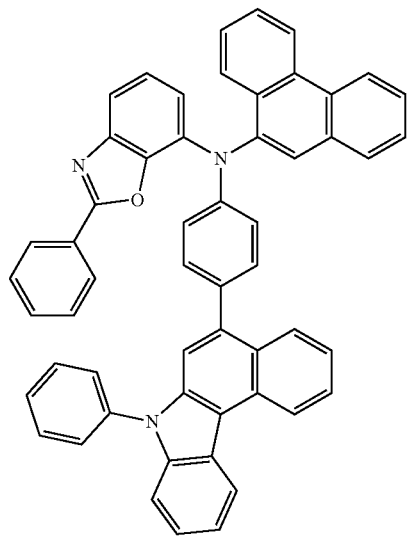
313
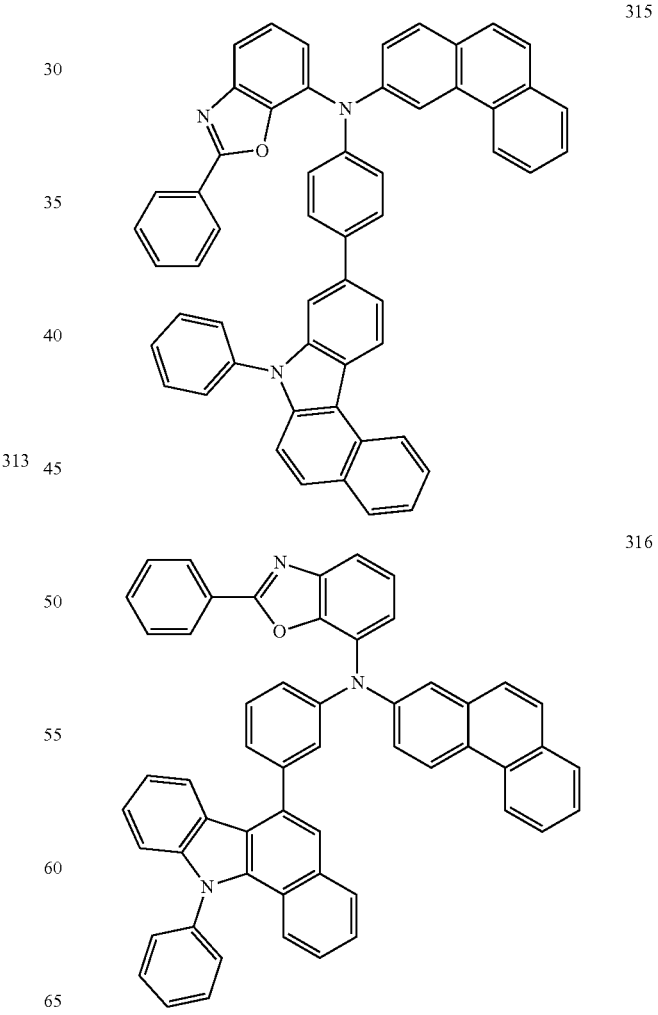
315
316

461
-continued
317
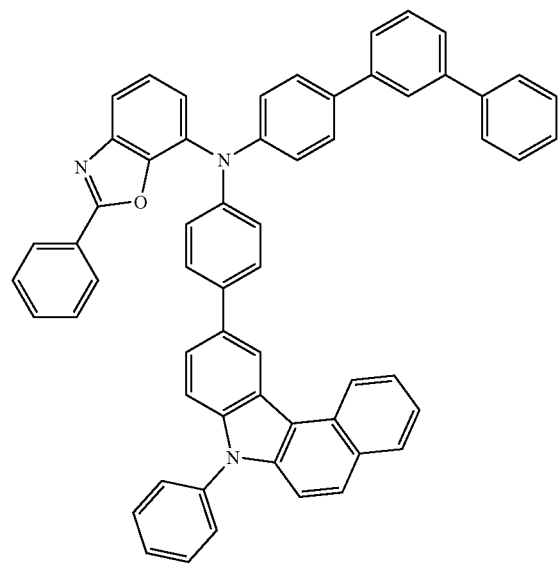
318
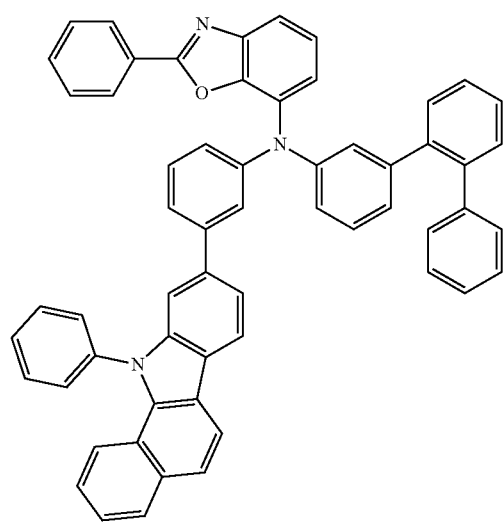
319
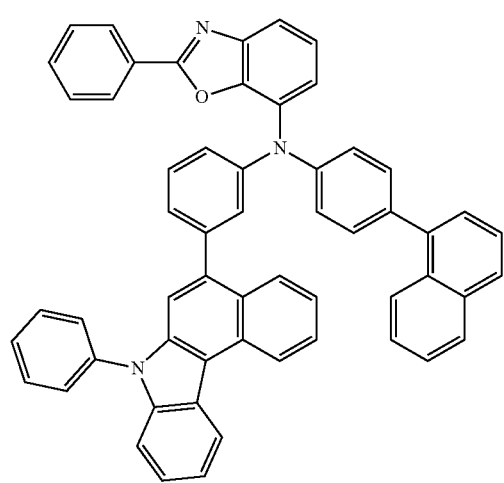
462
-continued
320
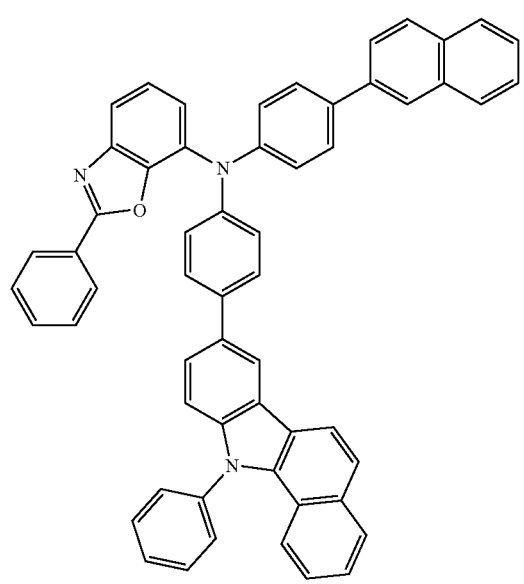
321
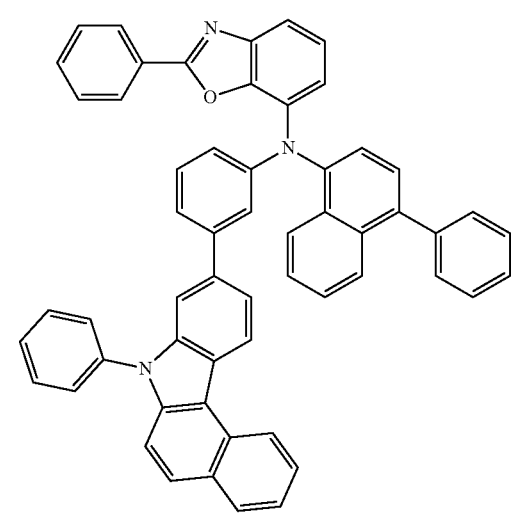
322
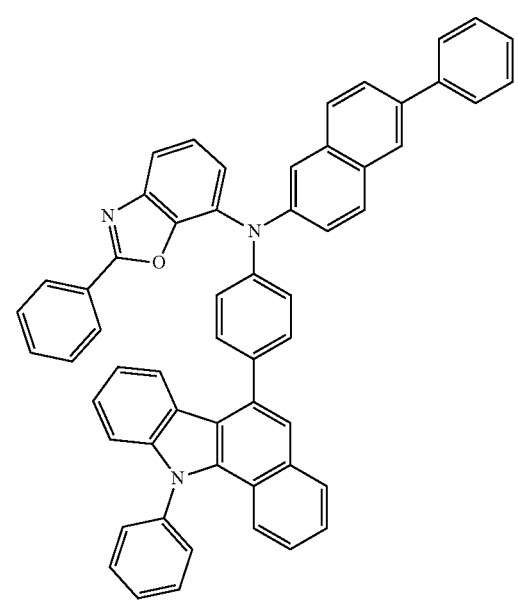

463
-continued
323
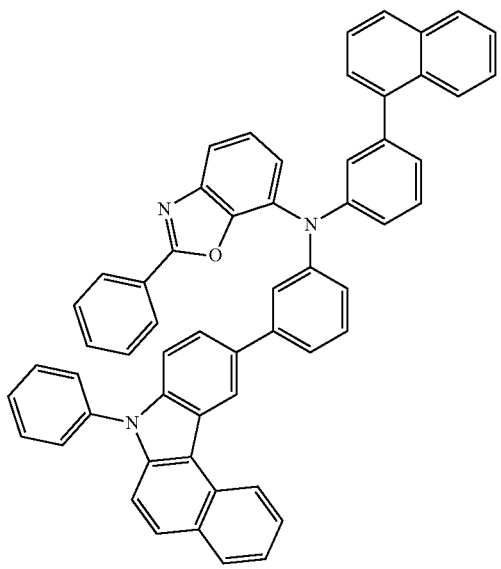
324
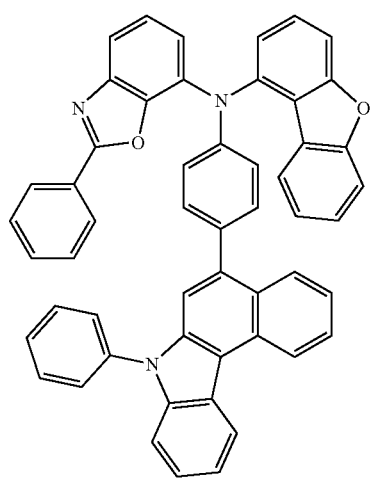
325
464
-continued
326
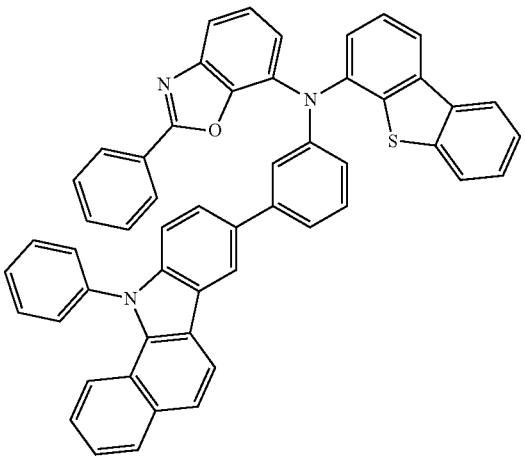 [SMILES: c1ccc(-c2nc3cccc(N(c4cccc(-c5ccc6c(c5)c5ccc7ccccc7c5n6-c5ccccc5)c4)c4cccc5c4sc4ccccc45)c3o2)cc1]
327
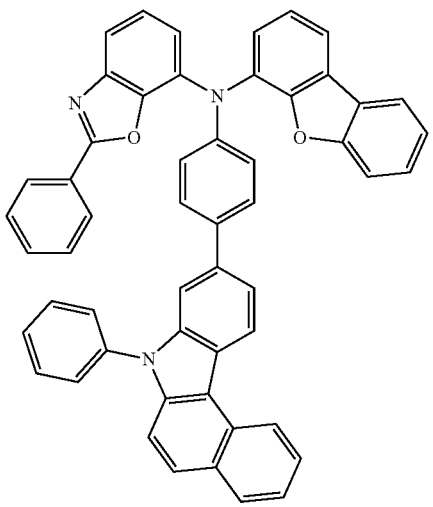
328
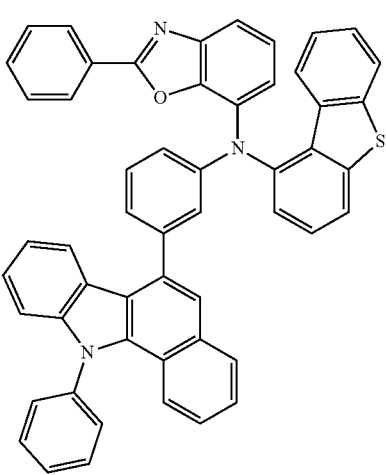

465
-continued
329
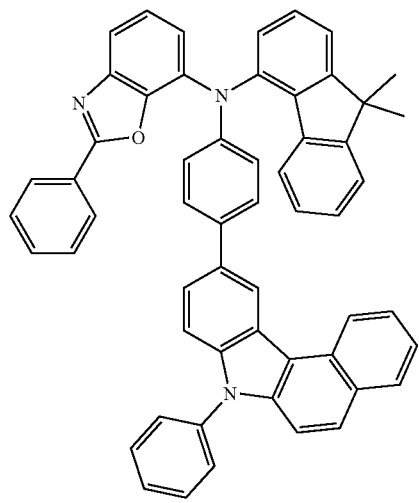
330
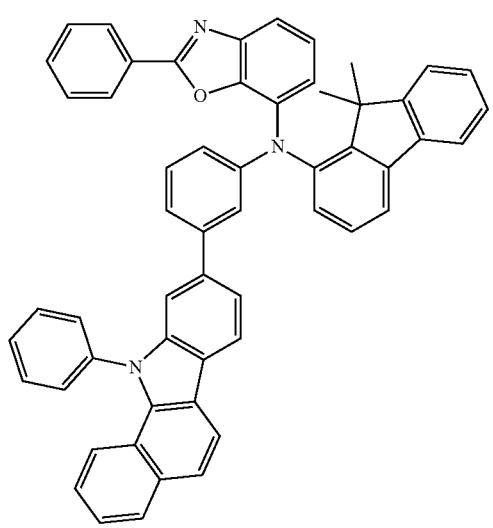
331
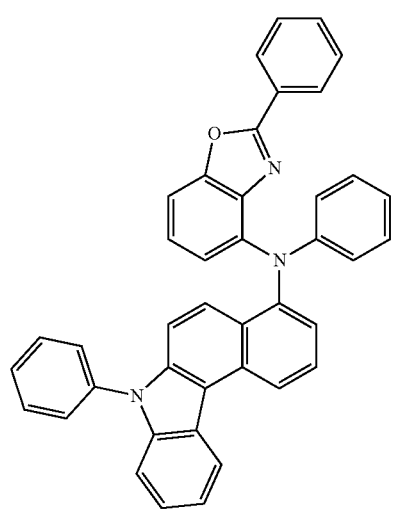
466
-continued
332
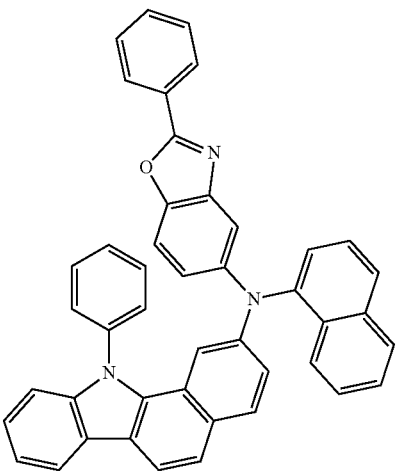
333
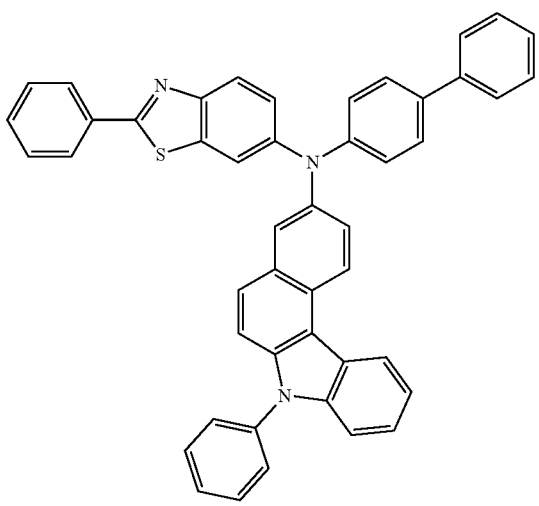 [SMILES: c1ccc(-c2ccc(N(c3ccc4c(ccc5c4c4ccccc4n5-c4ccccc4)c3)c3ccc4nc(-c5ccccc5)sc4c3)cc2)cc1]
334

467
-continued
335
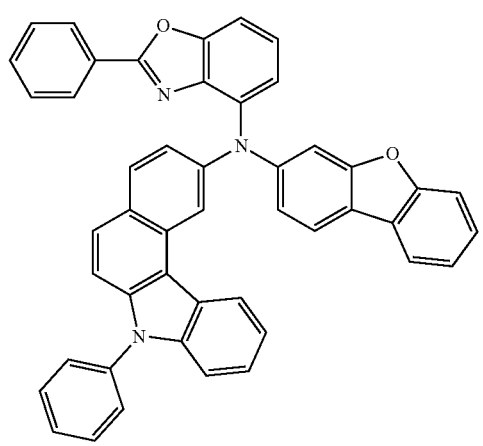 [SMILES: c1ccc(-c2nc3c(N(c4ccc5c(c4)oc4ccccc45)c4ccc5ccc6c(c5c4)c4ccccc4n6-c4ccccc4)cccc3o2)cc1]
336
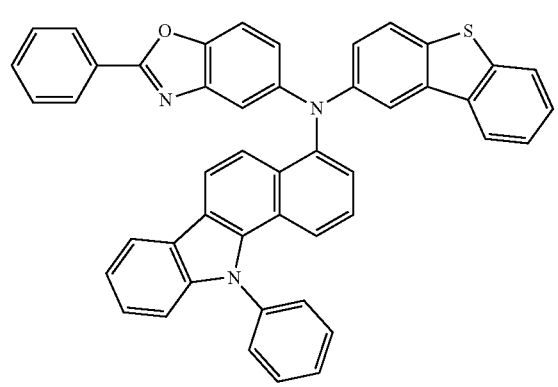
337
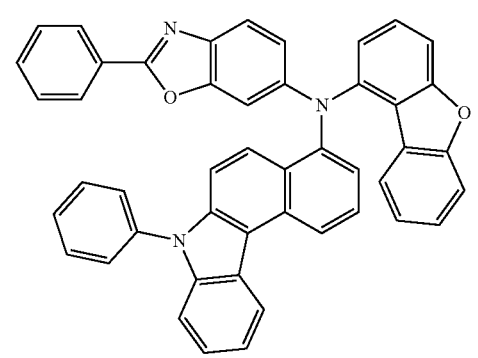
338
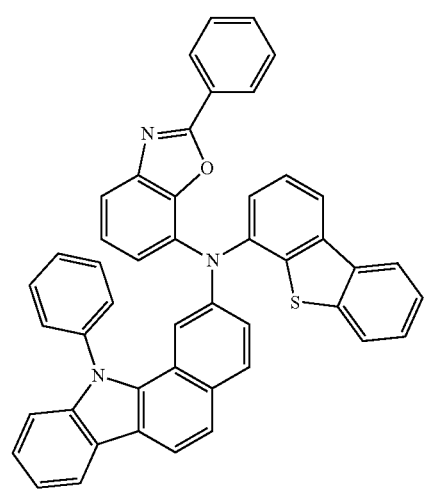
468
-continued
339
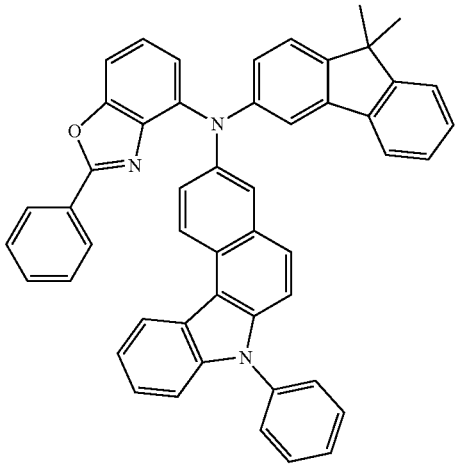
340
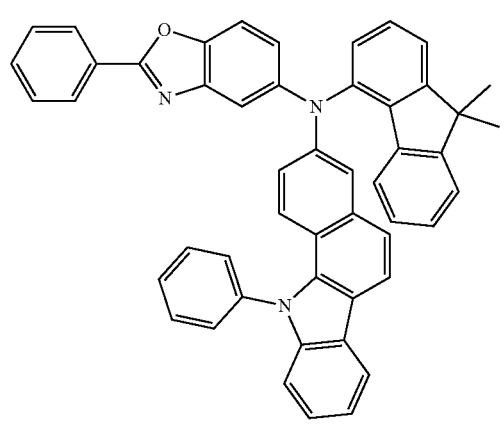
341
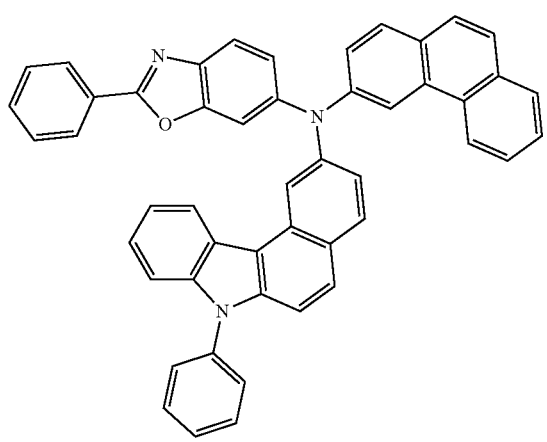

469
-continued
342
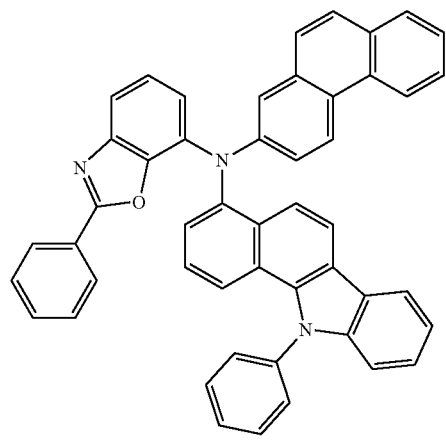
343
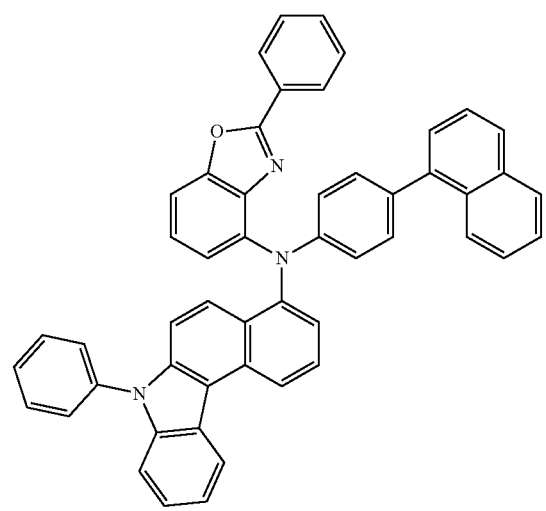 [SMILES: c1ccc(-c2nc3c(N(c4ccc(-c5cccc6ccccc56)cc4)c4cccc5c4ccc4c5c5ccccc5n4-c4ccccc4)cccc3o2)cc1]
344
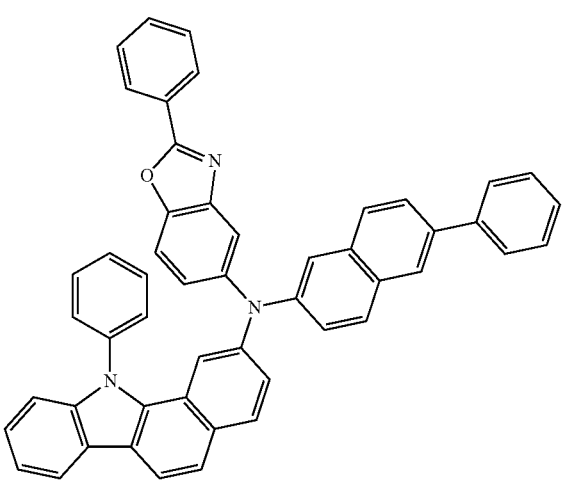
470
-continued
345
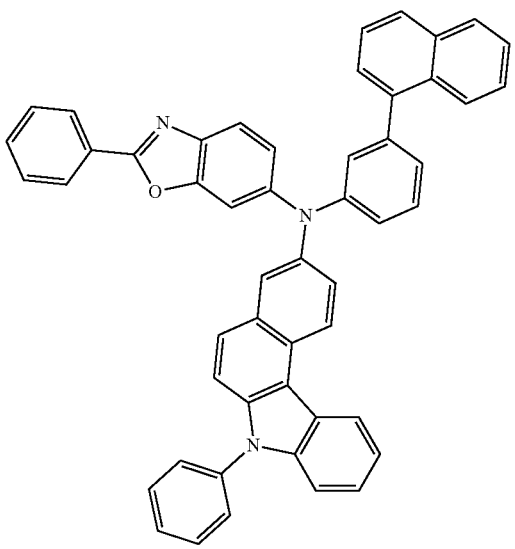
346
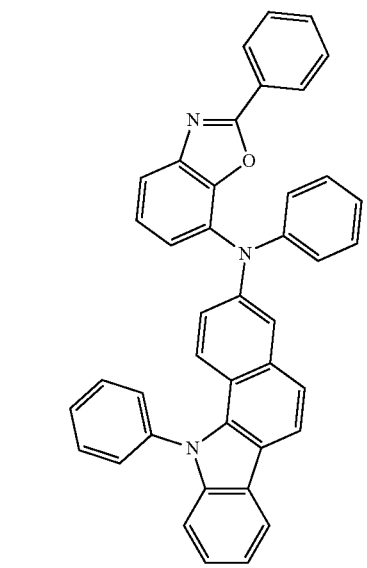
347
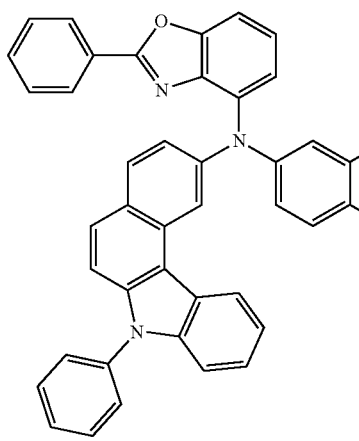

471
-continued
348
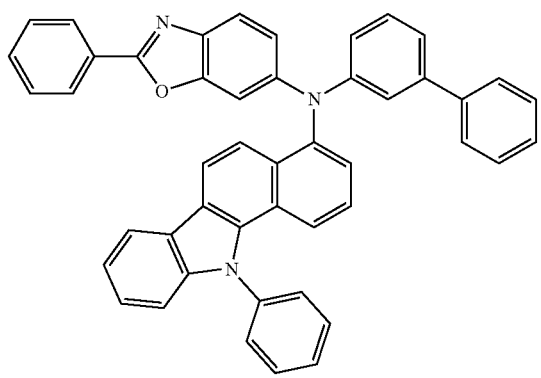
349
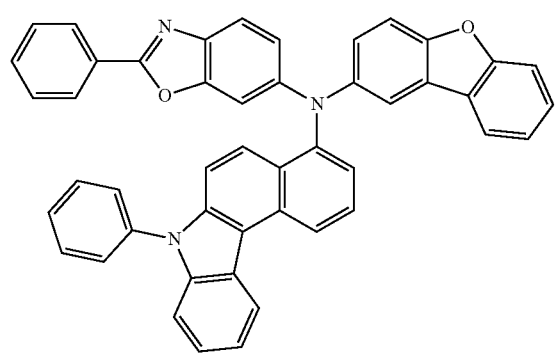
350
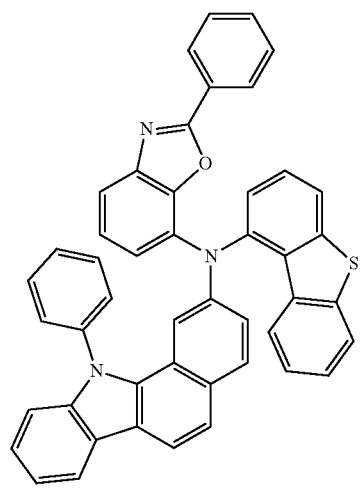
472
-continued
351
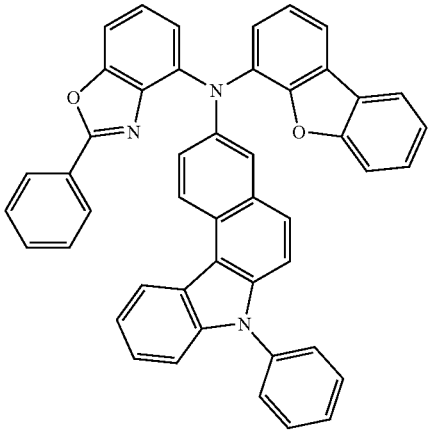
352
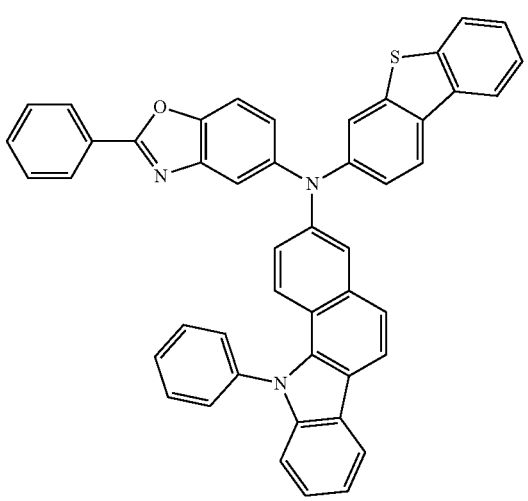
353
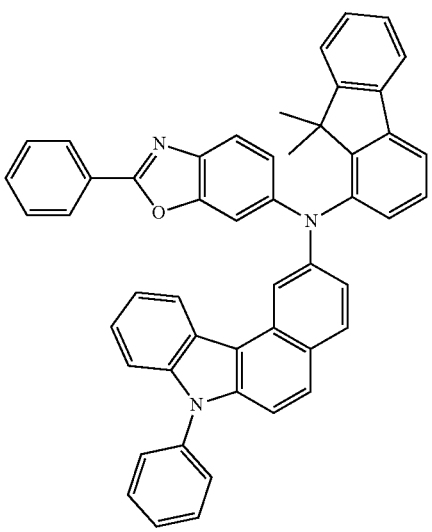

354
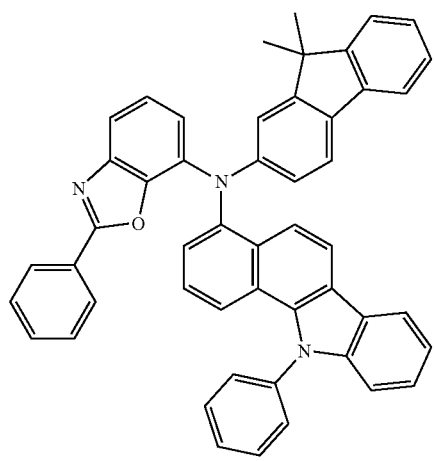
355
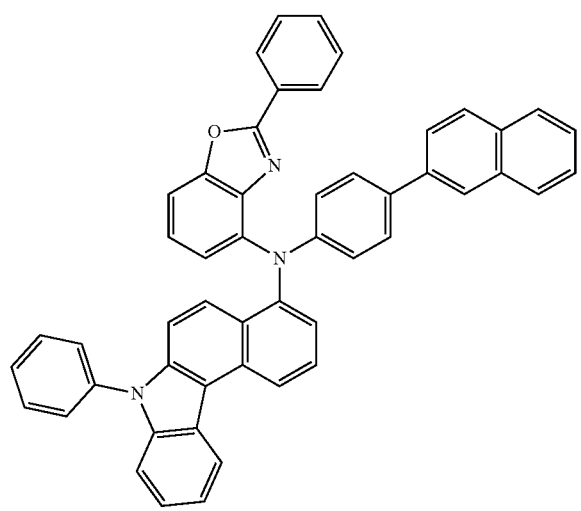
356
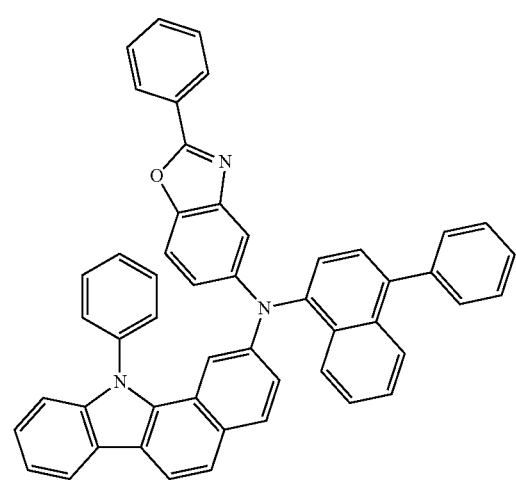
357
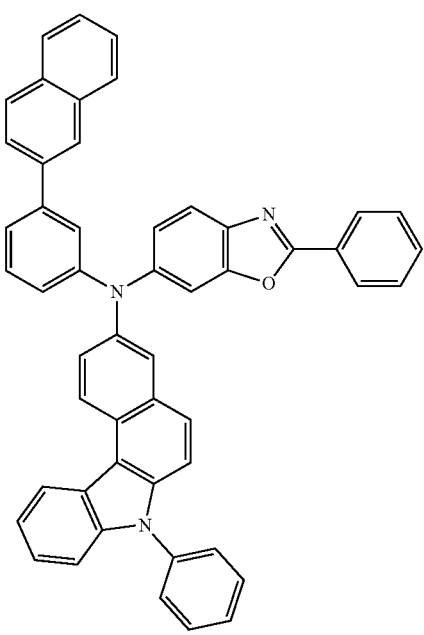
358
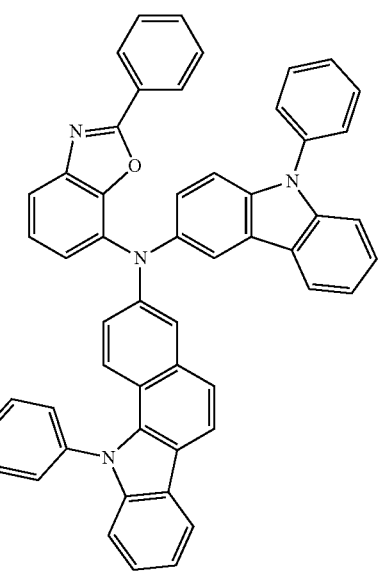
359
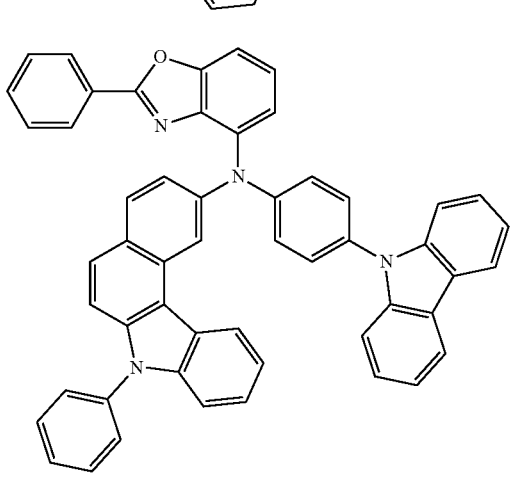

475
-continued
360
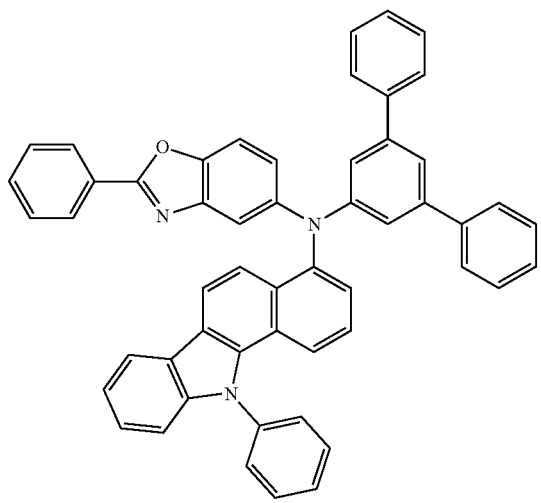
361
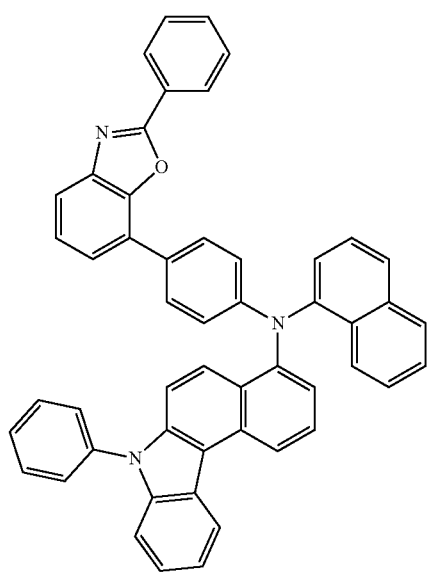
362
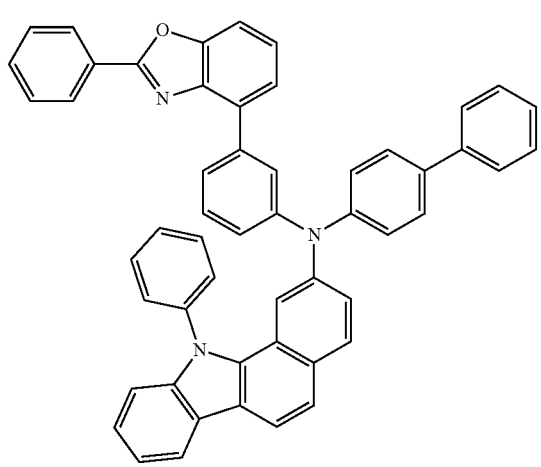
476
-continued
363
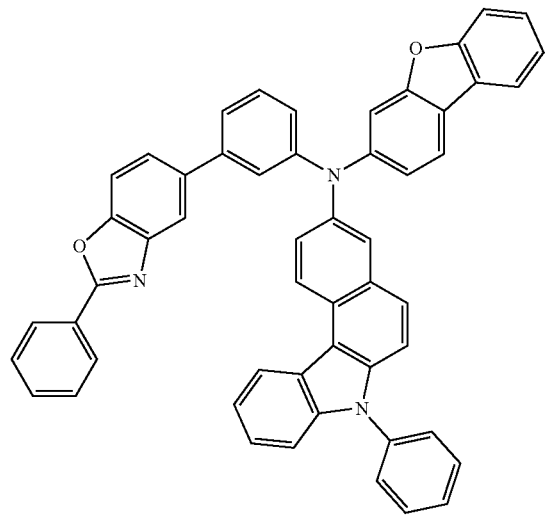
364
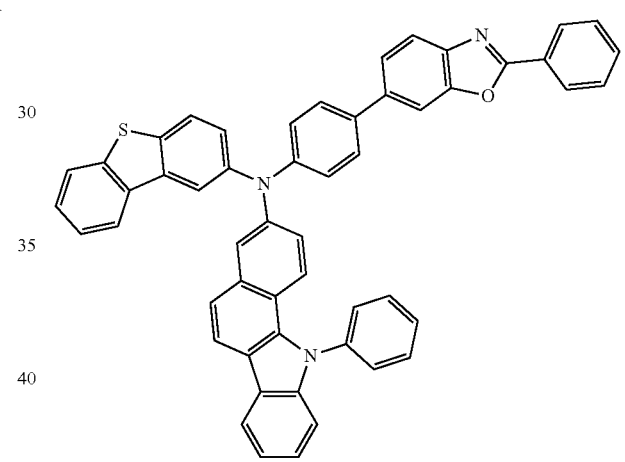
365
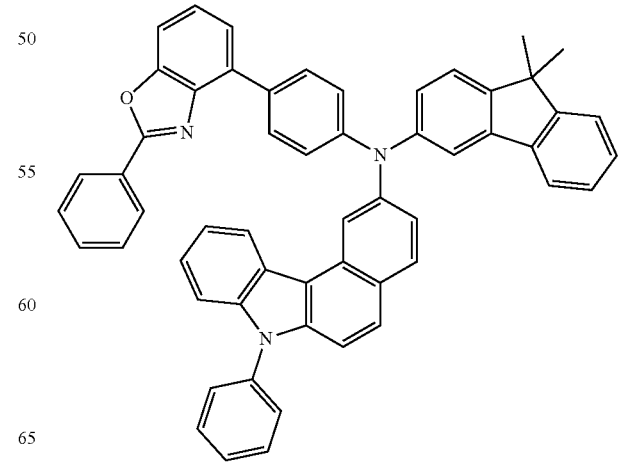

477 478
-continued -continued
366
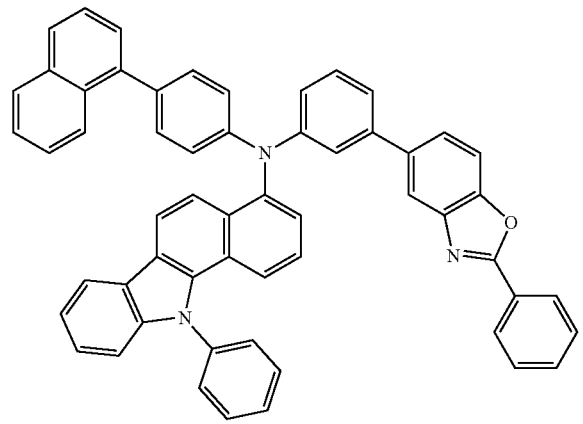
369
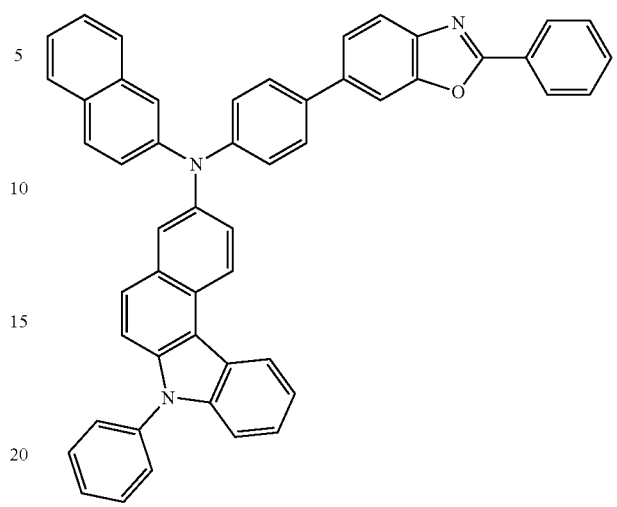
367
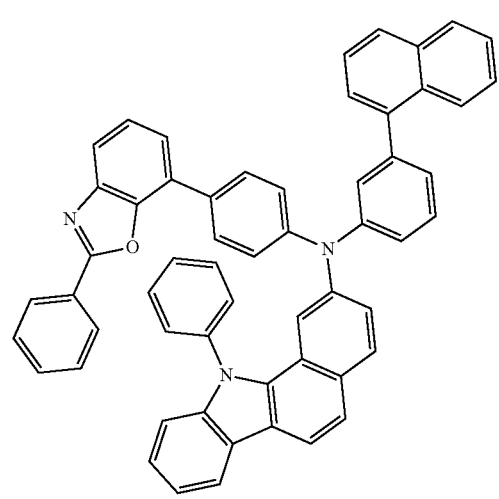
370
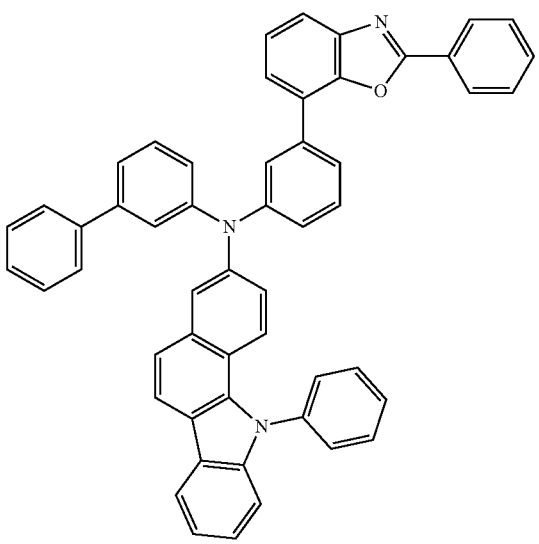
368
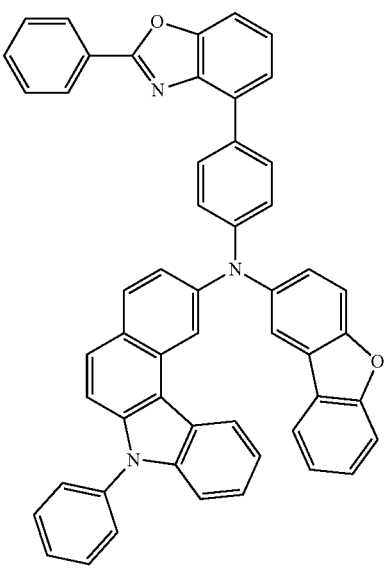
370

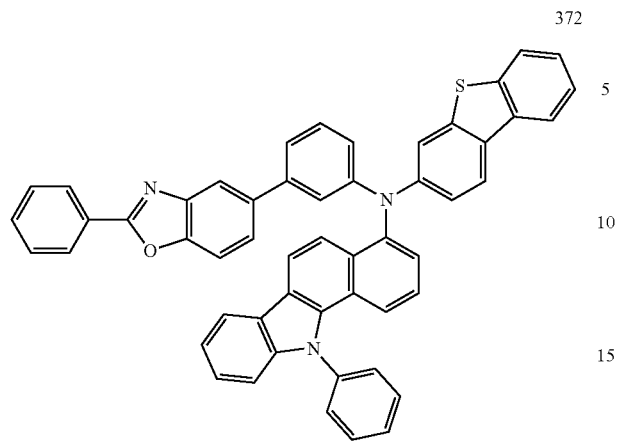
372
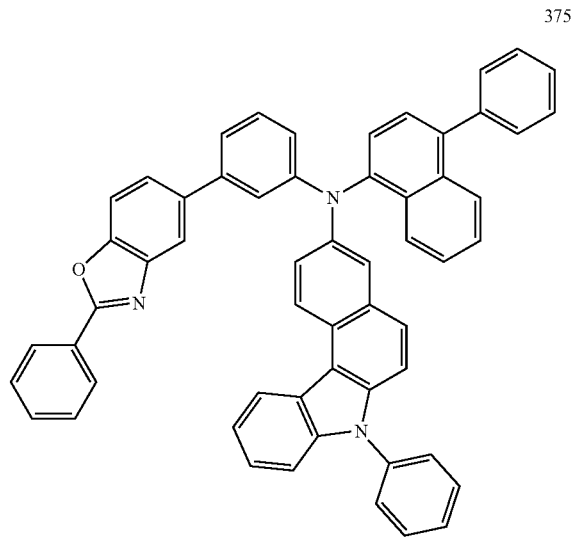
375
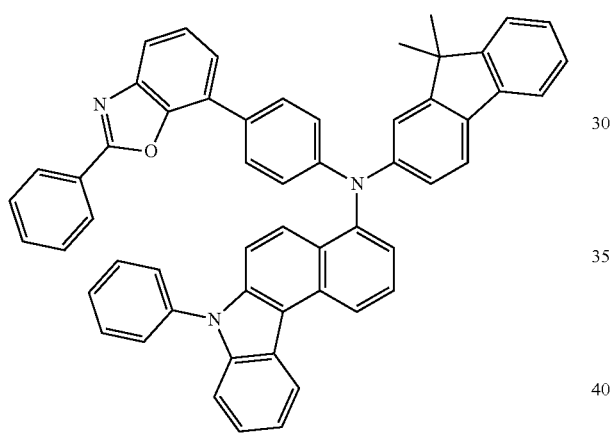
373
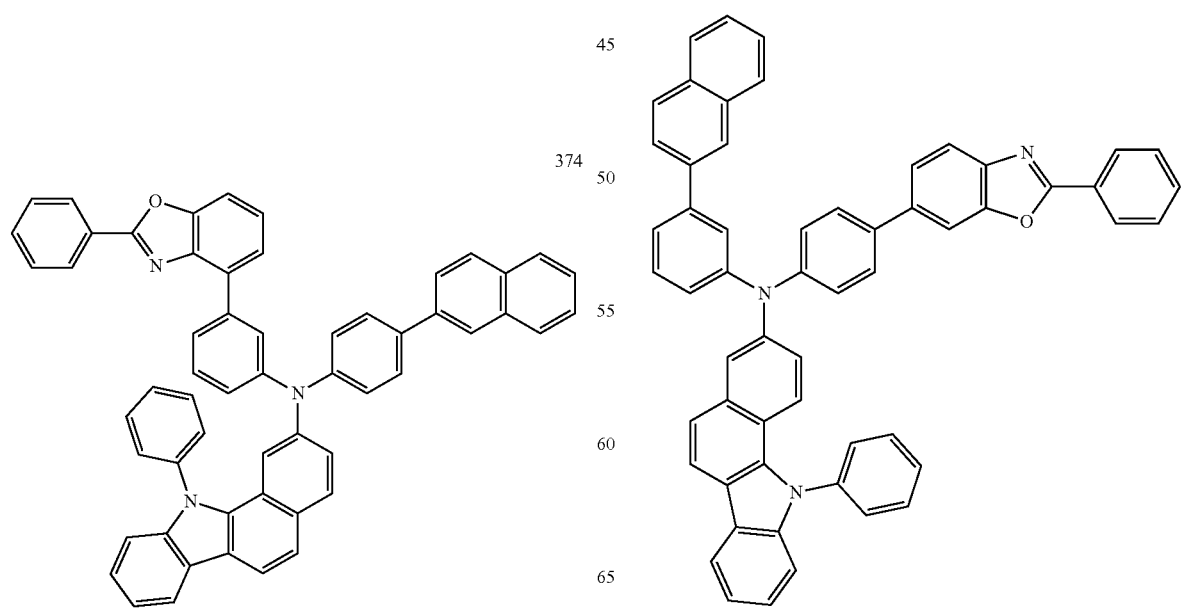

481 -continued
377
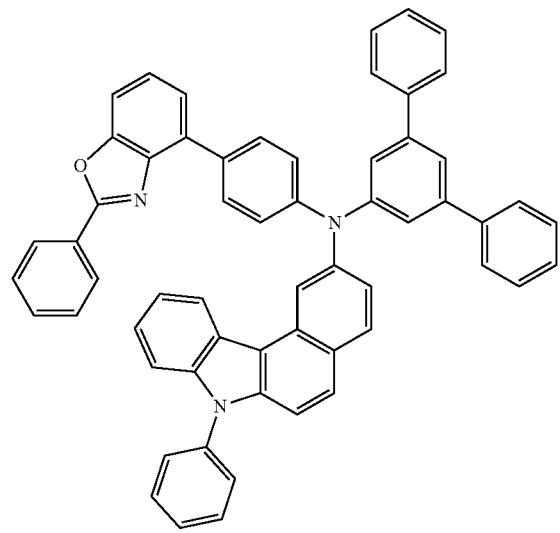
378
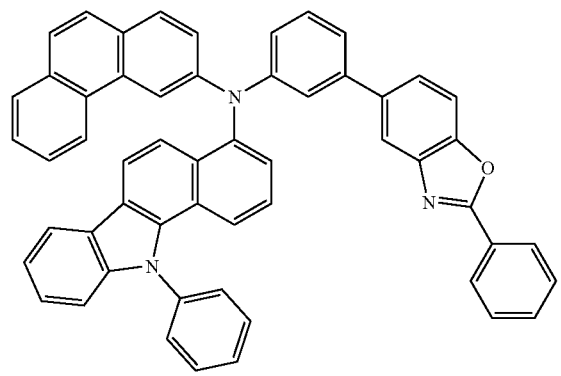
379
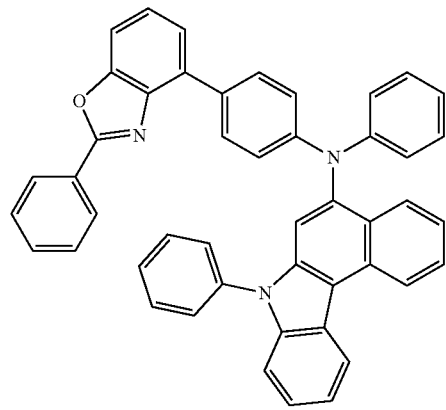
482 -continued
380
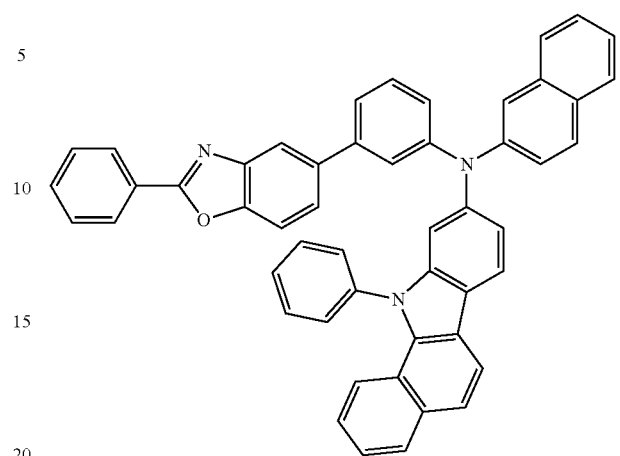
381
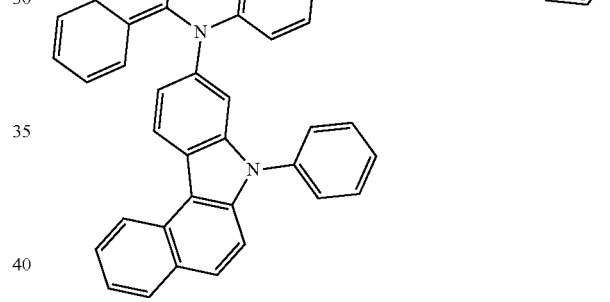
382
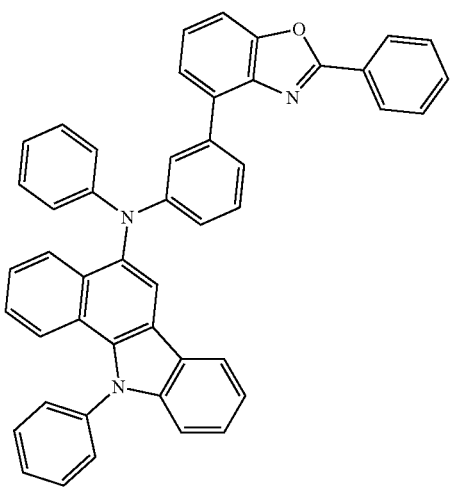

483
-continued
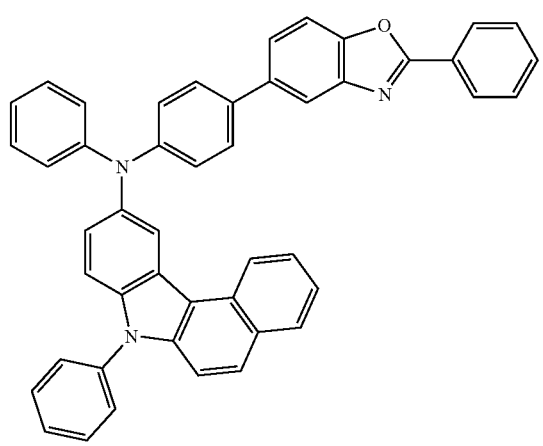
383
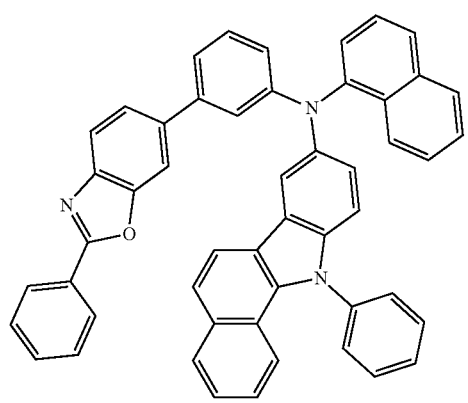
384
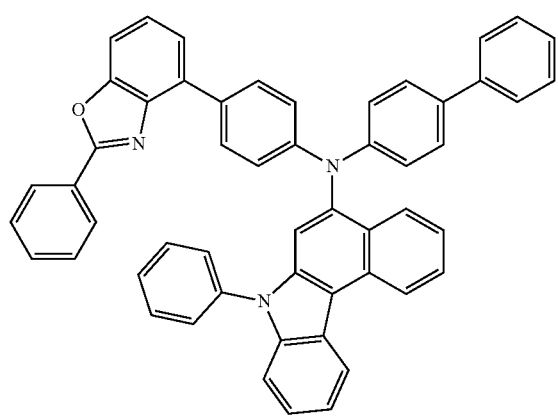
385
484
-continued
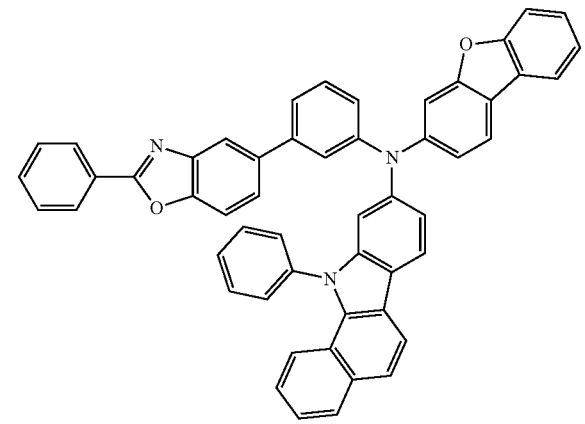
386
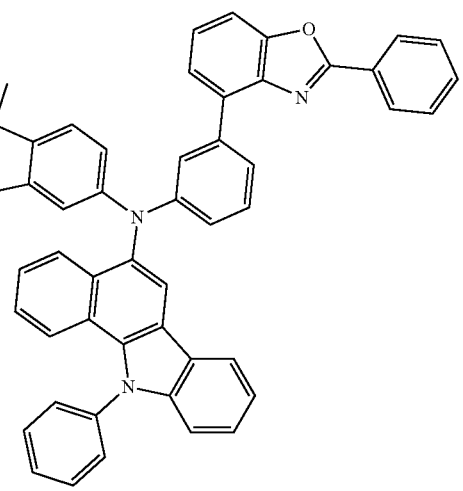
387
388

485
-continued
389
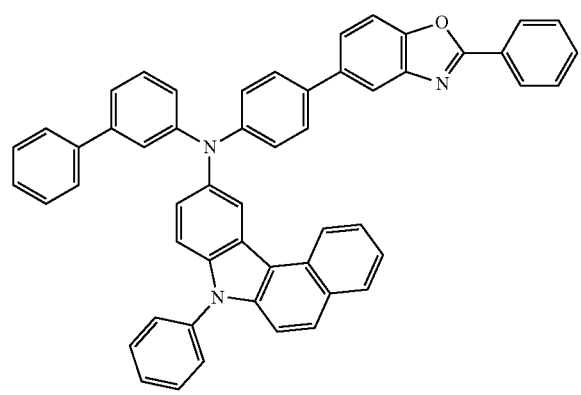
390
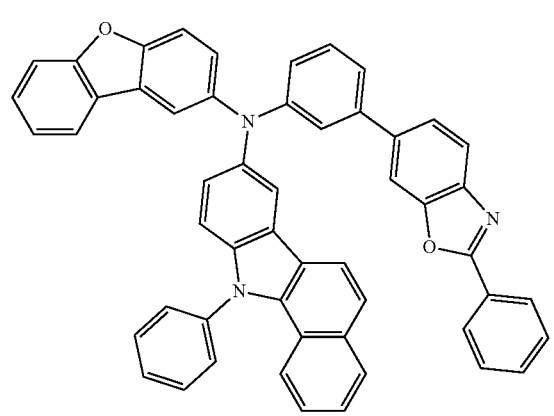
391
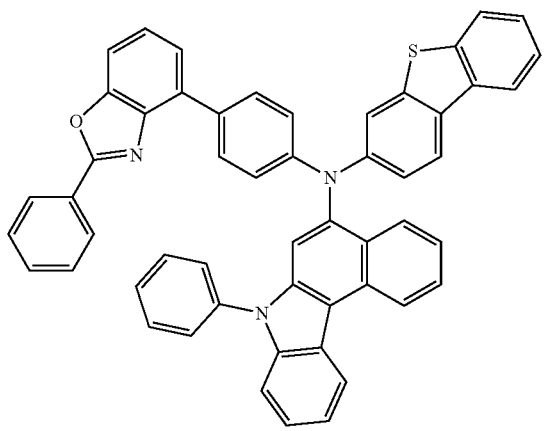
486
-continued
392
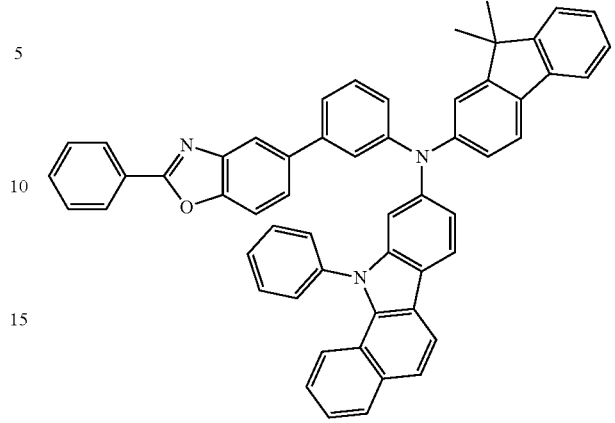
393
394
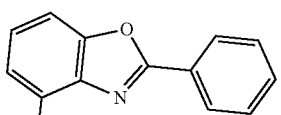

487
-continued
395
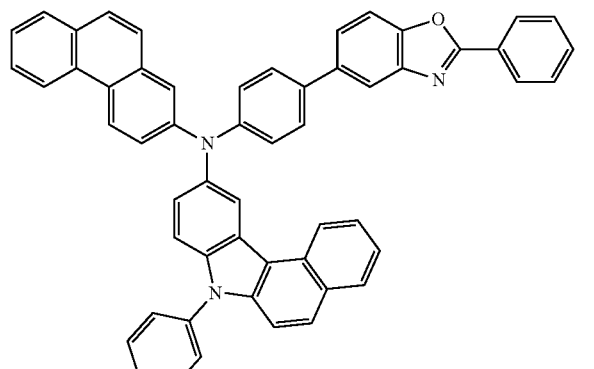
396
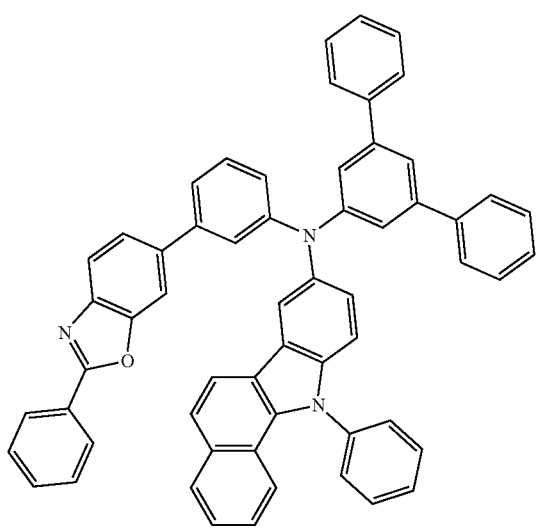
397
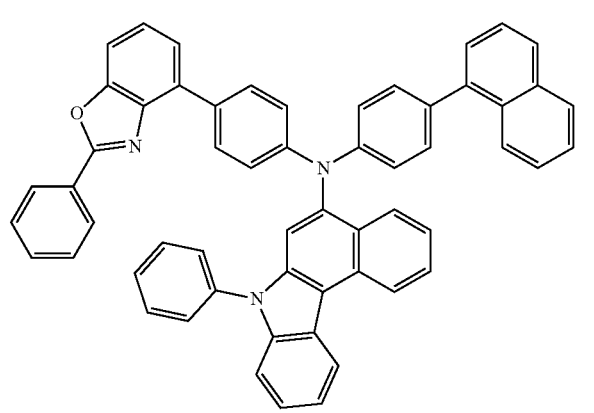
488
-continued
398
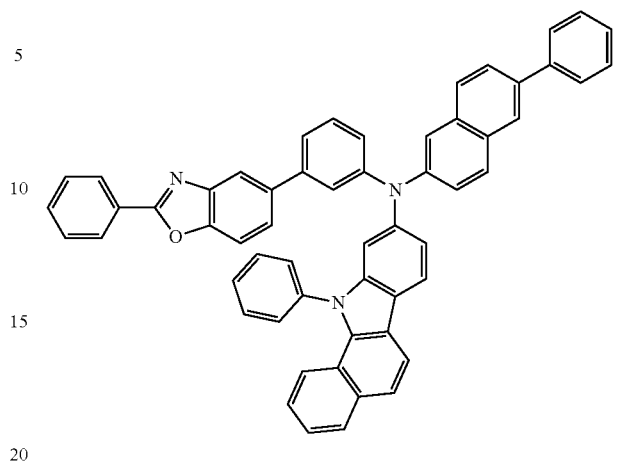
399
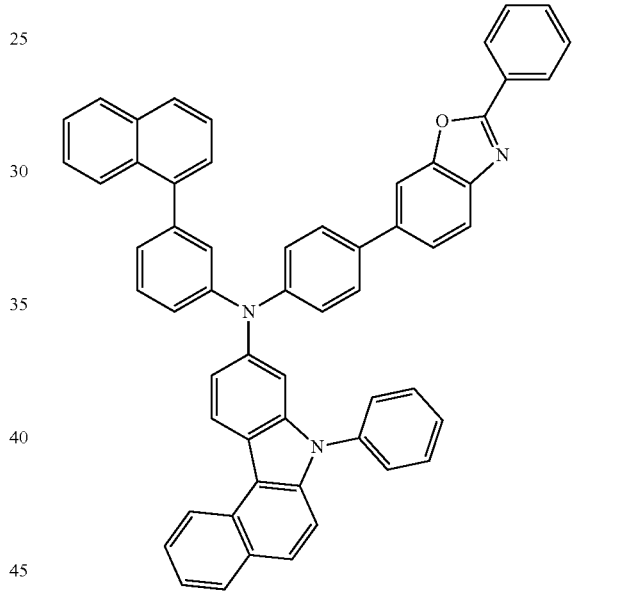
400
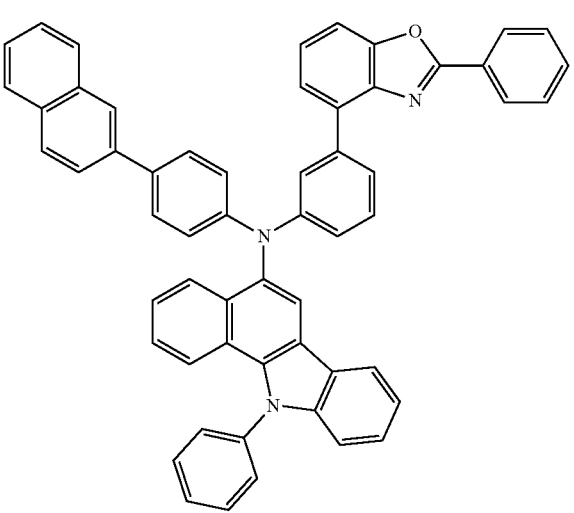

489
-continued
401
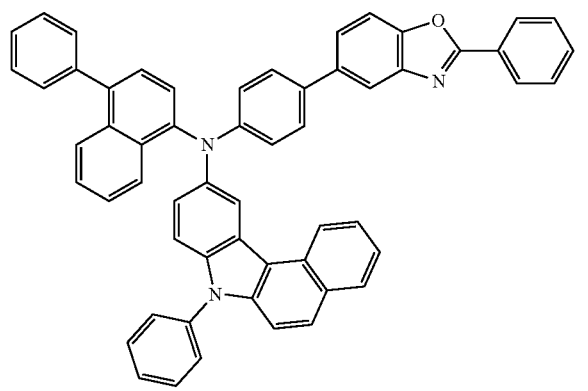
402
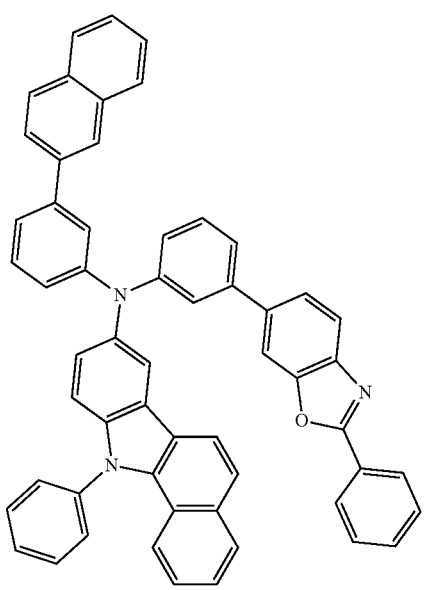
403
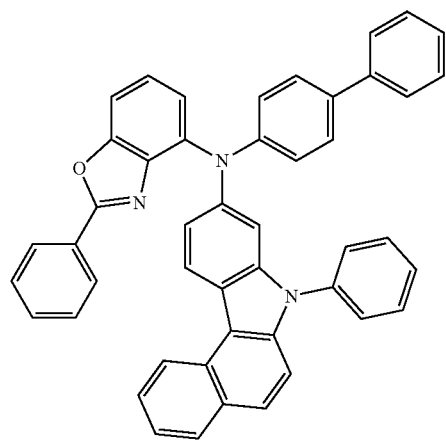 [SMILES: c1ccc(-c2ccc(N(c3ccc4c5c6ccccc6ccc5n(-c5ccccc5)c4c3)c3cccc4oc(-c5ccccc5)nc34)cc2)cc1]
490
-continued
404
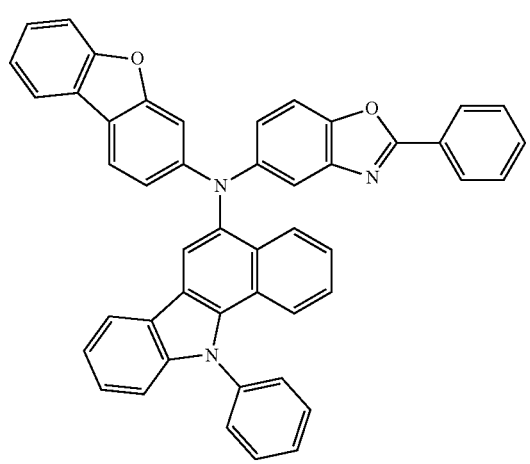
405
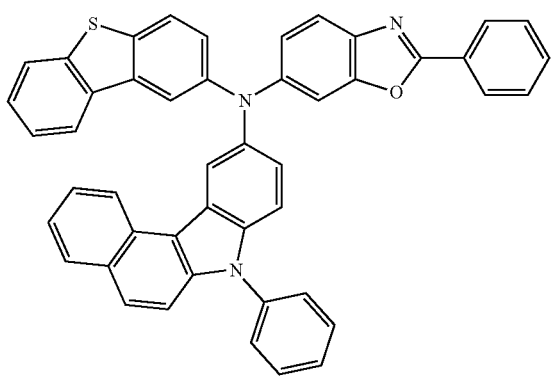
406
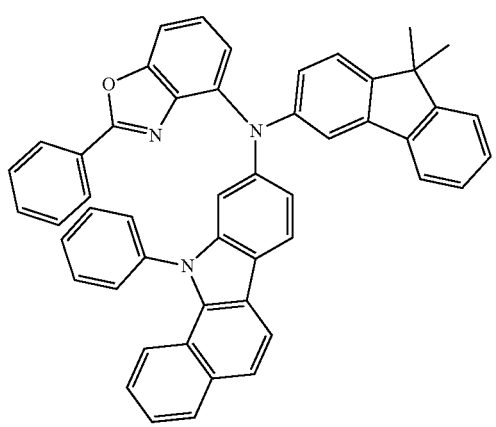

491
-continued
407
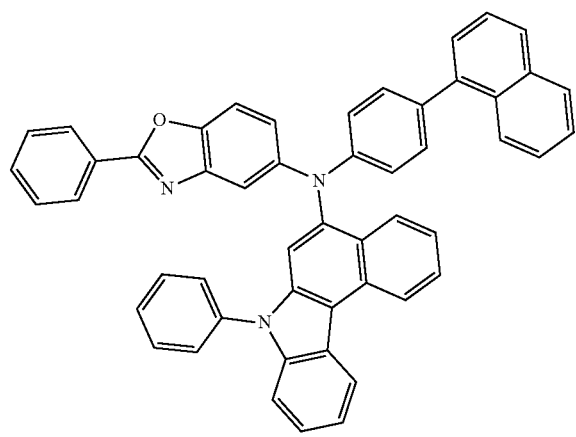
408
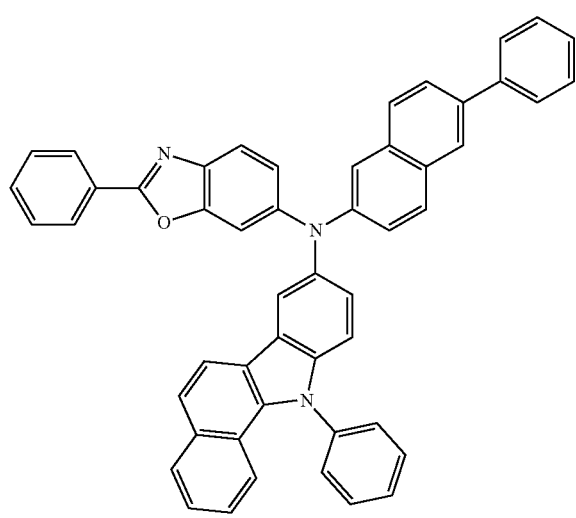
409
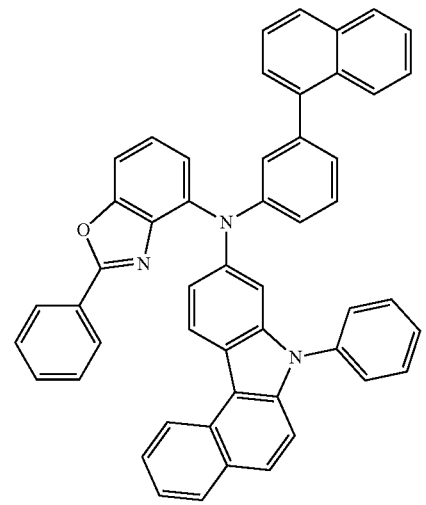
492
-continued
410
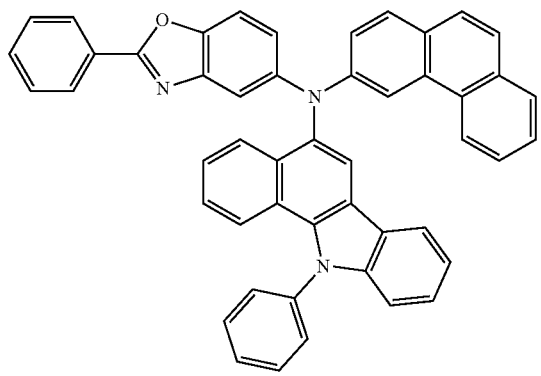
411
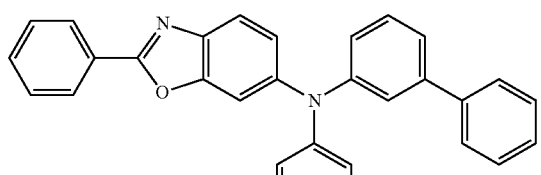
412
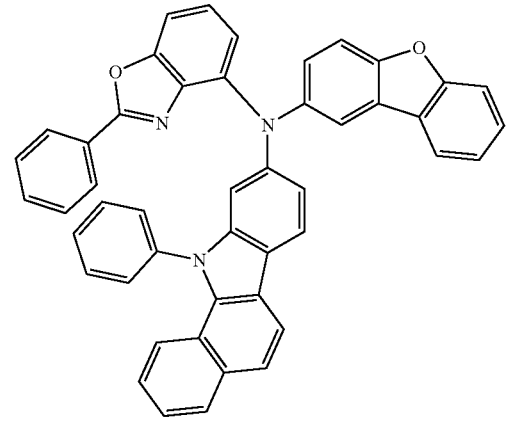
413
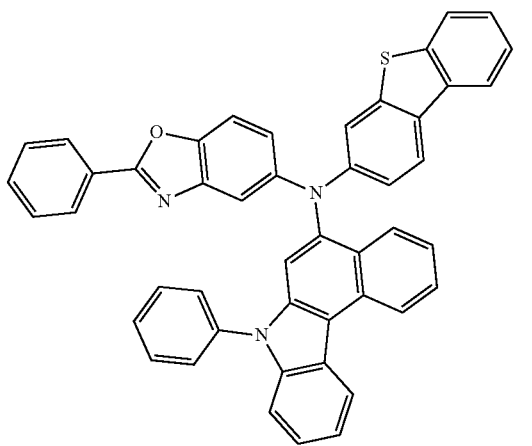

-continued
414
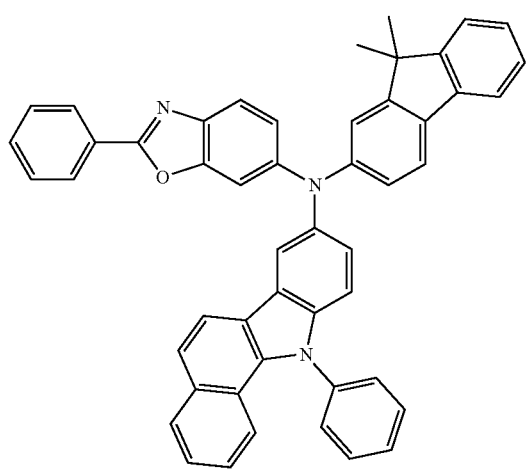 [SMILES: CC1(C)c2ccccc2-c2ccc(N(c3ccc4nc(-c5ccccc5)oc4c3)c3ccc4c(c3)c3ccc5ccccc5c3n4-c3ccccc3)cc21]
415
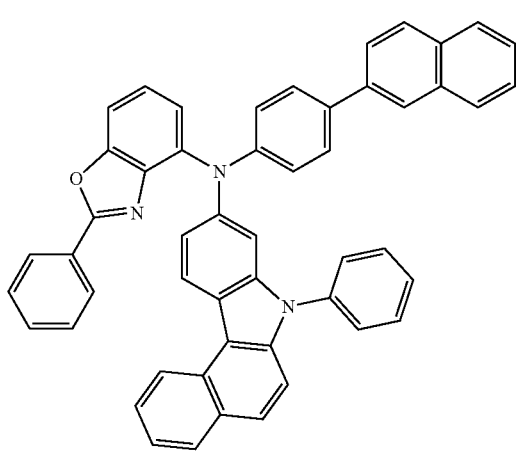
416
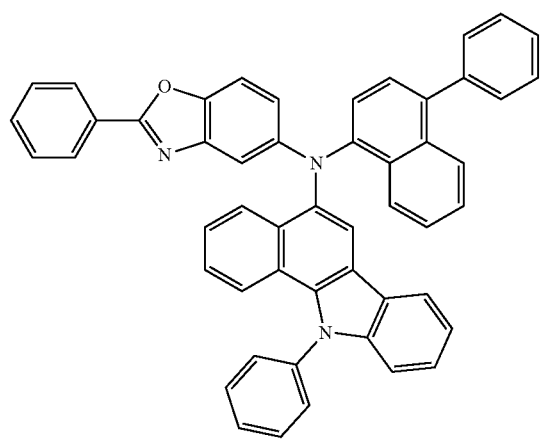
-continued
417
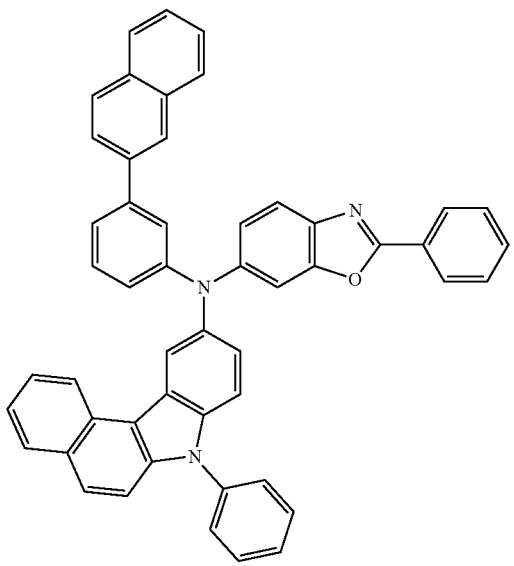
418
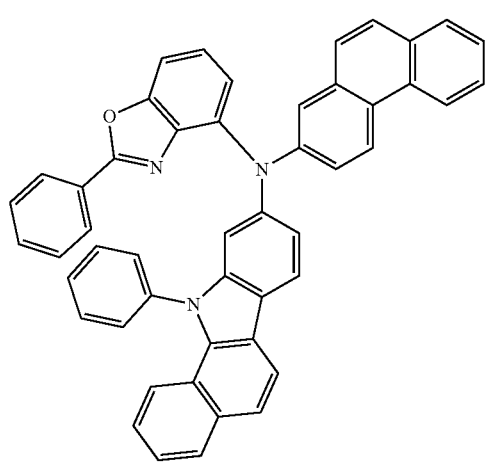
419
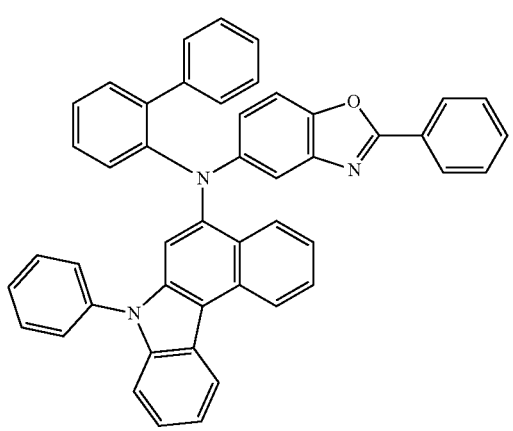

| 495 | 496 |
|---|---|
| -continued | -continued |
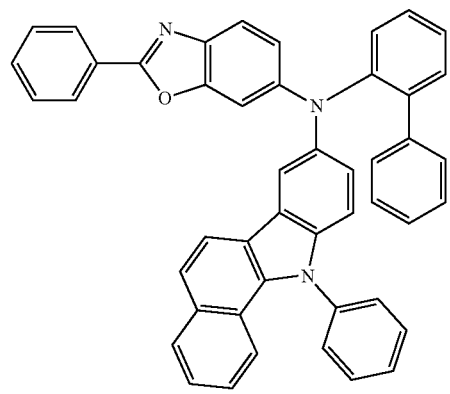
420
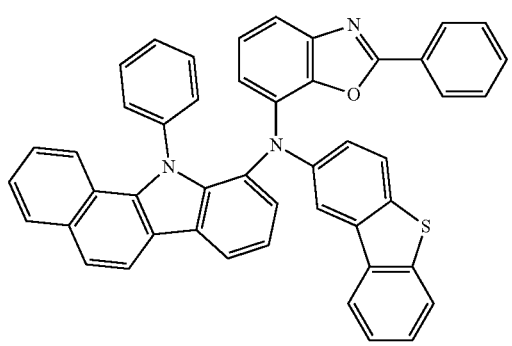
424
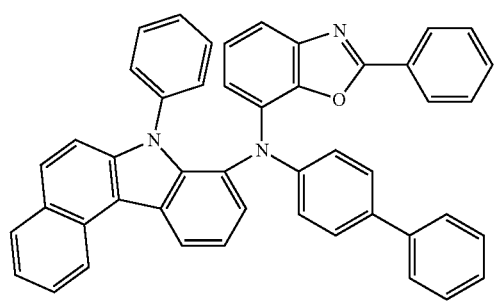
421
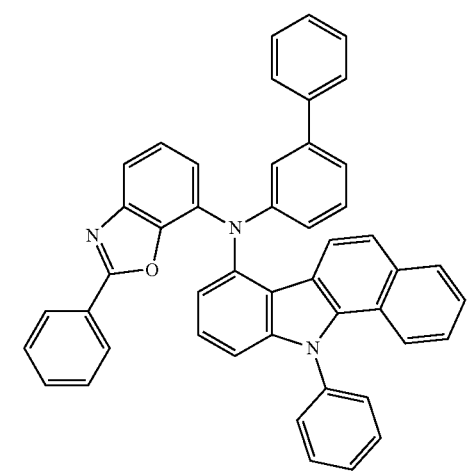
422
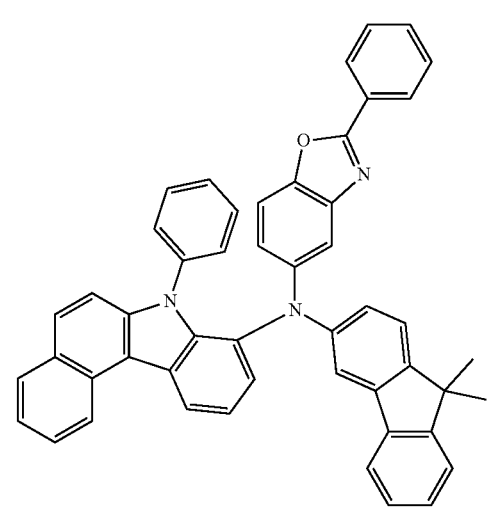
425
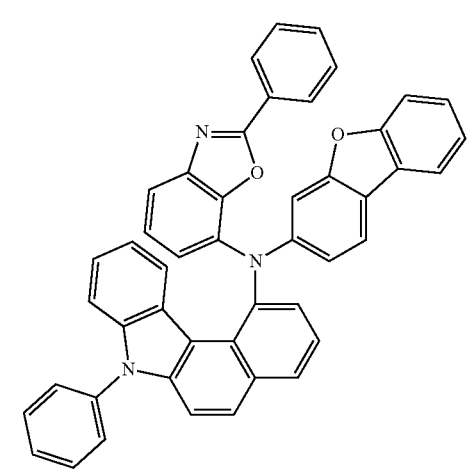
423
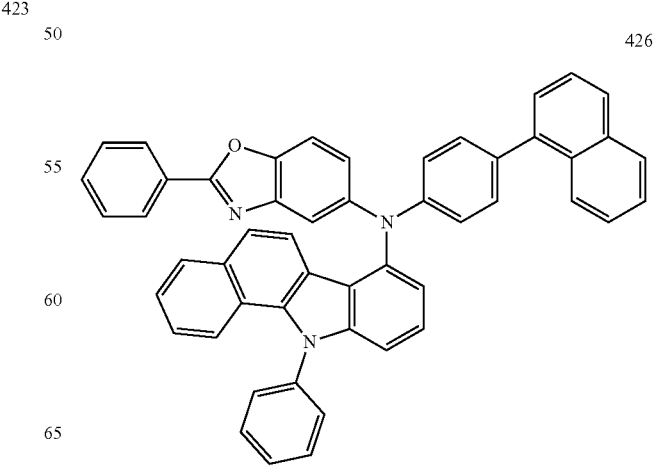
426

427
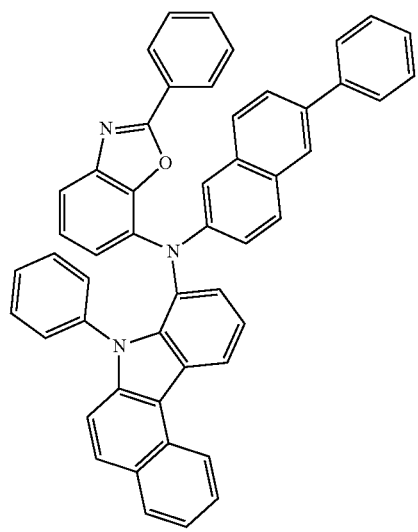
428
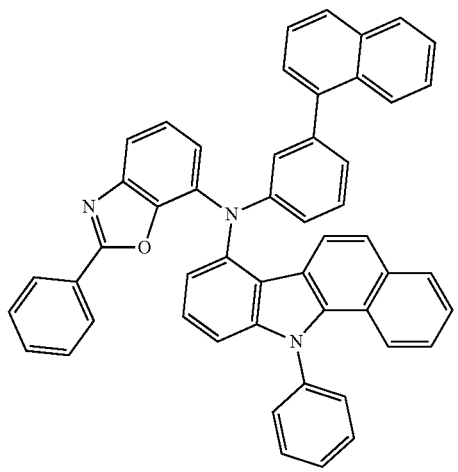
429
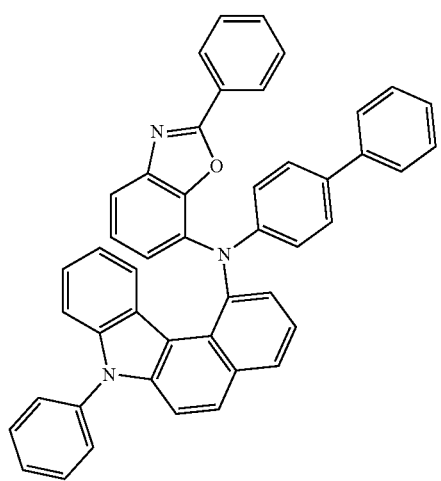
430
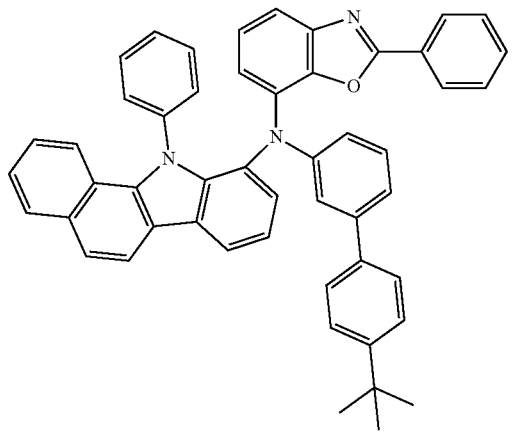
431
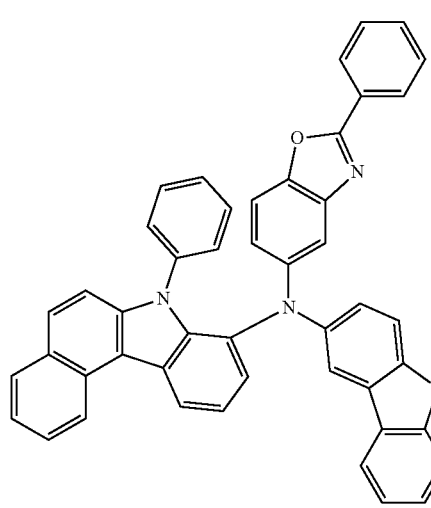
432
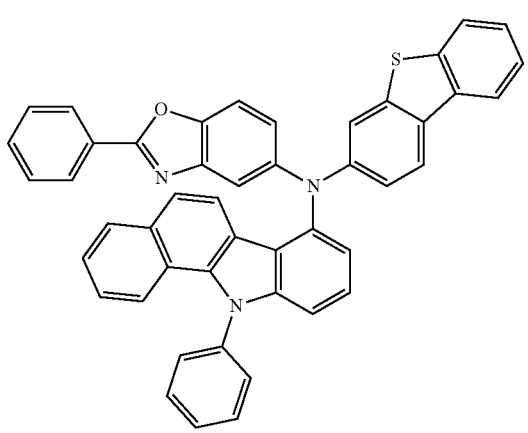

| 499 | 500 |
|---|---|
| -continued | -continued |
433
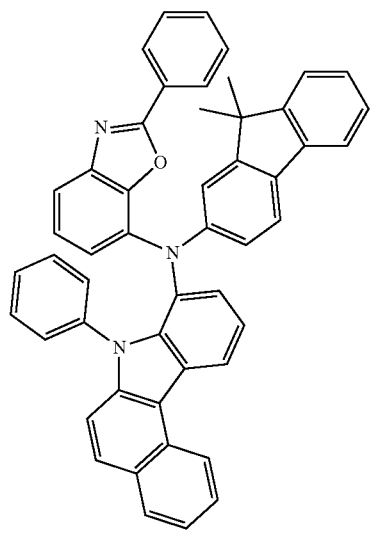
436
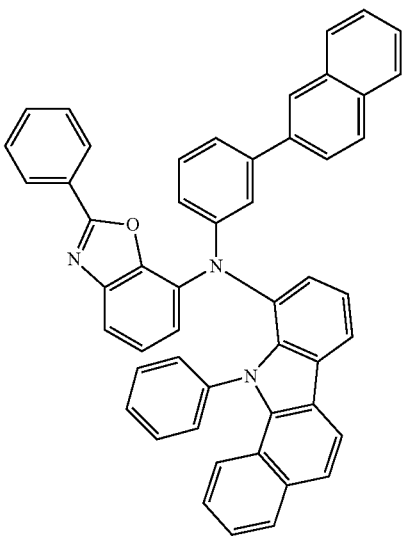
434
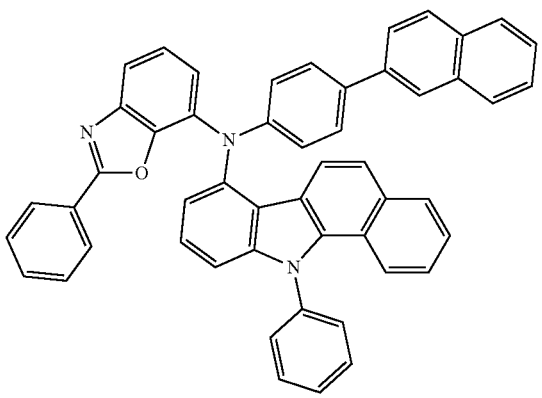 [SMILES: c1ccc(-c2nc3cccc(N(c4ccc(-c5ccc6ccccc6c5)cc4)c4cccc5c4c4ccc6ccccc6c4n5-c4ccccc4)c3o2)cc1]
437
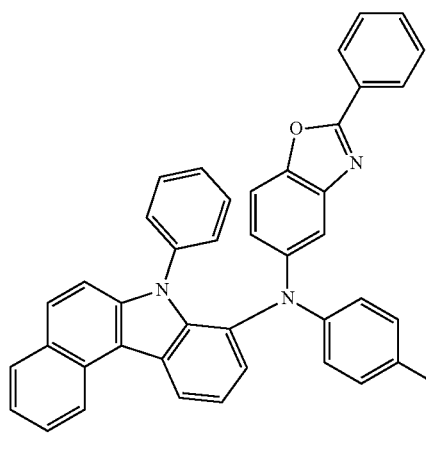
435
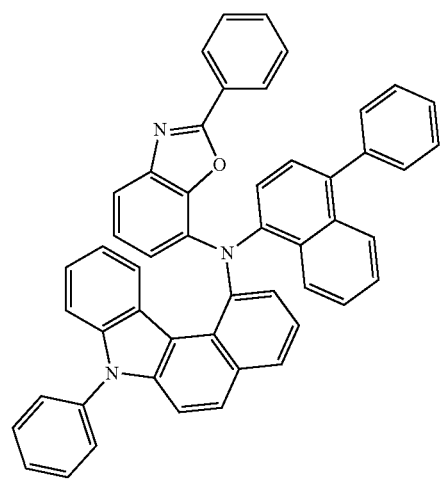
438
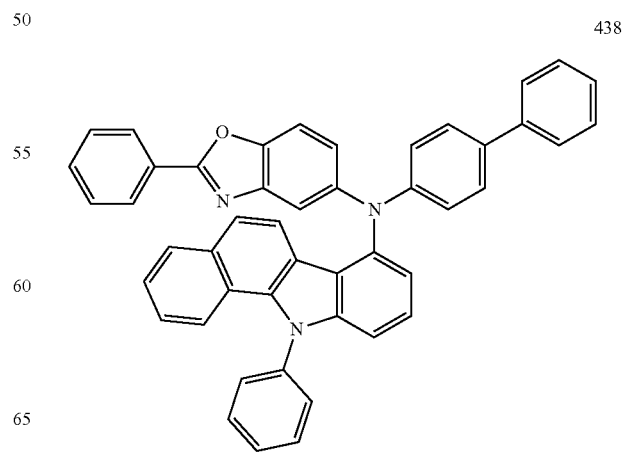

439
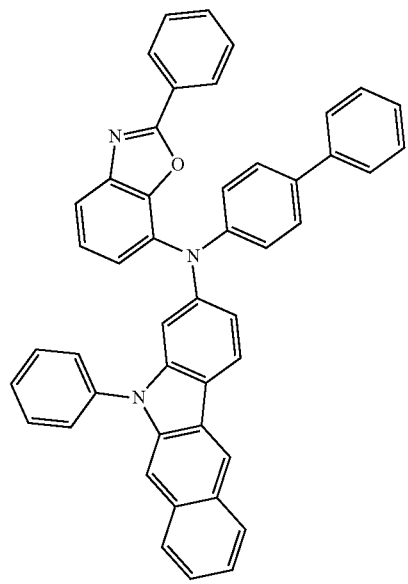
442
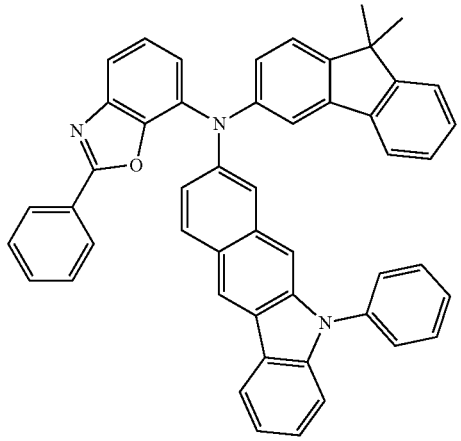
440
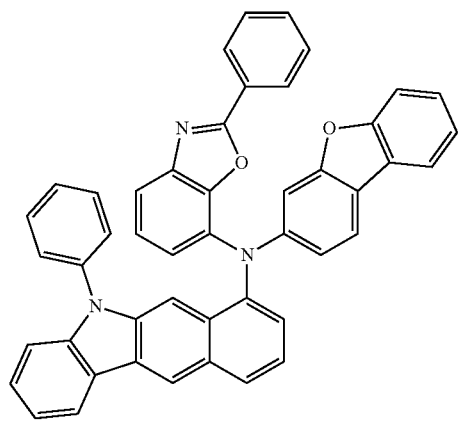
443
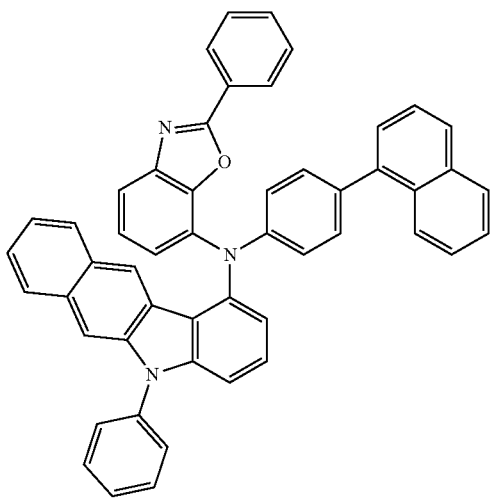
441
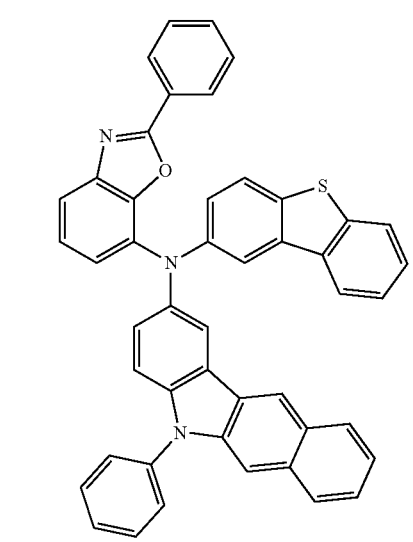
444
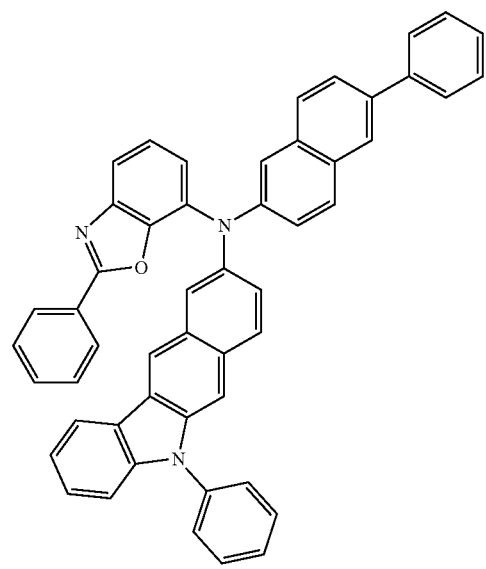

445
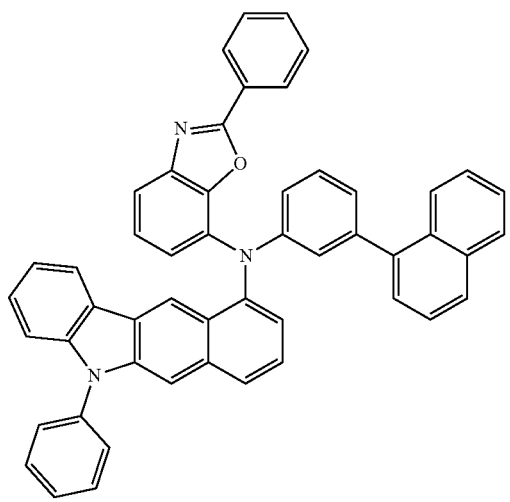
446
448
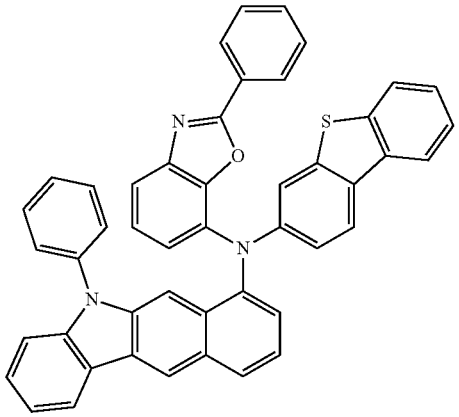
449
447
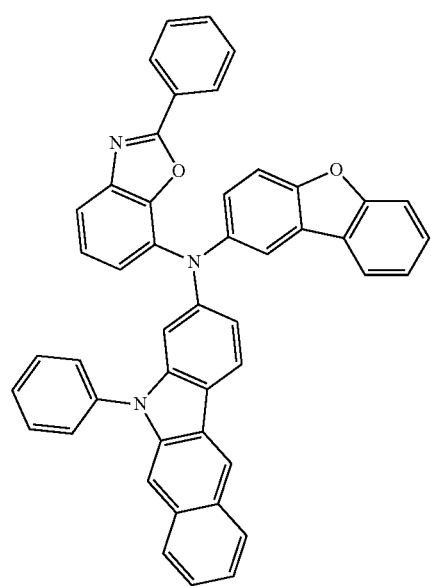
450
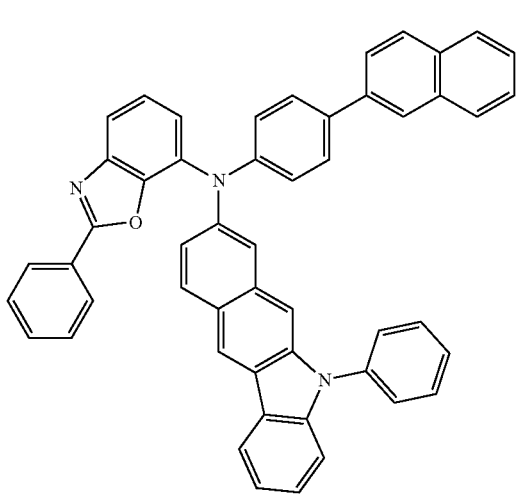

505
-continued
451
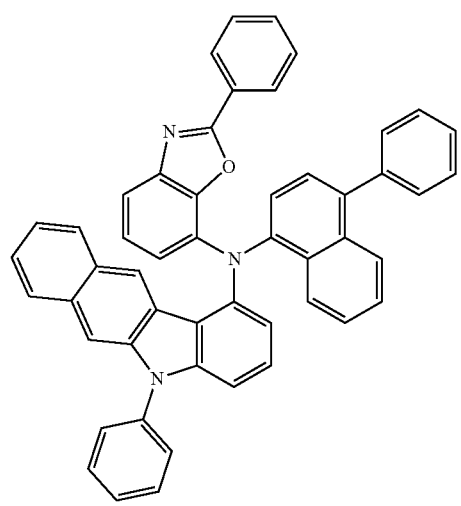
452
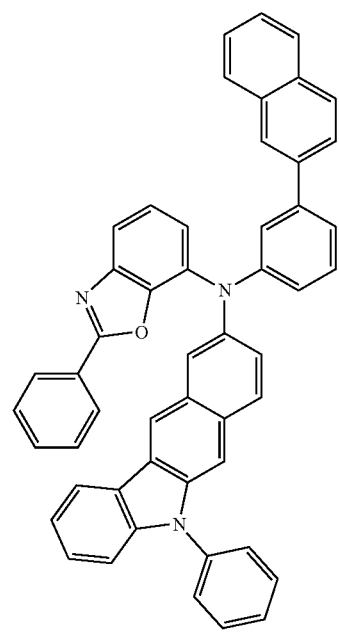
453
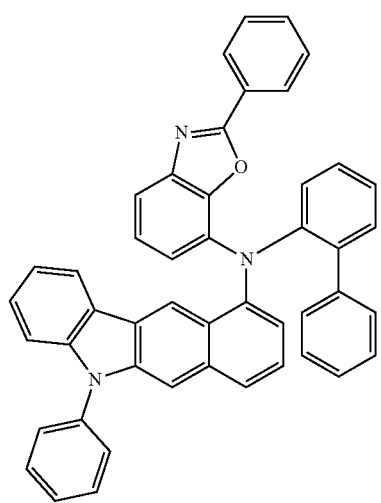
506
-continued
454
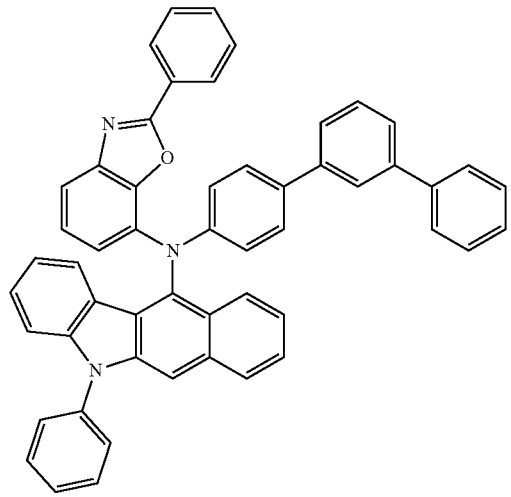
455
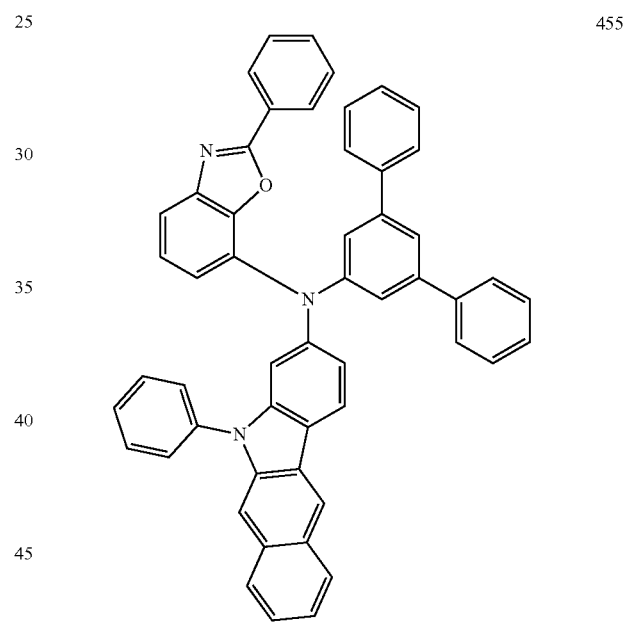
456
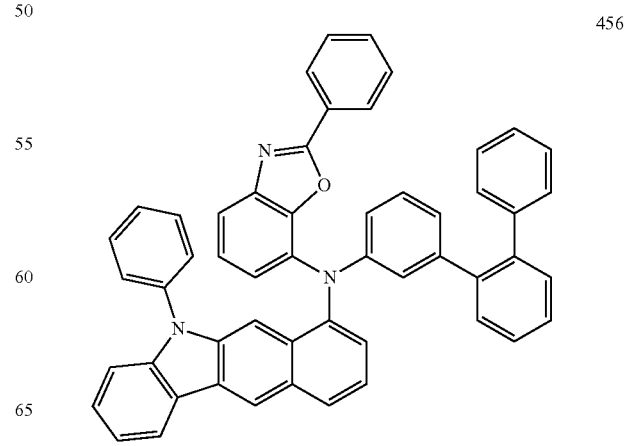

507
-continued
458
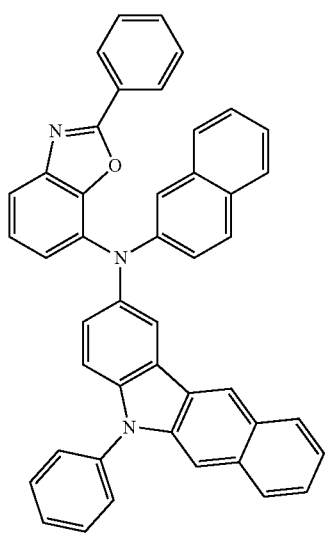
457
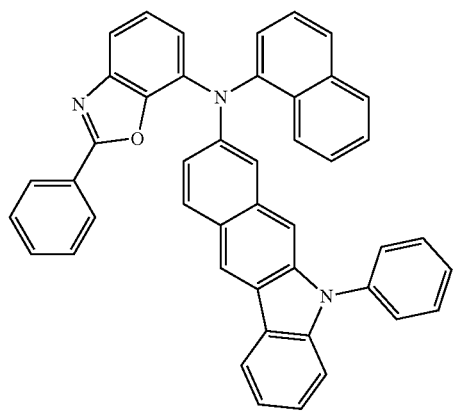
459
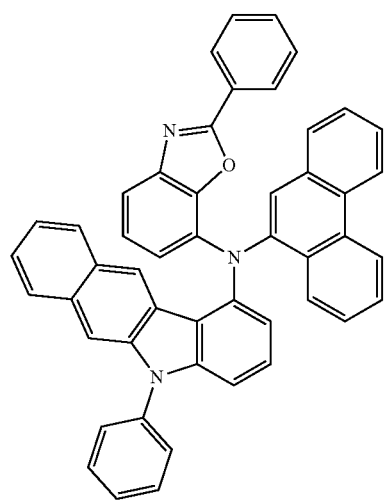
508
-continued
460
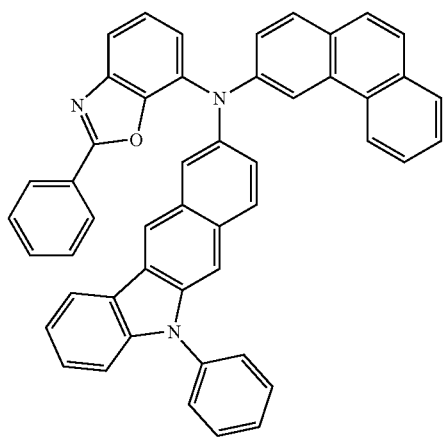
461
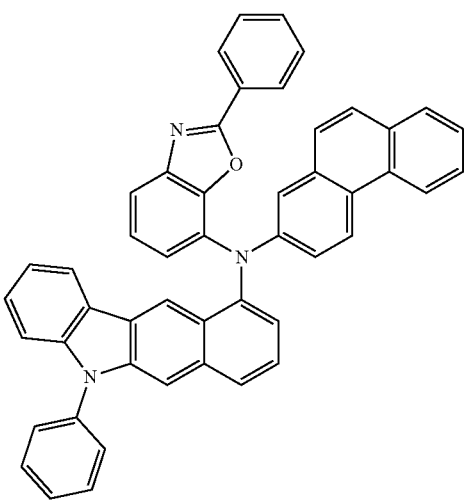
462
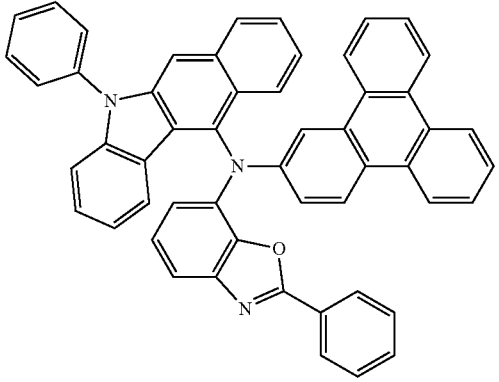

509
-continued
510
-continued
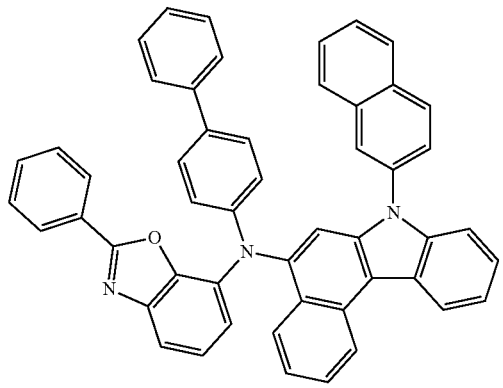
463
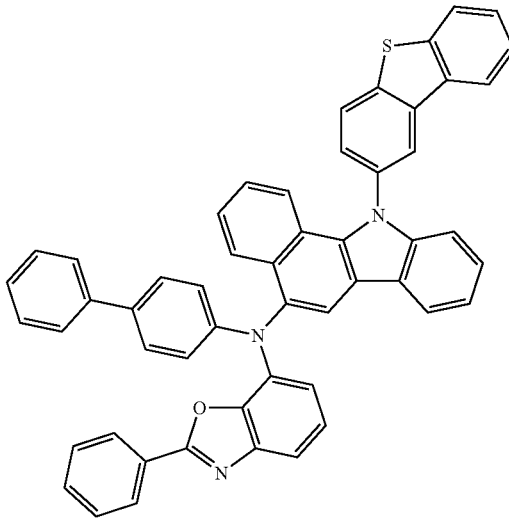
466
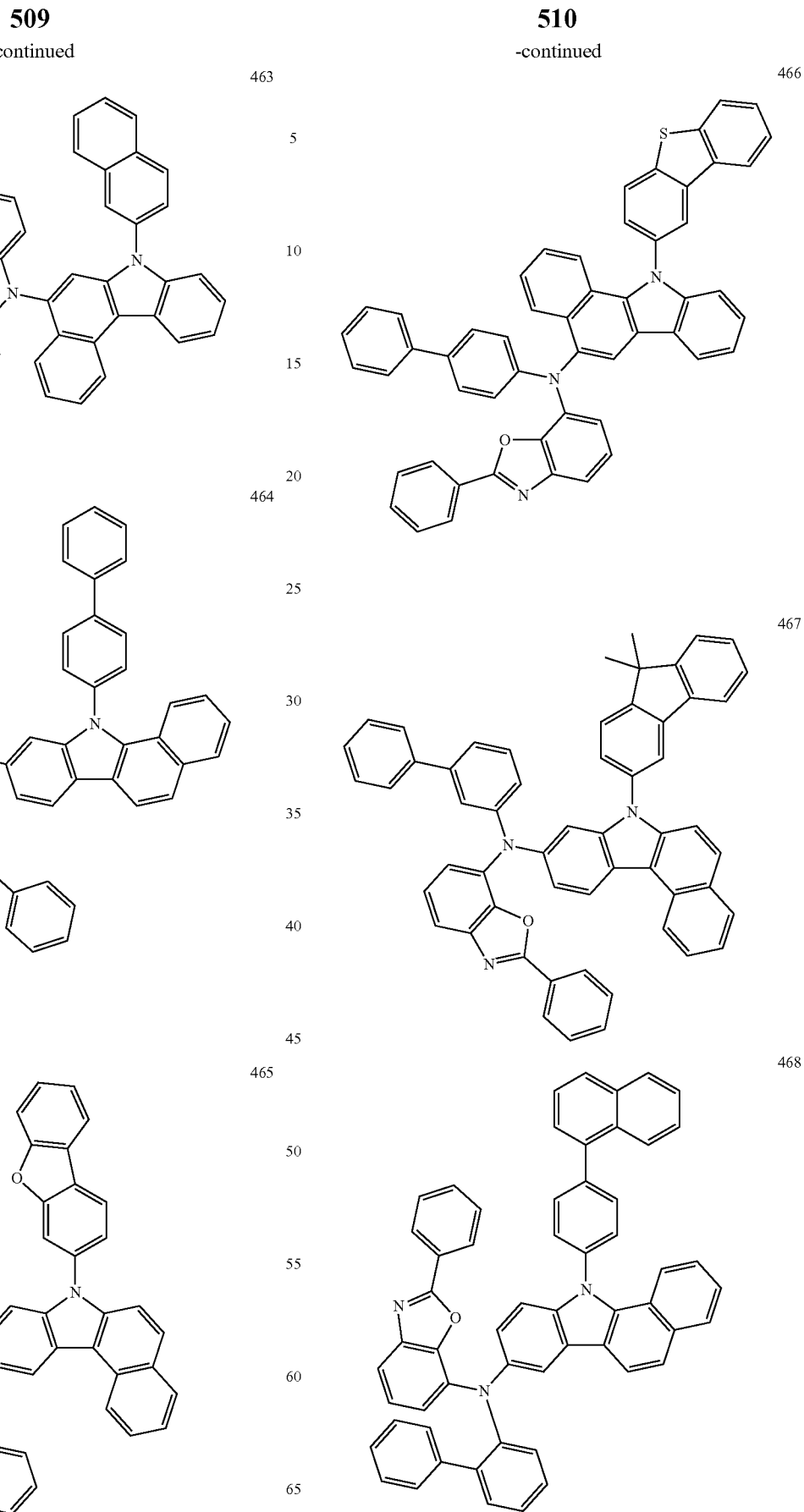
464
467
465
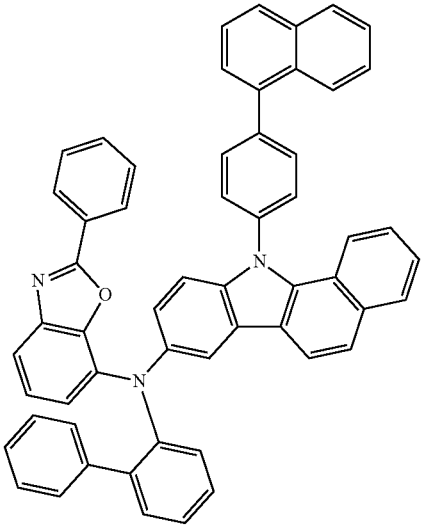
468

-continued
469
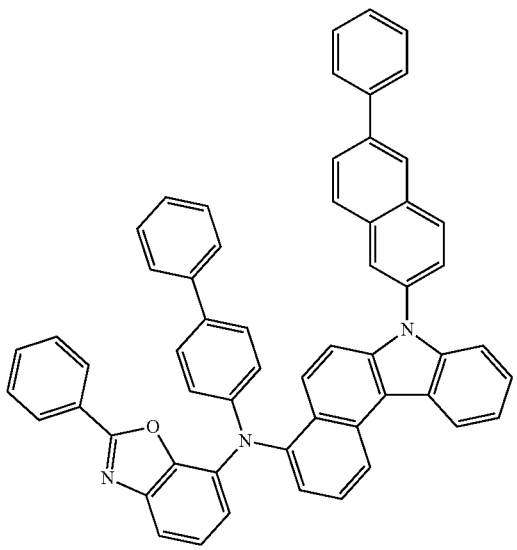
470
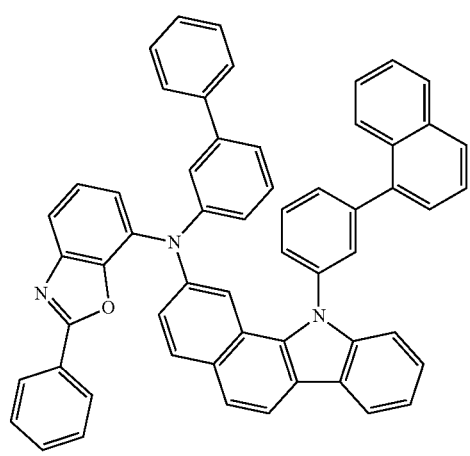 [SMILES: c1ccc(-c2cccc(N(c3ccc4ccc5c6ccccc6n(-c6cccc(-c7cccc8ccccc78)c6)c5c4c3)c3cccc4nc(-c5ccccc5)oc34)c2)cc1]
471
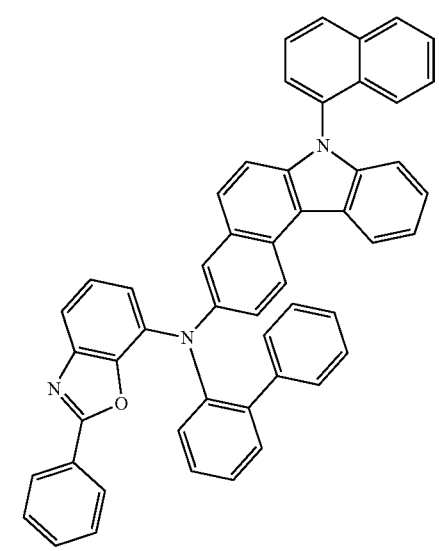
-continued
472
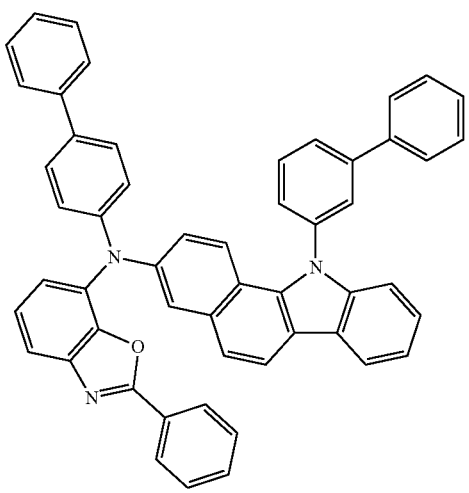
473
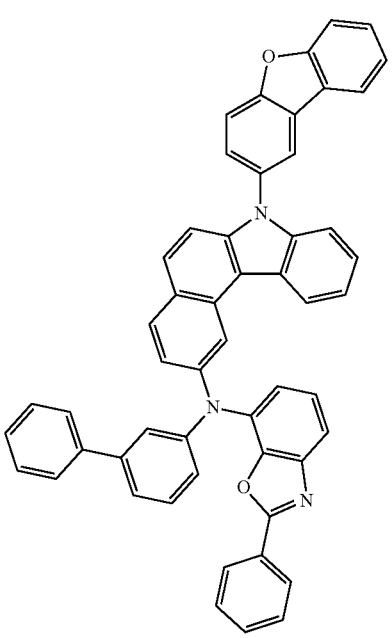
474
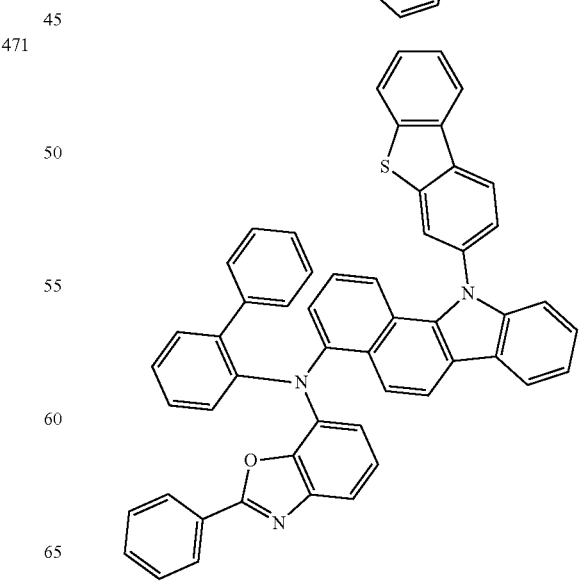

| 513 -continued | 514 -continued |
|---|---|
| 475 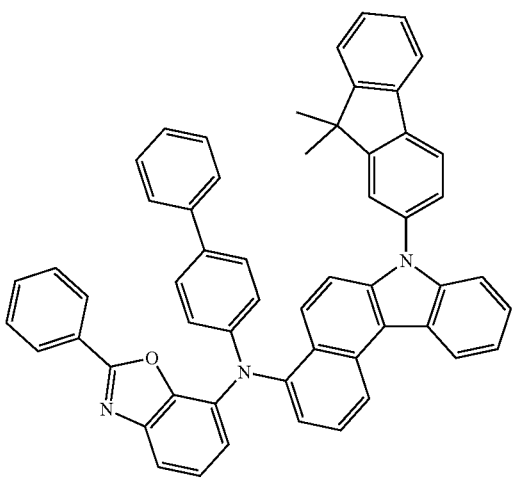 | 478 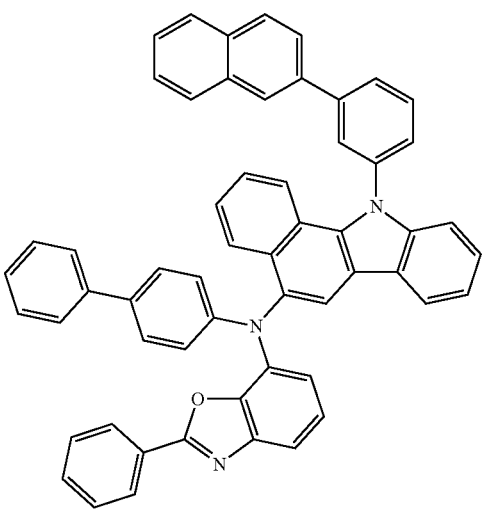 |
| 476 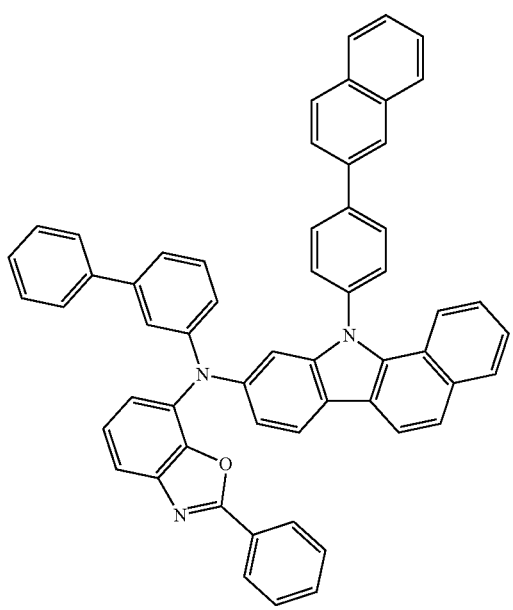 | 479 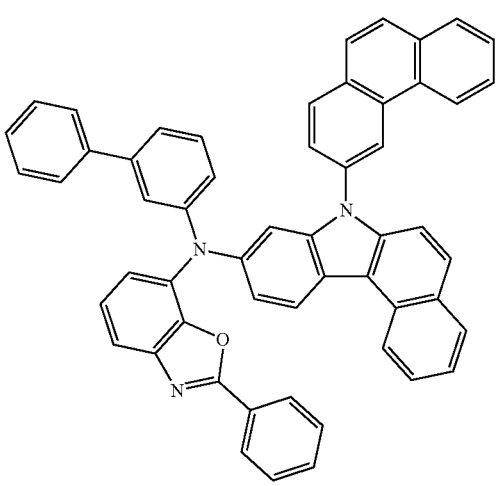 [SMILES: c1ccc(-c2cccc(N(c3ccc4c5c6ccccc6ccc5n(-c5ccc6ccc7ccccc7c6c5)c4c3)c3cccc4nc(-c5ccccc5)oc34)c2)cc1] |
| 477 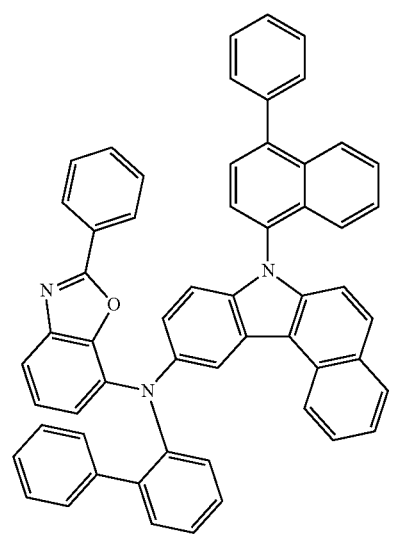 | 480 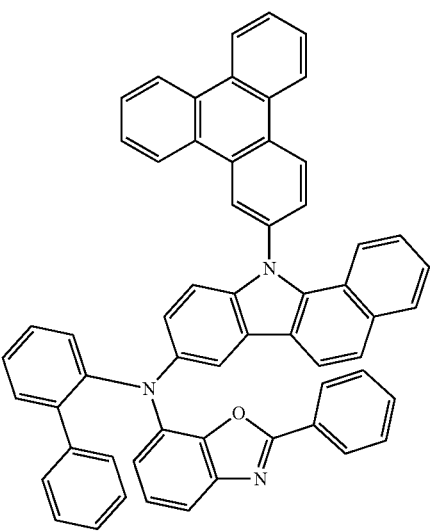 |

-continued
481
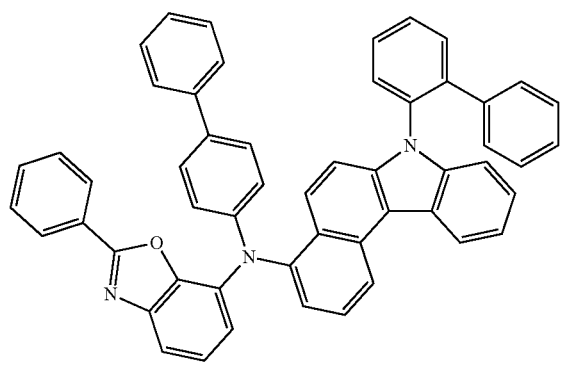
482
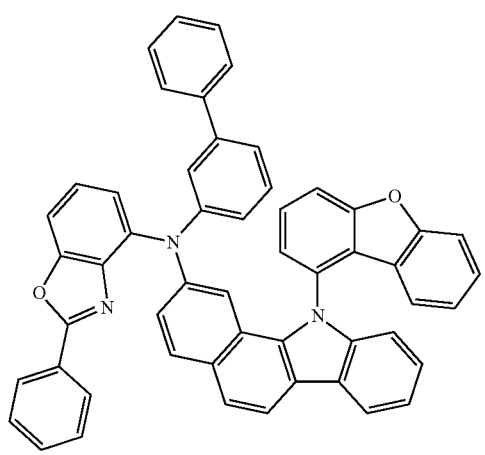
483
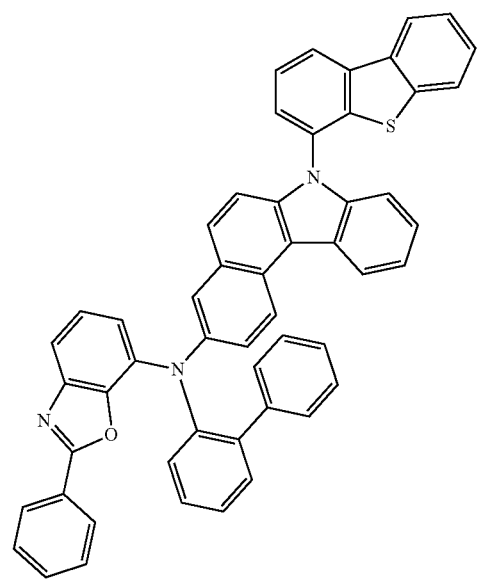
-continued
484
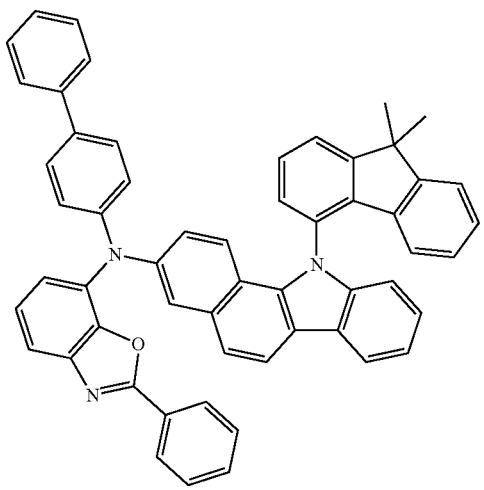
485
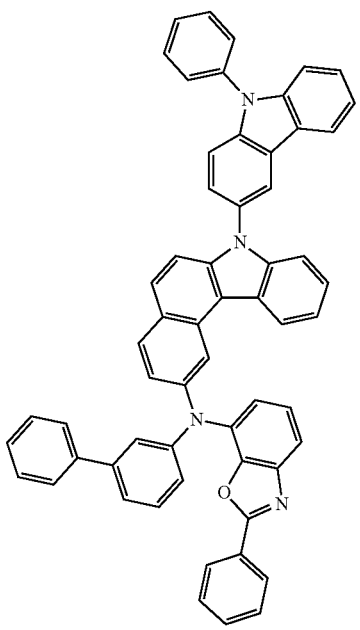
486
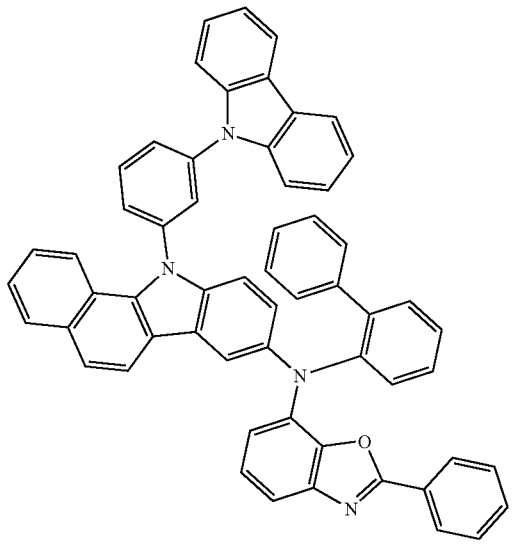

517
-continued
487
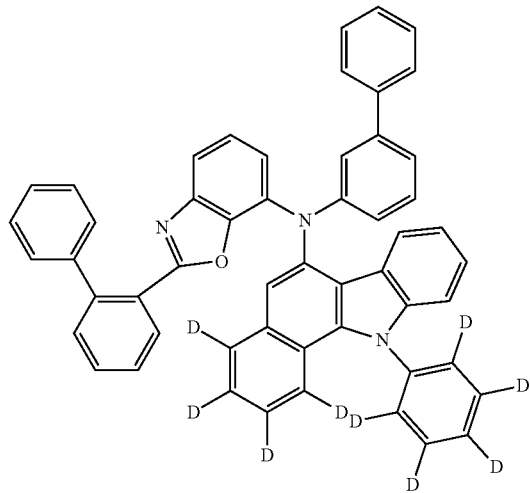
488
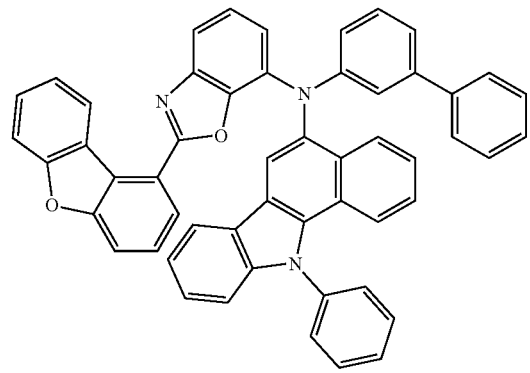
489
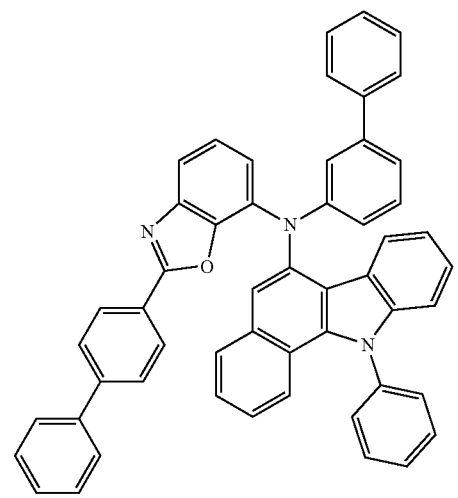
518
-continued
490
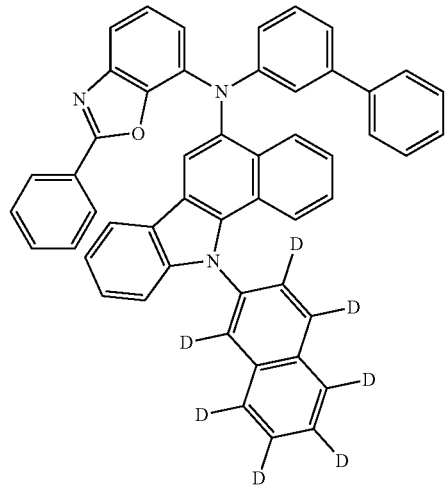
491
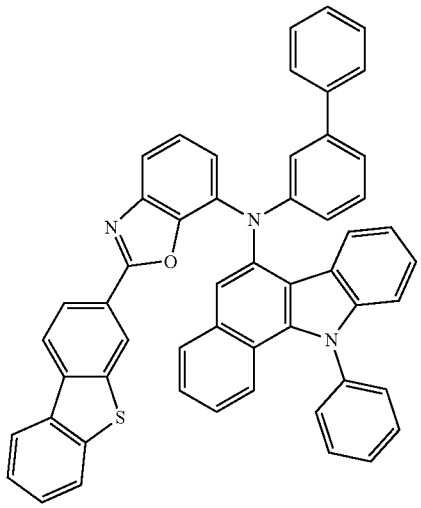
492
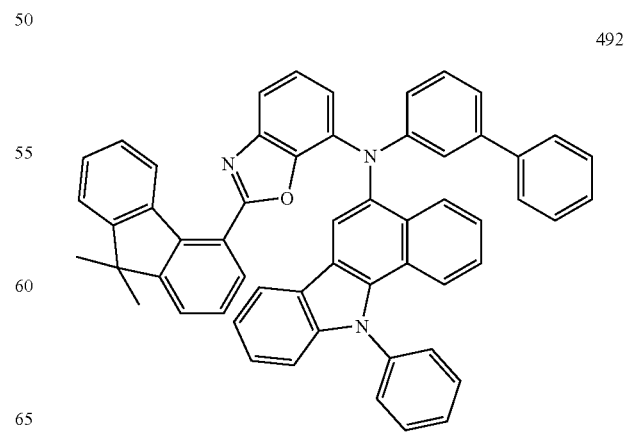

519
-continued
493
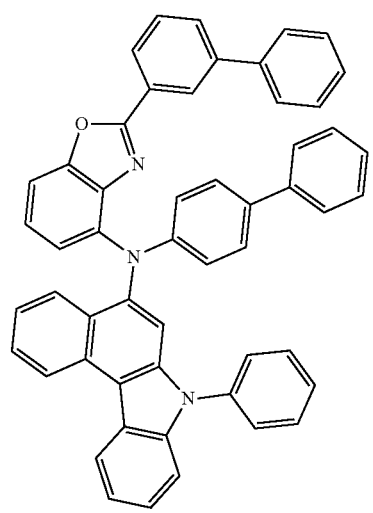
494
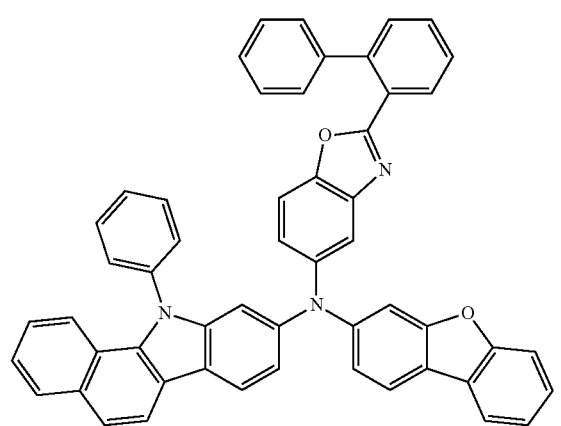
495
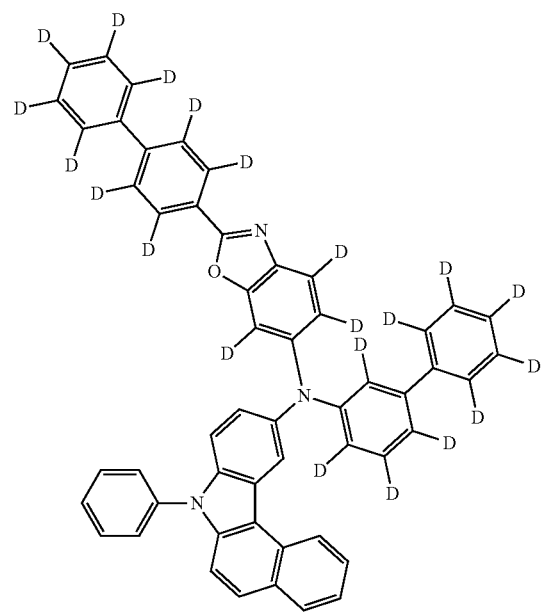
520
-continued
496
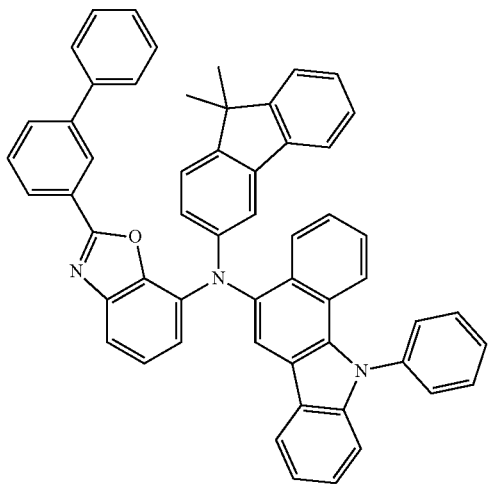
497
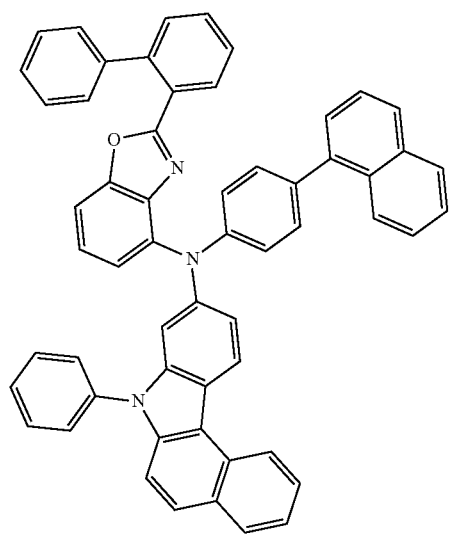
498
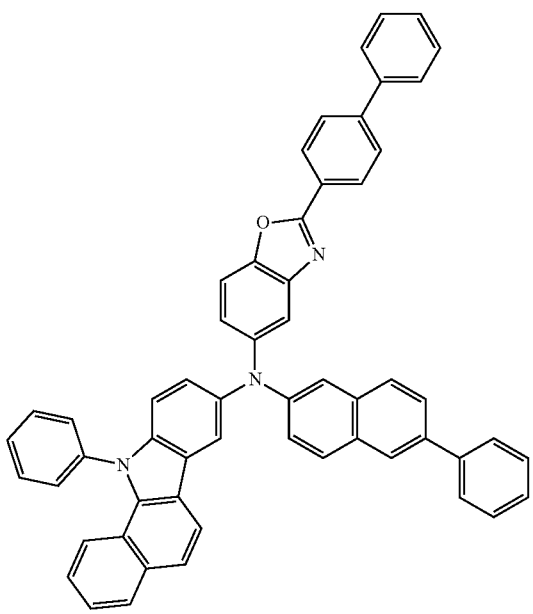

521
-continued
522
-continued
499
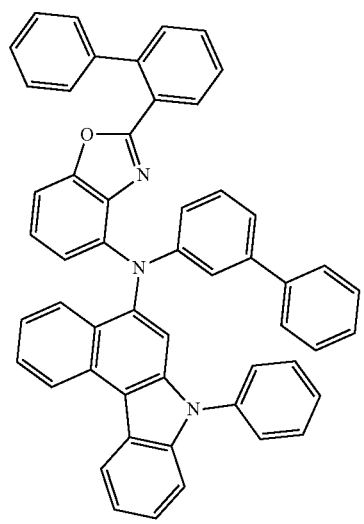
501
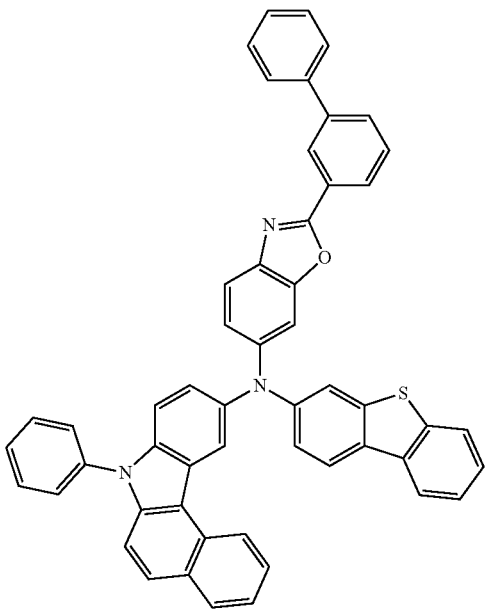
500
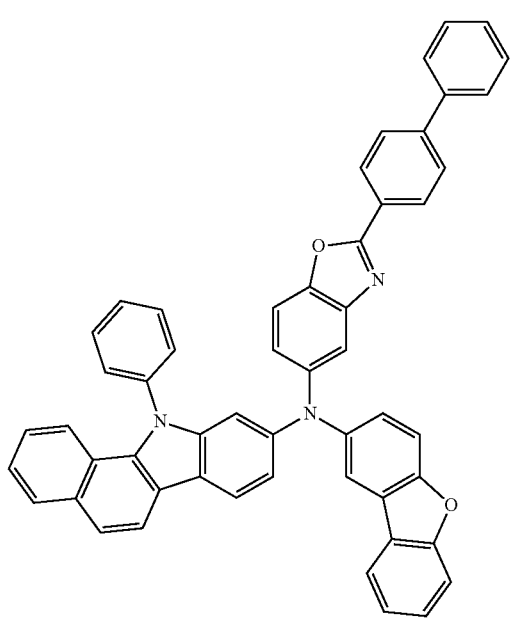
502
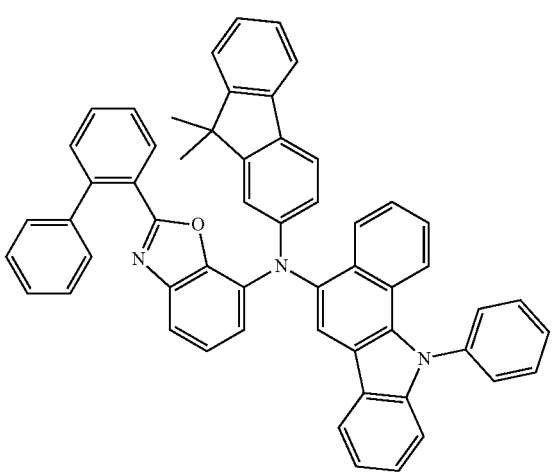

523
-continued
524
-continued
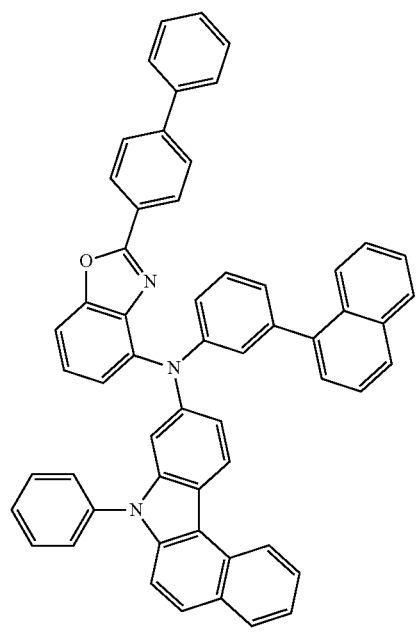
503
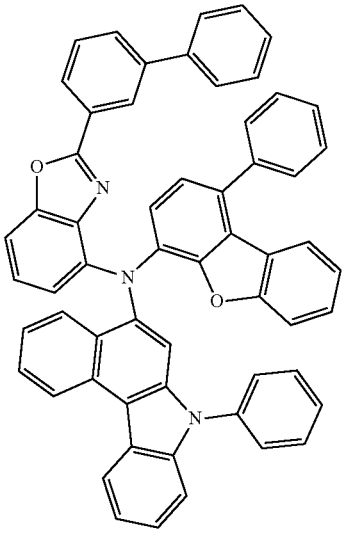
505
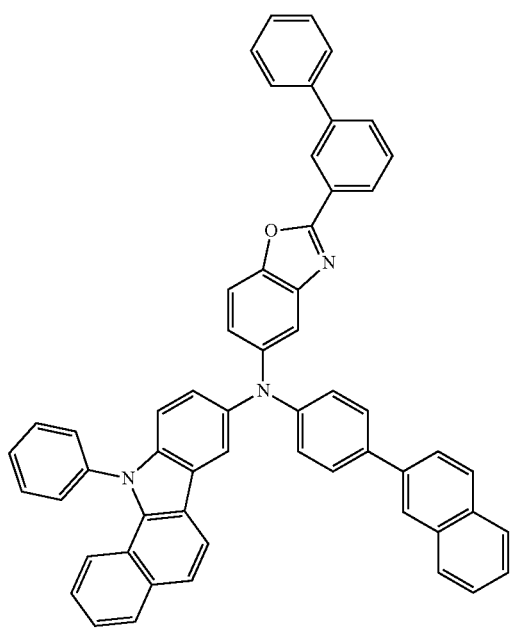
504
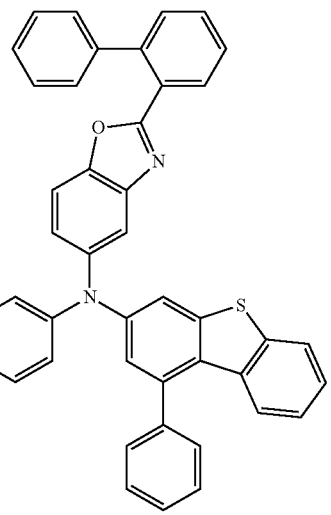
506

525
-continued

526
-continued

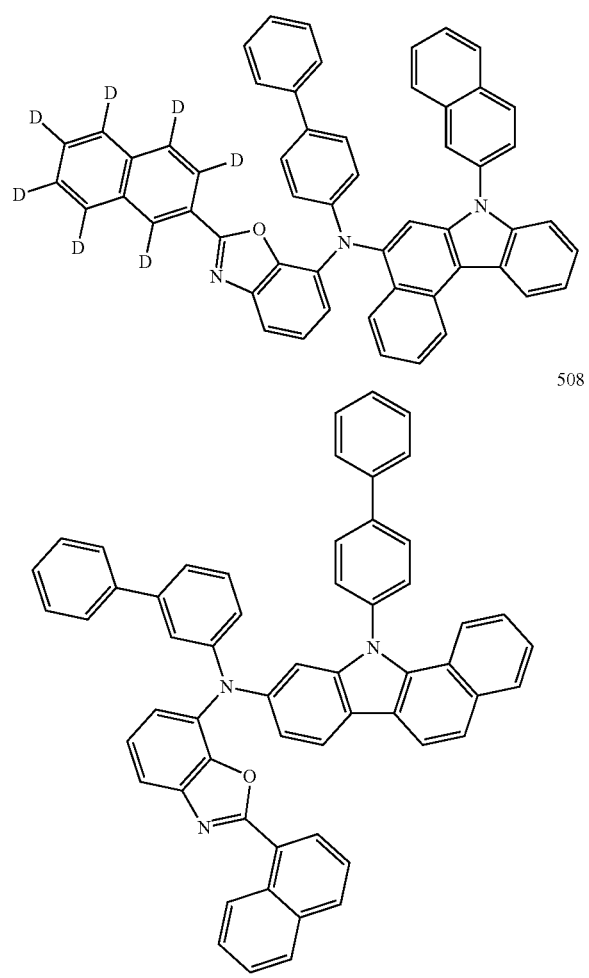

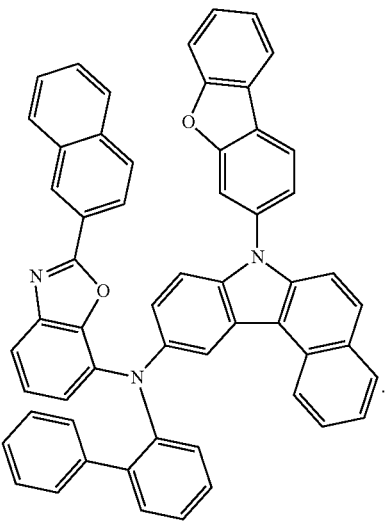

6. An organic electroluminescent device, comprising an anode and a cathode that are disposed opposite to each other, and a functional layer disposed between the anode and the cathode, wherein the functional layer comprises the arylamine compound according to claim 1.

7. The organic electroluminescent device according to claim 6, wherein the functional layer comprises an organic light-emitting layer, the organic light-emitting layer comprising the arylamine compound.

8. An electronic apparatus, comprising the organic electroluminescent device according to claim 6.

* * * * *

UNITED STATES PATENT AND TRADEMARK OFFICE
CERTIFICATE OF CORRECTION

PATENT NO. : 12,150,379 B2
APPLICATION NO. : 18/552891
DATED : November 19, 2024
INVENTOR(S) : Xianbin Xu and Lei Yang It is certified that error appears in the above-identified patent and that said Letters Patent is hereby corrected as shown below:

In the Claims

In Claim 1, Column 342, Line 55, 'Formula 1;' should read -- Formula 1: --.
In Claim 1, Column 343, Line 12, 'tert-butyl;' should read -- *tert*-butyl; --.

In Claim 1, Column 343, Lines 15-19, should read -- 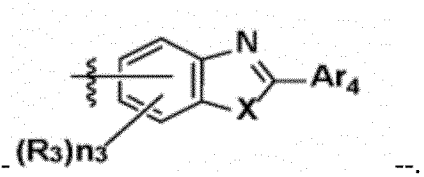 --.
In Claim 1, Column 345, Line 13, 'tert-butyl;' should read -- *tert*-butyl; --.
In Claim 1, Column 345, Line 26, 'tert-butyl;' should read -- *tert*-butyl; --.
In Claim 1, Column 345, Line 32, 'tert-butyl;' should read -- *tert*-butyl; --.

In Claim 5, Column 372, Lines 21-35, ' 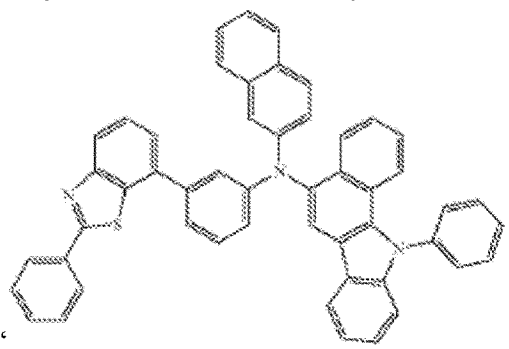 ' should read

Signed and Sealed this
Seventeenth Day of June, 2025

Coke Morgan Stewart
*Acting Director of the United States Patent and Trademark Office*

CERTIFICATE OF CORRECTION (continued)
U.S. Pat. No. 12,150,379 B2

Page 2 of 2

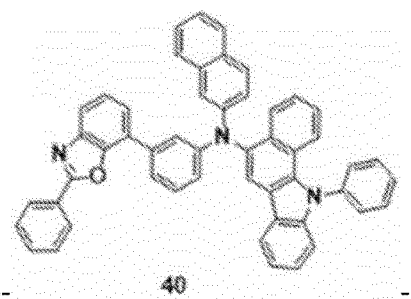

-- 40 --.

In Claim 5, Column 388, Lines 1-15, ' 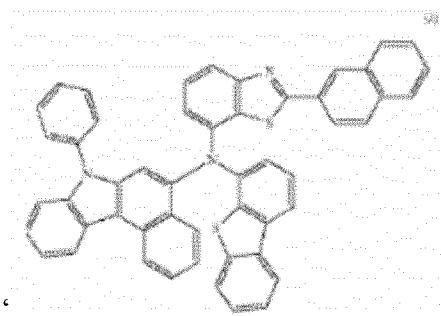 ' should read

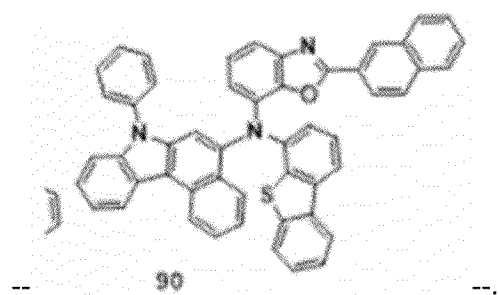

-- 90 --.

In Claim 5, Column 513, Lines 1-19, ' 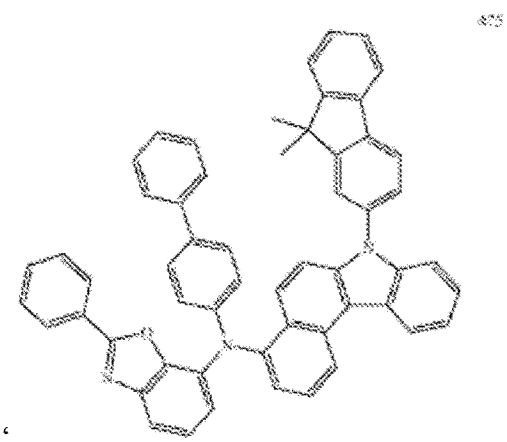 ' should read

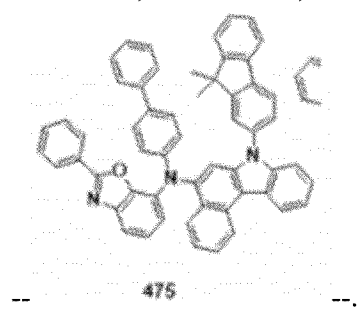

-- 475 --.